United States Patent
Reddy et al.

(10) Patent No.: US 11,629,146 B2
(45) Date of Patent: Apr. 18, 2023

(54) SUBSTITUTED [1,2,4]TRIAZOLO[4,3-A]PYRAZINES AS MODULATORS OF SODIUM CHANNEL ACTIVITY

(71) Applicant: Praxis Precision Medicines, Inc., Cambridge, MA (US)

(72) Inventors: Kiran Reddy, Boston, MA (US); Gabriel Martinez Botella, Wayland, MA (US); Andrew Mark Griffin, L'lle Bizard (CA); Brian Edward Marron, Durham, NC (US)

(73) Assignee: PRAXIS PRECISION MEDICINES, INC., Boston, MA (US)

( * ) Notice: Subject to any disclaimer, the term of this patent is extended or adjusted under 35 U.S.C. 154(b) by 456 days.

(21) Appl. No.: 16/464,468

(22) PCT Filed: Nov. 28, 2017

(86) PCT No.: PCT/US2017/063533
§ 371 (c)(1),
(2) Date: May 28, 2019

(87) PCT Pub. No.: WO2018/098499
PCT Pub. Date: May 31, 2018

(65) Prior Publication Data
US 2021/0188852 A1  Jun. 24, 2021

Related U.S. Application Data

(60) Provisional application No. 62/552,073, filed on Aug. 30, 2017, provisional application No. 62/458,306, filed on Feb. 13, 2017, provisional application No. 62/427,044, filed on Nov. 28, 2016.

(51) Int. Cl.
*A61K 31/4985* (2006.01)
*C07D 487/04* (2006.01)

(52) U.S. Cl.
CPC .................. *C07D 487/04* (2013.01)

(58) Field of Classification Search
CPC .......................... A61K 31/4985; C07D 487/04
USPC .......................................... 514/249; 544/236
See application file for complete search history.

(56) References Cited

U.S. PATENT DOCUMENTS

| | | |
|---|---|---|
| 3,845,770 A | 11/1974 | Theeuwes et al. |
| 4,112,095 A | 9/1978 | Allen, Jr. et al. |
| 4,230,705 A | 10/1980 | Allen, Jr. et al. |
| 4,242,515 A | 12/1980 | Trust et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hsieh et al. |
| 5,616,345 A | 4/1997 | Geoghegan et al. |
| 5,905,079 A | 5/1999 | Sargent et al. |
| 6,589,952 B2 | 7/2003 | Bakthavatchalam et al. |
| 7,863,279 B2 | 1/2011 | Even et al. |
| 8,030,305 B2 | 10/2011 | Lu et al. |
| 8,173,654 B2 | 5/2012 | Lu et al. |
| 8,198,448 B2 | 6/2012 | Albrecht et al. |
| 8,212,041 B2 | 7/2012 | Albrecht et al. |
| 8,217,177 B2 | 7/2012 | Albrecht et al. |
| 8,524,900 B2 | 9/2013 | Albrecht et al. |
| 8,937,060 B2 | 1/2015 | Cid-Nunez et al. |
| 8,952,034 B2 | 2/2015 | Corkey et al. |
| 9,066,954 B2 | 6/2015 | Albrecht et al. |
| 9,371,329 B2 | 6/2016 | Corkey et al. |
| 10,280,184 B2 | 5/2019 | Friedman et al. |
| 11,014,931 B2 | 5/2021 | Griffin et al. |
| 11,261,188 B2 | 3/2022 | Reddy et al. |
| 11,278,535 B2 | 3/2022 | Reddy et al. |
| 11,279,700 B2 | 3/2022 | Griffin et al. |
| 2002/0049208 A1 | 4/2002 | Bakthavatchalam et al. |
| 2009/0124609 A1 | 5/2009 | Albrecht et al. |
| 2009/0203707 A1 | 8/2009 | Rajamani et al. |
| 2010/0088778 A1 | 4/2010 | Mulley et al. |
| 2011/0021521 A1 | 1/2011 | Corkey et al. |
| 2012/0010192 A1 | 1/2012 | Kobayashi et al. |
| 2012/0065191 A1 | 3/2012 | Kiss et al. |
| 2012/0245164 A1 | 9/2012 | Auger et al. |
| 2013/0315895 A1 | 11/2013 | Farrell et al. |
| 2014/0066443 A1 | 3/2014 | Beshore et al. |
| 2014/0303158 A1 | 10/2014 | Corkey et al. |
| 2015/0038503 A1 | 2/2015 | Bourotte et al. |
| 2015/0344457 A1 | 12/2015 | Duncan et al. |

(Continued)

FOREIGN PATENT DOCUMENTS

| | | |
|---|---|---|
| CA | 1080712 A | 7/1980 |
| JP | 11-503437 A | 3/1999 |

(Continued)

OTHER PUBLICATIONS

US 8,754,103 B2, 06/2014, Corkey et al. (withdrawn)
File Registry on STN, RN 1347643-11-1, Entered STN: Dec. 2, 2011.
Berge et al., (1977). "Pharmaceutical salts," J. Pharmaceutical Sciences, 66(1): 1-19.
Burbano et al., (2018) "Characterization of a Novel Knock-In Mouse Model of KCNT1 Epileptic Encephalopathy (P2. 273)," Neurology, 90(15 Supplement), 2 pages. Abstract Only.

(Continued)

*Primary Examiner* — Douglas M Willis
(74) *Attorney, Agent, or Firm* — McCarter & English, LLP; Jonathan M. Sparks

(57) ABSTRACT

The present invention is directed to, in part, fused heteroaryl compounds and compositions useful for preventing and/or treating a disease or condition relating to aberrant function of a voltage-gated, sodium ion channel, for example, abnormal late/persistent sodium current. Methods of treating a disease or condition relating to aberrant function of a sodium ion channel including Dravet syndrome or epilepsy are also provided herein.

14 Claims, No Drawings

(56) References Cited

U.S. PATENT DOCUMENTS

| | | | |
|---|---|---|---|
| 2016/0159801 | A1 | 6/2016 | Quinn et al. |
| 2016/0235718 | A1 | 8/2016 | Baraban |
| 2016/0297799 | A1 | 10/2016 | Brookings et al. |
| 2016/0317536 | A1 | 11/2016 | Reich et al. |
| 2019/0308938 | A1 | 10/2019 | McCormack et al. |
| 2019/0389868 | A1 | 12/2019 | Reddy et al. |
| 2020/0179358 | A1 | 6/2020 | Reddy et al. |
| 2020/0247793 | A1 | 8/2020 | Reddy et al. |
| 2020/0377499 | A1 | 12/2020 | Griffin et al. |
| 2020/0377506 | A1 | 12/2020 | Reddy et al. |
| 2020/0377507 | A1 | 12/2020 | Griffin et al. |
| 2021/0087197 | A1 | 3/2021 | Griffin et al. |
| 2021/0163488 | A1 | 6/2021 | Griffin et al. |
| 2021/0171530 | A1 | 6/2021 | Reddy et al. |
| 2021/0188839 | A1 | 6/2021 | Reddy et al. |
| 2021/0188852 | A1 | 6/2021 | Reddy et al. |
| 2021/0355118 | A1 | 11/2021 | Reddy et al. |
| 2021/0403476 | A1 | 12/2021 | Reddy et al. |
| 2022/0024930 | A1 | 1/2022 | Griffin et al. |

FOREIGN PATENT DOCUMENTS

| | | |
|---|---|---|
| JP | 5340798 B2 | 11/2013 |
| JP | 2017001991 A | 1/2017 |
| WO | WO-2006061428 A2 | 6/2006 |
| WO | WO-2007075567 A1 | 7/2007 |
| WO | WO-2008008539 A2 | 1/2008 |
| WO | WO-2010053757 A1 | 5/2010 |
| WO | WO-2010056865 A1 | 5/2010 |
| WO | WO-2010074807 A1 | 7/2010 |
| WO | WO-2011014462 A1 | 2/2011 |
| WO | WO-2011056985 A2 | 5/2011 |
| WO | WO-2012003392 A1 | 1/2012 |
| WO | WO-2012065546 A1 | 5/2012 |
| WO | WO-2012154760 A1 | 11/2012 |
| WO | WO-2013006463 A1 | 1/2013 |
| WO | WO-2013043925 A1 | 3/2013 |
| WO | WO-2014179492 A1 | 11/2014 |
| WO | WO-2015095370 A1 | 6/2015 |
| WO | WO-2015158283 A1 | 10/2015 |
| WO | WO-2015194670 A1 | 12/2015 |
| WO | WO-2015197567 A1 | 12/2015 |
| WO | 2018067786 A1 | 4/2018 |
| WO | WO-2018098491 A1 | 5/2018 |
| WO | WO-2018098499 A1 | 5/2018 |
| WO | WO-2018098500 A1 | 5/2018 |
| WO | WO-2018148745 A1 | 8/2018 |
| WO | WO-2018187480 A1 | 10/2018 |
| WO | WO-2019035951 A1 | 2/2019 |
| WO | WO-2019232209 A1 | 12/2019 |
| WO | WO-2020069322 A1 | 4/2020 |
| WO | 20211108513 A1 | 6/2021 |
| WO | 20211108625 A1 | 6/2021 |

OTHER PUBLICATIONS

Cannon, J. G., (1995), "Chapter Nineteen: Analog Design," Burger's Medicinal Chemistry and Drug Discovery, Fifth Edition, vol. I: Principles and Practice, Wiley-Interscience, pp. 783-802.

Chaplan et al., (1994), "Quantitative assessment of tactile allodynia in the rat paw," J Neurosci Meth., 53:55-63.

Dorwald, F. Z., (2005). "Side Reactions in Organic Synthesis," Wiley: VCH, Weinheim, 37 pages.

Flynn et al., (1972), "Correlation and Prediction of Mass Transport across Membranes I: Influence of Alkyl Chain Length on Flux-Determining Properties of Barrier and Diffusant," Journal of Pharmaceutical Sciences, 61 (6): 838-852.

Fukaya et al., (2013), "Identification of a Novel Benzoxazolone Derivative as a Selective, Orally Active 18 kDa Translocator Protein (TSPO) Ligand," J. of Med. Chem., 56(20): 8191-8195.

Hackam et al., (2006), :Translation of research evidence from animals to humans,Δ JAMA, 296(14): 1731-1732.

Jordan et al., (2003), "Tamoxifen: a most unlikely pioneering medicine," Nat Rev Drug Discov., 2(3):205-213.

Kearney et al., (2001). "A gain-of-function mutation in the sodium channel gene Scn2a results in seizures and behavioral abnormalities," Neuroscience, 702(2):307-317. Abstract Only.

Kim et al., (1992), "An experimental model for peripheral neuropathy produced by segmental spinal nerve ligitation in the rat," Pain, 50:355-363.

Li et al., (2018). "Antisense oligonucleotide therapy for SCN2A gain-of-function epilepsies," American Epilepsy Society, 28 pages.

Patel et al., (2019), "Neuropathy following spinal nerve injury shares features with the irritable nociceptor phenotype: A back-translational study of oxcarbazepine," Eur J Pain, 23:183-197.

Petrou et al., (2018), "Abstract: Antisense oligonucleotide therpay SCNA2 gain-of-function epilepsis," American Epilepsy Society, available online at <http://www.aesnet.org/abstractslisting/antisense-oligonucleotide-therapy-for-scna2a-gain-of-function-epilepsies>, 2 pages.

Venkatesh et al., (2000), "Role of the developed scientist in compound lead selection and optimization," J Pharm Sci., 89(2):145-54.

Wagnon et al., (2015), "Convulsive seizures and SUDEP in a mouse model of SCN8A epileptic encephalopathy," Human Molecular Genetics, 24(2):506-515.

Wilen et al., (1977). "Strategies in optical resolutions," Tetrahedron, 33(21):2725-2736.

Woodland et al., (2015), "Discovery of Inhibitors of Trypanosomo brucei by Phenotypic Screening of a Focused Protein Kinase Library," ChemMedChem, 10(11): 1809-1820.

Zaza et al., (2008), "Pathophysiology and pharmacology of the cardiac 'late sodium current'," Pharmacology & Therapeutics, 119(3):326-339.

Final Office Action received for U.S. Appl. No. 16/638,725 dated Apr. 2, 2021, 8 pages.

International Preliminary Report and Patentability for International Patent Application No. PCT/US2018/018044 filed on Feb. 13, 2018, 7 pages.

International Preliminary Report and Patentability for International Patent Application No. PCT/US2018/026099 filed on Apr. 4, 2018, 6 pages.

International Preliminary Report and Patentability for International Patent Application No. PCT/US2017/063507 filed on Nov. 28, 2017, 6 pages.

International Preliminary Report and Patentability for International Patent Application No. PCT/US2017/063534 filed on Nov. 28, 2017, 8 pages.

International Preliminary Report and Patentability for International Patent Application No. PCT/US2018/000224 filed on Aug. 15, 2018, 6 pages.

International Search Report and Written Opinion dated Feb. 25, 2021, for PCT Application No. PCT/US2020/062179 filed on Nov. 25, 2020, 7 pages.

International Search Report and Written Opinion received for International Patent Application No. PCT/US2020/062317 dated Apr. 6, 2021, 14 pages.

Non-Final Office Action received for U.S. Appl. No. 16/638,725 dated Dec. 11, 2021, 16 pages.

Non-Final Office Action received for U.S. Appl. No. 16/887,906 dated Jun. 10, 2021, 18 pages.

Non-Final Office Action received for U.S. Appl. No. 16/464,483 dated Jun. 30, 2021, 22 pages.

Non-Final Office Action received for U.S. Appl. No. 16/485,581 dated Mar. 10, 2021, 8 pages.

Non-Final Office Action received for U.S. Appl. No. 17/102,586 dated Jan. 26, 2021, 14 pages.

Non-Final Office Action received for U.S. Appl. No. 16/500,795 dated Apr. 13, 2022, 18 pages.

Non-Final Office Action received for U.S. Appl. No. 16/885,605 dated Jan. 28, 2022, 10 pages.

Restriction Requirement received for U.S. Appl. No. 16/500,795 dated Dec. 16, 2021, 12 pages.

Albright et al. "Synthesis and anxiolytic activity of 6-(substituted-phenyl)-1,2,4-triazolo[4,3-b]pyridazines," *J. Med. Chem.* (1981) vol. 24, pp. 592-600.

Anderson et al. "Unexpected efficacy of a novel sodium channel modulator in Dravet Syndrome," Scientific Reports. 2017.

(56) References Cited

OTHER PUBLICATIONS

Anderson et al., "Antiepileptic activity of preferential inhibitors of persistent sodium current," Epilepsia (2014), 55(8), 1274-1283.
Baker et al. "The novel sodium channel modulator GS-458967 (GS967) is an effective treatment in a mouse model of SCN8A encephalopathy," Epilepsia, 2018, 1166-1176.
Barbieri et al. "Late sodium current blocker GS967 inhibits persistent currents induced by familial hemiplegic migraine type 3 mutations of the SCN1A gene," *The Journal of Headache and Pain* (2019) vol. 20, No. 107, pp. 1-13.
Belardinelli et al. "A Novel, Potent, and Selective Inhibitor of Cardiac Late Sodium Current Suppresses Experimental Arrhythmias," *J. Pharmacol. Exp. Ther.* (2013) vol. 344, pp. 23-32.
Guan et al. "Synthesis and anticonvulsant activity of a new 6-alkoxy-[1,2,4]-triazolo[4,3-b]pyridazine," *Eur. J. Med. Chem.* (2010) vol. 45, pp. 1746-1752.
Koltun et al. "Discovery of triazolopyridinone GS-462808, a late sodium current inhibitor (Late INai) of the cardiac Nav1.5 channel with improved efficacy and potency relative to ranolazine," *Bioorg. Med. Chem. Lett.* (2016) vol. 26, pp. 3207-3211.
PUBCHEM-CID 58763997 Create Date: Aug. 19, 2012 (14 pages).
PUBCHEM-CID 597467 Create Date: Mar. 27, 2005 (15 pages).
PUBCHEM-CID 82381512 Create Date: Oct. 20, 2014 (10 pages).
PUBCHEM-CID 89077556 Create Date: Feb. 13, 2015 (11 pages).
STN Chemical Structure Search Results (dated Apr. 14, 2019). (36 pages).
STN Chemical Structure Search Results (dated Apr. 2018). (55 pages).
STN Chemical Structure Search Results (dated Apr. 23, 2019). (45 pages).
STN Chemical Structure Search Results (dated Feb. 2018). (29 pages).
STN Chemical Structure Search Results (dated Jan. 15, 2020). (22 pages).
STN Chemical Structure Search Results (dated Jan. 2018). (23 pages).
STN Chemical Structure Search Results (dated Mar. 20, 2018). (264 pages).
STN Chemical Structure Search Results (dated Mar. 20, 2018). (83 pages).
STN Chemical Structure Search Results (dated Mar. 6, 2017). (480 pages).
STN Chemical Structure Search Results (dated Mar. 6, 2017). (511 pages).
STN Chemical Structure Search Results (dated May 18, 2016). (102 pages).
STN Chemical Structure Search Results (dated Nov. 1, 2017). (107 pages).
STN Chemical Structure Search Results (dated Nov. 21, 2017). (85 pages).
STN Chemical Structure Search Results (dated Nov. 3, 2017). (57 pages).
STN Chemical Structure Search Results (dated Nov. 6, 2017). (123 pages).
STN Chemical Structure Search Results (dated Nov. 6, 2017). (7 pages).
Wengert et al. "Prax330 reduces persistent and resurgent sodium channel currents and neuronal hyperexcitability of subiculum neurons in a mouse model of SCN8A epileptic encephalopathy," *Neuropharmacology* (2019) vol. 158, No. 107699, pp. 1-11.
Written Opinion of the International Searching Authority and International Search Report for PCT/US2017/063507 dated Mar. 29, 2019 (9 pages).
Written Opinion of the International Searching Authority and International Search Report for PCT/US2017/063533 dated Mar. 29, 2019 (10 pages).
Written Opinion of the International Searching Authority and International Search Report for PCT/US2017/063534 dated Mar. 28, 2019 (11 pages).
Written Opinion of the International Searching Authority and International Search Report for PCT/US2018/00224 dated Nov. 5, 2018 (8 pages).
Written Opinion of the International Searching Authority and International Search Report for PCT/US2018/018044 dated May 24, 2018 (10 pages).
Written Opinion of the International Searching Authority and International Search Report for PCT/US2018/026099 dated Aug. 10, 2018 (9 pages).
Written Opinion of the International Searching Authority and International Search Report for PCT/US2019/034653 dated Aug. 9, 2019 (9 pages).
Written Opinion of the International Searching Authority and International Search Report for PCT/US2019/053467 dated Jan. 14, 2020 (9 pages).
Zablocki et al. "Discovery of Dihydrobenzoxazepinone (GS-6615) Late Sodium Current Inhibitor (Late $I_{Na}i$), a Phase II Agent with Demonstrated Preclinical Anti-Ischemic and Antiarrhythmic Properties," *Journal of Medicinal Chemistry* (2016) vol. 59, pp. 9005-9017.
Eurasian Office Action for Application No. 202092908, dated Feb. 21, 2022, 7 pages.
Eurasian Office Action for Application No. 201991306, dated Feb. 25, 2021, 8 pages.
Eurasian Office Action for Application No. 201991306, dated Aug. 24, 2021, 6 pages.
European Office Action for Application No. 19810530.6, dated Feb. 17, 2022, 1 page.
European Office Action for Application No. 19810530.6, dated Jan. 31, 2022, 9 pages.
Indian Office Action for Application No. 202017056206, dated Jun. 14, 2022, 7 pages.
Japanese Office Action for Application No. 2019-548536, dated Oct. 26, 2021, 9 pages.
Singapore Office Action for Application No. 11202011879R. dated May 6, 2022, 10 pages.
U.S. Appl. No. 17/058,187, filed Nov. 24, 2020, U.S. Publication No. 2021-0163488, Published.
U.S. Appl. No. 17/280,485, filed Mar. 26, 2021, U.S. Publication No. 2021-0403476, Published.
U.S. Appl. No. 17/102,586, filed Nov. 24, 2020, U.S. Pat. No. 11,014,931, Issued.
U.S. Appl. No. 17/214,343, filed Mar. 26, 2021, U.S. Publication No. 2022-0024930, Published.
U.S. Appl. No. 17/025,018, filed Mar. 23, 2022, U.S. Publication No. 2022-0220118, Published.
U.S. Appl. No. 17/780,570, filed May 27, 2022, Pending.

SUBSTITUTED [1,2,4]TRIAZOLO[4,3-A]PYRAZINES AS MODULATORS OF SODIUM CHANNEL ACTIVITY

CROSS REFERENCE TO RELATED APPLICATIONS

This application is the national stage of International (PCT) Patent Application Serial No. PCT/US2017/063533, filed Nov. 28, 2017, which claims priority to and the benefit of U.S. Provisional Application No. 62/427,044 filed Nov. 28, 2016, U.S. Provisional Application No. 62/458,306 filed Feb. 13, 2017, and U.S. Provisional Application No. 62/552,073 filed Aug. 30, 2017, each of which is incorporated herein by reference in its entirety.

BACKGROUND

Sodium ion (Na+) channels primarily open in a transient manner and are quickly inactivated, thereby generating a fast Na+ current to initiate the action potential. The late or persistent sodium current (INaL) is a sustained component of the fast Na+ current of cardiac myocytes and neurons. Many common neurological and cardiac conditions are associated with abnormal INaL enhancement, which contributes to the pathogenesis of both electrical and contractile dysfunction in mammals (see, e.g., *Pharmacol Ther* (2008) 119:326-339). Accordingly, pharmaceutical compounds that selectively modulate sodium channel activity, e.g., abnormal INaL, are useful in treating such disease states.

SUMMARY OF THE INVENTION

Described herein are fused heteroaryl compounds and compositions useful for preventing and/or treating a disease, disorder, or condition, e.g., a disease, disorder, or condition relating to aberrant function of a sodium ion channel, e.g., abnormal late sodium current (INaL). In one aspect, the present disclosure features compounds of Formula (I):

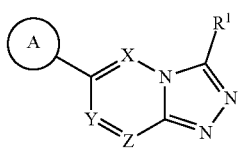

(I)

or a pharmaceutically acceptable salt thereof, wherein each of X, Y, and Z is independently N or $CR^2$, wherein at least one of X, Y, and Z is independently N; A is aryl or heteroaryl (e.g., monocyclic 6-membered aryl or heteroaryl), each of which is optionally substituted by one or more $R^3$; $R^2$ is hydrogen, alkyl, or halo; $R^1$ is hydrogen, alkyl, alkenyl, alkynyl, —$OR^b$, carbocyclyl, heterocyclyl, aryl, heteroaryl, wherein alkyl, alkenyl, alkynyl, carbocyclyl, heterocyclyl, aryl, and heteroaryl are optionally substituted with one or more $R^4$; each $R^3$ is independently alkyl, carbocyclyl, heterocyclyl, halo, cyano, nitro, —$OR^c$, —$N(R^d)_2$, —$C(O)R^c$, —$C(O)OR^c$, or —$C(O)N(R^d)_2$ wherein alkyl, carbocyclyl, and heterocyclyl are optionally substituted with one or more $R^5$; each of $R^4$ and $R^5$ is independently alkyl, carbocyclyl, heterocyclyl, aryl, heteroaryl, halo, cyano, nitro, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$, wherein alkyl, carbocyclyl, heterocyclyl, aryl, and heteroaryl are optionally substituted by one or more $R^7$; each $R^b$ is hydrogen; each $R^c$ is independently hydrogen, alkyl, carbocyclyl, heterocyclyl, aryl, or heteroaryl, wherein alkyl, aryl, and heteroaryl is optionally substituted by one or more $R^6$; each $R^d$ is independently hydrogen or alkyl, wherein each alkyl is optionally substituted by one or more $R^6$; each $R^6$ is independently alkyl, carbocyclyl, heterocyclyl, halo, cyano, nitro, or —OH; and each $R^7$ is independently alkyl, halo, or oxo.

In one aspect, the present disclosure provides a method of treating a neurological disorder or a psychiatric disorder, wherein the method comprises administering to a subject in need thereof a compound of Formula (I):

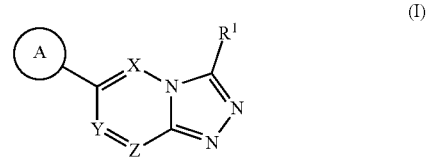

(I)

or a pharmaceutically acceptable salt thereof, wherein:
each of X, Y, and Z is independently N or $CR^2$, wherein at least one of X, Y, and Z is independently N;
A is aryl or heteroaryl ring, each of which is optionally substituted by one or more $R^3$;
$R^1$ is hydrogen, alkyl, alkenyl, alkynyl, —$OR^b$, carbocyclyl, heterocyclyl, aryl, or heteroaryl, wherein alkyl, alkenyl, alkynyl, carbocyclyl, heterocyclyl, aryl, and heteroaryl are optionally substituted with one or more $R^4$;
$R^2$ is hydrogen, alkyl, or halo;
each $R^3$ is independently alkyl, carbocyclyl, heterocyclyl, halo, cyano, nitro, —$OR^c$, —$N(R^d)_2$, —$C(O)R^c$, —$C(O)OR^c$, or —$C(O)N(R^d)_2$ wherein alkyl, carbocyclyl, and heterocyclyl are optionally substituted with one or more $R^5$;
each of $R^4$ and $R^5$ is independently alkyl, carbocyclyl, heterocyclyl, aryl, heteroaryl, halo, cyano, nitro, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$, wherein alkyl, carbocyclyl, heterocyclyl, aryl, and heteroaryl are optionally substituted by one or more $R^7$;
each $R^b$ is hydrogen;
each $R^c$ is independently hydrogen, alkyl, aryl, or heteroaryl, wherein alkyl, aryl, or heteroaryl is optionally substituted by one or more $R^6$;
$R^d$ is independently hydrogen or alkyl, wherein each alkyl is optionally substituted by one or more $R^6$;
each $R^6$ is independently alkyl, carbocyclyl, heterocyclyl, halo, cyano, nitro, or —OH; and
and each $R^7$ is independently alkyl, halo, or oxo.

In another aspect, the present disclosure provides a method of treating a neurological disorder or a psychiatric disorder, wherein the method comprises administering to a subject in need thereof a compound of Formula (I-2):

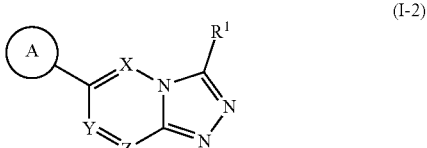

(I-2)

or a pharmaceutically acceptable salt thereof, wherein:

each of X, Y, and Z is independently N or $CR^2$, wherein at least one of X, Y, and Z is independently N;

A is aryl or heteroaryl ring, each of which is optionally substituted by one or more $R^3$;

$R^1$ is hydrogen, alkyl, alkenyl, alkynyl, —$OR^b$, —$N(R^d)_2$, carbocyclyl, heterocyclyl, aryl, or heteroaryl, wherein alkyl, alkenyl, alkynyl, carbocyclyl, heterocyclyl, aryl, and heteroaryl are optionally substituted with one or more $R^4$;

$R^2$ is hydrogen, alkyl, halo, $N(R^d)_2$, —$C(O)OR^c$, —$NR^dC(O)(R^c)$, or —$C(O)N(R^d)_2$, wherein the alkyl is optionally substituted with —OH or —O-alkyl;

each $R^3$ is independently alkyl, carbocyclyl, heterocyclyl, halo, cyano, nitro, —$OR^c$, —$N(R^d)_2$, —$C(O)R^c$, —$C(O)OR^c$, or —$C(O)N(R^d)_2$ wherein alkyl, carbocyclyl, and heterocyclyl are optionally substituted with one or more $R^5$;

each of $R^4$ and $R^5$ is independently alkyl, carbocyclyl, heterocyclyl, aryl, heteroaryl, halo, cyano, nitro, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$, wherein alkyl, carbocyclyl, heterocyclyl, aryl, and heteroaryl are optionally substituted by one or more $R^7$;

each $R^b$ is hydrogen, alkyl, heteroaryl, or aryl, wherein the alkyl or aryl is optionally substituted by one or more halogens;

each $R^c$ is independently hydrogen, alkyl, aryl, or heteroaryl, wherein alkyl, aryl, or heteroaryl is optionally substituted by one or more $R^6$;

$R^d$ is independently hydrogen or alkyl, wherein each alkyl is optionally substituted by one or more $R^6$; wherein two $R^d$ can be taken together with the nitrogen atom to which they are attached to form a heterocyclyl;

each $R^6$ is independently alkyl, carbocyclyl, heterocyclyl, halo, cyano, nitro, or —OH; and and each $R^7$ is independently alkyl, halo, or oxo.

In some embodiments, the neurological disorder is epilepsy.

In some embodiments, the neurological disorder is an epileptic encephalopathy.

In some embodiments, the epileptic encephalopathy comprises Dravet syndrome, infantile spasms, or Lennox-Gastaut syndrome.

In some embodiments, X is N and each of Y and Z is independently $CR^2$.

In some embodiments, wherein Y is N and each of X and Z is independently $CR^2$.

In some embodiments, Z is N and each of X and Y is independently $CR^2$.

In some embodiments, $R^2$ is hydrogen.

In some embodiments, A is aryl, substituted by 1-3 $R^3$.

In some embodiments, A is phenyl.

In some embodiments, A is heteroaryl substituted by 1-3 $R^3$.

In some embodiments, A is pyridyl.

In some embodiments, each $R^3$ is independently alkyl, halo, cyano, carbocyclyl, or —$OR^c$.

In some embodiments, $R^3$ is alkyl or —$OR^c$.

In some embodiments, $R^1$ is alkyl or carbocyclyl.

In some embodiments, $R^1$ is substituted alkyl.

In some embodiments, $R^1$ is alkyl substituted with halo, heterocyclyl, or —OH.

In some embodiments, $R^1$ is —$CF_3$.

In some embodiments, the compound is selected from:

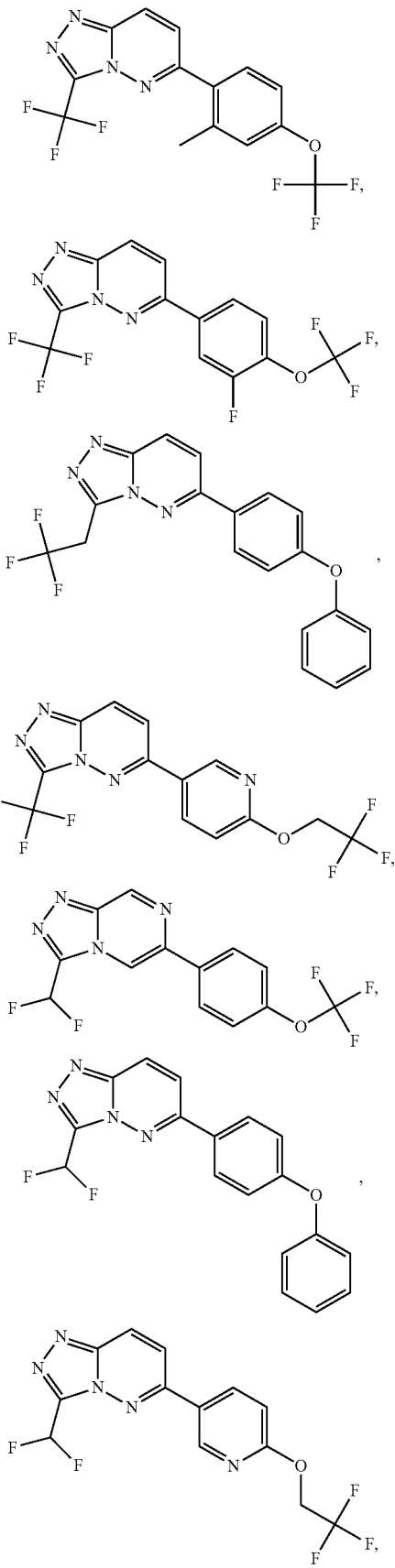

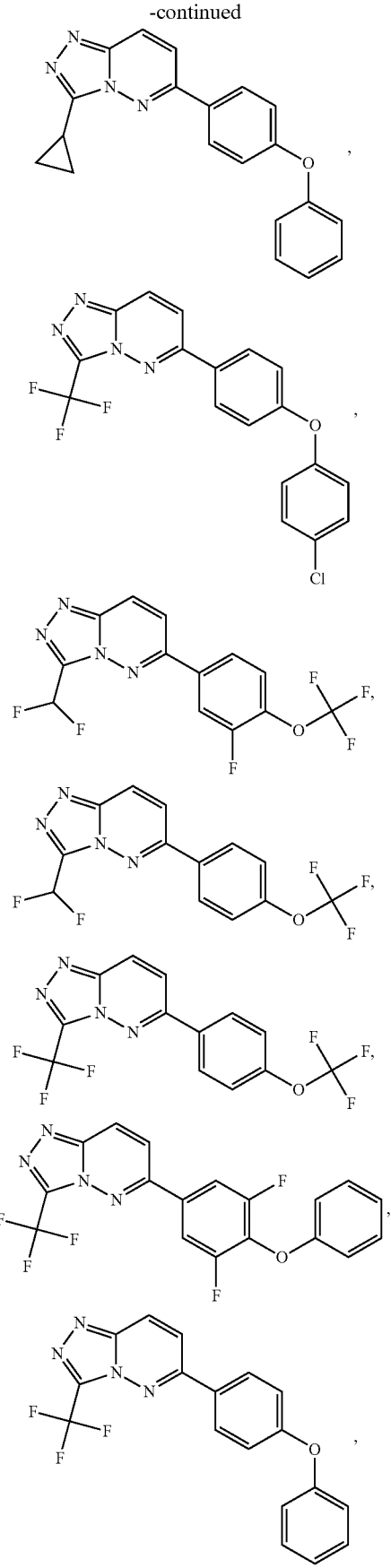
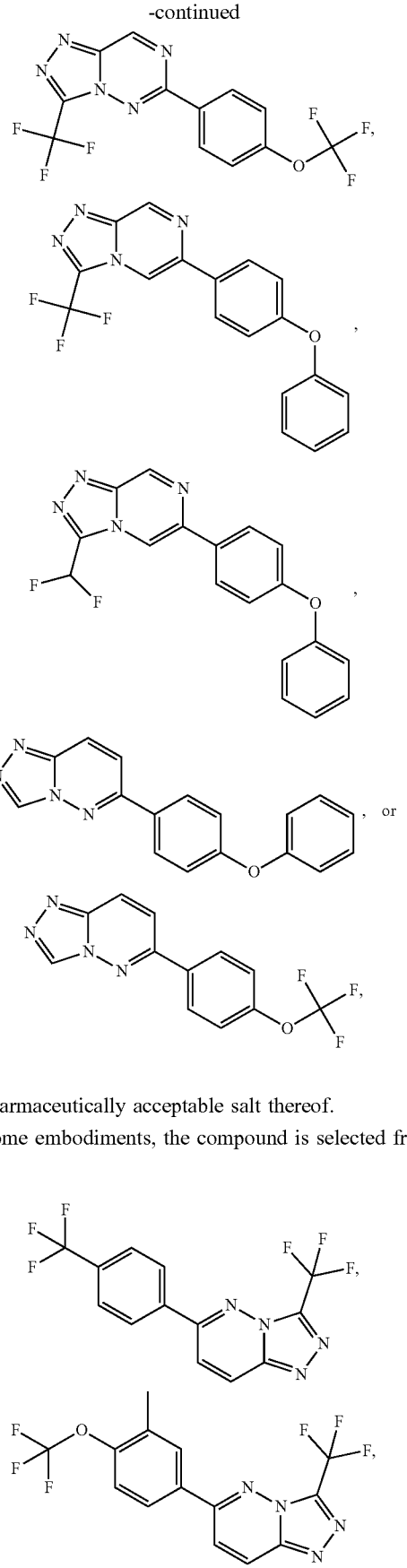
or a pharmaceutically acceptable salt thereof.
In some embodiments, the compound is selected from:
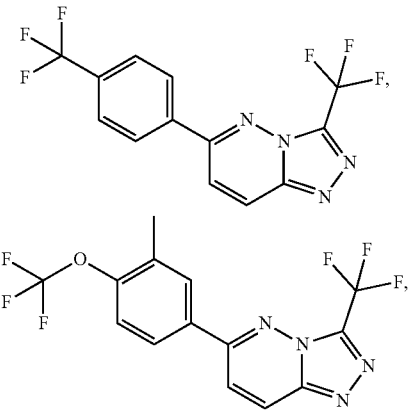

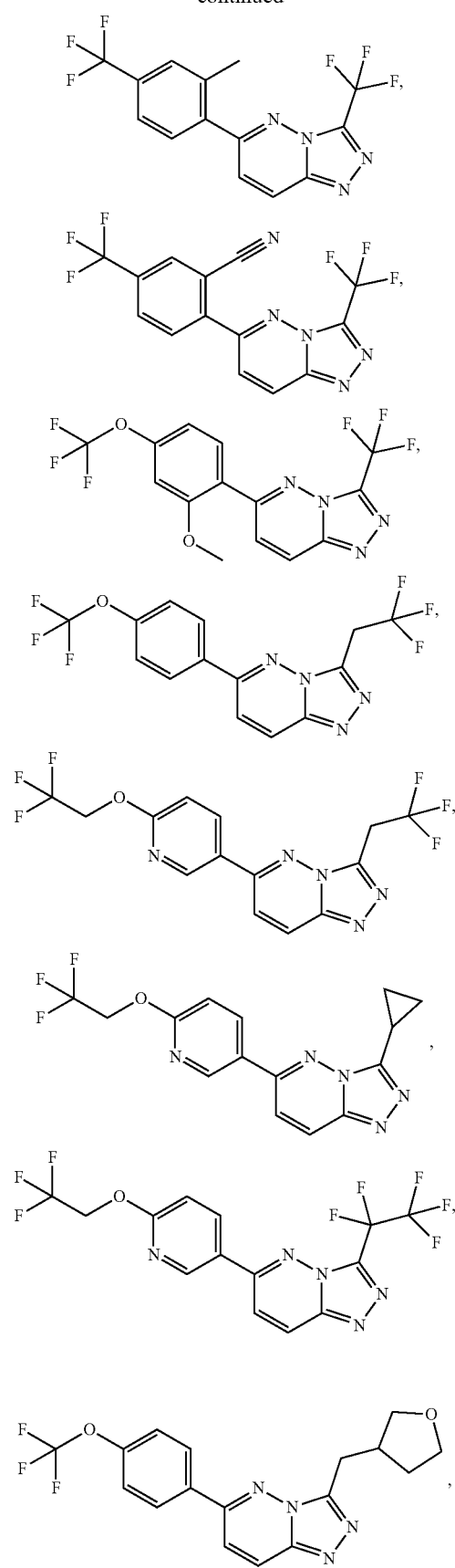
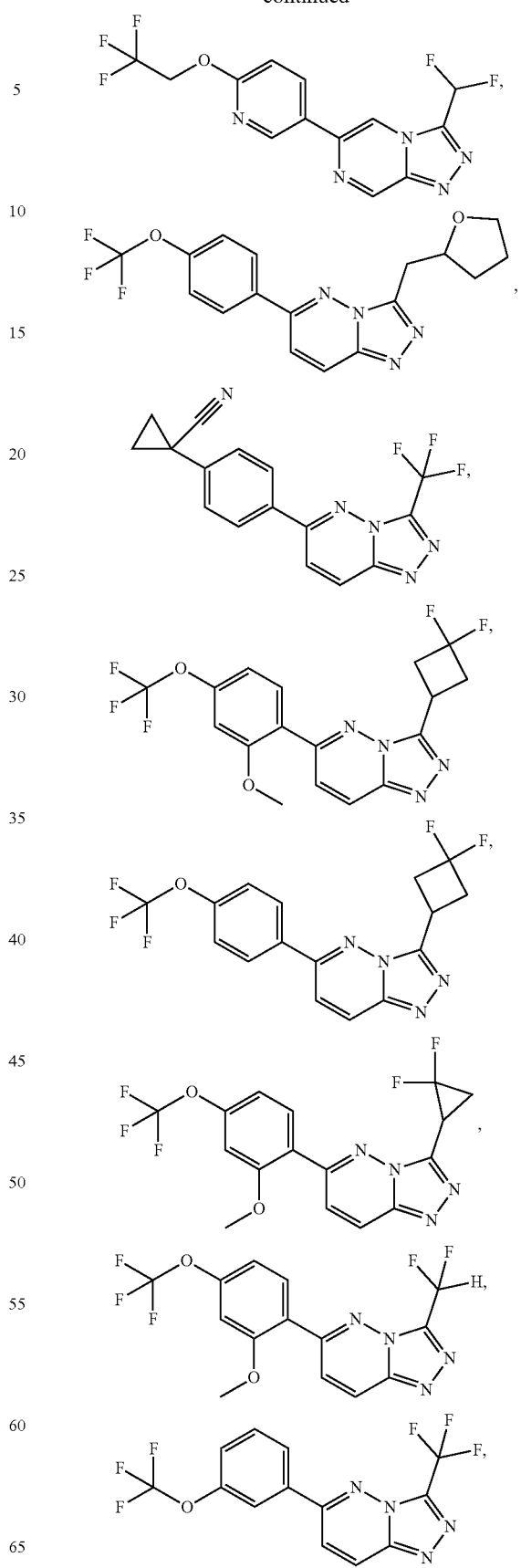

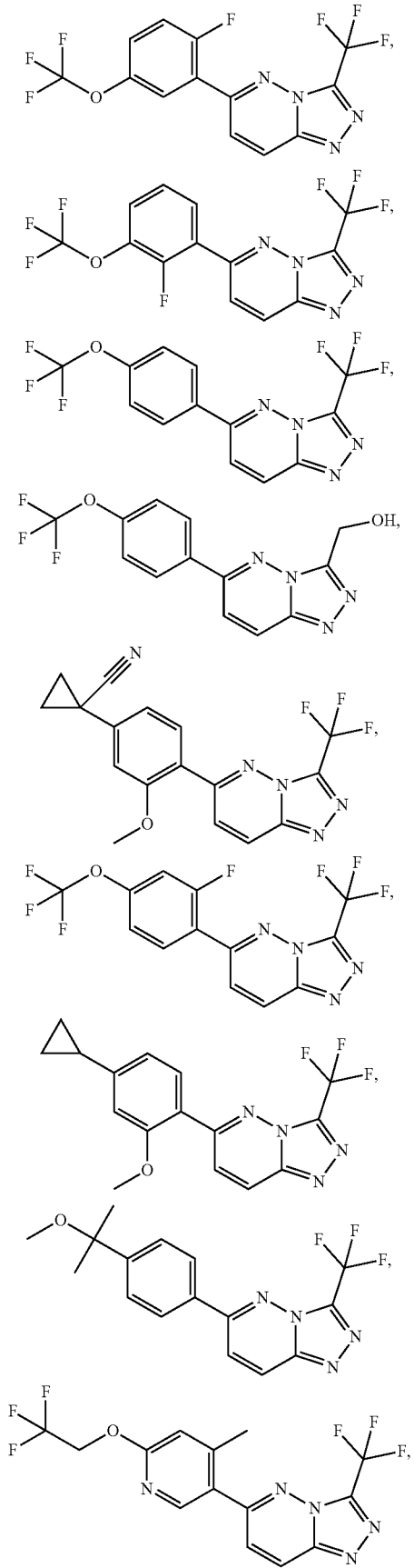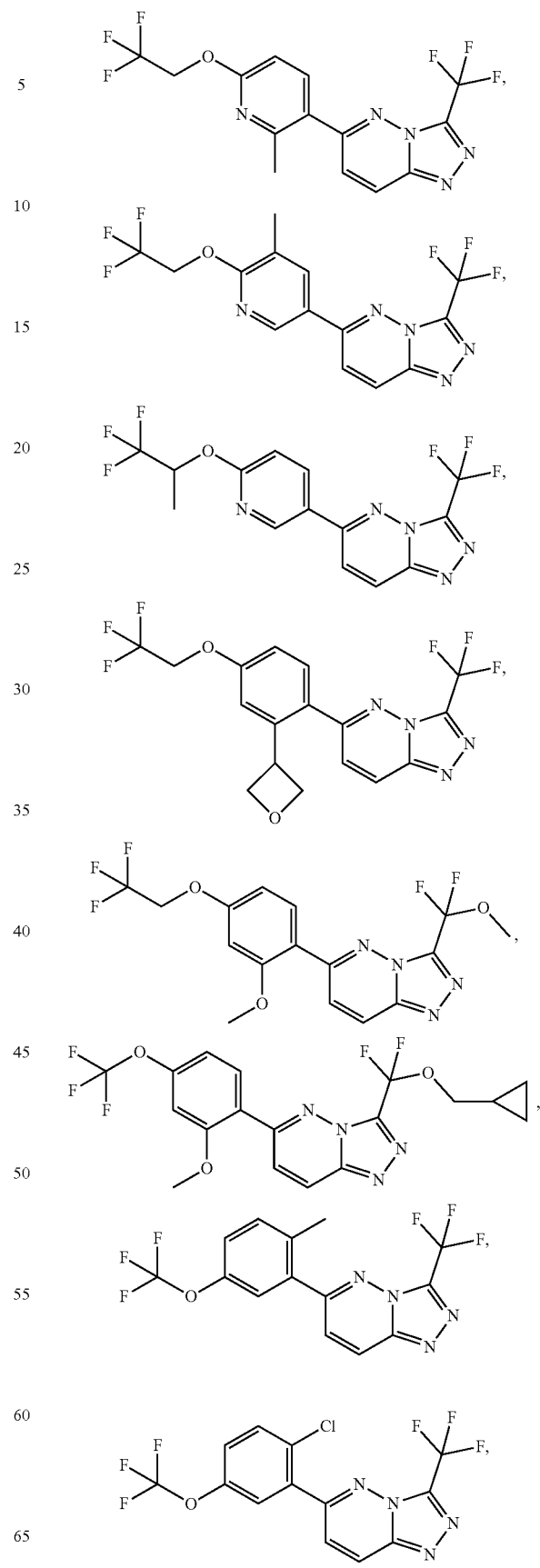

11
-continued
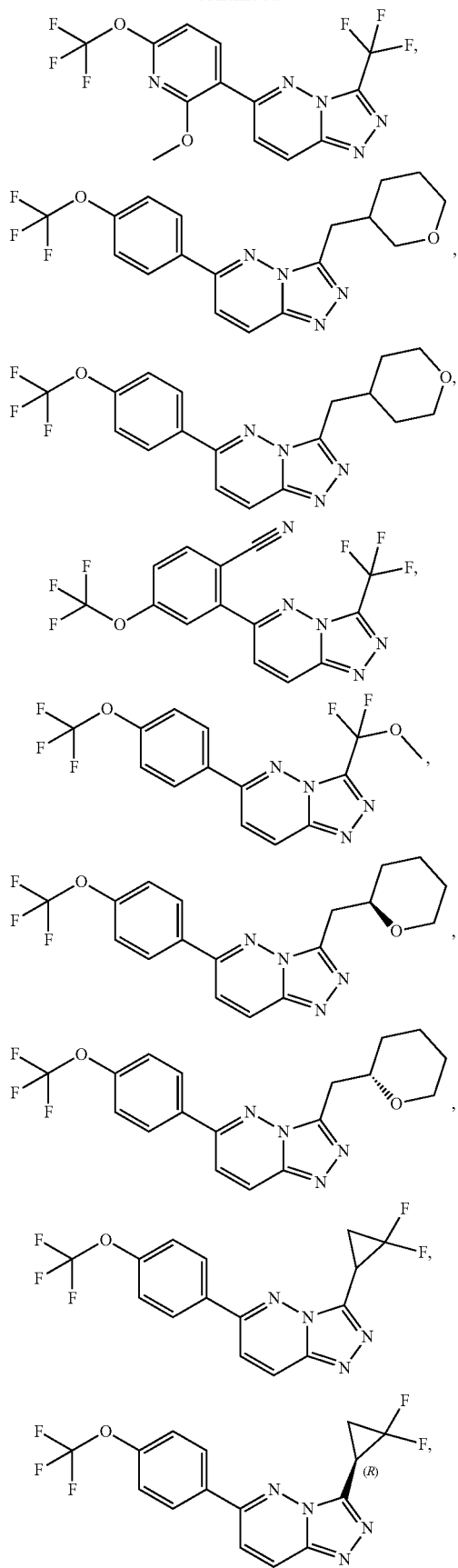
12
-continued
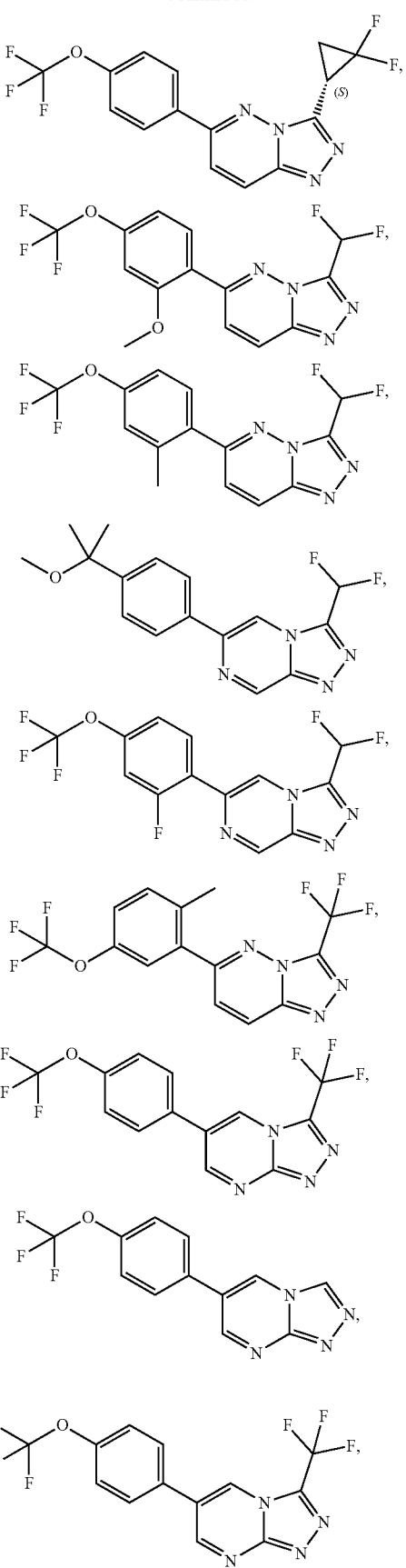

-continued
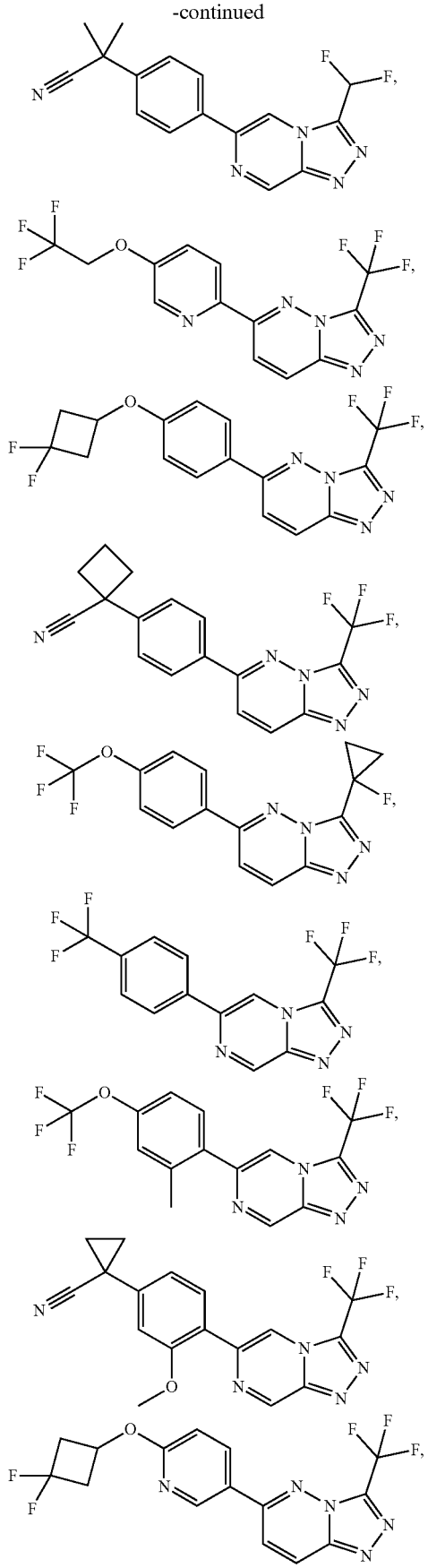
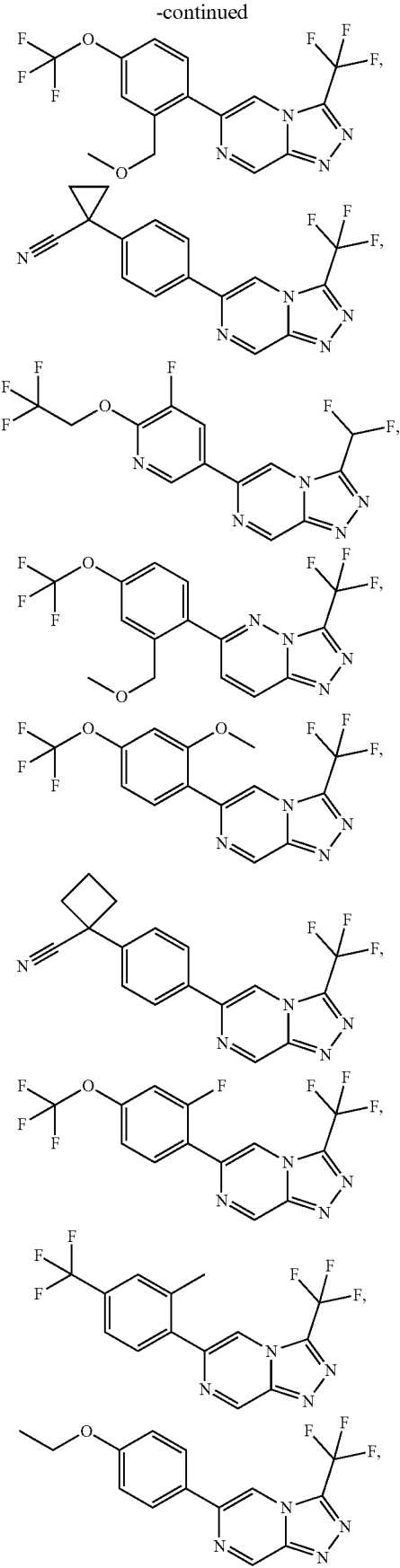

-continued
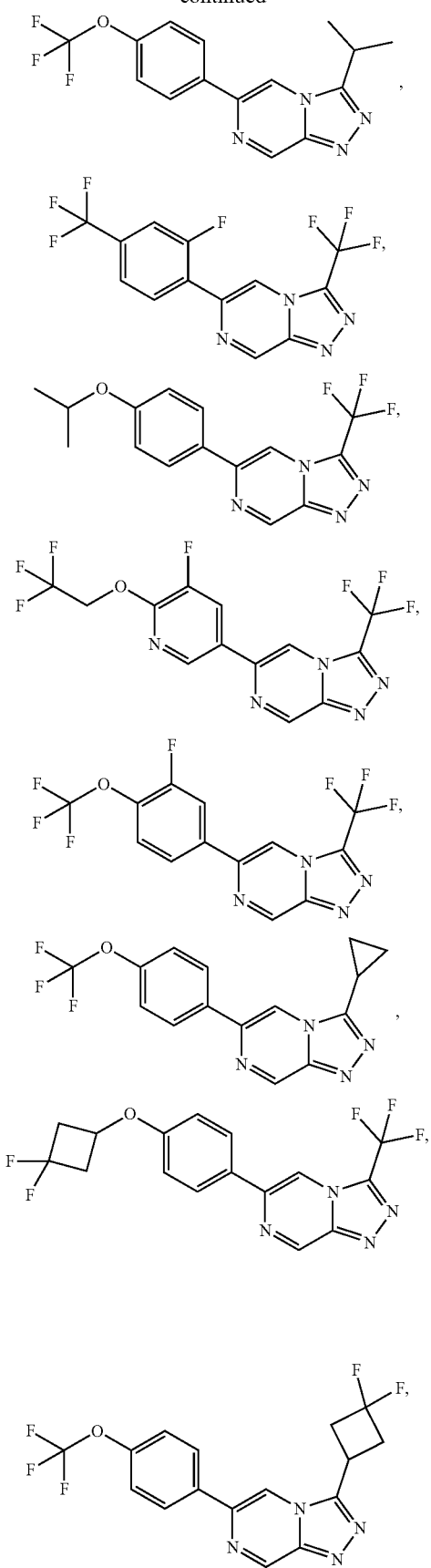
-continued
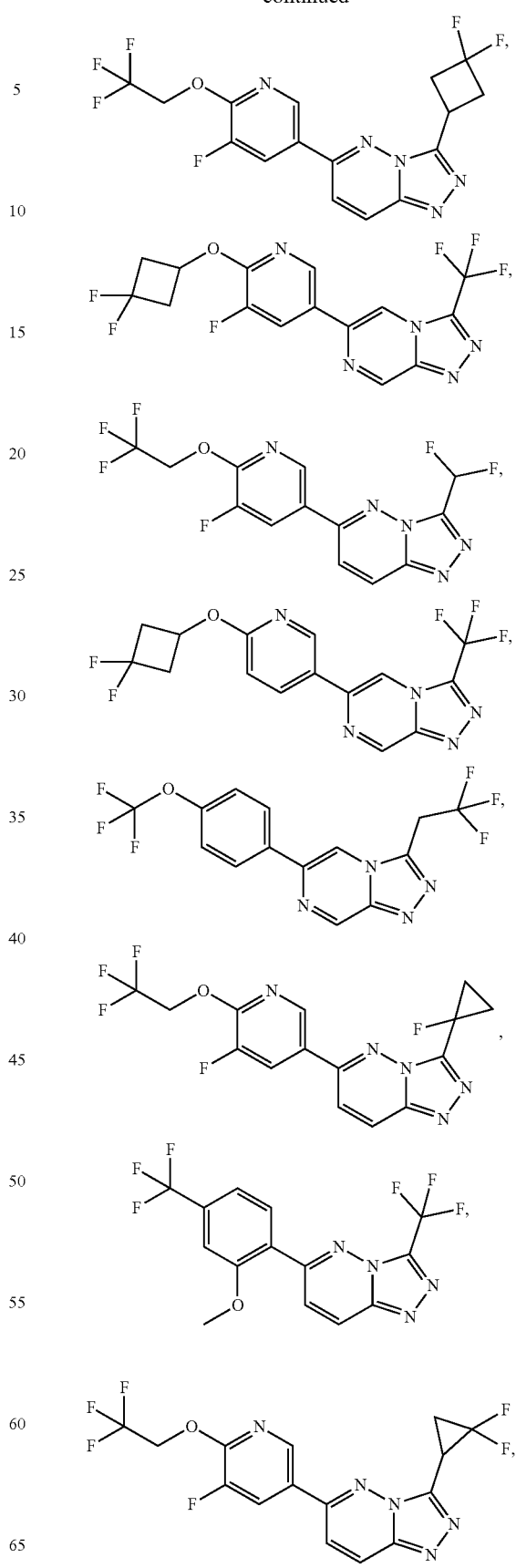

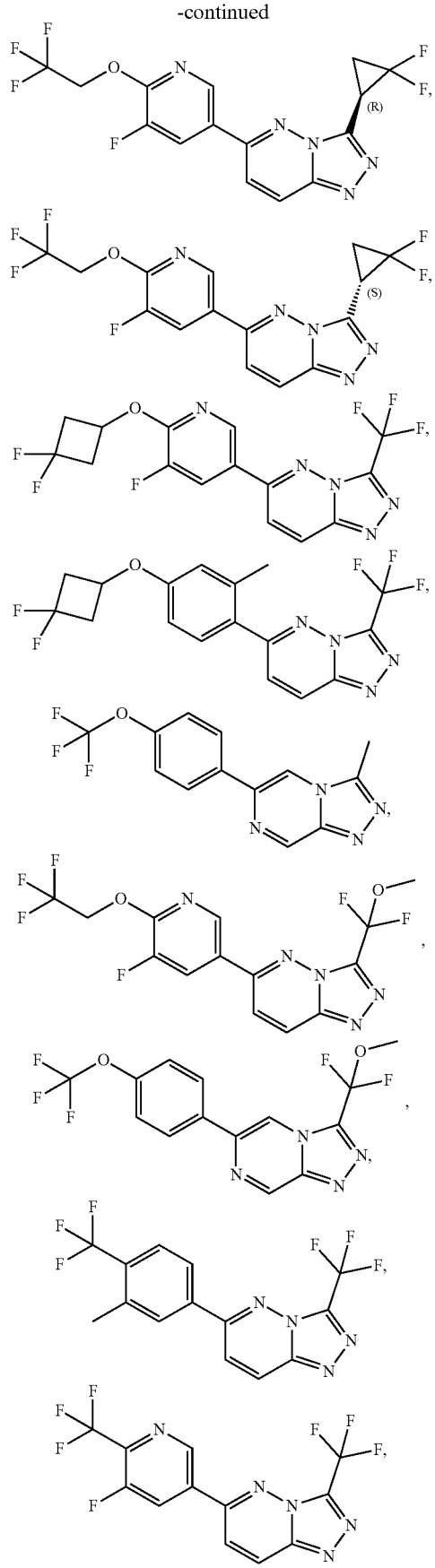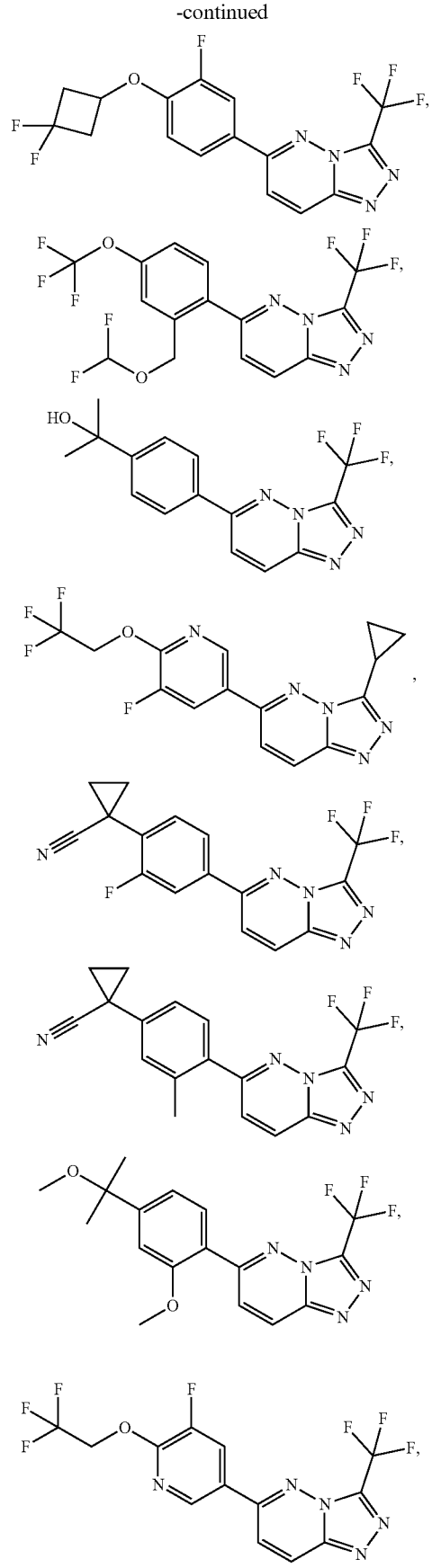

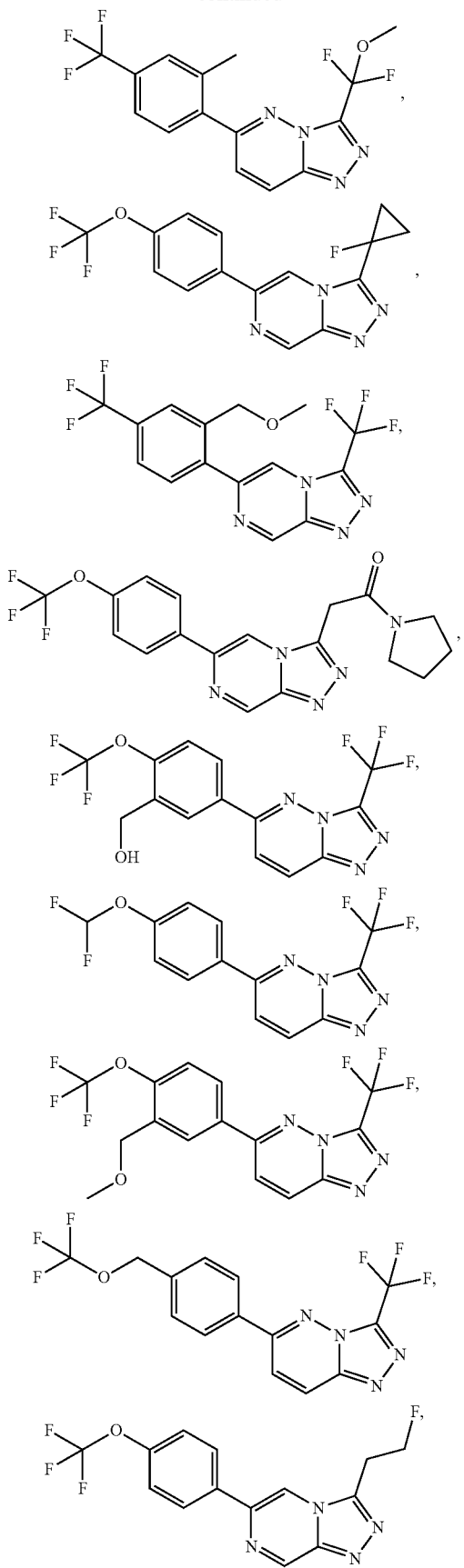
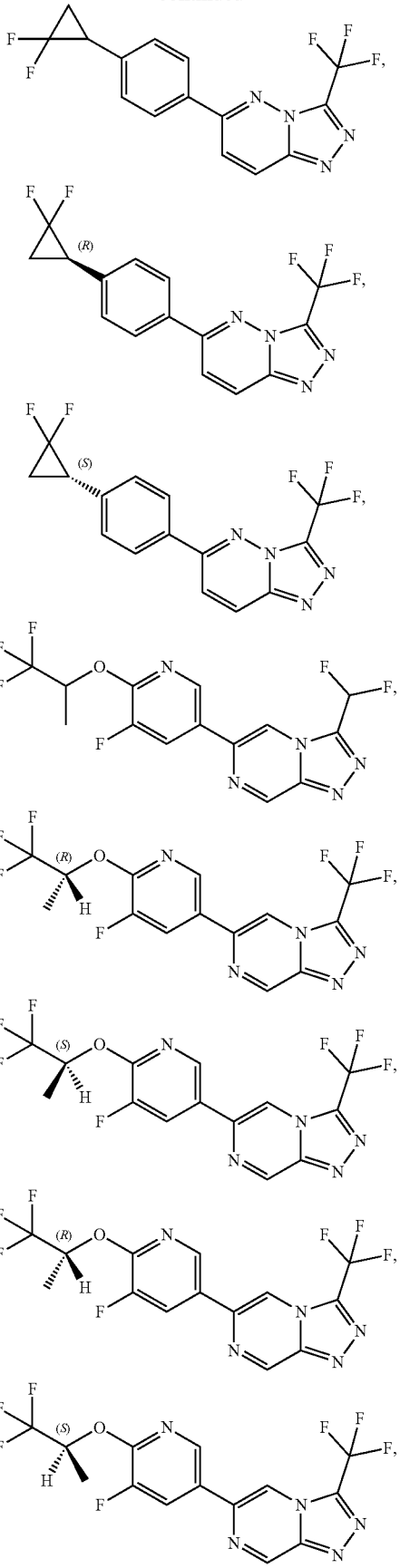

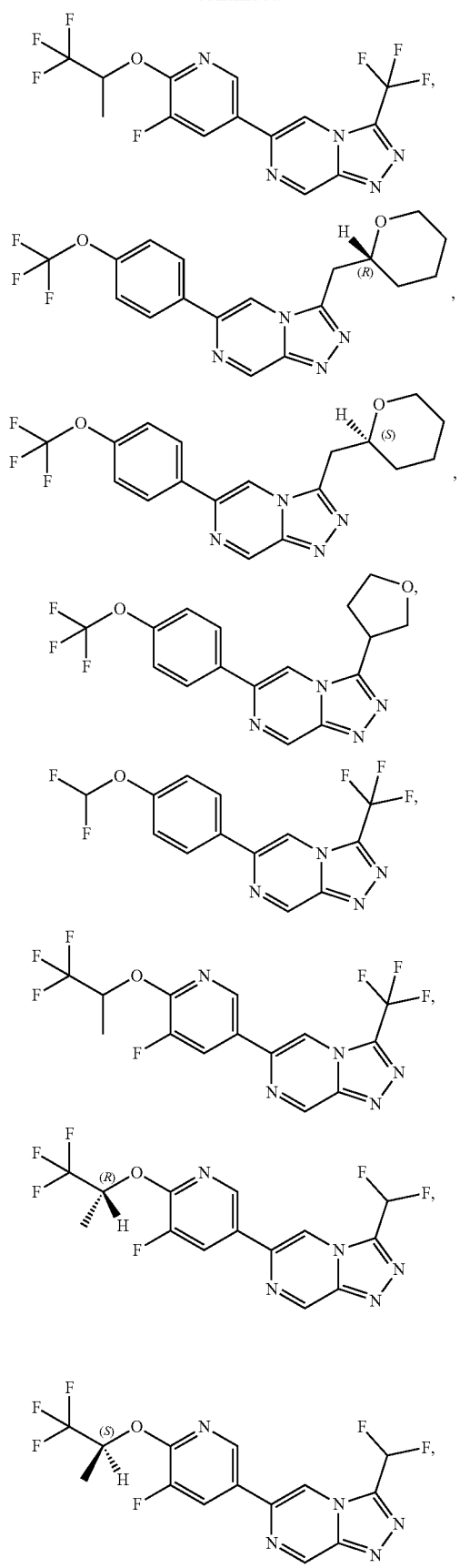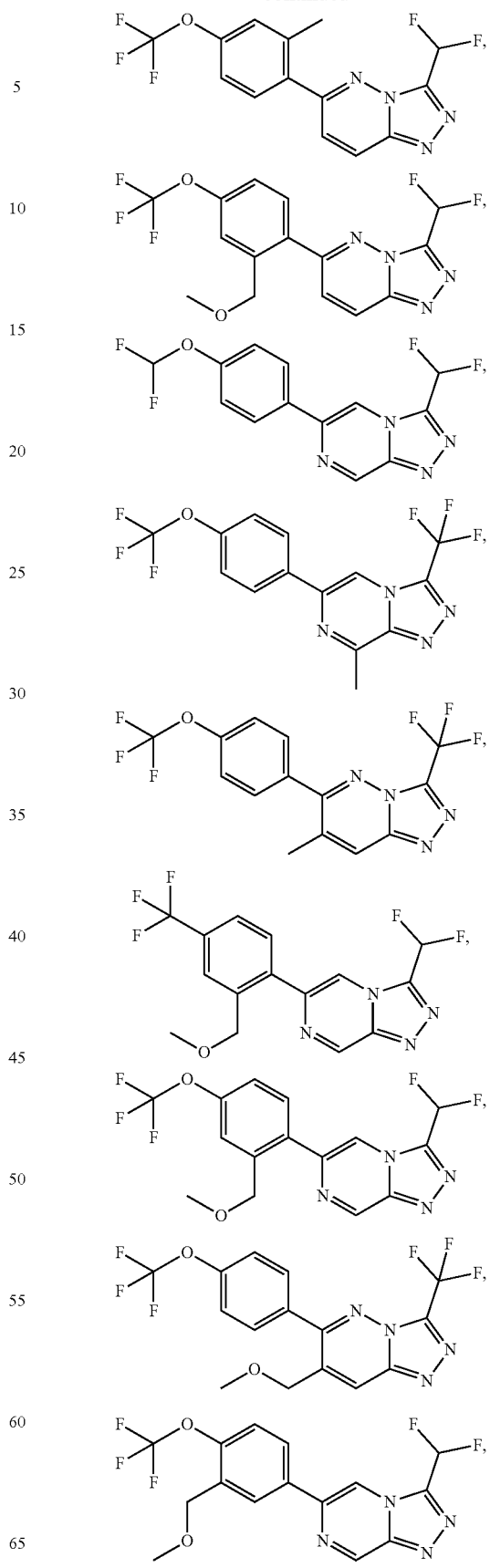

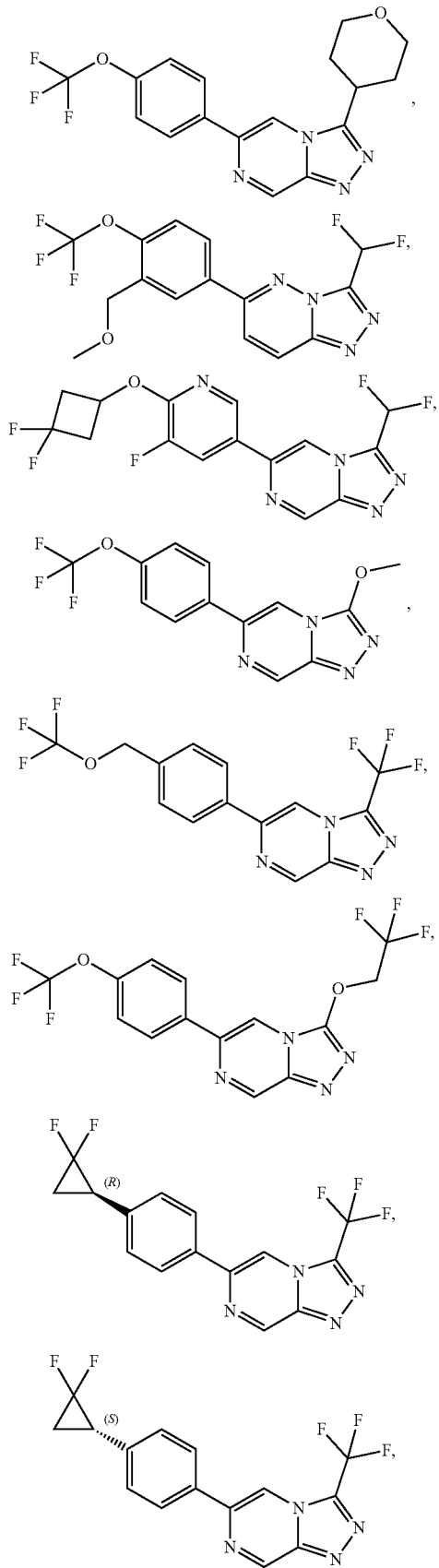
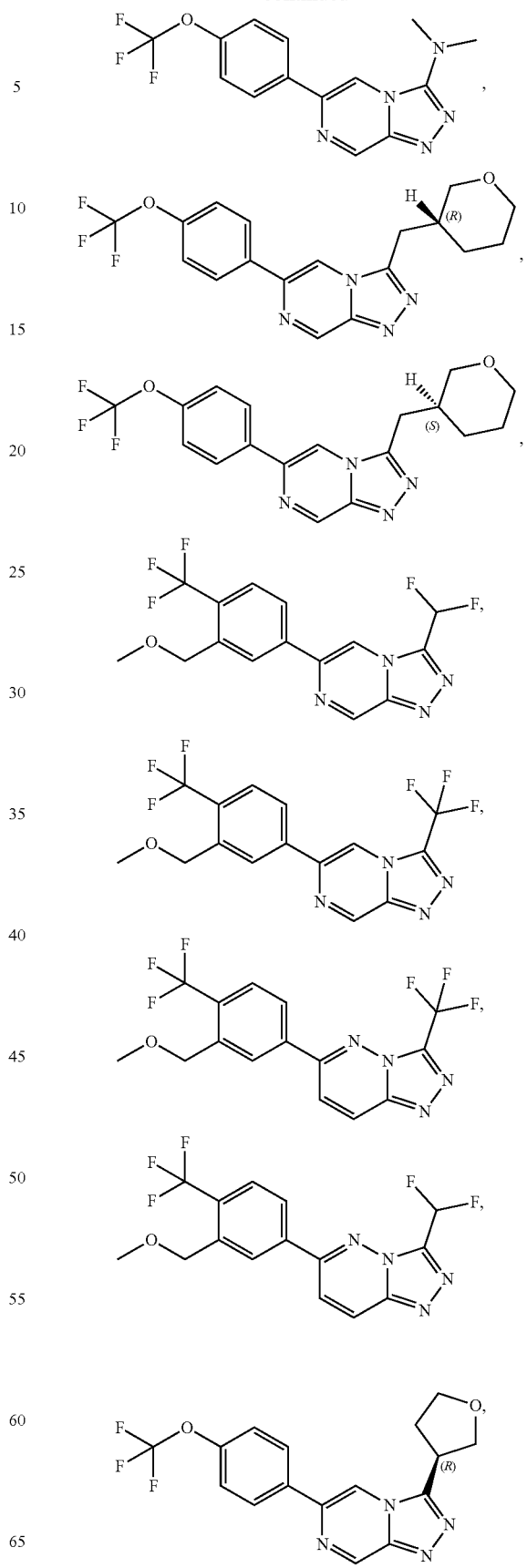

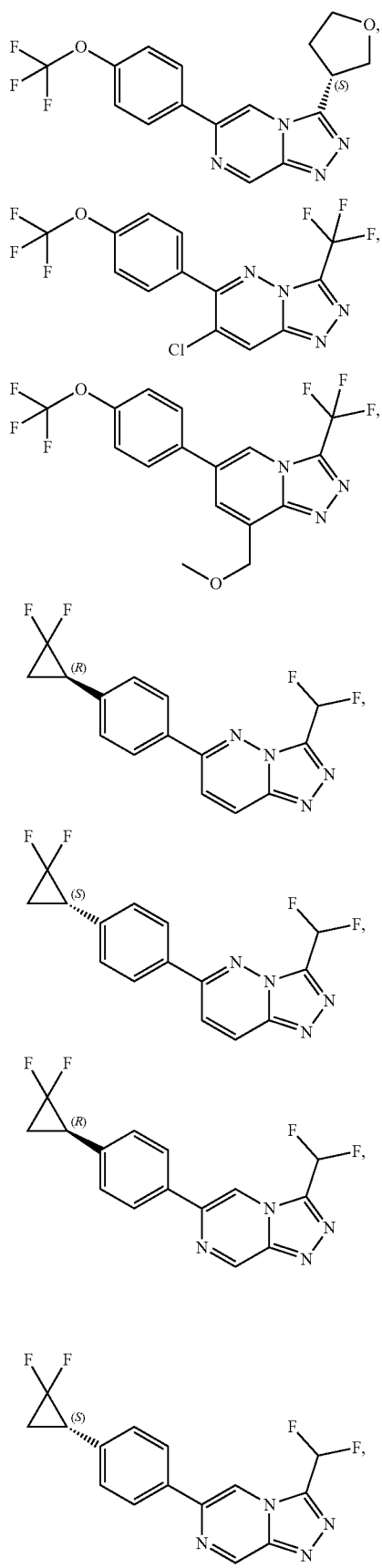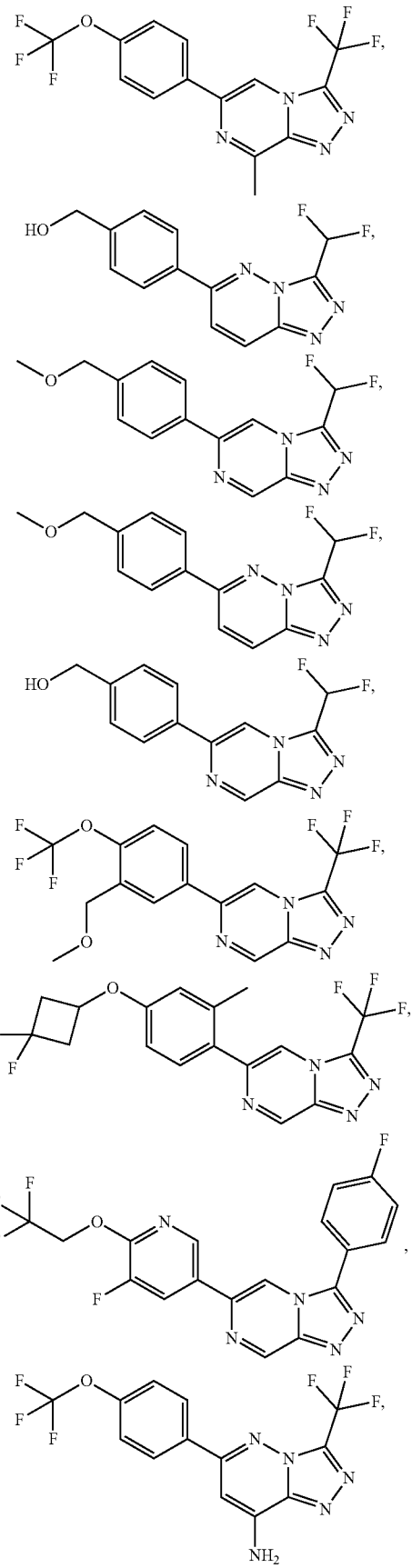

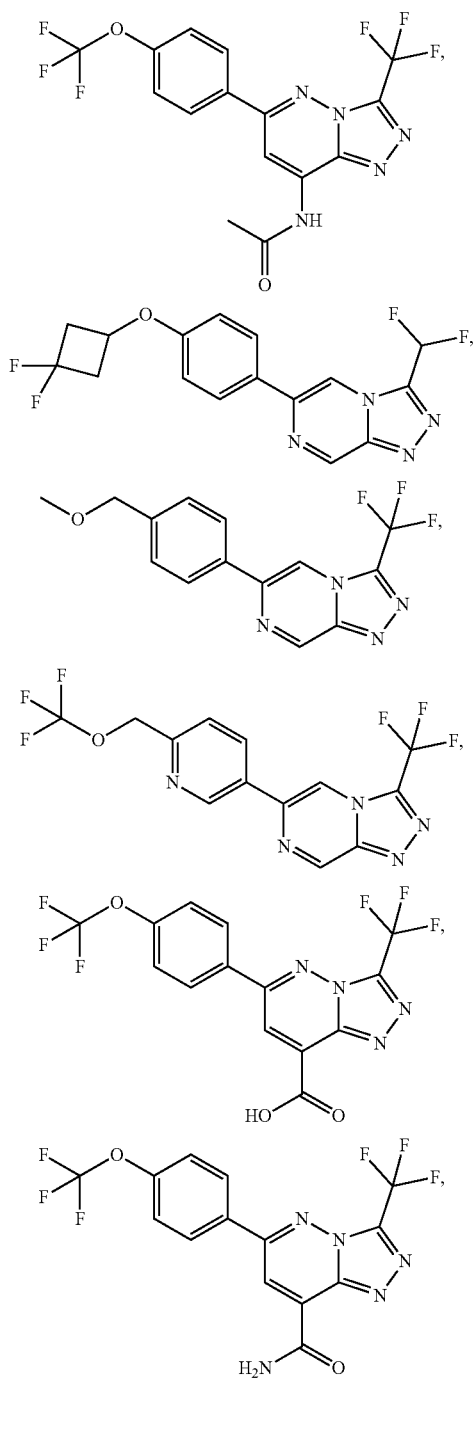
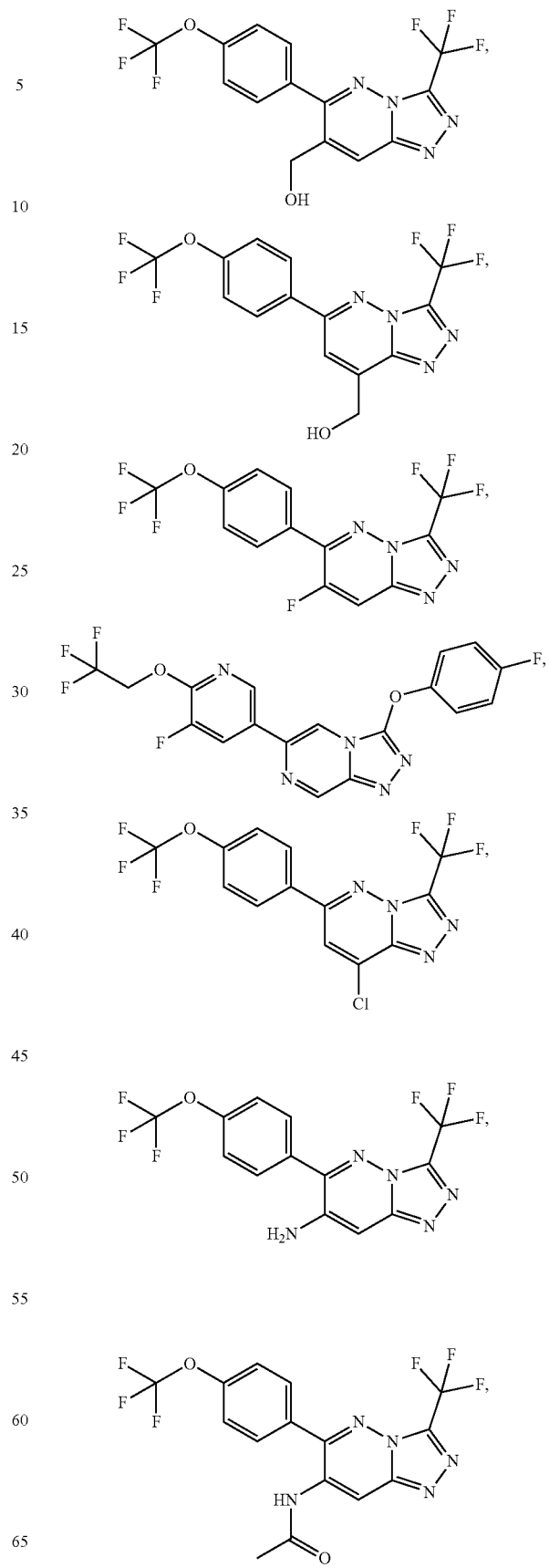

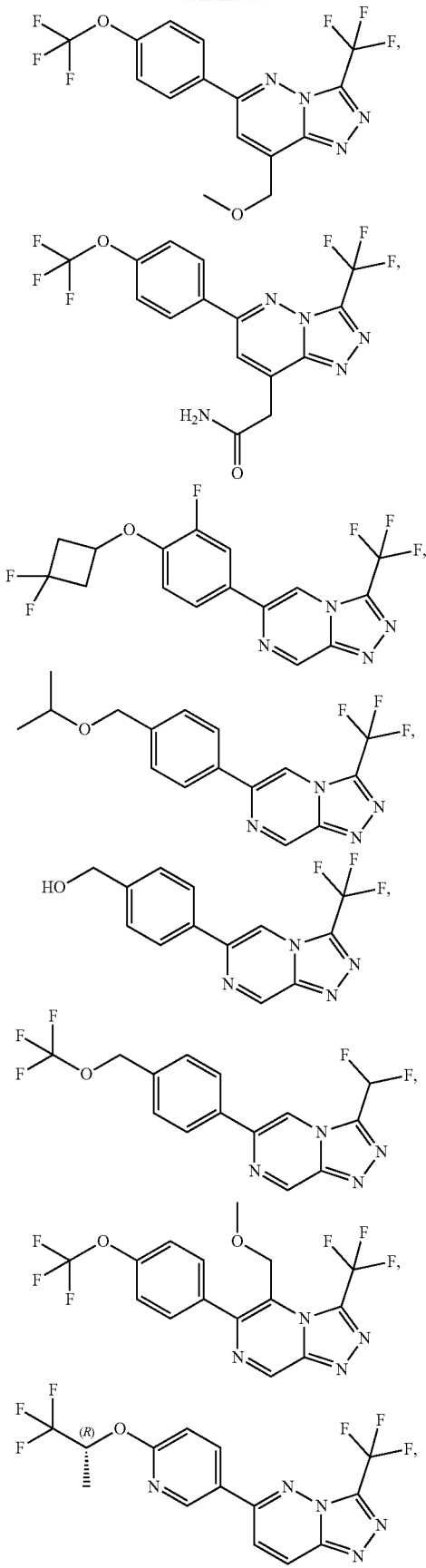
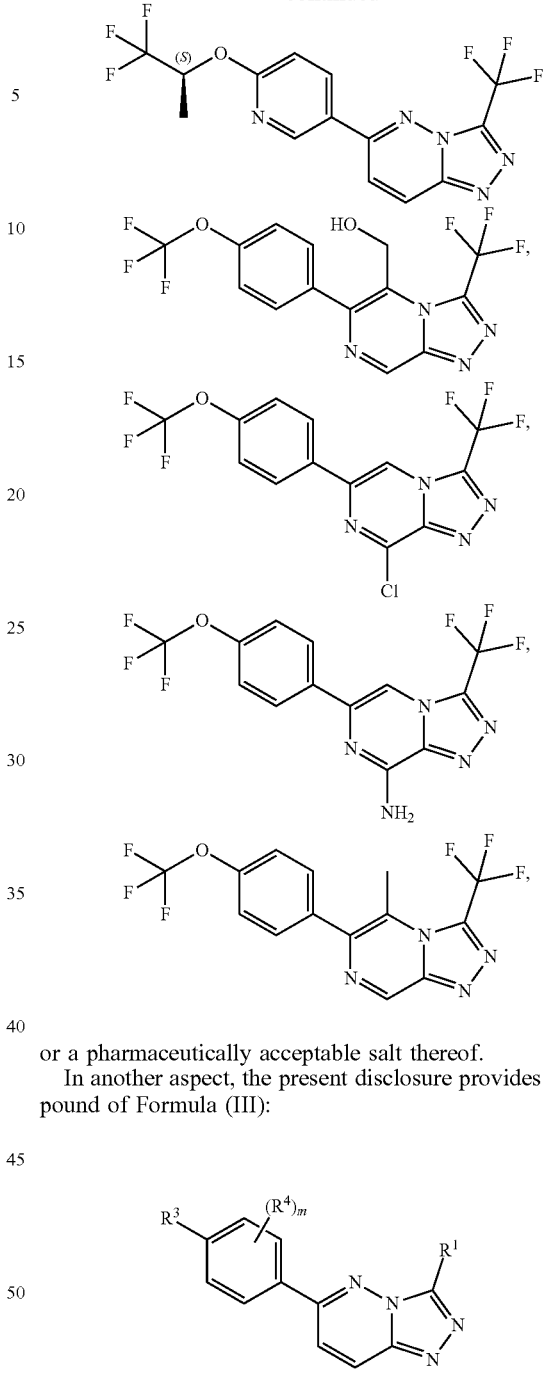

or a pharmaceutically acceptable salt thereof.

In another aspect, the present disclosure provides a compound of Formula (III):

(III)

or a pharmaceutically acceptable salt thereof, wherein:

$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^3$ is $C_{1-6}$alkyl, halo, cyano, nitro, $C_{3-8}$carbocyclyl, 3-8 membered heterocyclyl, —$OR^7$, —$N(R^d)_2$, —$C(O)R^c$, —$C(O)OR^c$, or —$C(O)N(R^d)_2$, wherein $C_{1-6}$alkyl, $C_{3-8}$carbocyclyl, or 3-8 membered heterocyclyl is optionally substituted with one or more $R^5$;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$, wherein $C_{1-6}$alkyl, $C_{3-8}$carbocyclyl, or 3-8 membered heterocyclyl are optionally substituted with one or more $R^5$;

m is 1 or 2;

each $R^5$ is independently halo, cyano, nitro, $C_{1-6}$alkyl, $C_{3-8}$carbocyclyl, 3-8 membered heterocyclyl, $-OR^c$, $-C(O)N(R^d)_2$, $-SO_2R^c$, $-SO_2OR^c$, $-SO_2N(R^d)_2$, $-NR^dC(O)(R^c)$, or $-N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano;

$R^7$ is $C_{1-6}$alkyl or $C_{3-8}$carbocyclyl wherein $C_{1-6}$alkyl or $C_{3-8}$carbocyclyl is optionally substituted with one or more $R^6$;

wherein the compound is not one of the following:

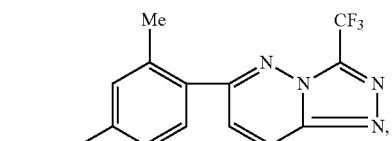

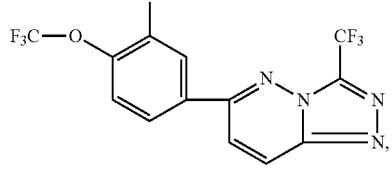


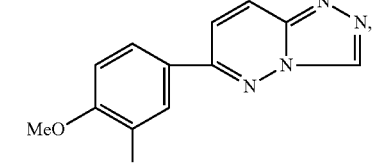

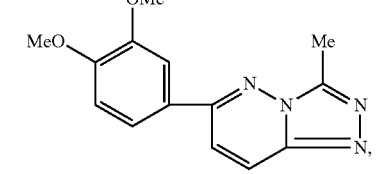

or a pharmaceutically acceptable salt thereof.

In some embodiments, $R^1$ is $C_{1-6}$haloalkyl optionally substituted with $-OR^c$ or $C_{3-4}$carbocyclyl optionally substituted with one or two halogens.

In some embodiments, $R^1$ is $CF_3$ or $CHF_2$.

In some embodiments, $R^3$ is $-OR^7$.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, $R^3$ is $-OCF_3$ or $-O-CH_2CF_3$.

In some embodiments, $R^4$ is independently $C_{1-6}$ alkyl, $-OR^c$, or halogen.

In some embodiments, $R^4$ is methyl or fluoride.

In some embodiments, m is 1.

In some embodiments, the compound is selected from:

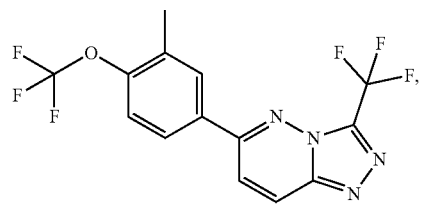

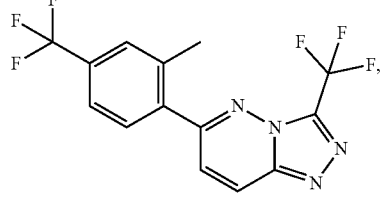

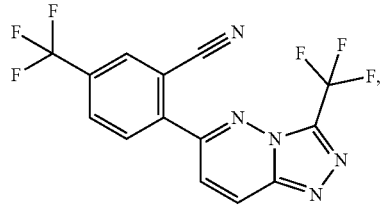

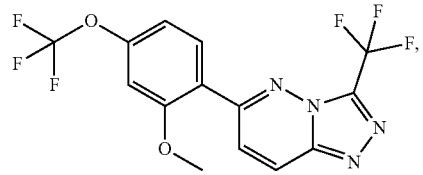 [SMILES: Cc1c(-c2ccc(OC(F)(F)F)cc2)ncc2nnc(C(F)(F)F)n12]

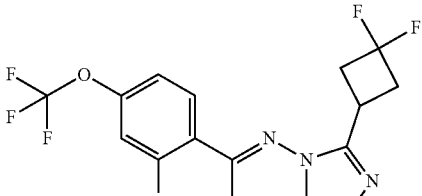

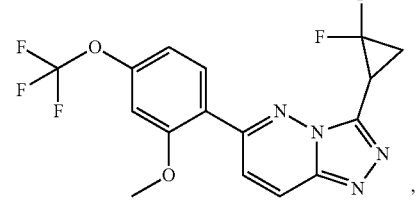

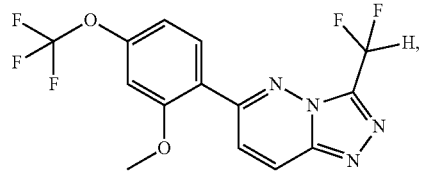

-continued
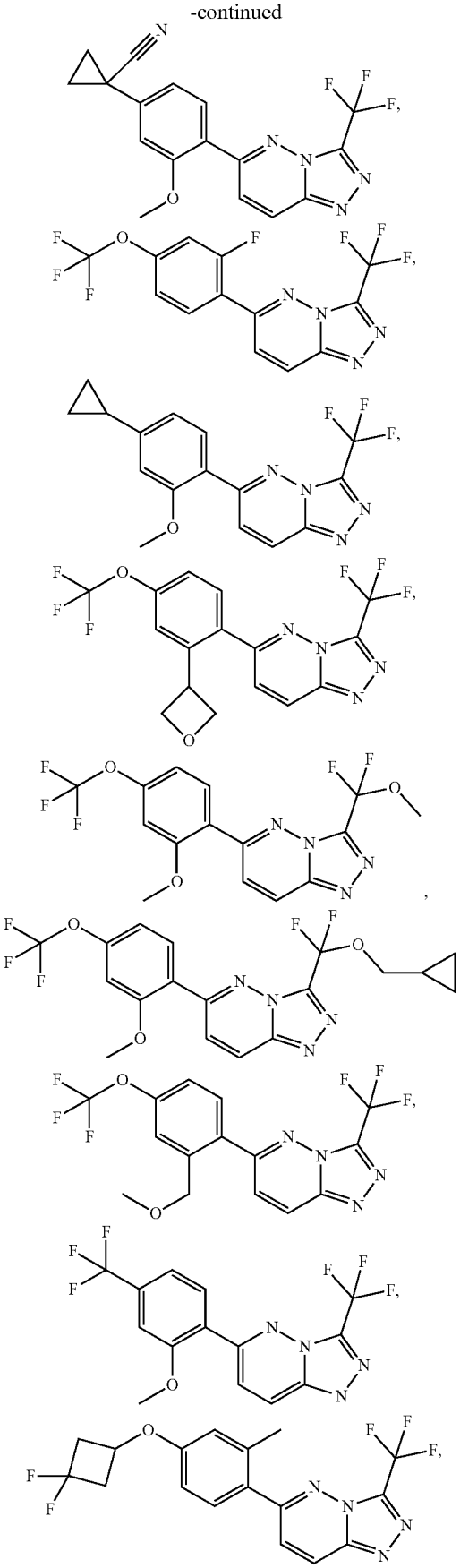
-continued
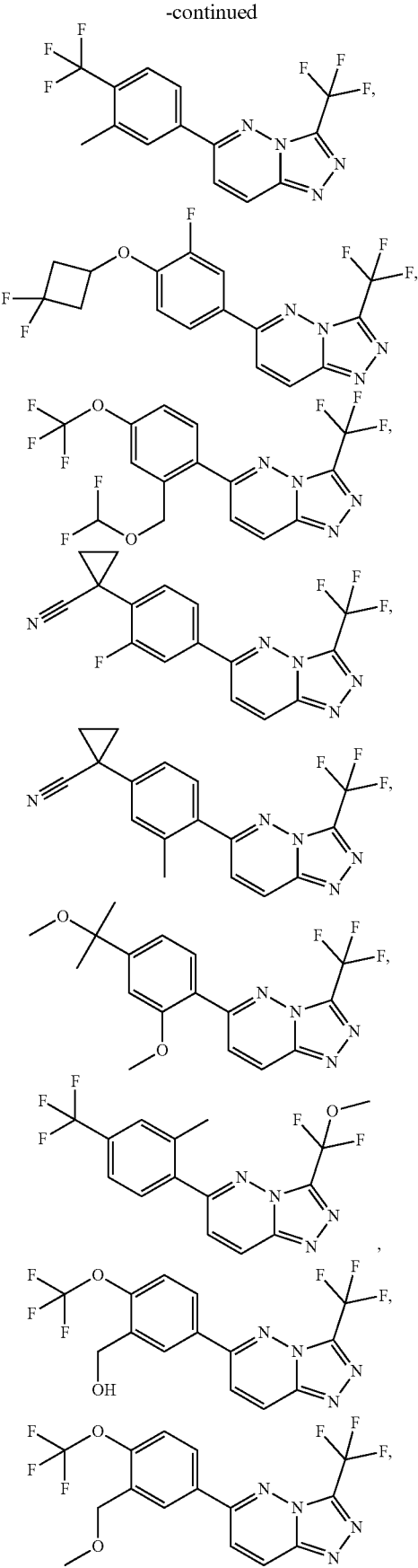

-continued

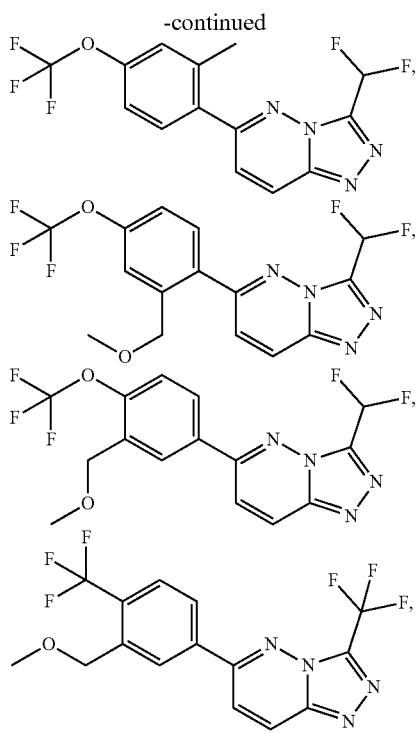

or a pharmaceutically acceptable salt thereof.

In another aspect, the present disclosure provides a compound of Formula (IIIa):

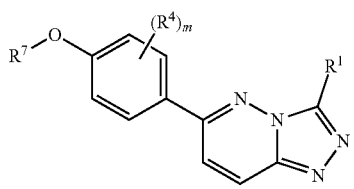

(IIIa)

or a pharmaceutically acceptable salt thereof, wherein:
$R^1$ is $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl are optionally substituted with one or more $R^5$;

m is 1 or 2;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano;

$R^7$ is $C_{1-6}$alkyl or $C_{3-8}$carbocyclyl wherein $C_{1-6}$alkyl or $C_{3-8}$carbocyclyl is optionally substituted with one or more $R^6$;

wherein the compound is not one of the following:

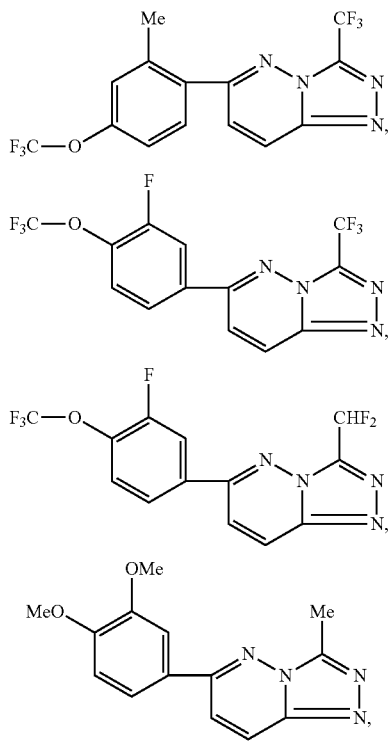

or a pharmaceutically acceptable salt thereof.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, —$OR^7$ is —$OCF_3$ or —O—$CH_2CF_3$.

In some embodiments, $R^4$ is independently $C_{1-6}$ alkyl, —$OR^c$, or halogen.

In some embodiments, $R^4$ is methyl or fluoride.

In some embodiments, m is 1.

In some embodiments, the compound is selected from:

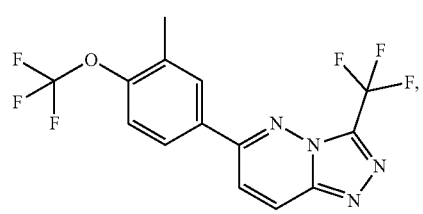

37
-continued
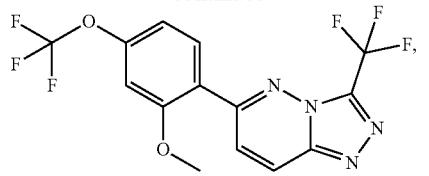
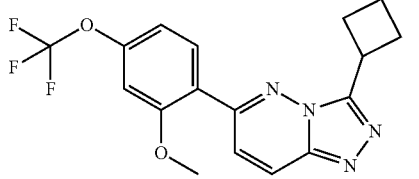
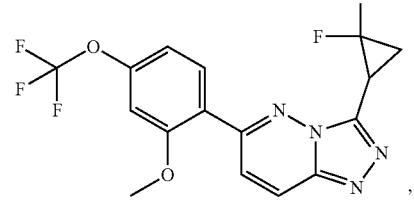
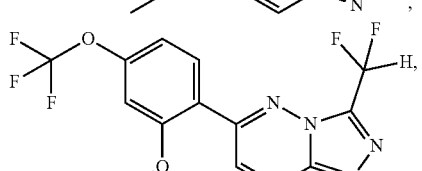
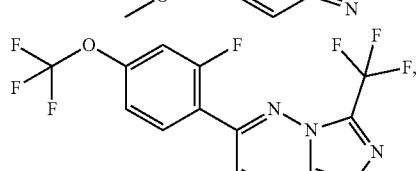
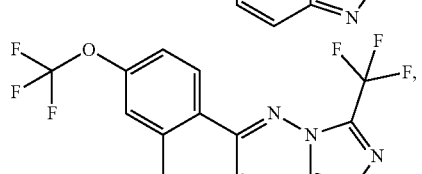
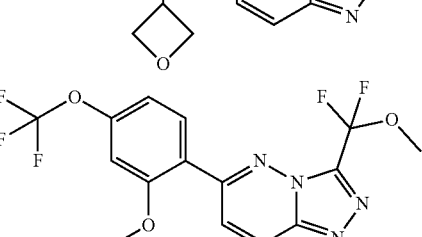
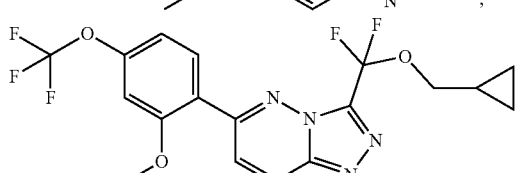
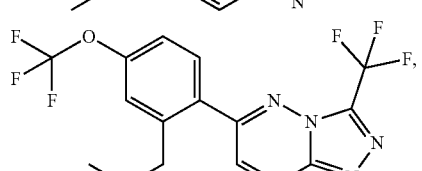
38
-continued
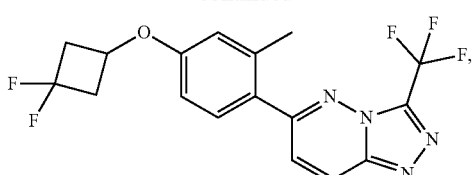
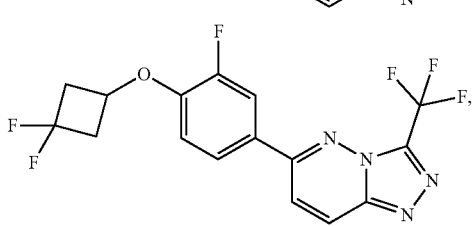
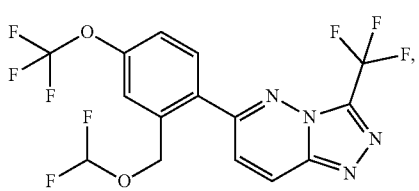
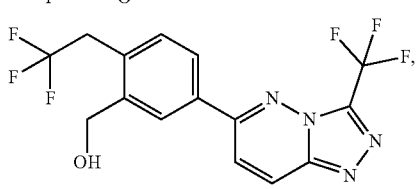
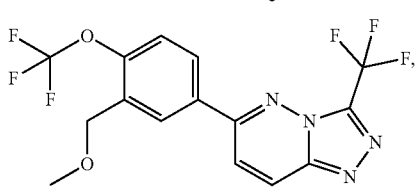
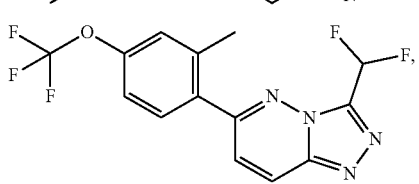
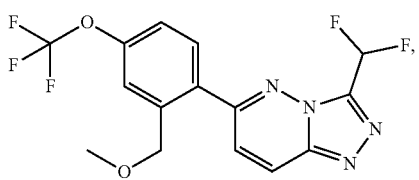
or a pharmaceutically acceptable salt thereof.

In another aspect, the present disclosure provides a compound of Formula (IV):

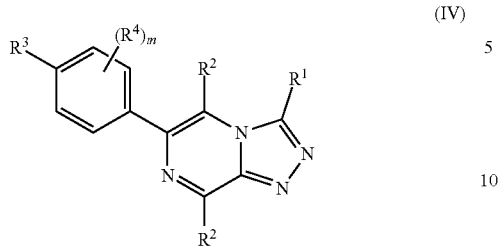

or a pharmaceutically acceptable salt thereof, wherein:

$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^2$ is independently hydrogen, $C_{1-6}$alkyl, or halo;

$R^3$ is $C_{1-6}$alkyl, halo, cyano, nitro, $C_{3-8}$carbocyclyl, 3-8 membered heterocyclyl, —$OR^7$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl is optionally substituted with one or more $R^5$;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl are optionally substituted with one or more $R^5$;

m is 1 or 2;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^3$ is —$OR^7$.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, $R^3$ is —$OCF_3$ or —$O$—$CH_2CF_3$.

In some embodiments, $R^4$ is independently $C_{1-6}$ alky, —$OR^c$, or halogen.

In some embodiments, $R^4$ is methyl or fluoride.

In some embodiments, m is 1.

In some embodiments, the compound is selected from:

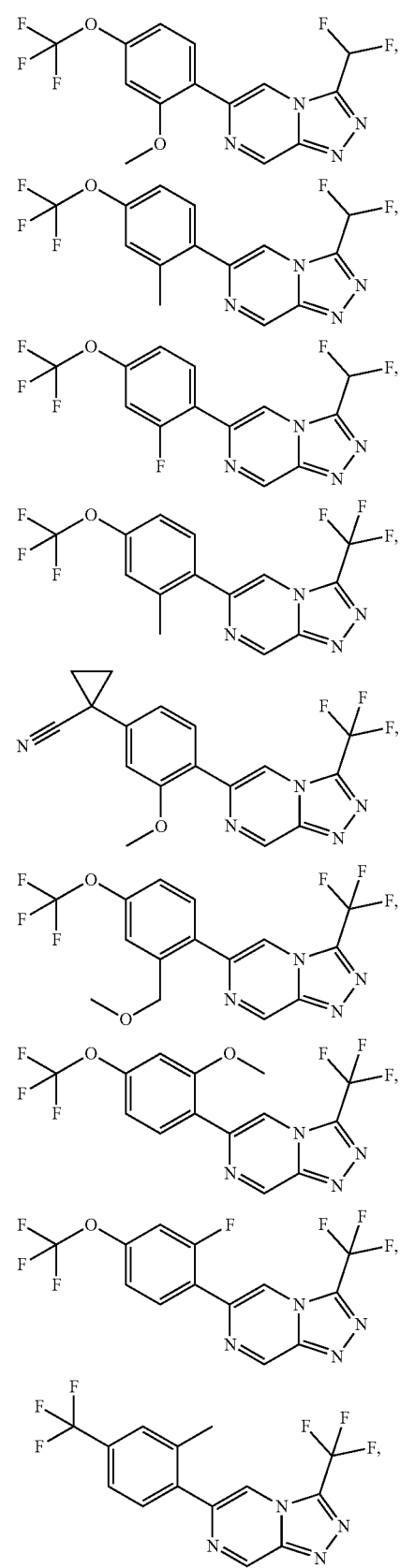

-continued

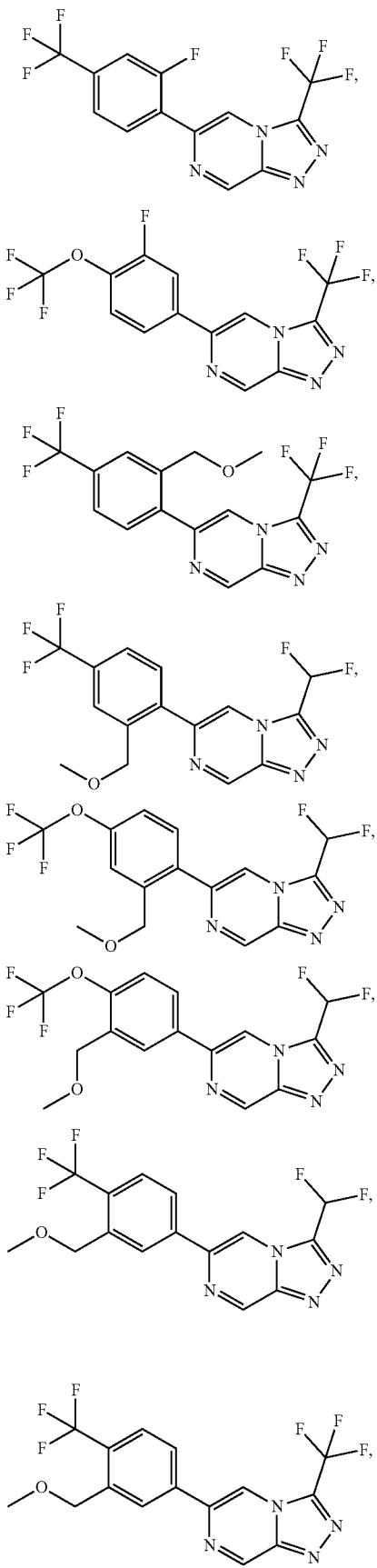

-continued

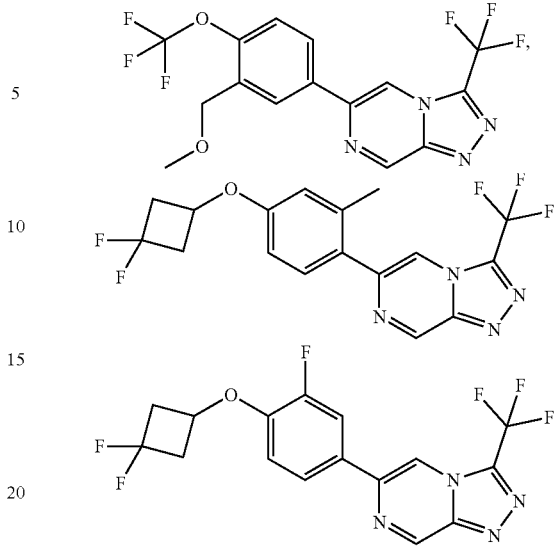

or a pharmaceutically acceptable salt thereof.

In another aspect, the present disclosure provides a compound of Formula (IVa):

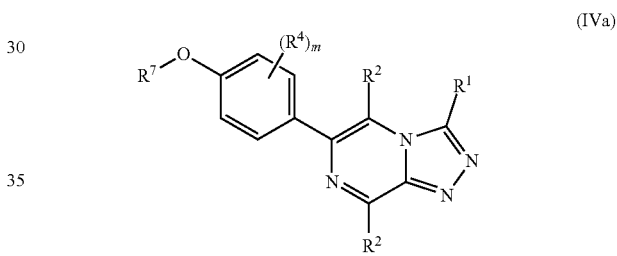

(IVa)

or a pharmaceutically acceptable salt thereof, wherein:

$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^2$ is independently hydrogen, $C_{1-6}$alkyl, or halo;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl are optionally substituted with one or more $R^5$;

m is 1 or 2;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, $-OR^7$ is $-OCF_3$ or $-O-CH_2CF_3$.

In some embodiments, $R^4$ is independently $C_{1-6}$ alkyl, $-OR^e$, or halogen.

In some embodiments, $R^4$ is methyl or fluoride.

In some embodiments, m is 1.

In some embodiments, the compound is selected from:

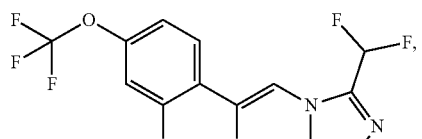
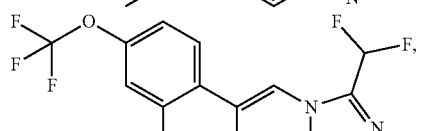

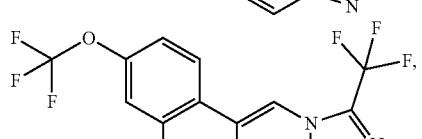
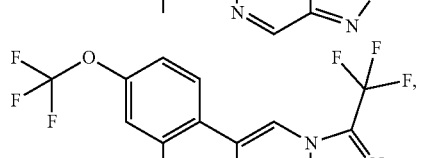
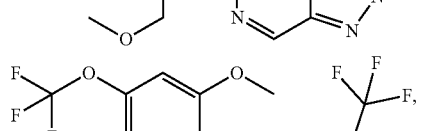
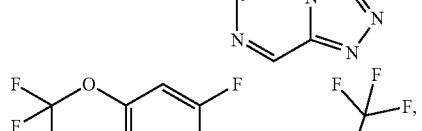
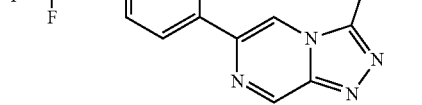

-continued

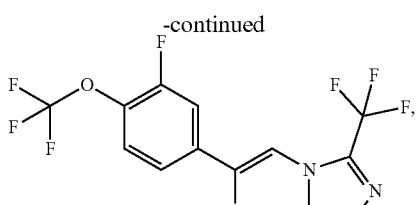
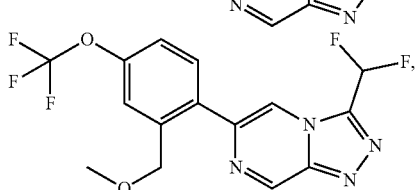
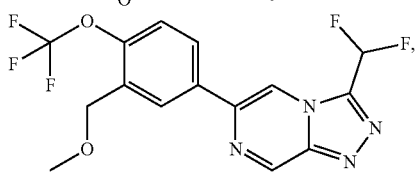
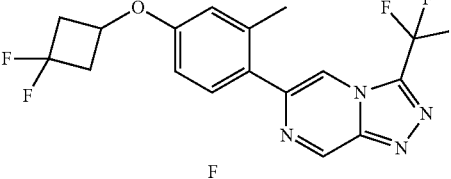
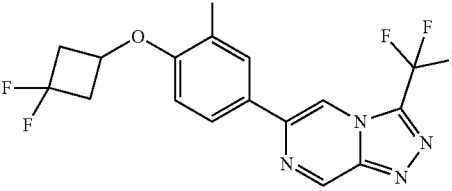

or a pharmaceutically acceptable salt thereof.

In another aspect, the present disclosure provides a compound of Formula (IVb):

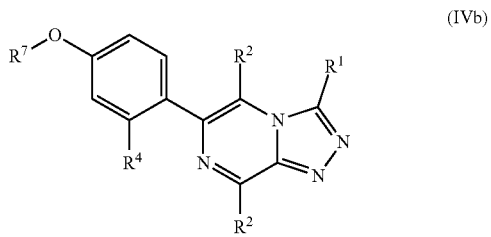

(IVb)

or a pharmaceutically acceptable salt thereof, wherein:

$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or $-OR^e$;

$R^2$ is independently hydrogen, $C_{1-6}$alkyl, or halo;

$R^4$ is $C_{1-6}$alkyl optionally substituted with one or more $R^5$;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, —$OR^7$ is —$OCF_3$ or —O—$CH_2CF_3$.

In some embodiments, $R^4$ is methyl.

In some embodiments, the compound is selected from:

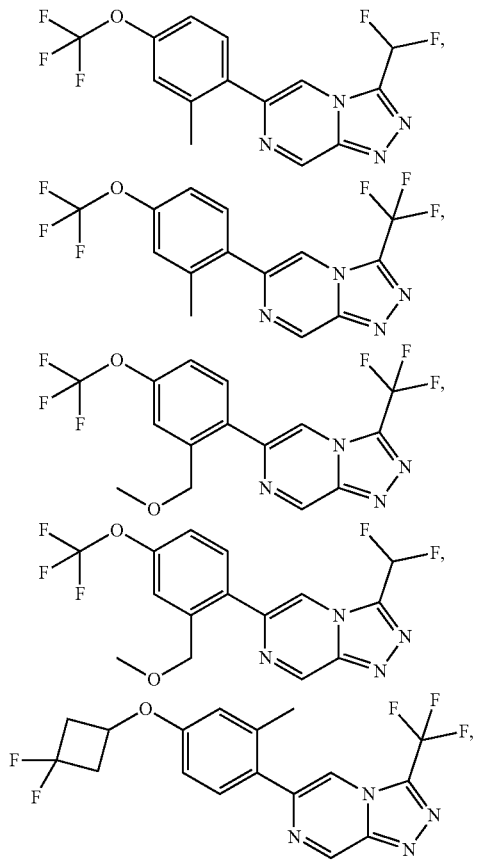

or a pharmaceutically acceptable salt thereof.

In another aspect, the present disclosure provides a compound of Formula (V):

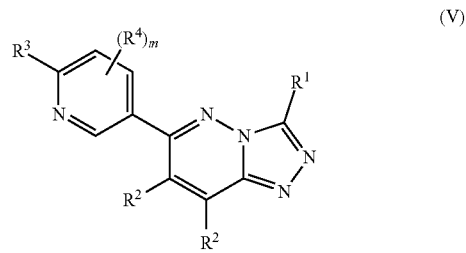

or a pharmaceutically acceptable salt thereof, wherein:

$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^2$ is independently hydrogen, $C_{1-6}$alkyl, or halo;

$R^3$ is $C_{1-6}$alkyl, halo, cyano, nitro, $C_{3-8}$carbocyclyl, 3-8 membered heterocyclyl, —$OR^7$, —$N(R^d)_2$, —$C(O)R^c$, —$C(O)OR^c$, or —$C(O)N(R^d)_2$, wherein $C_{1-6}$alkyl, $C_{3-8}$carbocyclyl, or 3-8 membered heterocyclyl is optionally substituted with one or more $R^5$;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl are optionally substituted with one or more $R^5$;

m is 1 or 2;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl;

wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^3$ is —$OR^7$.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, $R^3$ is —$OCF_3$ or —O—$CH_2CF_3$.

In some embodiments, $R^4$ is independently $C_{1-6}$ alkyl, —$OR^c$, or halogen.

In some embodiments, $R^4$ is methyl.

In some embodiments, $R^4$ is fluoride.

In some embodiments, m is 1.

In some embodiments, the compound is selected from:
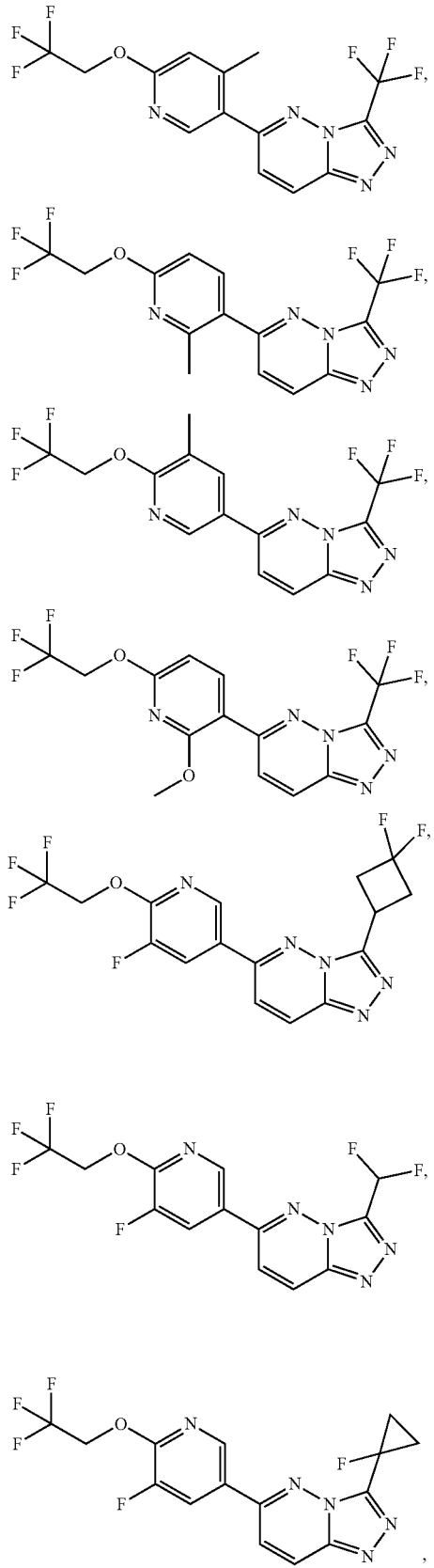
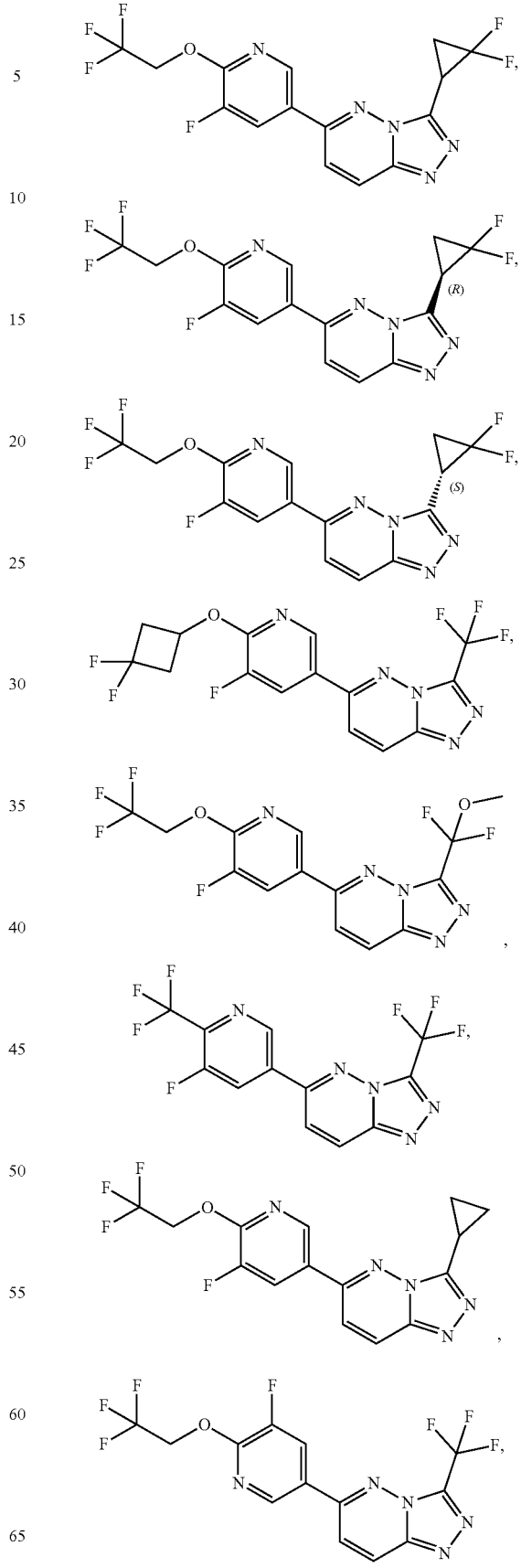

-continued

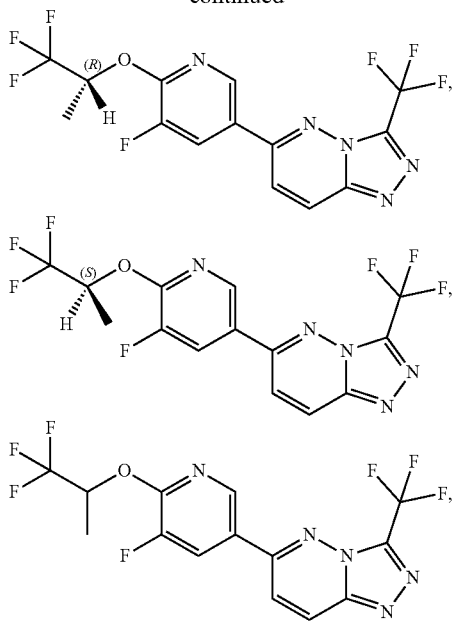

or a pharmaceutically acceptable salt thereof.

In another aspect, the present disclosure provides a compound of Formula (Va):

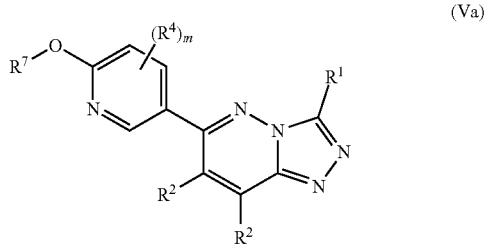

or a pharmaceutically acceptable salt thereof, wherein:
$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;
$R^2$ is independently hydrogen, $C_{1-6}$alkyl, or halo;
$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$, wherein $C_{1-6}$alkyl, $C_{3-8}$carbocyclyl, or 3-8 membered heterocyclyl are optionally substituted with one or more $R^5$;
m is 1 or 2;
each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$; each $R^c$ is independently hydrogen or $C_{1-6}$alkyl, wherein each $C_{1-6}$alkyl is optionally substituted with one or more $R^6$;
each $R^d$ is independently hydrogen or $C_{1-6}$alkyl;
each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and
$R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, —$OR^7$ is —$OCF_3$ or —O—$CH_2CF_3$.

In some embodiments, $R^4$ is independently $C_{1-6}$ alkyl, —$OR^c$, or halogen.

In some embodiments, $R^4$ is methyl.

In some embodiments, $R^4$ is fluoride.

In some embodiments, m is 1.

In some embodiments, the compound is selected from:

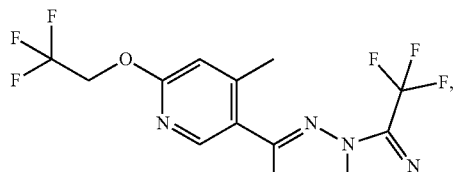

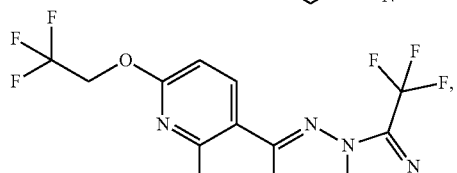

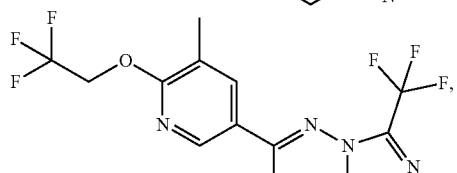

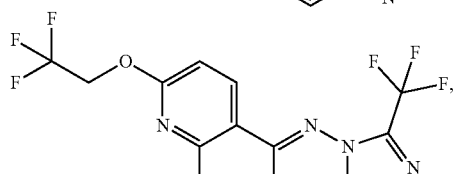

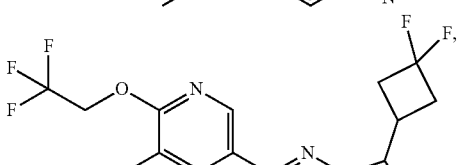

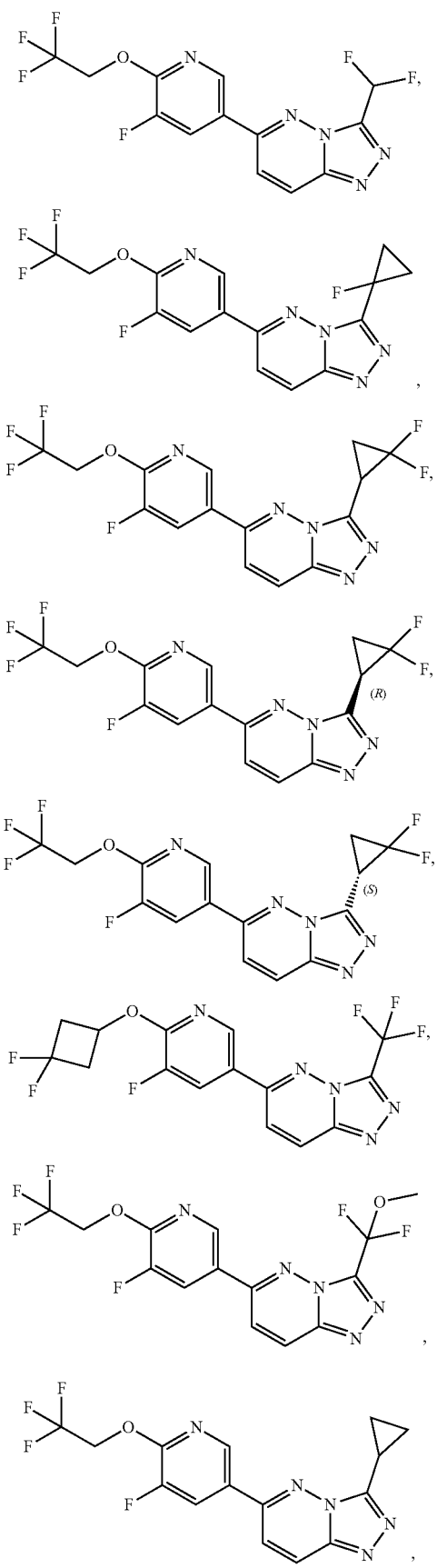

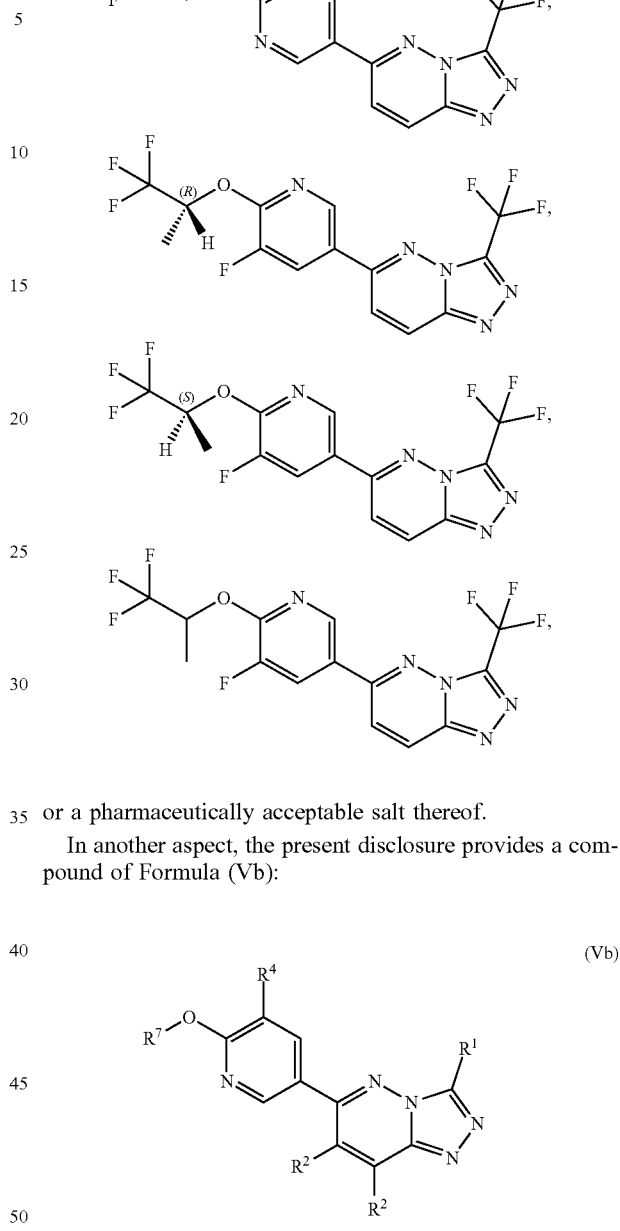

or a pharmaceutically acceptable salt thereof.

In another aspect, the present disclosure provides a compound of Formula (Vb):

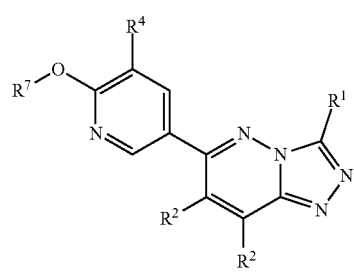

(Vb)

or a pharmaceutically acceptable salt thereof, wherein:

R$^1$ is hydrogen, C$_1$ alkyl, C$_{1-6}$haloalkyl, or C$_{3-8}$carbocyclyl, wherein C$_1$ alkyl, C$_{1-6}$haloalkyl, or C$_{3-8}$carbocyclyl is optionally substituted by one or more halo, 3-8 membered heterocyclyl, or —OR$^c$;

R$^2$ is independently hydrogen, C$_{1-6}$alkyl, or halo;

R$^4$ is halogen;

each R$^5$ is independently halo, cyano, nitro, C$_{1-6}$alkyl, C$_{3-8}$carbocyclyl, 3-8 membered heterocyclyl, —OR$^c$, —C(O)N(R$^d$)$_2$, —SO$_2$R$^c$, —SO$_2$OR$^c$, —SO$_2$N(R$^d$)$_2$, —NR$^d$C(O)(R$^c$), or —N(R$^d$)$_2$;

each R$^c$ is independently hydrogen or C$_{1-6}$alkyl, wherein each C$_{1-6}$alkyl is optionally substituted with one or more R$^6$;

each R$^d$ is independently hydrogen or C$_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, —$OR^7$ is —$OCF_3$ or —$O$—$CH_2CF_3$.

In some embodiments, $R^4$ is fluoride.

In some embodiments, the compound is selected from:

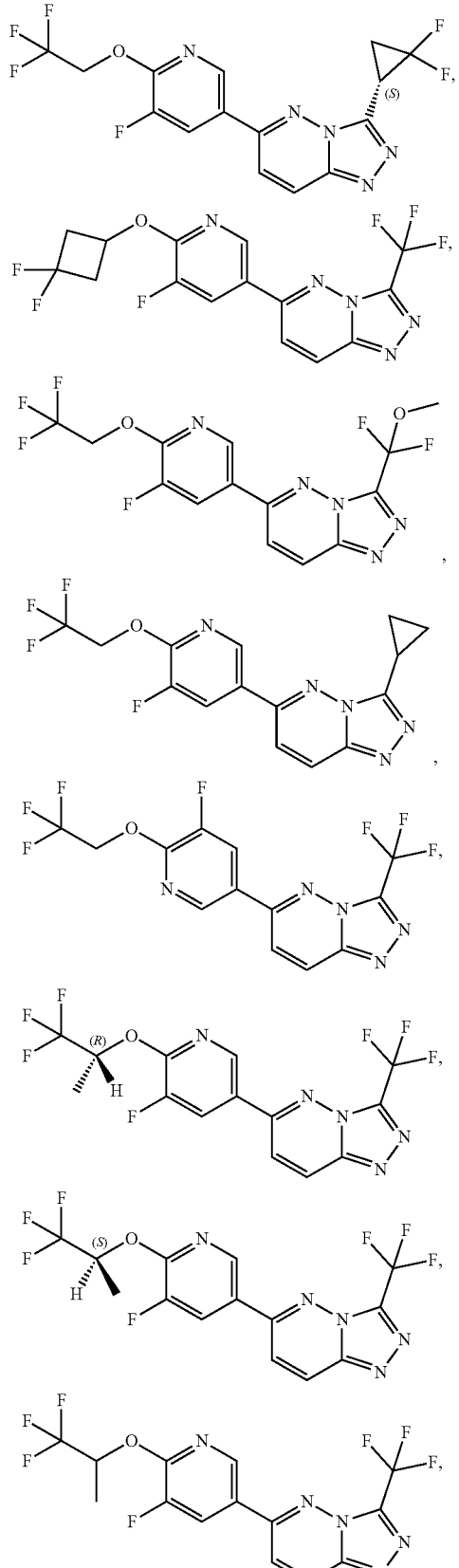

or a pharmaceutically acceptable salt thereof.-

In another aspect, the present disclosure provides a compound of Formula (VI):

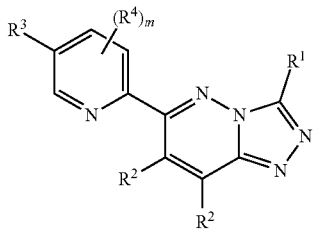

(VI)

or a pharmaceutically acceptable salt thereof, wherein:
$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^2$ is independently hydrogen, $C_{1-6}$alkyl, or halo;

$R^3$ is $C_{1-6}$alkyl, halo, cyano, nitro, $C_{3-8}$carbocyclyl, 3-8 membered heterocyclyl, —$OR^7$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl is optionally substituted with one or more $R^5$;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl are optionally substituted with one or more $R^5$;

m is 0, 1 or 2;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^3$ is —$OR^7$.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, $R^3$ is —$OCF_3$ or —$O$—$CH_2CF_3$.

In some embodiments, $R^4$ is independently $C_{1-6}$ alky, —$OR^c$, or halogen.

In some embodiments, $R^4$ is methyl or fluoride.

In some embodiments, m is 1 or 2.

In some embodiments, m is 1.

In some embodiments, the compound is:

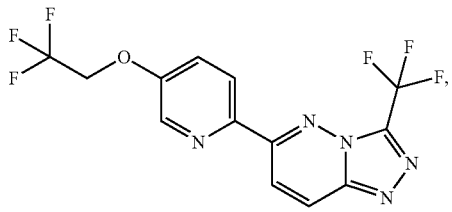 [SMILES: FC(F)(F)COc1ccc(-c2ccc3nnc(C(F)(F)F)n3n2)nc1]

or a pharmaceutically acceptable salt thereof.

In another aspect, the present disclosure provides a compound of Formula (VIa):

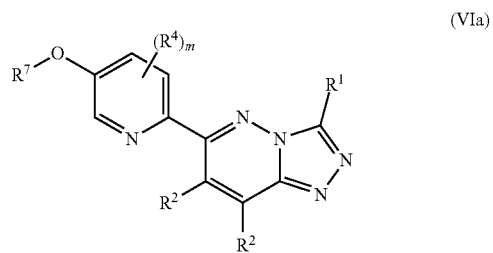

(VIa)

or a pharmaceutically acceptable salt thereof, wherein:
$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^2$ is independently hydrogen, $C_{1-6}$alkyl, or halo;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl are optionally substituted with one or more $R^5$;

m is 1 or 2;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, —$OR^7$ is —$OCF_3$ or —$O$—$CH_2CF_3$.

In some embodiments, R⁴ is independently $C_{1-6}$ alkyl, —OR$^c$, or halogen.

In some embodiments, R⁴ is methyl or fluoride.

In some embodiments, m is 1 or 2.

In some embodiments, m is 1.

In some embodiments, the compound is:

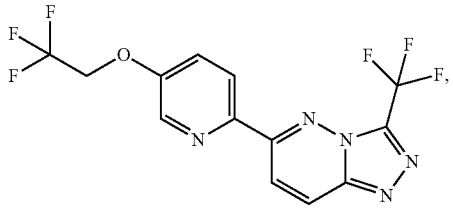 [SMILES: FC(F)(F)COc1ccc(-c2ccc3nnc(C(F)(F)F)n3n2)nc1]

or a pharmaceutically acceptable salt thereof.

In another aspect, the present disclosure provides a compound of Formula (VII):

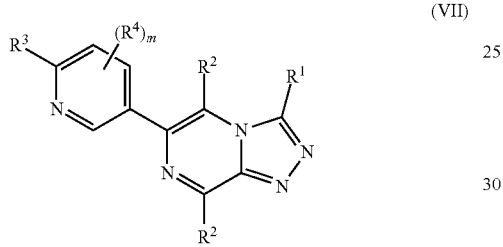

or a pharmaceutically acceptable salt thereof, wherein:

R¹ is hydrogen, $C_1$ alkyl, $C_{1-6}$haloalkyl, $C_{3-8}$carbocyclyl, phenyl, O-phenyl, wherein $C_1$ alkyl, $C_{1-6}$haloalkyl, $C_{3-8}$carbocyclyl, phenyl, or O-phenyl is optionally substituted by one or more halo, 3-8 membered heterocyclyl, or —OR$^c$;

R² is independently hydrogen, $C_{1-6}$alkyl, or halo;

R³ is $C_{1-6}$alkyl, halo, cyano, nitro, $C_{3-8}$carbocyclyl, 3-8 membered heterocyclyl, —OR⁷, —N(R$^d$)₂, —C(O)R$^c$, —C(O)OR$^c$, or —C(O)N(R$^d$)₂ wherein $C_{1-6}$alkyl, $C_{3-8}$carbocyclyl, or 3-8 membered heterocyclyl is optionally substituted with one or more R⁵;

R⁴ is $C_{1-6}$alkyl, halo, cyano, nitro, $C_{3-8}$carbocyclyl, 3-8 membered heterocyclyl, —OR$^c$, —N(R$^d$)₂, —C(O)R$^c$, —C(O)OR$^c$, or —C(O)N(R$^d$)₂ wherein $C_{1-6}$alkyl, $C_{3-8}$carbocyclyl, or 3-8 membered heterocyclyl are optionally substituted with one or more R⁵;

m is 0, 1 or 2;

each R⁵ is independently halo, cyano, nitro, $C_{1-6}$alkyl, $C_{3-8}$carbocyclyl, 3-8 membered heterocyclyl, —OR$^c$, —C(O)N(R$^d$)₂, —SO₂R$^c$, —SO₂OR$^c$, —SO₂N(R$^d$)₂, —NR$^d$C(O)(R$^c$), or —N(R$^d$)₂;

each R$^c$ is independently hydrogen or $C_{1-6}$alkyl, wherein each $C_{1-6}$alkyl is optionally substituted with one or more R⁶;

each R$^d$ is independently hydrogen or $C_{1-6}$alkyl;

each R⁶ is independently halogen, cyano, $C_{3-8}$carbocyclyl, or 3-8 membered heterocyclyl; wherein the $C_{3-8}$carbocyclyl is optionally substituted with one or more halogens or cyano; and R⁷ is $C_{1-6}$alkyl or $C_{3-8}$carbocyclyl wherein $C_{1-6}$alkyl or $C_{3-8}$carbocyclyl is optionally substituted with one or more R⁶.

In some embodiments, R¹ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —ORc.

In some embodiments, R¹ is $CF_3$ or $CHF_2$.

In some embodiments, R² is hydrogen.

In some embodiments, R³ is —OR⁷.

In some embodiments, R⁷ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, R⁷ is $C_{1-6}$alkyl optionally substituted with 1, 2, or 3 halogens.

In some embodiments, R³ is —OCF₃ or —O—CH₂CF₃.

In some embodiments, R⁴ is independently $C_{1-6}$ alkyl, —OR$^c$, or halogen.

In some embodiments, R⁴ is methyl or fluoride.

In some embodiments, m is 1 or 2.

In some embodiments, m is 1.

In some embodiments, the compound is selected from:

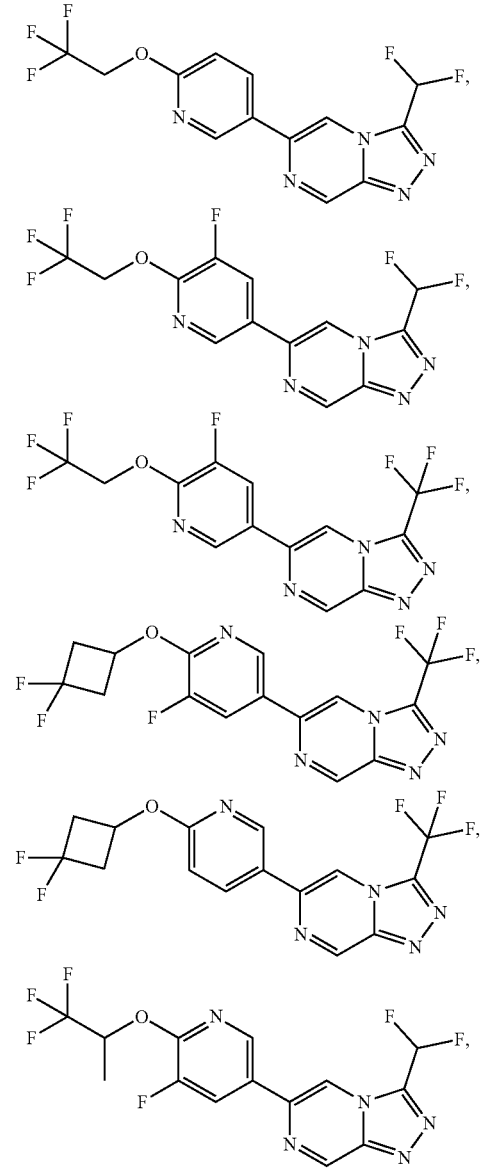

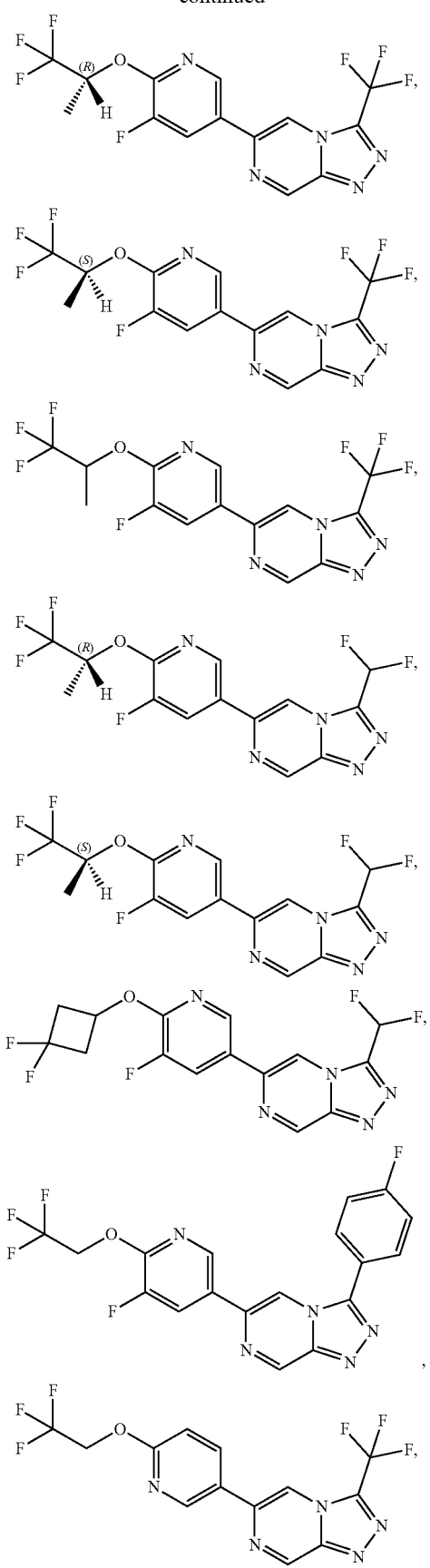
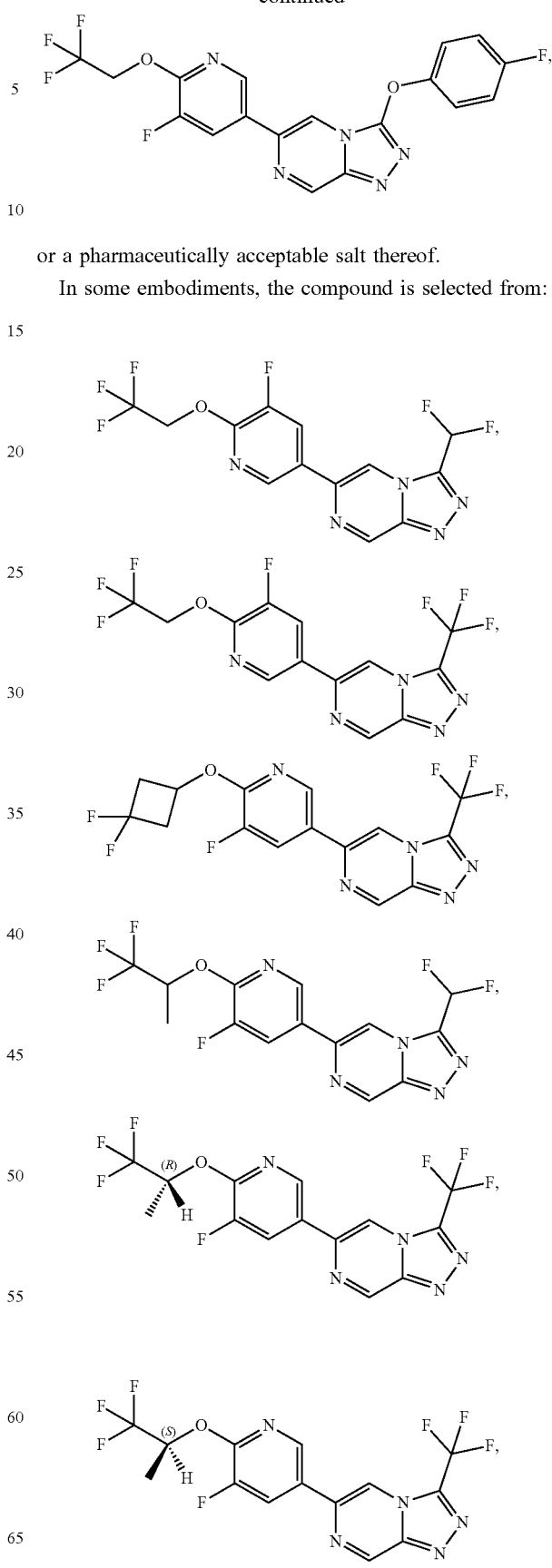
or a pharmaceutically acceptable salt thereof.
In some embodiments, the compound is selected from:

-continued

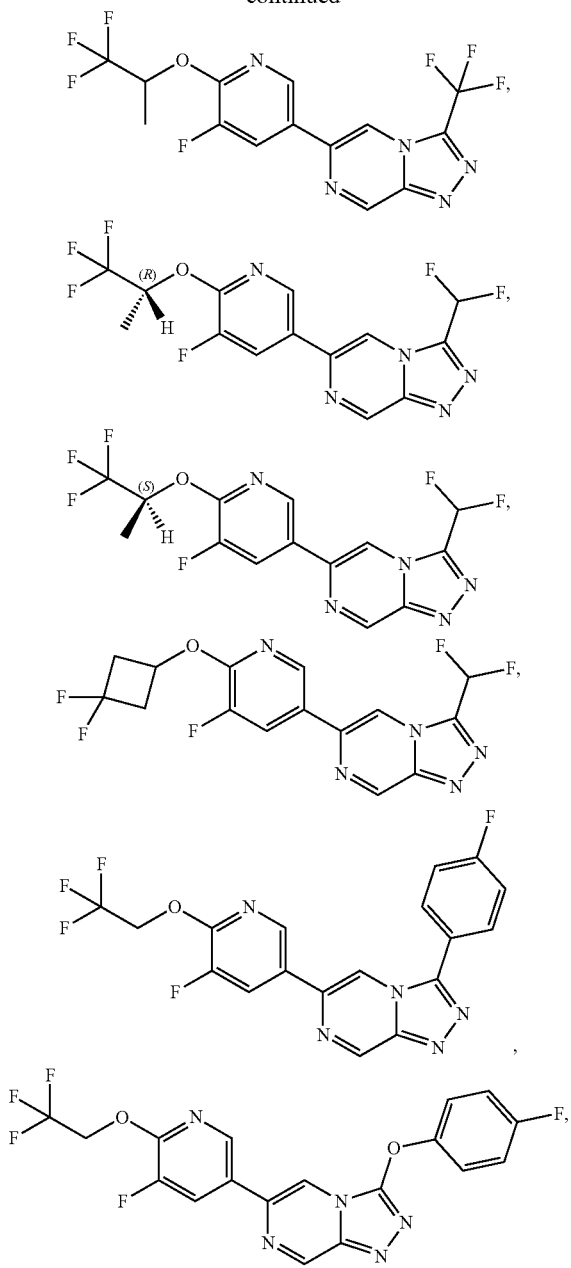

or a pharmaceutically acceptable salt thereof.

In another aspect, the present disclosure provides a compound of Formula (VIIa):

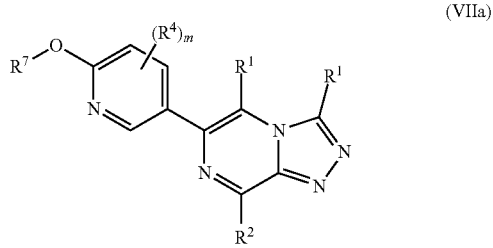

(VIIa)

or a pharmaceutically acceptable salt thereof, wherein:

$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^2$ is independently hydrogen, $C_{1-6}$alkyl, or halo;

$R^4$ is $C_{1-6}$alkyl, halo, cyano, nitro, $C_{3-8}$carbocyclyl, 3-8 membered heterocyclyl, —$OR^c$, —$N(R^d)_2$, —$C(O)R^c$, —$C(O)OR^c$, or —$C(O)N(R^d)_2$ wherein $C_{1-6}$alkyl, $C_{3-8}$carbocyclyl, or 3-8 membered heterocyclyl are optionally substituted with one or more $R^5$;

m is 0, 1 or 2;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or $C_{3-8}$carbocyclyl optionally substituted with 1, 2, or 3 substituents selected from halogen or cyano.

In some embodiments, $R^7$ is $C_{1-6}$alkyl optionally substituted with 1, 2, or 3 halogens.

In some embodiments, —$OR^7$ is —$OCF_3$ or —O—$CH_2CF_3$.

In some embodiments, $R^4$ is independently $C_{1-6}$ alkyl, —$OR^c$, or halogen.

In some embodiments, $R^4$ is methyl or fluoride.

In some embodiments, m is 1 or 2.

In some embodiments, m is 1.

In some embodiments, the compound is selected from:

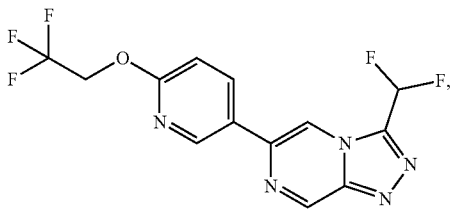

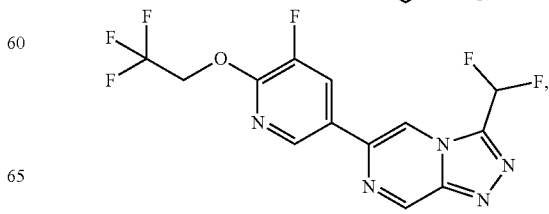

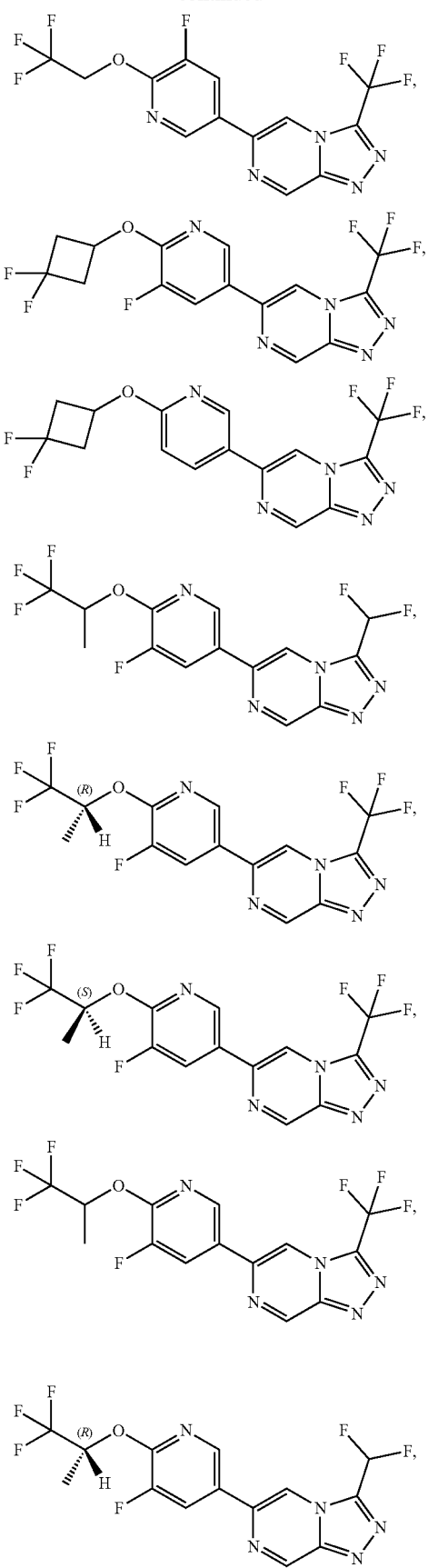
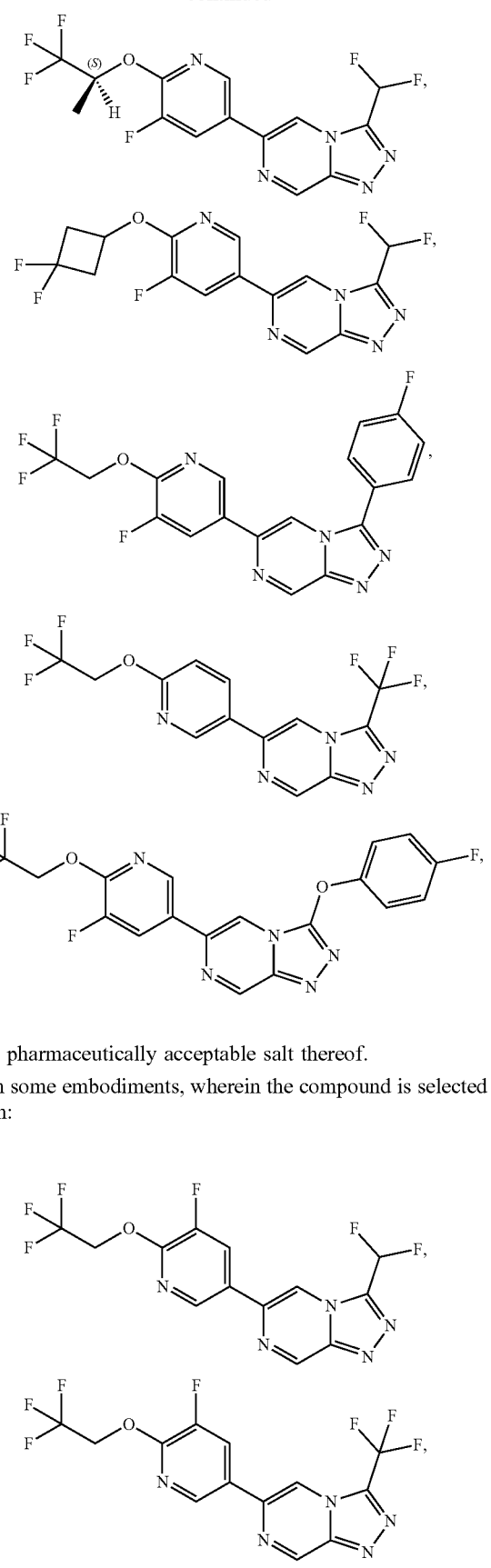
or a pharmaceutically acceptable salt thereof.
In some embodiments, wherein the compound is selected from:

-continued

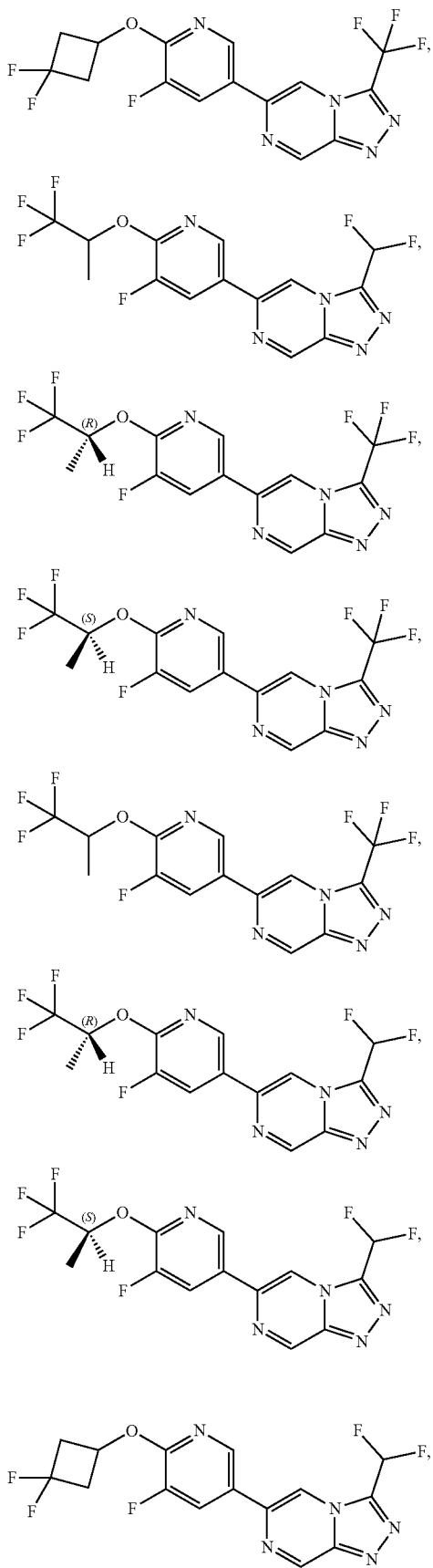

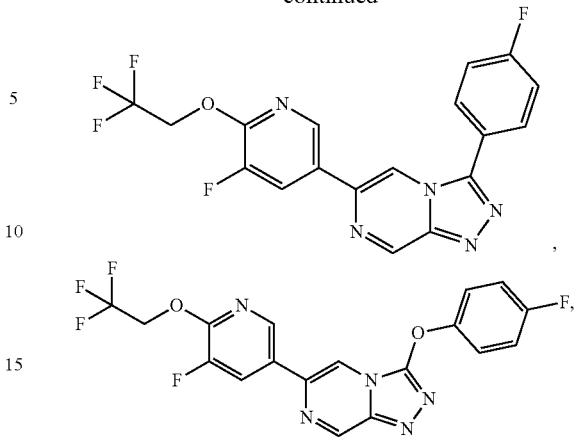

or a pharmaceutically acceptable salt thereof.

In another aspect, the present disclosure provides a compound of Formula (VIIb):

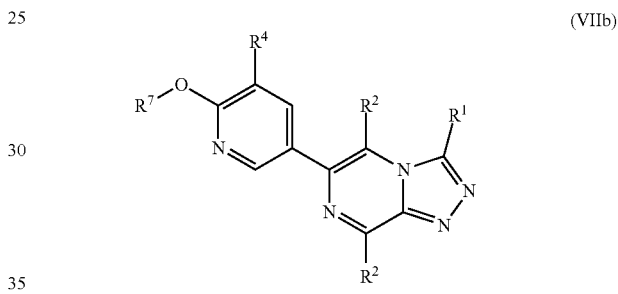

(VIIb)

or a pharmaceutically acceptable salt thereof, wherein:

$R^1$ is hydrogen, $C_1$ alkyl, $C_{1-6}$haloalkyl, or $C_{3-8}$carbocyclyl, wherein $C_1$ alkyl, $C_{1-6}$haloalkyl, or $C_{3-8}$carbocyclyl is optionally substituted by one or more halo, 3-8 membered heterocyclyl, or —$OR^c$;

$R^2$ is independently hydrogen, $C_{1-6}$alkyl, or halo;

$R^4$ is halogen;

each $R^5$ is independently halo, cyano, nitro, $C_{1-6}$alkyl, $C_{3-8}$carbocyclyl, 3-8 membered heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$;

each $R^c$ is independently hydrogen or $C_{1-6}$alkyl, wherein each $C_{1-6}$alkyl is optionally substituted with one or more $R^6$;

each $R^d$ is independently hydrogen or $C_{1-6}$alkyl;

each $R^6$ is independently halogen, cyano, $C_{3-8}$carbocyclyl, or 3-8 membered heterocyclyl; wherein the $C_{3-8}$carbocyclyl is optionally substituted with one or more halogens or cyano; and $R^7$ is $C_{1-6}$alkyl or $C_{3-8}$carbocyclyl wherein $C_{1-6}$alkyl or $C_{3-8}$carbocyclyl is optionally substituted with one or more $R^6$.

In some embodiments, $R^1$ is $C_{1-6}$haloalkyl optionally substituted with —$OR^c$ or $C_{3-4}$carbocyclyl optionally substituted with one or two halogens.

In some embodiments, $R^1$ is $CF_3$ or $CHF_2$.

In some embodiments, $R^2$ is hydrogen.

In some embodiments, $R^7$ is $C_{1-6}$alkyl optionally substituted with 1, 2, or 3 substituents selected from halogen or cyano; $C_{1-6}$alkyl substituted with $C_{3-8}$carbocyclyl optionally substituted with 1, 2, or 3 substituents selected from halogen or cyano; or C$_{3-8}$carbocyclyl optionally substituted with 1, 2, or 3 substituents selected from halogen or cyano.

In some embodiments, R$^7$ is C$_{1-6}$alkyl optionally substituted with 1, 2, or 3 halogens.

In some embodiments, —OR$^7$ is —OCF$_3$ or —O—CH$_2$CF$_3$.

In some embodiments, R$^4$ is fluoride.

In some embodiments, the compound is selected from:

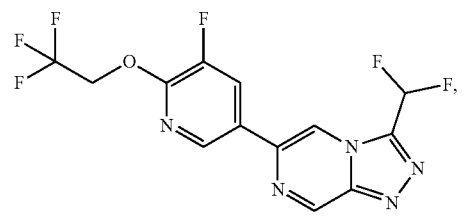

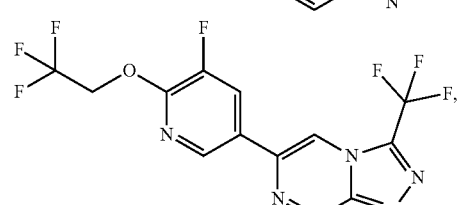

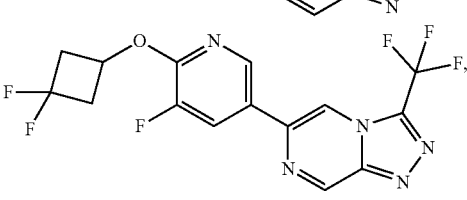

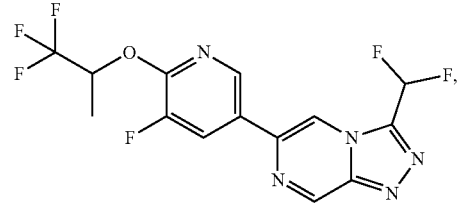

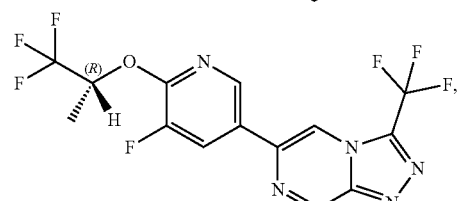

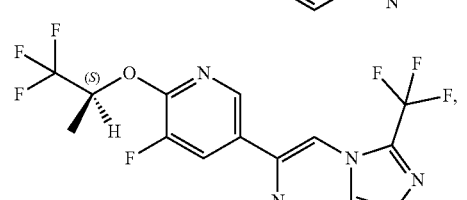

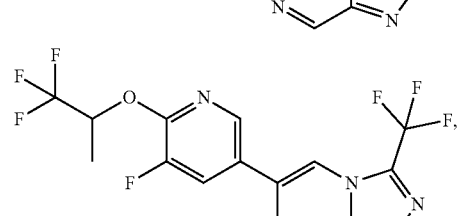

-continued

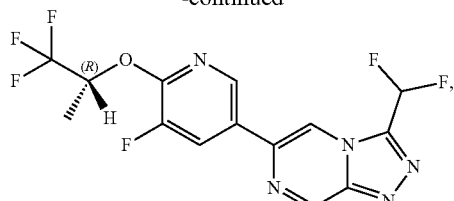

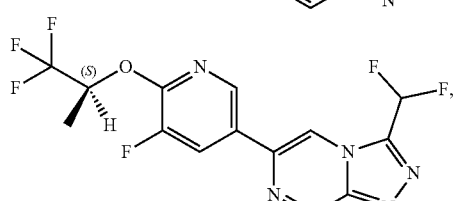

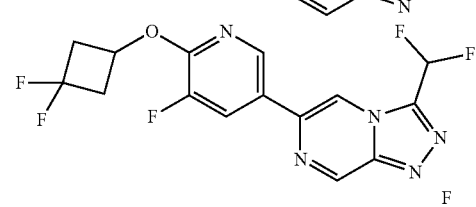

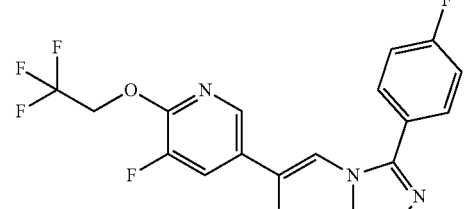

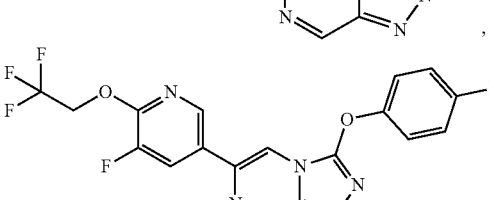

or a pharmaceutically acceptable salt thereof.

In another aspect, the present disclosure provides a compound of Formula (VIII):

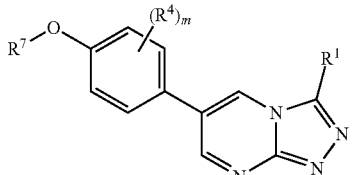

(VIII)

or a pharmaceutically acceptable salt thereof, wherein:

R$^1$ is hydrogen, C$_1$ alkyl, C$_{1-6}$haloalkyl, or C$_{3-8}$carbocyclyl, wherein C$_1$ alkyl, C$_{1-6}$haloalkyl, or C$_{3-8}$carbocyclyl is optionally substituted by one or more halo, 3-8 membered heterocyclyl, or —OR$^c$;

R$^4$ is C$_{1-6}$alkyl, —OR$^c$, or halogen;

m is 0, 1, or 2;

each R$^c$ is independently hydrogen or C$_{1-6}$alkyl, wherein each C$_{1-6}$alkyl is optionally substituted with one or more R$^6$;

each R⁶ is independently halogen, cyano, C₃₋₈carbocyclyl, or 3-8 membered heterocyclyl; wherein the C₃₋₈carbocyclyl is optionally substituted with one or more halogens or cyano; and R⁷ is C₁₋₆alkyl or C₃₋₈carbocyclyl wherein C₁₋₆alkyl or C₃₋₈carbocyclyl is optionally substituted with one or more R⁶.

In some embodiments, R¹ is C₁₋₆haloalkyl optionally substituted with —ORᶜ or C₃₋₄carbocyclyl optionally substituted with one or two halogens.

In some embodiments, R¹ is CF₃ or CHF₂.

In some embodiments, R⁷ is C₁₋₆alkyl optionally substituted with 1, 2, or 3 substituents selected from halogen or cyano; C₁₋₆alkyl substituted with C₃₋₈carbocyclyl optionally substituted with 1, 2, or 3 substituents selected from halogen or cyano; or C₃₋₈carbocyclyl optionally substituted with 1, 2, or 3 substituents selected from halogen or cyano.

In some embodiments, R⁷ is C₁₋₆alkyl optionally substituted with 1, 2, or 3 halogens.

In some embodiments, —OR⁷ is —OCF₃ or —O—CH₂CF₃.

In some embodiments, R⁴ is fluoride.
In some embodiments, R⁴ is methyl.
In some embodiments, m is 0.
In some embodiments, m is 1.
In some embodiments, the compound is selected from:

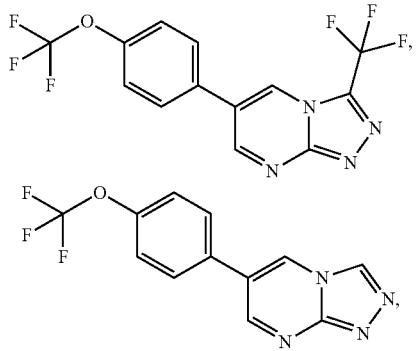

or a pharmaceutically acceptable salt thereof.

In another aspect, the present disclosure provides a compound of Formula (IX):

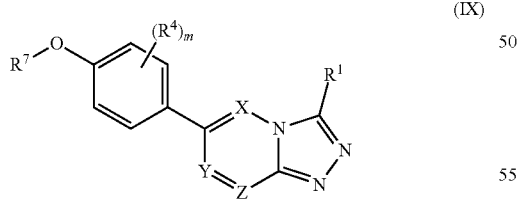

or a pharmaceutically acceptable salt thereof, wherein:
one of X, Y, and Z is N and the other two are CR²,
R¹ is hydrogen, C₁ alkyl, C₁₋₆haloalkyl, or C₃₋₈carbocyclyl, wherein C₁ alkyl, C₁₋₆ haloalkyl, or C₃₋₈carbocyclyl is optionally substituted by one or more halo, 3-8 membered heterocyclyl, or —ORᶜ;
one R² is hydrogen and the other R² is selected from C₁₋₆alkyl, halogen, —C(O)O(Rᶜ), —C(O)N(Rᵈ)₂, —NRᵈC(O)(Rᶜ), or —N(Rᵈ)₂; wherein the C₁₋₆alkyl is optionally substituted with —O(Rᵈ);

each Rᵈ is independently hydrogen or C₁₋₆alkyl;
R⁴ is C₁₋₆alkyl, —ORᶜ, or halogen;
m is 0, 1, or 2;
each Rᶜ is independently hydrogen or C₁₋₆alkyl, wherein each C₁₋₆alkyl is optionally substituted with one or more R⁶;

each R⁶ is independently halogen, cyano, C₃₋₈carbocyclyl, or 3-8 membered heterocyclyl; wherein the C₃₋₈carbocyclyl is optionally substituted with one or more halogens or cyano; and R⁷ is C₁₋₆alkyl or C₃₋₈carbocyclyl wherein C₁₋₆alkyl or C₃₋₈carbocyclyl is optionally substituted with one or more R⁶.

In some embodiments, X is N, Y and Z are CR².
In some embodiments, Y is N, and X and Z are CR².
In some embodiments, R¹ is C₁₋₆haloalkyl optionally substituted with —ORᶜ or C₃₋₄carbocyclyl optionally substituted with one or two halogens.

In some embodiments, R¹ is CF₃ or CHF₂.

In some embodiments, R⁷ is C₁₋₆alkyl optionally substituted with 1, 2, or 3 substituents selected from halogen or cyano; C₁₋₆alkyl substituted with C₃₋₈carbocyclyl optionally substituted with 1, 2, or 3 substituents selected from halogen or cyano; or C₃₋₈carbocyclyl optionally substituted with 1, 2, or 3 substituents selected from halogen or cyano.

In some embodiments, R⁷ is C₁₋₆alkyl optionally substituted with 1, 2, or 3 halogens.

In some embodiments, —OR⁷ is —OCF₃ or —O—CH₂CF₃.

In some embodiments, R⁴ is fluoride.
In some embodiments, R⁴ is methyl.
In some embodiments, m is 0.
In some embodiments, m is 1.
In some embodiments, the compound is selected from:

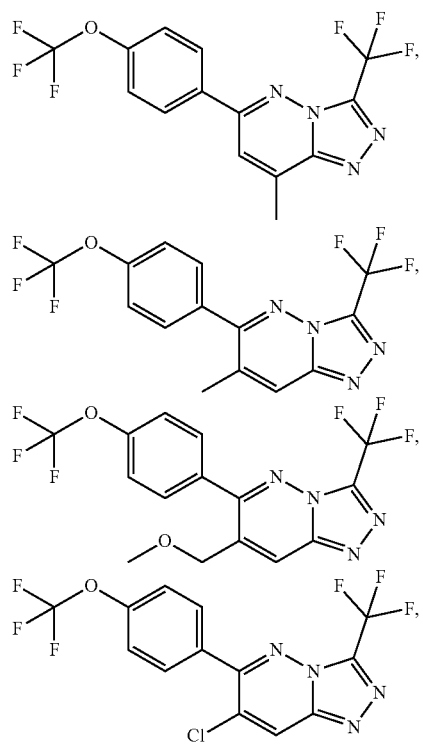

-continued
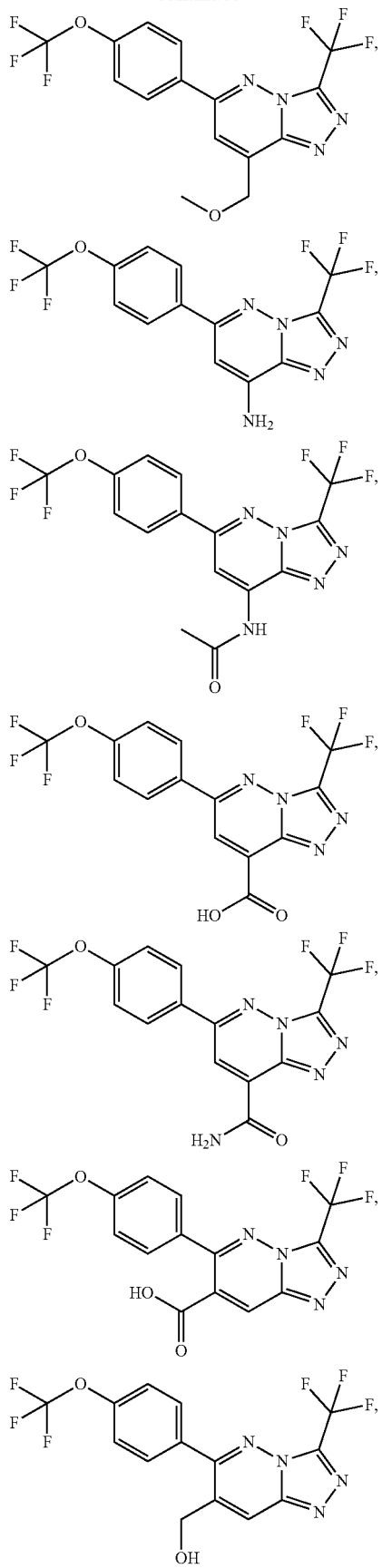
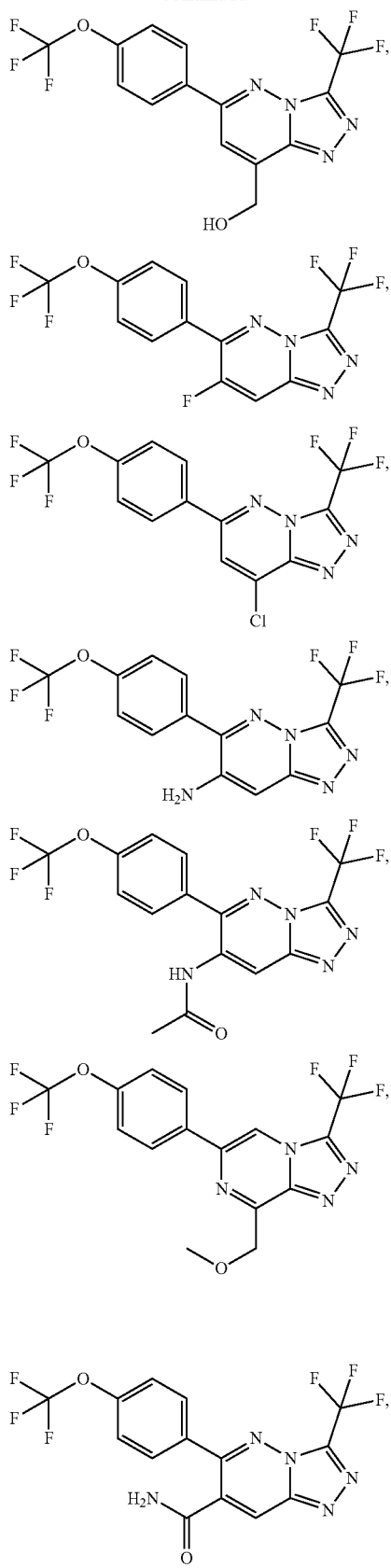
or a pharmaceutically acceptable salt thereof.

In another aspect, the present disclosure provides a compound selected from:
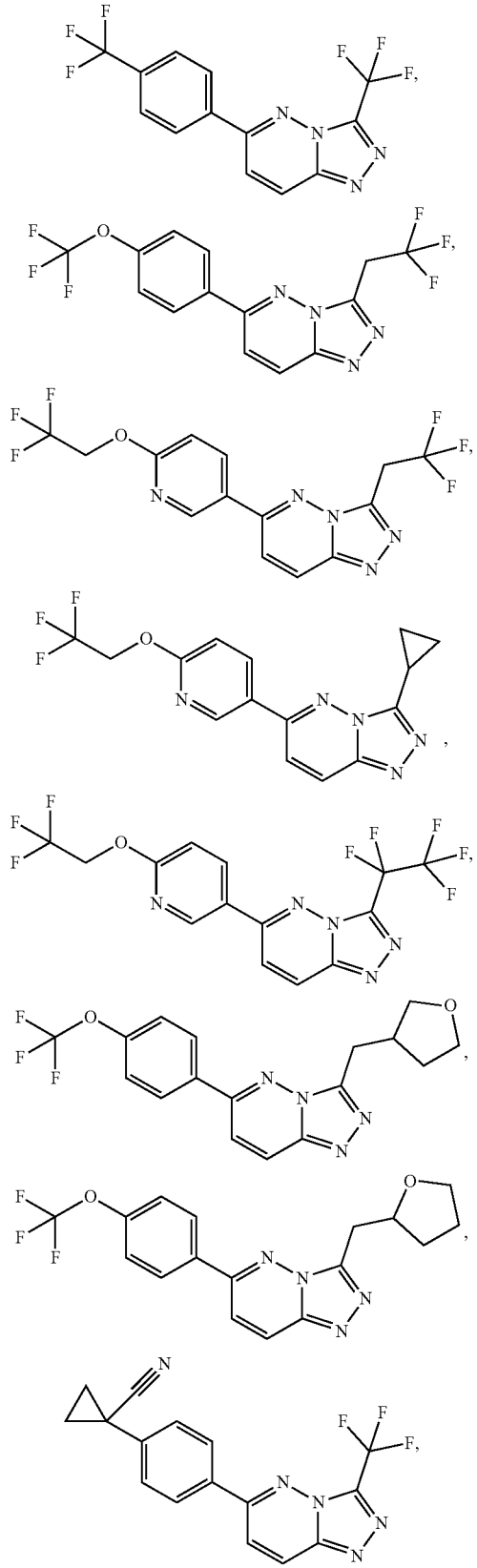
-continued
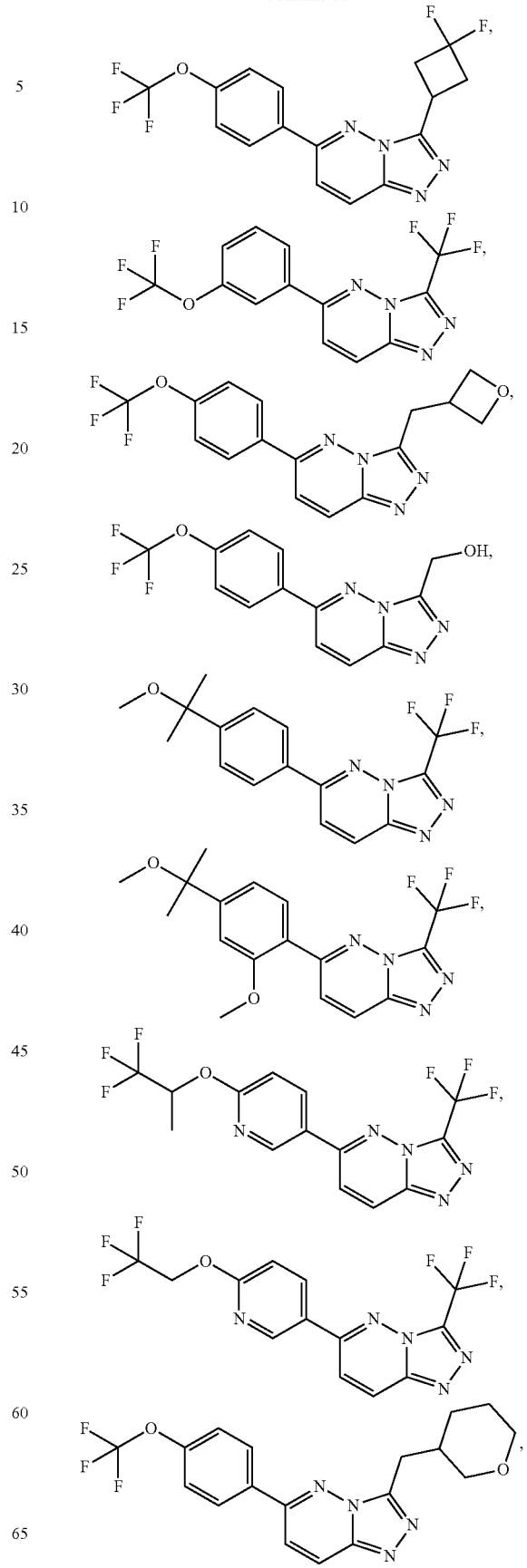

75
-continued
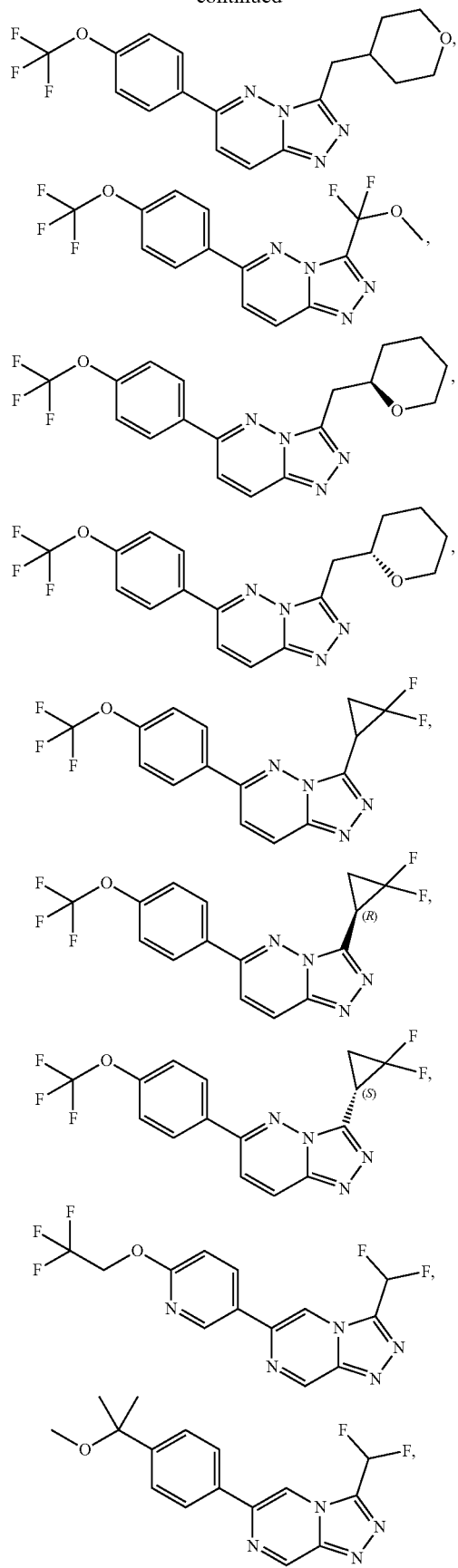
76
-continued
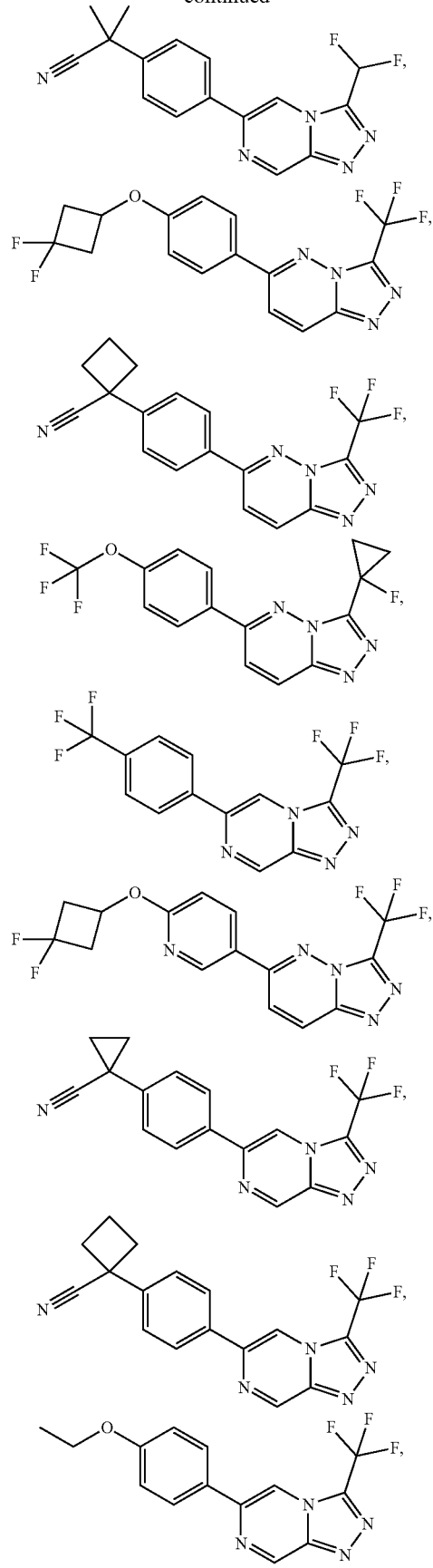

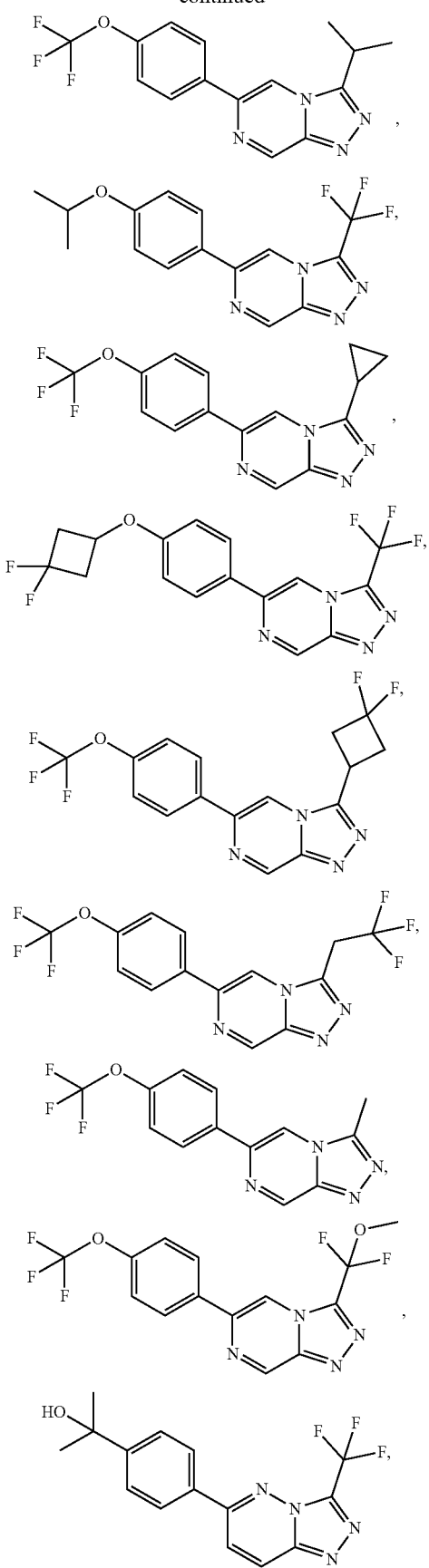
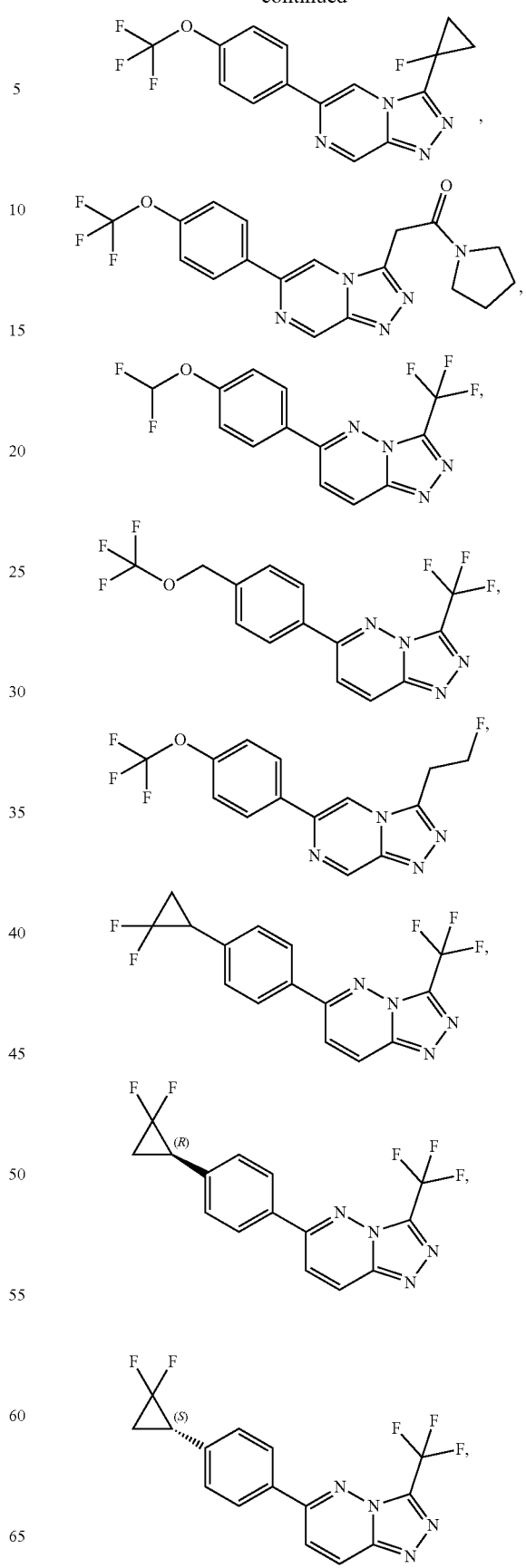

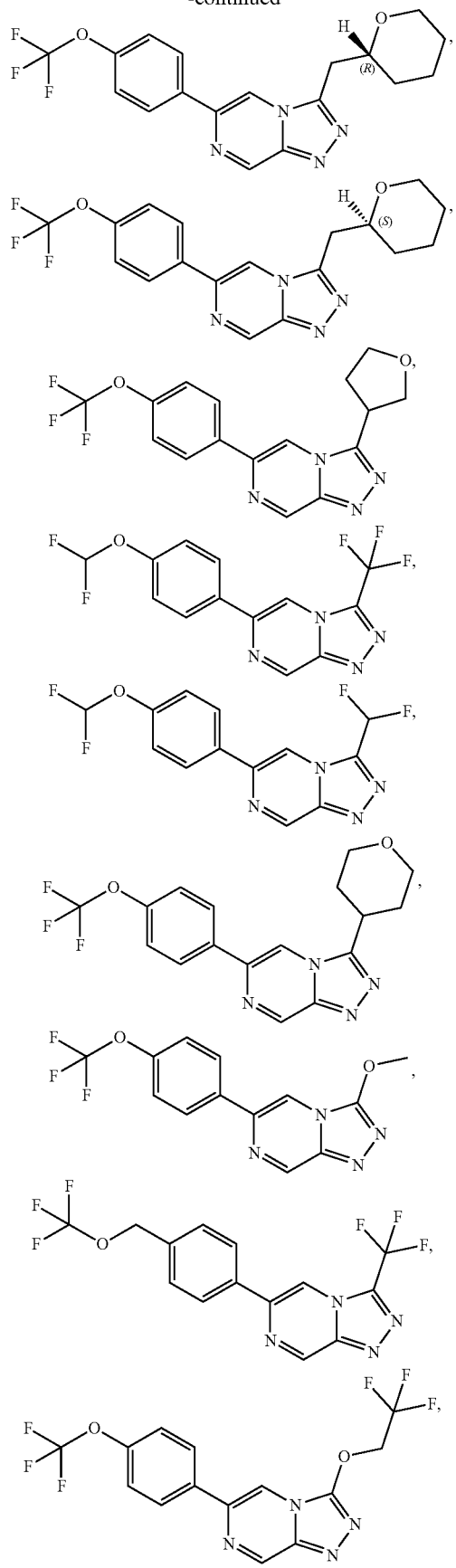
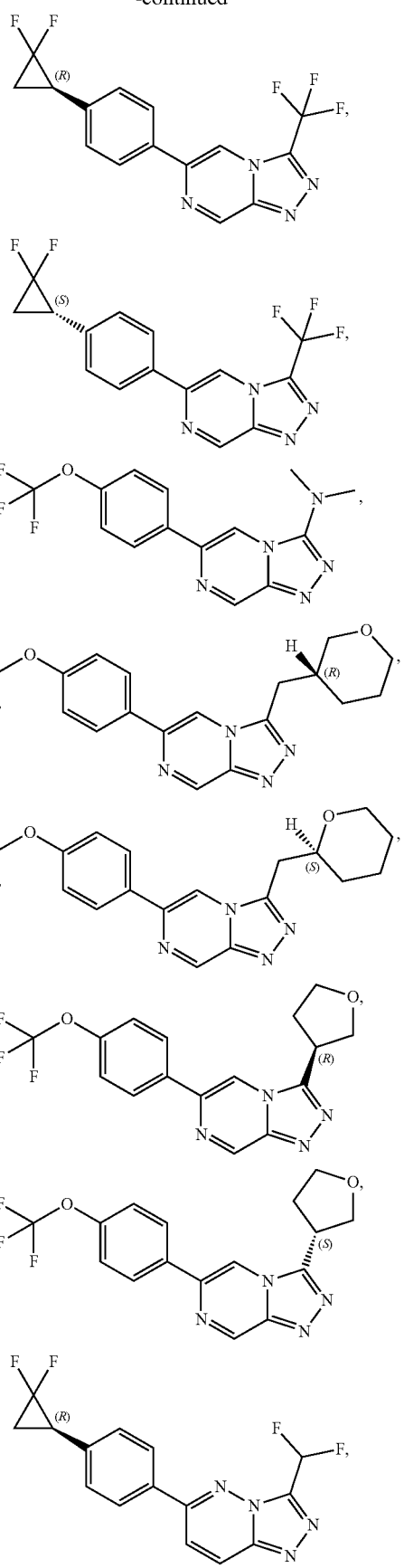

-continued
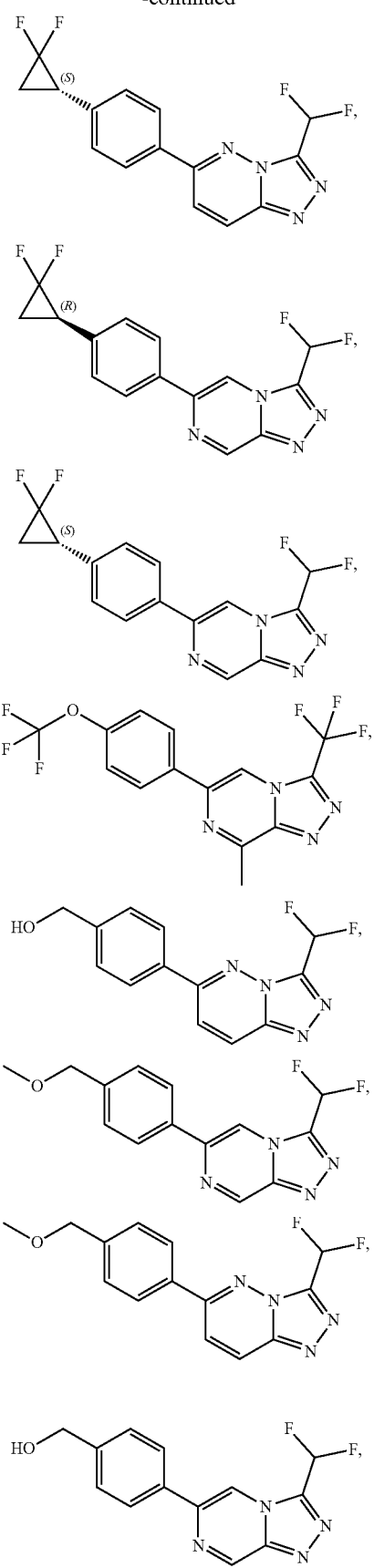
-continued
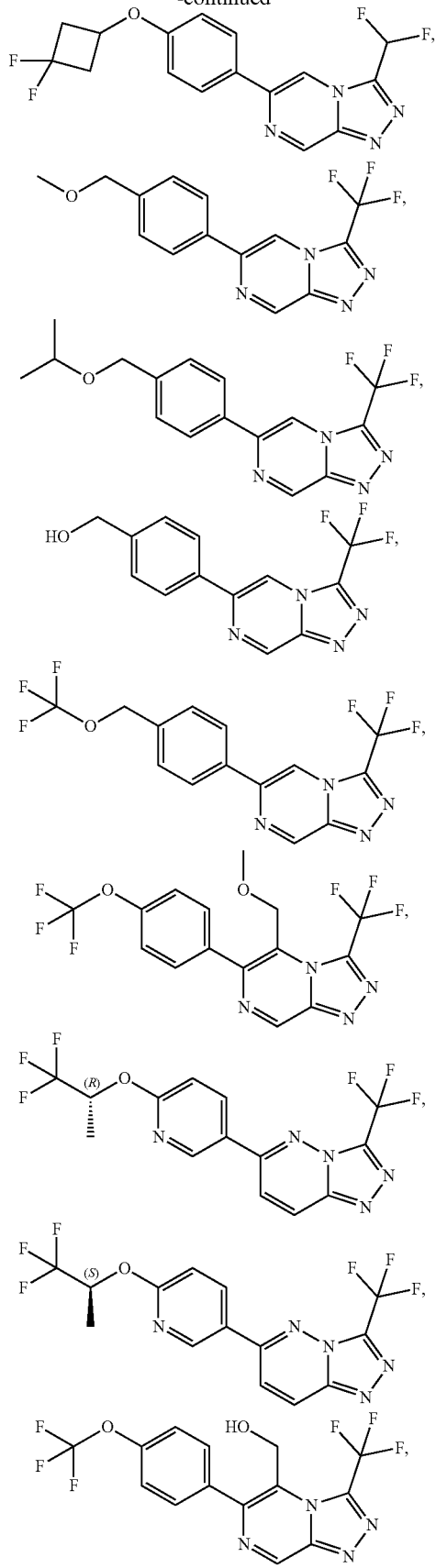

or a pharmaceutically acceptable salt thereof.

In another aspect, the present disclosure provides a pharmaceutical composition comprising a disclosed compound or pharmaceutically acceptable salt thereof, and a pharmaceutically acceptable carrier.

In another aspect, the present disclosure provides a method of treating a neurological disorder or a psychiatric disorder, wherein the method comprises administering to a subject in need thereof a disclosed compound or a pharmaceutically acceptable salt thereof or a disclosed pharmaceutical composition.

Other objects and advantages will become apparent to those skilled in the art from a consideration of the ensuing Detailed Description, Examples, and Claims.

DETAILED DESCRIPTION OF THE INVENTION

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include epilepsy or an epilepsy syndrome.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

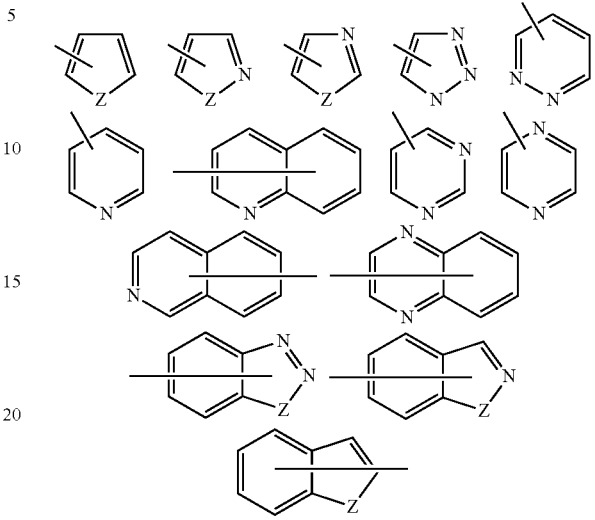

wherein each Z is selected from carbonyl, N, NR$^{65}$, O, and S; and R$^{65}$ is independently hydrogen, $C_1$-$C_8$ alkyl, $C_3$-$C_{10}$ carbocyclyl, 4-10 membered heterocyclyl, $C_6$-$C_{10}$ aryl, and 5-10 membered heteroaryl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

The term "cycloalkyl," as used herein, refers to a monocyclic saturated or partially unsaturated hydrocarbon ring system, for example, having 3-8 or 3-6 carbon atoms in its ring system, referred to herein as $C_{3-8}$ cycloalkyl or $C_{3-6}$ cycloalkyl, respectively. Exemplary cycloalkyl groups include, but are not limited to, cyclohexyl, cyclohexenyl, cyclopentyl, cyclopentenyl, cyclobutyl, and cyclopropyl.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

As used herein, "hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

As used herein, "cyano" refers to —CN.

As used herein, "halo" or "halogen" refers to fluoro (F), chloro (Cl), bromo (Br), and iodo (I). In certain embodiments, the halo group is either fluoro or chloro.

As used herein, "haloalkyl" refers to an alkyl group substituted with one or more halogen atoms.

As used herein, "nitro" refers to —NO$_2$.

As used herein, "oxo" refers to —C=O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

As used herein, a "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Compounds

In one aspect, the present invention features a compound of Formula (II):

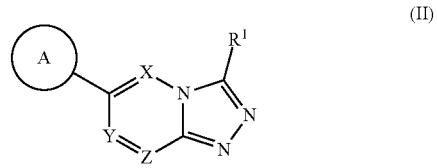

(II)

or a pharmaceutically acceptable salt thereof, wherein each of X, Y, and Z is independently N or $CR^2$, wherein at least one of X, Y, and Z is independently N; A is aryl or heteroaryl (e.g., a monocyclic 6-membered aryl or heteroaryl), optionally substituted by one or more $R^3$; $R^1$ is hydrogen, $C_1$ alkyl, haloalkyl, or carbocyclyl, wherein each alkyl and carbocyclyl is optionally substituted by halo, heterocyclyl, or —$OR^c$; $R^2$ is hydrogen, alkyl, or halo; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$ wherein the alkyl, carbocyclyl, and heterocyclyl are optionally substituted with one or more $R^5$; each $R^5$ is independently halo, cyano, nitro, alkyl, carbocyclyl, heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$; each $R^c$ is independently hydrogen, alkyl, carbocyclyl, or heterocyclyl, wherein each alkyl, carbocyclyl, or heterocyclyl is optionally substituted with one or more $R^6$; each $R^d$ is independently hydrogen or alkyl; and each $R^6$ is independently halo, carbocyclyl, or heterocyclyl.

In some embodiments, X is N. In some embodiments, X is N and Y is CR². In some embodiments, X is N and Z is CR². In some embodiments, X is N and each of Y and Z is independently CR². In some embodiments, R² is hydrogen.

In some embodiments, Y is N. In some embodiments, Y is N and X is CR². In some embodiments, Y is N and Z is CR². In some embodiments, Y is N and each of X and Z is independently CR². In some embodiments, R² is hydrogen.

In some embodiments, Z is N. In some embodiments, Z is N and X is CR². In some embodiments, Z is N and Y is CR². In some embodiments, Z is N and each of X and Y is independently CR². In some embodiments, R² is hydrogen.

In some embodiments, A is aryl (e.g., phenyl). In some embodiments, A is heteroaryl. In some embodiments, A is a 6-membered heteroaryl. In some embodiments, A is a nitrogen-containing heteroaryl (e.g., pyridyl).

In some embodiments, R¹ is hydrogen.

In some embodiments, R¹ is C₁ alkyl, haloalkyl, or carbocyclyl. In some embodiments, R¹ is haloalkyl, e.g., C₃-C₃ haloalkyl. In some embodiments, R¹ is C₃-C₃ haloalkyl, e.g., C₃-C₃ fluoroalkyl. In some embodiments, R¹ is —CF₃, —CHF₂, —CH₂CF₃, or CF₂CF₃. In some embodiments, R¹ is —CF₃.

In some embodiments, R¹ is C₁ alkyl substituted with heterocylyl or —OR$^c$. In some embodiments, R¹ is —CH₂— substituted with heterocylyl or —OR$^c$. In some embodiments, R¹ is —CH₂— substituted with an oxygen-containing heterocylyl or —OH. In some embodiments, R¹ is —CH₂— substituted with tetrahydrofuranyl (e.g., 1-tetrahydrofuranyl or 2-tetrahydrofuranyl), tetrahydropyranyl (e.g., 1-tetrahydropyranyl, 2-tetrahydropyranyl, or 3-tetrahydropyranyl), or —OH.

In some embodiments, R¹ is C₁ alkyl substituted with halo and —OR$^c$. In some embodiments, R¹ is —CF₂(OR$^c$). In some embodiments, R$^c$ is alkyl (e.g., CH₃, or —CH₂— substituted with carbocyclyl (e.g., isopropanyl)).

In some embodiments, R¹ is carbocyclyl. In some embodiments, R¹ is cyclopropyl or cyclobutyl. In some embodiments, R¹ is cyclopropyl or cyclobutyl substituted with 1-3 halo groups (e.g., 1-3 fluoro). In some embodiments, R¹ is difluorocyclopropyl or difluorocyclobutyl.

In some embodiments, each R³ is independently alkyl, halo, cyano, carbocyclyl, heterocyclyl, or —OR$^c$. In some embodiments, R³ is alkyl (e.g., C₁-C₄ alkyl). In some embodiments, R³ is C₁-C₄ alkyl. In some embodiments, R³ is methyl, ethyl, or isopropyl. In some embodiments, R³ is C₁-C₄ alkyl substituted with R⁵ (e.g., alkyl (e.g., methyl), halo (e.g., fluoro), cyano, carbocyclyl, or —OR$^c$ (e.g., —OH or —OCH₃)). In some embodiments, R³ is —CF₃, —C(CH₃)₂OH, —C(CH₃)₂OCH₃, or CH₂OCHF₂. In some embodiments, R³ is —CF₃.

In some embodiments, R³ is halo (e.g., fluoro or chloro).

In some embodiments, R³ is cyano.

In some embodiments, R³ is carbocyclyl. In some embodiments, R³ is unsubstituted carbocyclyl (e.g., unsubstituted cyclopropyl or unsubstituted cyclobutyl) or substituted carbocyclyl (e.g., substituted with cyano or halo).

In some embodiments, R³ is heterocyclyl. In some embodiments, R³ is an oxygen-containing heterocyclyl. In some embodiments, R³ is oxetanyl.

In some embodiments, R³ is —OR$^c$. In some embodiments, R³ is —OR$^c$, wherein R$^c$ is alkyl. In some embodiments, R³ is —OCF₃, —OCH₃, —OCH(CH₃)(CF₃), —OCH₂CH₂, —OCH(CH₃)₂, or —OCH₂CF₃. In some embodiments, R³ is —OR$^c$, wherein R$^c$ is carbocyclyl, e.g., optionally substituted with one or more R⁶. In some embodiments, R³ is carbocyclyl (e.g., cyclopropyl or cyclobutyl) optionally substituted with halo (e.g., fluoro) or cyano.

In another aspect, provided is a compound of Formula (III-2):

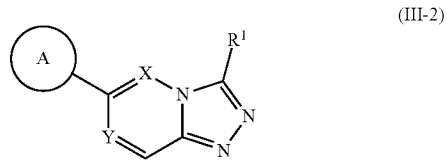

or a pharmaceutically acceptable salt thereof, wherein each one of X and Y is N and the other of X and Y is CR²; A is aryl or heteroaryl (e.g., a monocyclic 6-membered aryl or heteroaryl), optionally substituted by one or more R³; R¹ is hydrogen, C₁ alkyl, haloalkyl, or carbocyclyl, wherein each alkyl and carbocyclyl is optionally substituted by halo, heterocyclyl, or —OR$^c$; R² is hydrogen, alkyl, or halo; each R³ is independently alkyl, halo, cyano, nitro, carbocyclyl, heterocyclyl, —OR$^c$, —N(R$^d$)₂, —C(O)R$^c$, —C(O)OR$^c$, or —C(O)N(R$^d$)₂ wherein the alkyl, carbocyclyl, and heterocyclyl are optionally substituted with halo, cyano, nitro, alkyl, carbocyclyl, heterocyclyl, —OR$^c$, —C(O)N(R$^d$)₂, —SO₂R$^c$, —SO₂OR$^c$, —SO₂N(R$^d$)₂, —NR$^d$C(O)(R$^c$), or —N(R$^d$)₂; each R$^c$ is independently hydrogen or alkyl, wherein each alkyl is optionally substituted with one or more R⁶; each R$^d$ is independently hydrogen or alkyl, and each R⁶ is independently halo, carbocyclyl, or heterocyclyl.

In some embodiments, X is N. In some embodiments, X is N and Y is CR². In some embodiments, R² is hydrogen.

In some embodiments, X is CR². In some embodiments, X is CR² and Y is N. In some embodiments, R² is hydrogen.

In some embodiments, A is aryl (e.g., phenyl). In some embodiments, A is heteroaryl. In some embodiments, A is a 6-membered heteroaryl. In some embodiments, A is a nitrogen-containing heteroaryl (e.g., pyridyl).

In some embodiments, R¹ is hydrogen.

In some embodiments, R¹ is C₁ alkyl, haloalkyl, or carbocyclyl. In some embodiments, R¹ is haloalkyl, e.g., C₁-C₃ haloalkyl. In some embodiments, R¹ is C₁-C₃ haloalkyl, e.g., C₁-C₃ fluoroalkyl. In some embodiments, R¹ is —CF₃, —CHF₂, —CH₂CF₃, or CF₂CF₃. In some embodiments, R¹ is —CF₃.

In some embodiments, R¹ is C₁ alkyl substituted with heterocylyl or —OR$^c$. In some embodiments, R¹ is —CH₂— substituted with heterocylyl or —OR$^c$. In some embodiments, R¹ is —CH₂— substituted with an oxygen-containing heterocylyl or —OH. In some embodiments, R¹ is —CH₂— substituted with tetrahydrofuranyl (e.g., 1-tetrahydrofuranyl or 2-tetrahydrofuranyl), tetrahydropyranyl (e.g., 1-tetrahydropyranyl, 2-tetrahydropyranyl, or 3-tetrahydropyranyl), or —OH.

In some embodiments, R¹ is C₁ alkyl substituted with halo and —OR$^c$. In some embodiments, R¹ is —CF₂(OR$^c$). In some embodiments, R$^c$ is alkyl (e.g., CH₃, or —CH₂— substituted with carbocyclyl (e.g., isopropanyl)). In some embodiments, R¹ is carbocyclyl. In some embodiments, R¹ is cyclopropyl or cyclobutyl. In some embodiments, R¹ is cyclopropyl or cyclobutyl substituted with 1-3 halo groups (e.g., 1-3 fluoro). In some embodiments, R¹ is difluorocyclopropyl or difluorocyclobutyl.

In some embodiments, R³ is heterocyclyl. In some embodiments, R³ is an oxygen-containing heterocyclyl. In some embodiments, R³ is oxetanyl.

In some embodiments, each $R^3$ is independently alkyl, halo, cyano, carbocyclyl, heterocyclyl, or —$OR^c$. In some embodiments, $R^3$ is alkyl (e.g., $C_1$-$C_4$ alkyl). In some embodiments, $R^3$ is $C_1$-$C_4$ alkyl. In some embodiments, $R^3$ is methyl. In some embodiments, $R^3$ is substituted $C_1$ alkyl (e.g., wherein the $C_1$ alkyl is substituted with alkyl (e.g., methyl), halo (e.g., fluoro), cyano, carbocyclyl, or —$OR^c$ (e.g., —$OCH_3$)). In some embodiments, $R^3$ is —$CF_3$.

In some embodiments, $R^3$ is halo (e.g., fluoro or chloro).

In some embodiments, $R^3$ is cyano.

In some embodiments, $R^3$ is carbocyclyl. In some embodiments, $R^3$ is unsubstituted carbocyclyl (e.g., unsubstituted cyclopropyl) or substituted carbocyclyl (e.g., substituted with cyano or halo).

In some embodiments, $R^3$ is heterocyclyl. In some embodiments, $R^3$ is an oxygen-containing heterocyclyl. In some embodiments, $R^3$ is oxetanyl. In some embodiments, $R^3$ is —$OR^c$. In some embodiments, $R^3$ is —$OR^c$, wherein $R^c$ is alkyl. In some embodiments, $R^3$ is —$OCF_3$, —$OCH_3$, —$OCH(CH_3)(CF_3)$, or —$OCH_2CF_3$.

In some embodiments, the compound of Formulas (II) or (III) is not:

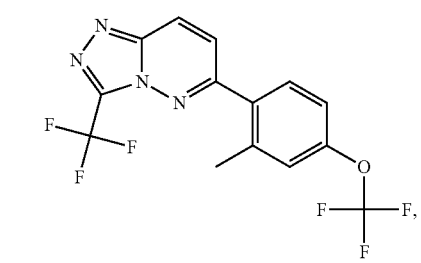

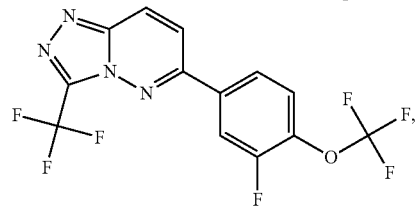

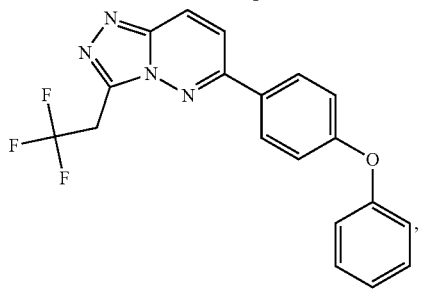

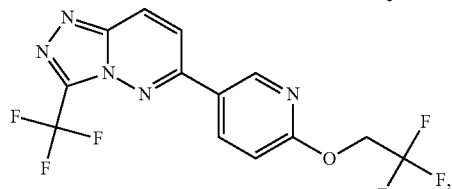

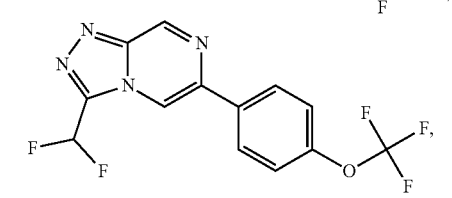

-continued

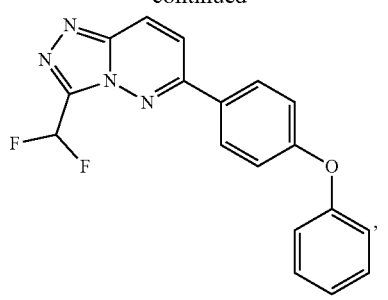

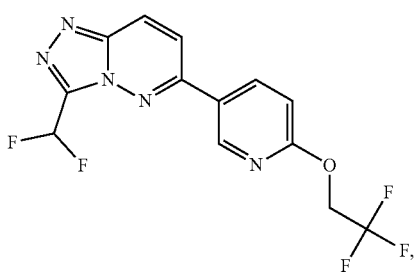

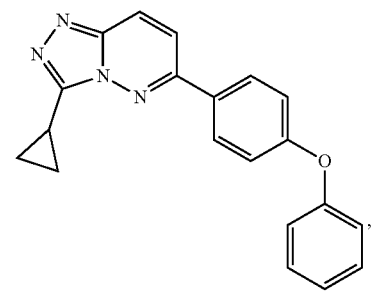

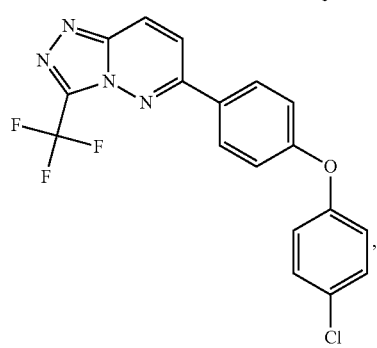

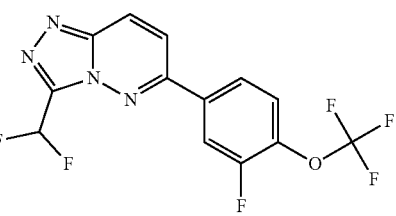

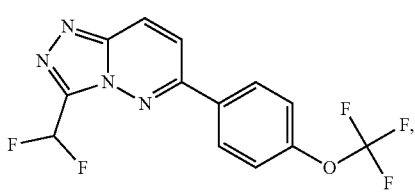

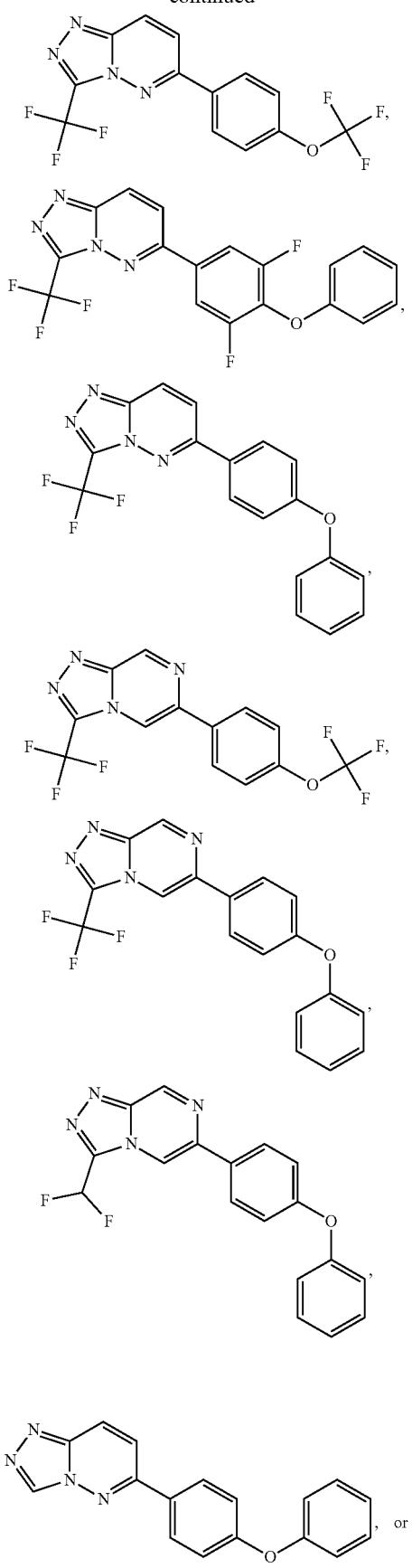

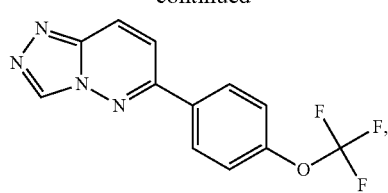

or a pharmaceutically acceptable salt thereof.

In another aspect, provided is a compound of Formula (IV-2):

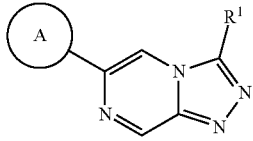

(IV-2)

or a pharmaceutically acceptable salt thereof, wherein A is aryl or heteroaryl (e.g., a monocyclic 6-membered aryl or heteroaryl), optionally substituted by one or more $R^3$; $R^1$ is hydrogen, alkyl, or carbocyclyl, wherein each alkyl and carbocyclyl is optionally substituted by halo, heterocyclyl, or —$OR^c$; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$ wherein the alkyl, carbocyclyl, and heterocyclyl are optionally substituted with halo, cyano, nitro, alkyl, carbocyclyl, heterocyclyl, carbocyclyl, heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$; each $R^c$ is independently hydrogen or alkyl, wherein alkyl is optionally substituted by one or more $R^6$; each $R^d$ is independently hydrogen or alkyl, wherein each alkyl is optionally substituted by one or more $R^6$; and each $R^6$ is independently alkyl, carbocyclyl, heterocyclyl, halo, cyano, nitro, or —OH.

In some embodiments, A is aryl (e.g., phenyl). In some embodiments, A is heteroaryl. In some embodiments, A is a 6-membered heteroaryl. In some embodiments, A is a nitrogen-containing heteroaryl (e.g., pyridyl).

In some embodiments, $R^1$ is haloalkyl, e.g., $C_3$-$C_3$ haloalkyl. In some embodiments, $R^1$ is $C_1$-$C_3$ haloalkyl, e.g., $C_3$-$C_3$ fluoroalkyl. In some embodiments, $R^1$ is —$CHF_2$.

In some embodiments, each $R^3$ is independently alkyl, halo, or —$OR^c$. In some embodiments, $R^3$ is alkyl (e.g., $C_1$-$C_4$ alkyl). In some embodiments, $R^3$ is $C_1$-$C_4$ alkyl. In some embodiments, $R^3$ is methyl or isopropanyl. In some embodiments, $R^3$ is substituted $C_1$-$C_4$ alkyl (e.g., wherein the $C_1$-$C_4$ alkyl is substituted with —$OR^c$ (e.g., —$OCH_3$)). In some embodiments, $R^3$ is halo (e.g., fluoro or chloro).

In some embodiments, $R^3$ is halo (e.g., fluoro).

In some embodiments, $R^3$ is —$OR^c$. In some embodiments, $R^3$ is —$OR^c$, wherein $R^c$ is alkyl. In some embodiments, $R^3$ is —$OCF_3$, —$OCH_3$, or —$OCH_2CF_3$. In some embodiments, $R^3$ is —$OCF_3$.

In some embodiments, the compound of Formula (IV) is not:

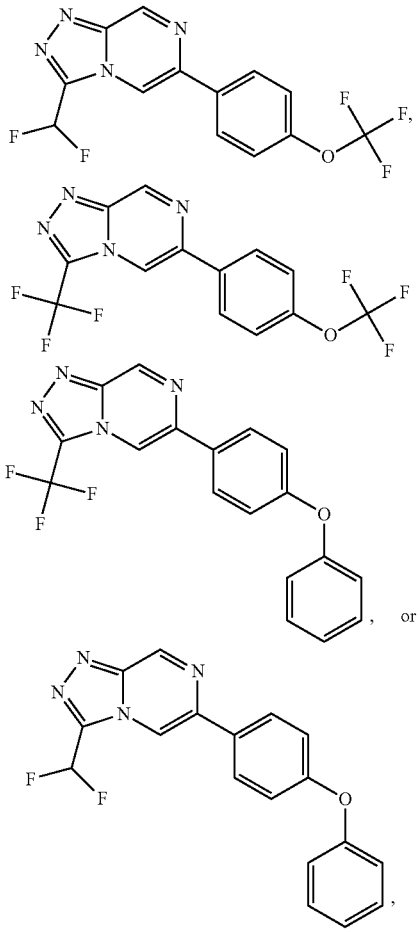

or a pharmaceutically acceptable salt thereof.

In another aspect, provided is a compound of Formula (V-2):

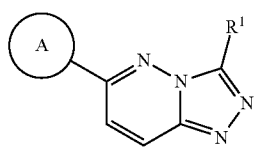

(V-2)

or a pharmaceutically acceptable salt thereof, wherein A is aryl or heteroaryl (e.g., a monocyclic 6-membered aryl or heteroaryl), optionally substituted by one or more $R^3$; $R^1$ is hydrogen, $C_1$ alkyl, haloalkyl, or carbocyclyl, wherein each alkyl and carbocyclyl is optionally substituted by halo, heterocyclyl, or —$OR^c$; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$, wherein the alkyl, carbocyclyl, and heterocyclyl are optionally substituted with halo, cyano, nitro, alkyl, carbocyclyl, heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$; each $R^c$ is hydrogen or alkyl, wherein alkyl is optionally substituted by one or more $R^6$; each $R^d$ is independently hydrogen or alkyl, wherein each alkyl is optionally substituted by one or more $R^6$; and each $R^6$ is independently alkyl, carbocyclyl, heterocyclyl, halo, cyano, nitro, or —OH.

In some embodiments, A is aryl (e.g., phenyl). In some embodiments, A is heteroaryl. In some embodiments, A is a 6-membered heteroaryl. In some embodiments, A is a nitrogen-containing heteroaryl (e.g., pyridyl).

In some embodiments, $R^1$ is $C_1$ alkyl, haloalkyl, or carbocyclyl. In some embodiments, $R^1$ is haloalkyl, e.g., $C_1$-$C_3$ haloalkyl. In some embodiments, $R^1$ is $C_1$-$C_3$ haloalkyl, e.g., $C_1$-$C_3$ fluoroalkyl. In some embodiments, $R^1$ is —$CF_3$, —$CHF_2$, —$CH_2CF_3$, or $CF_2CF_3$. In some embodiments, $R^1$ is —$CF_3$.

In some embodiments, $R^1$ is $C_1$ alkyl, wherein alkyl is substituted with heterocylyl or —$OR^c$. In some embodiments, $R^1$ is —$CH_2$— substituted with heterocylyl or —$OR^c$. In some embodiments, $R^1$ is —$CH_2$— substituted with an oxygen-containing heterocylyl or —OH. In some embodiments, $R^1$ is —$CH_2$— substituted with tetrahydrofuranyl (e.g., 1-tetrahydrofuranyl or 2-tetrahydrofuranyl) or —OH.

In some embodiments, $R^1$ is carbocyclyl. In some embodiments, $R^1$ is cyclopropyl or cyclobutyl. In some embodiments, $R^1$ is cyclopropyl or cyclobutyl, e.g., substituted cyclopropyl or substituted cyclobutyl. In some embodiments, $R^1$ is cyclopropyl or cyclobutyl substituted with 1-3 halo groups (e.g., 1-3 fluoro). In some embodiments, $R^1$ is difluorocyclopropyl or difluorocyclobutyl.

In some embodiments, each $R^3$ is independently alkyl, halo, cyano, carbocyclyl, heterocyclyl, or —$OR^c$. In some embodiments, $R^3$ is alkyl (e.g., $C_1$-$C_4$ alkyl). In some embodiments, $R^3$ is $C_1$-$C_4$ alkyl. In some embodiments, $R^3$ is methyl. In some embodiments, $R^3$ is substituted $C_1$ alkyl (e.g., wherein the $C_1$ alkyl is substituted with alkyl (e.g., methyl), halo (e.g., fluoro), cyano, carbocyclyl, or —$OR^c$ (e.g., —$OCH_3$)). In some embodiments, $R^3$ is —$CF_3$.

In some embodiments, $R^3$ is halo (e.g., fluoro). In some embodiments, $R^3$ is cyano.

In some embodiments, $R^3$ is carbocyclyl. In some embodiments, $R^3$ is unsubstituted carbocyclyl (e.g., unsubstituted cyclopropyl) or substituted carbocyclyl (e.g., substituted with cyano or halo).

In some embodiments, $R^3$ is —$OR^c$. In some embodiments, $R^3$ is —$OR^c$, wherein $R^c$ is alkyl (e.g., substituted alkyl or unsubstituted alkyl). In some embodiments, $R^3$ is —$OCF_3$, —$OCH_3$, —$OCH(CH_3)(CF_3)$, or —$OCH_2CF_3$.

In some embodiments, the compound of Formula (V) is not:

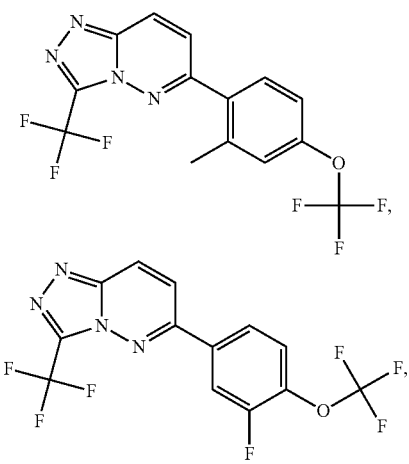

-continued
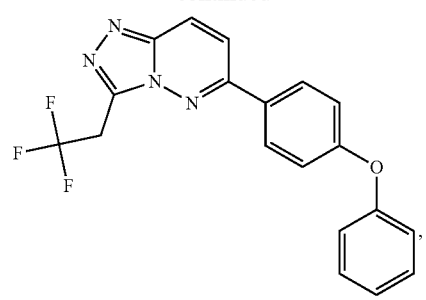
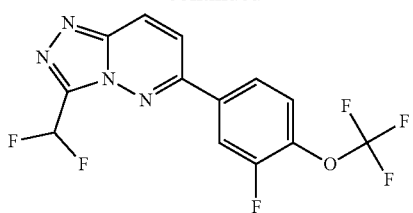
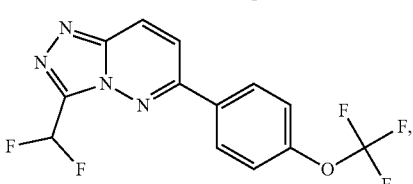
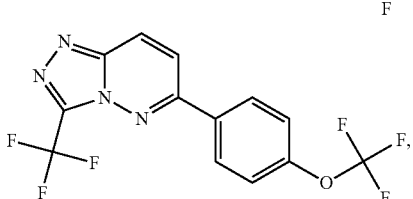
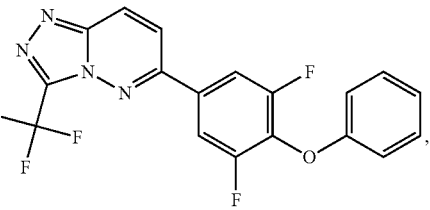
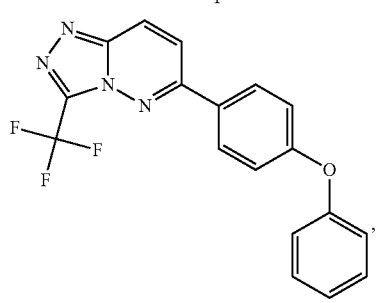
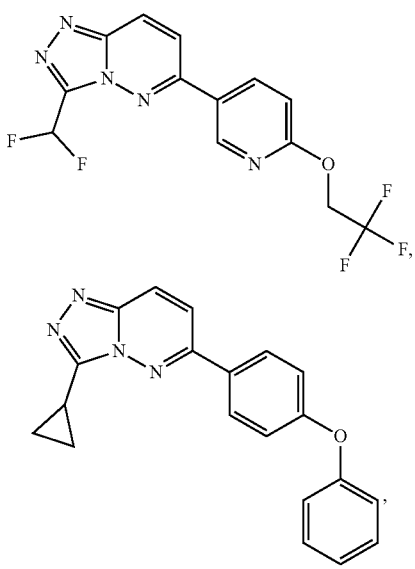
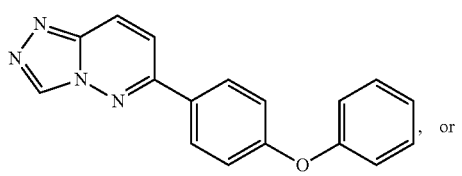, or
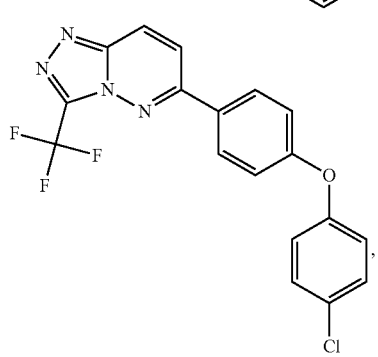
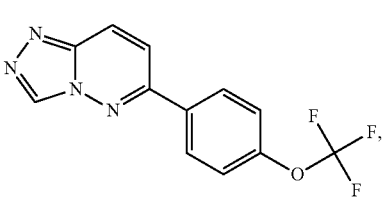
or a pharmaceutically acceptable salt thereof.

In another aspect, provided is a compound of Formula (V-3):

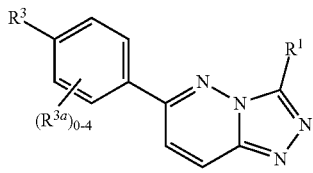

(V-3)

or a pharmaceutically acceptable salt thereof, wherein $R^1$ is hydrogen, $C_1$ alkyl, haloalkyl, or carbocyclyl, wherein each alkyl and carbocyclyl is optionally substituted by halo, heterocyclyl, or —$OR^c$; $R^3$ is alkyl, carbocyclyl, or —$OR^c$; each $R^{3a}$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$ wherein the alkyl, carbocyclyl, and heterocyclyl are optionally substituted with halo, cyano, nitro, alkyl, carbocyclyl, heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$; each $R^c$ is hydrogen or alkyl, wherein alkyl is optionally substituted by one or more $R^6$; each $R^d$ is independently hydrogen or alkyl, wherein each alkyl is optionally substituted by one or more $R^6$; and each $R^6$ is independently alkyl, carbocyclyl, heterocyclyl, halo, cyano, nitro, or —OH.

In some embodiments, $R^1$ is $C_1$ alkyl, haloalkyl, or carbocyclyl. In some embodiments, $R^1$ is haloalkyl, e.g., $C_1$-$C_3$ haloalkyl. In some embodiments, $R^1$ is $C_1$-$C_3$ haloalkyl, e.g., $C_1$-$C_3$ fluoroalkyl. In some embodiments, $R^1$ is —$CF_3$, —$CHF_2$, —$CH_2CF_3$, or $CF_2CF_3$. In some embodiments, $R^1$ is —$CF_3$.

In some embodiments, $R^1$ is $C_1$ alkyl, wherein alkyl is substituted with heterocylyl or —$OR^c$. In some embodiments, $R^1$ is —$CH_2$— substituted with heterocylyl or —$OR^c$. In some embodiments, $R^1$ is —$CH_2$— substituted with an oxygen-containing heterocylyl or —OH. In some embodiments, $R^1$ is —$CH_2$— substituted with tetrahydrofuranyl (e.g., 1-tetrahydrofuranyl or 2-tetrahydrofuranyl) or —OH.

In some embodiments, $R^1$ is carbocyclyl. In some embodiments, $R^1$ is cyclopropyl or cyclobutyl. In some embodiments, $R^1$ is cyclopropyl or cyclobutyl, e.g., substituted cyclopropyl or substituted cyclobutyl. In some embodiments, $R^1$ is cyclopropyl or cyclobutyl substituted with 1-3 halo groups (e.g., 1-3 fluoro). In some embodiments, $R^1$ is difluorocyclopropyl or difluorocyclobutyl.

In some embodiments, $R^3$ is independently alkyl, carbocyclyl, or —$OR^c$. In some embodiments, $R^3$ is alkyl (e.g., $C_1$-$C_4$ alkyl). In some embodiments, $R^3$ is unsubstituted alkyl (e.g., unsubstituted $C_1$-$C_4$ alkyl) or substituted alkyl (e.g., substituted $C_1$-$C_4$ alkyl). In some embodiments, $R^3$ is substituted $C_1$ alkyl (e.g., wherein the $C_1$ alkyl is substituted with alkyl (e.g., methyl), halo (e.g., fluoro), cyano, carbocyclyl, or —$OR^c$ (e.g., —$OCH_3$)). In some embodiments, $R^3$ is —$CF_3$.

In some embodiments, $R^3$ is —$OR^c$. In some embodiments, $R^3$ is —$OR^c$, wherein $R^c$ is alkyl (e.g., substituted alkyl or unsubstituted alkyl). In some embodiments, $R^3$ is —$OCF_3$, —$OCH_3$, —$OCH(CH_3)(CF_3)$, or —$OCH_2CF_3$.

In some embodiments, each $R^{3a}$ is independently alkyl, halo, cyano, carbocyclyl, heterocyclyl, or —$OR^c$. In some embodiments, $R^{3a}$ is alkyl (e.g., $C_1$-$C_4$ alkyl). In some embodiments, $R^{3a}$ is unsubstituted alkyl (e.g., unsubstituted $C_1$-$C_4$ alkyl) or substituted alkyl (e.g., substituted $C_1$-$C_4$ alkyl).

In some embodiments, $R^{3a}$ is halo (e.g., fluoro). In some embodiments, $R^{3a}$ is cyano.

In some embodiments, $R^{3a}$ is carbocyclyl. In some embodiments, $R^{3a}$ is unsubstituted carbocyclyl (e.g., unsubstituted cyclopropyl) or substituted carbocyclyl (e.g., substituted with cyano or halo).

In some embodiments, the compound of Formula (V-a) is not:

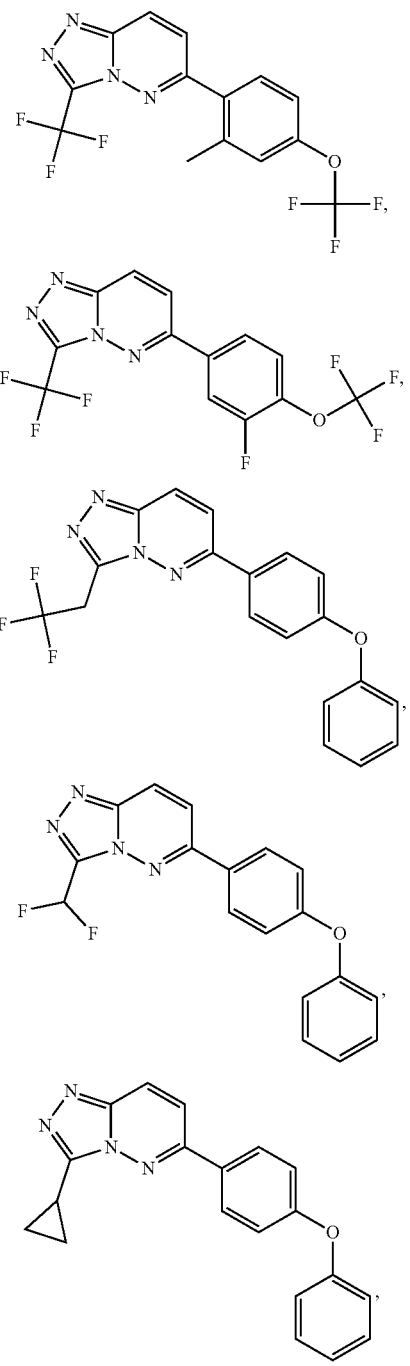

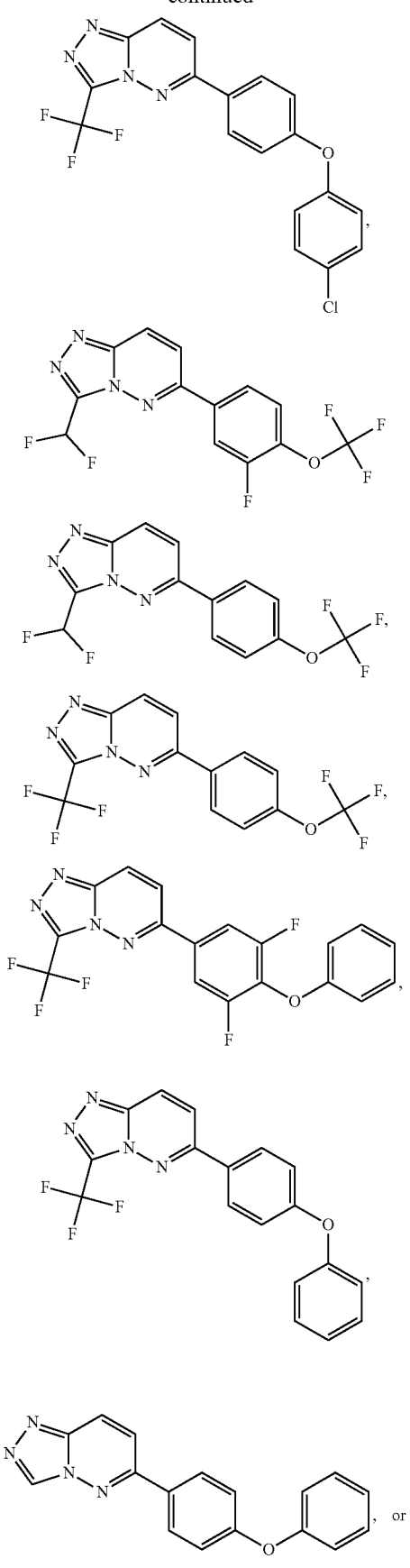

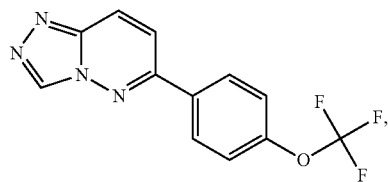

or a pharmaceutically acceptable salt thereof.

In another aspect, provided is a compound of Formula (V-4):

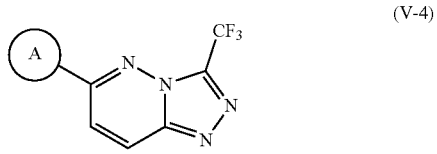

(V-4)

or a pharmaceutically acceptable salt thereof, wherein A is aryl or heteroaryl (e.g., a monocyclic 6-membered aryl or heteroaryl), optionally substituted by one or more $R^3$; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$ wherein the alkyl, carbocyclyl, and heterocyclyl are optionally substituted with halo, cyano, nitro, alkyl, carbocyclyl, heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$; each $R^c$ is hydrogen or alkyl, wherein alkyl is optionally substituted by one or more $R^6$; each $R^d$ is independently hydrogen or alkyl, wherein each alkyl is optionally substituted by one or more $R^6$; and each $R^6$ is independently alkyl, carbocyclyl, heterocyclyl, halo, cyano, nitro, or —OH.

In some embodiments, A is aryl (e.g., phenyl). In some embodiments, A is heteroaryl. In some embodiments, A is a 6-membered heteroaryl. In some embodiments, A is a nitrogen-containing heteroaryl (e.g., pyridyl).

In some embodiments, each $R^3$ is independently alkyl, halo, cyano, carbocyclyl, heterocyclyl, or —$OR^c$. In some embodiments, $R^3$ is alkyl (e.g., $C_1$-$C_4$ alkyl). In some embodiments, $R^3$ is unsubstituted alkyl (e.g., unsubstituted $C_1$-$C_4$ alkyl) or substituted alkyl (e.g., substituted $C_1$-$C_4$ alkyl). In some embodiments, $R^3$ is methyl. In some embodiments, $R^3$ is substituted $C_1$ alkyl (e.g., wherein the $C_1$ alkyl is substituted with alkyl (e.g., methyl), halo (e.g., fluoro), cyano, carbocyclyl, or —$OR^c$ (e.g., —$OCH_3$)). In some embodiments, $R^3$ is —$CF_3$.

In some embodiments, $R^3$ is halo (e.g., fluoro). In some embodiments, $R^3$ is cyano.

In some embodiments, $R^3$ is carbocyclyl. In some embodiments, $R^3$ is unsubstituted carbocyclyl (e.g., unsubstituted cyclopropyl) or substituted carbocyclyl (e.g., substituted with cyano or halo).

In some embodiments, $R^3$ is —$OR^c$. In some embodiments, $R^3$ is —$OR^c$, wherein $R^c$ is alkyl (e.g., substituted alkyl or unsubstituted alkyl). In some embodiments, $R^3$ is —$OCF_3$, —$OCH_3$, —$OCH(CH_3)(CF_3)$, or —$OCH_2CF_3$.

In some embodiments, the compound of Formula (V-b) is not:

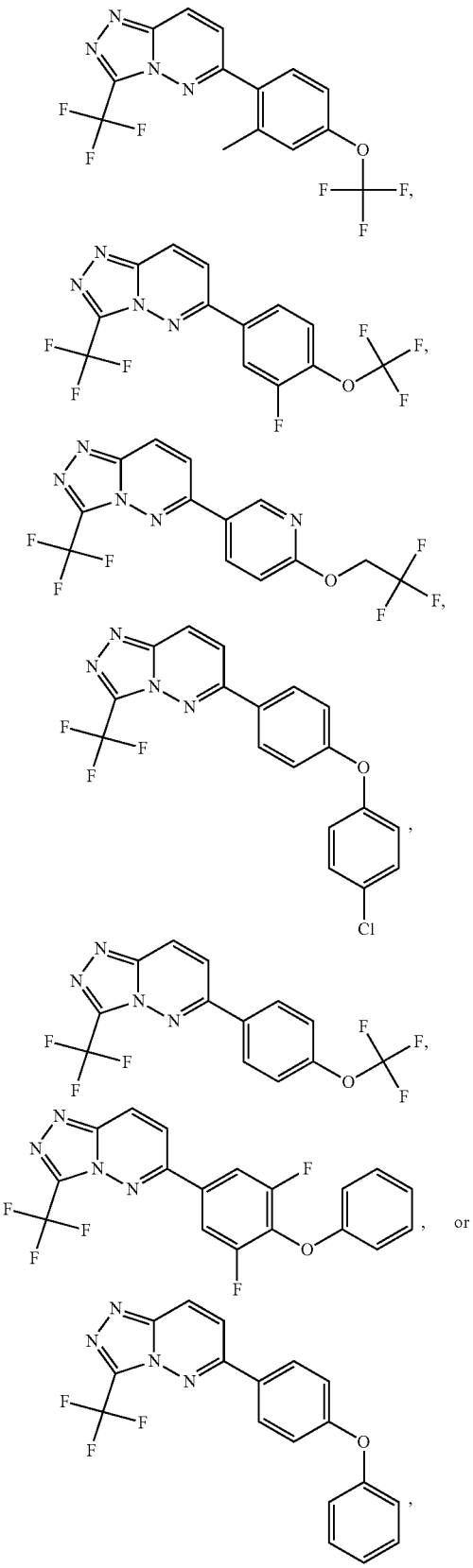

or a pharmaceutically acceptable salt thereof.

In another aspect, provided is a compound of Formula (VI-2):

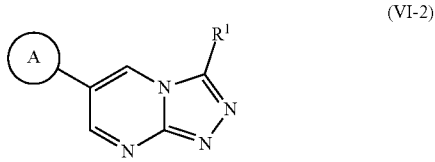

(VI-2)

or a pharmaceutically acceptable salt thereof, wherein A is aryl or heteroaryl (e.g., a monocyclic 6-membered aryl or heteroaryl), optionally substituted by one or more $R^3$; $R^1$ is hydrogen, $C_1$ alkyl, haloalkyl, or carbocyclyl, wherein each alkyl and carbocyclyl is optionally substituted by halo, heterocyclyl, or —$OR^c$; each $R^3$ is independently alkyl, halo, cyano, nitro, carbocyclyl, heterocyclyl, —$OR^c$, —$N(R^d)_2$, —$C(O)R^c$, —$C(O)OR^c$, or —$C(O)N(R^d)_2$ wherein the alkyl, carbocyclyl, and heterocyclyl are optionally substituted with halo, cyano, nitro, alkyl, carbocyclyl, heterocyclyl, —$OR^c$, —$C(O)N(R^d)_2$, —$SO_2R^c$, —$SO_2OR^c$, —$SO_2N(R^d)_2$, —$NR^dC(O)(R^c)$, or —$N(R^d)_2$; each $R^c$ is hydrogen or alkyl, wherein alkyl is optionally substituted by one or more $R^6$; each $R^d$ is independently hydrogen or alkyl, wherein each alkyl is optionally substituted by one or more $R^6$; and each $R^6$ is independently alkyl, carbocyclyl, heterocyclyl, halo, cyano, nitro, or —OH.

In some embodiments, A is aryl (e.g., phenyl).
In some embodiments, $R^1$ is hydrogen or haloalkyl.
In some embodiments, $R^1$ is hydrogen.
In some embodiments, $R^1$ is haloalkyl, e.g., $C_1$-$C_3$ haloalkyl. In some embodiments, $R^1$ is $C_1$-$C_3$ haloalkyl, e.g., $C_1$-$C_3$ fluoroalkyl. In some embodiments, $R^1$ is —$CF_3$.
In some embodiments, each $R^3$ is independently —$OR^c$. In some embodiments, $R^3$ is —$OR^c$, wherein $R^c$ is alkyl (e.g., substituted alkyl or unsubstituted alkyl). In some embodiments, $R^3$ is —$OCF_3$.

In any and all aspects, in some embodiments, the compound of Formulas (II), (III), (IV), (V), (V-a), (V-b), and (VI) is selected from:

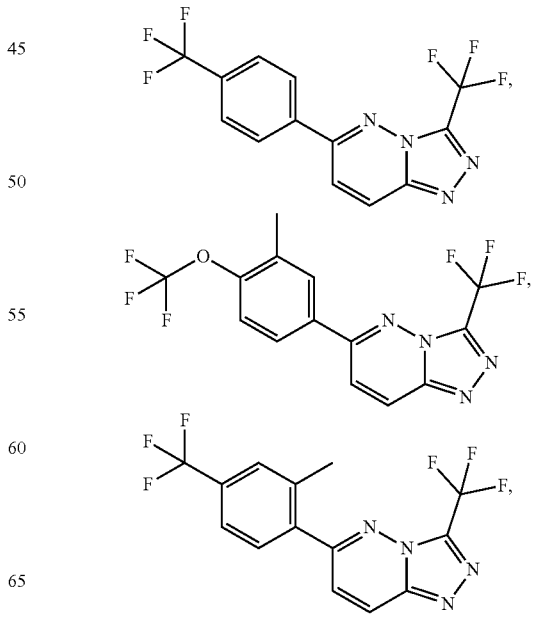

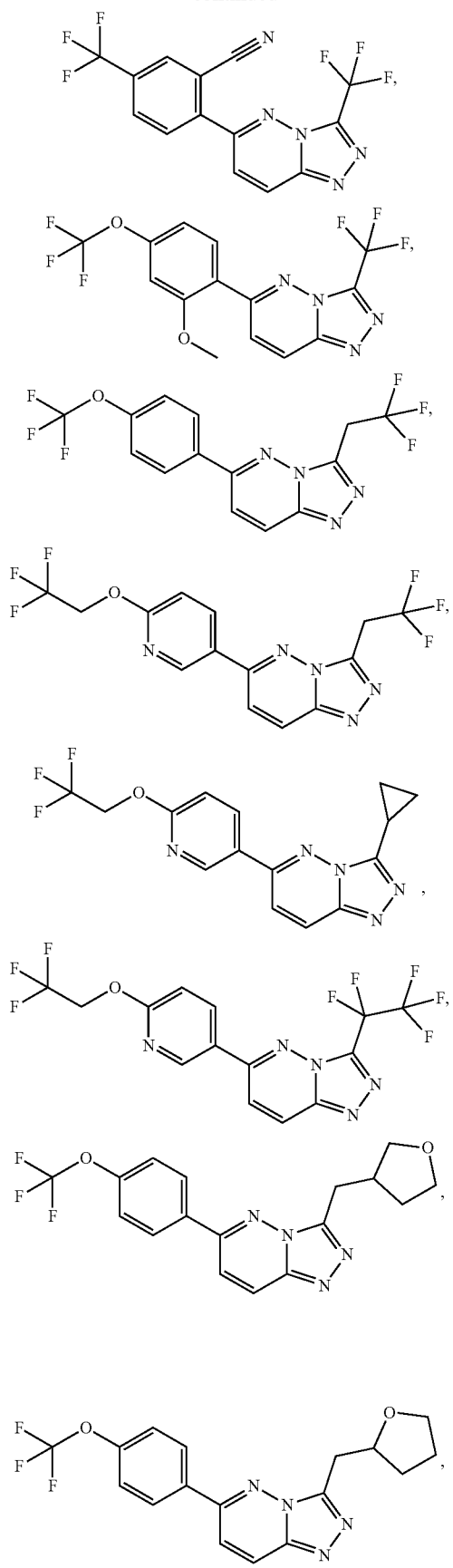
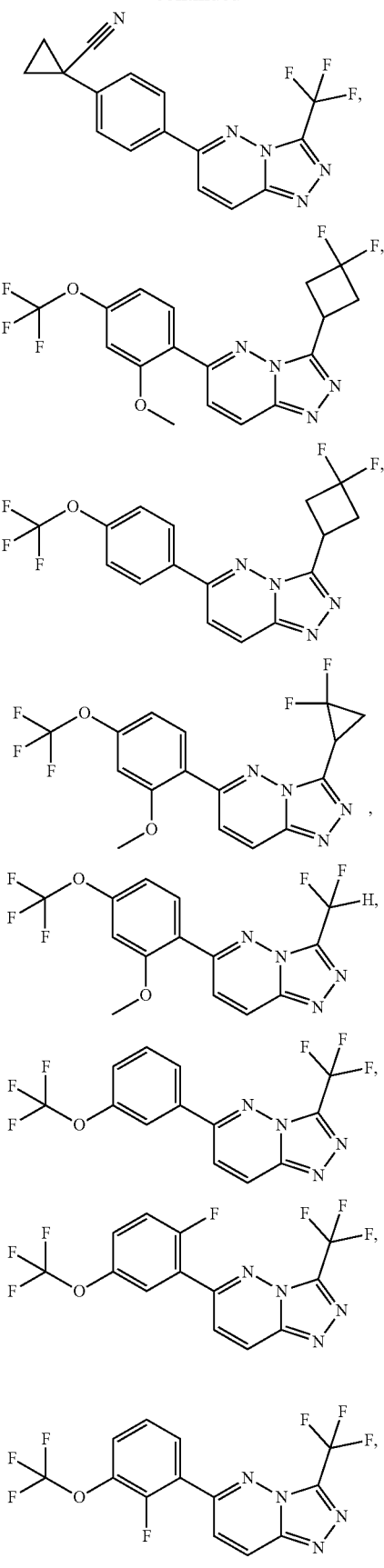

-continued
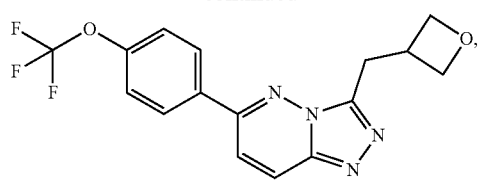
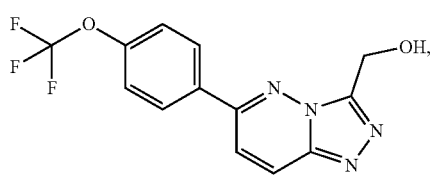
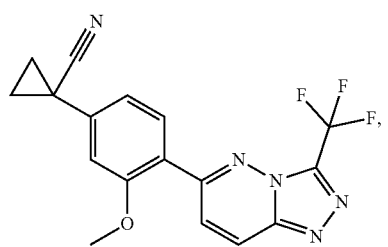
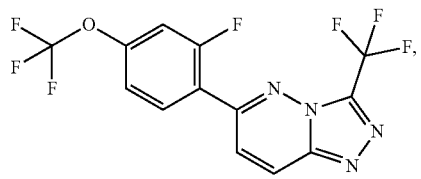
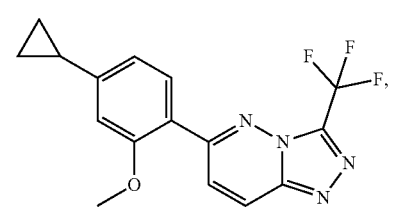
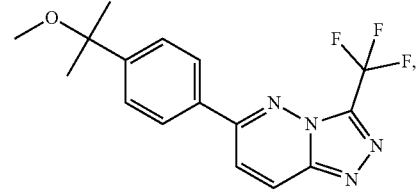
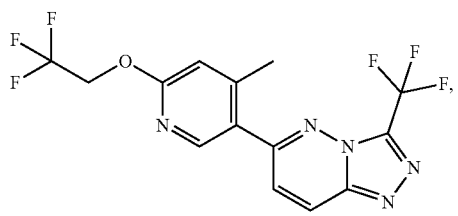
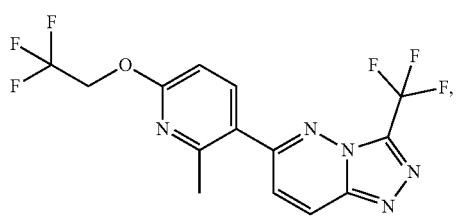
-continued
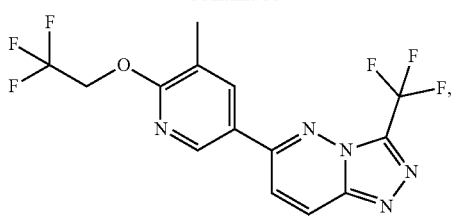
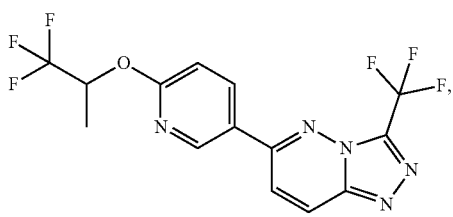
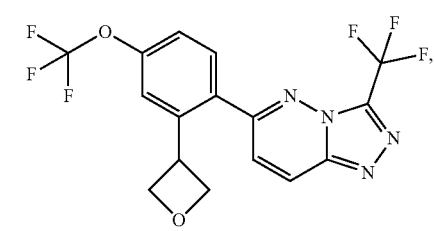
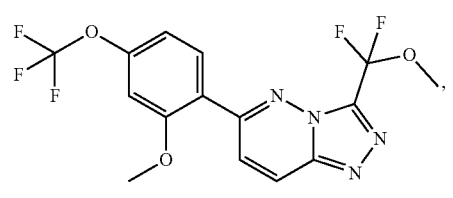
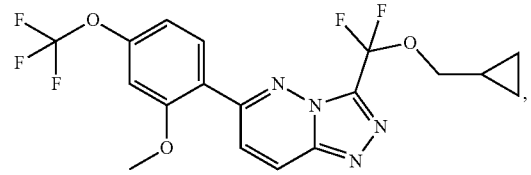
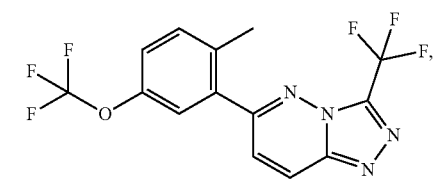
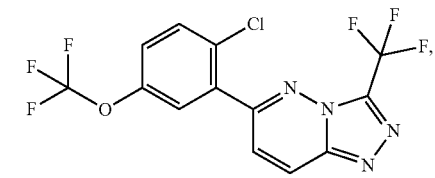
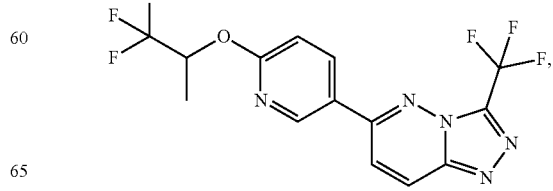

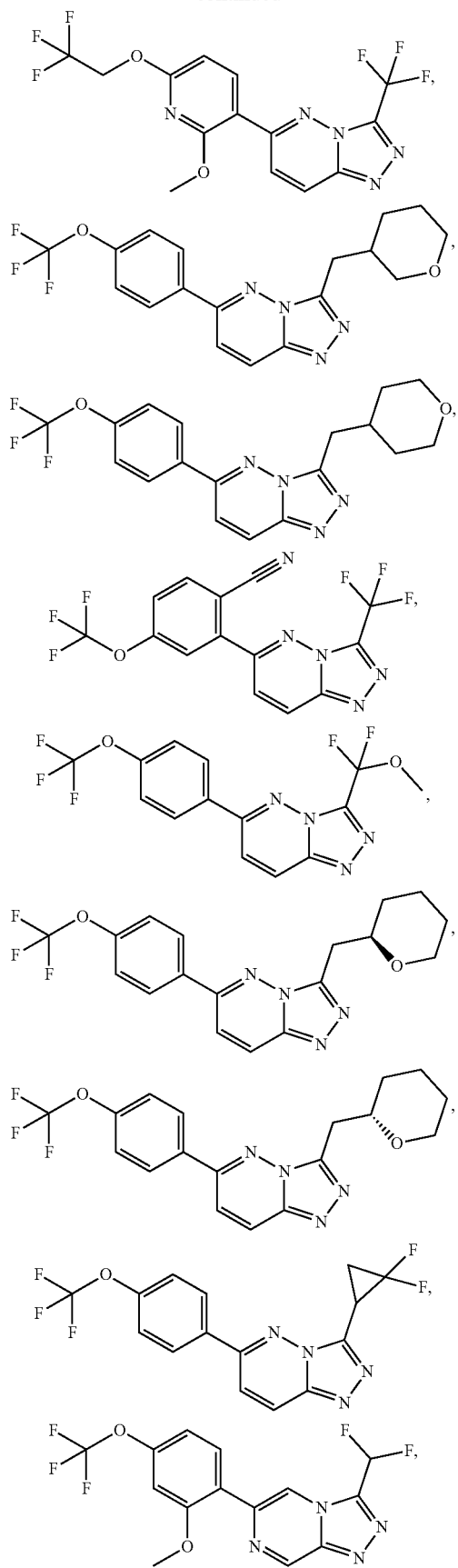
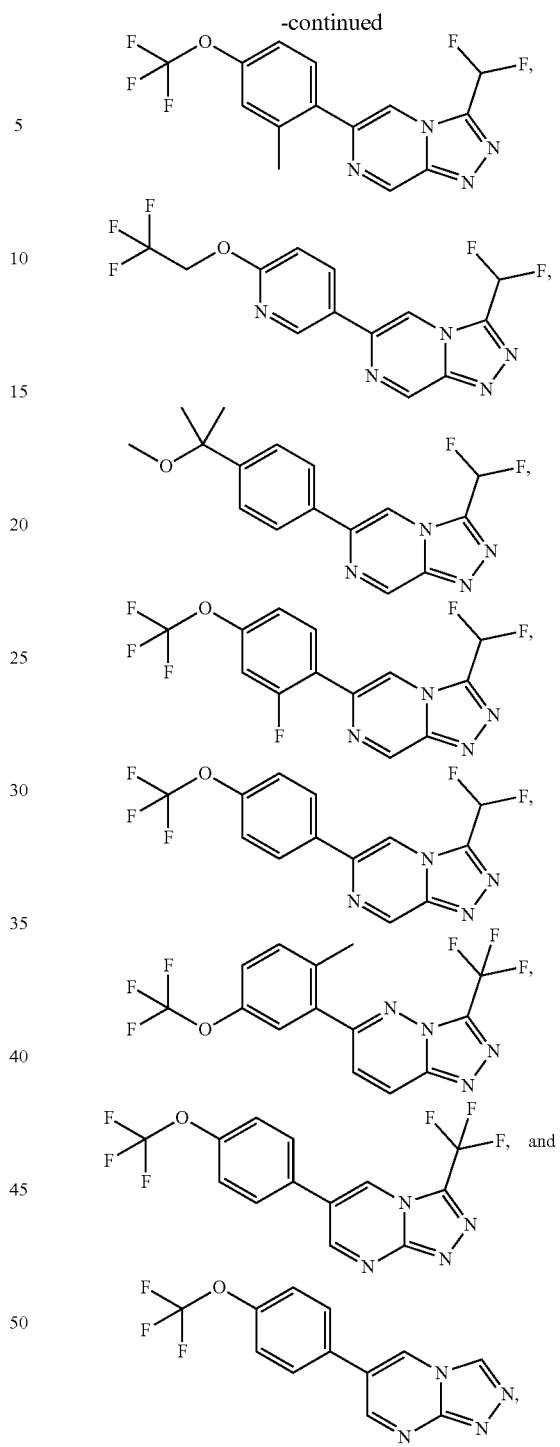

or a pharmaceutically acceptable salt thereof.

Methods of Treatment

Described herein are compounds and compositions thereof and their use to treat a disease, disorder, or condition relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. Compounds of the invention may also modulate all sodium ion channels, or may be specific to only one or a plurality of sodium ion channels, e.g., Nay 1.1, 1.2, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I); such as a compound of Formula (I) named herein.

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and actually turn blue. The return to consciousness is gradual and the person maybe confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) prior to administration of a compound described herein (e.g., a compound of Formula (I)).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound of Formula (I):

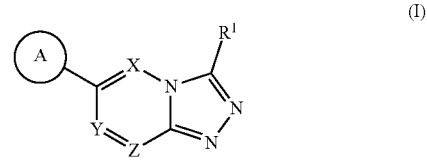

or a pharmaceutically acceptable salt thereof, wherein each of X, Y, and Z is independently N or $CR^2$, wherein at least one of X, Y, and Z is independently N; A is aryl or heteroaryl (e.g., monocyclic 6-membered aryl or heteroaryl), each of which is optionally substituted by one or more $R^3$; $R^2$ is hydrogen, alkyl, or halo; $R^1$ is hydrogen, alkyl, alkenyl, alkynyl, —$OR^b$, carbocyclyl, heterocyclyl, aryl, heteroaryl, wherein alkyl, alkenyl, alkynyl, carbocyclyl, heterocyclyl, aryl, and heteroaryl are optionally substituted with one or more $R^4$; each $R^3$ is independently alkyl, carbocyclyl, heterocyclyl, halo, cyano, nitro, —$OR^c$, —$N(R^d)_2$, —$C(O)R^c$, —$C(O)OR^c$, or —$C(O)N(R^d)_2$ wherein alkyl, carbocyclyl, and heterocyclyl are optionally substituted with one or more $R^5$; each of $R^4$ and $R^5$ is independently alkyl, carbocyclyl, heterocyclyl, aryl, heteroaryl, halo, cyano, nitro, —$OR^c$, —C(O)N(R$^d$)$_2$, —SO$_2$R$^c$, —SO$_2$OR$^c$, —SO$_2$N(R$^d$)$_2$, —NR$^d$C(O)(R$^c$), or —N(R$^d$)$_2$, wherein alkyl, carbocyclyl, heterocyclyl, aryl, and heteroaryl are optionally substituted by one or more R$^7$; each R$^b$ is hydrogen; each R$^c$ is independently hydrogen, alkyl, carbocyclyl, heterocyclyl, aryl, or heteroaryl, wherein alkyl, aryl, and heteroaryl is optionally substituted by one or more R$^6$; each R$^d$ is independently hydrogen or alkyl, wherein each alkyl is optionally substituted by one or more R$^6$; each R$^6$ is independently alkyl, carbocyclyl, heterocyclyl, halo, cyano, nitro, or —OH; and each R$^7$ is independently alkyl, halo, or oxo.

A compound of the present invention (e.g., a compound of Formula (I)) may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula (I)).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula (I)).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound of Formula (I):

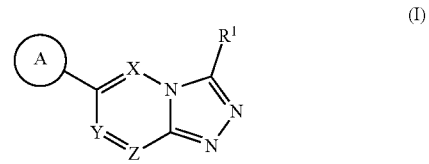

or a pharmaceutically acceptable salt thereof, wherein each of X, Y, and Z is independently N or CR$^2$, wherein at least one of X, Y, and Z is independently N; A is aryl or heteroaryl (e.g., monocyclic 6-membered aryl or heteroaryl), each of which is optionally substituted by one or more R$^3$; R$^2$ is hydrogen, alkyl, or halo; R$^1$ is hydrogen, alkyl, alkenyl, alkynyl, —OR$^b$, carbocyclyl, heterocyclyl, aryl, heteroaryl, wherein alkyl, alkenyl, alkynyl, carbocyclyl, heterocyclyl, aryl, and heteroaryl are optionally substituted with one or more R$^4$; each R$^3$ is independently alkyl, carbocyclyl, heterocyclyl, halo, cyano, nitro, —OR$^c$, —N(R$^d$)$_2$, —C(O)R$^c$, —C(O)OR$^c$, or —C(O)N(R$^d$)$_2$ wherein alkyl, carbocyclyl, and heterocyclyl are optionally substituted with one or more R$^5$; each of R$^4$ and R$^5$ is independently alkyl, carbocyclyl, heterocyclyl, aryl, heteroaryl, halo, cyano, nitro, —OR$^c$, —C(O)N(R$^d$)$_2$, —SO$_2$R$^c$, —SO$_2$OR$^c$, —SO$_2$N(R$^d$)$_2$, —NR$^d$C(O)(R$^c$), or —N(R$^d$)$_2$, wherein alkyl, carbocyclyl, heterocyclyl, aryl, and heteroaryl are optionally substituted by one or more R$^7$; each R$^b$ is hydrogen; each R$^c$ is independently hydrogen, alkyl, carbocyclyl, heterocyclyl, aryl, or heteroaryl, wherein alkyl, aryl, and heteroaryl is optionally substituted by one or more R$^6$; each R$^d$ is independently hydrogen or alkyl, wherein each alkyl is optionally substituted by one or more R$^6$; each R$^6$ is independently alkyl, carbocyclyl, heterocyclyl, halo, cyano, nitro, or —OH; and each R$^7$ is independently alkyl, halo, or oxo.

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) prior to administration of a compound described herein (e.g., a compound of Formula (I)).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) comprising administering to a subject in need thereof a compound of Formula (I):

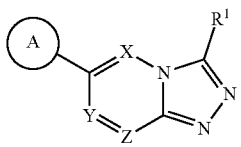

(I)

or a pharmaceutically acceptable salt thereof, wherein each of X, Y, and Z is independently N or CR², wherein at least one of X, Y, and Z is independently N; A is aryl or heteroaryl (e.g., monocyclic 6-membered aryl or heteroaryl), each of which is optionally substituted by one or more R³; R² is hydrogen, alkyl, or halo; R¹ is hydrogen, alkyl, alkenyl, alkynyl, —OR$^b$, carbocyclyl, heterocyclyl, aryl, heteroaryl, wherein alkyl, alkenyl, alkynyl, carbocyclyl, heterocyclyl, aryl, and heteroaryl are optionally substituted with one or more R⁴; each R³ is independently alkyl, carbocyclyl, heterocyclyl, halo, cyano, nitro, —OR$^c$, —N(R$^d$)₂, —C(O)R$^c$, —C(O)OR$^c$, or —C(O)N(R$^d$)₂ wherein alkyl, carbocyclyl, and heterocyclyl are optionally substituted with one or more R⁵; each of R⁴ and R⁵ is independently alkyl, carbocyclyl, heterocyclyl, aryl, heteroaryl, halo, cyano, nitro, —OR$^c$, —C(O)N(R$^d$)₂, —SO₂R$^c$, —SO₂OR$^c$, —SO₂N(R$^d$)₂, —NR$^d$C(O)(R$^c$), or —N(R$^d$)₂, wherein alkyl, carbocyclyl, heterocyclyl, aryl, and heteroaryl are optionally substituted by one or more R⁷; each R$^b$ is hydrogen; each R$^c$ is independently hydrogen, alkyl, carbocyclyl, heterocyclyl, aryl, or heteroaryl, wherein alkyl, aryl, and heteroaryl is optionally substituted by one or more R⁶; each R$^d$ is independently hydrogen or alkyl, wherein each alkyl is optionally substituted by one or more R⁶; each R⁶ is independently alkyl, carbocyclyl, heterocyclyl, halo, cyano, nitro, or —OH; and each R⁷ is independently alkyl, halo, or oxo.

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula (I)).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound of Formula (I):

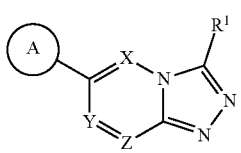

(I)

or a pharmaceutically acceptable salt thereof, wherein each of X, Y, and Z is independently N or CR², wherein at least one of X, Y, and Z is independently N; A is aryl or heteroaryl (e.g., monocyclic 6-membered aryl or heteroaryl), each of which is optionally substituted by one or more R³; R² is hydrogen, alkyl, or halo; R¹ is hydrogen, alkyl, alkenyl, alkynyl, —OR$^b$, carbocyclyl, heterocyclyl, aryl, heteroaryl, wherein alkyl, alkenyl, alkynyl, carbocyclyl, heterocyclyl, aryl, and heteroaryl are optionally substituted with one or more R⁴; each R³ is independently alkyl, carbocyclyl, heterocyclyl, halo, cyano, nitro, —OR$^c$, —N(R$^d$)₂, —C(O)R$^c$, —C(O)OR$^c$, or —C(O)N(R$^d$)₂ wherein alkyl, carbocyclyl, and heterocyclyl are optionally substituted with one or more R⁵; each of R⁴ and R⁵ is independently alkyl, carbocyclyl, heterocyclyl, aryl, heteroaryl, halo, cyano, nitro, —OR$^c$, —C(O)N(R$^d$)₂, —SO₂R$^c$, —SO₂OR$^c$, —SO₂N(R$^d$)₂, —NR$^d$C(O)(R$^c$), or —N(R$^d$)₂, wherein alkyl, carbocyclyl, heterocyclyl, aryl, and heteroaryl are optionally substituted by one or more R⁷; each R$^b$ is hydrogen; each R$^c$ is independently hydrogen, alkyl, carbocyclyl, heterocyclyl, aryl, or heteroaryl, wherein alkyl, aryl, and heteroaryl is optionally substituted by one or more R⁶; each R$^d$ is independently hydrogen or alkyl, wherein each alkyl is optionally substituted by one or more R⁶; each R⁶ is independently alkyl, carbocyclyl, heterocyclyl, halo, cyano, nitro, or —OH; and each R⁷ is independently alkyl, halo, or oxo.

Other Disorders

In some embodiments, a compound of the present invention (e.g., a compound of Formula (I)) may have appropriate pharmacokinetic properties such that they may active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy.

In any and all aspects, in some embodiments, the compound of Formula (I) is selected from:

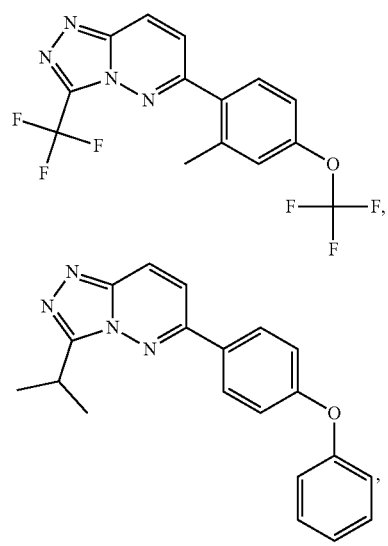

121
-continued
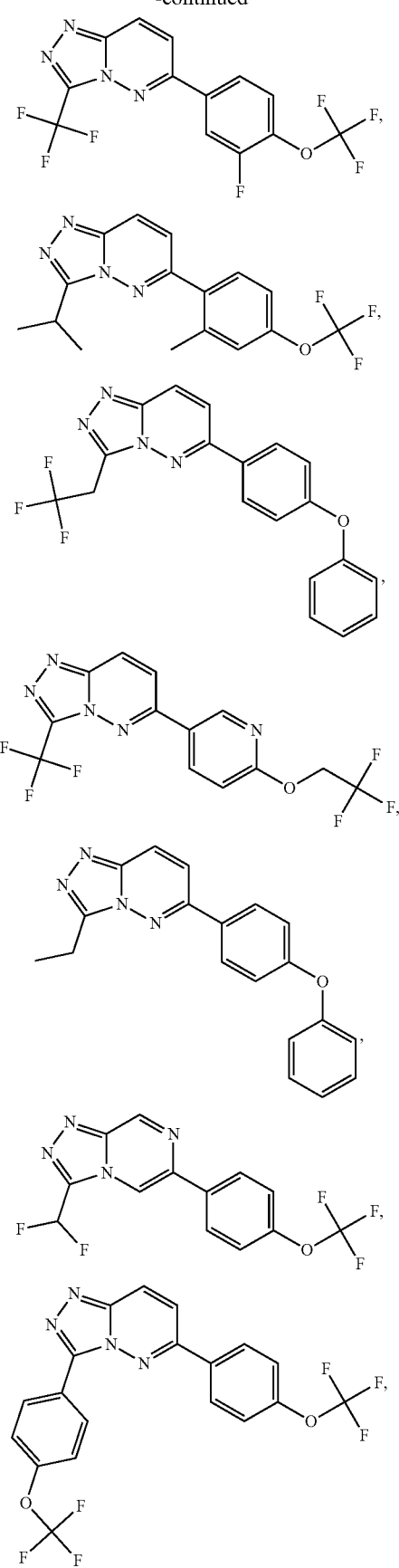
122
-continued
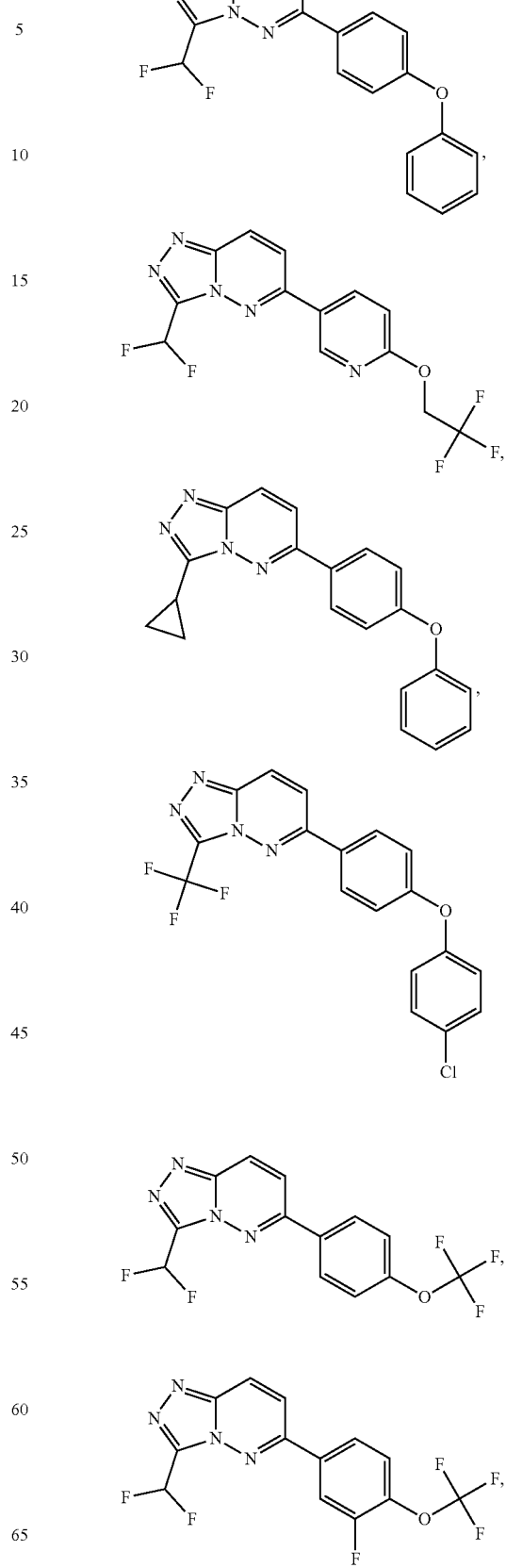

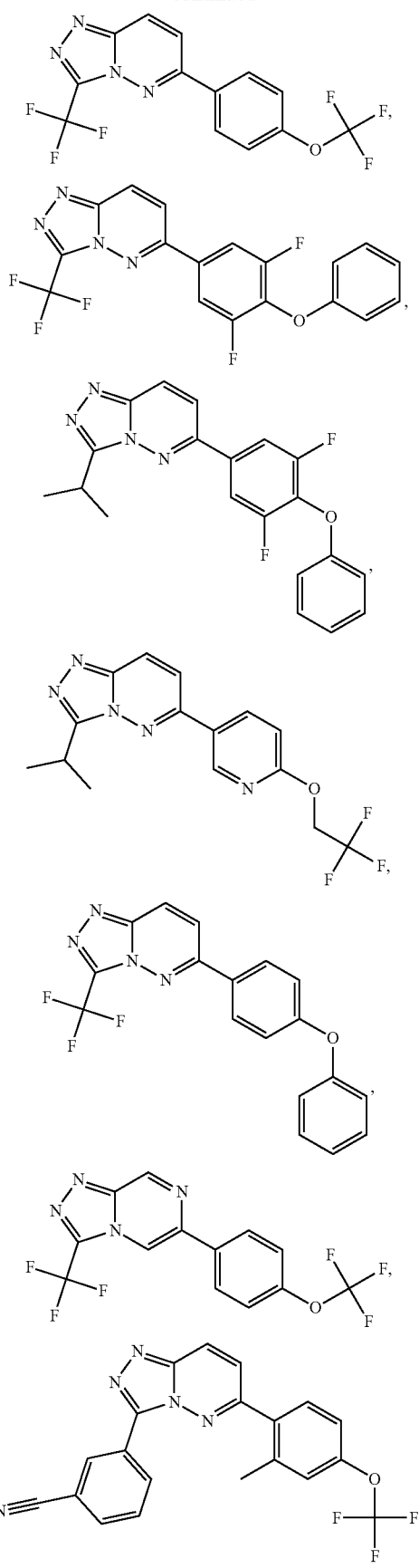
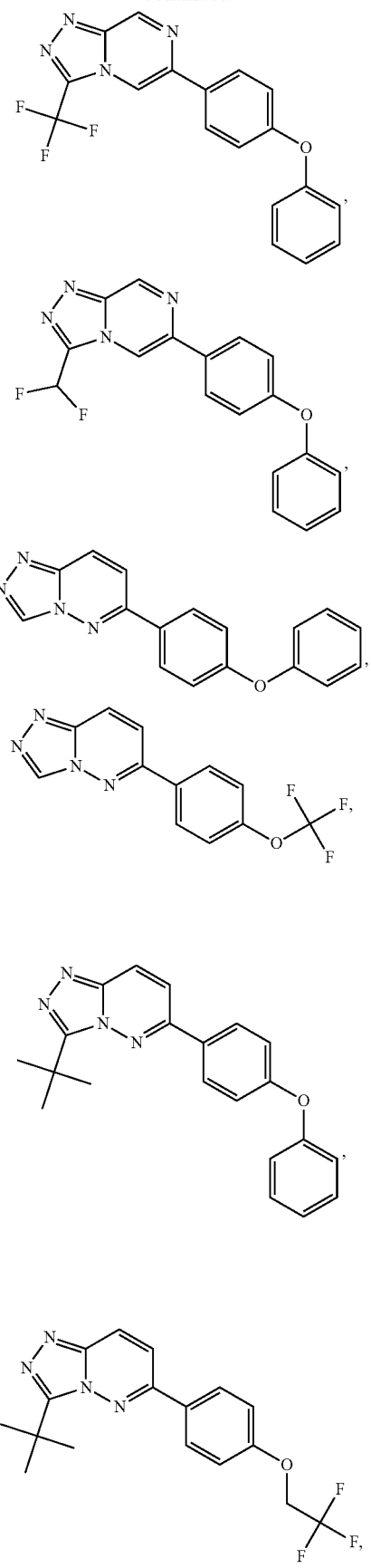

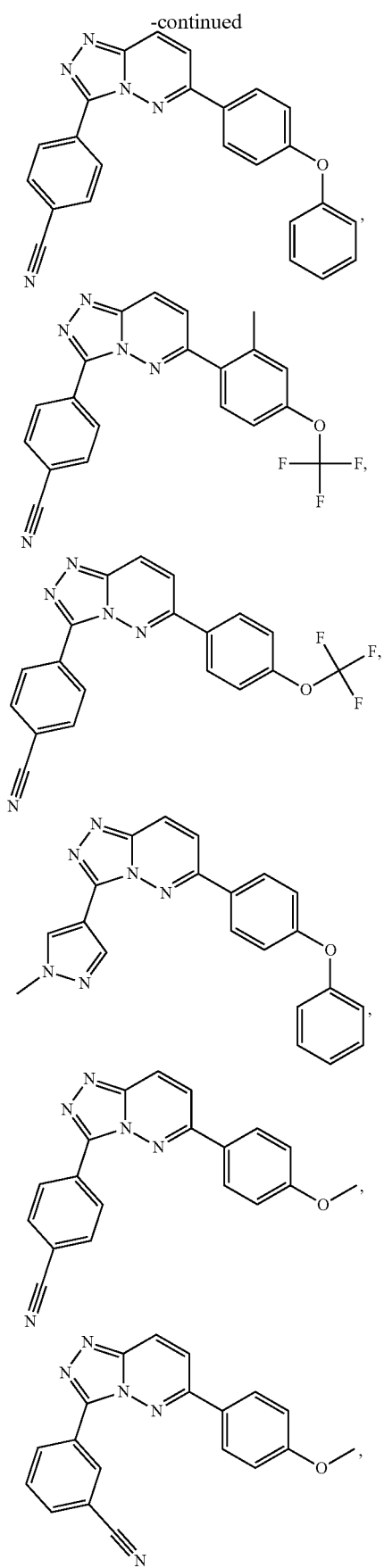
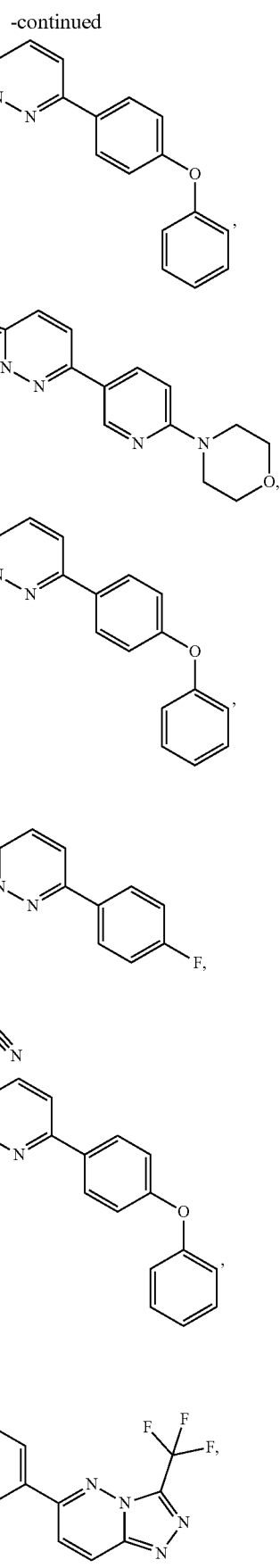

127
-continued
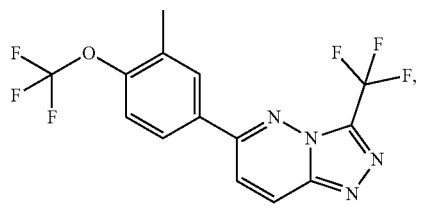
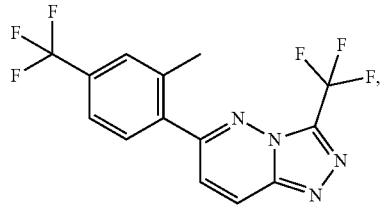
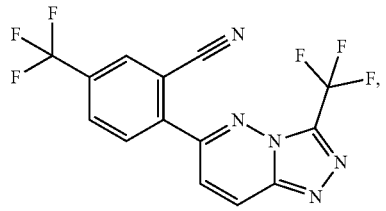
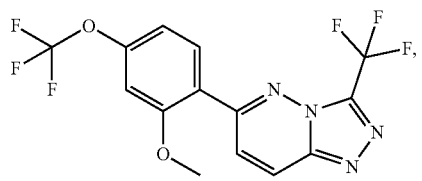
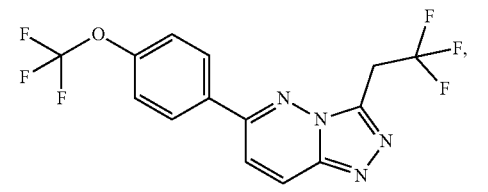
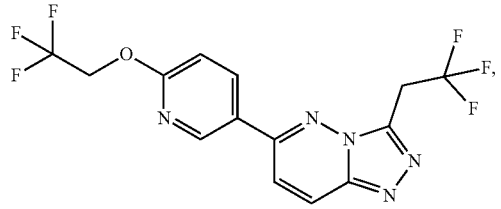
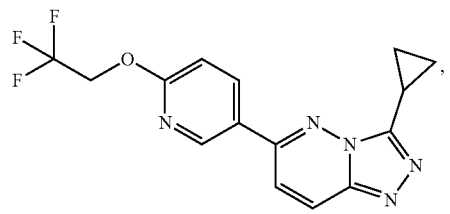
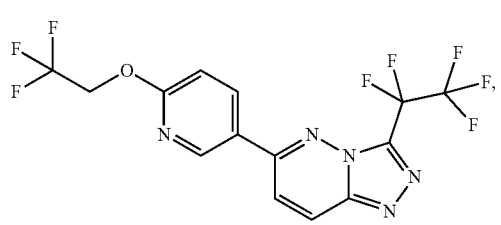
128
-continued
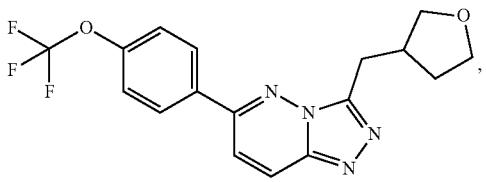
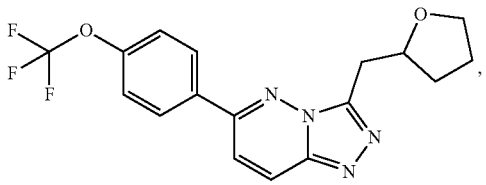
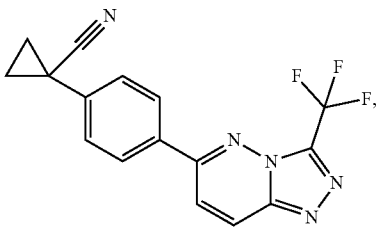
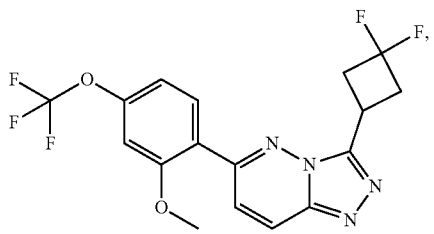
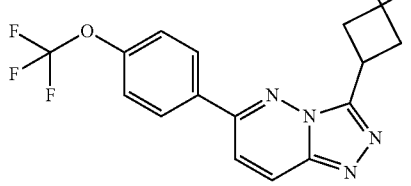
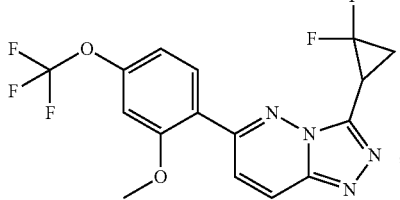
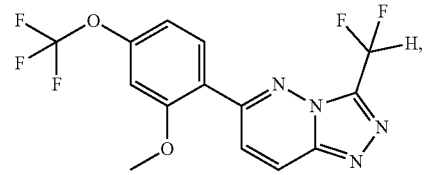
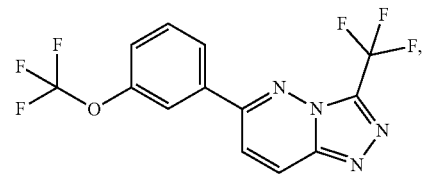

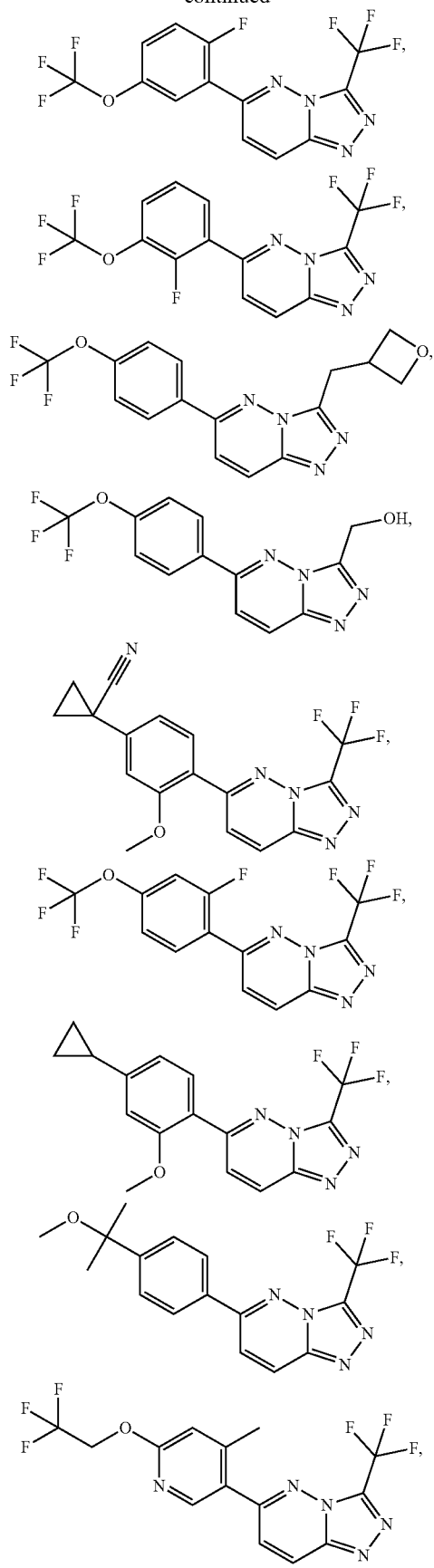
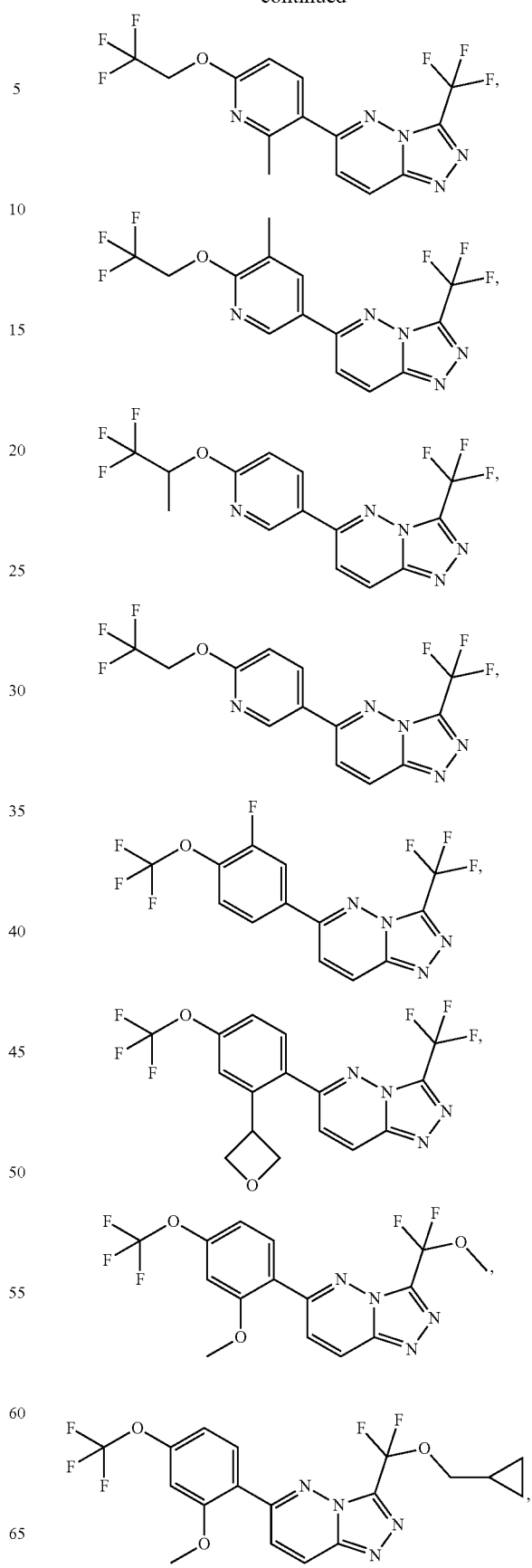

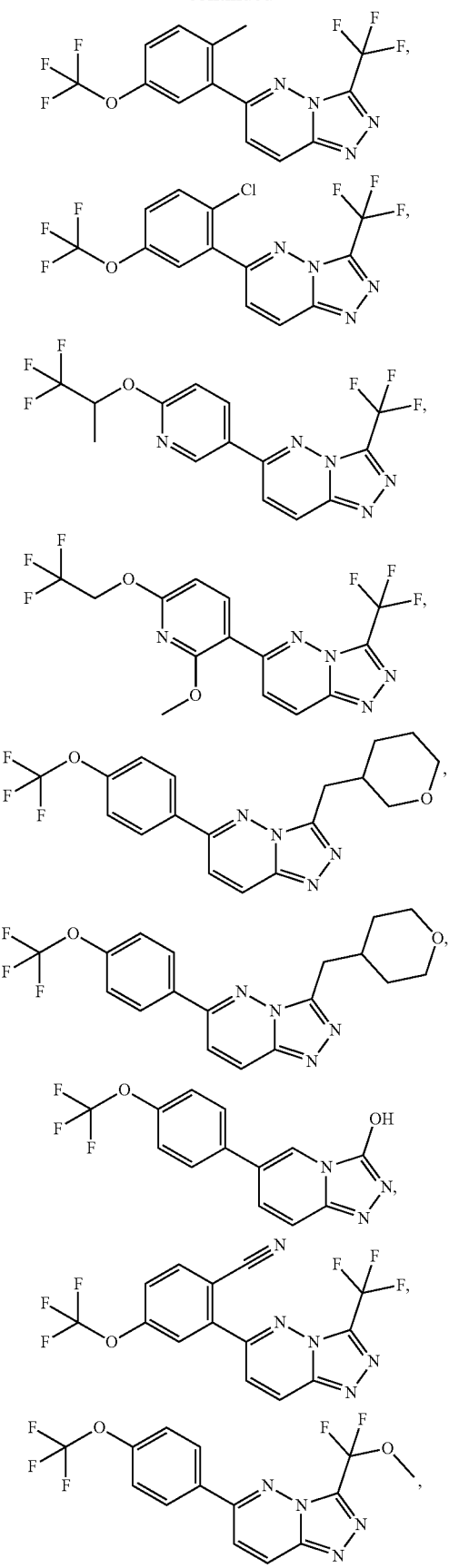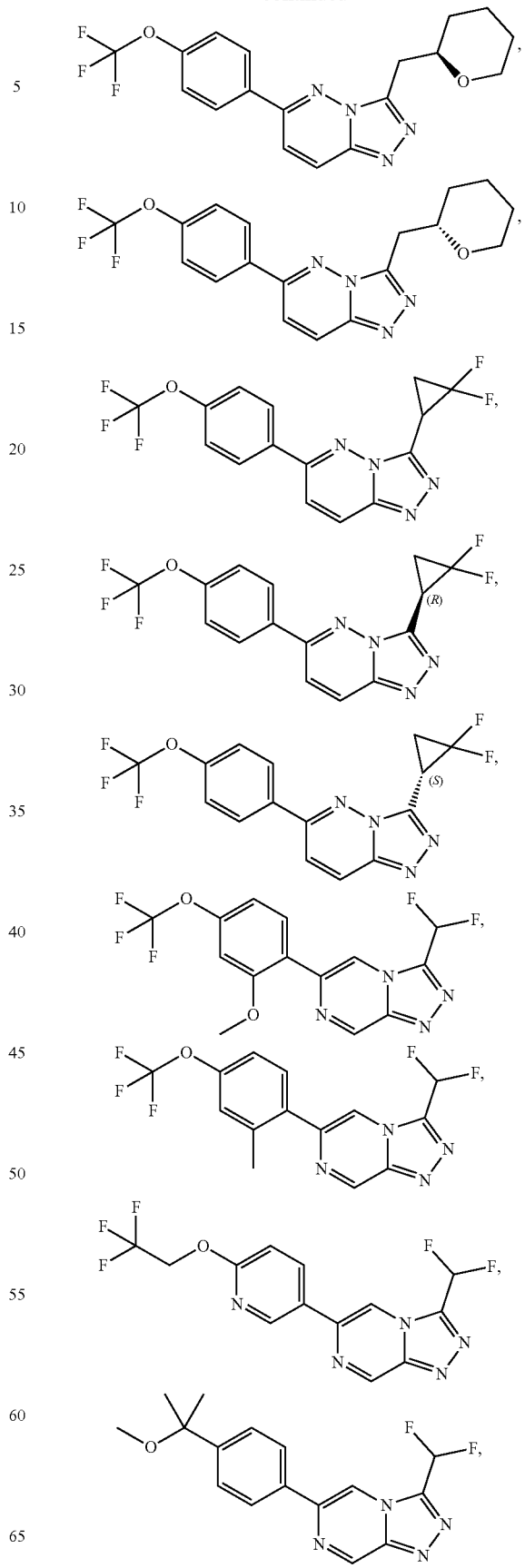

133
-continued
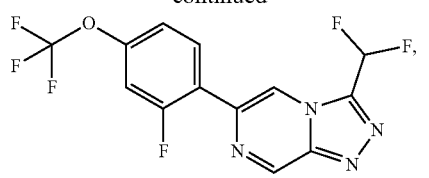

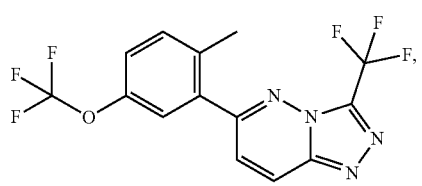
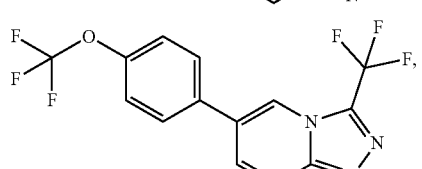
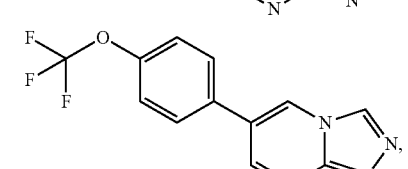
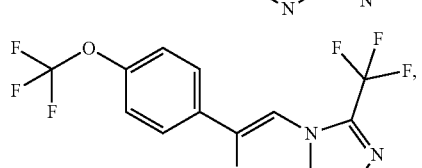
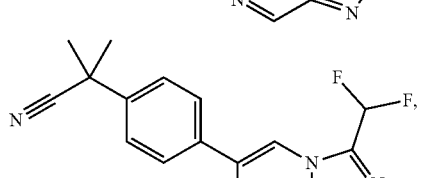
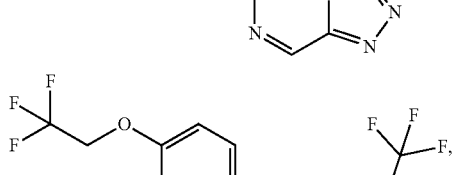
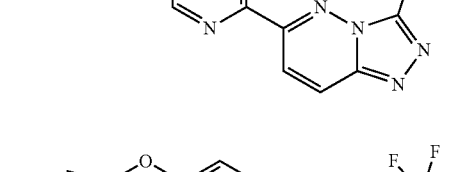
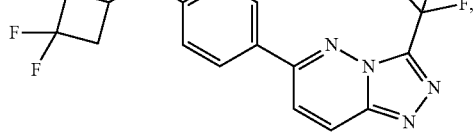
134
-continued
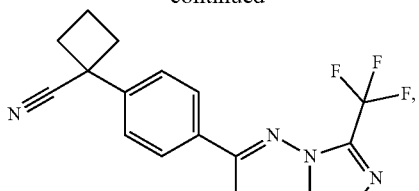
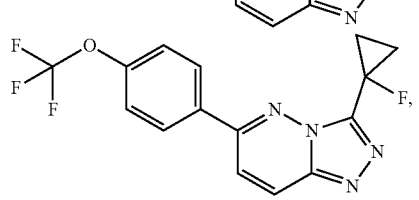
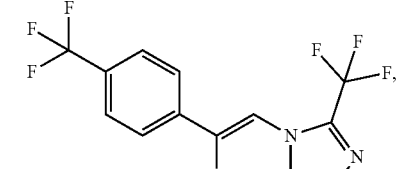
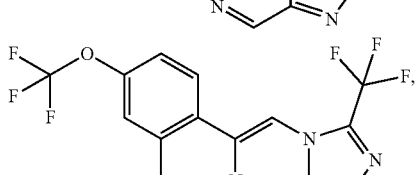
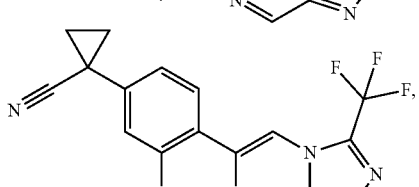
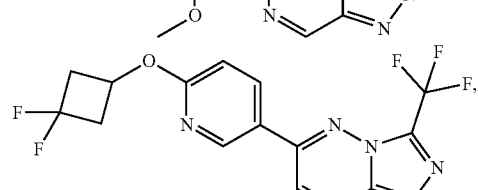
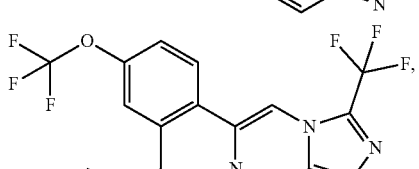
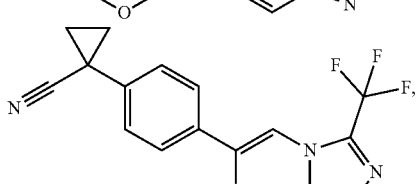
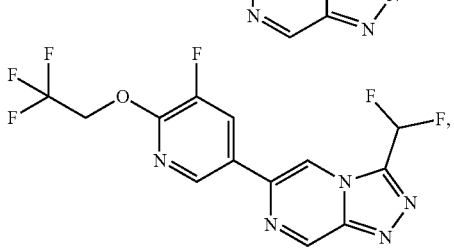

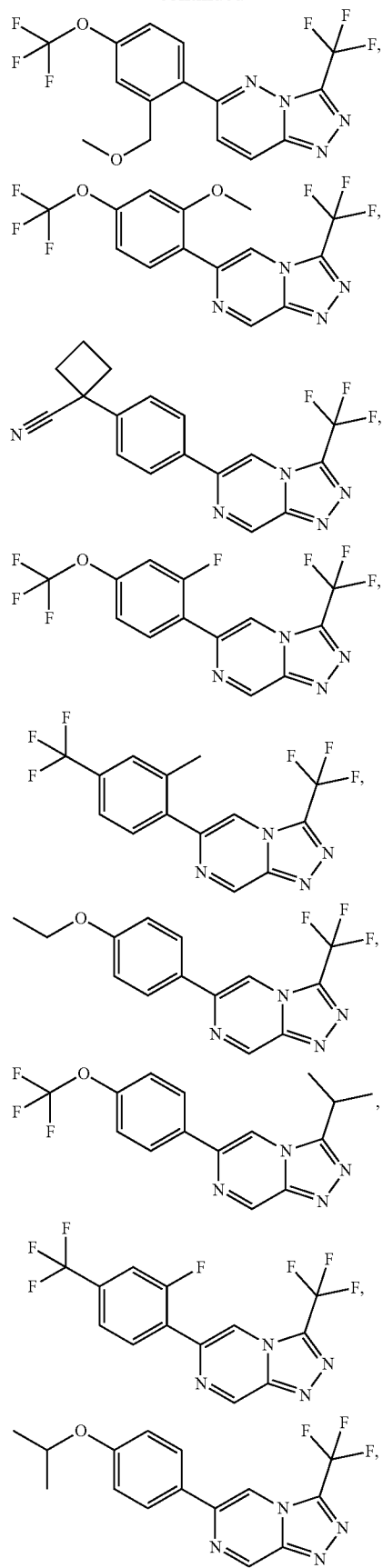
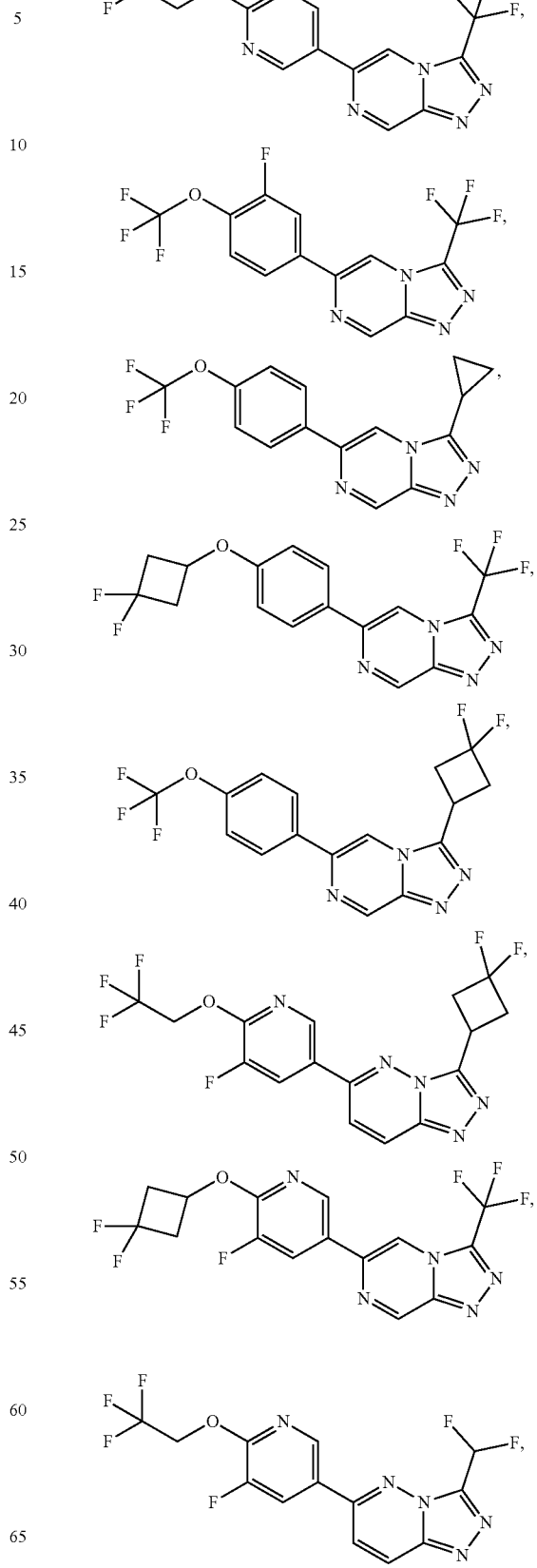

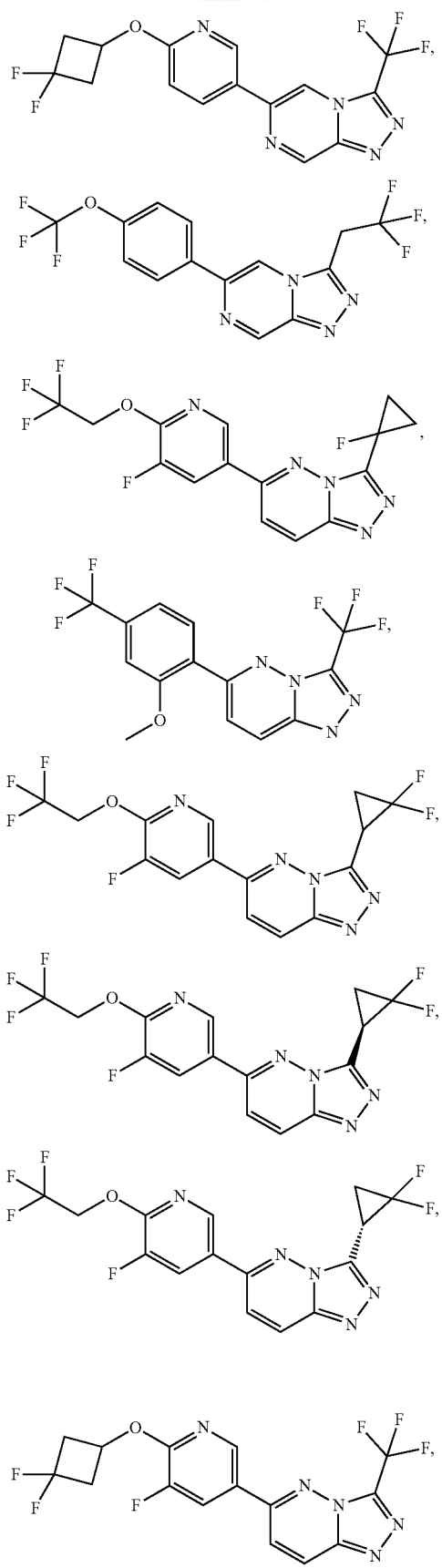
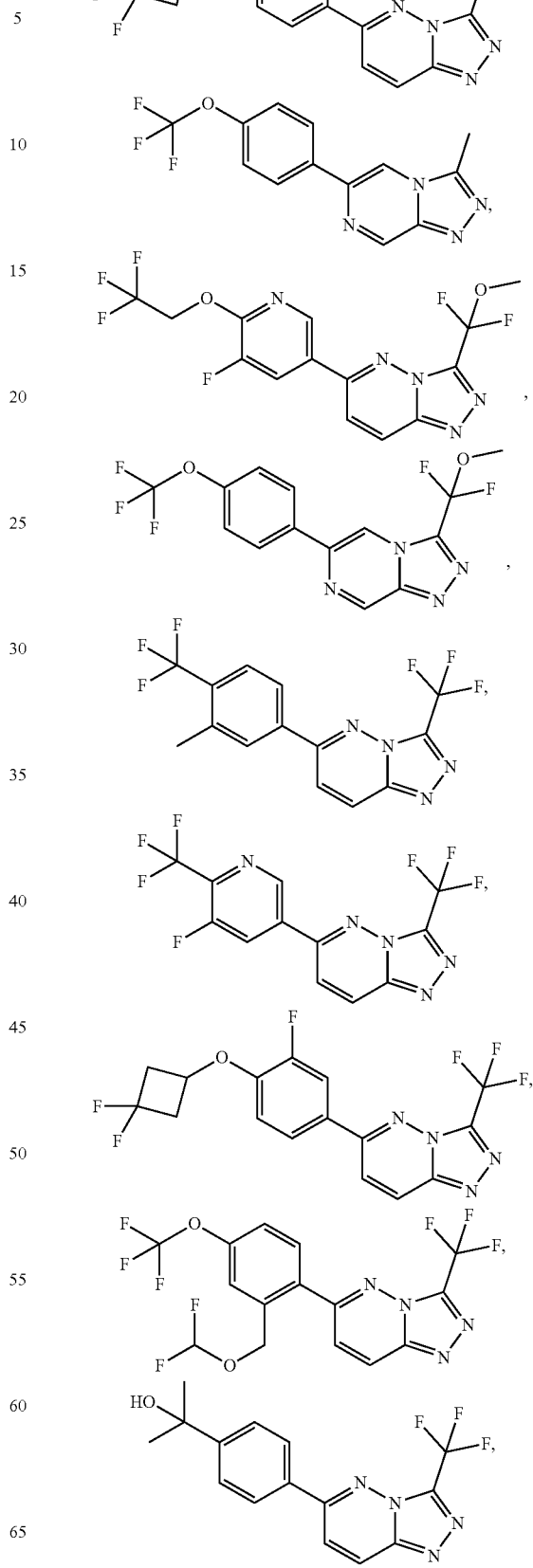

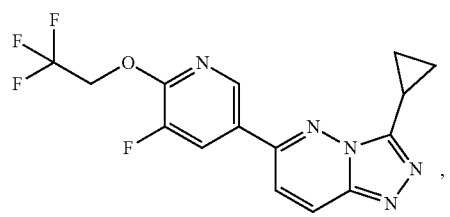
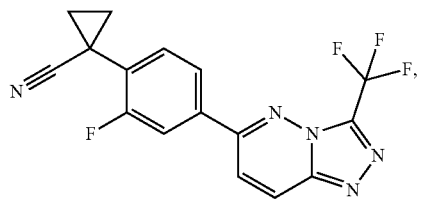
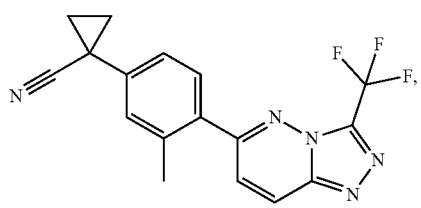
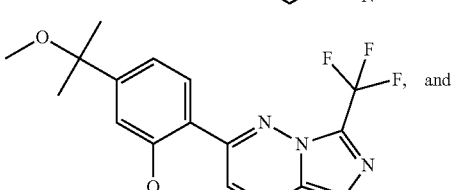
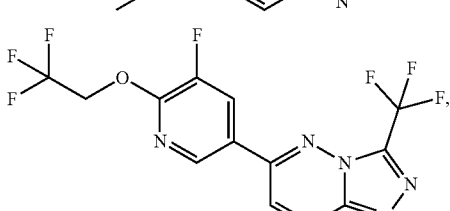
or a pharmaceutically acceptable salt thereof.
In some embodiments, the compound of Formula (I) is selected from:
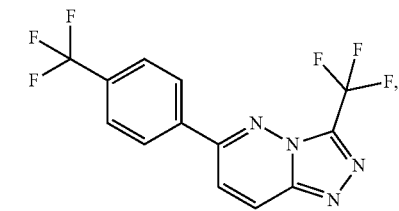
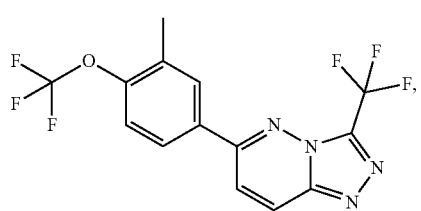
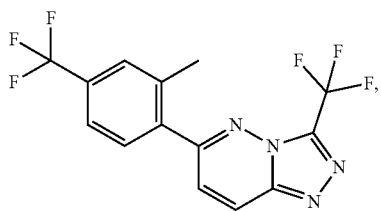
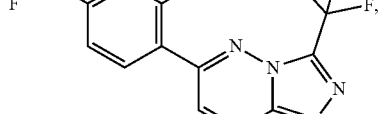
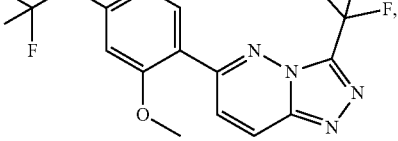
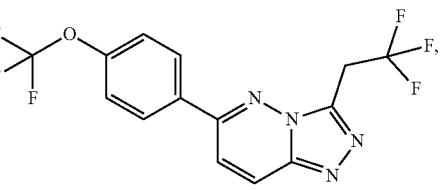
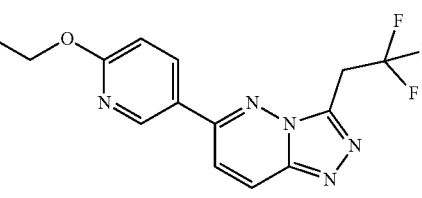
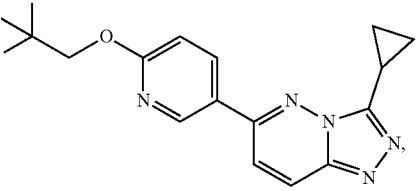
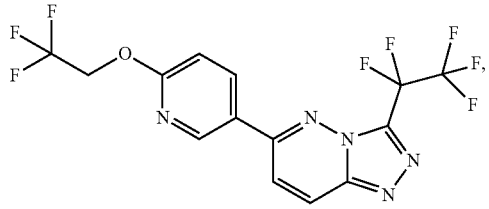
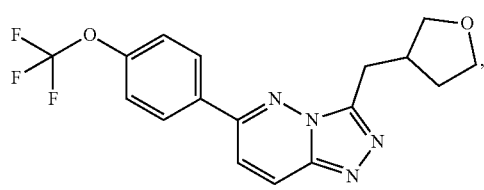

-continued

143
-continued
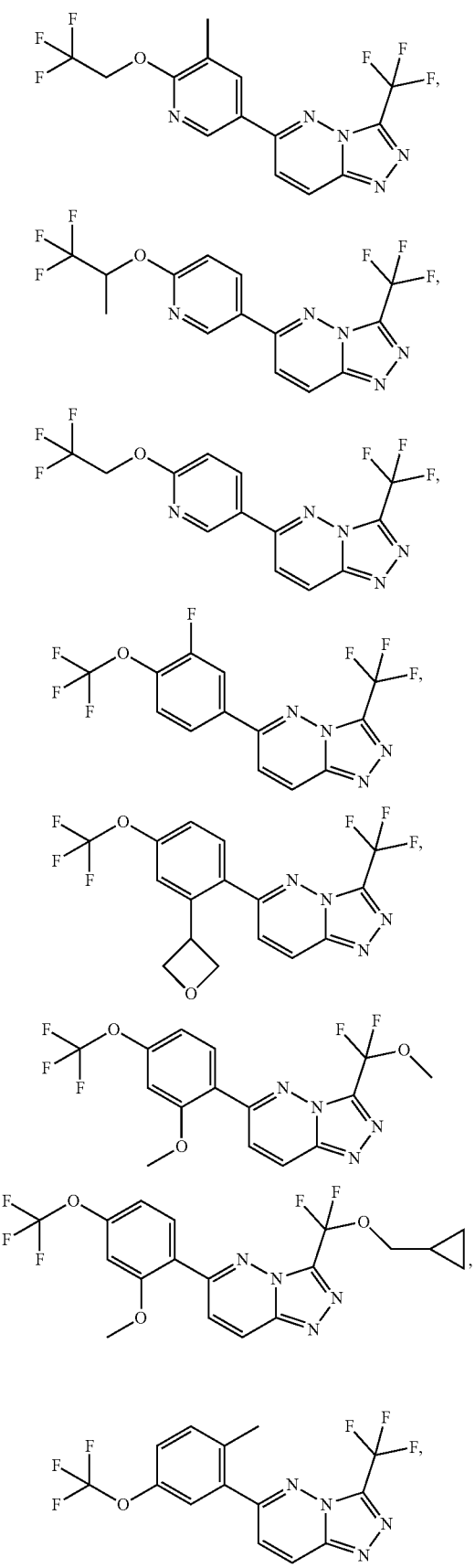
144
-continued
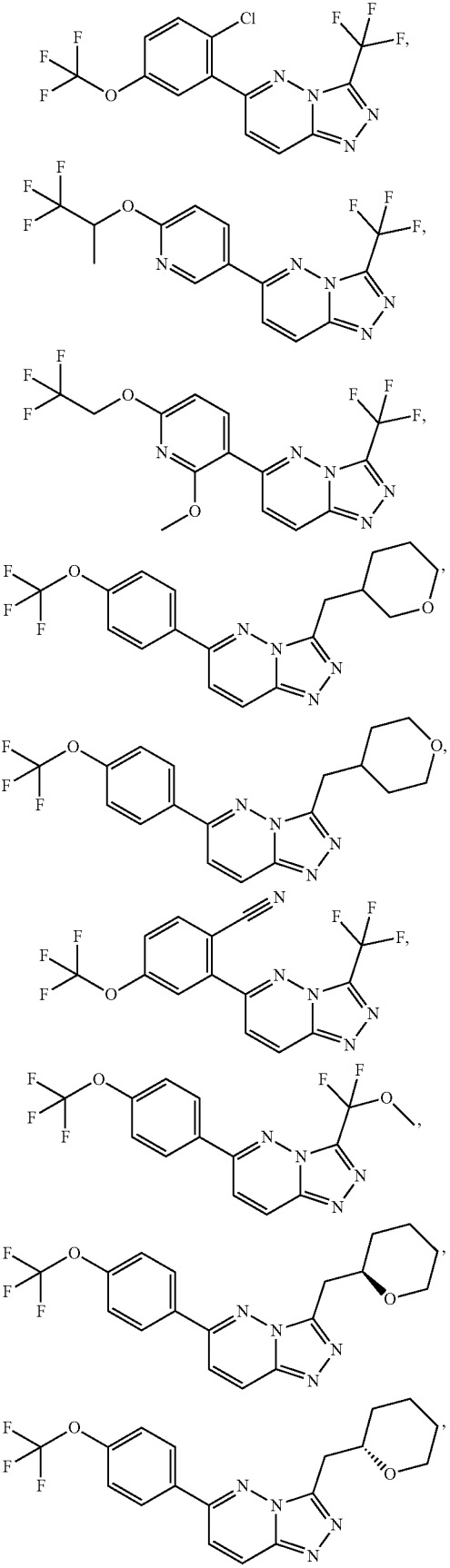

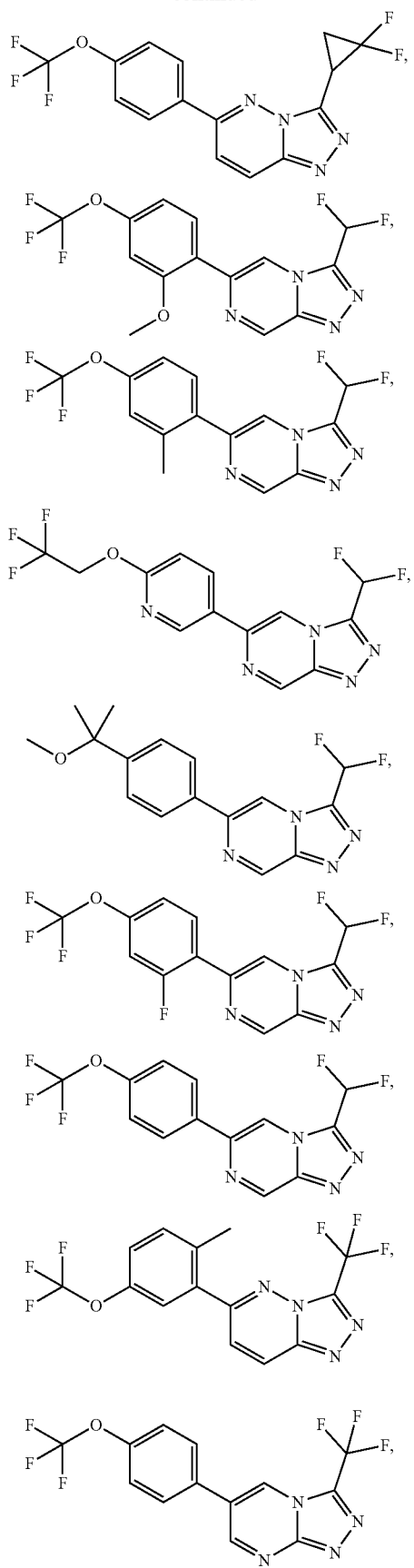
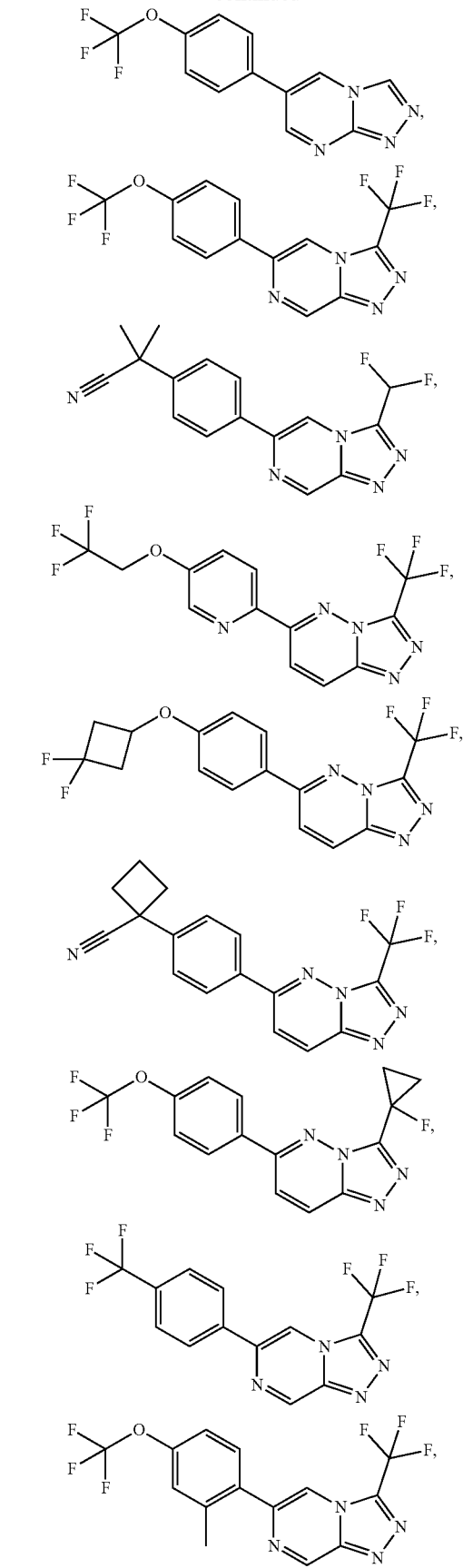

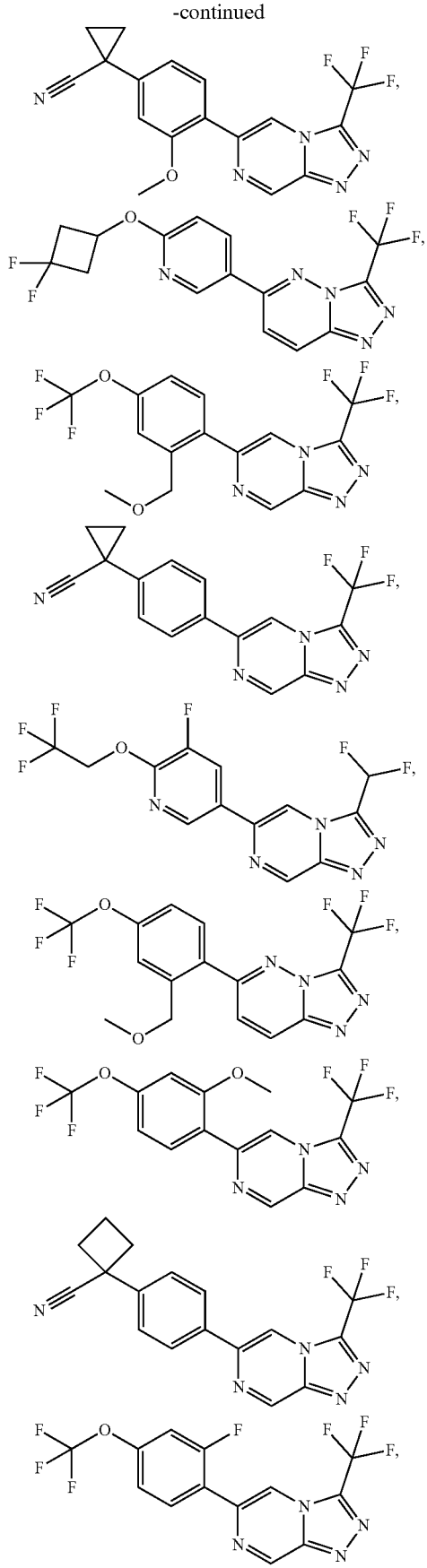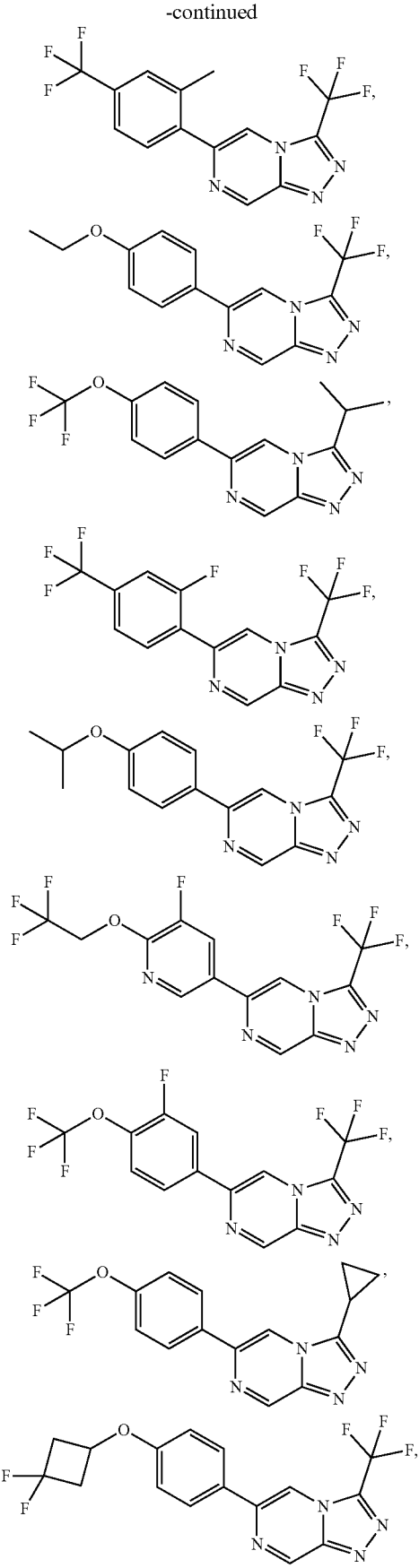

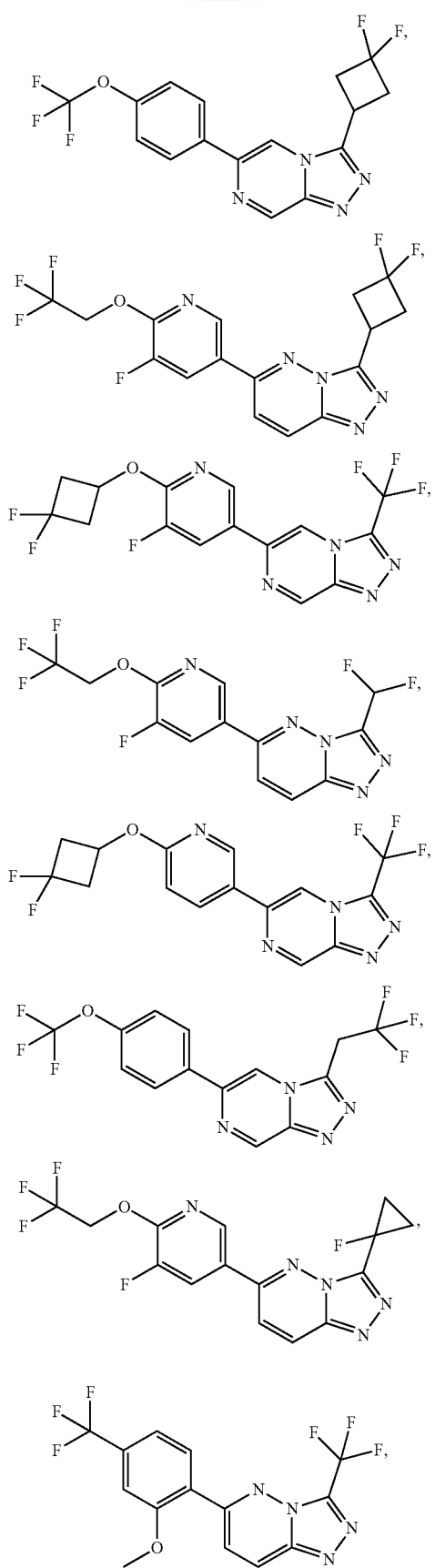
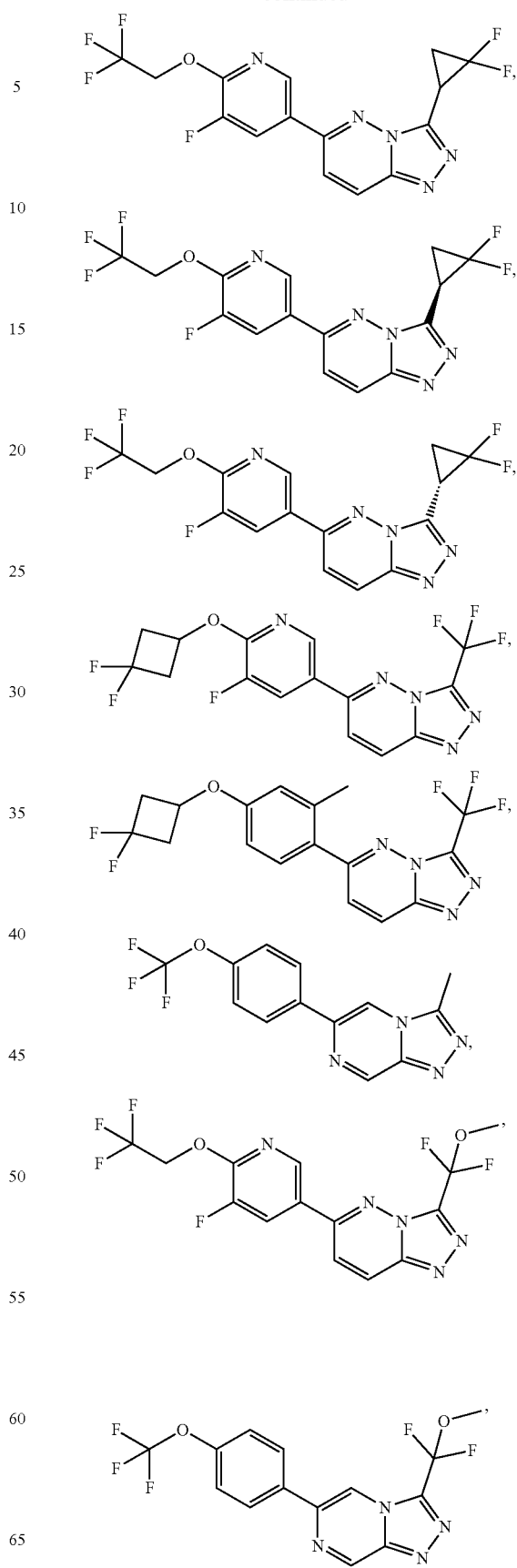

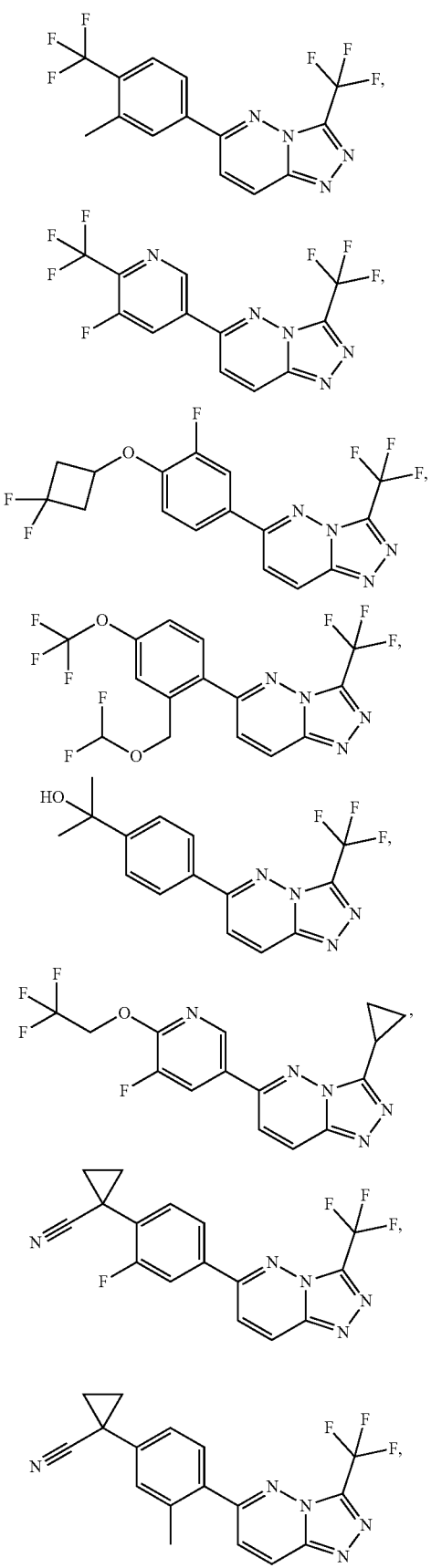

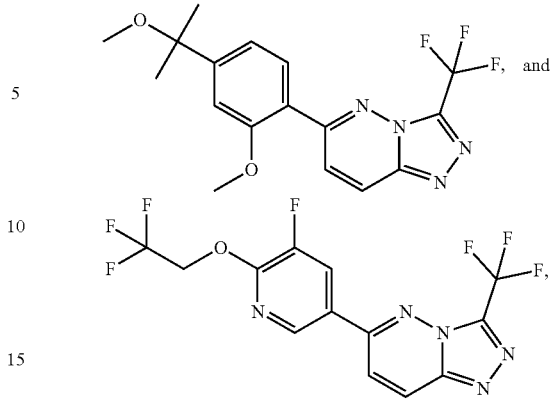

or a pharmaceutically acceptable salt thereof.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be Formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably Formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule).

The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (lnspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amioarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon)

captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the sodium channel blockers of the invention to treat neuropathic pain via inhibition of the Nay 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; benzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (EffexorXR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel blockers of the invention and therapeutic agent or agents, essentially contemporaneous administration of more than one formulation comprising the sodium channel blocker of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate $C_{18}$ (2.1 mm×30 mm, 3 µm); A=$H_2O$ (0.04% TFA) and B=$CH_3CN$ (0.02% TFA); 50° C.; 1.2 mL/min; 10-80% B over 0.9 minutes, then 80% B for 0.6 minutes); Method B (Chromolith Flash RP-18 endcapped $C_{18}$ (2 mm×25 mm); A=$H_2O$ (0.04% TFA) and B=$CH_3CN$ (0.02% TFA); 50° C.; 1.5 mL/min; 5-95% B over 0.7 minutes, then 95% B for 0.4 minutes); and Method C (Xtimate $C_{18}$ (2.1 mm×30 mm, 3 µm); A=$H_2O$ (0.04% TFA) and B=$CH_3CN$ (0.02% TFA); 50° C.; 0.8 mL/min; 10-80% B over 6 minutes, then 80% B for 0.5 minutes).

LIST OF ABBREVIATIONS

NIS N-iodosuccinimide
DMF N,N-dimethylformamide
THF tetrahydrofuran
MeOH methanol
DCM dichloromethane
LiHMDS lithium bis(trimethylsilyl)amide
EtOH ethanol
$Et_3N$ trimethylamine
Pd(dppf)$Cl_2$ [1,1'-bis(diphenylphosphino)ferrocene]palladium(II) dichloride
MeI methyliodide
$Et_3SiH$ triethylsilane
DBU 1,8-diazabicyclo(5.4.0)undec-7-ene
AcN acetonitrile
TMSCF$_3$ trifluoromethyltrimethylsilane
TBAB tetrabutylammonium bromide
Pd(t-$Bu_3P$)$_2$ bis(tri-tert-butylphosphine)palladium(0)
DAST diethylaminosulfur trifluoride
DIPEA N,N-diisopropylethylamine
HATU 1-[bis(dimethylamino)methylene]-1H-1,2,3-triazolo[4,5-b]pyridinium 3-oxide hexafluorophosphate
Pd(dba)$_3$ tris(dibenzylideneacetone)dipalladium(0)
XPhos 2-dicyclohexylphosphino-2',4',6'-triisopropylbiphenyl Example 1: Synthesis of Compound 1

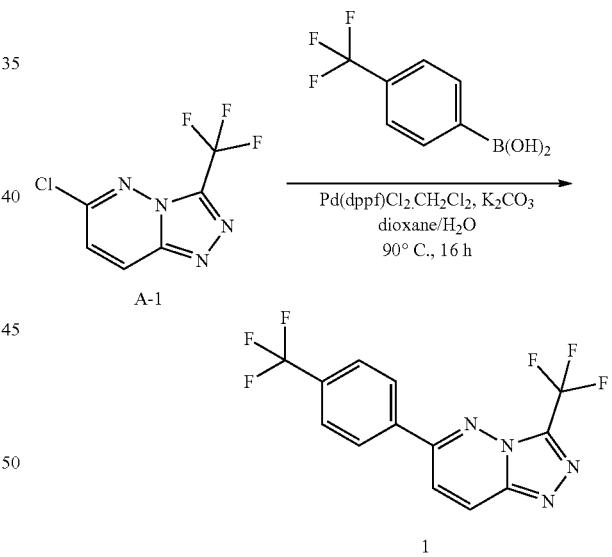

A mixture of A-1 (100.00 mg, 449.32 µmol), 4-(trifluoromethyl)phenylboronic acid (102.41 mg, 539.18 µmol), $K_2CO_3$ (124.20 mg, 898.64 µmol) and Pd(dppf)$Cl_2$.$CH_2Cl_2$ (55.04 mg, 67.40 µmol) in dioxane (6 mL) and water (600 µL) under $N_2$ was heated to 90° C. and stirred for 16 h. The reaction mixture was diluted with EtOAc (10 mL), filtered, and concentrated to give a residue that was purified by prep-TLC (silica gel, PE:EtOAc=2:1) to afford Compound 1 (26.00 mg) as a solid. $^1$H NMR: (400 MHz, CDCl$_3$) $\delta_H$=8.37 (d, 1H), 8.14 (d, 2H), 7.85 (d, 2H), 7.79 (d, 1H). LCMS: $R_t$=1.16 min using Method A, MS ESI calcd. for $C_{13}H_7F_6N_4$ [M+H]$^+$333.05, found 333.1.

Example 2: Synthesis of Compound 2

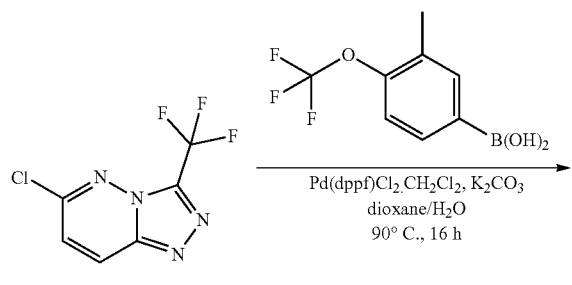

A mixture of A-1 (100.00 mg, 449.32 μmol), 3-methyl-4-(trifluoromethoxy)-phenylboronic acid (118.59 mg, 539.18 μmol), Pd(dppf)Cl$_2$.CH$_2$Cl$_2$ (55.04 mg, 67.40 μmol) and K$_2$CO$_3$ (124.20 mg, 898.64 μmol) in dioxane (6 mL) and water (600 μL) under N$_2$ was heated to 90° C. and stirred for 16 h. The reaction mixture was diluted with EtOAc (10 mL), filtered, and concentrated to give a residue that was purified by prep-HPLC (Kromasil (150 mm×25 mm, 10 μm) A=H$_2$O (0.05% NH$_4$OH) and B=CH$_3$CN; 50-80% B over 8 minutes) to afford Compound 2 (26.80 mg) as a solid. $^1$H NMR (400 MHz, CDCl$_3$) δ$_H$=8.31 (d, 1H), 7.95-7.85 (m, 2H), 7.74 (d, 1H), 7.41 (d, 1H), 2.45 (s, 3H). LCMS R$_t$=1.22 min using Method A, MS ESI calcd. for C$_{14}$H$_9$F$_6$N$_4$O [M+H]$^+$ 363.06, found 363.1.

Example 3: Synthesis of Compound 3

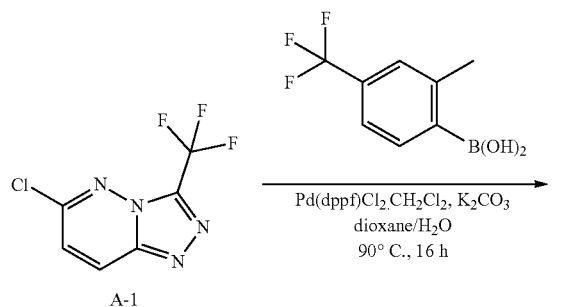

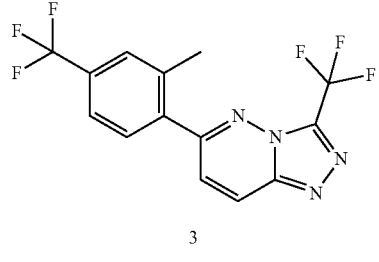

A mixture of A-1 (100.00 mg, 449.32 μmol), [2-methyl-4-(trifluoromethyl)phenyl]boronic acid (109.97 mg, 539.18 μmol), Pd(pddf)Cl$_2$.CH$_2$Cl$_2$ (55.04 mg, 67.40 μmol) and K$_2$CO$_3$ (124.20 mg, 898.63 μmol) in dioxane (6 mL) and water (600 μL) under N$_2$ was heated to 90° C. and stirred for 16 hours. The reaction mixture was diluted with EtOAc (10 mL), filtered, and concentrated to give a residue that was purified by prep-TLC (silica gel, PE:EtAOAc=2:1) to afford Compound 3 as a solid. $^1$H NMR (400 MHz, CDCl$_3$) δ$_H$=8.34 (d, 1H), 7.65-7.58 (m, 3H), 7.47 (d, 1H), 2.53 (s, 3H). LCMS R$_t$=1.18 min using Method A, MS ESI calcd. for C$_{14}$H$_9$F$_6$N$_4$ [M+H]$^+$ 347.1, found 347.1.

Example 4: Synthesis of Compound 4

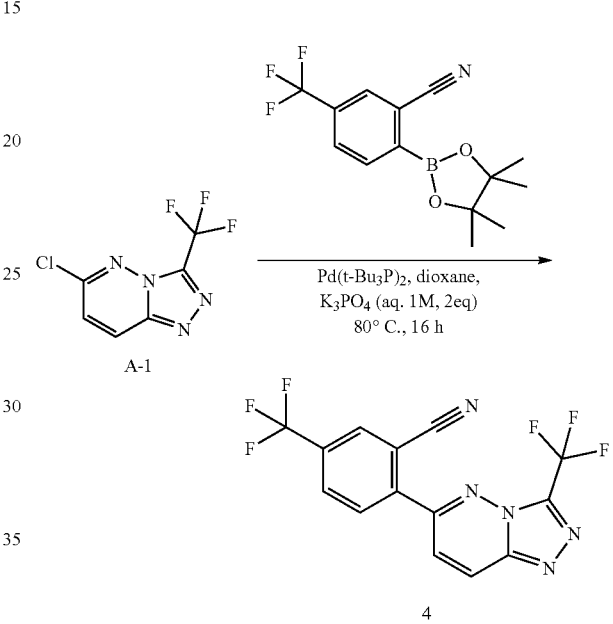

A mixture of A-1 (100.00 mg, 449.32 μmol), 2-(4,4,5,5-tetramethyl-1,3,2-dioxaborolan-2-yl)-5-(trifluoromethyl)benzonitrile (160.18 mg, 539.18 μmol), K$_3$PO$_4$ (190.75 mg, 898.64 μmol) and Pd(t-Bu$_3$P)$_2$ (22.96 mg, 44.93 μmol) in dioxane (10 mL) and H$_2$O (900 μL) was stirred at 80° C. for 16 hours in a 20 mL sealed tube under N$_2$. The reaction mixture was cooled to room temperature, concentrated, and purified by prep-TLC (silica gel, DCM:EtAOAc=5:1) to give Compound 4 as a solid. $^1$H NMR (400 MHz, CDCl$_3$) δ$_H$=8.48 (d, 1H), 8.20 (s, 1H), 8.13-8.03 (m, 2H), 7.78 (d, 1H). LCMS R$_t$=1.08 min using Method A, MS ESI calcd. for C$_{14}$H$_6$F$_6$N$_5$ [M+H]$^+$ 358.0, found 357.9.

Example 5: Synthesis of Compound 5

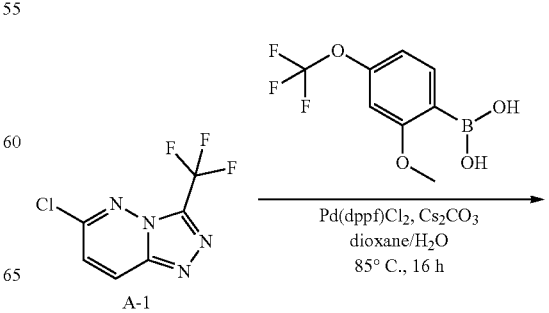

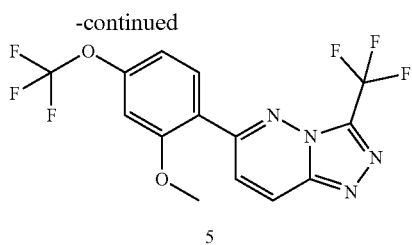

5

A mixture of A-1 (80.00 mg, 359.45 μmol), 2-methoxy-4-(trifluoromethoxy)phenylboronic acid (84.81 mg, 359.45 μmol), Pd(dppf)Cl$_2$·CH$_2$Cl$_2$ (29.35 mg, 35.95 μmol and Cs$_2$CO$_3$ (234.23 mg, 718.90 μmol) in dioxane (5 mL) and water (500 μL) was stirred at 85° C. for 16 hours in a 10 mL sealed tube under N$_2$. The reaction mixture was cooled to room temperature, concentrated, and purified by prep-TLC (silica gel, PE:EtAOAc=2:1) to give Compound 5 as a solid. $^1$H NMR (400 MHz, CDCl$_3$) δ$_H$=8.20 (d, 1H), 7.82 (d, 1H), 7.80 (d, 1H), 7.04 (d, 1H), 6.91 (s, 1H), 3.94 (s, 3H). LCMS R$_t$=1.18 min using Method A, MS ESI calcd. for C$_{14}$H$_9$F$_6$N$_4$O$_2$ [M+H]$^+$ 379.0, found 379.1.

Example 6: Synthesis of Compound 6

The resulting mixture was stirred at 120° C. for 1 hour in a microwave reactor. The mixture was concentrated, diluted with H$_2$O (10 mL), basified with solid NaHCO$_3$ to pH~9 and extracted with EtOAc (30 mL×2). The combined organic phase was washed with brine (10 mL), dried over Na$_2$SO$_4$, filtered and concentrated to give the crude product, which was purified by flash chromatography on silica gel (EtOAc in PE=25% to 33% to 50% to 66%) to afford A-4 as a solid. LCMS R$_t$=0.66 min using Method B, MS ESI calcd. for C$_7$H$_5$ClF$_3$N$_4$ [M+H]$^+$237.0, found 237.0.

Synthesis of Compound 6: A mixture of A-4 (100.00 mg, 422.69 μmol), 4-(trifluoromethoxy)phenylboronic acid (104.45 mg, 507.23 μmol), Pd(dppf)Cl$_2$·CH$_2$Cl$_2$ (34.52 mg, 42.27 μmol) and K$_2$CO$_3$ (116.84 mg, 845.38 μmol) in dioxane (10 mL) and H$_2$O (1 mL) was stirred at 90° C. for 4 hours. The mixture was diluted with EtOAc (20 mL), filtered through silica gel and eluted with EtOAc (30 mL×2), then concentrated to give a residue that was purified by prep-TLC (silica gel, PE:EtAOAc=2:1) to give Compound 6 (17.30 mg) as a solid. $^1$H NMR (400 MHz, CDCl$_3$) δ$_H$=8.26 (d, 1H), 8.08-8.02 (m, 2H), 7.63 (d, 1H), 7.43 (d, 2H), 4.27-4.16 (m, 2H). LCMS R$_t$=1.14 min using Method A, MS ESI calcd. For C$_{14}$H$_9$F$_6$N$_4$O [M+H]$^+$ 363.0, found 362.9.

Example 7: Synthesis of Compound 7

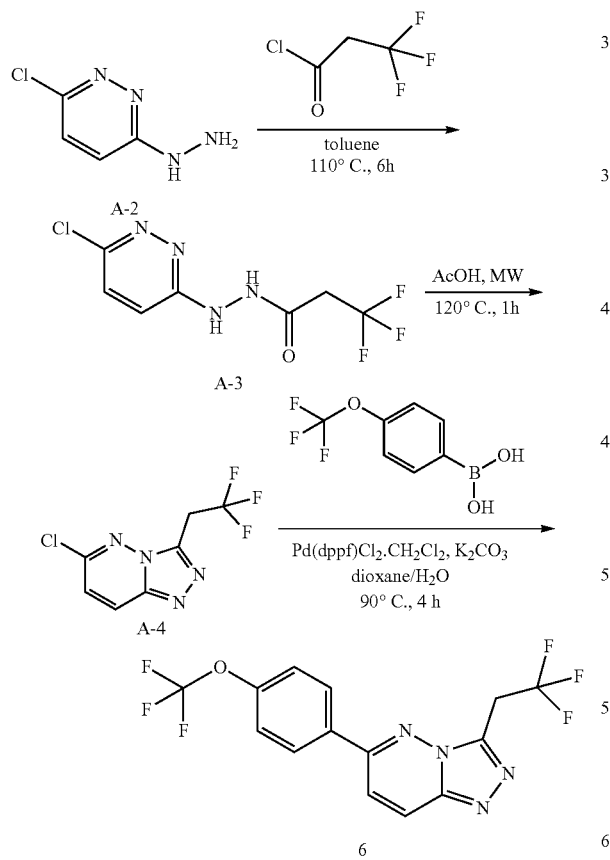

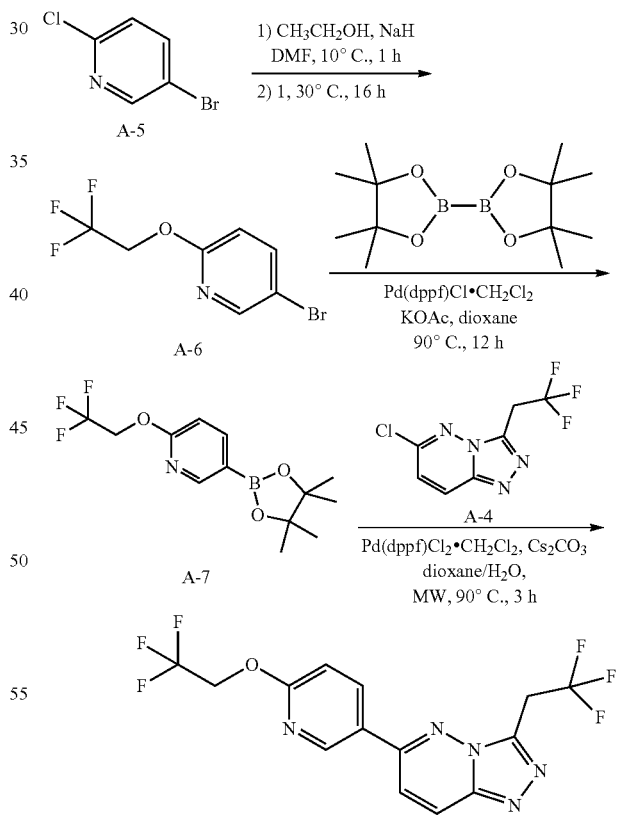

Synthesis of A-4: To a solution of A-2 (100.00 mg, 691.75 μmol) in toluene (10 mL) was added 3,3,3-trifluoropropanoyl chloride (121.61 mg, 830.10 μmol), and the mixture was stirred at 110° C. for 6 hours. The reaction mixture was concentrated, and to the residue was added AcOH (10 mL).

Synthesis of A-6: To a mixture of NaH (2.70 g, 67.55 mmol, 60% purity) in DMF (50 mL) was added 2,2,2-trifluoroethanol (4.86 mL, 67.55 mmol) dropwise at 10° C., and the mixture was stirred for 1 hr. A-5 (10.00 g, 51.96 mmol) was then added in one portion, and the reaction was stirred at 30° C. for 16 hrs. The reaction mixture was quenched with sat.NH₄Cl (250 mL), extracted with EtOAc (100 mL×3), and the combined organic phase was washed with brine (200 mL), dried over Na₂SO₄, filtered and concentrated. The resulting residue was purified by flash chromatography on silica gel (EtOAc in PE=0% to 5%) to give A-6 (11.00 g) as an oil. ¹H NMR (400 MHz, CDCl₃) δ$_H$=8.20 (d, 1H), 7.73 (dd, 1H), 6.80 (d, 1H), 4.73 (q, 2H).

Synthesis of A-7: A mixture of A-6 (2.00 g, 7.81 mmol), 4,4,5,5-tetramethyl-2-(4,4,5,5-tetramethyl-1,3,2-dioxaborolan-2-yl)-1,3,2-dioxaborolane (4.96 g, 19.52 mmol), Pd(dppf)Cl₂.CH₂Cl₂ (637.95 mg, 781.00 μmol) and KOAc (1.92 g, 19.52 mmol) was stirred at 90° C. for 12 hours. The mixture was concentrated and the residue was purified by flash chromatography on silica gel (EtOAc in PE=0% to 10%) to give A-7 (1.90 g, 6.27 mmol) as an oil. ¹H NMR (400 MHz, CDCl₃) δ$_H$=8.51 (d, 1H), 7.99 (dd, 1H), 6.83 (d, 1H), 4.79 (q, 2H), 1.34 (s, 12H).

Synthesis of Compound 7: A mixture of A-4 (100.00 mg, 422.69 μmol), A-7 (128.11 mg, 422.69 μmol), Cs₂CO₃ (275.44 mg, 845.38 μmol) and Pd(dppf)Cl₂.CH₂Cl₂ (34.52 mg, 42.27 μmol) in H₂O (500 μL) and dioxane (5 mL) was stirred at 90° C. for 3 hours in microwave reactor, at which point the desired product was observed by LCMS. The mixture was diluted with EtOAc (10 mL), filtered through silica gel and eluted with EtOAc (10 mL×2). The filtrate was concentrated and the residue was purified by prep-TLC (silica gel, EtOAc:DCM=1:2) to give Compound 7 (42.10 mg) as a solid. ¹H NMR (400 MHz, CDCl₃) δ$_H$=8.78 (d, 1H), 8.33 (dd, 2.4, 1H), 8.26 (d, 1H), 7.61 (d, 1H), 7.08 (d, 1H), 4.27, 4.88 (q, 2H), 4.21 (q, 2H). LCMS R$_t$=1.10 min using Method A, MS ESI calcd. For C₁₄H₁₀F₆N₅O [M+H]⁺ 378.1, found 377.9.

Example 8: Synthesis of Compound 8

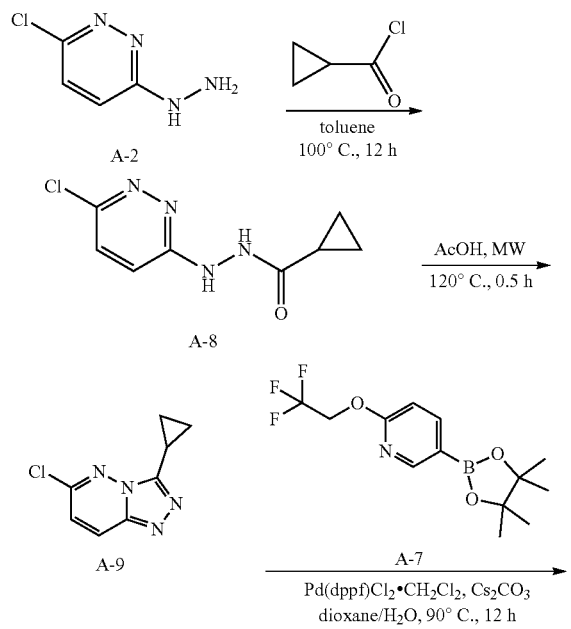

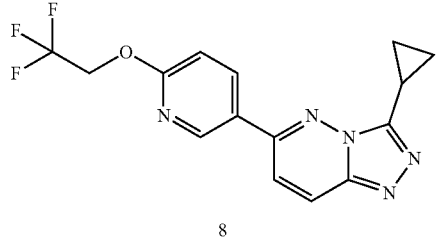

Synthesis of A-9: A mixture of A-2 (200.00 mg, 1.38 mmol) and cyclopropanecarbonyl chloride (150.54 μL, 1.66 mmol) in toluene (10 mL) was stirred at 100° C. for 12 hour. This mixture was concentrated and AcOH (10 mL) was added to the residue. The mixture was stirred at 120° C. for 0.5 hour in a microwave reactor, then the mixture was concentrated, diluted with H₂O (10 mL), basified with solid NaHCO₃ to pH ~9, extracted with EtOAc (30 mL×2), and the combined organic phase was washed with brine (10 mL), dried over Na₂SO₄, filtered and concentrated to give crude A-9 (170.00 mg). LCMS R$_t$=0.64 min using Method B, MS ESI calcd. for C₈H₈ClN₄ [M+H]⁺ 194.9, found 195.0.

Synthesis of Compound 8: A mixture of A-9 (150.00 mg, 770.73 μmol), A-7 (233.59 mg, 770.73 μmol), Cs₂CO₃ (502.24 mg, 1.54 mmol) and Pd(dppf)Cl₂.CH₂Cl₂ (62.94 mg, 77.07 μmol) in H₂O (500 μL) and dioxane (5 mL) was stirred at 90° C. for 12 hours. After cooling to room temperature, the mixture was diluted with EtOAc (10 mL), filtered through silica gel and eluted with EtOAc (10 mL×2), and the filtrated was concentrated to five a residue that was purified by prep-HPLC (Kromasil (150 mm×25 mm, 10 μm) A=H₂O (0.05% NH₄OH) and B=CH₃CN; 30-60% B over 8 minutes) to give Compound 8 (11.90 mg) as a solid. ¹H NMR (400 MHz, CDCl₃) δ$_H$=8.77 (d, 1H), 8.04 (dd, 1H), 8.15 (d, 1H), 7.47 (d, 1H), 7.06 (d1H), 4.87 (q, 2H), 2.65-2.53 (m, 1H), 1.50-1.39 (m, 2H), 1.29-1.22 (m, 2H). LCMS R$_t$=1.10 min using Method A, MS ESI calcd. for C₁₅H₁₃F₃N₅O [M+H]⁺ 336.1, found 336.1.

Example 9: Synthesis of Compound 9

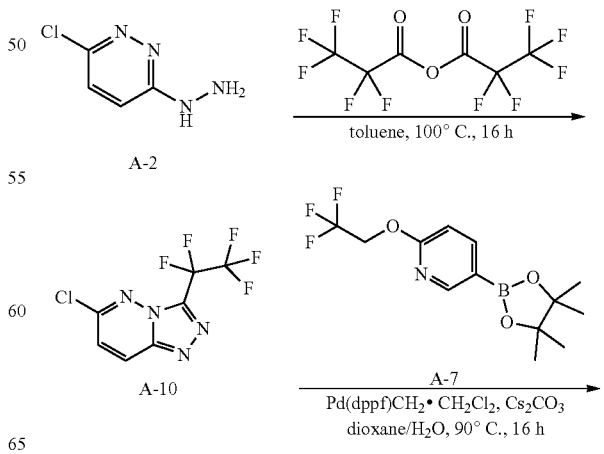

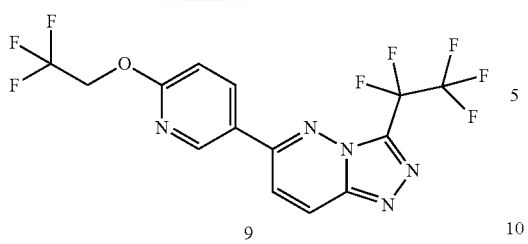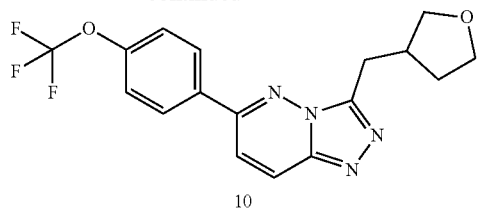

Synthesis of A-10: A mixture of A-2 (200.00 mg, 1.38 mmol) and 2,2,3,3,3-pentafluoropropanoyl 2,2,3,3,3-pentafluoropropanoate (327.03 μL, 1.66 mmol) in toluene (10 mL) was stirred at 100° C. for 16 hours. The mixture was concentrated, diluted with H$_2$O (10 mL), basified with solid NaHCO$_3$ to pH9, extracted with EtOAc (30 mL×2), and the combined organic phase was washed with brine (10 mL), dried over Na$_2$SO$_4$, filtered and concentrated to give A-10 as a solid. LCMS R$_t$=0.76 min using Method B, MS ESI calcd. for C$_7$H$_3$ClF$_5$N$_4$ [M+H]$^+$ 273.0, found 272.9.

Synthesis of Compound 9: A mixture of A-10 (130.00 mg, 476.96 μmol), A-7 (173.47 mg, 572.35 μmol), Cs$_2$CO$_3$ (310.81 mg, 953.92 μmol) and Pd(dppf)Cl$_2$.CH$_2$Cl$_2$ (38.95 mg, 47.70 μmol) in dioxane (10 mL) and H$_2$O (1 mL) was stirred at 90° C. for 16 hours. The mixture was diluted with EtOAc (10 mL), filtered through silica gel and eluted with EtOAc (10 m L×2). The filtrate was concentrated and the residue was purified by prep-HPLC (Kromasil (150 mm×25 mm, 10 μm) A=H$_2$O (0.05% NH$_4$OH) and B=CH$_3$CN; 45-75% B over 8 minutes to give Compound 9 (14.70 mg, 35.37 μmol) as a solid. $^1$H NMR (400 MHz, CDCl$_3$) δ$_H$=8.80 (d, 1H), 8.36 (d, 1H), 8.36 (d, 1H), 7.76 (d, 1H), 7.09 (d, 1H), 4.88 (q, 2H). LCMS R$_t$=1.18 min using Method A, MS ESI calcd. For C$_{14}$H$_8$F$_8$N$_5$O [M+H]$^+$ 414.1, found 414.0.

Example 10: Synthesis of Compound 10

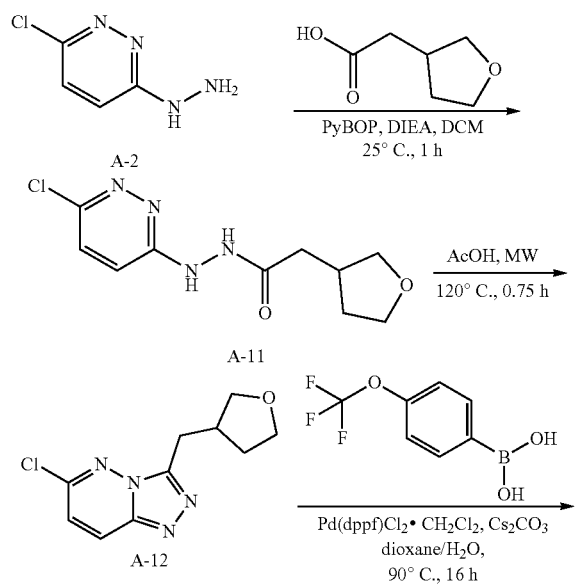

Synthesis of A-11: To a mixture of A-2 (100.00 mg, 691.75 μmol), PYBOP (539.97 mg, 1.04 mmol) in DCM (10.00 mL) was added 2-tetrahydrofuran-3-ylacetic acid (90.02 mg, 691.75 μmol) and DIPEA (362.44 μL, 2.08 mmol), and the mixture was stirred at 25° C. for 1 hour. The mixture was concentrated to give crude A-11 (800.00 mg), which was used directly without any further purification. LCMS R$_t$=0.18 min using Method B, MS ESI calcd. For C$_{10}$H$_{14}$ClN$_4$O$_2$ [M+H]$^+$ 257.1, found 257.0.

Synthesis of A-12: A mixture of A-11 (800.00 mg, 3.12 mmol, 1.00 eq) in AcOH (5 mL) was stirred at 120° C. for 0.75 hour in a microwave reactor. The mixture was concentrated, diluted with H$_2$O (10 mL), basified with solid NaHCO$_3$ to pH ~9, extracted with EtOAc (30 mL×2), and the combined organic phase was washed with brine (10 mL), dried over Na$_2$SO$_4$, filtered and concentrated to give the crude product that was purified by flash chromatography on silica gel (MeOH in DCM=0% to 3% to 5%) to give A-12 (180.00 mg) as an oil. LCMS R$_t$=0.68 min using Method B, MS ESI calcd. For C$_{10}$H$_{12}$ClN$_4$O [M+H]$^+$ 239.1, found 239.0.

Synthesis of Compound 10: A mixture of A-12 (180.00 mg, 754.18 μmol), [4-(trifluoromethoxy)phenyl]boronic acid (186.37 mg, 905.02 μmol), Pd(dppf)Cl$_2$.CH$_2$Cl$_2$ (61.59 mg, 75.42 μmol) and Cs$_2$CO$_3$ (491.45 mg, 1.51 mmol) in dioxane (5 mL) and H$_2$O (500 μL) was stirred at 90° C. for 16 hours. The mixture was concentrated and the residue purified by prep-TLC (silica gel, DCM:EtOAc=3:2) to Compound 10 (15.20 mg) as a solid. $^1$H NMR (400 MHz, CDCl$_3$) δ$_H$=8.19 (d, 1H), 8.04 (d, 2H), 7.55 (d, 1H), 7.42 (br d, 2H), 4.06-3.93 (m, 2H), 3.83 (q, 1H), 3.69 (dd, 1H), 3.37 (d, 2H), 3.11-2.96 (m, 1H), 2.25-2.12 (m, 1H), 1.91-1.76 (m, 1H). LCMS R$_t$=1.10 min using Method A, MS ESI calcd. For C$_{17}$H$_{16}$F$_3$N$_4$O$_2$ [M+H]$^+$ 365.1, found 365.3.

Example 11: Synthesis of Compound 11

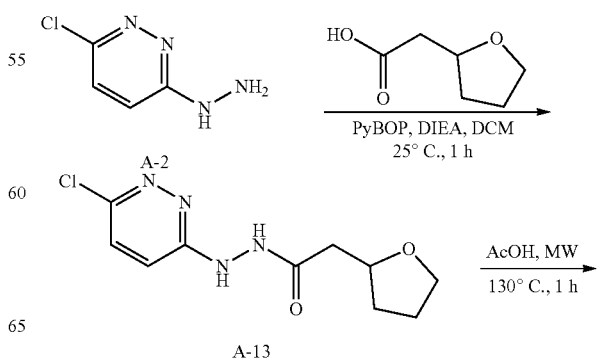

169

-continued

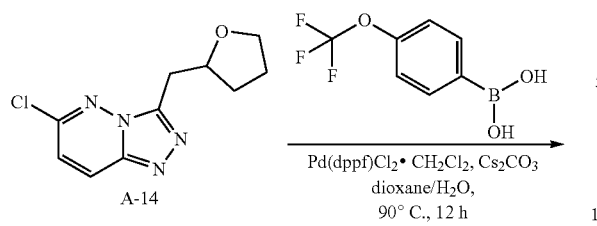

Example 12: Synthesis of Compound 12

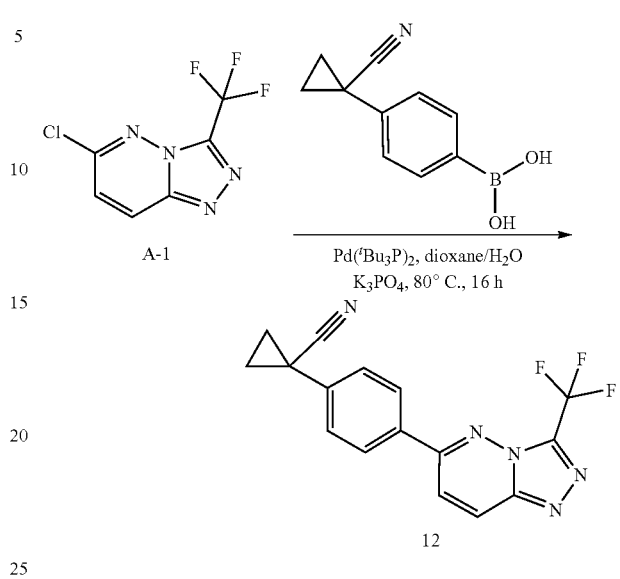

Synthesis of A-13: To a mixture of A-2 (83.00 mg, 574.16 µmol) and 2-tetrahydrofuran-2-ylacetic acid (74.72 mg, 574.16 µmol) in DCM (10 mL) was added PYBOP (448.18 mg, 861.23 µmol) and DIPEA (601.66 µL, 3.44 mmol), and the mixture was stirred at 25° C. for 16 hour. The mixture was concentrated to give A-13, which was used for next step without further purification. LCMS $R_t$=0.25 min using Method B, MS ESI calcd. For $C_{10}H_{14}ClN_4O_2$ [M+H]$^+$ 257.1, found 256.9.

Synthesis of A-14: A mixture of A-13 (800.00 mg, 3.12 mmol, 1.00 eq) in AcOH (6 mL) was stirred at 130° C. for 1 hour in microwave reactor. The mixture was concentrated, diluted with $H_2O$ (10 mL), basified with solid $NaHCO_3$ to pH~9, extracted with EtOAc (30 mL×2), and the combined organic phase was washed with brine (10 mL), dried over $Na_2SO_4$, filtered and concentrated to give a residue that was purified by flash chromatography on silica gel (MeOH in DCM=0% to 3% to 5%) to give A-14 (100.00 mg as an oil. LCMS $R_t$=0.66 min using Method B, MS ESI calcd. For $C_{10}H_{12}ClN_4O$ [M+H]$^+$ 239.1, found 239.0.

Synthesis of Compound 11: A mixture of A-14 (100.00 mg, 418.99 µmol), 4-(trifluoromethoxy)phenylboronic acid (103.54 mg, 502.79 µmol), Pd(dppf)Cl$_2$·CH$_2$Cl$_2$ (34.22 mg, 41.90 µmol) and Cs$_2$CO$_3$ (273.03 mg, 837.98 µmol) in dioxane (5 mL) and H$_2$O (500 µL) was stirred at 90° C. for 12 hour. The mixture was diluted with EtOAc (10 mL), and filtered through silica gel. The filtrate was concentrated and the residue was purified by prep-HPLC (Kromasil (150 mm×25 mm, 10 µm) A=H$_2$O (0.05% NH$_4$OH) and B=CH$_3$CN; 35-65% B over 8 minutes) to give Compound 11 (24.30 mg, 66.70 µmol) as a solid. $^1$H NMR (400 MHz, CDCl$_3$) δ$_H$=8.18 (d, 1H), 8.04 (d, 2H), 7.53 (d, 1H), 7.41 (d, 2H), 4.61 (quin, 1H), 4.02-3.90 (m, 1H), 3.85-3.74 (m, 1H), 3.60 (dd, 1H), 3.42 (dd, 1H), 2.20-2.08 (m, 1H), 2.06-1.91 (m, 2H), 1.89-1.77 (m, 1H). LCMS $R_t$=1.11 min using Method A, MS ESI calcd. For $C_{17}H_{16}F_3N_4O_2$ [M+H]$^+$ 365.1, found 365.0.

A mixture of A-1 (100.00 mg, 449.32 µmol), 4-(1-cyano-cyclopropyl)-phenylboronic acid (84.02 mg, 449.32 µmol), Pd(t-Bu$_3$P)$_2$ (45.92 mg, 89.86 µmol) and K$_3$PO$_4$ (190.75 mg, 898.64 µmol) in dioxane (8 mL) and H$_2$O (900 µL) was stirred at 80° C. for 16 hours under N. The mixture was concentrated and the residue purified by prep-TLC (silica gel, DCM:EtOAc=2:1) to give Compound 12 (73.82 mg, 224.19 µmol) as a solid. $^1$H NMR (400 MHz, CDCl$_3$) δ$_H$=8.32 (d, 1H), 8.03 (d, 2H), 7.77 (d, 1H), 7.50 (d, 2H), 1.91-1.85 (m, 2H), 1.55-1.50 (m, 2H). LCMS $R_t$=1.09 min using Method A, MS ESI calcd. for $C_{16}H_{11}F_3N_5$ [M+H]$^+$ 330.1, found 330.1.

Example 13: Synthesis of Compound 13

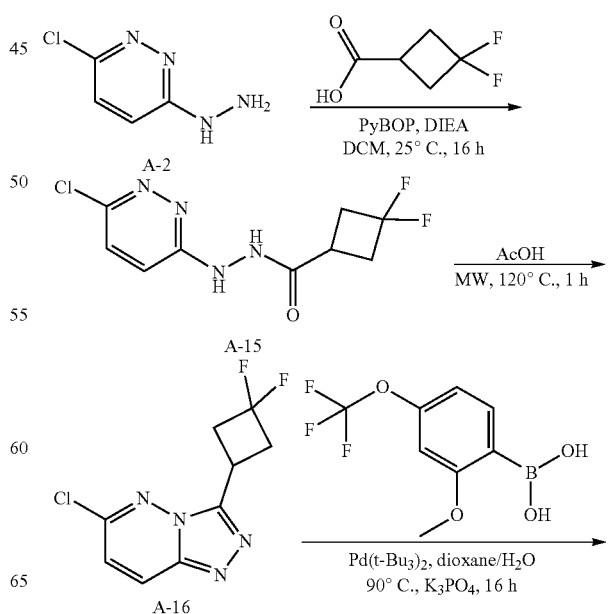

-continued

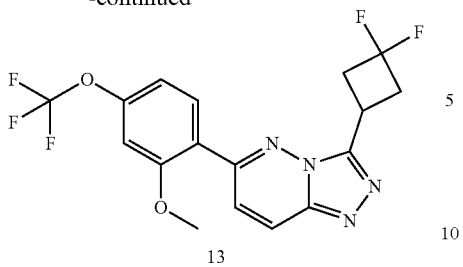

13

-continued

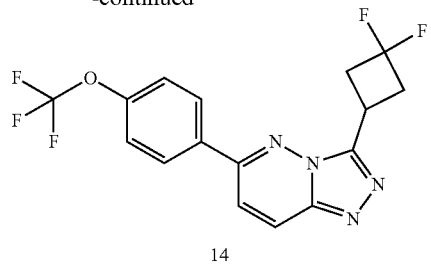

14

Synthesis of A-15: To a mixture of A-2 (400.00 mg, 2.77 mmol), 3,3-difluorocyclobutanecarboxylic acid (414.70 mg, 3.05 mmol) in DCM (30 mL) was added PYBOP (2.16 g, 4.16 mmol) and DIPEA (1.45 mL, 8.31 mmol), and the mixture was stirred at 25° C. for 16 hours. The reaction mixture was concentrated, diluted with NH$_4$Cl (30 mL), and extracted with EtOAc (40 mL×2). The combined organic phase was washed with brine (20 mL), dried over Na$_2$SO$_4$, filtered and concentrated to give crude A-15 (2.45 g) as an oil. LCMS R$_t$=0.40 min using Method B, MS ESI calcd. for C$_9$H$_{10}$ClF$_2$N$_4$O [M+H]$^+$ 263.0, found 262.9.

Synthesis of A-16: A solution of A-15 (2.45 g, 9.33 mmol) in AcOH (5 mL) was sealed and heated in microwave reactor at 120° C. for 1 hour. After cooling to room temperature, the reaction mixture was concentrated, diluted with sat.NaHCO$_3$ (50 mL), and extracted with DCM (50 mL×2). The combined organic phase was washed with brine (20 mL), dried over Na$_2$SO$_4$, filtered and concentrated to give a residue that was purified by flash chromatography on silica gel (silica gel, PE:EtOAc=5:1 to 1:1 to 1:2) to afford A-16 (500.00 mg, 2.04 mmol) as a solid. $^1$H NMR (400 MHz, DMSO-d$_6$) δ$_H$=8.45 (d, 1H), 7.50 (d, 1H), 3.98-3.87 (m, 1H), 3.23-3.12 (m, 4H).

Synthesis of Compound 13: A mixture of A-16 (100.00 mg, 408.78 μmol), [2-methoxy-4-(trifluoromethoxy)phenyl]boronic acid (96.45 mg, 408.78 μmol), Pd(t-Bu$_3$P)$_2$ (41.78 mg, 81.76 μmol) and K$_3$PO$_4$ (173.54 mg, 817.56 μmol) in dioxane (4 mL) and H$_2$O (400 μL) was stirred under N$_2$ at 90° C. for 16 hours. The mixture was cooled to room temperature, diluted with EtOAc (20 mL), filtered through silica gel and eluted with EtOAc (10 mL), and concentrated to give a residue that was purified by prep-HPLC (Kromasil (150 mm×25 mm, 10 μm) A=H$_2$O (0.05% NH$_4$OH) and B=CH$_3$CN; 46-76% B over 10 minutes to afford Compound 13 (100.70 mg, 246.83 μmol) as a solid. $^1$H NMR (400 MHz, CDCl$_3$) δ$_H$=8.07 (d, 1H), 7.71 (d, 1H), 7.58 (d, 1H), 7.05-6.98 (m, 1H), 6.91 (s, 1H), 4.07-3.96 (m, 1H), 3.93 (s, 3H), 3.40-3.25 (m, 2H), 3.22-3.09 (m, 2H). LCMS R$_t$=1.17 min using Method A, MS ESI calcd. for C$_{17}$H$_{14}$F$_5$N$_4$O$_2$ [M+H]$^+$ 401.1, found 401.0.

Example 14: Synthesis of Compound 14

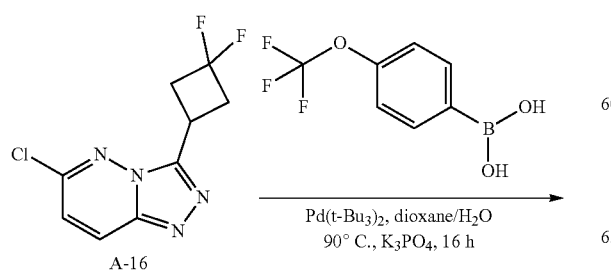

A mixture of A-16 (100.00 mg, 408.78 μmol), 4-(trifluoromethoxy)phenyl-boronic acid (84.18 mg, 408.78 μmol), K$_3$PO$_4$ (173.54 mg, 817.56 μmol) and Pd(t-Bu$_3$P)$_2$ (41.78 mg, 81.76 μmol) in dioxane (8 mL) and H$_2$O (800 μL) was stirred under N$_2$ at 90° C. for 16 hours. The mixture was cooled to room temperature and the mixture was concentrated a residue that was purified by prep-HPLC (Xtimate C$_{18}$ (150 mm×25 mm, 5 μm); A=H$_2$O (0.05% NH$_4$OH) and B=CH$_3$CN; 44-74% B over 10 minutes) to afford Compound 14 (78.40 mg, 207.43 μmol) as a solid. $^1$H NMR (400 MHz, CDCl$_3$) δ$_H$=8.21 (d, 1H), 8.04 (d, 2H), 7.58 (d, 1H), 7.42 (d, 2H), 4.07 (dquin, 1H), 3.43-3.29 (m, 2H), 3.25-3.14 (m, 2H). LCMS R$_t$=1.17 min using Method A, MS ESI calcd. for C$_{16}$H$_{12}$F$_5$N$_4$O [M+H]$^+$ 371.1, found 370.9.

Example 15: Synthesis of Compound 15

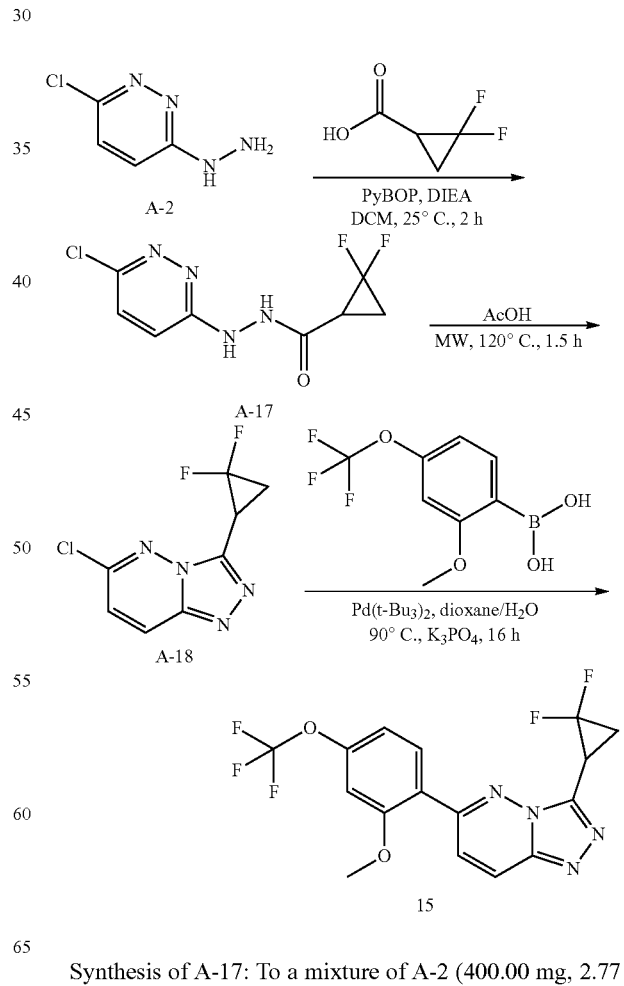

Synthesis of A-17: To a mixture of A-2 (400.00 mg, 2.77 mmol), 2,2-difluorocyclopropanecarboxylic acid (371.55 mg, 3.04 mmol) in DCM (30 mL) was added PYBOP (2.16 g, 4.15 mmol) and DIPEA (1.45 mL, 8.30 mmol), and the mixture was stirred at 25° C. for 2 hours. The reaction mixture was concentrated, diluted with NH$_4$Cl (50 mL), extracted with EtOAc (50 mL×2), and the combined organic phase was washed with brine (20 mL), dried over Na$_2$SO$_4$, filtered and concentrated to give A-17 (3.43 g, crude) as an oil. LCMS R$_t$=0.18 min using Method B, MS ESI calcd. for C$_8$H$_8$ClF$_2$N$_4$O [M+H]$^+$ 249.0, found 248.9.

Synthesis of A-18: A solution of A-17 (3.30 g, 13.27 mmol) in AcOH (5 mL) was sealed and heated in microwave reactor at 120° C. for 1.5 hours. After cooling to room temperature, the reaction mixture was concentrated, diluted with sat.NaHCO$_3$ (50 mL), and extracted with DCM (50 mL×2). The combined organic phase was washed with brine (20 mL), dried over Na$_2$SO$_4$, filtered and concentrated to give a residue that was purified by flash chromatography on silica gel (PE:EtOAc=5:1 to 1:1) to afford A-18 (300.00 mg, 1.30 mmol) as a solid. $^1$H NMR (400 MHz, CDCl$_3$) $\delta_H$=8.09 (d, 1H), 7.15 (d, 1H), 3.24 (ddd, 1H), 2.66-2.55 (m, 1H), 2.22-2.02 (m, 1H).

Synthesis of Compound 15: A mixture of 2-methoxy-4-(trifluoromethoxy)phenyl-boronic acid (102.32 mg, 433.65 μmol), A-18 (100.00 mg, 433.65 μmol), Pd(t-Bu$_3$P)$_2$ (44.32 mg, 86.73 μmol) and K$_3$PO$_4$ (184.10 mg, 867.30 μmol) in dioxane (8 mL) and H$_2$O (800 μL) was stirred under N$_2$ at 90° C. for 16 hours. The mixture was cooled to room temperature, diluted with EtOAc (20 mL), filtered through silica gel, and eluted with EtOAc (10 mL). The filtrate was concentrated to give a residue that was purified by prep-HPLC (Xtimate C$_{18}$ (150 mm×25 mm, 5 μm); A=H$_2$O (0.05% NH$_4$OH) and B=CH$_3$CN; 42-72% B over 10 minutes) to afford Compound 15 (38.20 mg, 96.35 μmol) as a solid. $^1$H NMR (400 MHz, CDCl$_3$) $\delta_H$=8.07 (d, 1H), 7.77 (d, 1H), 7.60 (d, 1H), 7.05-6.99 (m, 1H), 6.92-6.89 (m, 1H), 3.93 (s, 3H), 3.36-3.24 (m, 1H), 2.69-2.58 (m, 1H), 2.20-2.08 (m, 1H). LCMS R$_t$=1.16 min using Method A, MS ESI calcd. for C$_{16}$H$_{12}$F$_5$N$_4$O$_2$ [M+H]$^+$ 387.1, found 387.0.

Example 16: Synthesis of Compound 16

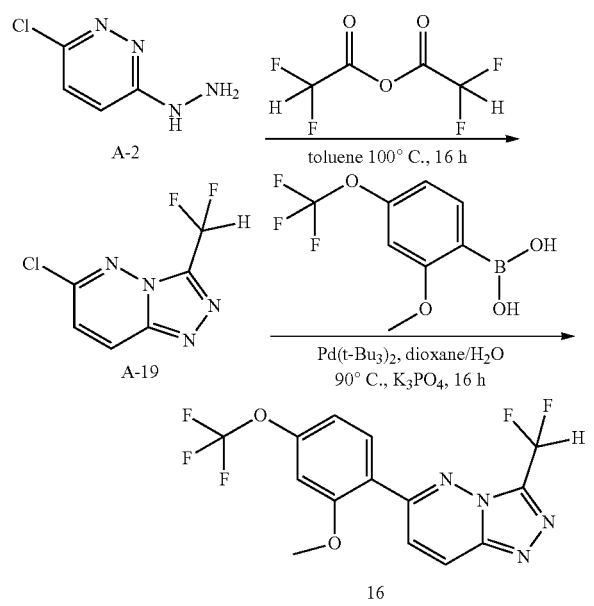

Synthesis of A-19: To a suspension of A-2 (500.00 mg, 3.46 mmol) in toluene (10 mL) was added (2,2-difluoroacetyl) 2,2-difluoroacetate (662.43 mg, 3.81 mmol) slowly. The reaction mixture was stirred at 110° C. for 16 hours. The reaction mixture was concentrated, diluted with sat.NaHCO$_3$ (30 mL), and the product was extracted with EtOAc (20 mL×2). The combined organic phase was washed with brine (10 mL), dried over Na$_2$SO$_4$, filtered and concentrated to give A-19 (600.00 mg, 2.91 mmol) as a solid. LCMS R$_t$=0.33 min using Method B, MS ESI calcd. for C$_6$H$_4$ClF$_2$N$_4$ [M+H]$^+$ 205.0, found 204.9.

Synthesis of Compound 16: A mixture of A-19 (100.00 mg, 488.85 μmol), [2-methoxy-4-(trifluoromethoxy)phenyl] boronic acid (115.35 mg, 488.85 μmol), Pd(t-Bu$_3$P)$_2$ (49.97 mg, 97.77 μmol) and K$_3$PO$_4$ (207.54 mg, 977.71 μmol) in H$_2$O (1 mL) and dioxane (5 mL) was stirred under N$_2$ at 90° C. for 16 hours. The mixture was cooled to room temperature, diluted with EtOAc (40 mL), filtered through silica gel, and eluted with EtOAc (10 mL). The filtrate was concentrated to give a residue that was purified by prep-HPLC (Xtimate C$_{18}$ (150 mm×25 mm, 5 μm); A=H$_2$O (0.05% NH$_4$OH) and B=CH$_3$CN; 39-69% B over 10 minutes) to afford Compound 16 (61.10 mg, 166.81 μmol) as a solid. $^1$H NMR (400 MHz, DMSO-d$_6$) $\delta_H$=8.52 (d, 1H), 7.92-7.53 (m, 3H), 7.30-7.27 (m, 1H), 7.21-7.14 (m, 1H), 3.91 (s, 3H). LCMS R$_t$=1.14 min using Method A, MS ESI calcd. for C$_{14}$H$_{10}$F$_5$N$_4$O$_2$ [M+H]$^+$ 361.1, found 360.9.

Example 17: Synthesis of Compound 17

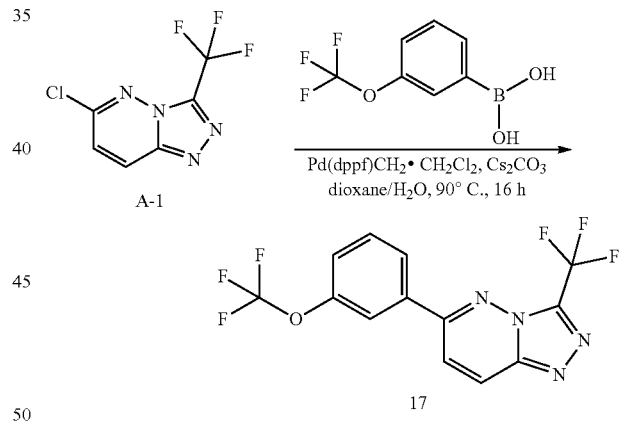

A mixture of A-1 (150.00 mg, 673.98 μmol), [3-(trifluoromethoxy)phenyl]-boronic acid (166.55 mg, 808.78 μmol), Cs$_2$CO$_3$ (439.19 mg, 1.35 mmol) and Pd(dppf)Cl$_2$.CH$_2$Cl$_2$ (82.56 mg, 101.10 μmol) in dioxane (3 mL) and H$_2$O (300 μL) under N$_2$ was stirred at 90° C. for 16 hours. The mixture was cooled to room temperature, diluted with EtOAc (30 mL), filtered through silica gel and eluted with EtOAc (10 mL). The filtrate was concentrated to a residue that was purified by prep-HPLC (Xtimate C$_{18}$ (150 mm×25 mm, 5 μm); A=H$_2$O (0.05% NH$_4$OH) and B=CH$_3$CN; 46-76% B over 10 minutes) to afford Compound 17 (50.28 mg, 142.96 μmol) as a solid. $^1$H NMR (400 MHz, CDCl$_3$) $\delta_H$=8.36 (d, 1H), 7.97 (d, 1H), 7.88 (s, 1H), 7.77 (d, 1H), 7.65 (t, 1H), 7.50-7.45 (m, 1H). LCMS R$_t$=1.19 min using Method A, MS ESI calcd. for C$_{13}$H$_7$F$_6$N$_4$O [M+H]$^+$ 349.0, found 348.9.

Example 18: Synthesis of Compound 18

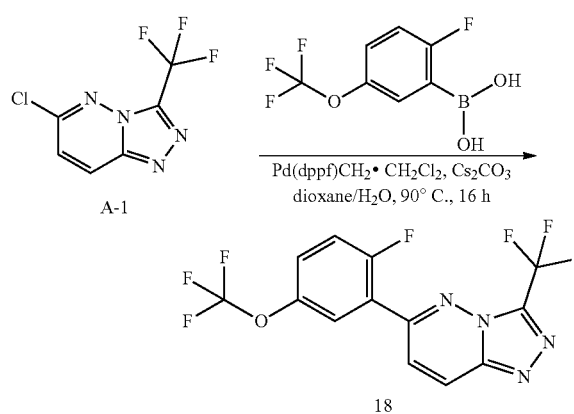

A mixture of A-1 (150.00 mg, 673.98 μmol), [2-fluoro-5-(trifluoromethoxy)phenyl]boronic acid (150.92 mg, 673.98 μmol) and $Cs_2CO_3$ (439.19 mg, 1.35 mmol) in dioxane (3 mL) and $H_2O$ (300 μL) was added Pd(dppf)$Cl_2 \cdot CH_2Cl_2$ (82.56 mg, 101.10 μmol) was stirred at 90° C. for 16 hours under $N_2$. After cooling to room temperature, the mixture was concentrated to give a residue that was purified by prep-TLC (silica gel, EtOAc:PE=1:2) to afford Compound 18 (22.78 mg, 62.21 μmol) as a solid. $^1$H NMR (400 MHz, CDCl$_3$) $\delta_H$=8.34 (d, 1H), 7.85-7.79 (m, 2H), 7.50-7.43 (m, 1H), 7.37-7.31 (t, 1H). LCMS $R_t$=1.19 min using Method A, MS ESI calcd. for $C_{13}H_6F_7N_4O$ [M+H]$^+$ 367.0, found 367.2.

Example 19: Synthesis of Compound 19

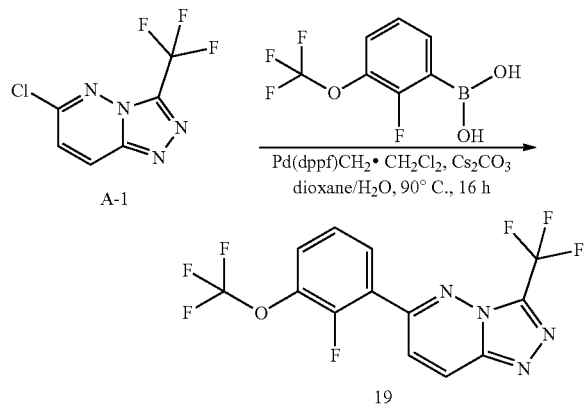

A mixture of A-1 (150.00 mg, 673.98 μmol), [2-fluoro-3-(trifluoromethoxy)phenyl]boronic acid (181.10 mg, 808.78 μmol), $Cs_2CO_3$ (439.19 mg, 1.35 mmol) and Pd(dppf)$Cl_2 \cdot CH_2Cl_2$ (82.56 mg, 101.10 μmol) in dioxane (3 mL) and $H_2O$ (300 μL) was stirred under nitrogen atmosphere at 90° C. for 16 hours. The mixture was diluted with EtOAc (15 mL), filtered through silica gel and eluted with EtOAc (15 mL×3). The filtrate was concentrated to give a residue that was purified by prep-TLC (silica gel, EtOAc:PE=1:2) and triturated from n-hexane (2 mL) to afford Compound 19 (21.69 mg, 57.90 μmol) as a solid. $^1$H NMR (400 MHz, CDCl$_3$) $\delta_H$=8.35 (d, 1H), 7.94-7.85 (m, 1H), 7.79 (dd, 1H), 7.58 (t, 1H), 7.45-7.39 (m, 1H). LCMS $R_t$=1.18 min using Method A, MS ESI calcd. for $C_{13}H_6F_7N_4O$ [M+H]$^+$367.0, found 366.9.

Example 20: Synthesis of Compound 20

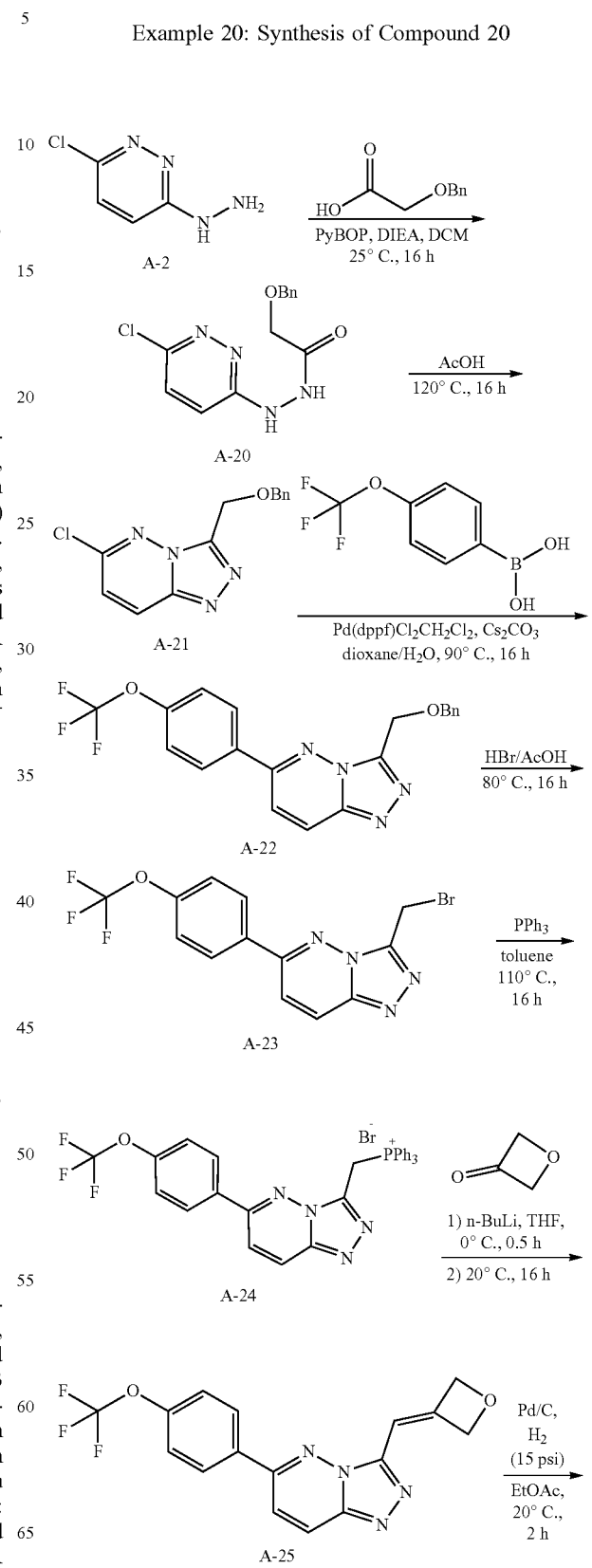

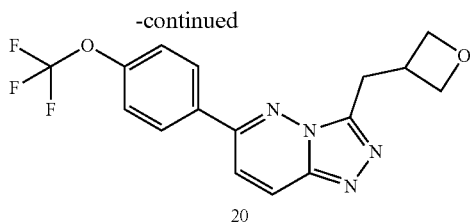

20

Synthesis of A-20: To a solution of A-2 (2.00 g, 13.84 mmol), 2-benzyloxyacetic acid (2.30 g, 13.84 mmol, 1.98 mL) and PYBOP (10.80 g, 20.76 mmol) in DCM (100 mL) was added DIPEA (7.25 mL, 41.52 mmol) and the mixture was stirred at 25° C. for 16 hour. The reaction mixture was concentrated, diluted with NH$_4$Cl (20 mL), extracted with EtOAc (30 mL×2), and the combined organic phase was washed with brine (15 mL), dried over Na$_2$SO$_4$, filtered, and concentrated to give crude A-20 (13.00 g) as an oil. LCMS R$_f$=0.67 min using Method B, MS ESI calcd. for C$_{13}$H$_{14}$ClN$_4$O$_2$ [M+H]$^+$ 293.1, found 293.0.

Synthesis of A-21: A mixture of A-20 (10.00 g, 34.16 mmol) in AcOH (50 mL) was stirred at 120° C. for 16 hours. After cooling to room temperature, the reaction mixture was concentrated, diluted with sat.NaHCO$_3$ (50 mL), extracted with EtOAc (80 mL×2), and the combined organic phase was washed with brine (20 mL), dried over Na$_2$SO$_4$, filtered, and concentrated to give a residue that was purified by flash chromatography on silica gel (PE:EtOAc=1:1 to 1:2) to afford A-21 (1.80 g, 5.71 mmol) as a solid. LCMS R$_f$=0.98 min using Method A, MS ESI calcd. for C$_{13}$H$_{12}$ClN$_4$O [M+H]$^+$ 275.1, found 274.9.

Synthesis of A-22: A mixture of A-21 (1.80 g, 6.55 mmol), [4-(trifluoromethoxy)phenyl]boronic acid (1.48 g, 7.20 mmol), Cs$_2$CO$_3$ (4.27 g, 13.10 mmol) and Pd(dppf)Cl$_2$·CH$_2$Cl$_2$ (802.64 mg, 982.50 µmol) in dioxane (30 mL) and H$_2$O (3 mL) was stirred at 90° C. for 16 hours. The mixture was cooled to room temperature, diluted with EtOAc (30 mL), filtered through silica gel, eluted with EtOAc (10 mL). The filtrate was concentrated to give a residue that was purified by flash chromatography on silica gel (PE:EtOAc=2:1 to 1:1) to afford A-22 (1.30 g, 2.88 mmol) as a solid. LCMS R$_f$=0.88 min using Method B, MS ESI calcd. for C$_{20}$H$_{16}$F$_3$N$_4$O$_2$ [M+H]$^+$ 401.1, found 401.1.

Synthesis of A-23: A mixture of A-22 (1.20 g, 3.00 mmol, 1.00 eq) in HBr/AcOH (10 mL) was stirred under N$_2$ at 80° C. for 16 hours. After cooling to room temperature, the mixture was concentrated, diluted with H$_2$O (30 mL), extracted by EtOAc (40 mL×2), and the combined organic phase was washed with brine (20 mL), dried over Na$_2$SO$_4$ filtered, and concentrated to give A-23 (800.00 mg) as a solid. LCMS R$_f$=0.83 min using Method B, MS ESI calcd. for C$_{13}$H$_8$BrF$_3$N$_4$O [M+H+2]$^+$375.0, found 375.0.

Synthesis of A-24: To a mixture of A-23 (1.10 g, 2.95 mmol) in toluene (20 mL) was added PPh$_3$ (773.74 mg, 2.95 mmol). The reaction was stirred at 110° C. for 16 hours. The reaction mixture was cooled and diluted with PE (20 mL), filtered, and dried to A-24 (800.00 mg) as a solid.

Synthesis of A-25: To a mixture of A-24 (700.00 mg, 1.10 mmol) in THF (10 mL) at 0° C. under N$_2$ was added n-BuLi (2.5 M, 528.00 µL), and the reaction mixture was stirred at 0° C. for 30 min. Oxetan-3-one (198.17 mg, 2.75 mmol) was then added, and the reaction mixture was stirred at 20° C. for 16 hours. The reaction was quenched with sat.NH$_4$Cl (10 mL), extracted with EtOAc (10 mL×3), and the combined organic phase was washed with brine (10 mL), dried over Na$_2$SO$_4$, filtered, and concentrated to give a residue that was purified by flash chromatography on silica gel (EtOAc in PE=30% to 50% to 80%) to afford A-25 (120.00 mg) as a solid. LCMS R$_f$=0.82 min using Method B, MS ESI calcd. for C$_{16}$H$_{12}$F$_3$N$_4$O$_2$ [M+H]$^+$349.1, found 349.1.

Synthesis of Compound 20: A mixture of A-25 (120.00 mg, 344.55 µmol) and wet Pd/C (50.00 mg) in EtOAc (10 mL) under N$_2$ was degassed and refilled with H$_2$. The reaction mixture was stirred under H$_2$ (15 psi) for 2 hours at 20° C. The reaction mixture was diluted with EtOAc (20 mL), filtered through a Celite pad, eluted with EtOAc (20 mL), and concentrated to give a residue that was purified by prep-HPLC (Xtimate C$_{18}$ (150 mm×25 mm, 5 µm); A=H$_2$O (0.05% NH$_4$OH) and B=CH$_3$CN; 27-57% B over 10 minutes) to afford Compound 20 (42.00 mg, 118.71 µmol) as a solid. $^1$H NMR (400 MHz, CDCl$_3$) δ$_H$=8.19 (d, 1H), 8.04 (d, 2H), 7.55 (d, 1H), 7.42 (d, 2H), 4.97 (t, 2H), 4.66 (t, 2H), 3.80-3.70 (m, 1H), 3.69-3.62 (m, 2H). LCMS R$_f$=0.76 min using Method B, MS ESI calcd. for C$_{16}$H$_{14}$F$_3$N$_4$O$_2$ [M+H]$^+$ 351.1, found 351.1.

Example 21: Synthesis of Compound 21

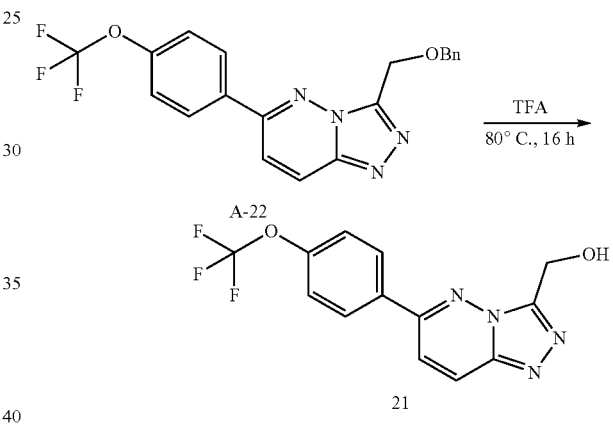

A mixture of A-21 (100.00 mg, 249.78 µmol) in TFA (3 mL) was stirred at 80° C. for 16 hours. After cooling to room temperature, the mixture was concentrated to give a residue that was purified by prep-HPLC (Xtimate C$_{18}$ (150 mm×25 mm, 5 µm); A=H$_2$O (0.05% NH$_4$OH) and B=CH$_3$CN; 22-52% B over 10 minutes) to afford Compound 21 (30.59 mg, 96.14 µmol) as a solid. $^1$H NMR (400 MHz, CDCl$_3$) δ$_H$=8.23 (d, 1H), 8.05 (d, 2H), 7.60 (d, 1H), 7.42 (d, 2H), 5.34 (d, 2H), 2.76 (t, 1H). LCMS R$_f$=0.99 min using Method A, MS ESI calcd. for C$_{13}$H$_{10}$F$_3$N$_4$O$_2$ [M+H]$^+$ 311.1, found 310.9.

Example 22: Synthesis of Compound 22

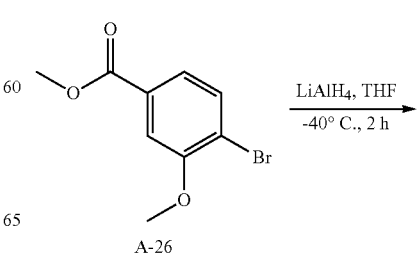

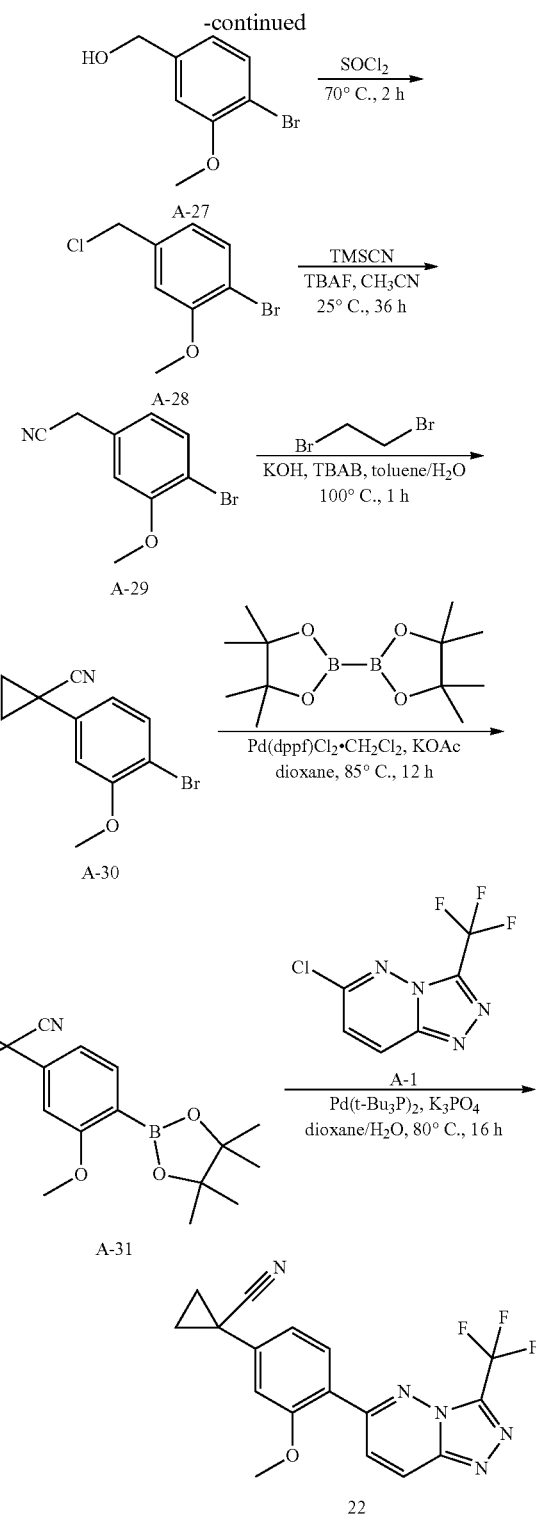

with water (30 mL×2) and brine (50 mL), dried over Na$_2$SO$_4$, filtered and concentrated to give A-27 (2.50 g, 11.52 mmol) as an oil. $^1$H NMR (400 MHZ DMSO-d$_6$) $\delta_H$=7.49 (d, 1H), 7.06 (s, 1H), 6.84 (d, 1H), 5.29 (t, 1H), 4.47 (d, 2H), 3.83 (s, 3H).

Synthesis of A-28: A mixture of A-27 (2.50 g, 11.52 mmol) in SOCl$_2$ (15 mL) was stirred at 70° C. for 2 hours. The mixture was concentrated, and the residue was diluted with EtOAc (150 mL). The organic phase was washed with water (30 mL) and brine (30 mL), dried over Na$_2$SO$_4$, filtered and concentrated to give A-28 (2.60 g, 11.04 mmol) as an oil. $^1$H NMR (400 MHz DMSO-d$_6$) $\delta_H$=7.57 (d, 1H), 7.20 (d, 1H), 6.97 (dd, 1H), 4.74 (s, 2H), 3.86 (s, 3H).

Synthesis of A-29: To a mixture of A-28 (2.60 g, 11.04 mmol) in CH$_3$CN (30 mL) was added TMSCN (2.08 mL, 16.56 mmol) and TBAF (1 M, 16.56 mL), and the mixture was stirred at 25° C. for 36 hours. The mixture was diluted with H$_2$O (50 mL) and extracted with EtOAc (100 mL×2), and the combined organic phase was washed with water (30 mL×2) and brine (50 mL), dried over Na$_2$SO$_4$, filtered and concentrated to give a residue that was purified by flash chromatography on silica gel (EtOAc in PE=5% to 10% to 15%) to afford A-29 (2.15 g, 9.51 mmol) as an oil. $^1$H NMR (400 MHz, CDCl$_3$) $\delta_H$=7.54 (d, 1H), 6.87 (d, 1H), 6.81 (dd, 1H), 3.93 (s, 3H), 3.74 (s, 2H).

Synthesis of A-30: To a mixture of A-29 (2.00 g, 8.85 mmol), TBAB (114.08 mg, 353.87 μmol), KOH (4.96 g, 88.47 mmol) in toluene (40 mL) and H$_2$O (4 mL) was added 1,2-dibromoethane (1.33 mL, 17.69 mmol) at 100° C., and the mixture was stirred at 100° C. for 1 hour. The mixture was diluted with EtOAc (150 mL), then washed with water (30 mL×2) and brine (30 mL), dried over Na$_2$SO$_4$, filtered and concentrated to give a residue that was purified by flash chromatography on silica gel (EtOAc in PE=5% to 10%) to afford A-30 (1.72 g) as a solid. $^1$H NMR (400 MHz CDCl$_3$) $\delta_H$=7.49 (d, 1H), 6.93 (d, 1H), 6.67 (dd, 1H), 3.93 (s, 3H), 1.79-1.72 (m, 2H), 1.45-1.38 (m, 2H).

Synthesis of A-31: A mixture of A-30 (500 mg, 1.98 mmol), 4,4,5,5-tetramethyl-2-(4,4,5,5-tetramethyl-1,3,2-dioxaborolan-2-yl)-1,3,2-dioxaborolane (1.51 g, 5.94 mmol), Pd(dppf)Cl$_2$.CH$_2$Cl$_2$ (242.54 mg, 297.00 μmol) and KOAc (388.63 mg, 3.96 mmol) in dioxane (25 mL) was stirred 85° C. for 12 hours under N$_2$. After cooling to room temperature, the mixture was concentrated, diluted with H$_2$O (30 mL), and extracted with EtOAc (100 mL×2). The combined organic phase was washed with water (20 mL×2) and brine (20 mL), dried over Na$_2$SO$_4$, filtered and concentrated to give a residue that was purified by flash chromatography on silica gel (EtOAc in PE=1% to 5% to 10%) to afford A-31 (510.00 mg) as an oil. $^1$H NMR (400 MHz CDCl$_3$) $\delta_H$=7.64 (d, 1H), 6.87 (d, 1H), 6.73 (dd, 1H), 3.87 (s, 3H), 1.78-1.72 (m, 2H), 1.47-1.41 (m, 2H), 1.35 (s, 12H).

Synthesis of Compound 22: A mixture of A-31 (403.27 mg, 1.35 mmol), A-1 (150.00 mg, 673.98 μmol), Pd(t-Bu$_3$P)$_2$ (51.67 mg, 101.10 μmol) and K$_3$PO$_4$ (286.13 mg, 1.35 mmol) in dioxane (10 mL) and H$_2$O (1.35 mL) was stirred at 80° C. for 16 hours in a 20 mL sealed tube under N$_2$. After cooling to room temperature, the mixture was concentrated, diluted with H$_2$O (20 mL), and extracted with EtOAc (50 mL×2). The combined organic phase was washed with water (20 mL×2) and brine (20 mL), dried over Na$_2$SO$_4$, filtered and concentrated to give a residue that was purified by prep-TLC (silica gel, EtOAc:DCM=1:2) to afford Compound 22 (147.51 mg) as a solid. $^1$H NMR (400 MHz, CDCl$_3$) $\delta_H$=8.18 (d, 1H), 7.83 (d, 1H), 7.74 (d, 1H), 7.16 (s, 1H), 6.89 (d, 1H), 3.97 (s, 3H), 1.90-1.81 (m, 2H), Synthesis of A-27: To a mixture of A-26 (3.00 g, 12.24 mmol) in THF (40 mL) was added LiAlH$_4$ (1.39 g, 36.72 mmol) at −40° C. under N$_2$, and the mixture was stirred at −40° C. for 2 hours. To the mixture was added H$_2$O (1.76 g) dropwise at −40° C., and the mixture was stirred at 0° C. for 0.5 hour, followed by stirring at 50° C. for 0.5 hour. The mixture was then filtered through Celite, eluted by THF (100 mL×2), concentrated, dissolved in EtOAc (200 mL), washed 1.56-1.49 (m, 2H). LCMS $R_t$=1.11 min using Method A, MS ESI calcd. for $C_{17}H_{13}F_3N_5O$ [M+H]$^+$ 360.1, found 360.0.

Example 23: Synthesis of Compound 23

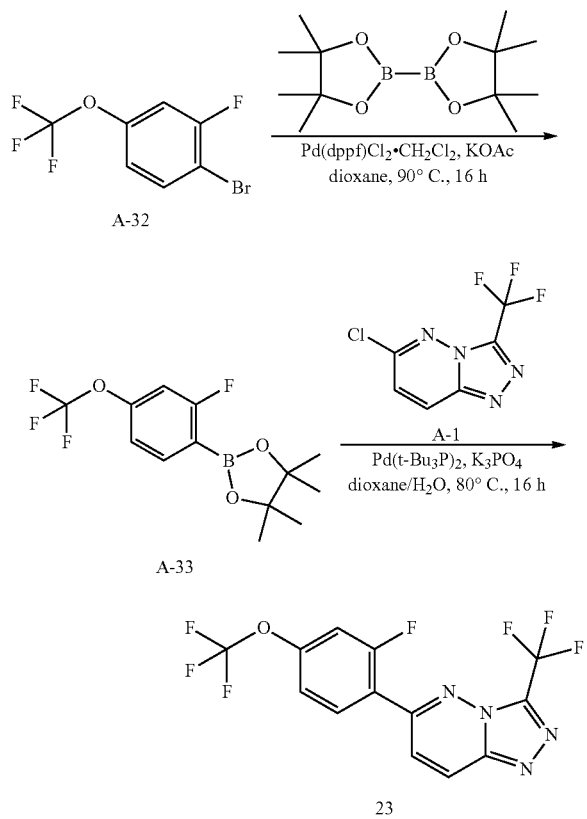

Synthesis of A-33: A mixture of A-32 (1.25 g, 4.83 mmol), 4,4,5,5-tetramethyl-2-(4,4,5,5-tetramethyl-1,3,2-dioxaborolan-2-yl)-1,3,2-dioxaborolane (3.68 g, 14.48 mmol), Pd(dppf)Cl$_2$.CH$_2$Cl$_2$ (394.13 mg, 482.63 µmol) and KOAc (947.30 mg, 9.65 mmol) in dioxane (30 mL) was stirred at 90° C. for 16 hours. After cooling to room temperature, the mixture was diluted with EtOAc (50 mL), filtered through silica gel, and concentrated to give a residue that was purified by flash chromatography on silica gel (EtOAc in PE=0% to 1%) to afford A-32 (1.29 g) as an oil. $^1$H NMR (400 MHz CDCl$_3$) $\delta_H$=7.78 (dd, 1H), 7.01 (d, 1H), 6.93 (d, 1H), 1.37 (s, 12H).

Synthesis of Compound 23: A mixture of A-33 (275.04 mg, 898.64 µmol), A-1 (100.00 mg, 449.32 µmol), Pd(t-Bu$_3$P)$_2$ (45.92 mg, 89.86 µmol), K$_3$PO$_4$ (190.75 mg, 898.64 µmol) in dioxane (8 mL) and H$_2$O (1 mL) was stirred at 80° C. for 16 hours. After cooling to room temperature, the mixture was concentrated to give a residue that was purified by prep-HPLC (Xtimate C$_{18}$ (150 mm×25 mm, 5 µm); A=H$_2$O (0.05% NH$_4$OH) and B=CH$_3$CN; 45-75% B over 10 minutes) to afford Compound 23 (107.00 mg) as a solid. $^1$H NMR (400 MHz DMSO-d$_6$) $\delta_H$=8.73 (d, 1H), 8.02-7.96 (m, 2H), 7.72 (br d, 1H), 7.53 (br d, 1H). LCMS $R_t$=1.197 min using Method A, MS ESI calcd. for $C_{13}H_6F_7N_4O$ [M+H]$^+$ 367.0, found 366.9.

Example 24: Synthesis of Compound 24

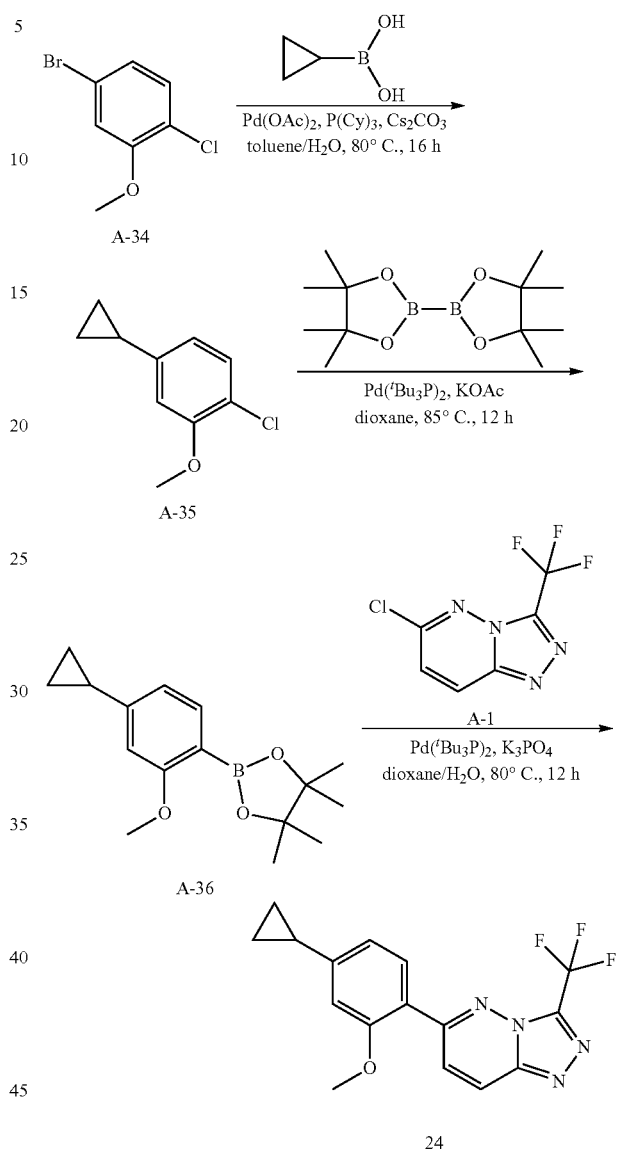

Synthesis of A-35: A mixture of cyclopropylboronic acid (1.94 g, 22.58 mmol), A-34 (3.07 mL, 22.58 mmol), Pd(OAc)$_2$ (506.84 mg, 2.26 mmol), Cs$_2$CO$_3$ (14.71 g, 45.16 mmol) and P(Cy)$_3$ (1.82 mL, 5.65 mmol) in H$_2$O (8 mL) and toluene (80 mL) was stirred at 80° C. for 16 hours under N$_2$. After cooling to room temperature, the mixture was washed with water (20 mL) and brine (20 mL), dried over Na$_2$SO$_4$, filtered and concentrated to give a residue that was purified by flash chromatography on silica gel (EtOAc in PE=0% to 1% to 2%) to afford A-35 (2.70 g, 14.78 mmol) as an oil. $^1$H NMR (400 MHz, CDCl$_3$) $\delta_H$=7.22 (d, 1H), 6.68 (d, 1H), 6.59 (dd, 1H), 3.90 (s, 3H), 1.93-1.84 (m, 1H), 1.02-0.94 (m, 2H), 0.72-0.66 (m, 2H).

Synthesis of A-36: A mixture of A-35 (2.29 g, 9.03 mmol), A-1 (550.00 mg, 3.01 mmol), KOAc (679.42 mg, 6.92 mmol) and Pd($^t$Bu$_3$P)$_2$ (153.89 mg, 301.00 µmol) in dioxane (25 mL) was stirred at 85° C. for 12 hours under N$_2$. The mixture was concentrated, diluted with H$_2$O (30 mL), and extracted with EtOAc (50 mL×2). The combined organic phase was washed with water (20 mL×2) and brine (20 mL), dried over Na₂SO₄, filtered and concentrated to give a residue that was purified by flash chromatography on silica gel (EtOAc in PE=0% to 1% to 2%) to afford A-36 (350.00 mg) as a solid. ¹H NMR (400 MHZ CDCl₃) $\delta_H$=7.58 (d, 1H), 6.67-6.58 (m, 2H), 3.83 (s, 3H), 1.96-1.84 (m, 1H), 1.34 (s, 12H), 1.02-0.94 (m, 2H), 0.78-0.70 (m, 2H).

Synthesis of Compound 24: A mixture of A-36 (310.42 mg, 1.13 mmol), A-1 (140.00 mg, 629.04 μmol), Pd(t-Bu₃P)₂ (48.22 mg, 94.36 μmol) and K₃PO₄ (267.05 mg, 1.26 mmol) in dioxane (10 mL) and H₂O (1.35 mL) was stirred at 80° C. for 12 hours in a 20 mL sealed tube under N₂. The mixture was concentrated, diluted with H₂O (20 mL), and extracted with EtOAc (50 mL×2). The combined organic phase was washed with water (20 mL×2) and brine (20 mL), dried over Na₂SO₄, filtered and concentrated to give a residue that was purified by prep-TLC (silica gel, EtOAc: DCM=1:3) to afford Compound 24 (42.91 mg) as a solid. ¹H NMR (400 MHz, CDCl₃) $\delta_H$=8.13 (d, 1H), 7.85 (d, 1H), 7.66 (d, 1H), 6.85-6.76 (m, 2H), 3.91 (s, 3H), 2.04-1.93 (m, 1H), 1.14-1.04 (m, 2H), 0.85-0.77 (m, 2H). LCMS $R_t$=1.21 min using Method A, MS ESI calcd. for $C_{16}H_{14}F_3N_4O$ [M+H]⁺ 335.1, found 334.9.

Example 25: Synthesis of Compound 25

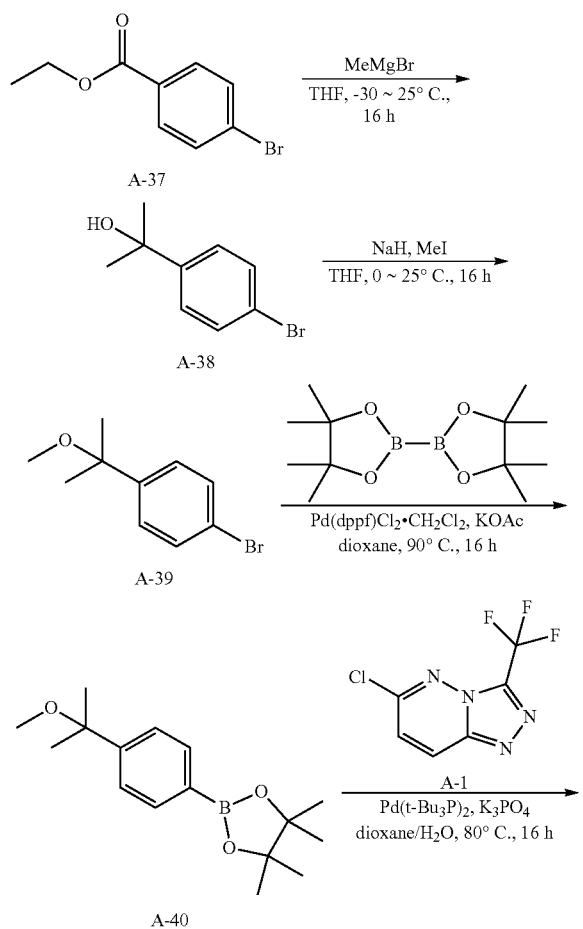

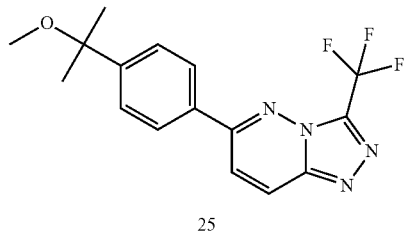

25

Synthesis of A-38: To a mixture of A-37 (2.14 mL, 13.10 mmol) in THF (80 mL) was added MeMgBr (3 M, 26.20 mL, 6.00 eq) dropwise at −30° C. The reaction mixture was allowed to warm to room temperature and stirred at 25° C. for 16 hours. The reaction was quenched with sat.NH₄Cl (200 mL), extracted with EtOAc (200 mL×2), and the combined organic layers were washed with H₂O (200 mL×2), brine (100 mL), dried over Na₂SO₄, filtered and concentrated to give A-38 (2.80 g, crude) as an oil. ¹H NMR (400 MHZ DMSO-d₆) $\delta_H$=7.50-7.44 (m, 2H), 7.44-7.38 (m, 2H), 5.10 (s, 1H), 1.40 (s, 6H).

Synthesis of A-39: To a mixture of A-38 (2.80 g, 13.02 mmol) in THF (30 mL) was added NaH (1.04 g, 26.04 mmol, 60% purity) and CH₃I (1.62 mL, 26.04 mmol) at 0° C. and the mixture was stirred at 25° C. for 16 hours. The mixture was quenched with a saturated solution of NH₄Cl (50 mL), extracted with EtOAc (100 mL×2), and the combined organic phase was washed with brine (30 mL), dried over Na₂SO₄, filtered and concentrated to A-39 (2.70 g, 11.78 mmol) as an oil. ¹H NMR (400 MHz CDCl₃) $\delta_H$=7.47 (d, 2H), 7.29 (d, 2H), 3.07 (s, 3H), 1.51 (s, 6H).

Synthesis of A-40: A mixture of A-39 (1.30 g, 5.67 mmol), 4,4,5,5-tetramethyl-2-(4,4,5,5-tetramethyl-1,3,2-dioxaborolan-2-yl)-1,3,2-dioxaborolane (4.32 g, 17.01 mmol), Pd(dppf)Cl₂·CH₂Cl₂ (695.06 mg, 850.50 μmol) and KOAc (1.11 g, 11.34 mmol) in dioxane (70 mL) was stirred at 90° C. for 16 hours. After cooling to room temperature, the mixture was diluted with EtOAc (100 mL), filtered through silica gel and eluted with EtOAc (100 mL×2). The filtrate was concentrated to give a residue that was purified by flash chromatography on silica gel (PE) to afford A-40 (950.00 mg, 3.44 mmol) as a solid. ¹H NMR (400 MHz CDCl₃) $\delta_H$=7.81 (d, 2H), 7.43 (d, 2H), 3.08 (s, 3H), 1.53 (s, 6H), 1.35 (s, 12H).

Synthesis of Compound 25: A mixture of A-40 (372.28 mg, 1.35 mmol), A-1 (150.00 mg, 673.98 μmol), Pd(t-Bu₃P)₂ (34.44 mg, 67.40 μmol) and K₃PO₄ (286.13 mg, 1.35 mmol) in dioxane (10 mL) and H₂O (1 mL) was stirred at 80° C. for 16 hours. After cooling to room temperature, the mixture was concentrated to give a residue that was purified by prep-TLC (silica gel, PE:EtOAc=2:1) and prep-HPLC (Xtimate C₁₈ (150 mm×25 mm, 5 μm); A=H₂O (0.05% NH₄OH) and B=CH₃CN; 55-85% B over 10 minutes) to afford Compound 25 (23.00 mg) as a solid. ¹H NMR (400 MHz, CDCl₃+D₂O) $\delta_H$=8.30 (d, 1H), 8.01 (d, 2H), 7.79 (d, 1H), 7.63 (d, 2H), 3.14 (s, 3H), 1.59 (s, 6H). LCMS $R_t$=1.14 min using Method A, MS ESI calcd. for $C_{16}H_{16}F_3N_4O$ [M+H]⁺ 337.1, found 336.9.

Example 26: Synthesis of Compound 26

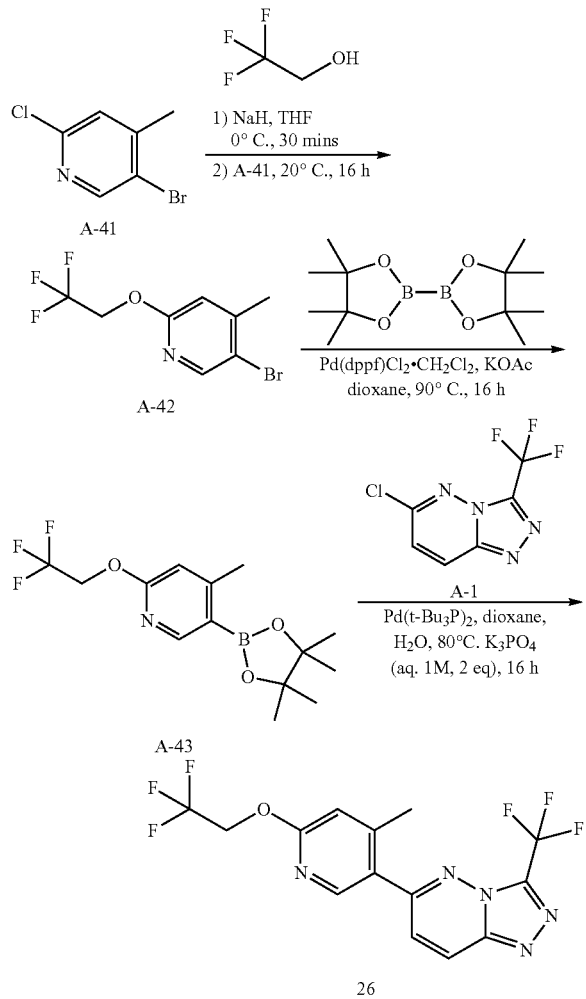

Synthesis of A-42: To a solution of 2,2,2-trifluoroethanol (522.51 µL, 7.26 mmol) was added NaH (290.40 mg, 7.26 mmol, 60% purity) in DMF (20 mL) at 0° C. slowly, and the mixture was stirred at 0° C. for 30 mins. Then to the mixture was added A-40 (1.00 g, 4.84 mmol), and the mixture was stirred at 20° C. for 16 hours. The reaction was quenched with a saturation solution of NH$_4$Cl (30 mL) and extracted with EtOAc (50 mL×2). The combined organic phase was washed with brine (30 mL), dried over Na$_2$SO$_4$, filtered, and concentrated to give a residue that was purified by flash chromatography on silica gel (EtOAc in PE=0% to 1%) to afford A-42 (900 mg) as an oil. LCMS R$_t$=0.89 min using Method B, MS ESI calcd. for C$_8$H$_8$BrF$_3$NO [M+H+2]$^+$ 272.0, found 271.9.

Synthesis of A-43: A mixture of A-42 (900 mg, 3.33 mmol), 4,4,5,5-tetramethyl-2-(4,4,5,5-tetramethyl-1,3,2-dioxaborolan-2-yl)-1,3,2-dioxaborolane (1.27 g, 5.00 mmol), KOAc (654.15 mg, 6.67 mmol) and Pd(dppf)Cl$_2$.CH$_2$Cl$_2$ (544.33 mg, 666.54 µmol) in dioxane (20 mL) was stirred at 90° C. for 16 hours. After cooling to room temperature, the mixture was diluted with H$_2$O (20 mL×3), and extracted with EtOAc (50 mL×2). The combined organic phase was washed with brine (50 mL), dried over Na$_2$SO$_4$, filtered and concentrated to give a residue that was purified by flash chromatography on silica gel (EtOAc in PE=0% to 1%) to afford A-43 (600 mg, 1.52 mmol) as an oil. $^1$H NMR (400 MHz, CDCl$_3$) δ$_H$=8.44 (s, 1H), 6.65 (s, 1H), 4.78 (q, 2H), 2.48 (s, 3H), 1.34 (s, 12H). LCMS R$_t$=0.98 min using Method B, MS ESI calcd. for C$_{14}$H$_{20}$BF$_3$NO$_3$ [M+H]$^+$ 318.1, found 318.4.

Synthesis of Compound 26: A mixture of A-43 (320.59 mg, 1.01 mmol), A-1 (150.00 mg, 673.98 µmol), Pd(t-Bu$_3$P)$_2$ (51.67 mg, 101.10 µmol) and K$_3$PO$_4$ (286.13 mg, 1.35 mmol) in dioxane (8 mL) and H$_2$O (1 mL) was stirred at 80° C. for 16 hours. After cooling to room temperature, the mixture was concentrated and purified by prep-TLC (silica gel, EtOAc:DCM=1:3) and prep-HPLC (Kromasil (150 mm×25 mm, 10 µm) A=H$_2$O (0.05% NH$_4$OH) and B=CH$_3$CN; 50-60% B over 8 minutes) to afford Compound 26 (24.13 mg, 63.43 µmol) as a solid. $^1$H NMR (400 MHz, CDCl$_3$) δ$_H$=8.36-8.30 (m, 2H), 7.51 (d, 1H), 6.92 (s, 1H), 4.85 (q, 2H), 2.53 (s, 3H). LCMS R$_t$=0.84 min using Method B, MS ESI calcd. for C$_{14}$H$_{10}$F$_6$N$_5$O [M+H]$^+$378.1, found 378.1.

Example 27: Synthesis of Compound 27

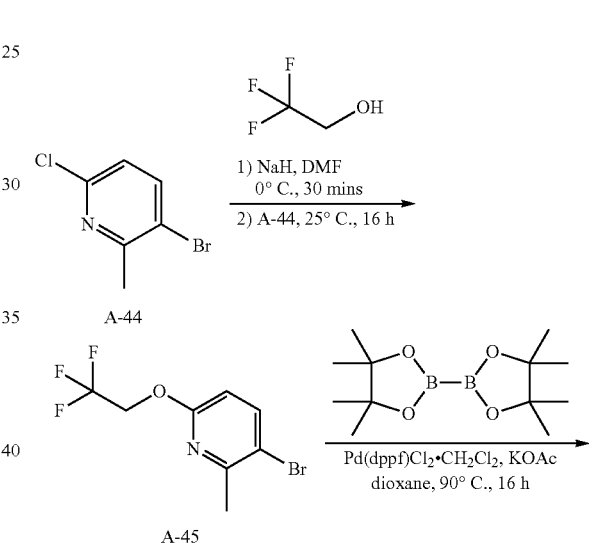

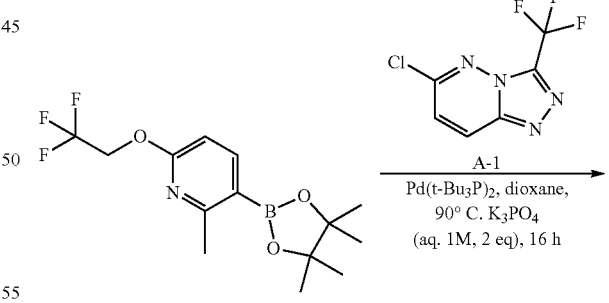

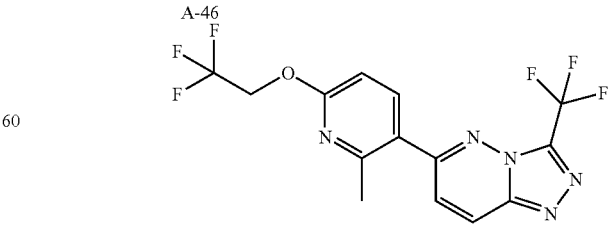

Synthesis of A-45: To a mixture of NaH (387.20 mg, 9.68 mmol, 60% purity) in DMF (20 mL) was added 2,2,2-trifluoroethanol (731.52 µL, 10.16 mmol) under $N_2$ at 0° C. and the mixture was stirred at 0° C. for 0.5 hour. Then 3-bromo-6-chloro-2-methyl-pyridine (1.00 g, 4.84 mmol) was added, and the mixture was stirred at 25° C. for 16 hours. The mixture was quenched with $NH_4Cl$ (80 mL) and extracted with EtOAc (40 mL×2). The combined organic was washed by brine (20 mL), dried over $Na_2SO_4$, filtered and concentrated to give a residue that was purified by flash chromatography on silica gel (PE) to give A-45 (500.00 mg, 1.85 mmol) as an oil. $^1$H NMR (400 MHz, $CDCl_3$) $\delta_H$=7.70 (d, 1H), 6.60 (d, 1H), 4.74 (q, 2H), 2.55 (s, 3H).

Synthesis of A-46: A-45 (200.00 mg, 740.60 µmol), 4,4,5,5-tetramethyl-2-(4,4,5,5-tetramethyl-1,3,2-dioxaborolan-2-yl)-1,3,2-dioxaborolane (564.20 mg, 2.22 mmol), Pd(dppf)$Cl_2$·$CH_2Cl_2$ (60.48 mg, 74.06 µmol) and KOAc (145.36 mg, 1.48 mmol) in dioxane (5 mL) was stirred under $N_2$ at 90° C. for 16 hours. The mixture was cooled to room temperature, diluted with EtOAc (10 mL), filtered through silica gel, eluted with EtOAc (10 mL) and the filtrate was concentrated to give a residue that was purified by flash chromatography on silica gel (PE:EtOAc=50:1) to afford A-46 (200.00 mgl) as an oil. $^1$H NMR (400 MHZ $CDCl_3$) $\delta_H$=7.97 (d, 1H), 6.64 (d, 1H), 4.80 (q, 2H), 2.65 (s, 3H), 1.34 (s, 12H).

Synthesis of Compound 27: A mixture of A-46 (170.98 mg, 539.18 µmol), A-1 (100.00 mg, 449.32 µmol), $K_3PO_4$ (190.75 mg, 898.64 µmol) and Pd(t-$Bu_3P)_2$ (45.92 mg, 89.86 µmol) in dioxane (6 mL) and $H_2O$ (1 mL) was stirred at 90° C. for 16 hours. The mixture was cooled to room temperature, diluted with EtOAc (20 mL), filtered and concentrated to give a residue that was purified by prep-HPLC (Xtimate $C_{18}$ (150 mm×25 mm, 5 µm); A=$H_2O$ (0.05% $NH_4OH$) and B=$CH_3CN$; 46-76% B over 10 minutes) to afford Compound 27 (53.15 mg, 138.45 µmol) as a solid. $^1$H NMR (400 MHz, $CDCl_3$) $\delta_H$=8.31 (d, 1H), 7.81 (d, 1H), 7.47 (d, 1H), 6.90 (d, 1H), 4.87 (q, 2H), 2.64 (s, 3H). LCMS $R_t$=3.42 min in using Method C, MS ESI calcd. for $C_{14}H_{10}F_6N_5O$ [M+H]$^+$ 378.1, found 377.9.

Example 28: Synthesis of Compound 28

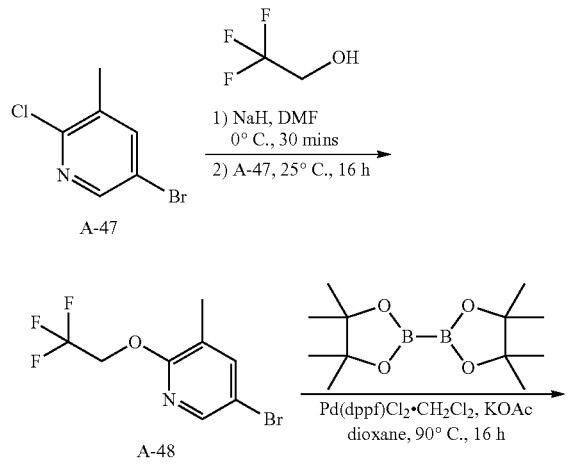

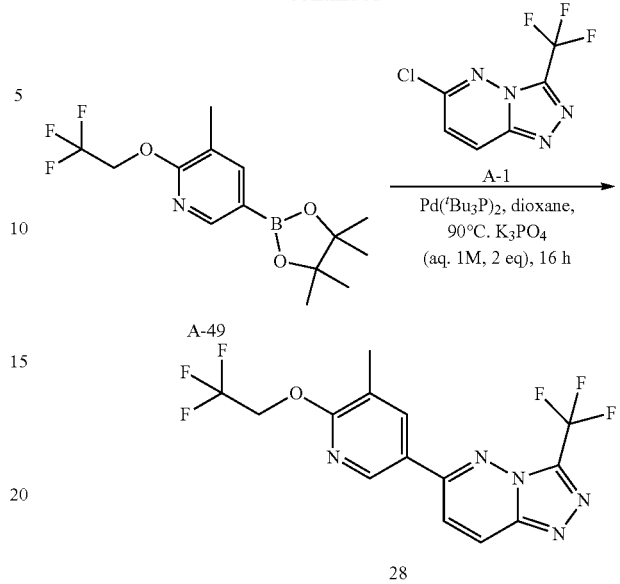

Synthesis of A-48: To a mixture of NaH (387.47 mg, 9.69 mmol, 60% purity) in DMF (20 mL) was added 2,2,2-trifluoroethanol (732.02 µL, 10.17 mmol) under $N_2$ at 0° C. and the mixture was stirred at 0° C. for 0.5 hour. Then A-47 (1.00 g, 4.84 mmol) was added and the yellow mixture was stirred at 25° C. for 16 hours. The mixture was quenched with $NH_4Cl$ (80 mL) and extracted with EtOAc (50 mL×2). The combine organic phase was washed with brine (20 mL), dried over $Na_2SO_4$, filtered and concentrated to give a residue that was purified by flash chromatography on silica gel (PE) to afford A-48 (480.00 mg) as an oil. $^1$H NMR (400 MHz, $CDCl_3$) $\delta_H$=8.02 (d, 1H), 7.57 (d, 1H), 4.73 (q, 2H), 2.23 (s, 3H).

Synthesis of A-49: A mixture of A-48 (200.00 mg, 740.60 µmol), 4,4,5,5-tetramethyl-2-(4,4,5,5-tetramethyl-1,3,2-dioxaborolan-2-yl)-1,3,2-dioxaborolane (564.20 mg, 2.22 mmol), Pd(dppf)$Cl_2$·$CH_2Cl_2$ (60.48 mg, 74.06 µmol) and KOAc (72.68 mg, 740.60 µmol) in dioxane (5 mL) was stirred under $N_2$ at 90° C. for 16 hours. The mixture was cooled to room temperature, diluted with EtOAc (10 mL), filtered through silica gel, eluted with EtOAc (10 mL) and concentrated to give a residue that was purified by flash chromatography on silica gel (PE:EtOAc=50:1) to afford A-49 (180.00 mg) as an oil. LCMS $R_t$=1.00 min using Method B, MS ESI calcd. for $C_{14}H_{20}BF_3NO_3$ [M+H]+ 318.1, found 318.1.

Synthesis of Compound 28: A mixture of A-49 (170.98 mg, 539.18 µmol), A-1 (100.00 mg, 449.32 µmol), $K_3PO_4$ (190.75 mg, 898.64 µmol) and Pd(t-$Bu_3P)_2$ (45.92 mg, 89.86 µmol) in dioxane (6 mL) and $H_2O$ (1 mL) was stirred under $N_2$ at 90° C. for 16 hoursMS. The mixture was cooled to room temperature, diluted with EtOAc (20 mL), filtered and concentrated to give a residue that was purified by prep-HPLC (Xtimate $C_{18}$ (150 mm×25 mm, 5 µm); A=$H_2O$ (0.05% $NH_4OH$) and B=$CH_3CN$; 46-76% B over 10 minutes) to afford Compound 28 (31.40 mg) as a solid. $^1$H NMR (400 MHz $CDCl_3$) $\delta_H$=8.62 (s, 1H), 8.32 (d, 1H), 8.16 (s, 1H), 7.74 (d, 1H), 4.88 (q, 2H), 2.39 (s, 3H). LCMS $R_t$=3.52 min using Method C, MS ESI calcd. for $C_{14}H_{10}F_6N_5O$ [M+H]$^+$ 378.1, found 377.9.

Example 29: Synthesis of Compound 29

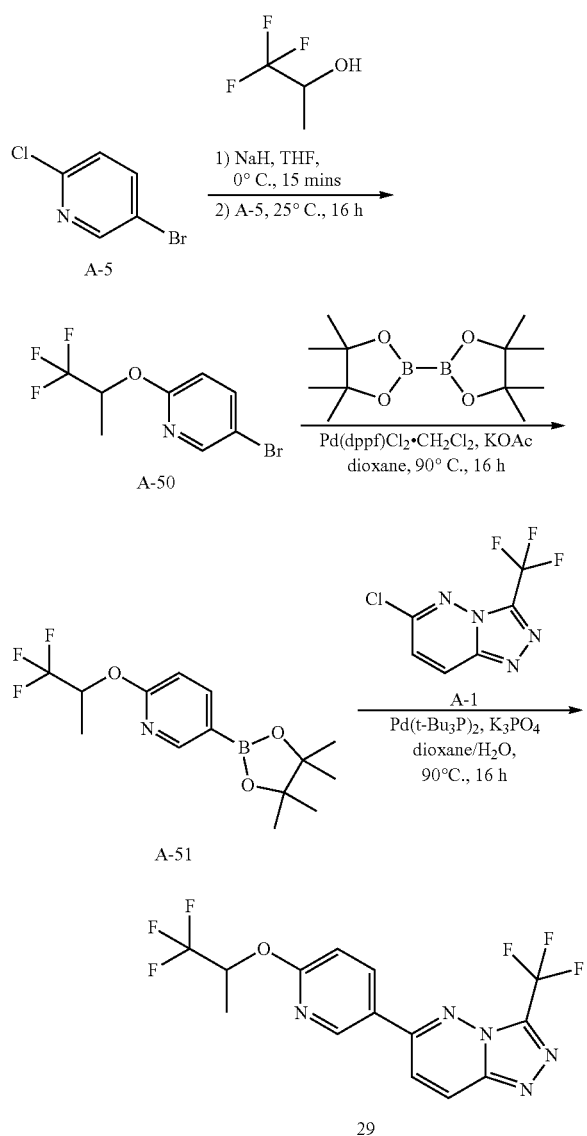

29

Synthesis of A-50: To a mixture of 1,1,1-trifluoropropan-2-ol (1.19 g, 10.40 mmol, 941.53 μL) in DMF (20 mL) was added NaH (415.71 mg, 10.40 mmol, 60% purity) at 0° C. The reaction was stirred at 0° C. for 15 min, and then A-5 (1.00 g, 5.20 mmol, 1.00 eq) was added at 0° C. The reaction mixture was allowed to warm to 25° C. and stirred for 16 hours. The mixture was quenched with sat.NH$_4$Cl (100 mL) and extracted with EtOAc (100 mL×2). The combined organic layers were washed with H$_2$O (100 mL), brine (100 mL), dried over Na$_2$SO$_4$, filtered and concentrated to give a residue that was purified by flash chromatography on silica gel (EtOAc in PE=0% to 1%) to afford A-50 (1.00 g, 3.67 mmol) as an oil. LCMS R$_t$=0.94 min using Method B, MS ESI calcd. for C$_8$H$_8$BrF$_3$NO [M+H]$^+$ 270.0, found 269.9.

Synthesis of A-51: A mixture of A-50 (500.00 mg, 1.85 mmol), 4,4,5,5-tetramethyl-2-(4,4,5,5-tetramethyl-1,3,2-dioxaborolan-2-yl)-1,3,2-dioxaborolane (1.41 g, 5.55 mmol), Pd(dppf)Cl$_2$·CH$_2$Cl$_2$ (151.08 mg, 185.00 μmol) and KOAc (363.12 mg, 3.70 mmol) in dioxane (10 mL) was stirred at 90° C. for 16 hours. After cooling to room temperature, the mixture was concentrated to give a residue that was purified by flash chromatography on silica gel (EtOAc in PE=0% to 1%) to afford A-51 (400.00 mg) as a solid. $^1$H NMR (400 MHZ, CDCl$_3$) δ$_H$=8.51 (d, 1H), 7.98 (dd, 1H), 6.79 (d, 1H), 5.87 (td, 1H), 1.49 (d, 3H), 1.34 (s, 12H).

Synthesis of Compound 29: A mixture of A-51 (320.59 mg, 1.01 mmol), A-1 (150.00 mg, 673.98 μmol), Pd(t-Bu$_3$P)$_2$ (34.44 mg, 67.40 μmol) and K$_3$PO$_4$ (286.13 mg, 1.35 mmol) in dioxane (10 mL) and H$_2$O (1 mL) was stirred at 90° C. for 16 hours. After cooling to room temperature, the mixture was concentrated to give a residue that was purified by prep-HPLC (Xtimate C$_{18}$ (150 mm×25 mm, 5 μm); A=H$_2$O (0.05% NH$_4$OH) and B=CH$_3$CN; 45-75% B over 10 minutes) to afford Compound 29 (72.61 mg, 192.48 μmol) as a solid. $^1$H NMR (400 MHz, CDCl$_3$) δ$_H$=8.79 (d, 1H), 8.34 (dt, 2H), 7.74 (d, 1H), 7.03 (d, 1H), 5.90 (td, 1H), 1.56 (d, 3H). LCMS R$_t$=1.21 min using Method A, MS ESI calcd. for C$_{14}$H$_{10}$F$_6$N$_5$O [M+H]$^+$ 378.1, found 377.9.

Example 30: Synthesis of Compound 30

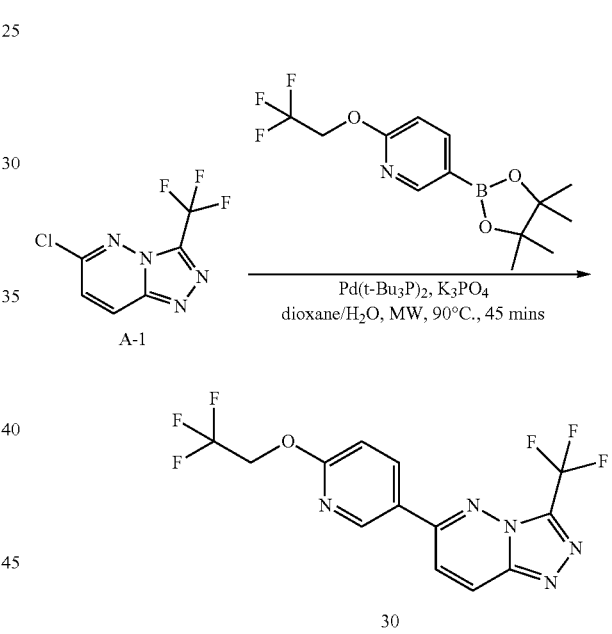

30

A mixture of A-1 (150.00 mg, 673.98 μmol), 5-(4,4,5,5-tetramethyl-1,3,2-dioxaborolan-2-yl)-2-(2,2,2-trifluoroethoxy)pyridine (204.27 mg, 673.98 μmol), K$_3$PO$_4$ (286.13 mg, 1.35 mmol), and Pd(t-Bu$_3$P)$_2$ (34.44 mg, 67.40 μmol) in dioxane (3 mL) and H$_2$O (1 mL) was stirred at 90° C. in a microwave reactor for 45 mins. After cooling to room temperature, the mixture was diluted with EtOAc (10 mL), filtered through Celite and eluted with EtOAc (10 mL×3). The combined organic phase was washed with brine (10 mL), dried over Na$_2$SO$_4$, filtered and concentrated to give a residue that was purified by flash chromatography on silica gel (EtOAc in DCM=20% to 40% to 60%) and triturated form i-Pr$_2$O (3 mL) to afford Compound 30 (33.50 mg) as a solid. $^1$H NMR (400 MHz, CDCl$_3$) δ$_H$=8.80 (d, 1H), 8.40-8.31 (m, 2H), 7.75 (d, 1H), 7.09 (d, 1H), 4.88 (q, 2H). LCMS R$_t$=0.84 min using Method B, MS ESI calcd. for C$_{13}$H$_8$F$_6$N$_5$O [M+H]$^+$ 364.1, found 364.0.

Example 31: Synthesis of Compound 31

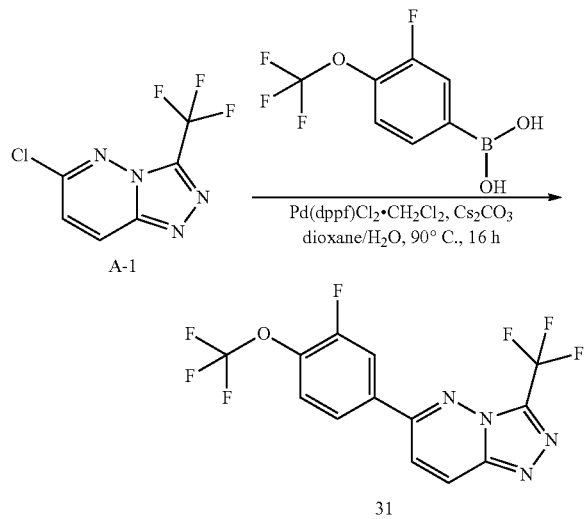

A mixture of A-1 (150.00 mg, 673.98 µmol), [3-fluoro-4-(trifluoromethoxy)phenyl]boronic acid (181.10 mg, 808.78 µmol), Pd(dppf)Cl$_2$·CH$_2$Cl$_2$ (82.56 mg, 101.10 µmol) and Cs$_2$CO$_3$ (439.19 mg, 1.35 mmol) in dioxane (3 mL) and H$_2$O (300 µL) was stirred at 90° C. for 16 hours. The mixture was cooled to room temperature, diluted with EtOAc (30 mL), filtered through silica gel and eluted with EtOAc (10 mL). The filtrate was concentrated to give a residue that was purified by prep-HPLC (Xtimate C$_{18}$ (150 mm×25 mm, 5 µm); A=H$_2$O (0.05% NH$_4$OH) and B=CH$_3$CN; 46-76% B over 10 minutes) to afford Compound 31 (35.50 mg) as a solid. $^1$H NMR (400 MHz, CDCl$_3$) $\delta_H$=8.37 (d, 1H), 7.93 (dd, 1H), 7.87-7.82 (m, 1H), 7.74 (d, 1H), 7.54 (t, 1H). LCMS R$_t$=1.21 min using Method A, MS ESI calcd. for C$_{13}$H$_6$F$_7$N$_4$O [M+H]$^+$ 367.0, found 366.9.

Example 32: Synthesis of Compound 32

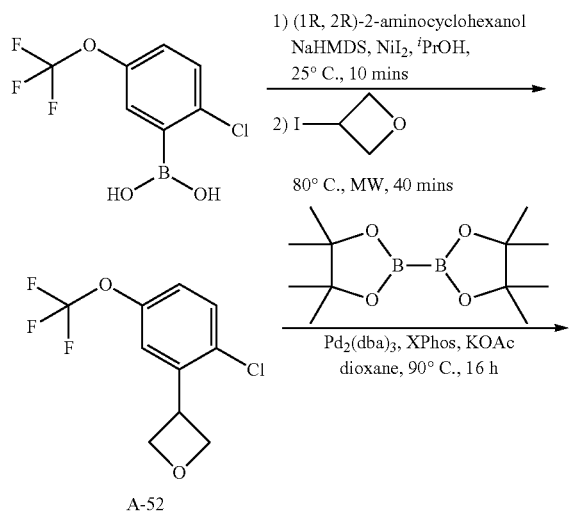

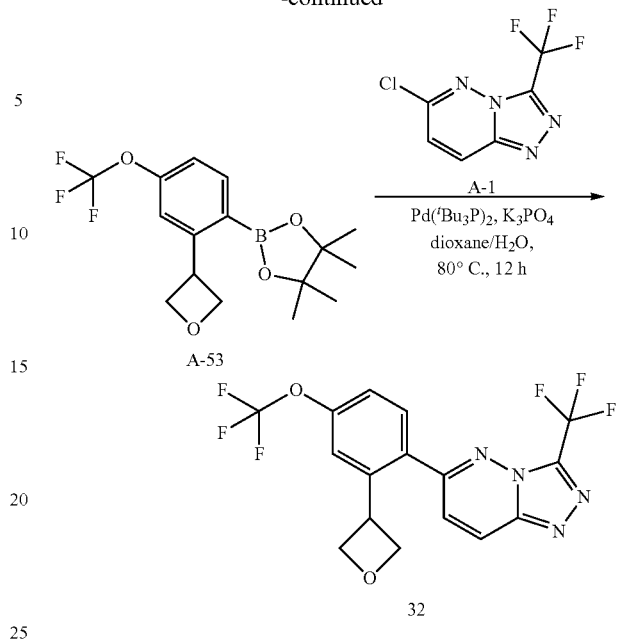

Synthesis of A-52: To a mixture of [2-chloro-5-(trifluoromethoxy)phenyl]boronic acid (4.81 g, 20.00 mmol), NiI$_2$ (312.53 mg, 1.00 mmol) and (1R,2R)-2-aminocyclohexanol (115.18 mg, 1.00 mmol) in t-PrOH (20 mL) was added NaHMDS (1 M, 20.00 mL) under N$_2$, then the mixture was stirred at 25° C. for 10 minutes. A solution of 3-iodooxetane (1.84 g, 10.00 mmol) in i-PrOH (1 mL) was added and the mixture was stirred at 80° C. for 40 minutes under microwave conditions. After cooling to room temperature, the mixture was quenched with a saturated solution of NH$_4$Cl (30 mL) and extracted with EtOAc (50 mL×2). The combined organic phase was then washed with brine (15 mL), dried over Na$_2$SO$_4$, filtered and concentrated to give the crude product, which was purified by flash chromatography on silica gel (EtOAc in PE=0% to 2.5% to 5%) to give A-52 (820.00 mg) as an oil. $^1$H NMR (400 MHZ, CDCl$_3$) $\delta_H$=7.39 (d, 1H), 7.29 (d, 1H), 7.11 (dd, 1H), 5.13-5.06 (m, 2H), 4.84-4.77 (m, 2H), 4.67-4.57 (m, 1H).

Synthesis of A-53: A mixture of A-52 (800.00 mg, 3.17 mmol), 4,4,5,5-tetramethyl-2-(4,4,5,5-tetramethyl-1,3,2-dioxaborolan-2-yl)-1,3,2-dioxaborolane (2.41 g, 9.51 mmol), Pd$_2$(dba)$_3$ (290.28 mg, 317.00 µmol), XPhos (377.80 mg, 792.50 µmol) and KOAc (622.21 mg, 6.34 mmol) in dioxane (30 mL) was stirred at 90° C. for 16 hours under N$_2$. After cooling to room temperature, the mixture was concentrated to a residue that was dissolved in H$_2$O (30 mL), and extracted with EtOAc (50 mL×2). The combined organic phase was washed with water (20 mL×2) and brine (20 mL), dried over Na$_2$SO$_4$, filtered, and the residue was purified by flash chromatography on silica gel (EtOAc in PE=0% to 2% to 3%) to give A-53 (500 mg, crude) as an oil. The crude product was used for next step directly without any further purification.

Synthesis of Compound 32: A mixture of A-53 (500.00 mg, 1.45 mmol), A-1 (70.00 mg, 314.52 µmol), Pd(t-Bu$_3$P)$_2$ (24.11 mg, 47.18 µmol) and K$_3$PO$_4$ (133.53 mg, 629.04 µmol) in dioxane (6 mL) and H$_2$O (600 µL) was stirred at 80° C. for 12 hours in 20 mL sealed tube under N$_2$. After cooling to room temperature, the mixture was concentrated and the residue was diluted with H$_2$O (20 mL) and extracted with EtOAc (30 mL×2). The combined organic phase was washed with water (15 mL×2) and brine (20 mL), dried over Na₂SO₄, filtered and purified by prep-TLC (silica gel, EtOAc:PE=1:1) to give Compound 32 (25.11 mg) as a solid. ¹H NMR (400 MHz, CDCl₃) $\delta_H$=8.36 (d, 1H), 7.68 (d, 1H), 7.55 (d, 1H), 7.43 (d, 1H), 7.35 (dd, 1H), 5.00-4.94 (m, 2H), 4.72-4.66 (m, 2H), 4.65-4.56 (m, 1H). LCMS $R_t$=1.14 min using Method A, MS ESI calcd. for $C_{16}H_{11}F_6N_4O_2$ [M+H]⁺ 405.1, found 405.2.

Example 33: Synthesis of Compound 33

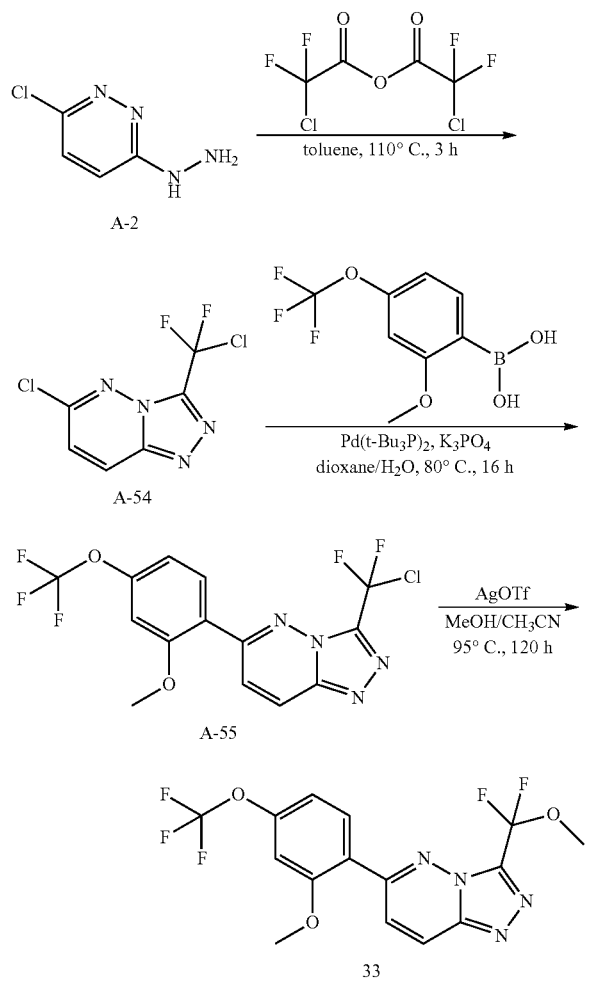

Synthesis of A-54: A mixture of A-2 (3.00 g, 20.75 mmol) and (2-chloro-2,2-difluoro-acetyl) 2-chloro-2,2-difluoro-acetate (5.55 g, 22.83 mmol) in toluene (30 mL) was stirred at 110° C. for 3 hours. The mixture was concentrated, dissolved in sat.NaHCO₃ (50 mL), and extracted with EtOAc (150 mL×2). The combined organic phase was washed with brine (50 mL), dried over Na₂SO₄, filtered and concentrated to give A-54 (3.60 g, 15.06 mmol) as a solid. ¹H NMR (400 MHz, CDCl₃) $\delta_H$=8.22 (d, 1H), 7.35 (d, 1H). LCMS $R_t$=0.69 min using Method B, MS ESI calcd. for $C_6H_3Cl_2F_2N_4$ [M+H]⁺ 239.0, found 238.9.

Synthesis of A-55: A mixture of A-54 (400.00 mg, 1.67 mmol), [2-methoxy-4-(trifluoromethoxy)phenyl]boronic acid (394.04 mg, 1.67 mmol), Pd(t-Bu₃P)₂ (128.02 mg, 250.50 μmol) and K₃PO₄ (708.98 mg, 3.34 mmol) in dioxane (14 mL) and H₂O (2 mL) was stirred at 80° C. for 16 hours under N₂. After cooling to room temperature, the mixture was concentrated, diluted with H₂O (50 mL), and extracted with EtOAc (100 mL×2). The combined organic phase was washed with water (30 mL×2) and brine (50 mL), dried over Na₂SO₄, filtered, and concentrated, and the crude product was purified by flash chromatography on silica gel (EtOAc in PE=20% to 40% to 60%) to give A-55 (400.00 mg) as a solid. ¹H NMR (400 MHz CDCl₃) $\delta_H$=8.19 (d, 1H), 7.87-7.78 (m, 2H), 7.04 (d, 1H), 6.92 (s, 1H), 3.95 (s, 3H).

Synthesis of Compound 33: To a mixture of A-55 (120.00 mg, 304.04 μmol) in MeOH (3 mL) and CH₃CN (4 mL) was added AgOTf (390.61 mg, 1.52 mmol), and the mixture was stirred at 95° C. for 120 hours. The mixture was then diluted with H₂O (20 mL) and extracted with EtOAc (50 mL×2). The combined organic phase was washed with water (20 mL×2), dried over Na₂SO₄, filtered and concentrated to give the crude product. The crude product was purified by prep-TLC (silica gel, EtOAc:PE=1:2), triturated from i-Pr₂O (1 mL), and dried to give Compound 33 (18.04 mg) as a solid. ¹H NMR (400 MHz CDCl₃) $\delta_H$=8.14 (d, 1H), 7.80 (d, 1H), 7.73 (d, 1H), 7.03 (d, 1H), 6.90 (s, 1H), 3.93 (s, 3H), 3.90 (s, 3H). LCMS $R_t$=1.16 min using Method A, MS ESI calcd. for $C_{15}H_{12}F_5N_4O_3$ [M+H]⁺ 391.1, found 391.0.

Example 34: Synthesis of Compound 34

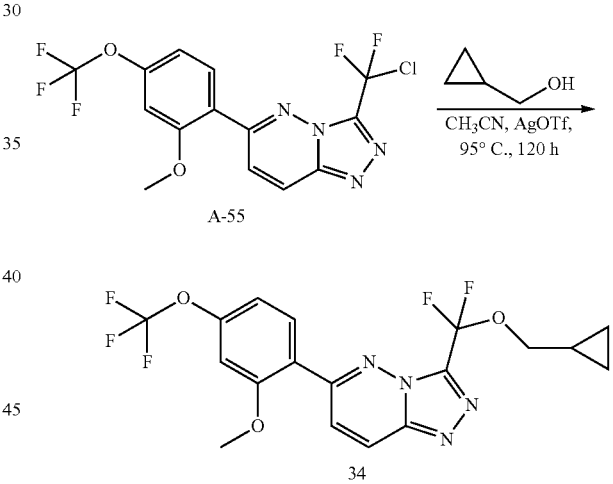

To a mixture of A-55 (120.00 mg, 304.04 μmol) and cyclopropylmethanol (1.93 mL, 24.32 mmol) in CH₃CN (4 mL) was added AgOTf (390.61 mg, 1.52 mmol), and the mixture was stirred at 95° C. for 120 hours. The mixture was then diluted with H₂O (20 mL), and extracted with EtOAc (50 mL×2). The combined organic phase was washed with water (20 mL×2), dried over Na₂SO₄, filtered and concentrated to give the crude product, which was purified by prep-TLC (silica gel, EtOAc:PE=1:2) and prep-HPLC (Kromasil (150 mm×25 mm, 10 μm) A=H₂O (0.05% NH₄OH) and B=CH₃CN; 48-78% B over 8 minutes) to afford Compound 34 (3.52 mg) as a solid. ¹H NMR (400 MHz DMSO-d₆) $\delta_H$=8.51 (d, 1H), 7.84 (d, 1H), 7.71 (d, 1H), 7.29 (s, 1H), 7.19 (d, 1H), 3.97 (d, 2H), 3.91 (s, 3H), 1.21-1.12 (m, 1H), 0.59-0.52 (m, 2H), 0.36-0.29 (m, 2H). LCMS $R_t$=1.24 min using Method A, MS ESI calcd. for $C_{18}H_{16}F_5N_4O_3$ [M+H]⁺ 431.1, found 430.9.

Example 35: Synthesis of Compound 35

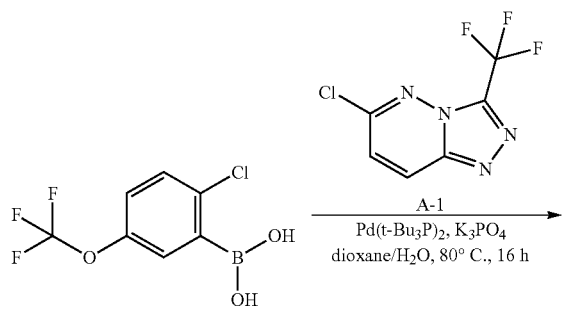

A mixture of A-1 (1.00 g, 4.49 mmol), [2-chloro-5-(trifluoromethoxy)phenyl]-boronic acid (1.19 g, 4.94 mmol), Pd(t-Bu₃P)₂ (344.44 mg, 673.50 μmol) and K₃PO₄ (1.91 g, 8.98 mmol) in dioxane (30 mL) and H₂O (4 mL) was stirred at 80° C. for 16 hours under N₂. The mixture was diluted with H₂O (50 mL) and extracted with EtOAc (100 mL×2). The combined organic phase was washed with brine (50 mL), dried over Na₂SO₄, filtered, concentrated, and purified by flash chromatography on silica gel (EtOAc in PE=5% to 10% to 15%) to give the impure product, which was triturated from PE (10 mL) and dried to give Compound 35 (1.09 g) as a solid. ¹H NMR (400 MHz CDCl₃) δ$_H$=8.32 (d, 1H), 7.67 (d, 1H), 7.63 (d, 1H), 7.53 (d, 1H), 7.41 (dd, 1H). LCMS R$_t$=1.19 min using Method A, MS ESI calcd. for C₁₃H₆ClF₆N₄O [M+H]⁺ 383.0, found 382.8.

Example 36: Synthesis of Compound 36

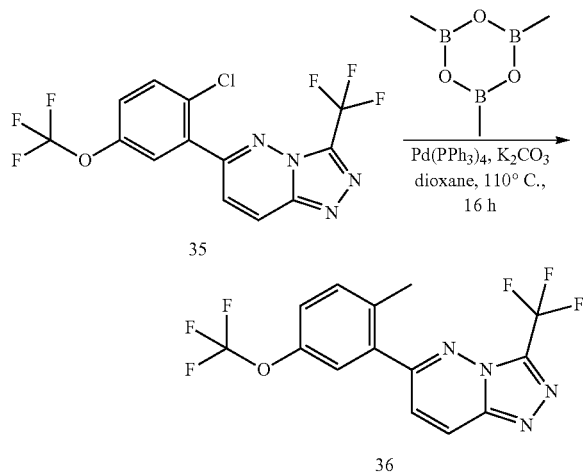

A mixture of Compound 35 (50.00 mg, 130.67 μmol), 2,4,6-trimethyl-1,3,5,2,4,6-trioxatriborinane (49.21 mg, 392.01 μmol), K₂CO₃ (27.09 mg, 196.01 μmol) and Pd(PPh₃)₄ (15.10 mg, 13.07 μmol) in dioxane (3 mL) was stirred at 110° C. for 16 hours. The mixture was cooled to room temperature, diluted with EtOAc (10 mL), filtered with silica gel, and eluted with EtOAc (5 mL), concentrated, and purified by prep-HPLC (Xtimate C₁₈ (150 mm×25 mm, 5 μm); A=H₂O (0.05% NH₄OH) and B=CH₃CN; 45-75% B over 10 minutes) to give Compound 36 (33.50 mg) as a solid. ¹H NMR (400 MHz CDCl₃) δ$_H$=8.34 (d, 1H), 7.48 (d, 1H), 7.44 (d, 1H), 7.37-7.30 (m, 2H), 2.48 (s, 3H). LCMS R$_t$=1.19 min using Method A, MS ESI calcd. for C₁₄H₉F₆N₄O [M+H]⁺ 363.1, found 362.8.

Example 37: Synthesis of Compound 37

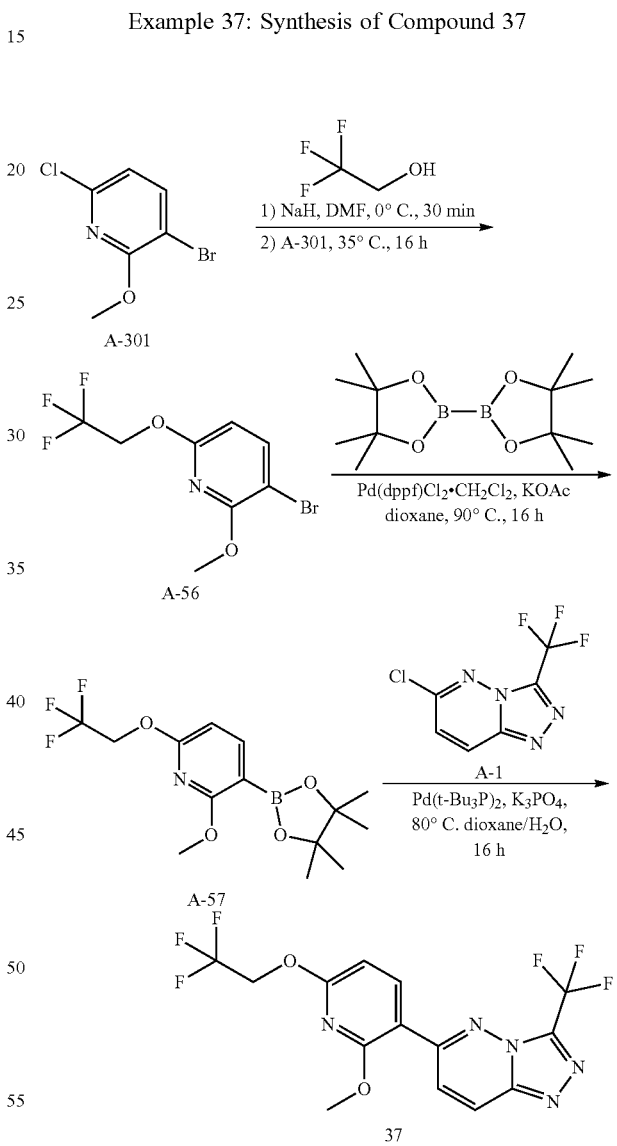

Synthesis of A-56: To a solution of 2,2,2-trifluoroethanol (971.22 μL, 13.49 mmol) in DMF (20 mL) was added NaH (540.00 mg, 13.50 mmol, 60% purity) in portions at 0° C., and the mixture was stirred at 0° C. for 30 mins. Then 3-bromo-6-chloro-2-methoxy-pyridine (700.00 mg, 3.15 mmol) was added, and the mixture was stirred at 35° C. for 16 hours. The mixture was then quenched with a saturated solution of NH₄Cl (60 mL) and extracted with EtOAc (50 mL×2). The combined organic phase was washed with brine (30 mL), dried over Na$_2$SO$_4$, filtered and concentrated, and the residue was purified by flash chromatography on silica gel (PE) to give A-56 (600.00 mg) as an oil. $^1$H NMR (400 MHz CDCl$_3$) $\delta_H$=7.73 (d, 1H), 6.38 (d, 1H), 4.73 (q, 2H), 3.99 (s, 3H).

Synthesis of A-57: A mixture of A-56 (500.00 mg, 1.75 mmol), 4,4,5,5-tetramethyl-2-(4,4,5,5-tetramethyl-1,3,2-dioxaborolan-2-yl)-1,3,2-dioxaborolane (1.33 g, 5.25 mmol), Pd(dppf)Cl$_2$.CH$_2$Cl$_2$ (285.82 mg, 350.00 µmol) and KOAc (343.49 mg, 3.50 mmol) in dioxane (10 mL) was stirred at 90° C. for 16 hours. The mixture was then concentrated and the residue was purified by flash chromatography on silica gel (EtOAc in PE=0% to 2%) to give A-57 as a solid. $^1$H NMR (400 MHz, CDCl$_3$) $\delta_H$=7.97 (d, 1H), 6.41 (d, 1H), 4.82-4.73 (m, 2H), 3.95 (s, 3H), 1.34 (s, 12H).

Synthesis of Compound 37: A mixture of A-57 (299.35 mg, 898.64 µmol), A-1 (100.00 mg, 449.32 µmol), K$_3$PO$_4$ (190.75 mg, 898.64 µmol) and Pd(t-Bu$_3$P)$_2$ (45.92 mg, 89.86 µmol) in dioxane (10 mL) and H$_2$O (900 µL) was stirred at 80° C. for 16 hours. The mixture was then concentrated and purified by prep-HPLC (Kromasil (150 mm×25 mm, 10 µm) A=H$_2$O (0.05% NH$_4$OH) and B=CH$_3$CN; 53-63% B over 8 minutes) to give Compound 37 (53.76 mg) as a solid. $^1$H NMR (400 MHz CDCl$_3$) $\delta_H$=8.27-8.18 (m, 2H), 8.01 (d, 1H), 6.68 (d, 1H), 4.85 (q, 2H), 4.08 (s, 3H). LCMS R$_f$=0.91 min using Method B, MS ESI calcd. for C$_{14}$H$_{10}$F$_6$N$_5$O$_2$ [M+H]$^+$ 394.1, found 394.1.

Example 38: Synthesis of Compound 38

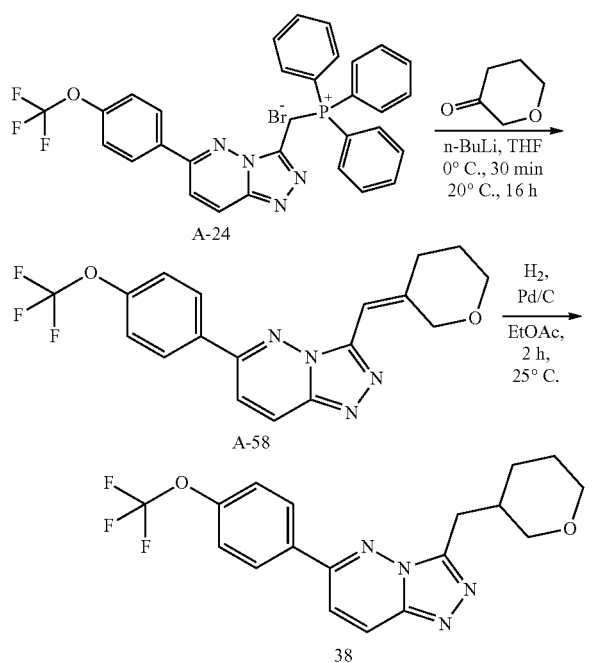

Synthesis of A-58: To a mixture of A-24 (500.00 mg, 786.89 µmol) in THF (10 mL) at 0° C. under N$_2$ was added n-BuLi (2.5 M, 377.71 µL). The reaction mixture was stirred at 0° C. for 30 min, then tetrahydropyran-3-one (196.96 mg, 1.97 mmol) was added. The mixture was stirred at 20° C. for 16 hours. The mixture was quenched with NH$_4$Cl (50 mL), extracted with EtOAc (50 mL×2). The combined organic phase was washed with brine (20 mL), dried over Na$_2$SO$_4$, filtered and concentrated, and the residue was purified by flash chromatography on silica gel (EtOAc:PE=2:1) to give A-58 (100.00 mg) as a solid. $^1$H NMR (400 MHZ, CDCl$_3$) $\delta_H$=8.20 (dd, 1H), 8.08-8.04 (m, 2H), 7.54 (dd, 1H), 7.42 (d, 2H), 6.74 (d, 1H), 5.02 (s, 1H), 4.35 (s, 1H), 3.95-3.83 (m, 2H), 3.33 (t, 1H), 2.70 (t, 1H), 1.97-1.86 (m, 2H).

Synthesis of Compound 38: A mixture of A-58 (100.00 mg, 265.72 µmol) and Pd/C (80.00 mg) in EtOAc (20 mL) under N$_2$ was degassed, and refilled with H$_2$. The mixture was stirred under an H$_2$ balloon (15 psi) at 25° C. for 2 hours. The mixture was the diluted with EtOAc (10 mL), filtered with silica gel, eluted with EtOAc (5 mL) and concentrated, and the residue was purified by prep-HPLC (Xtimate C$_{18}$ (150 mm×25 mm, 5 µm); A=H$_2$O (0.05% NH$_4$OH) and B=CH$_3$CN; 40-70% B over 10 minutes to give Compound 38 (42.50 mg, 110.71 µmol) as a solid. $^1$H NMR (400 MHz, CDCl$_3$) $\delta_H$=8.21-8.16 (m, 1H), 8.06-8.02 (m, 2H), 7.56-7.50 (m, 1H), 7.42 (d, 2H), 3.97 (dd, 1H), 3.87 (td, 1H), 3.52-3.42 (m, 1H), 3.40-3.27 (m, 1H), 3.20 (d, 2H), 2.41 (tdd, 1H), 1.99-1.89 (m, 1H), 1.74-1.59 (m, 2H), 1.49-1.37 (m, 1H). LCMS R$_f$=1.12 min using Method A, MS ESI calcd. for C$_{18}$H$_{18}$F$_3$N$_4$O$_2$ [M+H]$^+$ 379.1, found 378.9.

Example 39: Synthesis of Compound 39

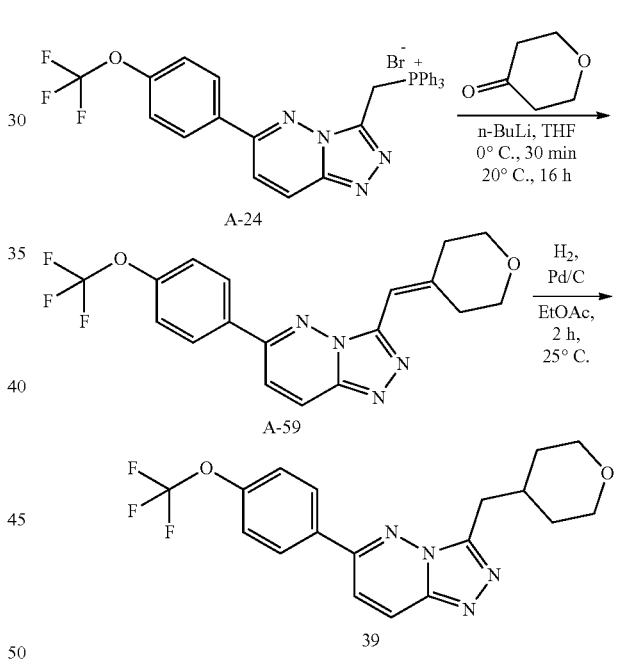

Synthesis of A-59: To a mixture of A-24 (500.00 mg, 786.89 µmol) in THF (10 mL) at 0° C. under N$_2$ was added n-BuLi (2.5 M, 377.71 µL). The reaction mixture was stirred at 0° C. for 30 mins, and then tetrahydropyran-4-one (180.70 µL, 1.97 mmol) was added. The mixture was stirred at 20° C. for 16 hours. The mixture was quenched by sat.NH$_4$Cl (30 mL), extracted with EtOAc (30 mL×2), and the combined organic was washed with brine (15 mL), dried over Na$_2$SO$_4$, filtered and concentrated to give a residue that was purified by flash chromatography on silica gel (EtOAc) to give A-59 (100.00 mg) as a solid. LCMS R$_f$=0.82 min using Method B, MS ESI calcd. for C$_{18}$H$_{16}$F$_3$N$_4$O$_2$ [M+H]$^+$ 377.1, found 377.0.

Synthesis of Compound 39: A mixture of A-59 (100.00 mg, 265.72 µmol, 1.00 eq) and Pd/C (50.00 mg) in EtOAc (20.00 mL) under N$_2$ was degassed and refilled with H$_2$. The mixture was stirred under an H₂ balloon (15 psi) at 25° C. for 2 hours. The mixture was diluted with EtOAc (10 mL), filtered with silica gel, eluted with EtOAc (5 mL), and concentrated to give a residue that was purified by flash chromatography on silica gel (EtOAc) and prep-TLC (silica gel, EtOAc) to give Compound 39 (7.80 mg) as a solid. ¹H NMR (400 MHz, CDCl₃) $\delta_H$=8.19 (d, 1H), 8.04 (d, 2H), 7.54 (d, 1H), 7.42 (br d, 2H), 3.99 (dd, 2H), 3.47-3.37 (m, 2H), 3.25 (d, 2H), 2.43-2.29 (m, 1H), 1.73 (br d, 2H), 1.58-1.49 (m, 2H). LCMS $R_t$=1.12 min using Method A, MS ESI calcd. for $C_{18}H_{18}F_3N_4O_2$ [M+H]⁺ 379.1, found 378.9.

Example 40: Synthesis of Compound 40

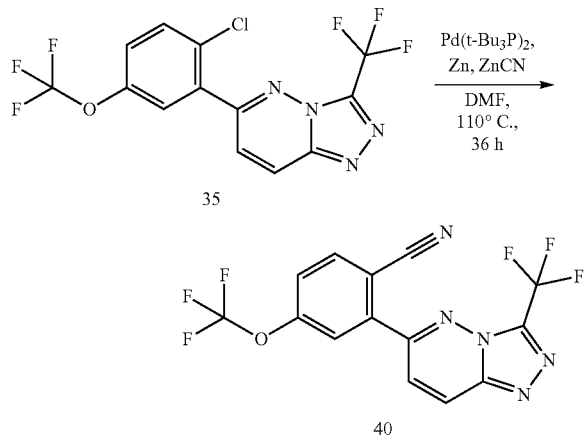

A mixture of Compound 35 (500.00 mg, 1.31 mmol), Zn(CN)₂ (461.46 mg, 3.93 mmol), Zn (8.57 mg, 131.00 μmol) and Pd(t-Bu₃P)₂ (133.90 mg, 262.00 μmol) in DMF (20 mL) was stirred at 110° C. for 36 hours in a 20 mL sealed tube under N₂. The mixture was diluted with H₂O (50 mL) and extracted with EtOAc (100 mL×2). The combined organic phase was washed with water (40 mL×2) and brine (50 mL), dried over Na₂SO₄, filtered and concentrated to give a residue that was purified by prep-HPLC (Xtimate C₁₈ (150 mm×25 mm, 5 μm); A=H₂O (0.05% NH₄OH) and B=CH₃CN; 40-70% B over 10 minutes to give Compound 40 (24.90 mg) as a solid. ¹H NMR (400 MHz, CDCl₃) $\delta_H$=8.46 (d, 1H), 8.00 (d, 1H), 7.77 (d, 1H), 7.71 (s, 1H), 7.59-7.55 (m, 1H). LCMS $R_t$=1.25 min using Method A, MS ESI calcd. for $C_{14}H_6F_6N_5O$ [M+H]⁺ 373.0, found 374.0.

Example 41: Synthesis of Compound 41

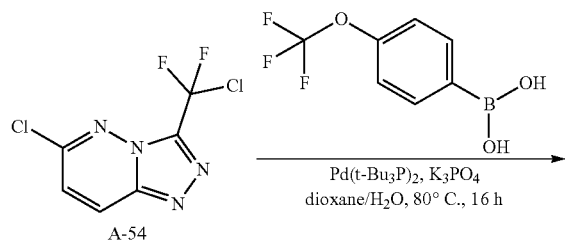

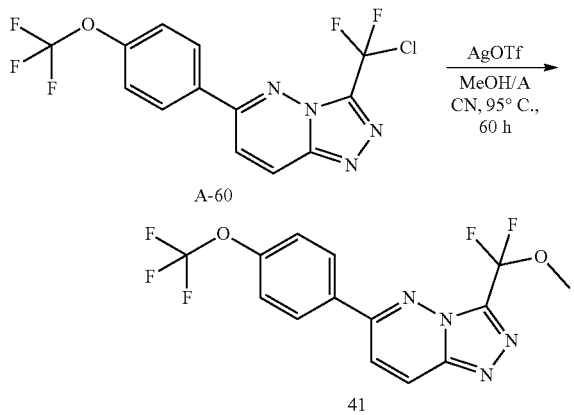

Synthesis of A-60: A mixture of A-54 (1.00 g, 4.18 mmol), [4-(trifluoromethoxy)phenyl]boronic acid (1.03 g, 5.02 mmol), Pd(t-Bu₃P)₂ (213.62 mg, 418.00 μmol) and K₃PO₄ (1.77 g, 8.36 mmol) in dioxane (20 mL) and H₂O (2 mL) was stirred at 80° C. for 16 hours. The mixture was then concentrated to give a residue that was purified by flash chromatography on silica gel (EtOAc in PE=10% to 50% to 100%) to give A-59 (1.20 g, 2.52 mmol) as a solid. ¹H NMR (400 MHz CDCl₃) $\delta_H$=8.33 (d, 1H), 8.10 (d, 2H), 7.78 (d, 1H), 7.44 (d, 2H). LCMS $R_t$=0.88 min using Method B, MS ESI calcd. for $C_{13}H_7ClF_5N_4O$ [M+H]⁺ 365.0, found 365.0.

Synthesis of Compound 41: To a mixture of A-59 (50.00 mg, 137.11 μmol) in MeOH (1 mL) and CH₃CN (1 mL) was added AgOTf (176.15 mg, 685.55 μmol), and the mixture was stirred at 95° C. for 60 hours. The mixture was then diluted with H₂O (20 mL) and extracted with EtOAc (30 mL×2). The combined organic phase was washed with water (10 mL×2) and brine (20 mL), dried over Na₂SO₄, filtered and concentrated to give a residue that was purified by prep-TLC (silica gel, EtOAc:PE=1:1) to give Compound 41 (6.42 mg) as a solid. ¹H NMR (400 MHz, CDCl₃) $\delta_H$=8.28 (d, 1H), 8.08 (d, 2H), 7.69 (d, 1H), 7.42 (d, 2H), 3.93 (s, 3H). LCMS $R_t$=1.14 min using Method A, MS ESI calcd. for $C_{14}H_{10}F_5N_4O_2$ [M+H]⁺ 361.1, found 360.9.

Example 42: Synthesis of Compounds 42 and 43

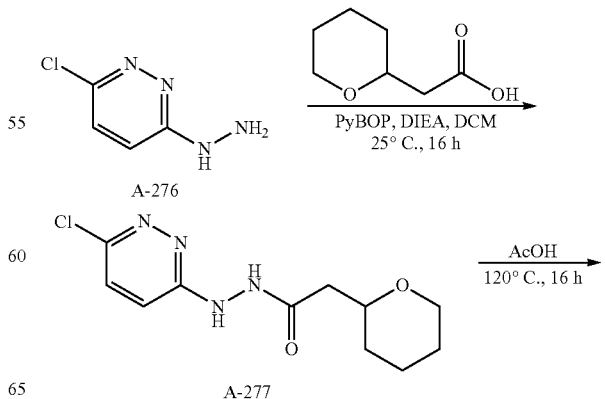

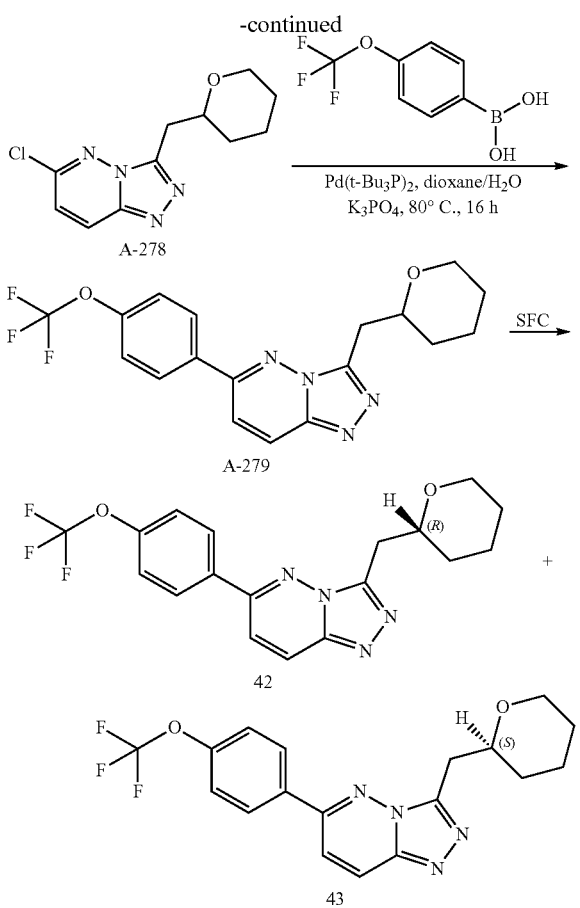

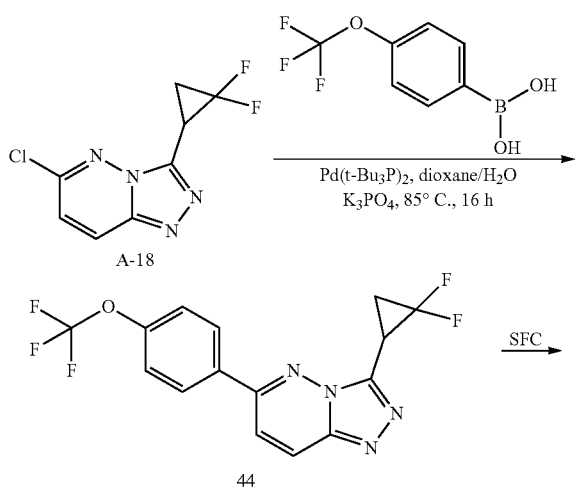

To a mixture of 2-tetrahydropyran-2-ylacetic acid (498.65 mg, 3.46 mmol) and (6-chloropyridazin-3-yl)hydrazine (500 mg, 3.46 mmol) in DCM (20 mL) was added PyBOP (2.70 g, 5.19 mmol) and DIPEA (1.81 mL, 10.38 mmol). The mixture was stirred at 25° C. for 16 hours. The reaction was diluted with sat.NH$_4$Cl (20 mL), and the mixture was extracted with DCM (20 mL×2). The combined organic phase was washed with brine (10 mL), dried over Na$_2$SO$_4$, filtered and concentrated to give the crude product (2800 mg, 7.83 mmol, crude) as a solid. LCMS R$_f$=0.67 min in 1.5 min chromatography, 5-95AB, purity 75.67%, MS ESI calcd. for C$_{11}$H$_{16}$ClN$_4$O$_2$ [M+H]$^+$ 271.1, found 271.0.

A mixture of N'-(6-chloropyridazin-3-yl)-2-tetrahydropyran-2-yl-acetohydrazide (2.80 g, 10.34 mmol) in acetic acid (8 mL) was stirred at 120° C. for 16 hours. After cooling to r.t., the mixture was concentrated, the residue was diluted with EtOAc (20 mL), neutralized with sat.NaHCO$_3$ to pH=9, and extracted with EtOAc (20 mL×2). Then the combined organic phase was washed with brine (15 mL), dried over Na$_2$SO$_4$ and concentrated to give the crude product. The crude product was purified by flash chromatography on silica gel (EtOAc in PE=50% to 70% to 100%) to give the product (420 mg) as a solid. $^1$H NMR (400 MHz, CDCl$_3$) δ$_H$=8.05 (d, 1H), 7.08 (d, 1H), 4.02-3.90 (m, 2H), 3.48-3.39 (m, 2H), 3.30-3.22 (m, 1H), 1.91-1.81 (m, 1H), 1.77-1.71 (m, 1H), 1.64-1.42 (m, 4H).

A mixture of 6-chloro-3-(tetrahydropyran-2-ylmethyl)-[1,2,4]triazolo[4,3-b]pyridazine (420 mg, 1.66 mmol), [4-(trifluoromethoxy)phenyl]boronic acid (410.72 mg, 1.99 mmol), Pd(t-Bu$_3$P)$_2$ (169.88 mg, 0.33 mmol) and K$_3$PO$_4$ (705.71 mg, 3.32 mmol) in 1,4-dioxane (10 mL) and water (2 mL) was stirred at 80° C. under N$_2$ for 16 hours. After cooling to r.t., the mixture was concentrated, the residue was diluted with NH$_4$Cl (20 mL) and extracted with EtOAc (20 mL×2). Then the combined organic phase was washed with brine (15 mL), dried over Na$_2$SO$_4$ and concentrated to give the crude product. The crude product was purified by flash chromatography on silica gel (EtOAc in PE=70% to 100%) to give the impure product. Then the impure product was triturated from i-Pr$_2$O (10 mL) to give the (440 mg, 70% yield) as a solid. $^1$H NMR (400 MHz, CDCl$_3$) δ$_H$=8.17 (d, 1H), 8.05 (d, 2H), 7.52 (d, 1H), 7.41 (d, 2H), 4.10-3.93 (m, 2H), 3.61-3.52 (m, 1H), 3.51-3.42 (m, 1H), 3.40-3.31 (m, 1H), 1.93-1.83 (m, 1H), 1.80-1.72 (m, 1H), 1.58-1.44 (m, 4H).

The product was separated by SFC (C2 (250 mm×30 mm, 10 μm); A=CO$_2$ and B=EtOH (0.1% NH$_3$H$_2$O); 38° C.; 60 mL/min; 20% B; 10 min run; 12 injections, Rt of peak 1=7.2 min, Rt of Peak 2=8.8 min) to give the product of 3-[[(2R)-tetrahydropyran-2-yl]methyl]-6-[4-(trifluoromethoxy)phenyl]-[1,2,4]triazolo[4,3-b]pyridazine (133.87 mg) (Peak 1, Rt=6.26 min in SFC) as a solid and 3-[[(2S)-tetrahydropyran-2-yl]methyl]-6-[4-(trifluoromethoxy)phenyl]-[1,2,4]triazolo[4,3-b]pyridazine (135.71 mg, 0.37 mmol (Peak 2: Rt=6.93 min in SFC) as a solid.

Note: the enantiomers were randomly assigned.

Compound 42: $^1$H NMR (400 MHz, DMSO-d$_6$+D$_2$O) δ$_H$=8.37 (d, 1H), 8.22 (d, 2H), 7.89 (d, 1H), 7.58 (d, 2H), 3.96-3.86 (m, 1H), 3.82-3.73 (m, 1H), 3.40-3.23 (m, 3H), 1.80-1.64 (m, 2H), 1.51-1.31 (m, 4H). LCMS R$_f$=1.29 min in 2 min chromatography, 10-80AB, purity 100%, MS ESI calcd. for C$_{18}$H$_{18}$F$_3$N$_4$O$_2$ [M+H]$^+$ 379.1, found 379.0.

Compound 43: $^1$H NMR (400 MHz, DMSO-d$_6$+D$_2$O) δ$_H$=8.26 (d, 1H), 8.16 (d, 2H), 7.84 (d, 1H), 7.58-7.47 (m, 2H), 3.95-3.85 (m, 1H), 3.79-3.68 (m, 1H), 3.39-3.22 (m, 3H), 1.76-1.61 (m, 2H), 1.45-1.28 (m, 4H).

LCMS R$_f$=1.29 min in 2 min chromatography, 10-80AB, purity 100%, MS ESI calcd. for C$_{18}$H$_{18}$F$_3$N$_4$O$_2$ [M+H]$^+$ 379.1, found 379.0.

Example 43: Synthesis of Compounds 44, 45, and 46

-continued

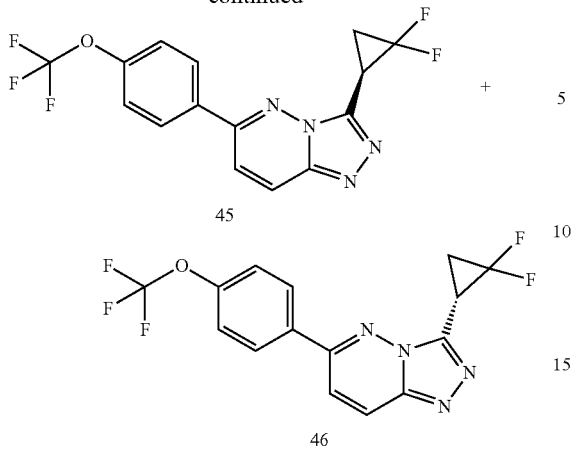

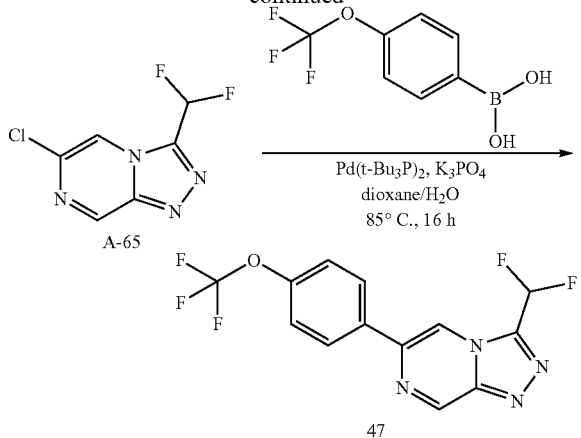

A mixture of A-18 (100.00 mg, 433.65 μmol), [4-(trifluoromethoxy)-phenyl]boronic acid (98.23 mg, 477.02 μmol), Pd(t-Bu$_3$P)$_2$ (22.16 mg, 43.37 μmol) and K$_3$PO$_4$ (184.10 mg, 867.30 μmol) in dioxane (2 mL) and H$_2$O (200 μL) was stirred at 85° C. for 16 hours. The mixture was diluted with EtOAc (10 mL), filtered through silica gel, eluted with EtOAc (10 mL) and concentrated to give a residue that was purified by prep-HPLC (Xbridge (150 mm×25 mm, 5 μm); A=H$_2$O (0.05% NH$_4$HCO$_3$) and B=CH$_3$CN; 5-65% B over 10 minutes) to give Compound 44 (25.89 mg, 72.67 μmol) as a solid. $^1$H NMR (400 MHz, MeOD-<d$_4$) δ$_H$=8.31 (d, 1H), 8.29-8.22 (m, 2H), 7.98 (d, 1H), 7.51 (d, 2H), 3.62-3.46 (m, 1H), 2.58-2.41 (m, 1H), 2.37-2.25 (m, 1H). LCMS R$_t$=1.13 min using Method A, MS ESI calcd. for C$_{15}$H$_{10}$F$_5$N$_4$O [M+H]$^+$ 357.1, found 356.9. Compound 44 was purified by SFC (Chiralcel AD (250 mm×30 mm, 5 μm); A=CO$_2$ and B=EtOH (0.1% NH$_3$H$_2$O); 38° C.; 50 mL/min; 15% B over 10 minutes; multiple injections) to afford Enantiomer 1, randomly assigned as Compound 45 (Rt=7.0 min) and Enantiomer 2, randomly assigned as Compound 46 (Rt=8.2 min). Compound 45 (120.64 mg) NMR (400 MHz, CDCl$_3$) δ=8.21 (d, 1H), 8.07 (d, 2H), 7.59 (d, 1H), 7.43 (d, 2H), 3.39-3.29 (m, 1H), 2.71-2.60 (m, 1H), 2.23-2.13 (m, 1H). LCMS R$_t$=1.22 min using Method A, MS ESI calcd. for C$_{15}$H$_{10}$F$_5$N$_4$O [M+H]$^+$ 357.1, found 357.0. Compound 46 (130.7 mg) $^1$H NMR (400 MHz, CDCl$_3$) δ=8.21 (d, 1H), 8.07 (d, 2H), 7.59 (d, 1H), 7.43 (d, 2H), 3.40-3.28 (m, 1H), 2.71-2.61 (m, 1H), 2.24-2.13 (m, 1H). LCMS R$_t$=1.22 min using Method A, MS ESI calcd. for C$_{15}$H$_{10}$F$_5$N$_4$O [M+H]$^+$ 357.1, found 357.0.

Example 44: Synthesis of Compound 47

Synthesis of A-64: A mixture of A-63 (10.00 g, 67.12 mmol) in EtOH (80 mL) was stirred under N$_2$ at 80° C. for 16 hours. The mixture was concentrated to give the crude product, which was triturated from H$_2$O (20 mL) to give A-64 (1.60 g, 11.07 mmol) as a solid. $^1$H NMR (400 MHz, CDCl$_3$) δ$_H$=8.10-8.01 (m, 2H), 6.03 (br s, 1H), 3.85 (br s, 2H).

Synthesis of A-65: A mixture of A-64 (1.99 g, 11.42 mmol) in toluene (20 mL) was stirred at 120° C. for 72 hours. The mixture was diluted with H$_2$O (50 mL) and extracted with EtOAc (50 mL×2). The combined organic phase was washed with brine (20 mL), dried over Na$_2$SO$_4$, filtered and concentrated to give a residue that was purified by flash chromatography on silica gel (PE:EtOAc=5:1 to 1:1) to give A-65 (600.00 mg) as a solid. LCMS R$_t$=0.19 min using Method B, MS ESI calcd. for C$_6$H$_4$ClF$_2$N$_4$ [M+H]$^+$ 205.0, found 204.8.

Synthesis of Compound 47: A mixture of A-65 (50.00 mg, 244.43 μmol), [4-(trifluoromethoxy)phenyl]boronic acid (50.33 mg, 244.43 μmol), K$_3$PO$_4$ (103.77 mg, 488.85 μmol) and Pd(t-Bu$_3$P)$_2$ (24.98 mg, 48.89 μmol) in dioxane (2 mL) and H$_2$O (200 μL) under N$_2$ was heated to 85° C. and stirred for 16 hours. After cooling, the mixture was diluted with EtOAc (10 mL), filtered through a Celite pad, and eluted with EtOAc (10 mL). The filtrate was concentrated, and the residue was purified by prep-HPLC (Xtimate C$_{18}$ (150 mm×25 mm, 5 μm); A=H$_2$O (0.05% NH$_4$OH) and B=CH$_3$CN; 42-72% B over 10 minutes) to give Compound 47 (3.04 mg, 9.21 μmol) as a solid. $^1$H NMR (400 MHz DMSO-d$_6$) δ$_H$=9.69 (s, 1H), 9.23 (s, 1H), 8.25 (d, 2H), 7.85 (t, 1H), 7.56 (d, 2H). LCMS R$_t$=0.82 min using Method B, MS ESI calcd. for C$_{13}$H$_8$F$_5$N$_4$O [M+H]$^+$ 331.1, found 330.9.

Example 45: Synthesis of Compound 48

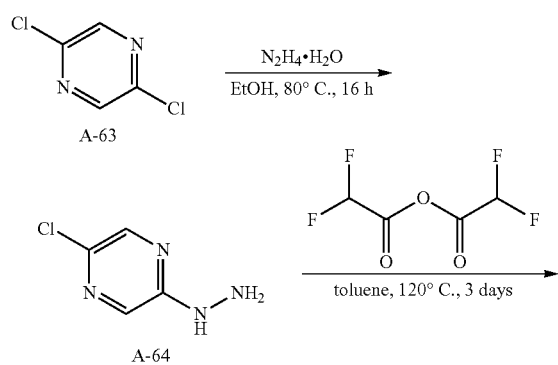

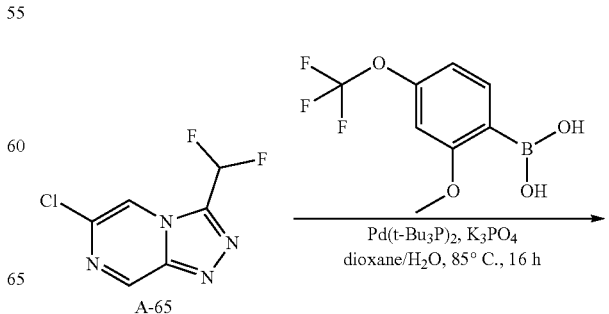

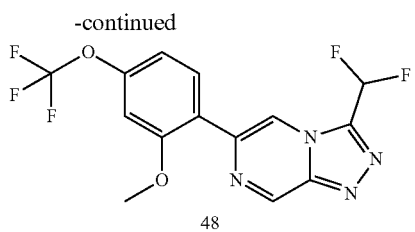

48

A mixture of A-65 (100.00 mg, 488.85 µmol, 1.00 eq), [2-methoxy-4-(trifluoromethoxy)phenyl]boronic acid (115.35 mg, 488.85 µmol), K$_3$PO$_4$ (207.54 mg, 977.70 µmol) and Pd(t-Bu$_3$P)$_2$ (49.97 mg, 97.77 µmol) in dioxane (3 mL) and H$_2$O (300 µL) under N$_2$ was heated to 85° C. and stirred for 16 hours. The reaction mixture was diluted with EtOAc (10 mL), filtered through a Celite pad, and eluted with EtOAc (10 mL). The filtrate was concentrated and the residue was purified by prep-TLC (silica gel, PE:EtOAc=1:1) to afford Compound 48 (13.14 mg, 36.48 µmol) as a solid. $^1$H NMR (400 MHz MeOD-d$_4$) $\delta_H$=9.54 (d, 1H), 9.18 (d, 1H), 8.33 (d, 1H), 7.60 (t, 1H), 7.15-7.07 (m, 2H), 4.04 (s, 3H). LCMS R$_t$=1.16 min using Method A, MS ESI calcd. for C$_{14}$H$_{10}$F$_5$N$_4$O$_2$ [M+H]$^+$ 361.1, found 360.9.

Example 46: Synthesis of Compound 49

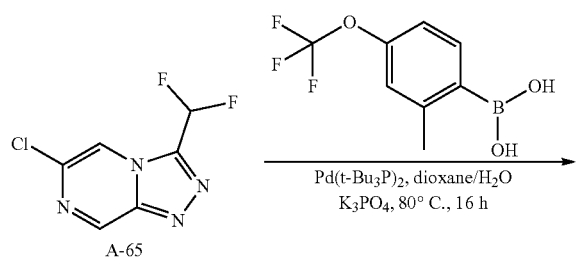

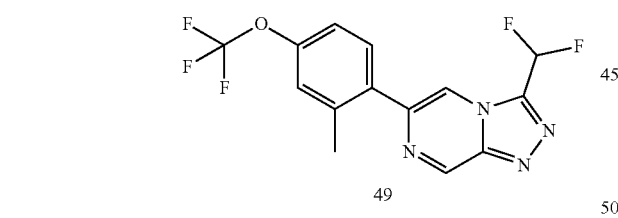

49

A mixture of A-65 (50.00 mg, 244.42 µmol), [2-methyl-4-(trifluoromethoxy)phenyl]boronic acid (59.14 mg, 268.86 µmol), K$_3$PO$_4$ (103.77 mg, 488.84 µmol) and Pd(t-Bu$_3$P)$_2$ (24.98 mg, 48.88 µmol) in dioxane (2 mL) and H$_2$O (200 µL) was stirred under N$_2$ at 80° C. for 16 hours. The mixture was diluted with EtOAc (5 mL), filtered through silica gel, eluted with EtOAc (10 mL). The filtrate was concentrated to give a residue that was purified by prep-HPLC (Xtimate C$_{18}$ (150 mm×25 mm, 5 µm); A=H$_2$O (0.05% NH$_4$OH) and B=CH$_3$CN; 40-70% B over 10 minutes) to give Compound 49 (7.26 mg) as a solid. $^1$H NMR (400 MHz, MeOD-d$_4$) $\delta_H$=9.52 (d, 1H), 8.62 (d, 1H), 7.70-7.43 (m, 2H), 7.32-7.22 (m, 2H), 2.44 (s, 3H). LCMS R$_t$=1.27 min using Method A, MS ESI calcd. for C$_{14}$H$_{10}$F$_5$N$_4$O [M+H]$^+$345.1, found 344.9.

Example 47: Synthesis of Compound 50

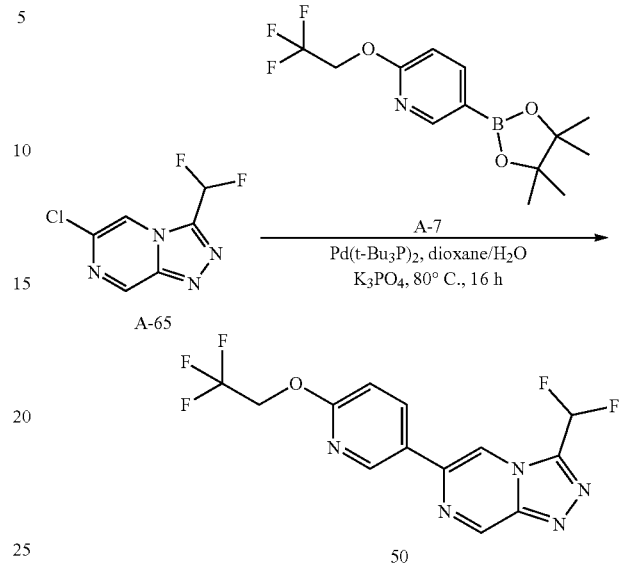

50

A mixture of A-65 (50.00 mg, 244.42 µmol), 5-(4,4,5,5-tetramethyl-1,3,2-dioxaborolan-2-yl)-2-(2,2,2-trifluoroethoxy)pyridine (81.49 mg, 268.86 µmol), K$_3$PO$_4$ (103.77 mg, 488.84 µmol) and Pd(t-Bu$_3$P)$_2$ (24.98 mg, 48.88 µmol) in dioxane (2 mL) and H$_2$O (200 µL) was stirred under N$_2$ at 80° C. for 16 hours. The mixture was diluted with EtOAc (5 mL), filtered through silica gel, and eluted with EtOAc (5 mL). The filtrate was concentrated to give a residue that was purified by prep-HPLC (Xtimate C$_{18}$ (150 mm×25 mm, 5 µm); A=H$_2$O (0.05% NH$_4$OH) and B=CH$_3$CN; 35-65% B over 10 minutes) to afford Compound 50 (18.08 mg) as a solid. $^1$H NMR (400 MHz, DMSO-d$_6$) $\delta_H$=9.69 (s, 1H), 9.23 (s, 1H), 8.93 (d, 1H), 8.51 (dd, 1H), 7.82 (t, 1H), 7.20 (d, 1H), 5.09 (q, 2H). LCMS R$_t$=1.20 min using Method A, MS ESI calcd. for C$_{13}$H$_9$F$_5$N$_5$O [M+H]$^+$ 346.1, found 345.9.

Example 48: Synthesis of Compound 51

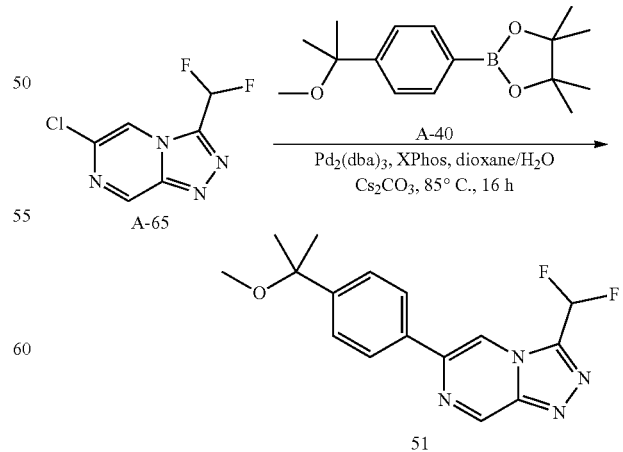

51

A mixture of A-65 (100.00 mg, 488.83 µmol), 2-[4-(1-methoxy-1-methyl-ethyl)phenyl]-4,4,5,5-tetramethyl-1,3,2- dioxaborolane (148.51 mg, 537.71 μmol), Pd$_2$(dba)$_3$ (67.14 mg, 73.32 μmol), XPhos (81.56 mg, 171.09 μmol) and Cs$_2$CO$_3$ (318.54 mg, 977.66 μmol) in dioxane (3 mL) and H$_2$O (300 μL) was stirred at 85° C. for 16 hours. The mixture was diluted with EtOAc (10 mL), filtered through silica gel, eluted with EtOAc (20 mL) and concentrated to give a residue that was purified by prep-HPLC (Xbridge (150 mm×25 mm, 5 μm); A=H$_2$O (0.05% NH$_4$HCO$_3$) and B=CH$_3$CN; 27-57% B over 10 minutes) to afford Compound 51 (43.81 mg) as a solid. $^1$H NMR (400 MHz, MeOD-d$_4$) δ$_H$=9.53 (d, 1H), 8.88 (d, 1H), 8.08 (d, 2H), 7.73-7.46 (m, 3H), 3.12 (s, 3H), 1.57 (s, 6H). LCMS R$_t$=1.16 min using Method A, MS ESI calcd. for C$_{16}$H$_{17}$F$_2$N$_4$O [M+H]$^+$ 319.1, found 318.9.

Example 49: Synthesis of Compound 52

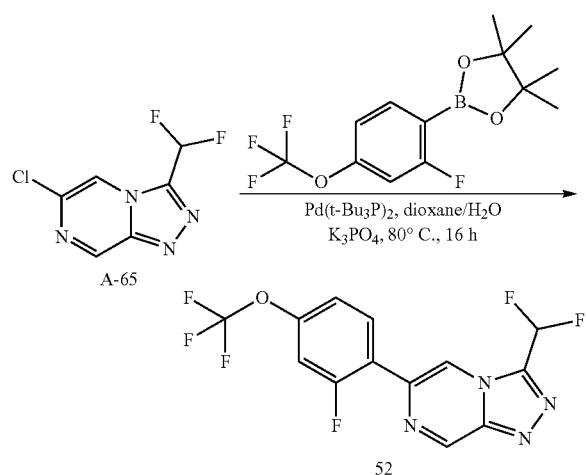

A mixture A-65 (50.00 mg, 244.42 μmol), 2-[2-fluoro-4-(trifluoromethoxy)phenyl]-4,4,5,5-tetramethyl-1,3,2-dioxaborolane (74.81 mg, 244.42 μmol), K$_3$PO$_4$ (103.77 mg, 488.84 μmol) and Pd(t-Bu$_3$P)$_2$ (24.98 mg, 48.88 μmol) in H$_2$O (200 μL) and dioxane (2 mL) was stirred under N$_2$ at 80° C. for 16 hours. The mixture was diluted with EtOAc (20 mL), filtered through silica gel, and eluted with EtOAc (10 mL). The filtrate was concentrated to give a residue that was purified by prep-HPLC (Xtimate C$_{18}$ (150 mm×25 mm, 5 μm); A=H$_2$O (0.05% NH$_4$OH) and B=CH$_3$CN; 40-70% B over 10 minutes) to afford Compound 52 (6.68 mg) as a solid. $^1$H NMR (400 MHz, DMSO-d$_6$) δ$_H$=9.72 (d, 1H), 8.96 (d, 1H), 8.17 (t, 1H), 7.87 (t, 1H), 7.64 (dd, 1H), 7.47 (d, 1H). LCMS R$_t$=1.28 min using Method A, MS ESI calcd. for C$_{13}$H$_7$F$_6$N$_4$O [M+H]$^+$ 349.0, found 348.9.

Example 50: Synthesis of Compound 54

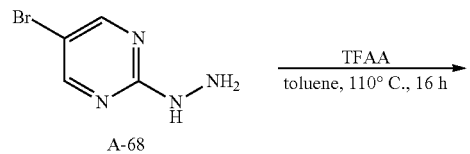

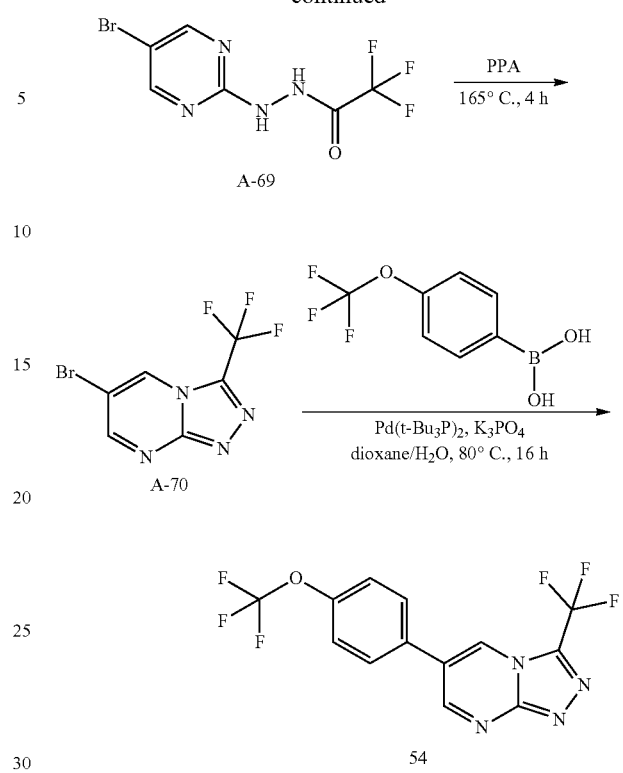

Synthesis of A-69: A mixture of A-68 (1.00 g, 5.29 mmol) and TFAA (1.11 g, 5.29 mmol, 735.80 μL) in toluene (20 mL) was stirred at 110° C. for 16 hours. After cooling to room temperature, the mixture was diluted with H$_2$O (10 mL) and extracted with EtOAc (30 mL×2). The combined organic phase was washed with brine (15 mL), dried over Na$_2$SO$_4$, filtered and concentrated to give A-69 (1.30 g, 4.56 mmol) as a solid. $^1$H NMR (400 MHz, CDCl$_3$) δ$_H$=8.87-8.56 (m, 1H), 8.41 (s, 2H)

Synthesis of A-70: A mixture of A-69 (300.00 mg, 1.05 mmol) and PPA (6.00 g) was stirred at 165° C. for 4 hours. The mixture was then diluted with H$_2$O (20 mL) and basified with Na$_2$CO$_3$ (solid) to pH~9, and then extracted with EtOAc (50 mL×2). The combined organic phase was washed with water (20 mL×2) and brine (20 mL), dried over Na$_2$SO$_4$, filtered and concentrated to give a residue that was purified by flash chromatography on silica gel (EtOAc in PE=10% to 15%) to afford A-70 (190.00 mg, 630.75 μmol) as a solid. $^1$H NMR (400 MHz, CDCl$_3$) δ$_H$=9.07 (d, 1H), 8.99 (d, 1H). LCMS R$_t$=0.681 min using Method B, MS ESI calcd. for C$_6$H$_3$BrF$_3$N$_4$ [M+H]$^+$ 266.9, found 266.8.

Synthesis of Compound 54: A mixture of A-70 (100.00 mg, 374.52 μmol), [4-(trifluoromethoxy)phenyl]boronic acid (115.69 mg, 561.78 μmol) Pd(t-Bu$_3$P)$_2$ (28.71 mg, 56.18 μmol) and K$_3$PO$_4$ (159.00 mg, 749.04 μmol) in dioxane (5 mL) and H$_2$O (1 mL) was stirred at 80° C. for 16 hours under N$_2$. The mixture was then concentrated to give a residue that was purified by prep-TLC (silica gel, PE:EtOAc=2:1) to afford Compound 54 (7.92 mg) as a solid. $^1$H NMR (400 MHz, CDCl$_3$) δ$_H$=9.20 (d, 1H), 9.03 (d, 1H), 7.67 (m, 2H), 7.46 (d, 2H). LCMS R$_t$=1.29 mins using Method A, MS ESI calcd. for C$_{13}$H$_7$F$_6$N$_4$O [M+H]$^+$ 349.0, found 348.9.

Example 51: Synthesis of Compound 55

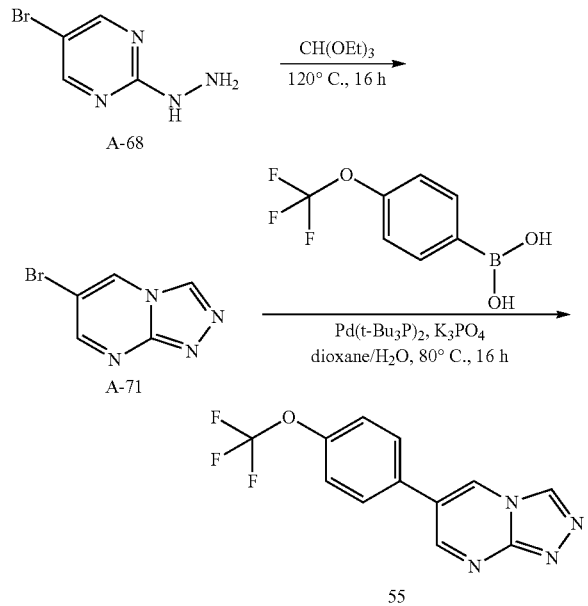

Synthesis of A-71: A mixture of A-68 (500.00 mg, 2.65 mmol) in CH(OEt)$_3$ (882.54 μL, 5.30 mmol) was stirred at 120° C. for 16 hours The mixture was diluted with EtOH (5 mL) and the solid formed was collected by filtration, washed with EtOH (5 mL×3) and dried in oven to afford A-71 (400.00 mg, 1.99 mmol) as a solid. $^1$H NMR (400 MHz, CDCl$_3$) $δ_H$=8.81 (s, 1H), 8.68 (d, 1H), 8.62 (d, 1H). LCMS R$_t$=0.15 min using Method B, MS ESI calcd. for C$_5$H$_4$BrN$_4$ [M+H+2]$^+$ 201.0, found 200.9.

Synthesis of Compound 55: A mixture of A-71 (150.00 mg, 753.73 μmol), [4-(trifluoromethoxy)phenyl]boronic acid (232.82 mg, 1.13 mmol), Pd(t-Bu$_3$P)$_2$ (57.78 mg, 113.06 μmol) and K$_3$PO$_4$ (319.99 mg, 1.51 mmol) in dioxane (7 mL) and H$_2$O (2 mL) was stirred at 80° C. for 16 hours under N$_2$. The mixture was concentrated to give a residue that was purified by flash chromatography on silica gel (EtOAc in PE=20% to 60% to 100%) and prep-HPLC (Kromasil (150 mm×25 mm, 10 μm) A=H$_2$O (0.05% NH$_4$OH) and B=CH$_3$CN; 25-55% B over 8 minutes) to afford Compound 55 (17.21 mg, 60.66 μmol) as a solid. $^1$H NMR (400 MHz CDCl$_3$) $δ_H$=9.08 (d, 1H), 9.01 (d, 1H), 8.58 (s, 1H), 7.69-7.63 (m, 2H), 7.43 (d, 2H). LCMS R$_t$=1.10 min using Method A, MS ESI calcd. for C$_{12}$H$_8$F$_3$N$_4$O [M+H]$^+$ 281.1, found 280.9.

Example 52. Synthesis of Compound 56

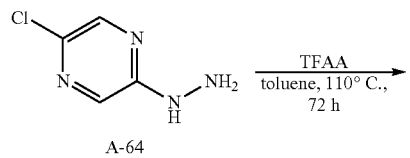

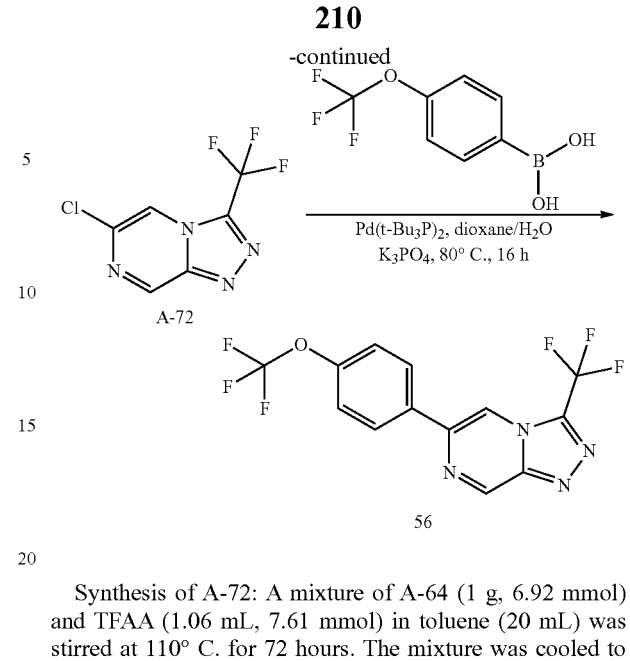

Synthesis of A-72: A mixture of A-64 (1 g, 6.92 mmol) and TFAA (1.06 mL, 7.61 mmol) in toluene (20 mL) was stirred at 110° C. for 72 hours. The mixture was cooled to room temperature, concentrated, and the residue was basified with sat.NaHCO$_3$ until pH=7-8. The mixture was extracted with EtOAc (20 mL×2), and the combined organic phase was washed with brine (10 mL), dried over Na$_2$SO$_4$, filtered and concentrated to give the crude product, which was purified by flash chromatography on silica gel (MeOH in DCM=0% to 5% to 10%) to afford A-72 (150 mg) as a solid. LCMS R$_t$=0.41 min using Method B, MS ESI calcd. for C$_6$H$_3$ClF$_3$N$_4$ [M+H]$^+$ 223.0, found 222.8.

Synthesis of Compound 56: A mixture of A-72 (100 mg, 449.33 μmol), [4-(trifluoromethoxy)phenyl]boronic acid (111.03 mg, 539.19 μmol), Pd(t-Bu$_3$P)$_2$ (34.44 mg, 67.40 μmol) and K$_3$PO$_4$ (190.76 mg, 898.65 μmol) in dioxane (3 mL) and H$_2$O (0.3 mL) was stirred at 80° C. for 16 hours. The mixture was cooled to room temperature, diluted with EtOAc (5 mL), filtered through silica gel, eluted with EtOAc (10 mL) and the filtrate was concentrated to give the crude product that was purified by prep-HPLC (Waters Xbridge (150 mm×25 mm, 5 μm) A=H$_2$O (10 mM NH$_4$HCO$_3$) and B=CH$_3$CN; 50-80% B over 10 minutes) to afford Compound 54 (16.13 mg) as a solid. $^1$H NMR (400 MHz, CDCl$_3$) $δ_H$=9.60 (s, 1H), 8.42 (s, 1H), 8.04 (d, 2H), 7.41 (d, 2H). LCMS R$_t$=1.16 min using Method A, MS ESI calcd. for C$_{13}$H$_7$F$_6$N$_4$O [M+H]$^+$ 349.0, found 348.7.

Example 53. Synthesis of Compound 57

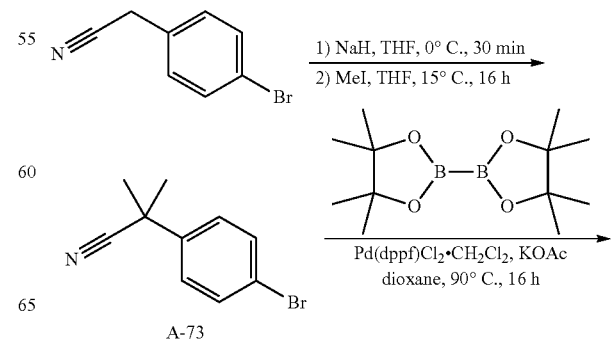

212

Example 54. Synthesis of Compound 58

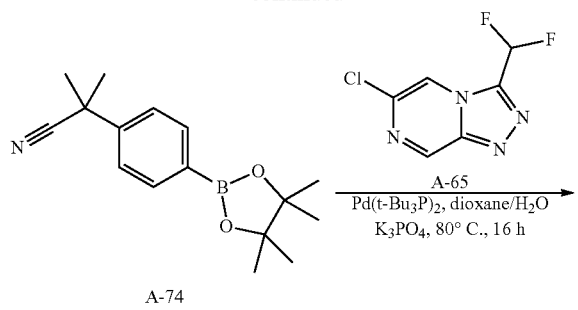

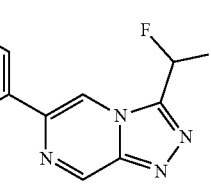

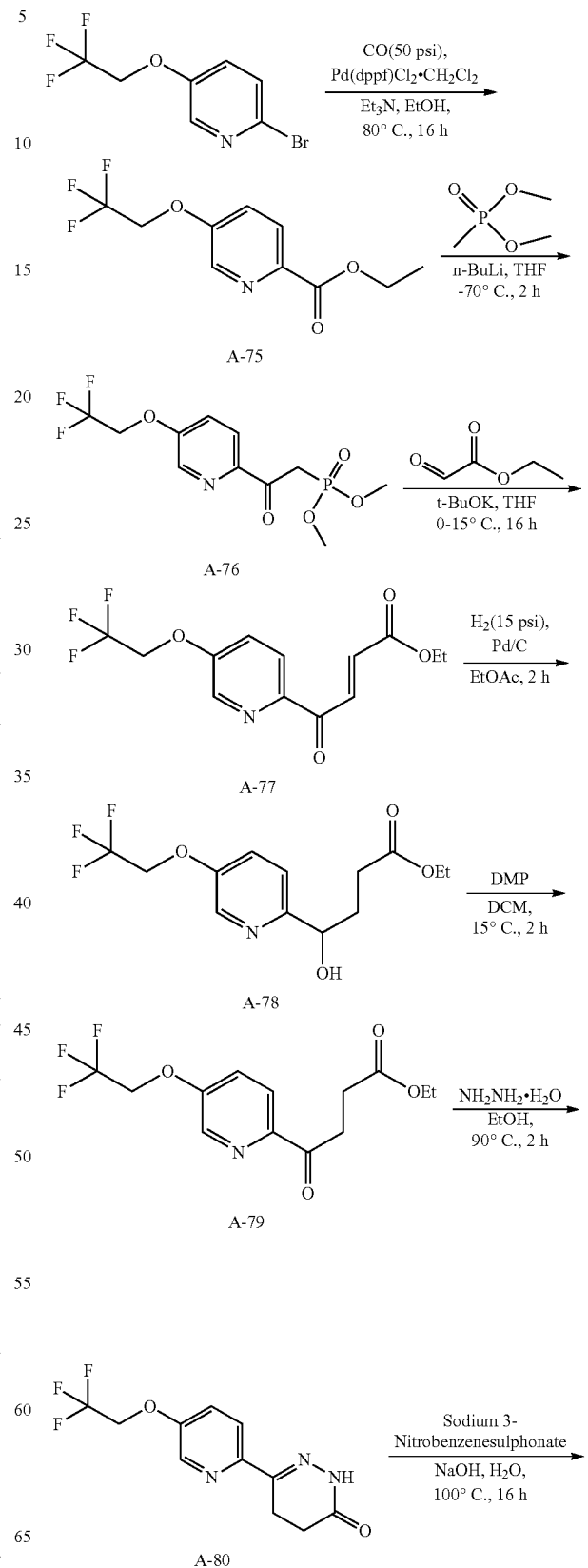

211

-continued

Synthesis of A-73: To a solution of 2-(4-bromophenyl) acetonitrile (2.00 g, 10.20 mmo) in THF (20 mL) was added NaH (1.22 g, 30.60 mmol, 60% purity) at 0° C. The mixture was stirred at 0° C. for 30 mins, then MeI (4.34 g, 30.60 mmol, 1.90 mL, 3.00 eq) was added to the mixture. The mixture was stirred at 15° C. for 16 hours. The mixture was quenched with sat.NH$_4$Cl (50 mL) and extracted with EtOAc (50 mL×2). The combined organic phase was washed with brine (20 mL), dried over Na$_2$SO$_4$, filtered and concentrated to give the crude product that was purified by flash chromatography on silica gel (PE:EtOAc=20:1 to 10:1) to afford A-73 (400.00 mg) as an oil. $^1$H NMR (400 MHZ, CDCl$_3$) $\delta_H$=7.53 (d, 2H), 7.36 (d, 2H), 1.72 (s, 6H).

Synthesis of A-74: A mixture of A-73 (400 mg, 1.78 mmol), 4,4,5,5-tetramethyl-2-(4,4,5,5-tetramethyl-1,3,2-dioxaborolan-2-yl)-1,3,2-dioxaborolane (543.92 mg, 2.14 mmol), KOAc (525.54 mg, 5.35 mmol) and Pd(dppf)Cl$_2$.CH$_2$Cl$_2$ (218.65 mg, 267.74 μmol) in dioxane (10 mL) was stirred at 90° C. for 16 hours. The mixture was cooled to room temperature, diluted with EtOAc (10 mL), filtered through silica gel, eluted with EtOAc (10 mL) and concentrated to give the crude product, which was purified by flash chromatography on silica gel (PE:EtOAc=50:1 to 20:1 to 15:1) to afford A-74 (360 mg) as a solid. $^1$H NMR (400 MHz CDCl$_3$) $\delta_H$=7.84 (d, 2H), 7.49 (d, 2H), 1.74 (s, 6H), 1.36 (s, 12H).

Synthesis of Compound 57: A mixture of A-74 (0.1 g, 488.84 μmol), A-70 (159.07 mg, 586.61 μmol), Pd(t-Bu$_3$P)$_2$ (49.96 mg, 97.77 μmol) and K$_3$PO$_4$ (207.53 mg, 977.68 μmol) in dioxane (3 mL) and H$_2$O (0.3 mL) was stirred at 80° C. for 16 hours. The mixture was cooled to room temperature, diluted with EtOAc (5 mL), filtered through silica gel, eluted with EtOAc (10 mL) and concentrated to give the crude product. The crude product was purified by prep-HPLC (Waters Xbridge (150 mm×25 mm, 5 μm) A=H$_2$O (10 mM NH$_4$HCO$_3$) and B=CH$_3$CN; 23-53% B over 10 minutes) to afford Compound 57 (15.48 mg) as a solid. $^1$H NMR (400 MHz, MeOD-d$_4$) $\delta_H$=9.53 (d, 1H), 8.92 (d, 1H), 8.15 (d, 2H), 7.73-7.45 (m, 3H), 1.78 (s, 6H). LCMS R$_t$=1.02 min using Method A, MS ESI calcd. for C$_{16}$H$_{14}$F$_2$N$_5$ [M+H]$^+$ 314.1, found 313.9.

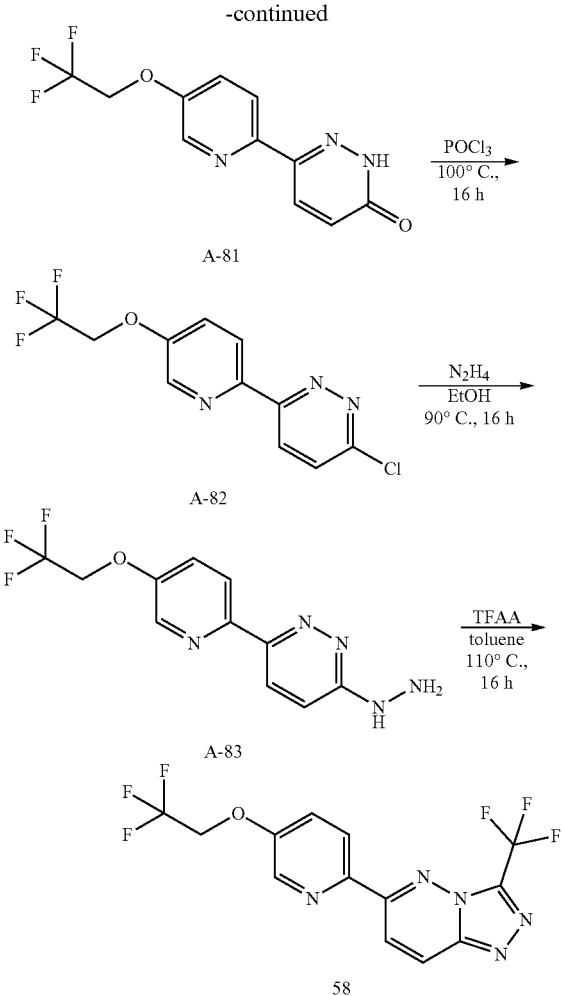

Synthesis of A-75: A mixture of 2-bromo-5-(2,2,2-trifluoroethoxy)pyridine (2 g, 7.81 mmol), Pd(dppf)Cl$_2$.CH$_2$Cl$_2$ (637.95 mg, 781.19 μmol) and Et$_3$N (2.37 g, 23.44 mmol, 3.26 mL) was degassed and refilled with CO. The reaction mixture was stirred under CO (50 psi) for 16 hours at 80° C., at which point the desired product was observed by LCMS. The reaction mixture was diluted with EtOAc (20 mL), and filtered through a Celite pad, eluted with EtOAc (20 mL) and concentrated. The residue was purified by flash chromatography on silica gel (PE/EtOAc=5/1 to 2/1 to 1/1) to afford A-75 (1.5 g) as a solid. $^1$H NMR (400 MHz, CDCl$_3$) $\delta_H$=8.48 (d, 1H), 8.16 (d, 1H), 7.34 (dd, 1H), 4.55-4.38 (m, 4H), 1.45 (t, 3H).

Synthesis of A-76: To a solution of [methoxy(methyl)phosphoryl]oxymethane (548.66 mg, 4.42 mmol, 472.99 μL) in THF (15 mL) under N$_2$ was added n-BuLi (2.5 M, 1.61 mL) drop wise at −70° C., and the reaction was stirred at −70° C. for 30 min. A-75 (500 mg, 2.01 mmol) was added, and the reaction was stirred at −70° C. for 1.5. The reaction was quenched with sat.NH$_4$Cl (20 mL), and extracted with EtOAc (20 mL×3). The combined organic phase was washed with brine (20 mL), dried over Na$_2$SO$_4$, filtered and concentrated to give a residue was purified by flash chromatography on silica gel (PE/EtOAc=5/1 to 2/1 to 1/1) to afford A-76 (500 mg, 1.53 mmol) as a solid. $^1$H NMR (400 MHz, CDCl$_3$) $\delta_H$=8.42 (d, 1H), 8.13 (d, 1H), 7.35 (dd, 1H), 4.50 (q, 2H), 3.99 (d, 2H), 3.81 (s, 3H), 3.78 (s, 3H).

Synthesis of A-77: To a solution of A-76 (460.52 mg, 1.41 mmol) and ethyl 2-oxoacetate (574.75 mg, 2.81 mmol) in THF (10 mL) at 0° C. was added z-BuOK (205.32 mg, 1.83 mmol). The reaction mixture was stirred at 15° C. for 16 hours. The reaction was quenched with sat.NH$_4$Cl (20 mL), extracted with EtOAc (20 mL×3), and the combined organic phase was washed with brine (20 mL), dried over Na$_2$SO$_4$, filtered and concentrated. The residue was purified by flash chromatography on silica gel (PE/EtOAc=5/1 to 2/1) to afford A-77 (350 mg) as a solid. LCMS R$_f$=0.84 min using Method B, MS ESI calcd. for C$_{13}$H$_{13}$F$_3$NO$_4$ [M+H]$^+$ 304.1, found 304.0.

Synthesis of A-78: A mixture of A-77 (350 mg, 1.15 mmol, 1 eq) and Pd/C (100 mg) in N$_2$ was degassed and refilled with H$_2$ (15 psi). The reaction mixture was stirred under H$_2$ (15 psi) at 15° C. for 2 hours. The reaction mixture was diluted with EtOAc (20 mL), filtered through a Celite pad, and eluted with EtOAc (10 mL). The filtrate was concentrated to afford A-78 (300 mg) as a solid. $^1$H NMR (400 MHz, CDCl$_3$) $\delta_H$=8.29 (t, 1H), 7.31 (d, 2H), 4.85-4.76 (m, 1H), 4.42 (q, 2H), 4.13 (q, 2H), 2.58-2.36 (m, 2H), 2.25-2.13 (m, 1H), 2.01-1.90 (m, 1H), 1.26 (t, 3H).

Synthesis of A-79: To a solution of A-78 (300 mg, 976.36 μmol, 1 eq) in DCM (10 mL) was added Dess-Martin (621.17 mg, 1.46 mmol). The reaction mixture was stirred at 15° C. for 2 hours. The reaction mixture was treated with sat.Na$_2$SO$_3$ (10 mL) and extracted with DCM (20 mL×3). The combined organic phase was washed with sat.NaHCO$_3$ (10 mL), dried over Na$_2$SO$_4$, filtered, concentrated, and the residue was purified by flash chromatography on silica gel (PE/EtOAc=20/1 to 10/1 to 5/1) to afford A-79 (230 mg) as a solid. $^1$H NMR (400 MHz, CDCl$_3$) $\delta_H$=8.40 (d, 1H), 8.08 (d, 1H), 7.34 (dd, 1H), 4.49 (q, 2H), 4.16 (q, 2H), 3.52 (t, 2H), 2.75 (t, 2H), 1.27 (t, 3H).

Synthesis of A-80: A mixture A-79 (230 mg, 753.48 μmol) and NH$_2$NH$_2$.H$_2$O (188.60 mg, 3.77 mmol) in EtOH (5 mL) was heated to 90° C. and stirred for 2 hours. After cooling, the reaction mixture was concentrated and the residue was treated with H$_2$O (10 mL), and the mixture was extracted with EtOAc (10 mL×3). The combined organic phase was washed with brine (10 mL), dried over Na$_2$SO$_4$, filtered and concentrated to afford A-80 (200 mg) as a solid. LCMS R$_f$=0.68 min using Method B, MS ESI calcd. for C$_{11}$H$_{11}$F$_3$N$_3$O$_2$ [M+H]$^+$ 274.1, found 273.9.

Synthesis of A-81: To a mixture of A-80 (150 mg, 549.03 μmol) and sodium 3-nitrobenzenesulfonate (247.23 mg, 1.10 mmol) in H$_2$O (10 mL) was added NaOH (87.84 mg, 2.20 mmol). The reaction mixture was stirred at 100° C. for 16 hours. After cooling, the reaction mixture was adjust to pH=8 with 1M HCl solution, and then the mixture was extracted with EtOAc (20 mL×3). The combined organic phase was washed with brine (10 mL), dried over Na$_2$SO$_4$, filtered and concentrated to afford A-81 (80 mg) as a solid. $^1$H NMR (400 MHz, CDCl$_3$) $\delta_H$=11-29 (s, 1H), 8.42-8.35 (m, 2H), 8.13 (d, 1H), 7.37 (dd, 1H), 7.08 (d, 1H), 4.48 (q, 2H).

Synthesis of A-82: A mixture A-81 (80 mg, 294.99 μmol) in POCl$_3$ (1 mL) was heated to 100° C. and stirred for 16 hours. After cooling, the reaction mixture was concentrated, and the residue was dissolved in DCM (10 mL) then treated with sat.NaHCO$_3$ to pH=8. The mixture was extracted with DCM (10 mL×3), and the combined organic phase was washed with brine (10 mL), dried over Na$_2$SO$_4$, filtered and concentrated to afford A-82 (70 mg, 241.68 μmol) as a solid. LCMS R$_f$=0.79 min using Method B, MS ESI calcd. for C$_{11}$H$_8$ClF$_3$N$_3$O [M+H]$^+$ 290.0, found 289.9.

Synthesis of A-83: To a solution of A-82 (70 mg, 241.68 µmol) in EtOH (5 mL) was added hydrazine (87.41 µL, 2.42 mmol). The reaction mixture was stirred at 90° C. for 16 hours. After cooling, the reaction mixture was concentrated to afford crude A-83 (70 mg) as a solid. LCMS $R_t$=0.64 min using Method B, MS ESI calcd. for $C_{11}H_{11}F_3N_5O$ $[M+H]^+$ 286.1, found 285.9.

Synthesis of Compound 58: To a mixture of A-83 (65 mg, 227.89 µmol) in toluene (5 mL) was added TFAA (34.87 µL, 250.68 µmol). The reaction mixture was stirred at 110° C. for 16 hours. After cooling, the reaction mixture was concentrated, and the residue was purified by prep-HPLC (Phenomenex Gemini (150 mm×25 mm, 10 µm); A=$H_2O$ (0.05% $NH_4OH$) and B=$CH_3CN$; 45-70% B over 9 minutes) to afford Compound 58 (36.03 mg) as a solid. $^1$H NMR (400 MHz, $CDCl_3$) $\delta_H$=8.54-8.48 (m, 2H), 8.45 (d, 1H), 8.30 (d, 1H), 7.47 (dd, 1H), 4.53 (q, 2H). LCMS $R_t$=0.82 min using Method B, MS ESI calcd. for $C_{13}H_8F_6N_5O$ $[M+H]^+$ 364.1, found 364.0.

Example 55. Synthesis of Compound 59

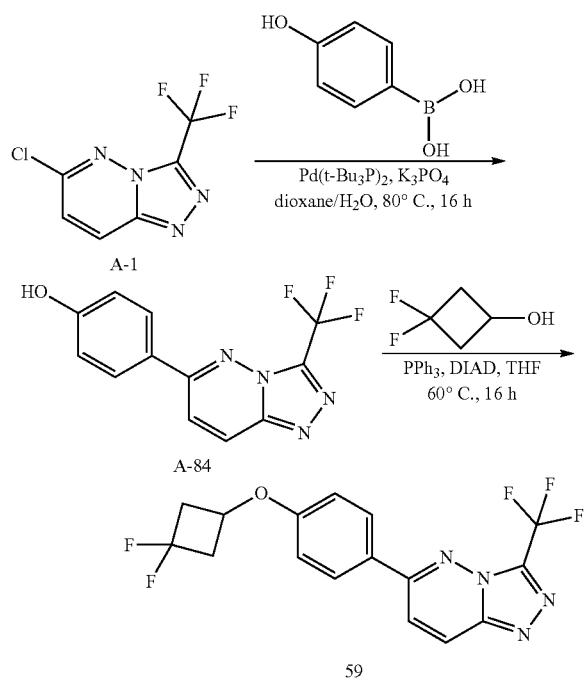

Synthesis of A-84: A mixture of A-1 (200 mg, 0.90 mmol), (4-hydroxyphenyl)boronic acid (185.92 mg, 1.35 mmol), $Pd(t-Bu_3P)_2$ (68.88 mg, 0.13 mmol) and $K_3PO_4$ (381.02 mg, 1.8 mmol) in 1,4-dioxane (10 mL) and water (2 mL) was stirred at 80° C. for 16 hours under $N_2$. After cooling to room temperature, the mixture was concentrated to a residue that was diluted with $H_2O$ (30 mL) and extracted with EtOAc (50 mL×5). The combined organic phase was washed with brine (20 mL), dried over $Na_2SO_4$, filtered and concentrated to give the crude product, which was purified by flash chromatography on silica gel (EtOAc in PE=20% to 60% to 100%) to afford A-84 (200 mg) as a solid. $^1$H NMR (400 MHZ, DMSO-$d_6$) $\delta_H$=10.26 (s, 1H), 8.59 (d, 1H), 8.15 (d, 1H), 8.01 (d, 2H), 6.98 (d, 2H). LCMS $R_t$=0.72 min using Method B, MS ESI calcd. for $C_{12}H_8F_3N_4O$ $[M+H]^+$ 281.1, found 280.9.

Synthesis of Compound 59: To a mixture of A-84 (40 mg, 0.14 mmol), 3,3-difluorocyclobutanol (18.52 mg, 0.17 mmol) and $Ph_3P$ (74.89 mg, 0.29 mmol) in THF (2 mL) was added DIAD (57.73 mg, 0.29 mmol) under $N_2$ at 60° C. The mixture was stirred at 60° C. for 16 hours. After cooling to room temperature, the mixture was concentrated to the crude product that was purified by prep-TLC (silica gel, DCM) and prep-HPLC (Phenomenex Gemini (250 mm×50 mm, 10 µm) A=$H_2O$ (0.05% $NH_4OH$) and B=$CH_3CN$; 58-68% B over 8 minutes) to afford Compound 59 (7.80 mg, 20.8 µmol) as a solid. $^1$H NMR (400 MHz, $CDCl_3$) $\delta_H$=8.26 (d, 1H), 8.01 (d, 2H), 7.74 (d, 1H), 6.99 (d, 2H), 4.81-4.70 (m, 1H), 3.23-3.10 (m, 2H), 2.90-2.75 (m, 2H). LCMS $R_t$=1.29 min using Method A, MS ESI calcd. for $C_{16}H_{12}F_5N_4O$ $[M+H]^+$ 371.1, found 371.0.

Example 56. Synthesis of Compound 60

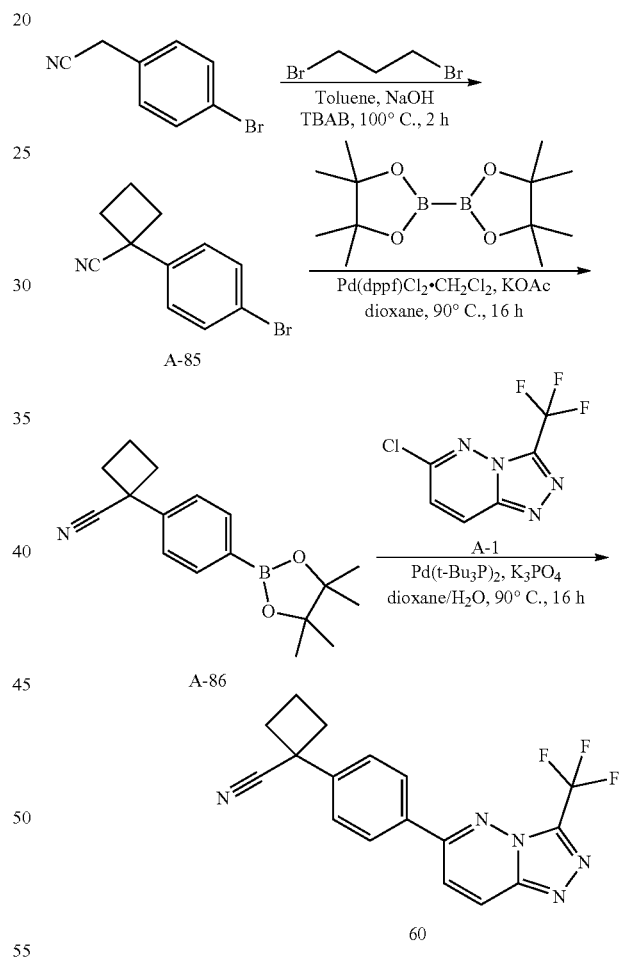

Synthesis of A-85: To a solution of 2-(4-bromophenyl)acetonitrile (5000 mg, 25.5 mmol) and TBAB (328.88 mg, 1.02 mmol) in toluene (30 mL) was added KOH (7155.43 mg, 127.52 mmol) (75% in $H_2O$), followed by 1,3-dibromopropane (10298.41 mg, 51.01 mmol), and the mixture was stirred at 100° C. for 2 hours. The mixture was then poured into water (50 mL) and extracted with EtOAc (100 mL×2). The combined organic phase was washed with brine (10 mL), dried over $Na_2SO_4$, filtered and concentrated to give the crude product, which was purified by flash chromatography on silica gel (DCM in PE=20% to 40% to 60%)

to afford A-85 (1600 mg) as a solid. $^1$H NMR (400 MHz, DMSO-d$_6$) $\delta_H$=7.64 (d, 2H), 7.43 (d, 2H), 2.78-2.70 (m, 2H), 2.64-2.56 (m, 2H), 2.27 (m, 1H), 2.05-1.95 (m, 1H).

Synthesis of A-86: A mixture of A-85 (1600 mg, 6.78 mmol), 4,4,5,5-tetramethyl-2-(4,4,5,5-tetramethyl-1,3,2-dioxaborolan-2-yl)-1,3,2-dioxaborolane (5162.48 mg, 20.33 mmol), KOAc (1330.09 mg, 13.55 mmol) and Pd(dppf)Cl$_2$·CH$_2$Cl$_2$ (829.44 mg, 1.02 mmol) in 1,4-dioxane (20 mL) was stirred at 90° C. for 16 hours. After cooling to room temperature, the mixture was filtered through Celite, eluted with EtOAc (50 mL×2) concentrated to give a residue that was purified by flash chromatography on silica gel (EtOAc in PE=5% to 15% to 60%). The impure product was triturated from i-Pr$_2$O (20 mL) and dried in oven to afford A-86 (1250 mg, 4.41 mmol) as a solid. $^1$H NMR (400 MHz, DMSO-d$_6$) $\delta_H$=7.85 (d, 2H), 7.43 (d, 2H), 2.90-2.78 (m, 2H), 2.70-2.59 (m, 2H), 2.45 (m, 1H), 2.09 (m, 1H), 1.36 (s, 12H).

Synthesis of Compound 60: A mixture of A-86 (152.68 mg, 0.54 mmol), A-1 (100 mg, 0.45 mmol), K$_3$PO$_4$ (181.52 mg, 0.90 mmol) and Pd(t-Bu$_3$P)$_2$ (45.92 mg, 0.09 mmol) in 1,4-dioxane (7 mL) and water (1 mL) was stirred at 90° C. for 16 hours. After cooling to room temperature, the mixture was concentrated and purified by prep-TLC (silica gel, PE:EtOAc=1:1) to give the crude product, which was triturated from i-Pr$_2$O (10 mL) and dried in oven to afford Compound 60 (58.8 mg, 0.17 mmol) as a solid. $^1$H NMR (400 MHz, DMSO-d$_6$) $\delta_H$=8.33 (d, 1H), 8.08 (d, 2H), 7.79 (d, 1H), 7.66 (d, 2H), 2.97-2.86 (m, 2H), 2.74-2.65 (m, 2H), 2.58-2.45 (m, 1H), 2.23-2.10 (m, 1H). LCMS R$_t$=1.29 min using Method A, MS ESI calcd. for C$_{17}$H$_{13}$F$_3$N$_5$ [M+H]$^+$ 344.1, found 343.9.

Example 57. Synthesis of Compound 61

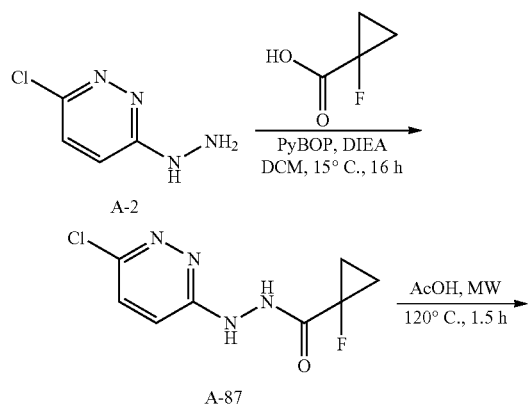

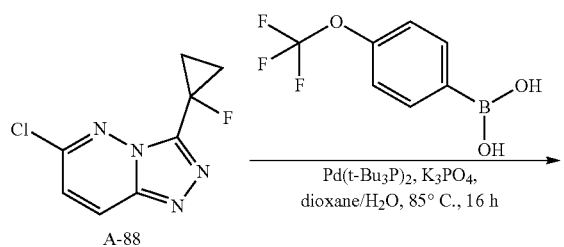

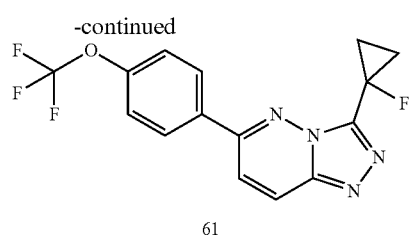

Synthesis of A-87: To a mixture of A-2 (300 mg, 2.08 mmol), 1-fluorocyclopropanecarboxylic acid (237.59 mg, 2.28 mmol) in DCM (5 mL) was added PyBOP (1618.71 mg, 3.11 mmol) and DIPEA (803.13 mg, 6.23 mmol) and the mixture was stirred at 15° C. for 16 hours. The reaction mixture was concentrated, diluted with NH$_4$Cl (50 mL), and extracted with EtOAc (50 mL×2). The combined organic phase was washed with brine (20 mL), dried over Na$_2$SO$_4$, filtered and concentrated to give the crude product of A-87 (2000 mg, 8.68 mmol) as an oil, which was used in the next step without further purification.

Synthesis of A-88: A solution of A-87 (2 g, 8.67 mmol) in acetic acid (10 mL) was sealed and heated in microwave reactor at 120° C. for 1.5 hours. After cooling to room temperature, the reaction mixture was concentrated, then diluted with sat.NaHCO$_3$ (50 mL) and extracted with DCM (50 mL×2). The combined organic phase was washed with brine (20 mL), dried over Na$_2$SO$_4$, filtered and concentrated to give the crude product, which was purified by flash chromatography on silica gel (PE:EtOAc=5:1 to 1:1) to afford A-88 (250 mg, 1.18 mmol) as a solid. $^1$H NMR (400 MHz, CDCl$_3$) $\delta_H$=8.12 (d, 1H), 7.21 (d, 1H), 1.75-1.66 (m, 2H), 1.53-1.46 (m, 2H).

Synthesis of Compound 61: A mixture of A-88 (100 mg, 0.47 mmol), [4-(trifluoromethoxy)phenyl]boronic acid (106.54 mg, 0.5200 mmol), Pd(t-BuP$_3$)$_2$ (36.05 mg, 0.07 mmol) and K$_3$PO$_4$ (129.82 mg, 0.9400 mmol) in 1,4-dioxane (3 mL) and water (0.3 mL) was stirred at 85° C. for 16 hours. The mixture was cooled to room temperature, diluted with EtOAc (5 mL), filtered through silica gel, eluted with EtOAc (10 mL), and concentrated to give the crude product, which was purified by prep-HPLC (Phenomenex Gemini (250 mm×50 mm, 10 µm) A=H$_2$O (0.05% NH$_4$OH) and B=CH$_3$CN; 50-80% B over 8 minutes) to afford Compound 61 (36.2 mg, 0.11 mmol) as a solid. $^1$H NMR (400 MHz, DMSO-d$_6$) $\delta_H$=8.57 (d, 1H), 8.26 (d, 2H), 8.09 (d, 1H), 7.63 (d, 2H), 1.76-1.62 (m, 2H), 1.51-1.45 (m, 2H). LCMS R$_t$=1.23 min using Method A, MS ESI calcd. for C$_{15}$H$_{11}$F$_4$N$_4$O [M+H]$^+$ 339.1, found 338.9.

Example 58. Synthesis of Compound 62

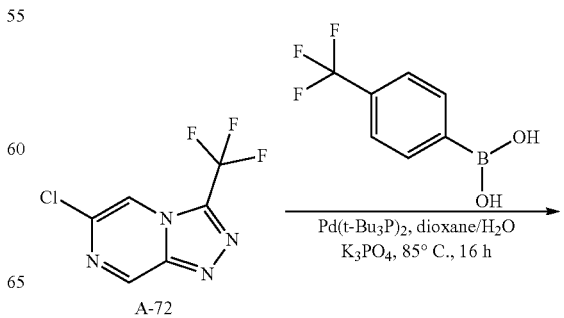

-continued

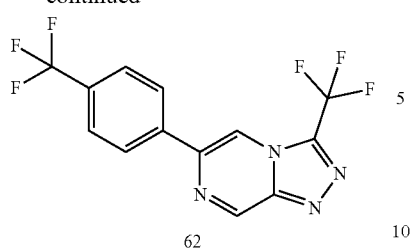

62

To a solution of A-72 (200 mg, 0.90 mmol) in 1,4-dioxane (2 mL) and water (0.20 mL) was added [4-(trifluoromethyl)phenyl]boronic acid (204.81 mg, 1.08 mmol), Pd(t-Bu₃P)₂ (68.89 mg, 0.13 mmol) and K₃PO₄ (381.56 mg, 1.8 mmol). The resulting mixture was stirred at 85° C. under N₂ for 16 hours. The reaction mixture was cooled to room temperature, filtered through Celite, and the filtrate was concentrated to give the crude product that was purified by prep-HPLC (Phenomenex Gemini (250 mm×50 mm, 10 μm) A=H₂O (0.05% NH₄OH) and B=CH₃CN; 50-80% B over 8 minutes) to afford Compound 62 (38.43 mg, 0.12 mmol) as a solid. $^1$H NMR (400 MHz, CDCl₃) δ$_H$=9.64 (s, 1H), 8.49 (s, 1H), 8.13 (d, 2H), 7.83 (d, 2H). LCMS R$_t$=1.22 mins using Method A, MS ESI calcd. for C₁₃H₇F₆N₄ [M+H]⁺ 333.0, found 332.9.

Example 59. Synthesis of Compound 63

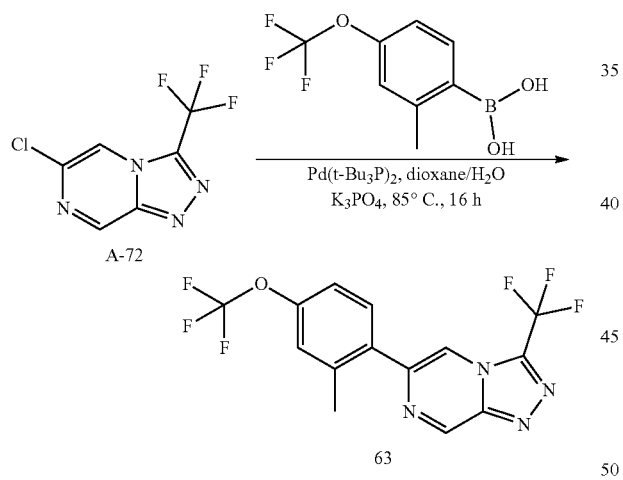

To a solution of A-72 (150 mg, 0.6700 mmol) in 1,4-dioxane (3 mL) and water (0.30 mL) was added [2-methyl-4-(trifluoromethoxy)phenyl]boronic acid (177.89 mg, 0.81 mmol), Pd(t-Bu₃P)₂ (51.67 mg, 0.10 mmol) and K₃PO₄ (286.17 mg, 1.35 mmol). The resulting mixture was stirred at 85° C. under N₂ for 16 hours. The reaction mixture was cooled to room temperature, filtered through Celite, concentrated, and purified by prep-HPLC (Phenomenex Gemini (250 mm×50 mm, 10 μm) A=H₂O (0.05% NH₄OH) and B=CH₃CN; 50-80% B over 8 minutes) to afford Compound 63 (21.69 mg, 0.06 mmol) as a solid. $^1$H NMR (400 MHz, CDCl₃) δ$_H$=9.60 (s, 1H), 8.18 (s, 1H), 7.48 (d, 1H), 7.25-7.19 (m, 2H), 2.44 (s, 3H). LCMS R$_t$=1.26 mins using Method A, MS ESI calcd. for C₁₄H₉F₆N₄O [M+H]⁺ 363.1, found 363.0.

Example 60. Synthesis of Compound 64

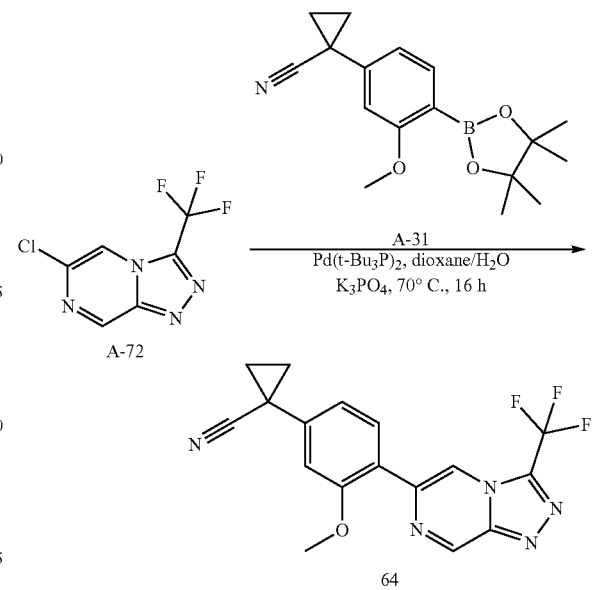

A mixture of A-72 (200 mg, 0.90 mmol), A-31 (349.5 mg, 1.17 mmol), Pd(t-Bu₃P)₂ (68.88 mg, 0.13 mmol) and K₃PO₄ (340 mg, 1.6 mmol) in 1,4-dioxane (10 mL) and water (2 mL) was stirred at 70° C. for 16 hours under N₂.S After cooling to room temperature, the mixture was diluted with H₂O (30 mL), and extracted with EtOAc (50 mL×2). The combined organic phase was washed with water (20 mL×2) and brine (20 mL), dried over Na₂SO₄, filtered and concentrated to give the crude product. The crude product was purified by prep-TLC (silica gel, DCM:MeOH=100:1), triturated from CH₃CN (0.5 mL), and dried in oven to afford Compound 64 (9.24 mg, 0.03 mmol) as a solid. $^1$H NMR (400 MHz, CDCl₃) δ$_H$=9.56 (s, 1H), 9.01 (s, 1H), 8.23 (d, 1H), 7.14 (s, 1H), 6.92 (dd, 1H), 4.04 (s, 3H), 1.87-1.81 (m, 2H), 1.54-1.49 (m, 2H). LCMS R$_t$=1.16 min using Method A, MS ESI calcd. for C₁₇H₁₃F₃N₅O [M+H]⁺ 360.1, found 360.0.

Example 61. Synthesis of Compound 65

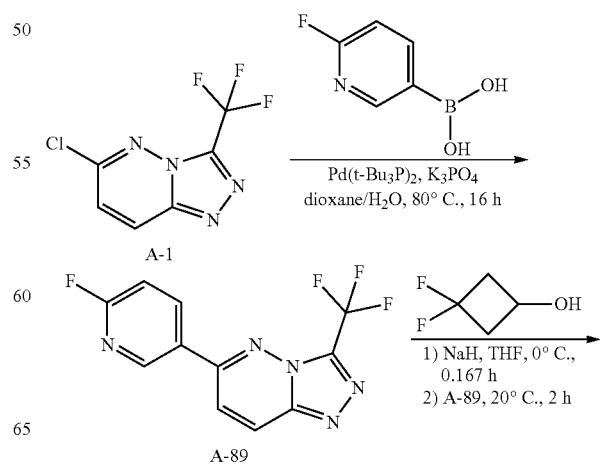

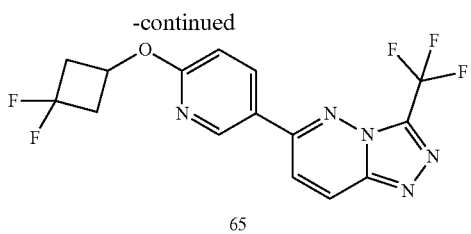

65

Synthesis of A-89: A mixture of Pd(t-Bu₃P)₂ (68.88 mg, 0.13 mmol), K₃PO₄ (381.02 mg, 1.8 mmol), A-1 (200 mg, 0.90 mmol) and (6-fluoro-3-pyridyl)boronic acid (189.94 mg, 1.35 mmol) in 1,4-dioxane (10 mL) and water (2 mL) was stirred at 80° C. for 16 hours under N₂. After cooling to room temperature, the mixture was concentrated, diluted with H₂O (30 mL), and extracted with EtOAc (100 mL×2). The combined organic phase was washed with brine (20 mL), dried over Na₂SO₄, filtered and concentrated to give the crude product, which was purified by flash chromatography on silica gel (EtOAc in PE=20% to 60% to 100%) to afford A-89 (140 mg, 0.49 mmol) as a solid. ¹H NMR (400 MHz, CDCl₃) $\delta_H$=8.87 (d, 1H), 8.53 (ddd, 1H), 8.39 (d, 1H), 7.77 (d, 1H), 7.20 (dd, 1H).

Synthesis of Compound 65: To a mixture of 3,3-difluorocyclobutanol (28 mg, 0.26 mmol) in THF (5 mL) was added NaH (14 mg, 0.35 mmol), and the mixture was stirred at 0° C. for 10 minutes. To the mixture was added A-89 (50 mg, 0.18 mmol), and the mixture was stirred at 20° C. for 2 hours. The mixture was quenched with sat. NH₄Cl (10 mL) and extracted with EtOAc (30 mL×2). The combined organic phase was washed with brine (10 mL), dried over Na₂SO₄, filtered, and concentrated to give the crude product, which was purified by prep-TLC (silica gel, PE:EtOAc=1:3) to afford Compound 65 (54.57 mg, 0.15 mmol) as a solid. ¹H NMR (400 MHz, CDCl₃) $\delta_H$=8.79 (d, 1H), 8.36-8.28 (m, 2H), 7.74 (d, 1H), 6.97 (d, 1H), 5.30-5.19 (m, 1H), 3.25-3.12 (m, 2H), 2.86-2.70 (m, 2H). LCMS $R_t$=1.21 min using Method A, MS ESI calcd. for C₁₅H₁₁F₅N₅O [M+H]⁺ 372.1, found 372.0.

Example 62. Synthesis of Compound 66

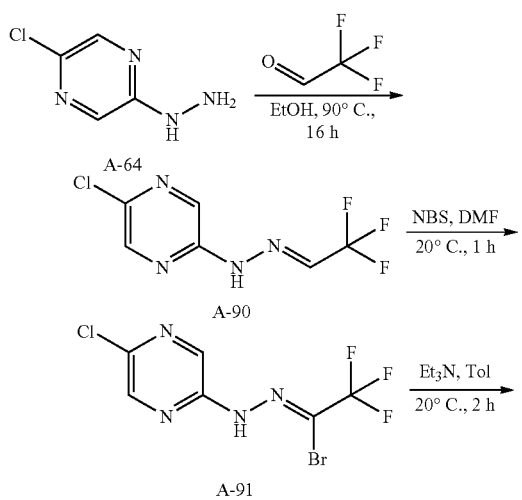

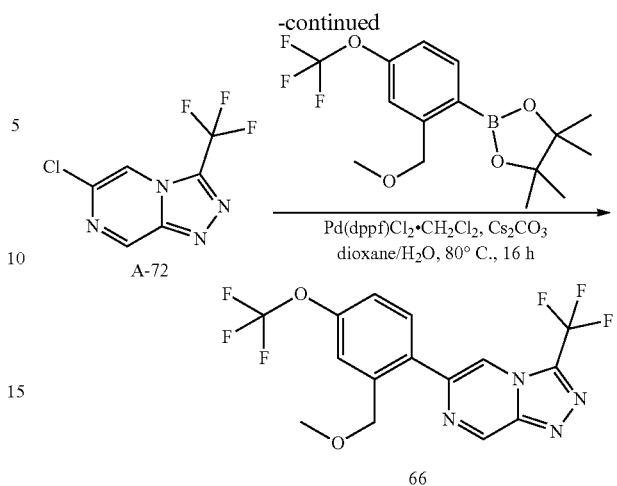

66

Synthesis of A-90: A mixture of A-64 (5 g, 34.59 mmol) and 2,2,2-trifluoroacetaldehyde (5.65 g, 43.23 mmol) in ethanol (25 mL) was stirred at 90° C. for 16 hours. After cooling to room temperature, the mixture was concentrated, triturated from/7-hexanes (20 mL), and dried to afford A-90 (7500 mg, 33.34 mmol) as a solid. ¹H NMR (400 MHz, CDCl₃) $\delta_H$=8.50 (br s, 1H), 8.49 (d, 1H), 8.15 (d, 1H), 7.16-7.11 (m, 1H).

Synthesis of A-91: To a mixture of A-90 (7500 mg, 33.4 mmol) in DMF (30 mL) was added a solution of NBS (6241.93 mg, 35.07 mmol) in DMF (30 mL). The mixture was stirred at 20° C. for 1 hour. The mixture was diluted with H₂O (200 mL) and extracted with n-hexanes (200 mL×3). The combined organic phase was washed with water (50 mL×2) and brine (50 mL), dried over Na₂SO₄, filtered and concentrated to afford A-91 (9500 mg, 31.31 mmol) as a solid. ¹H NMR (400 MHz, CDCl₃) $\delta_H$=8.60 (br s, 1H), 8.47 (d, 1H), 8.21 (d, 1H).

Synthesis of A-72: To a mixture of A-91 (9.5 g, 31.3 mmol) in toluene (20 mL) was added Et₃N (6.32 g, 62.61 mmol). The mixture was stirred at 20° C. for 2 hours. The mixture was diluted with H₂O (50 mL) and extracted with EtOAc (100 mL×2). The combined organic phase was washed with water (20 mL×2) and brine (20 mL), dried over Na₂SO₄, filtered, and concentrated to give the crude product, which was purified by flash chromatography on silica gel (EtOAc in PE=0% to 5% to 10%) to afford A-72 (4100 mg, 17.03 mmol) as a solid. ¹H NMR (400 MHz, CDCl₃) $\delta_H$=9.38 (d, 1H), 8.25 (s, 1H). LCMS $R_t$=0.35 min using Method B, MS ESI calcd. for C₆H₃ClF₃N₄ [M+H]⁺ 223.0, found 222.8.

Synthesis of Compound 66: A mixture of A-72 (100 mg, 0.45 mmol), 2-[2-(methoxymethyl)-4-(trifluoromethoxy)phenyl]-4,4,5,5-tetramethyl-1,3,2-dioxaborolane (179.07 mg, 0.54 mmol), Pd(dppf)Cl₂.CH₂Cl₂ (55.04 mg, 0.07 mmol) and Cs₂CO₃ (292.95 mg, 0.90 mmol) in 1,4-dioxane (3 mL) and water (0.50 mL) was stirred at 80° C. for 16 hours. The mixture was cooled to room temperature, diluted with EtOAc (5 mL), filtered through silica gel, eluted with EtOAc (5 mL), and concentrated to give the crude product, which was purified by prep-HPLC (Xbridge (150 mm×25 mm, 5 µm); A=H₂O (0.05% NH₄HCO₃) and B=CH₃CN; 42-72% B over 10 minutes) to afford Compound 66 (85.78 mg, 0.22 mmol) as a solid. ¹H NMR (400 MHz, CDCl₃) $\delta_H$=9.59 (d, 1H), 8.68 (s, 1H), 7.75 (d, 1H), 7.45 (s, 1H), 7.37 (d, 1H), 4.47 (s, 2H), 3.46 (s, 3H). LCMS $R_t$=1.24 min using Method A, MS ESI calcd. for $C_{15}H_{11}F_6N_4O_2$ [M+H]$^+$ 393.1, found 393.0.

Example 63. Synthesis of Compound 67

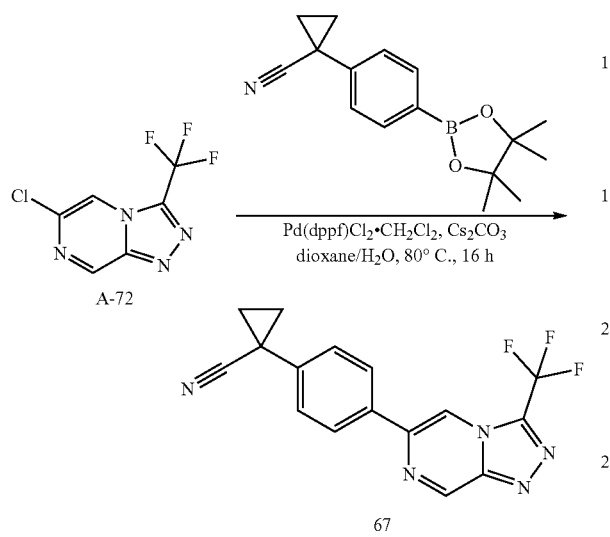

A mixture of 1-[4-(4,4,5,5-tetramethyl-1,3,2-dioxaborolan-2-yl)phenyl]cyclopropanecarbonitrile (199.54 mg, 0.74 mmol), A-72 (150 mg, 0.67 mmol), Pd(dppf)Cl$_2$.CH$_2$Cl$_2$ (82.56 mg, 0.10 mmol) and Cs$_2$CO$_3$ (439.43 mg, 1.35 mmol) in 1,4-dioxane (2 mL) and water (0.20 mL) was stirred at 80° C. for 16 hours. The mixture was cooled to room temperature, diluted with EtOAc (5 mL), filtered through silica gel, eluted with EtOAc (5 mL) and concentrated to give the crude product, which was purified by flash chromatography on silica gel (PE:EtOAc=5:1 to 1:1) to afford Compound 67 (77.03 mg, 0.24 mmol) as a solid. $^1$H NMR (400 MHz, DMSO-d$_6$) $\delta_H$=9.76 (d, 1H), 9.01 (s, 1H), 8.20 (d, 2H), 7.49 (d, 2H), 1.86-1.82 (m, 2H), 1.63-1.59 (m, 2H). LCMS $R_t$=1.11 min using Method A, MS ESI calcd. for $C_{16}H_{11}F_3N_5$ [M+H]$^+$ 330.1, found 329.9.

Example 64. Synthesis of Compound 68

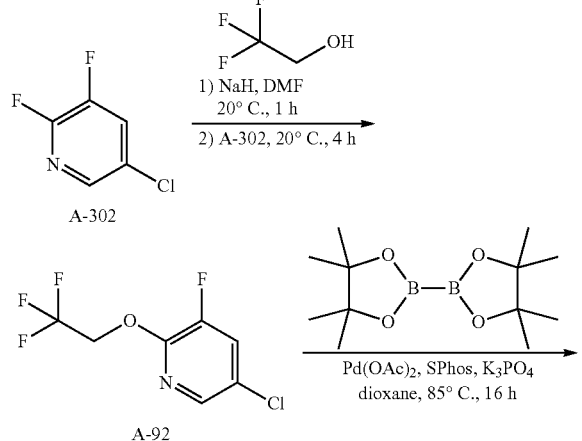

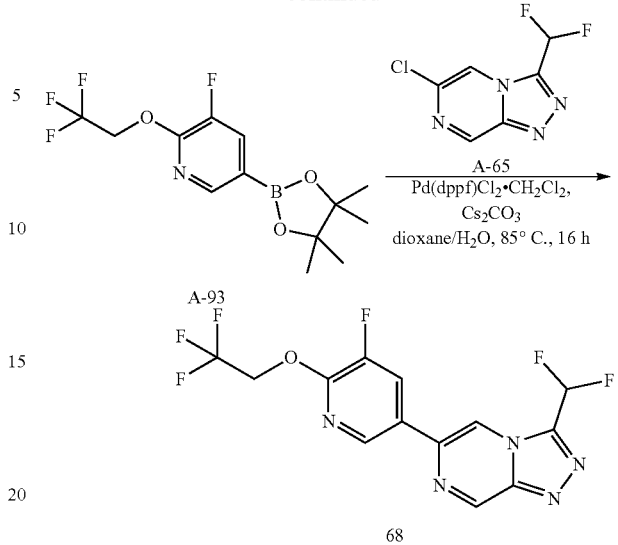

Synthesis of A-92: To a suspension of NaH (2.94 g, 73.56 mmol) in THF (50 mL) was added 2,2,2-trifluoroethanol (7.36 g, 73.56 mmol) slowly at 20° C., and the mixture was stirred for 1 hour. 5-chloro-2,3-difluoro-pyridine (10 g, 66.88 mmol) was then added, and the mixture was stirred at 20° C. for another 4 hours. The mixture was quenched with sat.NH$_4$Cl (50 mL) and extracted with EtOAc (100 mL×2). The combined organic phase was washed with brine (50 mL), dried over Na$_2$SO$_4$, filtered and concentrated to afford A-92 (15000 mg, 65.34 mmol) as an oil. $^1$H NMR (400 MHz, CDCl$_3$) $\delta_H$=7.83 (d, 1H), 7.38 (dd, 1H), 4.73 (q, 2H).

Synthesis of A-93: A mixture of A-92 (8 g, 34.85 mmol), 4,4,5,5-tetramethyl-2-(4,4,5,5-tetramethyl-1,3,2-dioxaborolan-2-yl)-1,3,2-dioxaborolane (26.55 g, 104.55 mmol), K$_3$PO$_4$ (14.79 g, 69.7 mmol), SPhos (4.29 g, 10.45 mmol) and Pd(OAc)$_2$ (782.4 mg, 3.48 mmol) in 1,4-dioxane (250 mL) was stirred at 85° C. for 16 hours. After cooling to room temperature, the mixture was filtered through Celite and eluted with EtOAc (50 mL×2). The filtrate was concentrated and diluted with EtOAc (200 mL), washed with water (100 mL×2) and brine (100 mL), dried over Na$_2$SO$_4$, filtered and concentrated to give the crude product, which was purified by flash chromatography on silica gel (EtOAc in PE=0 to 10% to 40%) to afford A-93 (3 g, 4.6021 mmol) as an oil. $^1$H NMR (400 MHz, CDCl$_3$) $\delta_H$=8.26 (d, 1H), 7.72 (dd, 1H), 4.87 (q, 2H), 1.35 (s, 12H). LCMS $R_t$=0.94 min using Method B, MS ESI calcd. for $C_{13}H_{17}BF_4NO_3$ [M+H]$^+$322.1, found 322.3.

Synthesis of Compound 68: A mixture of 3-fluoro-5-(4,4,5,5-tetramethyl-1,3,2-dioxaborolan-2-yl)-2-(2,2,2-trifluoroethoxy)pyridine (163.24 mg, 0.51 mmol), A-65 (80 mg, 0.39 mmol), Pd(dppf)Cl$_2$.CH$_2$Cl$_2$ (39.97 mg, 0.08 mmol) and Cs$_2$CO$_3$ (254.83 mg, 0.78 mmol) in 1,4-dioxane (3 mL) and water (0.50 mL) at 85° C. for 16 hours. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-TLC (PE:EtOAc=1:1) to afford Compound 68 (29.36 mg, 0.0798 mmol) as a solid. $^1$H NMR (400 MHz, DMSO-d$_6$) $\delta_H$=9.69 (s, 1H), 9.29 (s, 1H), 8.78 (d, 1H), 8.53

(dd, 1H), 7.81 (t, 1H), 5.19 (q, 2H). LCMS $R_t$=1.12 min using Method A, MS ESI calcd. for $C_{13}H_8F_6N_5O$ [M+H]$^+$ 364.1, found 363.9.

Example 65. Synthesis of Compound 69

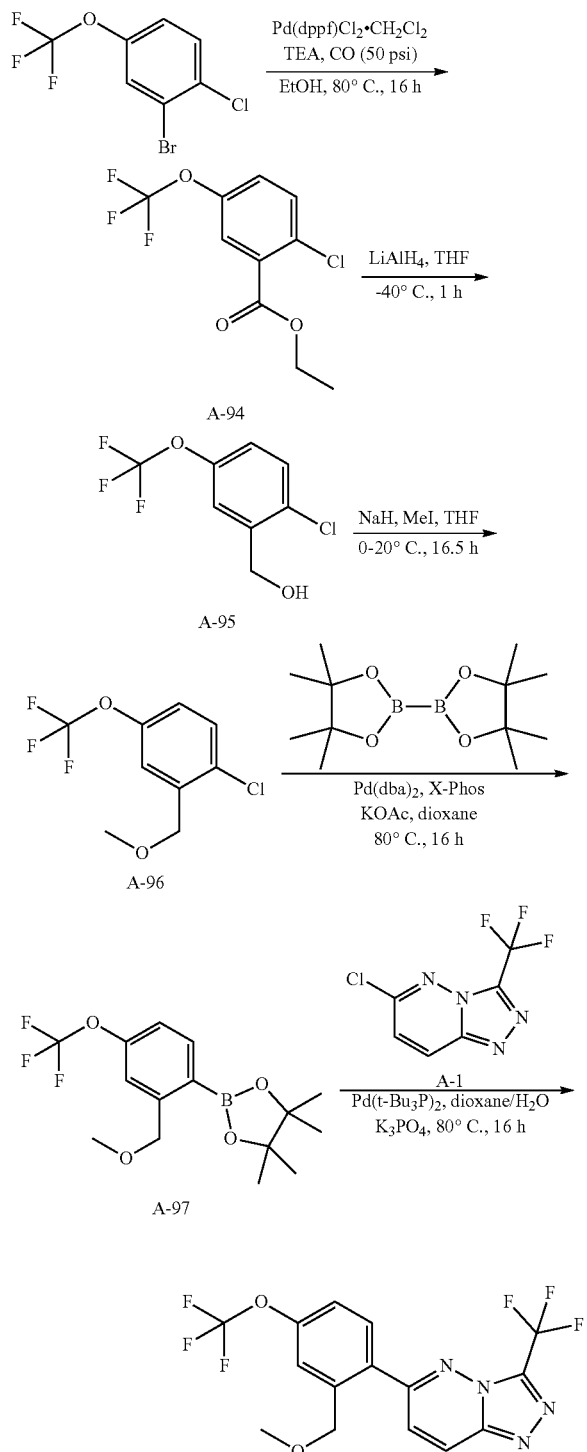

Synthesis of A-94: A mixture of 2-bromo-1-chloro-4-(trifluoromethoxy)benzene (5.00 g, 18.15 mmol), Pd(dppf)Cl$_2$·CH$_2$Cl$_2$ (1.48 g, 1.82 mmol) and Et$_3$N (7.55 mL, 54.45 mmol) in EtOH (30.00 mL) was degassed, and refilled with CO. The reaction was stirred under CO (50 psi) for 16 hours at 80° C. The reaction mixture was diluted with EtOH (20 mL), filtered through Celite, concentrated, and purified by flash chromatography on silica gel (EtOAc in PE=0%~5%) to afford A-94 (2.40 g, 8.93 mmol) as an oil. $^1$H NMR (400 MHz, CDCl$_3$) $\delta_H$=7.66-7.59 (m, 1H), 7.42 (d, 1H), 7.24-7.19 (m, 1H), 4.36 (q, 2H), 1.35 (t, 3H).

Synthesis of A-95: To a solution of A-94 (2.40 g, 8.93 mmol) in THF (30 mL) at −40° C. was added LiAlH$_4$ (406.67 mg, 10.72 mmol) slowly. The reaction was stirred at −40° C. for 1 hour. The reaction was quenched with sat.NH$_4$Cl (0.4 mL), diluted with EtOAc (30 mL), and the solid formed was filtered through Celite and eluted with EtOAc (30 mL). The filtrate was concentrated and purified by flash chromatography on silica gel (EtOAc in PE=0% to 10% to 20%) to afford A-95 (1.50 g, 6.62 mmol) as a solid. $^1$H NMR (400 MHz, CDCl$_3$) $\delta_H$=7.45-7.42 (m, 1H), 7.38 (d, 1H), 7.13-7.08 (m, 1H), 4.80 (d, 2H), 2.04 (t, 1H).

Synthesis of A-96: To a solution of A-96 (1.50 g, 6.62 mmol, 1.00 eq) in THF (20 mL) at 0° C. was added NaH (317.76 mg, 7.94 mmol, 60% purity) slowly. The mixture was stirred at 0° C. for 30 min, then MeI (1.24 mL, 19.86 mmol) was added, and the reaction was stirred at 20° C. for 16 hours. The reaction mixture was quenched with sat.NH$_4$Cl (50 mL), extracted with EtOAc (50 mL×3). The combined organic phase was washed with brine (50 mL), dried over Na$_2$SO$_4$, filtered, and concentrated, and the residue was purified by flash chromatography on silica gel (EtOAc in PE=0% to 5% to 10%) to afford A-96 (1.40 g, 5.82 mmol) as an oil. $^1$H NMR (400 MHz CDCl$_3$) $\delta_H$=7.43-7.32 (m, 2H), 7.09 (dd, 1H), 4.54 (s, 2H), 3.50 (s, 3H).

Synthesis of A-97: A mixture of A-96 (400.00 mg, 1.66 mmol), 4,4,5,5-tetramethyl-2-(4,4,5,5-tetramethyl-1,3,2-dioxaborolan-2-yl)-1,3,2-dioxaborolane (505.85 mg, 1.99 mmol), KOAc (325.82 mg, 3.32 mmol), X-Phos (197.84 mg, 415.00 μmol) and Pd$_2$(dba)$_3$ (152.01 mg, 166.00 μmol) in dioxane (6 mL) was stirred under N$_2$ at 80° C. for 16 hours. The mixture was cooled to room temperature, concentrated, and the residue was purified by flash chromatography on silica gel (PE:EtOAc=1:0 to 50:1) to afford A-97 (300.00 mg, 903.29 μmol) as an oil. LCMS $R_t$=0.99 min using Method B, MS ESI calcd. for $C_{15}H_{21}BF_3O_4$ [M+H]+ 333.1, found 332.7.

Synthesis of Compound 69: A mixture of A-97 (298.46 mg, 898.64 μmol), A-1 (100.00 mg, 449.32 μmol), Pd(t-Bu$_3$P)$_2$ (45.92 mg, 89.86 μmol) and K$_3$PO$_4$ (190.75 mg, 898.64 μmol) was stirred under N$_2$ at 80° C. for 16 hours. The mixture was cooled to room temperature, diluted with EtOAc (10 mL), filtered through Celite, eluted with EtOAc (5 mL), and concentrated to give the crude product, which was purified by prep-HPLC (Kromasil (150 mm×25 mm, 10 μm) A=H$_2$O (0.05% NH$_4$OH) and B=CH$_3$CN; 53-63% B over 8 minutes) to afford Compound 69 (32.30 mg, 81.58 μmol) as a solid. $^1$H NMR (400 MHz, CDCl$_3$) $\delta_H$=8.32 (d, 1H), 7.65-7.55 (m, 3H), 7.35 (d, 1H), 4.65 (s, 2H), 3.37 (s, 3H). LCMS $R_t$=0.87 min using Method B, MS ESI calcd. for $C_{15}H_{11}F_6N_4O_2$ [M+H]$^+$ 393.1, found 392.9.

Example 66. Synthesis of Compound 70

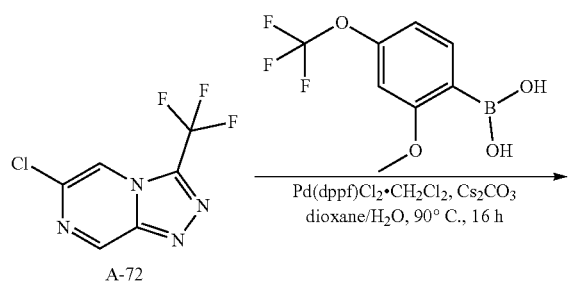

A mixture of [2-methoxy-4-(trifluoromethoxy)phenyl]boronic acid (127.22 mg, 0.54 mmol), A-72 (100 mg, 0.45 mmol), Pd(dppf)Cl$_2$·CH$_2$Cl$_2$ (73.39 mg, 0.09 mmol) and Cs$_2$CO$_3$ (292.77 mg, 0.90 mmol) in 1,4-dioxane (3 mL) and water (0.50 mL) was stirred at 90° C. for 16 hours under N$_2$. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 μm); A=H$_2$O (0.05% NH$_4$OH) and B=CH$_3$CN; 63-73% B over 8 minutes) to afford Compound 70 (5.62 mg) as a solid. $^1$H NMR (400 MHZ, CDCl$_3$) $\delta_H$=9.57 (d, 1H), 8.98 (s, 1H), 8.28 (d, 1H), 7.05 (d, 1H), 6.92 (s, 1H), 4.01 (s, 3H). LCMS R$_f$=1.24 min using Method A, MS ESI calcd. for C$_{14}$H$_9$F$_6$N$_4$O$_2$ [M+H]$^+$ 379.1, found 378.9.

Example 67. Synthesis of Compound 71

A mixture of A-86 (152.68 mg, 0.54 mmol), A-72 (100 mg, 0.45 mmol), Pd(dppf)Cl$_2$.DCM (73.39 mg, 0.09 mmol) and Cs$_2$CO$_3$ (292.77 mg, 0.90 mmol) in 1,4-dioxane (3 mL) and water (0.50 mL) was stirred at 90° C. for 16 hours. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 μm); A=H$_2$O (0.05% NH$_4$OH) and B=CH$_3$CN; 55-65% B over 8 minutes) to afford Compound 71 (29.77 mg, 0.09 mmol) as a solid. $^1$H NMR (400 MHz, CDCl$_3$) $\delta_H$=9.61 (d, 1H), 8.44 (s, 1H), 8.03 (d, 2H), 7.62 (d, 2H), 2.96-2.86 (m, 2H), 2.74-2.64 (m, 2H), 2.57-2.43 (m, 1H), 2.22-2.09 (m, 1H). LCMS R$_f$=1.12 min using Method A, MS ESI calcd. for C$_{17}$H$_{13}$F$_3$N$_5$ [M+H]$^+$ 344.1, found 344.0.

Example 68. Synthesis of Compound 72

A mixture of 2-[2-fluoro-4-(trifluoromethoxy)phenyl]-4,4,5,5-tetramethyl-1,3,2-dioxaborolane (165.02 mg, 0.5400 mmol), A-72 (100 mg, 0.45 mmol), Pd(dppf)Cl$_2$.DCM (73.39 mg, 0.09 mmol) and Cs$_2$CO$_3$ (292.77 mg, 0.90 mmol) in 1,4-dioxane (3 mL) and water (0.5 mL) was stirred at 90° C. for 16 hours. After cooling to room temperature, the mixture was filtered through silica gel, and eluted with EtOAc (20 mL×2). The organic phase was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 μm); A=H$_2$O (0.05% NH$_4$OH) and B=CH$_3$CN; 61-71% B over 8 minutes) to afford Compound 72 (36.18 mg, 0.10 mmol) as a solid. $^1$H NMR (400 MHz, DMSO-d$_6$) $\delta_H$=9.81 (d, 1H), 8.90 (s, 1H), 8.15 (t, 1H), 7.65 (d, 1H), 7.47 (d, 1H). LCMS R$_t$=1.23 min using Method A, MS ESI calcd. for C$_{13}$H$_6$F$_7$N$_4$O [M+H]$^+$ 367.0, found 366.9.

Example 69. Synthesis of Compound 73

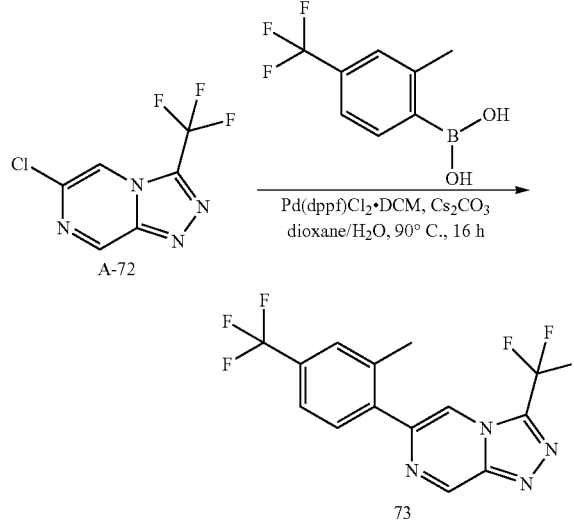

A mixture of A-72 (100 mg, 0.45 mmol), [2-methyl-4-(trifluoromethyl)phenyl]boronic acid (109.97 mg, 0.54 mmol), Pd(dppf)Cl$_2$.DCM (73.39 mg, 0.09 mmol) and Cs$_2$CO$_3$ (292.77 mg, 0.90 mmol) in 1,4-dioxane (3 mL) and water (0.5 mL) was stirred at 90° C. for 16 hours. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 µm); A=H$_2$O (0.05% NH$_4$OH) and B=CH$_3$CN; 63-73% B over 8 minutes) to afford Compound 73 (69.69 mg, 0.20 mmol) as an oil. $^1$H NMR (400 MHz, CDCl$_3$) $\delta_H$=9.61 (d, 1H), 8.21 (s, 1H), 7.65-7.55 (m, 3H), 2.49 (s, 3H). LCMS R$_t$=1.19 min using Method A, MS ESI calcd. for C$_{14}$H$_9$F$_6$N$_4$ [M+H]$^+$ 347.1, found 346.9.

Example 70. Synthesis of Compound 74

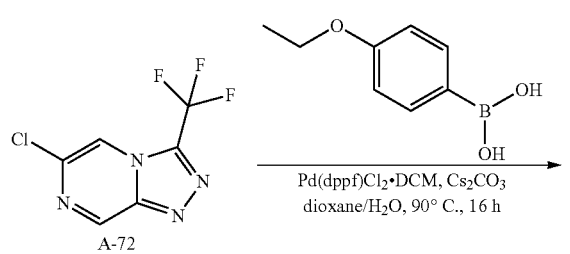

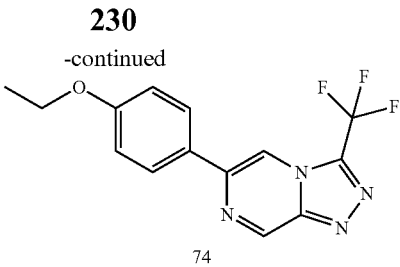

A mixture of A-72 (100 mg, 0.45 mmol), (4-ethoxyphenyl)boronic acid (89.49 mg, 0.54 mmol), Pd(dppf)Cl$_2$.DCM (73.39 mg, 0.09 mmol) and Cs$_2$CO$_3$ (146.39 mg, 0.45 mmol) in 1,4-dioxane (3 mL) and water (0.50 mL) was stirred at 90° C. for 16 hours. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 µm); A=H$_2$O (0.05% NH$_4$OH) and B=CH$_3$CN; 58-68% B over 8 minutes) to afford Compound 74 (31.15 mg, 0.10 mmol) as a solid. $^1$H NMR (400 MHz, CDCl$_3$) $\delta_H$=9.56 (d, 1H), 8.33 (s, 1H), 7.92 (d, 2H), 7.05 (d, 2H), 4.13 (q, 2H), 1.48 (t, 3H).

LCMS R$_t$=1.13 min using Method A, MS ESI calcd. for C$_{14}$H$_{12}$F$_3$N$_4$O [M+H]$^+$ 309.1, found 308.9.

Example 71. Synthesis of Compound 75

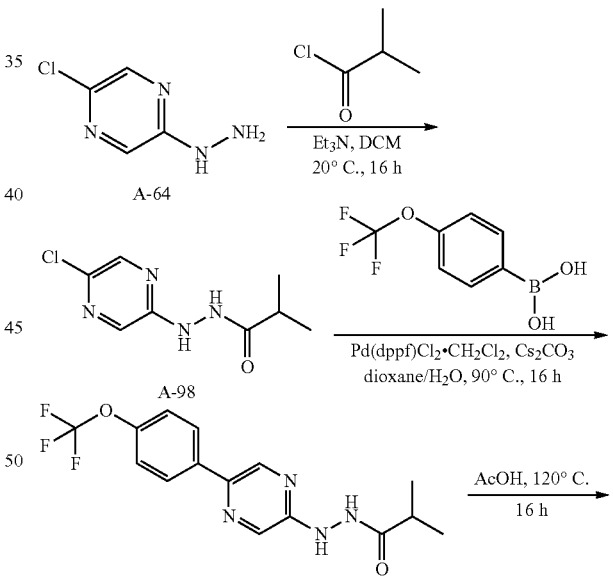

Synthesis of A-98: To a mixture of A-64 (1 g, 6.92 mmol) and Et$_3$N (1.91 mL, 13.84 mmol) in DCM (20 mL) was added 2-methylpropanoyl chloride (810.77 mg, 7.61 mmol).

The reaction mixture was stirred at 20° C. for 16 hours. The reaction mixture was quenched with sat.NaHCO$_3$ (50 mL) and extracted with DCM (30 mL×3). The combined organic phase was washed with brine (20 mL), dried over Na$_2$SO$_4$, filtered, and concentrated to afford A-98 (1500 mg, 7.0 mmol) as a solid. $^1$H NMR (400 MHz, CDCl$_3$) $\delta_H$=8.12 (d, 1H), 7.91 (d, 1H), 7.47 (s, 1H), 6.78 (s, 1H), 2.56-2.47 (m, 1H), 1.25 (d, 6H).

Synthesis of A-99: A mixture of A-98 (500 mg, 2.33 mmol), [4-(trifluoromethoxy)-phenyl]boronic acid (527.66 mg, 2.56 mmol), Pd(dppf)Cl$_2$.CH$_2$Cl$_2$ (190.23 mg, 0.23 mmol) and Cs$_2$CO$_3$ (1.52 g, 4.66 mmol) in 1,4-dioxane (10 mL) and water (1 mL) under N$_2$ was stirred at 90° C. for 16 hours. After cooling, the reaction mixture was diluted with EtOAc (20 mL), filtered through a Celite pad, eluted with EtOAc (10 mL), and concentrated to give a residue that was purified by flash chromatography on silica gel (EtOAc in PE=0% to 20% to 40%) to afford A-99 (250 mg, 0.73 mmol) as a solid.

$^1$H NMR (400 MHz, CDCl$_3$) $\delta_H$=8.53 (d, 1H), 8.20 (d, 1H), 7.92 (d, 2H), 7.58 (d, 1H), 7.31 (d, 2H), 6.87 (d, 1H), 2.60-2.53 (m, 1H), 1.28 (d, 6H).

Synthesis of Compound 75: A mixture of A-99 (150 mg, 0.44 mmol) in acetic acid (3 mL) was stirred at 120° C. for 16 hours. After cooling, the reaction mixture was concentrated and the mixture was diluted with sat.NaHCO$_3$ (30 mL) and extracted with EtOAc (30 mL×2). The combined organic phase was washed with brine (30 mL), dried over Na$_2$SO$_4$, filtered and concentrated to give a crude product that was purified by flash chromatography on silica gel (EtOAc in PE=0% to 20% to 40%) to afford Compound 75 (90.4 mg, 0.27 mmol) as a solid. $^1$H NMR (400 MHz, CDCl$_3$) $\delta_H$=9.42 (d, 1H), 8.14 (d, 1H), 8.00 (d, 2H), 7.38 (d, 2H), 3.49 (spt, 1H), 1.61 (d, 6H). LCMS R$_t$=1.15 min using Method A, MS ESI calcd. for C$_{15}$H$_{14}$F$_3$N$_4$O [M+H]$^+$ 323.1, found 322.9.

Example 72. Synthesis of Compound 76

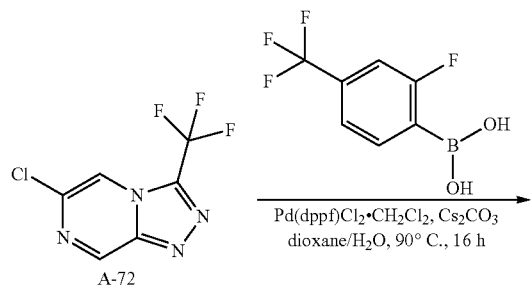

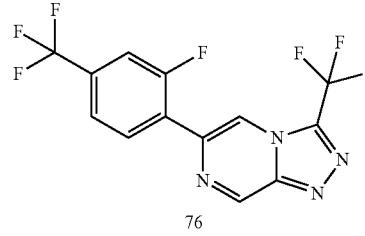

76

A mixture of A-72 (100 mg, 0.45 mmol), [2-fluoro-4-(trifluoromethyl)phenyl]boronic acid (112.11 mg, 0.54 mmol), Pd(dppf)Cl$_2$.CH$_2$Cl$_2$ (73.39 mg, 0.09 mmol) and Cs$_2$CO$_3$ (292.77 mg, 0.90 mmol) in 1,4-dioxane (3 mL) and water (0.5 mL) was stirred at 90° C. for 16 hours under N$_2$. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 μm); A=H$_2$O (0.05% NH$_4$OH) and B=CH$_3$CN; 58-68% B over 8 minutes) to afford Compound 76 (22.67 mg, 0.06 mmol) as a solid. $^1$H NMR (400 MHz, CDCl$_3$) $\delta_H$=9.63 (d, 1H), 8.80 (s, 1H), 8.45 (t, 1H), 7.65 (d, 1H), 7.55 (d, 1H). LCMS R$_t$=1.18 min using Method A, MS ESI calcd. for C$_{13}$H$_6$F$_7$N$_4$ [M+H]$^+$ 351.0, found 350.9.

Example 73. Synthesis of Compound 77

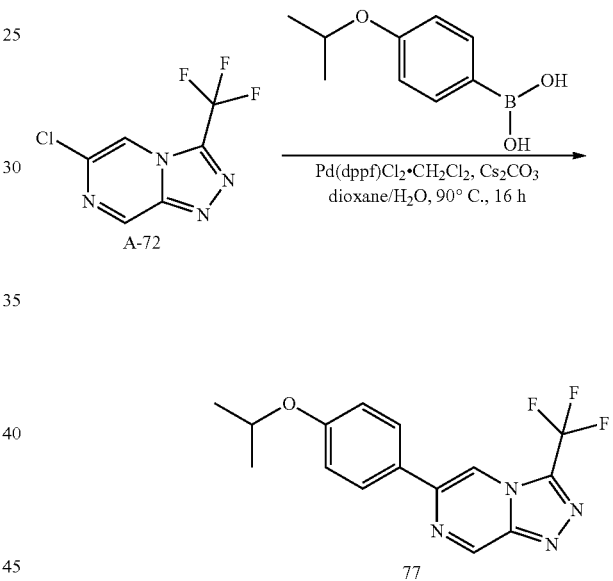

A mixture of A-72 (100 mg, 0.45 mmol), (4-isopropoxyphenyl)boronic acid (105.15 mg, 0.58 mmol), Pd(dppf)Cl$_2$.CH$_2$Cl$_2$ (73.39 mg, 0.09 mmol) and Cs$_2$CO$_3$ (292.77 mg, 0.90 mmol) in 1,4-dioxane (3 mL) and water (0.50 mL) was stirred at 90° C. for 16 hours under N$_2$. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 μm); A=H$_2$O (0.05% NH$_4$OH) and B=CH$_3$CN; 63-73% B over 8 minutes) to afford Compound 77 (23.16 mg, 0.07 mmol) as a solid. $^1$H NMR (400 MHz, CDCl$_3$) $\delta_H$=9.56 (d, 1H), 8.32 (s, 1H), 7.91 (d, 2H), 7.04 (d, 2H), 4.66 (quin, 1H), 1.40 (d, 6H). LCMS R$_t$=1.17 min using Method A, MS ESI calcd. for C$_{15}$H$_{14}$F$_3$N$_4$O [M+H]$^+$ 323.1, found 322.9.

Example 74. Synthesis of Compound 78

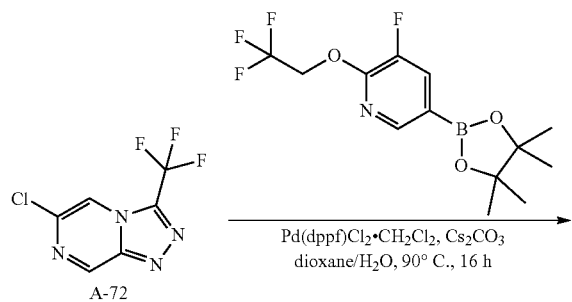

A mixture of 3-fluoro-5-(4,4,5,5-tetramethyl-1,3,2-dioxaborolan-2-yl)-2-(2,2,2-trifluoroethoxy)pyridine (173.12 mg, 0.54 mmol), A-72 (100 mg, 0.45 mmol), Pd(dppf)Cl$_2$·CH$_2$Cl$_2$ (73.39 mg, 0.09 mmol) and Cs$_2$CO$_3$ (292.77 mg, 0.90 mmol) in 1,4-dioxane (3 mL) and water (0.5 mL) was stirred at 90° C. for 16 hours under N$_2$. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 μm); A=H$_2$O (0.05% NH$_4$OH) and B=CH$_3$CN; 58-68% B over 8 minutes) to afford Compound 78 (45.53 mg, 0.12 mmol) as a solid. $^1$H NMR (400 MHz, CDCl$_3$) $\delta_H$=9.60 (d, 1H), 8.54 (d, 1H), 8.41 (s, 1H), 8.09 (dd, 1H), 4.94 (q, 2H). LCMS R$_t$=1.16 min using Method A, MS ESI calcd. for C$_{13}$H$_7$F$_7$N$_5$O [M+H]$^+$ 382.0, found 381.

Example 75. Synthesis of Compound 79

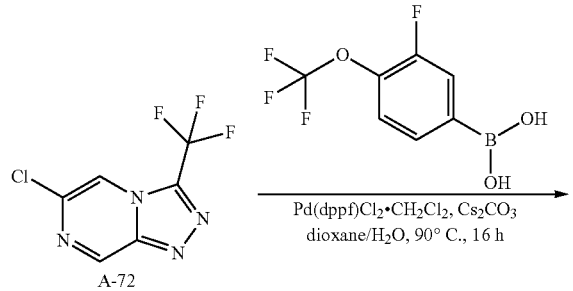

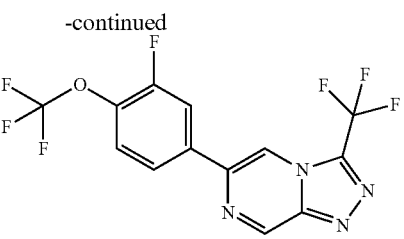

A mixture of A-72 (100 mg, 0.45 mmol), [3-fluoro-4-(trifluoromethoxy)phenyl]boronic acid (120.73 mg, 0.54 mmol), Pd(dppf)Cl$_2$·DCM (73.39 mg, 0.09 mmol) and Cs$_2$CO$_3$ (292.77 mg, 0.90 mmol) in 1,4-dioxane (3 mL) and water (0.5 mL) was stirred at 90° C. for 16 hours. After cooling to r.t, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by prep-HPLC (Phenomenex Gemini (250 mm×50 mm, 10 μm); A=H$_2$O (0.05% NH$_4$OH) and B=CH$_3$CN; 60-70% B over 8 minutes) to afford Compound 79 (27.15 mg, 0.07 mmol) as a solid. $^1$H NMR (400 MHz, CDCl$_3$) $\delta_H$=9.60 (d, 1H), 8.43 (s, 1H), 7.92 (dd, 1H), 7.79 (td, 1H), 7.53-7.47 (m, 1H). LCMS R$_t$=1.20 min using Method A, MS ESI calcd. for C$_{13}$H$_6$F$_7$N$_4$O [M+H]$^+$ 367.0, found 366.9.

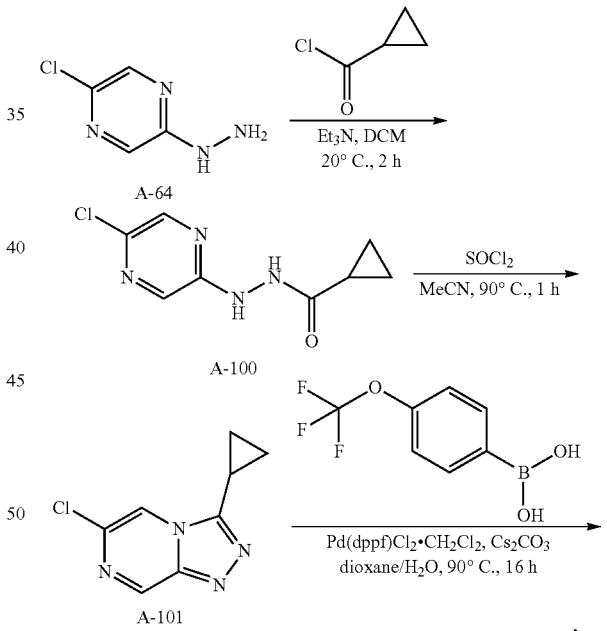

Synthesis of A-100: To a mixture of A-64 (500 mg, 3.46 mmol) and Et$_3$N (0.96 mL, 6.92 mmol) in DCM (10 mL) was added cyclopropanecarbonyl chloride (433.85 mg, 4.15 mmol) dropwise. The reaction mixture was stirred at 20° C.

for 2 hours. The reaction mixture was quenched with sat.NaHCO$_3$ (50 mL), extracted with DCM (30 mL×3). The combined organic phase was washed with brine (20 mL), dried over Na$_2$SO$_4$, filtered and concentrated, and the residue was purified by flash chromatography on silica gel (EtOAc in PE=0% to 20% to 50%) to afford A-100 (500 mg, 2.35 mmol) as a solid.

$^1$H NMR (400 MHz, CDCl$_3$) δ$_H$=8.12 (s, 1H), 7.94 (s, 1H), 7.59 (s, 1H), 6.81 (s, 1H), 1.56-1.48 (m, 1H), 1.10-1.05 (m, 2H), 0.95-0.88 (m, 2H).

Synthesis of A-101: To a mixture of N'-(5-chloropyrazin-2-yl)cyclopropanecarbohydrazide (350 mg, 1.65 mmol) in MeCN (10 mL) was added SOCl$_2$ (0.36 mL, 4.94 mmol). The reaction mixture was stirred at 90° C. for 1 hour. After cooling, the reaction mixture was concentrated and the resulting mixture was treated with sat.NaHCO$_3$ (20 mL) and extracted with EtOAc (20 mL×3). The combined organic phase was washed with brine (20 mL), dried over Na$_2$SO$_4$, filtered and concentrated to provide a residue that was purified by flash chromatography on silica gel (EtOAc in PE=0% to 20% to 50%) to afford A-101 (130 mg, 0.67 mmol) as a solid. $^1$H NMR (400 MHz, CDCl$_3$) δ$_H$=9.14 (d, 1H), 8.10 (d, 1H), 2.10-2.02 (m, 1H), 1.35-1.26 (m, 4H).

Synthesis of Compound 80: A mixture of A-101 (130 mg, 0.67 mmol), [4-(trifluoromethoxy)phenyl]boronic acid (165.07 mg, 0.8 mmol), Cs$_2$CO$_3$ (435.25 mg, 1.34 mmol), and Pd(dppf)Cl$_2$·CH$_2$Cl$_2$ (81.82 mg, 0.1 mmol) and in 1,4-dioxane (3 mL) and water (0.3 mL) was stirred at 90° C. for 16 hours under N$_2$. The mixture was cooled to room temperature, diluted with EtOAc (20 mL), filtered through silica gel and eluted with EtOAc (20 mL). The filtrate was concentrated to give the crude product, which was purified by prep-HPLC (Xbridge (150 mm×25 mm, 5 μm); A=H$_2$O (0.05% NH$_4$HCO$_3$) and B=CH$_3$CN; 40-70% B over 10 minutes) to afford Compound 80 (74.19 mg, 0.23 mmol) as a solid. $^1$H NMR (400 MHz, CDCl$_3$) δ$_H$=9.38 (d, 1H), 8.31 (d, 1H), 8.03 (d, 2H), 7.38 (d, 2H), 2.19-2.11 (m, 1H), 1.38-1.27 (m, 4H). LCMS R$_t$=1.12 min using Method A, ESI calcd. for C$_{15}$H$_{12}$F$_3$N$_4$O [M+H]$^+$ 321.1, found 320.9.

Example 77. Synthesis of Compound 81

Synthesis of A-102: A mixture of A-72 (300 mg, 1.35 mmol), (4-hydroxyphenyl)boronic acid (241.7 mg, 1.75 mmol), Pd(dppf)Cl$_2$·CH$_2$Cl$_2$ (220.16 mg, 0.27 mmol) and Cs$_2$CO$_3$ (878.32 mg, 2.7 mmol) in 1,4-dioxane (15 mL) and water (3 mL) was stirred at 90° C. for 16 hours. After cooling to room temperature, the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by flash chromatography on silica gel (EtOAc in PE=0 to 30% to 100%) to afford A-102 (180 mg, 0.59 mmol) as a solid. LCMS R$_t$=0.69 min using Method B, MS ESI calcd. for C$_{12}$H$_8$F$_3$N$_4$O [M+H]$^+$ 281.1, found 280.9.

Synthesis of Compound 81: To a mixture of A-102 (180 mg, 0.61 mmol), 3,3-difluorocyclobutanol (98.5 mg, 0.91 mmol) and PPh$_3$ (286.81 mg, 1.09 mmol) in THF (3 mL) was added DEAD (190.43 mg, 1.09 mmol) at 0° C. The mixture was allowed to warm and then was stirred at 70° C. for 16 hours. After cooling to room temperature, the mixture was concentrated to give the crude product, which was purified by prep-TLC (silica gel, PE:EtOAc=3:1) and prep-HPLC (Phenomenex Gemini (250 mm×50 mm, 10 μm); A=H$_2$O (0.05% NH$_4$OH) and B=CH$_3$CN; 48-78% B over 8 minutes) to afford Compound 81 (5.08 mg, 0.01 mmol) as a solid. $^1$H NMR (400 MHz, CDCl$_3$) δ$_H$=9.51 (d, 1H), 8.34 (s, 1H), 7.93 (d, 2H), 6.97 (d, 2H), 4.83-4.65 (m, 1H), 3.23-3.06 (m, 2H), 2.91-2.75 (m, 2H). LCMS R$_t$=1.19 min using Method A, MS ESI calcd. for C$_{16}$H$_{12}$F$_5$N$_4$O [M+H]$^+$ 371.1, found 371.0.

Example 78. Synthesis of Compound 82

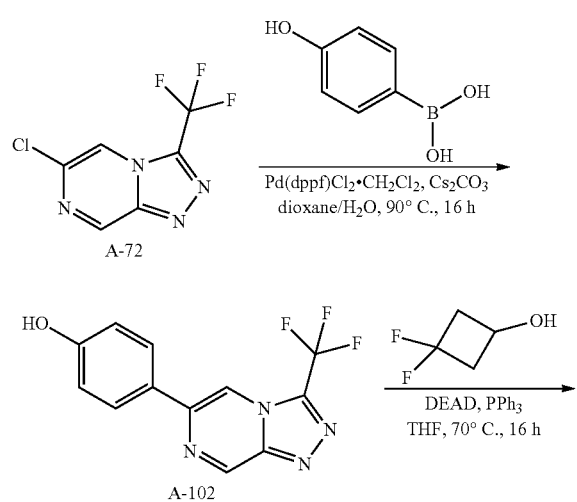

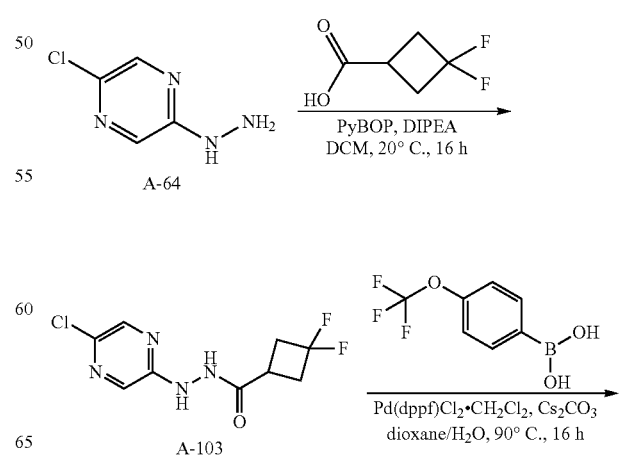

237

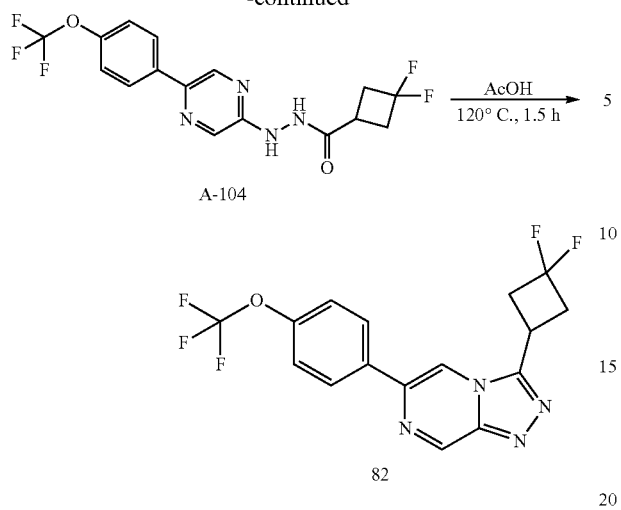

238

Example 79. Synthesis of Compound 83

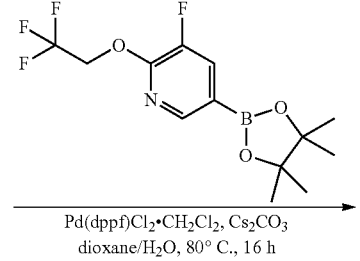

Synthesis of A-103: To a mixture of A-64 (500 mg, 3.46 mmol), 3,3-difluorocyclobutanecarboxylic acid (517.81 mg, 3.8 mmol) and PyBOP (2.7 g, 5.19 mmol) in DCM (30 mL) was added DIPEA (1.21 mL, 6.92 mmol). The reaction mixture was stirred at 20° C. for 16 hours. The reaction was quenched with sat.NH$_4$Cl (50 mL) and extracted with DCM (50 mL×3). The combined organic phase was washed with brine (20 mL), dried over Na$_2$SO$_4$, filtered, and concentrated to give the crude product, which was purified by flash chromatography on silica gel (EtOAc in PE=20% to 50%) to afford A-103 (600 mg, 1.64 mmol) as a solid. $^1$H NMR (400 MHz, DMSO-d$_6$) δ$_H$=10.10 (s, 1H), 9.12 (s, 1H), 8.19 (d, 1H), 7.83 (d, 1H), 3.03-2.95 (m, 1H), 2.84-2.66 (m, 4H).

Synthesis of A-104: A mixture of A-103 (250 mg, 0.95 mmol), [4-(trifluoromethoxy)-phenyl]boronic acid (294.03 mg, 1.43 mmol), Pd(dppf)Cl$_2$.CH$_2$Cl$_2$ (194.33 mg, 0.24 mmol) and Cs$_2$CO$_3$ (620.24 mg, 1.9 mmol) in 1,4-dioxane (3 mL) and water (0.3 mL) was stirred at 90° C. for 16 hours under N$_2$. The mixture was cooled to room temperature, diluted with EtOAc (30 mL), filtered through silica gel and eluted with EtOAc (30 mL). The filtrate was concentrated to give the crude product, which was purified by flash chromatography on silica gel (EtOAc in PE=20% to 50%) to afford A-104 (150 mg, 0.39 mmol) as a solid. $^1$H NMR (400 MHz, DMSO-d$_6$) δ$_H$=10.12 (s, 1H), 9.12 (s, 1H), 8.70 (d, 1H), 8.11-8.06 (m, 3H), 7.44 (d, 2H), 3.08-2.99 (m, 1H), 2.84-2.73 (m, 4H).

Synthesis of Compound 82: A mixture of A-104 (150 mg, 0.39 mmol) in acetic acid (2 mL) was stirred in microwave reactor at 120° C. for 1.5 hours. The mixture was cooled to room temperature and concentrated, and the residue was neutralized with 1N NaHCO$_3$ to pH=7-8 and extracted with EtOAc (20 mL×2). The combined organic phase was washed with brine (10 mL), dried over Na$_2$SO$_4$ and filtered, and the filtrate was concentrated to give the crude product, which was purified by prep-HPLC (Xbridge (150 mm×25 mm, 5 μm); A=H$_2$O (0.05% NH$_4$HCO$_3$) and B=CH$_3$CN; 38-78% B over 10 minutes) to afford Compound 82 (44.06 mg, 0.12 mmol) as a solid.

$^1$H NMR (400 MHz, DMSO-d$_6$) δ$_H$=9.46 (d, 1H), 8.97 (s, 1H), 8.22 (d, 2H), 7.52 (d, 2H), 4.16-4.03 (m, 1H), 3.33-3.07 (m, 4H). LCMS R$_t$=1.17 min using Method A, MS ESI calcd. for C$_{16}$H$_{12}$F$_5$N$_4$O [M+H]$^+$ 371.1, found 371.0.

A mixture of A-16 (100 mg, 0.41 mmol), 3-fluoro-5-(4,4,5,5-tetramethyl-1,3,2-dioxaborolan-2-yl)-2-(2,2,2-trifluoroethoxy)pyridine (196.88 mg, 0.61 mmol), Pd(dppf)Cl$_2$.CH$_2$Cl$_2$ (83.46 mg, 0.1 mmol), and Cs$_2$CO$_3$ (266.36 mg, 0.82 mmol) in 1,4-dioxane (3 mL) and water (0.3 mL) was stirred at 80° C. for 16 hours under N$_2$. The mixture was cooled to room temperature, diluted with EtOAc (30 mL), filtered through silica gel and eluted with EtOAc (30 mL). The filtrate was concentrated to give the crude product, which was purified by prep-HPLC (Xtimate C$_{18}$ (150 mm×25 mm, 5 μm); A=H$_2$O (0.05% NH$_4$HCO$_3$) and B=CH$_3$CN; 40-65% B over 9.5 minutes) to afford Compound 83 (61.78 mg, 0.15 mmol) as a solid. $^1$H NMR (400 MHz, CDCl$_3$) δ$_H$=8.53 (d, 1H), 8.24 (d, 1H), 8.11 (dd, 1H), 7.55 (d, 1H), 4.95 (q, 2H), 4.14-3.98 (m, 1H), 3.42-3.15 (m, 4H). LCMS R$_t$=1.16 min using Method A, MS ESI calcd. for C$_{16}$H$_{12}$F$_6$N$_5$O [M+H]$^+$ 404.1, found 404.0.

Example 80. Synthesis of Compound 84

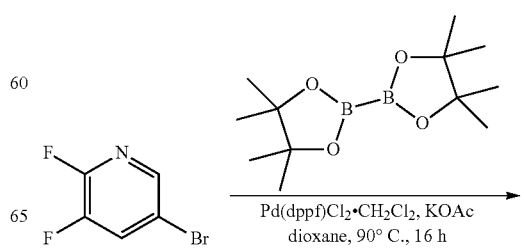

239

-continued

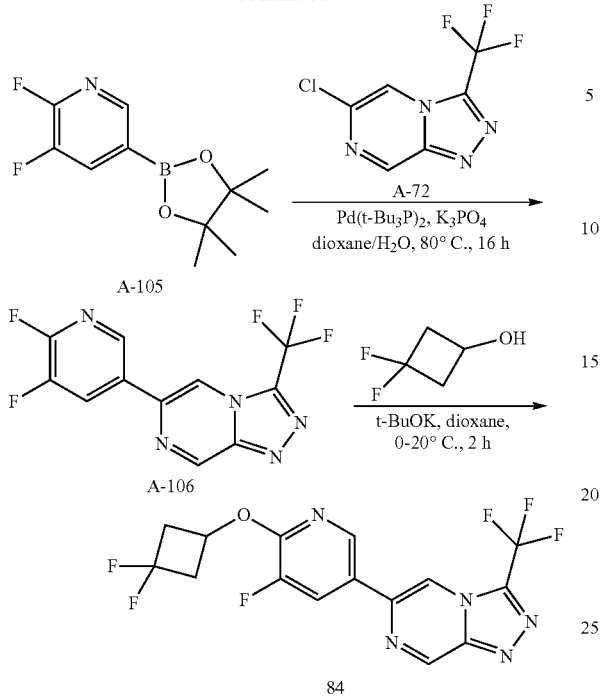

Synthesis of A-105: A mixture of 5-bromo-2,3-difluoropyridine (2 g, 10.31 mmol), 4,4,5,5-tetramethyl-2-(4,4,5,5-tetramethyl-1,3,2-dioxaborolan-2-yl)-1,3,2-dioxaborolane (3.4 g, 13.4 mmol), Pd(dppf)Cl$_2$·CH$_2$Cl$_2$ (1.26 g, 1.55 mmol) and KOAc (2.02 g, 20.62 mmol) in 1,4-dioxane (100 mL) was stirred at 90° C. for 16 hours. After cooling to room temperature, the mixture was filtered through silica gel and eluted with EtOAc (50 mL×2). The mixture was concentrated and diluted with EtOAc (150 mL), washed with water (100 mL×2) and brine (80 mL), dried over Na$_2$SO$_4$, filtered and concentrated to give the crude product, which was purified by flash chromatography on silica gel (EtOAc in PE=0 to 10%) to afford A-105 (2200 mg, 2.32 mmol) as a solid. LCMS R$_t$=0.88 min using Method B, MS ESI calcd. for C$_{11}$H$_{15}$BF$_2$NO$_2$ [M+H+2]$^+$242.1, found 242.0.

Synthesis of A-106: A mixture of A-105 (324.91 mg, 1.35 mmol), A-72 (200 mg, 0.90 mmol), Pd(t-Bu$_3$P)$_2$ (91.85 mg, 0.18 mmol) and K$_3$PO$_4$ (381.56 mg, 1.8 mmol) in 1,4-dioxane (10 mL) and water (2 mL) was stirred at 80° C. for 16 hours under N$_2$. After cooling to room temperature, the mixture was concentrated to give the crude product, which was purified by flash chromatography on silica gel (EtOAc in PE=0 to 30%) to afford A-106 (100 mg, 0.32 mmol) as a solid. $^1$H NMR (400 MHz CDCl$_3$) δ$_H$=9.62 (d, 1H), 8.58 (s, 1H), 8.48 (s, 1H), 8.31-8.24 (m, 1H). LCMS R$_t$=0.74 min using Method B, MS ESI calcd. for C$_{11}$H$_5$F$_5$N$_5$ [M+H]$^+$ 302.0, found 301.8.

Synthesis of Compound 84: To a mixture of A-106 (50 mg, 0.16 mmol) and 3,3-difluorocyclobutanol (34.06 mg, 0.32 mmol) in 1,4-dioxane (2 mL) was added t-BuOK (35.35 mg, 0.32 mmol) at 0° C. The mixture was stirred at 20° C. for 2 hours. The mixture was concentrated to give the crude product, which was purified by prep-HPLC (Phenomenex Gemini (250 mm×50 mm, 10 μm); A=H$_2$O (0.05% NH$_4$OH) and B=CH$_3$CN; 50-80% B over 8 minutes) to afford Compound 84 (13.63 mg, 0.04 mmol) as a solid. $^1$H NMR (400 MHz, CDCl$_3$) δ$_H$=9.59 (d, 1H), 8.51 (d, 1H), 8.39 (s, 1H), 8.03 (dd, 1H), 5.33-5.23 (m, 1H), 3.27-3.14 (m, 2H), 2.93-2.79 (m, 2H).

240

LCMS R$_t$=1.18 min using Method A, MS ESI calcd. for C$_{15}$H$_{10}$F$_6$N$_5$O [M+H]$^+$ 390.1, found 390.0.

Example 81. Synthesis of Compound 85

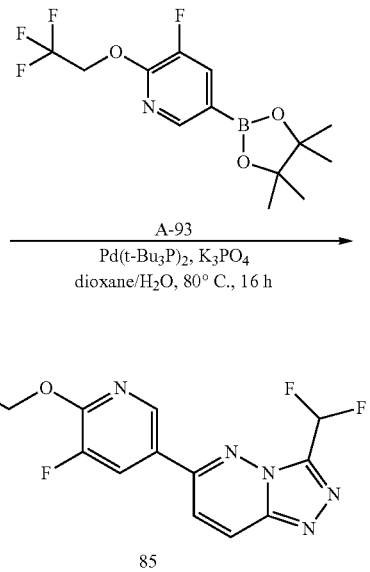

A mixture of A-67 (99.02 mg, 0.48 mmol), A-93 (202.05 mg, 0.63 mmol), K$_3$PO$_4$ (205.54 mg, 0.97 mmol) and Pd(t-Bu$_3$P)$_2$ (37.11 mg, 0.07 mmol) in 1,4-dioxane (3 mL) and water (0.50 mL) was stirred at 80° C. for 16 hours. After cooling to room temperature, the mixture was concentrated to give the crude product, which was purified by prep-HPLC (Phenomenex Gemini (250 mm×50 mm, 10 μm); A=H$_2$O (0.05% NH$_4$OH) and B=CH$_3$CN; 40-70% B over 8 minutes) to afford Compound 85 (108.7 mg, 0.30 mmol) as a solid. $^1$H NMR (400 MHz DMSO-d$_6$) δ$_H$=8.86 (d, 1H), 8.67 (d, 1H), 8.56 (dd, 1H), 8.21 (d, 1H), 7.83 (t, 1H), 5.22 (q, 2H). LCMS R$_t$=1.14 min using Method A, MS ESI calcd. for C$_{13}$H$_8$F$_6$N$_5$O [M+H]$^+$ 364.1, found 364.0.

Example 82. Synthesis of Compound 86

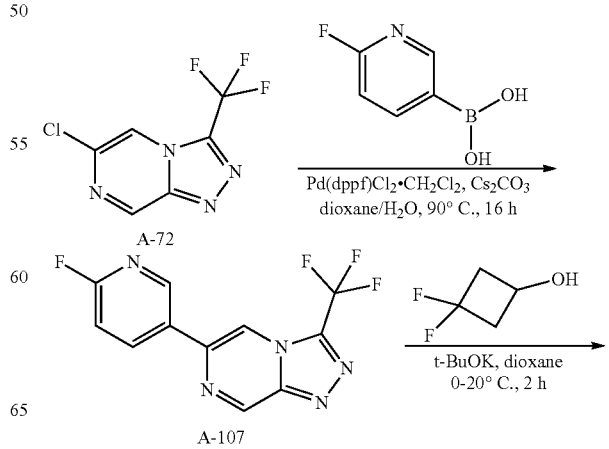

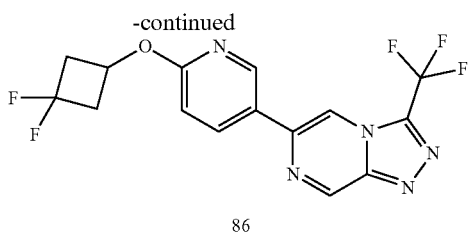

86

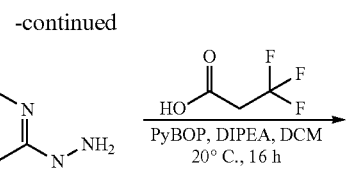

A-109

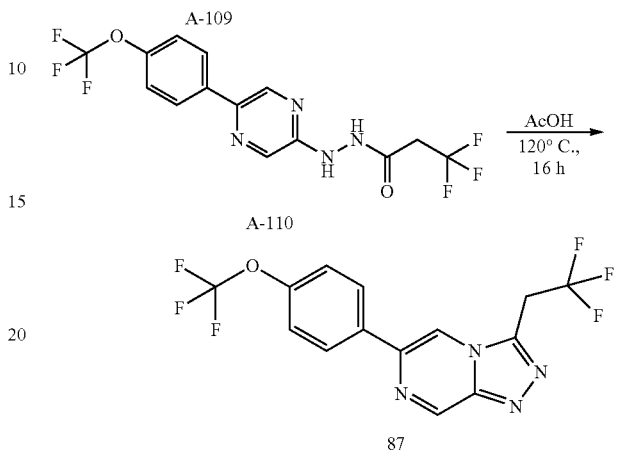

Synthesis of A-107: A mixture of A-72 (200 mg, 0.90 mmol), (6-fluoro-3-pyridyl)boronic acid (151.95 mg, 1.08 mmol), Pd(dppf)Cl$_2$.CH$_2$Cl$_2$ (146.77 mg, 0.18 mmol) and Cs$_2$CO$_3$ (585.55 mg, 1.8 mmol) in 1,4-dioxane (15 mL) and water (3 mL) was stirred at 90° C. for 16 hours. The mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product, which was purified by flash chromatography on silica gel (EtOAc in PE=0 to 30% to 50%) to afford A-107 (140 mg, 0.40 mmol) as a solid.

$^1$H NMR (400 MHz, CDCl$_3$) $\delta_H$=9.62 (d, 1H), 8.84 (d, 1H), 8.47-8.40 (m, 2H), 7.15 (dd, 1H). LCMS R$_t$=0.69 min using Method B, MS ESI calcd. for C$_{11}$H$_6$F$_4$N$_5$ [M+H]$^+$ 284.0, found 283.9.

Synthesis of Compound 86: To a mixture of 3,3-difluorocyclobutanol (25.19 mg, 0.23 mmol) and A-107 (33 mg, 0.12 mmol) in 1,4-dioxane (4 mL) was added t-BuOK (26.15 mg, 0.23 mmol) at 20° C. The mixture was stirred at 20° C. for 2 hours. The mixture was quenched with sat. NH$_4$Cl (10 mL) and extracted with EtOAc (20 mL×2). The combined organic phase was washed with brine (15 mL), dried over Na$_2$SO$_4$, filtered and concentrated to give the crude product, which was purified by prep-TLC (silica gel, PE:EtOAc=1:1) and prep-HPLC (Phenomenex Gemini (250 mm×50 mm, 10 μm); A=H$_2$O (0.05% NH$_4$OH) and B=CH$_3$CN; 55-65% B over 8 minutes) to afford Compound 86 (1.72 mg, 0.05 mmol) as a solid. $^1$H NMR (400 MHz, CDCl$_3$) $\delta_H$=9.59 (d, 1H), 8.75 (d, 1H), 8.36 (s, 1H), 8.20 (dd, 1H), 6.94 (d, 1H), 5.30-5.18 (m, 1H), 3.24-3.11 (m, 2H), 2.85-2.71 (m, 2H). LCMS R$_t$=1.14 min using Method A, MS ESI calcd. for C$_{15}$H$_{11}$F$_5$N$_5$O [M+H]$^+$ 372.1, found 372.0.

Example 83. Synthesis of Compound 87

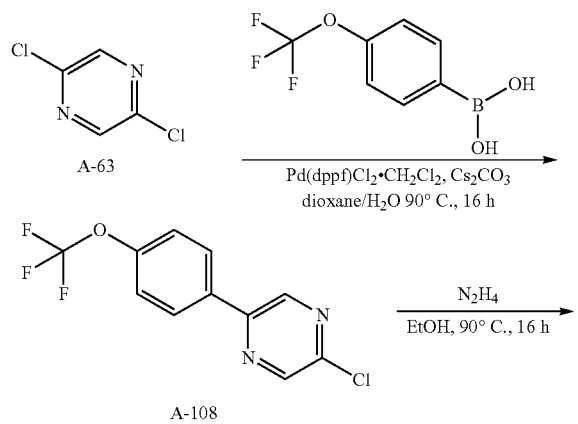

Synthesis of A-108: A mixture of A-63 (1 g, 6.71 mmol), [4-(trifluoromethoxy)phenyl]-boronic acid (1.52 g, 7.38 mmol), Pd(dppf)Cl$_2$.CH$_2$Cl$_2$ (822.23 mg, 1.01 mmol) and Cs$_2$CO$_3$ (4373.74 mg, 13.42 mmol) in 1,4-dioxane (20 mL) and water (4 mL) under N$_2$ was stirred at 90° C. for 16 hours. After cooling, the reaction mixture was diluted with EtOAc (20 mL), and filtered through a Celite pad, eluted with EtOAc (20 mL), and concentrated. The residue was purified by flash chromatography on silica gel (EtOAc in PE=0% to 3% to 8%) to afford A-108 (250 mg, 0.91 mmol) as a solid. $^1$H NMR (400 MHz, CDCl$_3$) $\delta_H$=8.79 (d, 1H), 8.65 (d, 1H), 8.05 (d, 2H), 7.37 (d, 2H)

Synthesis of A-109: A mixture of A-108 (250 mg, 0.91 mmol) and hydrazine (175.05 mg, 5.46 mmol) in ethanol (5 mL) was stirred at 90° C. for 16 hours. After cooling, the reaction mixture was concentrated, and the residue was diluted with sat.NaHCO$_3$ (10 mL), and extracted with EtOAc (10 mL×3). The combined organic phase was washed with brine (10 mL), dried over Na$_2$SO$_4$, filtered and concentrated afford A-109 (170 mg, 0.63 mmol) as a solid. $^1$H NMR (400 MHz, DMSO-d$_6$) $\delta_H$=8.60 (d, 1H), 8.23-8.17 (m, 2H), 8.05 (d, 2H), 7.41 (d, 2H), 4.36 (s, 2H).

Synthesis of A-110: To a mixture of A-109 (80 mg, 0.3 mmol), 3,3,3-trifluoropropanoic acid (41.7 mg, 0.33 mmol) and PyBOP (231.1 mg, 0.44 mmol) in DCM (30 mL) was added DIPEA (0.1 mL, 0.59 mmol). The reaction mixture was stirred at 20° C. for 16 hours. The reaction was quenched with sat.NH$_4$Cl (50 mL) and extracted with DCM (50 mL×3). The combined organic phase was washed with brine (20 mL), dried over Na$_2$SO$_4$, filtered and concentrated to afford A-110 (200 mg, 0.28 mmol) as an oil. LCMS R$_t$=0.81 min using Method B, MS ESI calcd. for C$_{14}$H$_n$F$_6$N$_4$O$_2$ [M+H]$^+$ 381.1, found 381.0.

Synthesis of Compound 87: A mixture of A-110 (200 mg, 0.53 mmol) in acetic acid (2 mL) was stirred at 120° C. for 16 hours. The mixture was cooled to room temperature and concentrated, and the residue was neutralized with 1N NaHCO$_3$ to pH=7-8 and extracted with EtOAc (20 mL×2). The combined phase organic was washed with brine (10 mL), dried over Na$_2$SO$_4$, filtered, and concentrated to give the crude product, which was purified by prep-HPLC (Xbridge (150 mm×25 mm, 5 μm); A=H₂O (0.05% NH₄HCO₃) and B=CH₃CN; 46-76% B over 6 minutes) to afford Compound 87 (25.13 mg, 0.07 mmol) as a solid. ¹H NMR (400 MHz, DMSO-d₆) $\delta_H$=9.57 (s, 1H), 9.33 (s, 1H), 8.23 (d, 2H), 7.57 (d, 2H), 4.61 (q, 2H). LCMS R$_f$=1.16 min using Method A, MS ESI calcd. for $C_{14}H_9F_6N_4O$ [M+H]⁺ 363.1, found 363.0.

Example 84 Synthesis of Compound 88

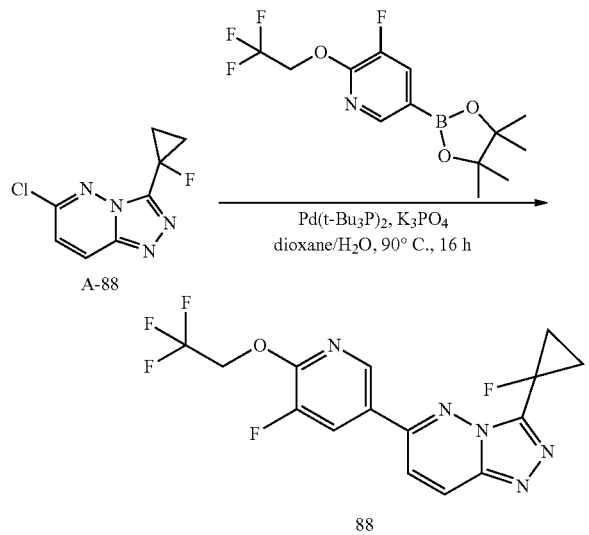

A mixture of A-88 (100 mg, 0.47 mmol), K₃PO₄ (199.71 mg, 0.94 mmol), 3-fluoro-5-(4,4,5,5-tetramethyl-1,3,2-dioxaborolan-2-yl)-2-(2,2,2-trifluoroethoxy)pyridine (226.53 mg, 0.71 mmol), and Pd(t-Bu₃P)₂ (36.06 mg, 0.07 mmol) and in 1,4-dioxane (3 mL) and water (0.3 mL) was stirred at 90° C. for 16 hours under N₂. The mixture was cooled to room temperature, diluted with EtOAc (20 mL), filtered through silica gel and eluted with EtOAc (20 mL). The filtrate was concentrated to give the crude product, which was purified by prep-HPLC (Xbridge (150 mm×25 mm, 5 μm); A=H₂O (0.05% NH₄HCO₃) and B=CH₃CN; 40-80% B over 10 minutes) to afford Compound 88 (61.29 mg, 0.16 mmol) as a solid. ¹H NMR (400 MHz DMSO-d₆) $\delta_H$=8.82 (d, 1H), 8.59 (d, 1H), 8.47 (dd, 1H), 8.13 (d, 1H), 5.22 (q, 2H), 1.76-1.66 (m, 2H), 1.52-1.44 (m, 2H). LCMS R$_f$=1.14 min using Method A, MS ESI calcd. for $C_{15}H_{11}F_5N_5O$ [M+H]⁺372.1, found 372.0.

Example 85. Synthesis of Compound 89

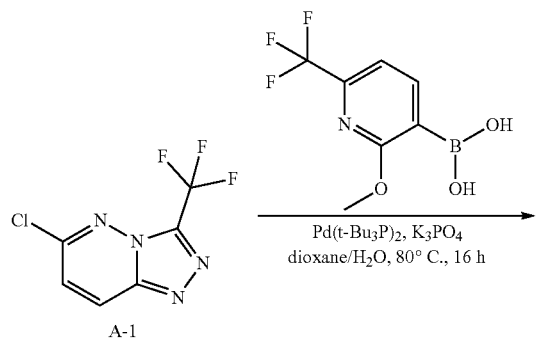

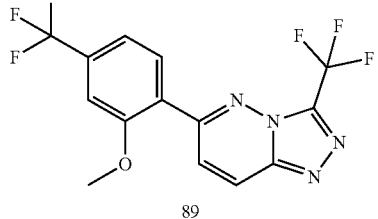

A mixture of [2-methoxy-4-(trifluoromethyl)phenyl]boronic acid (118.59 mg, 0.54 mmol), A-1 (100 mg, 0.45 mmol), K₃PO₄ (190.78 mg, 0.9 mmol) and Pd(t-Bu₃P)₂ (34.44 mg, 0.07 mmol) in 1,4-dioxane (2 mL) and water (0.2 mL) was stirred at 80° C. for 16 hours under N₂. The mixture was filtered through silica gel, and concentrated to the crude product, which was purified by prep-HPLC (Xbridge (150 mm×25 mm, 5 μm); A=H₂O (0.05% NH₄HCO₃) and B=CH₃CN; 52-72% B over 6.5 minutes) to afford Compound 89 (32.47 mg, 0.09 mmol) as a solid. ¹H NMR (400 MHz, DMSO-d₆) $\delta_H$=8.62 (d, 1H), 7.94 (d, 1H), 7.80 (d, 1H), 7.61-7.51 (m, 2H), 3.97 (s, 3H). LCMS R$_f$=1.22 min using Method A, MS ESI calcd. for $C_{14}H_9F_6N_4O$ [M+H]⁺ 363.1, found 363.0.

Example 86. Synthesis of Compounds 90, 91, and 92

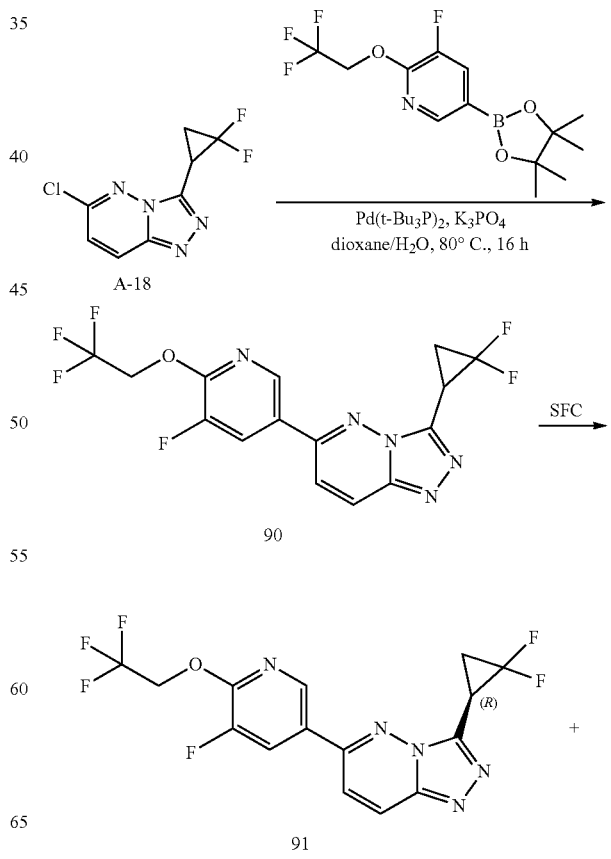

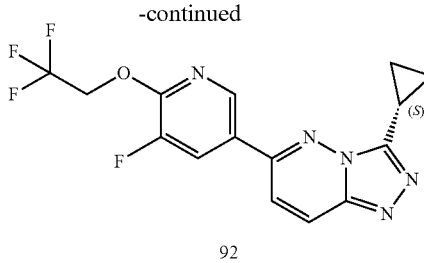

92

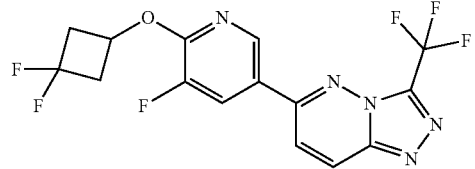

93

A mixture of A-18 (69.39 mg, 0.30 mmol), 3-fluoro-5-(4,4,5,5-tetramethyl-1,3,2-dioxaborolan-2-yl)-2-(2,2,2-trifluoroethoxy)pyridine (125.61 mg, 0.39 mmol), $K_3PO_4$ (127.77 mg, 0.60 mmol) and $Pd(t-Bu_3P)_2$ (23.07 mg, 0.05 mmol) in 1,4-dioxane (3 mL) and water (0.50 mL) was stirred at 80° C. for 16 hours. After cooling to room temperature, the mixture was diluted with $H_2O$ (20 mL) and extracted with EtOAc (50 mL×2). The combined organic phase was washed with brine (20 mL), dried over $Na_2SO_4$, filtered and concentrated to give the crude product, which was purified by flash chromatography on silica gel (EtOAc in PE=0 to 10% to 80%) to afford Compound 90 (90 mg). Compound 90 was purified by SFC (Chiralcel OJ (250 mm×30 mm, 5 μm); A=$CO_2$ and B=EtOH (0.1% $NH_3H_2O$); 38° C.; 60 mL/min; 15% B over 6 minutes; multiple injections) to afford Enantiomer 1, randomly assigned as Compound 91 (Rt=4.5 min) and Enantiomer 2, randomly assigned as Compound 92 (Rt=4.9 min). Compound 91 (25.85 mg, 0.07 mmol) NMR (CDCl$_3$, 00 MHZ) $\delta_H$=8.55 (d, 1H), 8.23 (d, 1H), 8.15 (dd, 1H), 7.56 (d, 1H), 4.95 (q, 2H), 3.37-3.29 (m, 1H), 2.70-2.60 (m, 1H), 2.25-2.15 (m, 1H). LCMS $R_t$=1.14 min using Method A, MS ESI calcd. for $C_{15}H_{10}F_6N_5O$ [M+H]$^+$ 390.1, found 390.0. Compound 92 (8.36 mg, 0.02 mmol) NMR (400 MHz, CDCl$_3$) $\delta_H$=8.55 (d, 1H), 8.23 (d, 1H), 8.15 (dd, 1H), 7.56 (d, 1H), 4.95 (q, 2H), 3.36-3.28 (m, 1H), 2.70-2.61 (m, 1H), 2.25-2.15 (m, 1H). LCMS $R_t$=1.16 min using Method A, MS ESI calcd. for $C_{15}H_{10}F_6N_5O$ [M+H]$^+$ 390.1, found 390.0.

Synthesis of A-111: A mixture of A-1 (200 mg, 0.90 mmol), 2,3-difluoro-5-(4,4,5,5-tetramethyl-1,3,2-dioxaborolan-2-yl)pyridine (281.59 mg, 1.17 mmol), $Pd(t-Bu_3P)_2$ (91.85 mg, 0.18 mmol) and $K_3PO_4$ (381.56 mg, 1.8 mmol) in 1,4-dioxane (10 mL) and water (1.5 mL) was stirred at 90° C. for 16 hours under $N_2$. After cooling to room temperature, the mixture was concentrated to give the crude product, which was purified by flash chromatography on silica gel (EtOAc in PE=0 to 50% to 100%) to afford A-111 (250 mg, 0.83 mmol) as a solid. $^1$H NMR (400 MHz, CDCl$_3$) $\delta_H$=8.62 (s, 1H), 8.42 (d, 1H), 8.32 (dt, 1H), 7.77 (d, 1H). LCMS $R_t$=0.76 min using Method B, MS ESI calcd. for $C_{11}H_5F_5N_5$ [M+H]$^+$ 302.0, found 301.9.

Synthesis of Compound 93: To a mixture of A-111 (50 mg, 0.17 mmol) and 3,3-difluorocyclobutanol (26.92 mg, 0.25 mmol) in 1,4-dioxane (2 mL) was added t-BuOK (37.26 mg, 0.33 mmol) at 0° C. The mixture was stirred at 20° C. for 2 hours. The mixture was concentrated to give the crude product, which was purified by prep-HPLC (Phenomenex Gemini (250 mm×50 mm, 10 μm); A=$H_2O$ (0.05% $NH_4OH$) and B=$CH_3CN$; 48-78% B over 8 minutes) to give the product of Compound 93 (8.04 mg, 0.02 mmol) as a solid. $^1$H NMR (400 MHz, CDCl$_3$) $\delta_H$=8.55 (d, 1H), 8.34 (d, 1H), 8.11 (dd, 1H), 7.73 (d, 1H), 5.36-5.23 (m, 1H), 3.27-3.16 (m, 2H), 2.94-2.81 (m, 2H). LCMS $R_t$=1.22 min using Method A, MS ESI calcd. for $C_{15}H_{10}F_6N_5O$ [M+H]$^+$ 390.1, found 390.0.

Example 87. Synthesis of Compound 93

Example 88. Synthesis of Compound 94

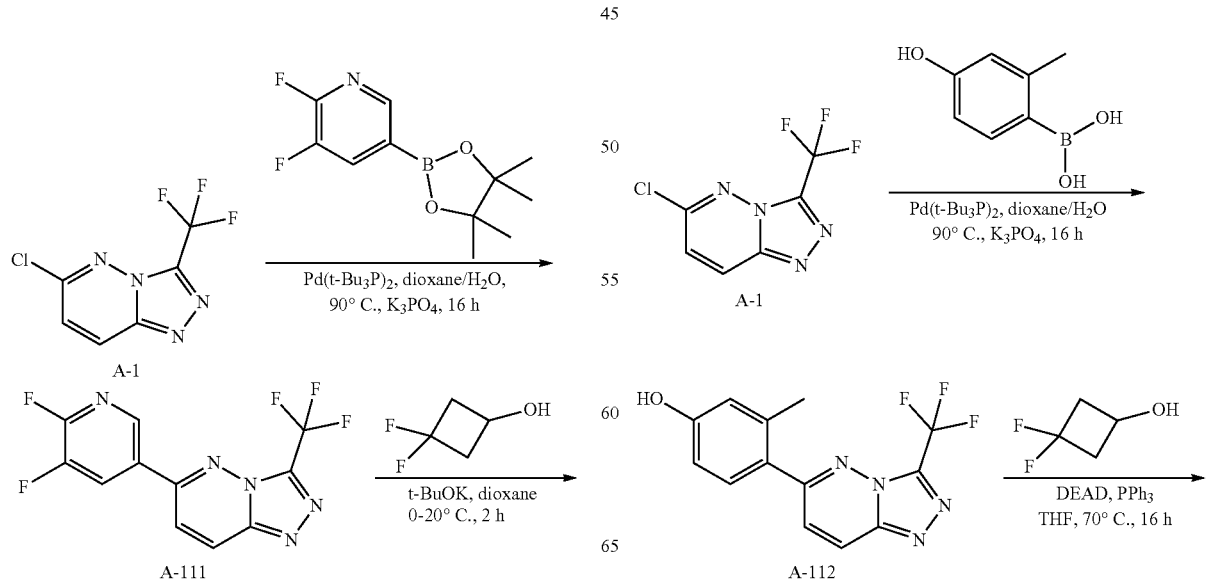

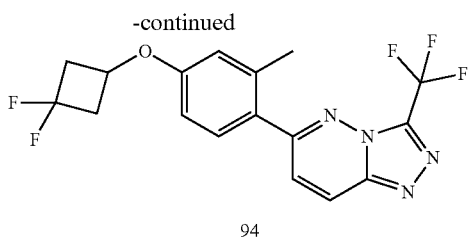

94

Synthesis of A-112: A mixture of A-1 (300 mg, 1.35 mmol), (4-hydroxy-2-methyl-phenyl)boronic acid (266.29 mg, 1.75 mmol), Pd(t-Bu$_3$P)$_2$ (137.77 mg, 0.27 mmol) and K$_3$PO$_4$ (572.34 mg, 2.7 mmol) in 1,4-dioxane (10 mL) and water (1.5 mL) was stirred at 90° C. for 16 hours under N$_2$. After cooling to room temperature, the mixture was concentrated to give the crude product, which was purified by flash chromatography on silica gel (EtOAc in PE=0 to 100%) to afford A-112 (300 mg, 0.97 mmol) as a solid. LCMS R$_t$=0.73 min using Method B, MS ESI calcd. for C$_{13}$H$_{10}$F$_3$N$_4$O [M+H]$^+$ 295.1, found 294.9.

Synthesis of Compound 94: To a mixture of A-112 (100 mg, 0.34 mmol), 3,3-difluorocyclobutanol (55.1 mg, 0.51 mmol) and PPh$_3$ (160.46 mg, 0.61 mmol) in THF (3 mL) was added DEAD (106.54 mg, 0.61 mmol) at 0° C. under N$_2$. The mixture was allowed to warm and stir at 70° C. for 16 hours. After cooling to room temperature, the mixture was concentrated to give the crude product, which was purified by prep-HPLC (Phenomenex Gemini (250 mm×50 mm, 10 μm); A=H$_2$O (0.05% NH$_4$OH) and B=CH$_3$CN; 55-85% B over 8 minutes) to afford Compound 94 (7.45 mg, 0.02 mmol) as a solid. $^1$H NMR (400 MHz, CDCl$_3$) δ$_H$=8.25 (d, 1H), 7.50-7.44 (m, 2H), 6.84-6.78 (m, 2H), 4.80-4.65 (m, 1H), 3.22-3.09 (m, 2H), 2.88-2.73 (m, 2H), 2.49 (s, 3H). LCMS R$_t$=1.21 min using Method A, MS ESI calcd. for C$_{17}$H$_{14}$F$_5$N$_4$O [M+H]$^+$ 385.1, found 385.0.

Example 89. Synthesis of Compound 95

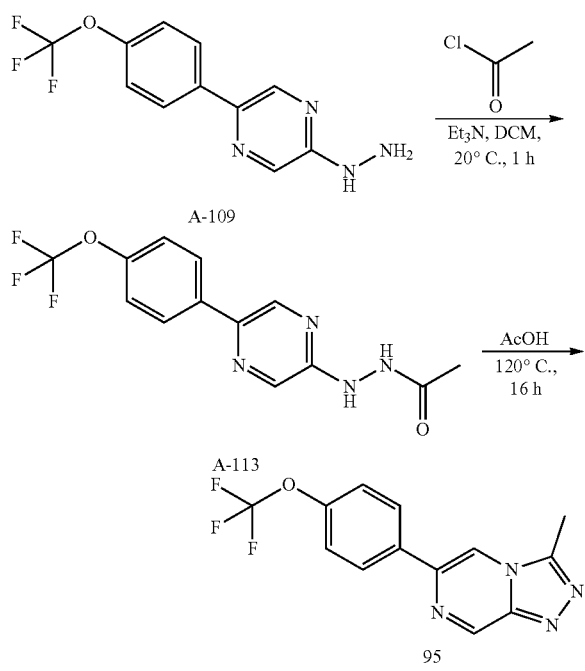

Synthesis of A-113: To a mixture of A-109 (100 mg, 0.37 mmol) and Et$_3$N (0.15 mL, 1.11 mmol) in DCM (3 mL) was added acetyl chloride (58.1 mg, 0.74 mmol). The reaction mixture was stirred at 20° C. for 1 hour. The reaction mixture was concentrated, diluted with sat.NaHCO$_3$ (15 mL), and extracted with EtOAc (10 mL×2). The combined organic phase was washed with brine (10 mL), dried over Na$_2$SO$_4$, filtered and concentrated afford A-113 (150 mg, 0.48 mmol) as an oil. LCMS R$_t$=0.745 min using Method B, MS ESI calcd. for C$_{13}$H$_{12}$F$_3$N$_4$O$_2$ [M+H]$^+$ 313.1, found 312.9.

Synthesis of Compound 95: A mixture of A-113 (150 mg, 0.48 mmol) in acetic acid (3 mL) was heated to 120° C. and stirred for 16 hours. The reaction mixture was concentrated, diluted with sat.NaHCO$_3$ (10 mL), and extracted with EtOAc (15 mL×2). The combined organic phase was washed with brine (10 mL), dried over Na$_2$SO$_4$, filtered, concentrated, and purified by flash chromatography on silica gel (EtOAc in PE, 0% to 40% to 100%) to afford Compound 95 (59.99 mg, 0.21 mmol) as a solid. $^1$H NMR (400 MHz, DMSO-d$_6$) δ$_H$=9.45 (d, 1H), 9.03 (d, 1H), 8.25 (d, 2H), 7.54 (d, 2H), 2.81 (s, 3H). LCMS R$_t$=1.09 min using Method A, MS ESI calcd. for C$_{13}$H$_{10}$F$_3$N$_4$O [M+H]$^+$ 295.1, found 294.9.

Example 90. Synthesis of Compound 96

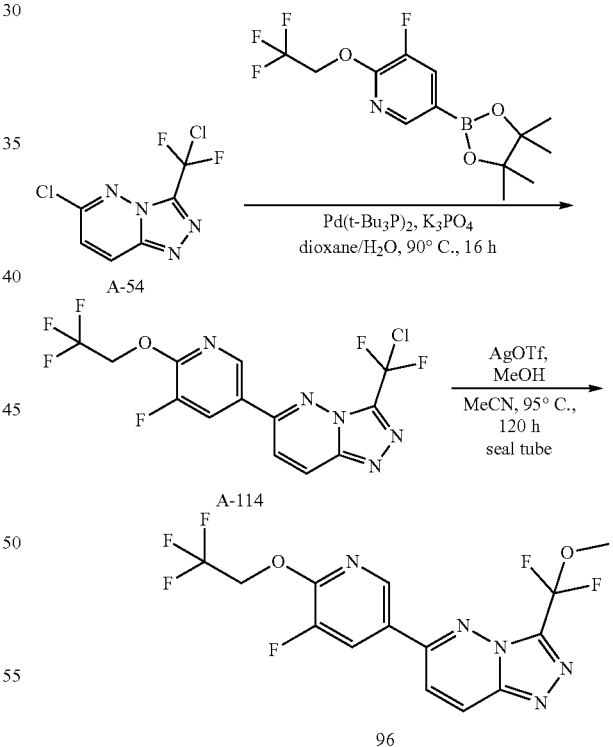

Synthesis of A-114: A mixture of A-54 (150 mg, 0.63 mmol), 3-fluoro-5-(4,4,5,5-tetramethyl-1,3,2-dioxaborolan-2-yl)-2-(2,2,2-trifluoroethoxy)pyridine (302.26 mg, 0.94 mmol), Pd(t-Bu$_3$P)$_2$ (48.11 mg, 0.09 mmol) and K$_3$PO$_4$ (266.47 mg, 1.26 mmol) in 1,4-dioxane (3 mL) and water (0.3 mL) under N$_2$ was stirred at 90° C. for 16 hours. After cooling, the reaction mixture was diluted with EtOAc (10 mL), filtered through a Celite pad, eluted with EtOAc (10 mL), concentrated, and purified by flash chromatography on silica gel (EtOAc in PE, 0% to 20% to 40%) to afford A-114 (160 mg, 0.4024 mmol) as a solid. $^1$H NMR (400 MHz DMSO-d$_6$) δ$_H$=8.84 (d, 1H), 8.76 (d, 1H), 8.47 (dd, 1H), 8.29 (d, 1H), 5.22 (q, 2H).

Synthesis of Compound 96: To a mixture of A-114 (160 mg, 0.4 mmol) in methanol (2 mL) and MeCN (2 mL) was added AgOTf (516.9 mg, 2.01 mmol), then the mixture was sealed and stirred at 95° C. for 120 hoursMS. After cooling, the mixture was diluted with H$_2$O (15 mL) and extracted with EtOAc (30 mL×2). The combined organic phase was washed with brine (20 mL), dried over Na$_2$SO$_4$, filtered, concentrated, and purified by flash chromatography on silica gel (EtOAc in PE, 0% to 20% to 40%) to afford Compound 96 (26.07 mg, 0.07 mmol) as a solid. $^1$H NMR (400 MHz, CDCl$_3$) δ$_H$=8.56 (d, 1H), 8.31 (d, 1H), 8.16 (dd, 1H), 7.67 (d, 1H), 4.95 (q, 2H), 3.94 (s, 3H). LCMS R$_t$=1.15 min using Method A, MS ESI calcd. for C$_{14}$H$_{10}$F$_6$N$_5$O$_2$ [M+H]$^+$ 394.1, found 394.0.

Example 91. Synthesis of Compound 97

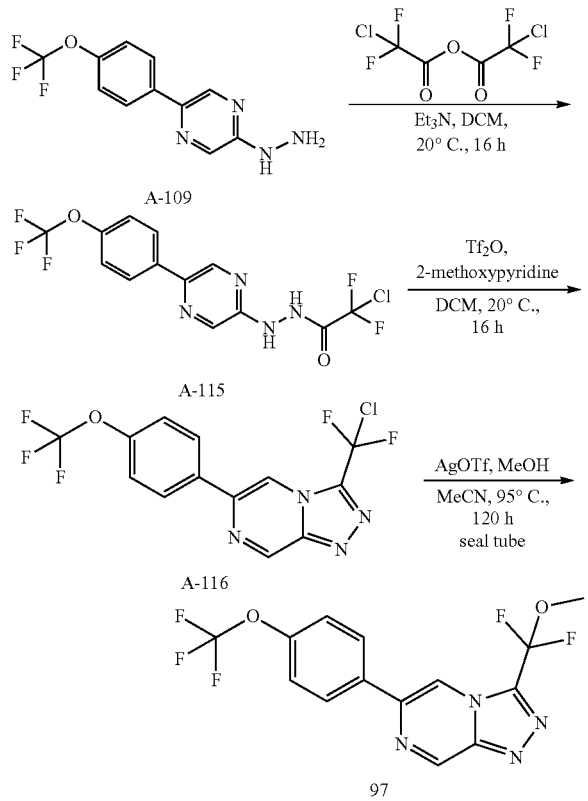

Synthesis of A-115: To a mixture of A-109 (200 mg, 0.74 mmol) and Et$_3$N (0.2 mL, 1.48 mmol) in DCM (5 mL) was added (2-chloro-2,2-difluoro-acetyl) 2-chloro-2,2-difluoro-acetate (197.8 mg, 0.81 mmol). The reaction mixture was stirred at 20° C. for 16 hours. The reaction mixture was concentrated, diluted with sat.NaHCO$_3$ (20 mL), and was extracted with EtOAc (20 mL×2). The combined organic phase was washed with brine (10 mL), dried over Na$_2$SO$_4$, filtered and concentrated to afford A-115 (300 mg, 0.78 mmol) as an oil, which was used directly in next step. LCMS R$_t$=0.83 min using Method B, MS ESI calcd. for C$_{13}$H$_9$ClF$_5$N$_4$O$_2$ [M+H]$^+$ 383.0, found 382.9.

Synthesis of A-116: To a mixture of A-115 (300 mg, 0.78 mmol) and 2-methoxypyridine (102.66 mg, 0.94 mmol) in DCM (5 mL) was added Tf$_2$O (243.31 mg, 0.86 mmol). The reaction mixture was stirred at 20° C. for 16 hours. The reaction mixture was concentrated, diluted with sat-.NaHCO$_3$ (10 mL), extracted with EtOAc (15 mL×2). The combined organic phase was washed with brine (10 mL), dried over Na$_2$SO$_4$, filtered, concentrated, and purified by flash chromatography on silica gel (EtOAc in PE, 0% to 10% to 20%) to afford A-116 (30 mg, 0.08 mmol) as a solid. $^1$H NMR (400 MHz CDCl$_3$) δ$_H$=9.59 (d, 1H), 8.45 (s, 1H), 8.04 (d, 2H), 7.41 (d, 2H).

Synthesis of Compound 97: A mixture of A-116 (30 mg, 0.08 mmol) and AgOTf (211.38 mg, 0.82 mmol) in MeCN (1 mL) and methanol (1 mL) was sealed and stirred at 95° C. for 120 hours. After cooling, the mixture was diluted with H$_2$O (15 mL) and extracted with EtOAc (30 mL×2). The combined organic phase was washed with brine (20 mL), dried over Na$_2$SO$_4$, filtered, concentrated, and purified by flash chromatography (EtOAc in PE, 0% to 20% to 40%) to afford Compound 97 (11.95 mg, 0.03 mmol) as a solid. $^1$H NMR (400 MHz CDCl$_3$) δ$_H$=9.53 (d, 1H), 8.47 (s, 1H), 8.02 (d, 2H), 7.40 (d, 2H), 3.98 (s, 3H). LCMS R$_t$=1.17 min using Method A, MS ESI calcd. for C$_{14}$H$_{10}$F$_5$N$_4$O$_2$ [M+H]$^+$ 361.1, found 361.0.

Example 92. Synthesis of Compound 98

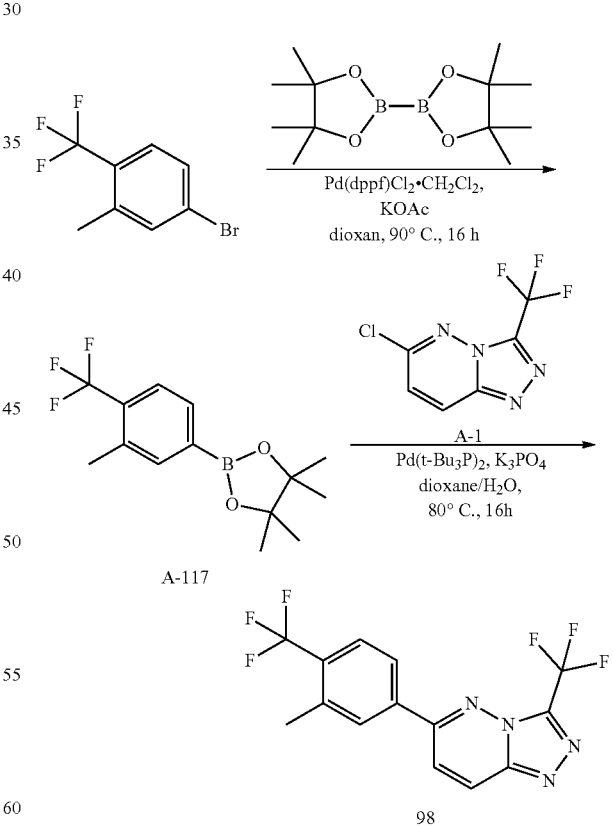

Synthesis of A-117: A mixture of 4-bromo-2-methyl-1-(trifluoromethyl)benzene (500 mg, 2.09 mmol), 4,4,5,5-tetramethyl-2-(4,4,5,5-tetramethyl-1,3,2-dioxaborolan-2-yl)-1,3,2-dioxaborolane (690.55 mg, 2.72 mmol) and Pd(dppf)Cl$_2$.CH$_2$Cl$_2$ (160.35 mg, 0.31 mmol) and KOAc (410.58 mg, 4.18 mmol) in 1,4-dioxane (5 mL) was stirred at 90° C. for 16 hours. The mixture was filtered through silica gel, eluted with EtOAc (10 mL×2), and the filtrate was concentrated to the crude product, which was purified by flash chromatography on silica gel (PE:EtOAc=10:1) to afford A-117 (300 mg, 1.05 mmol) as a solid. $^1$H NMR (400 MHz, CDCl$_3$) $\delta_H$=7.71-7.59 (m, 2H), 7.52 (d, 1H), 2.41 (d, 3H), 1.28 (s, 12H).

Synthesis of Compound 98: A mixture of A-1 (150 mg, 0.67 mmol), A-117 (250.67 mg, 0.88 mmol), K$_3$PO$_4$ (286.17 mg, 1.35 mmol) and Pd(t-Bu$_3$P)$_2$ (51.67 mg, 0.1 mmol) in 1,4-dioxane (2 mL) and water (0.2 mL) was stirred at 90° C. for 16 hours. After cooling to room temperature, the suspension was diluted with EtOAc (10 mL), filtered through silica gel, eluted with EtOAc (20 mL), and concentrated to give the crude product which was purified by prep-HPLC (Xbridge (150 mm×25 mm, 5 µm); A=H$_2$O (0.05% NH$_4$HCO$_3$) and B=CH$_3$CN; 58-65% B over 6 minutes) to afford Compound 98 (19.86 mg, 0.06 mmol) as a solid. $^1$H NMR (400 MHz, CDCl$_3$) $\delta_H$=8.35 (d, 1H), 7.97-7.88 (m, 2H), 7.85-7.81 (m, 1H), 7.78 (d, 1H), 2.64 (s, 3H) LCMS R$_t$=1.25 min using Method A, MS ESI calcd. for C$_{14}$H$_9$F$_6$N$_4$ [M+H]$^+$ 347.1, found 346.9.

Example 93. Synthesis of Compound 99

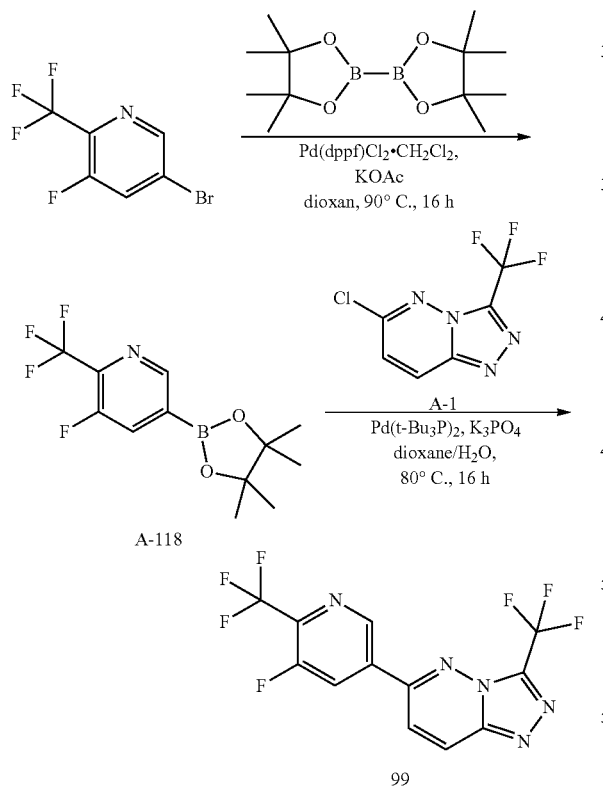

99

Synthesis of A-118: A mixture of 5-bromo-3-fluoro-2-(trifluoromethyl)pyridine (163.95 mg, 0.82 mmol), 4,4,5,5-tetramethyl-2-(4,4,5,5-tetramethyl-1,3,2-dioxaborolan-2-yl)-1,3,2-dioxaborolane (270.61 mg, 1.07 mmol), KOAc (160.9 mg, 1.64 mmol) and Pd(dppf)Cl$_2$.CH$_2$Cl$_2$ (62.84 mg, 0.12 mmol) in 1,4-dioxane (4 mL) was stirred at 90° C. under N$_2$ for 16 hours. The mixture was cooled to room temperature, diluted with EtOAc (10 mL), filtered through silica gel, and eluted with EtOAc (20 mL). The combined filtrates were concentrated to give the crude product, which was purified by flash chromatography on silica gel (PE:EtOAc=10:1) to afford A-118 (100 mg, 0.34 mmol) as a solid. $^1$H NMR (400 MHz, CDCl$_3$) $\delta_H$=8.82-8.75 (m, 1H), 7.93 (d, 1H), 1.37 (s, 12H).

Synthesis of Compound 99: A mixture of A-1 (100 mg, 0.45 mmol), A-118 (143.85 mg, 0.49 mmol), K$_3$PO$_4$ (190.78 mg, 0.9 mmol) and Pd(t-Bu$_3$P)$_2$ (34.44 mg, 0.07 mmol) in 1,4-dioxane (2 mL) and water (0.2 mL) was stirred at 80° C. under the N$_2$ for 16 hours. After cooling to room temperature, the suspension was diluted with EtOAc (10 mL), filtered through silica gel, eluted with EtOAc (20 mL), and concentrated to give a crude product that was purified by prep-TLC (silica gel, PE:EtOAc=1:1) to afford Compound 99 (32.76 mg, 0.09 mmol) as a solid. $^1$H NMR (400 MHz, DMSO-d$_6$) $\delta_H$=9.28 (s, 1H), 8.88 (d, 1H), 8.78 (d, 1H), 8.34 (d, 1H). LCMS R$_t$=1.15 min using Method A, MS ESI calcd. for C$_{12}$H$_5$F$_7$N$_5$ [M+H]$^+$ 352.0, found 351.9.

Example 94. Synthesis of Compound 100

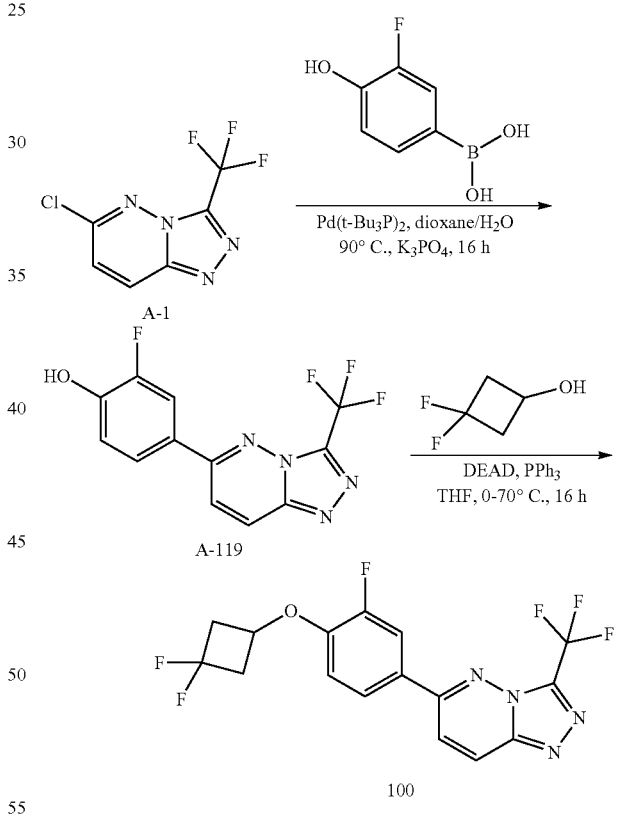

100

Synthesis of A-119: A mixture of A-119 (300 mg, 1.35 mmol), (3-fluoro-4-hydroxy-phenyl)boronic acid (273.22 mg, 1.75 mmol), Pd(t-Bu$_3$P)$_2$ (137.77 mg, 0.27 mmol) and K$_3$PO$_4$ (572.34 mg, 2.7 mmol) in 1,4-dioxane (15 mL) and water (3 mL) was stirred at 90° C. for 16 hours. After cooling to room temperature, the mixture was concentrated and purified by flash chromatography on silica gel (EtOAc in PE=0 to 100%) to afford A-119 (250 mg, 0.83 mmol) as a solid. $^1$H NMR (400 MHz DMSO-d$_6$) $\delta_H$=10.78 (s, 1H), 8.63 (d, 1H), 8.19 (d, 1H), 7.96 (d, 1H), 7.87 (d, 1H), 7.18 (t, 1H).

Synthesis of Compound 100: To a mixture of A-119 (100 mg, 0.34 mmol), 3,3-difluorocyclobutanol (54.37 mg, 0.50 mmol) and PPh$_3$ (158.32 mg, 0.60 mmol) in THF (3 mL) was added DEAD (105.12 mg, 0.60 mmol) at 0° C. under N$_2$. The mixture was heat and stirred at 70° C. for 16 hours, at which point the desired product was observed by LCMS. After cooling to room temperature, the mixture was concentrated and purified by flash chromatography on silica gel (EtOAc in PE=0 to 100%) and prep-HPLC (Phenomenex Gemini (250 mm×50 mm, 10 µm); A=H$_2$O (0.05% NH$_4$OH) and B=CH$_3$CN; 50-80% B over 8 minutes) to afford Compound 100 (51.33 mg, 0.13 mmol) as a solid. $^1$H NMR (400 MHz CDCl$_3$) $\delta_H$=8.29 (d, 1H), 7.85 (dd, 1H), 7.77 (d, 1H), 7.71 (d, 1H), 6.97 (t, 1H), 4.87-4.24 (m, 1H), 3.24-3.11 (m, 2H), 2.98-2.82 (m, 2H). LCMS R$_t$=1.20 min using Method A, MS ESI calcd. for C$_{16}$H$_{11}$F$_6$N$_4$O [M+H]$^+$ 389.1, found 389.0.

Example 95. Synthesis of Compound 101

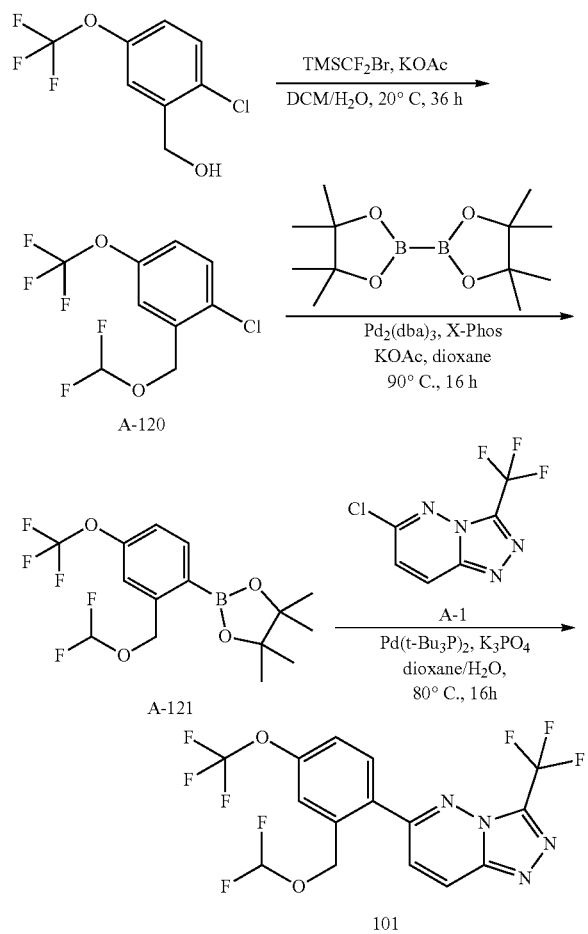

Synthesis of A-120: To a mixture of [2-chloro-5-(trifluoromethoxy)phenyl]methanol (200 mg, 0.88 mmol) and KOAc (519.76 mg, 5.3 mmol) in DCM (0.50 mL) and water (0.50 mL) was added [bromo(difluoro)methyl]-trimethylsilane (537.82 mg, 2.65 mmol), then the mixture was stirred at 20° C. for 36 hours. The mixture was diluted with DCM (30 mL), and the organic phase was washed with water (15 mL) and brine (15 mL), dried over Na$_2$SO$_4$, filtered and concentrated to give the crude product, which was purified by flash chromatography on silica gel (EtOAc in PE=0% to 2%) to afford A-120 (160 mg, 0.58 mmol) as an oil. $^1$H NMR (400 MHz DMSO-d$_6$) $\delta_H$=7.67 (d, 1H), 7.54 (d, 1H), 7.45 (dd, 1H), 6.88 (t, 1H), 5.03 (s, 2H)

Synthesis of A-121: A mixture of A-120 (110 mg, 0.40 mmol), 4,4,5,5-tetramethyl-2-(4,4,5,5-tetramethyl-1,3,2-dioxaborolan-2-yl)-1,3,2-dioxaborolane (302.98 mg, 1.19 mmol), X-Phos (47.4 mg, 0.10 mmol), KOAc (78.06 mg, 0.80 mmol) and Pd$_2$(dba)$_3$ (36.42 mg, 0.04 mmol) in 1,4-dioxane (3 mL) was stirred at 90° C. for 16 hours. After cooling to room temperature, the mixture was concentrated to give the crude product, which was purified by flash chromatography on silica gel (EtOAc in PE=0 to 10%) to afford A-121 (50 mg, 0.14 mmol) as an oil. $^1$H NMR (400 MHz, CDCl$_3$) $\delta_H$=7.89 (d, 1H), 7.34 (s, 1H), 7.17 (d, 1H), 6.57-6.15 (m, 1H), 5.20 (s, 2H), 1.35 (s, 12H).

Synthesis of Compound 101: A mixture of A-121 (50 mg, 0.14 mmol), A-1 (30.23 mg, 0.14 mmol), Pd(t-Bu$_3$P)$_2$ (13.88 mg, 0.03 mmol) and K$_3$PO$_4$ (28.84 mg, 0.14 mmol) in 1,4-dioxane (3 mL) and water (0.50 mL) was stirred at 90° C. for 16 hours under N$_2$. After cooling to room temperature, the mixture was filtered through silica gel, eluted with EtOAc (20 mL×2), concentrated, diluted with EtOAc (30 mL), washed with water (10 mL×2) and brine (10 mL), dried over Na$_2$SO$_4$, filtered and concentrated to give the crude product, which was purified by Prep-HPLC (Phenomenex Gemini (250 mm×50 mm, 10 µm); A=H$_2$O (0.05% NH$_4$OH) and B=CH$_3$CN; 50-80% B over 8 minutes) to afford Compound 101 (9.08 mg, 0.02 mmol) as a solid. $^1$H NMR (400 MHz, CDCl$_3$) $\delta_H$=8.36 (br d, 1H), 7.66 (d, 1H), 7.59 (s, 1H), 7.55 (d, 1H), 7.41 (br d, 1H), 6.48-6.08 (m, 1H), 5.20 (s, 2H). LCMS R$_t$=1.23 min using Method A, MS ESI calcd. for C$_{15}$H$_9$F$_8$N$_4$O$_2$ [M+H]$^+$ 429.1, found 429.0.

Example 96. Synthesis of Compound 102

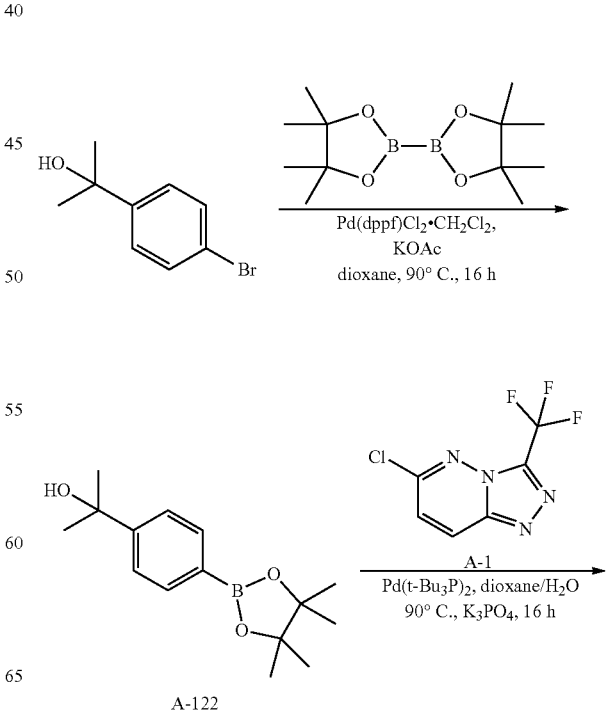

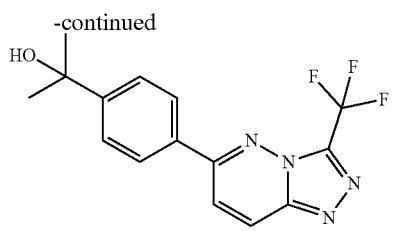

102

Synthesis of A-122: A mixture of 2-(4-bromophenyl)propan-2-ol (250 mg, 1.16 mmol), A-122 (885.47 mg, 3.49 mmol), Pd(dppf)Cl$_2$·CH$_2$Cl$_2$ (189.84 mg, 0.23 mmol) and KOAc (228.14 mg, 2.32 mmol) in 1,4-dioxane (15 mL) was stirred at 90° C. for 16 hours under N$_2$. After cooling to room temperature, the mixture was concentrated and purified by flash chromatography on silica gel (EtOAc in PE=0 to 50%) to afford A-122 (250 mg, 0.95 mmol) as a solid. $^1$H NMR (400 MHz DMSO-d$_6$) δ$_H$=7.61 (d, 2H), 7.47 (d, 2H), 5.05 (s, 1H), 1.40 (s, 6H), 1.28 (s, 12H).

Synthesis of Compound 102: To a mixture of A-122 (250 mg, 0.95 mmol), A-1 (200 mg, 0.90 mmol), Pd(t-Bu$_3$P)$_2$ (91.85 mg, 0.18 mmol) and K$_3$PO$_4$ (381.56 mg, 1.8 mmol) in 1,4-dioxane (15 mL) and water (2 mL) was stirred at 90° C. for 16 hours under N$_2$. After cooling to room temperature, the mixture was concentrated and purified by flash chromatography on silica gel (EtOAc in PE=0 to 70%) to afford Compound 102 (19.98 mg, 0.06 mmol) as a solid. $^1$H NMR (400 MHz, DMSO-d$_6$) δ$_H$=8.67 (d, 1H), 8.21 (d, 1H), 8.06 (d, 2H), 7.70 (d, 2H), 5.21 (s, 1H), 1.47 (s, 6H). LCMS R$_t$=1.04 min using Method A, MS ESI calcd. for C$_{15}$H$_{14}$F$_3$N$_4$O [M+H]$^+$ 323.1, found 323.0.

Example 97. Synthesis of Compound 103

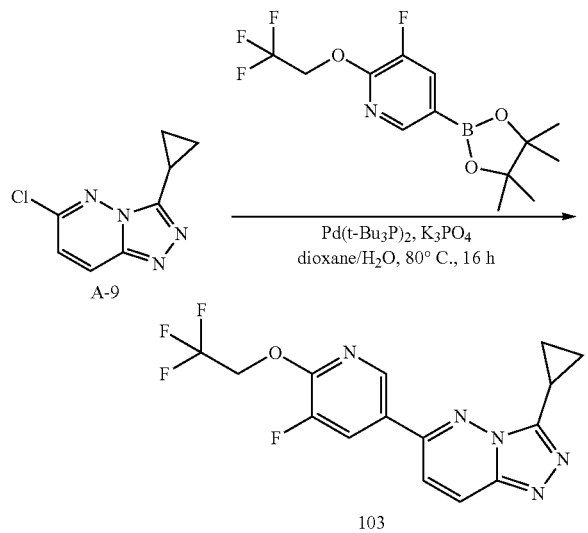

103

Synthesis of Compound 103: A mixture of A-9 (150 mg, 0.77 mmol), 3-fluoro-5-(4,4,5,5-tetramethyl-1,3,2-dioxaborolan-2-yl)-2-(2,2,2-trifluoroethoxy)pyridine (296.96 mg, 0.92 mmol), K$_3$PO$_4$ (327.25 mg, 1.54 mmol) and Pd(t-Bu$_3$P)$_2$ (59.08 mg, 0.12 mmol) in 1,4-dioxane (3 mL) and water (0.50 mL) was stirred at 80° C. for 16 hours under N$_2$. After cooling to room temperature, the mixture was concentrated and purified by prep-HPLC (Phenomenex Gemini (250 mm×50 mm, 10 μm); A=H$_2$O (0.05% NH$_4$OH) and B=CH$_3$CN; 48-58% B over 8 minutes) to afford Compound 103 (40.99 mg, 0.11 mmol) as a solid. $^1$H NMR (400 MHz, CDCl$_3$) δ$_H$=8.54 (d, 1H), 8.16 (d, 2H), 7.47 (d, 1H), 4.94 (q, 2H), 2.63-2.55 (m, 1H), 1.46-1.42 (m, 2H), 1.29-1.24 (m, 2H). LCMS R$_t$=1.13 min using Method A, MS ESI calcd. for C$_{15}$H$_{12}$F$_4$N$_5$O [M+H]$^+$ 354.1, found 354.0.

Example 98. Synthesis of Compound 104

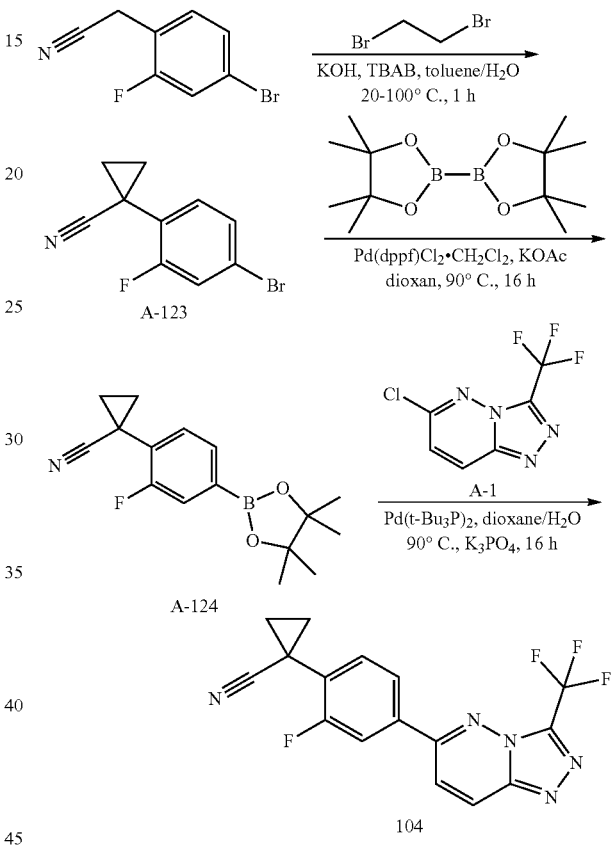

104

Synthesis of A-123: To a mixture of 2-(4-bromo-2-fluorophenyl)acetonitrile (1 g, 4.67 mmol), TBAB (60.25 mg, 0.19 mmol) and KOH (2.62 g, 46.72 mmol) in toluene (40 mL) and water (4 mL) was added 1,2-dibromoethane (1.76 g, 9.34 mmol) at 20° C., then the mixture was stirred at 100° C. for 1 hour. After cooling to room temperature, the mixture was diluted with H$_2$O (40 mL) and extracted with EtOAc (80 mL×2). The combined organic phase was washed with brine (50 mL), dried over Na$_2$SO$_4$, filtered and concentrated to give the crude product, which was purified by flash chromatography on silica gel (DCM in PE=0 to 10%) to afford A-123 (587 mg, 2.34 mmol) as an a solid. $^1$H NMR (400 MHz, CDCl$_3$) δ$_H$=7.32-7.28 (m, 2H), 7.25-7.20 (m, 1H), 1.73-1.69 (m, 2H), 1.40-1.36 (m, 2H). LCMS R$_t$=0.81 min using Method B, MS ESI calcd. for C$_{10}$H$_7$BrFN [M+H]$^+$ 240.0, not found.

Synthesis of A-124: A mixture of A-123 (587 mg, 2.45 mmol), 4,4,5,5-tetramethyl-2-(4,4,5,5-tetramethyl-1,3,2-dioxaborolan-2-yl)-1,3,2-dioxaborolane (1.86 g, 7.34 mmol), KOAc (479.93 mg, 4.89 mmol) and Pd(dppf)Cl$_2$·CH$_2$Cl$_2$ (187.44 mg, 0.37 mmol) in 1,4-dioxane (20 mL) was stirred at 90° C. for 16 hours under N$_2$. After cooling to room temperature, the mixture was diluted with H$_2$O (20 mL) and extracted with EtOAc (50 mL×2). The combined organic phase was washed with brine (20 mL), dried over Na$_2$SO$_4$, filtered, and concentrated to give the crude product, which was purified by flash chromatography on silica gel (EtOAc in PE=0 to 10%) to afford A-124 (1420.7 mg, 2.66 mmol) as a solid. $^1$H NMR (400 MHz, CDCl$_3$) $\delta_H$=7.55 (dd, 1H), 7.50 (d, 1H), 7.34 (t, 1H), 1.73-1.67 (m, 2H), 1.44-1.41 (m, 2H), 1.34 (s, 12H).

Synthesis of Compound 104: A mixture of A-124 (322.54 mg, 1.12 mmol), A-1 (100 mg, 0.45 mmol), K$_3$PO$_4$ (190.78 mg, 0.90 mmol) and Pd(t-Bu$_3$P)$_2$ (34.44 mg, 0.07 mmol) in 1,4-dioxane (4 mL) and water (0.90 mL) was stirred at 90° C. for 16 hours under N$_2$. After cooling to room temperature, the mixture was concentrated to give the crude product, which was purified by Prep-HPLC (Phenomenex Gemini (250 mm×50 mm, 10 μm); A=H$_2$O (0.05% NH$_4$OH) and B=CH$_3$CN; 48-58% B over 8 minutes) to afford Compound 104 (10.01 mg, 0.03 mmol) as a solid. $^1$H NMR (400 MHz, CDCl$_3$) $\delta_H$=8.37 (d, 1H), 7.84-7.78 (m, 2H), 7.75 (d, 1H), 7.60 (t, 1H), 1.84-1.79 (m, 2H), 1.56-1.52 (m, 2H). LCMS R$_t$=1.12 min using Method A, MS ESI calcd. for C$_{16}$H$_{10}$F$_4$N$_5$ [M+H]$^+$ 348.1, found 348.0.

Example 99. Synthesis of Compound 105

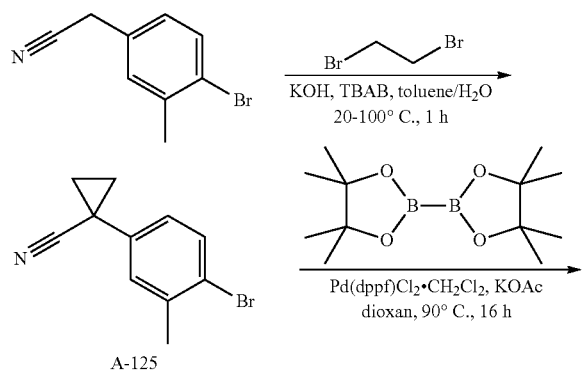

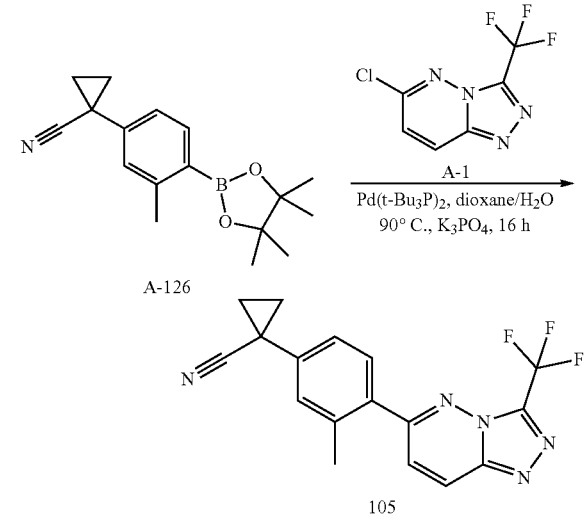

Synthesis of A-125: To a mixture of 2-(4-bromo-3-methyl-phenyl)acetonitrile (1 g, 4.76 mmol), TBAB (61.38 mg, 0.19 mmol) and KOH (2.67 g, 47.6 mmol) in toluene (40 mL) and water (4 mL) was added 1,2-dibromoethane (1.79 g, 9.52 mmol) at 20° C., then the mixture was stirred at 100° C. for 1 hour. After cooling to room temperature, the mixture was diluted with H$_2$O (40 mL) and extracted with EtOAc (70 mL×2). The combined organic phase was washed with brine (40 mL), dried over Na$_2$SO$_4$, filtered and concentrated to give the crude product, which was purified by flash chromatography on silica gel (DCM in PE=0 to 10%) to afford A-125 (643 mg, 1.0 mmol) as a solid. $^1$H NMR (400 MHz, +CDCl$_3$) $\delta_H$=7.50 (d, 1H), 7.20 (d, 1H), 6.94 (dd, 1H), 2.41 (s, 3H), 1.75-1.71 (m, 2H), 1.40-1.36 (m, 2H).

Synthesis of A-126: A mixture of A-125 (643 mg, 2.72 mmol), 4,4,5,5-tetramethyl-2-(4,4,5,5-tetramethyl-1,3,2-dioxaborolan-2-yl)-1,3,2-dioxaborolane (2.07 g, 8.17 mmol), KOAc (534.53 mg, 5.45 mmol) and Pd(dppf)Cl$_2$.CH$_2$Cl$_2$ (208.76 mg, 0.41 mmol) in 1,4-dioxane (20 mL) was stirred at 90° C. for 16 hours under N$_2$. After cooling to room temperature, the mixture was diluted with H$_2$O (20 mL) and extracted with EtOAc (40 mL×2). The combined organic phase was washed with brine (20 mL), dried over Na$_2$SO$_4$, filtered and concentrated to give the crude product, which was purified by flash chromatography on silica gel (EtOAc in PE=0 to 10%) to afford A-126 (1309.8 mg, 4.43 mmol) as a solid. $^1$H NMR (400 MHz, CDCl$_3$) $\delta_H$=7.73 (d, 1H), 7.10 (s, 1H), 7.03 (dd, 1H), 2.54 (s, 3H), 1.74-1.70 (m, 2H), 1.44-1.41 (m, 2H), 1.34 (s, 12H).

Synthesis of Compound 105: A mixture of A-126 (381.7 mg, 1.35 mmol), A-1 (100 mg, 0.45 mmol), K$_3$PO$_4$ (190.78 mg, 0.90 mmol) and Pd(t-Bu$_3$P)$_2$ (34.44 mg, 0.07 mmol) in 1,4-Dioxane (4 mL) and Water (0.90 mL) was stirred at 90° C. for 16 hours under N$_2$. After cooling to room temperature, the mixture was concentrated to give the crude product, which was purified by prep-HPLC (Phenomenex Gemini (250 mm×50 mm, 10 μm); A=H$_2$O (0.05% NH$_4$OH) and B=CH$_3$CN; 50-60% B over 8 minutes) to afford Compound 105 (11.38 mg, 0.03 mmol) as a solid. $^1$H NMR (400 MHz, DMSO-d$_6$) $\delta_H$=8.65 (d, 1H), 7.83 (d, 1H), 7.60 (d, 1H), 7.40-7.33 (m, 2H), 2.42 (s, 3H), 1.85-1.80 (m, 2H), 1.63-1.58 (m, 2H). LCMS R$_t$=1.12 min using Method A, MS ESI calcd. for C$_{17}$H$_{13}$F$_3$N$_5$ [M+H]$^+$ 344.1, found 344.0.

Example 100: Synthesis of Compound 106

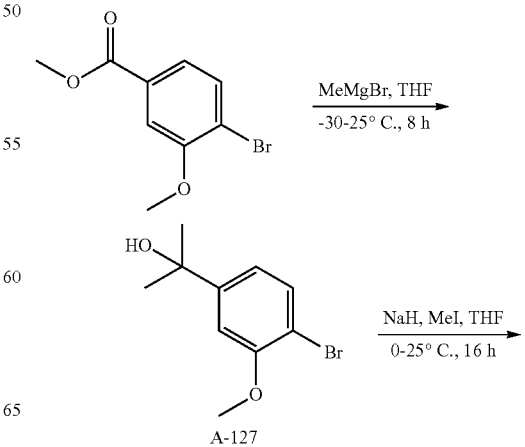

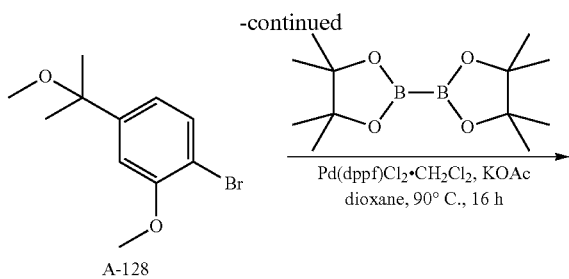

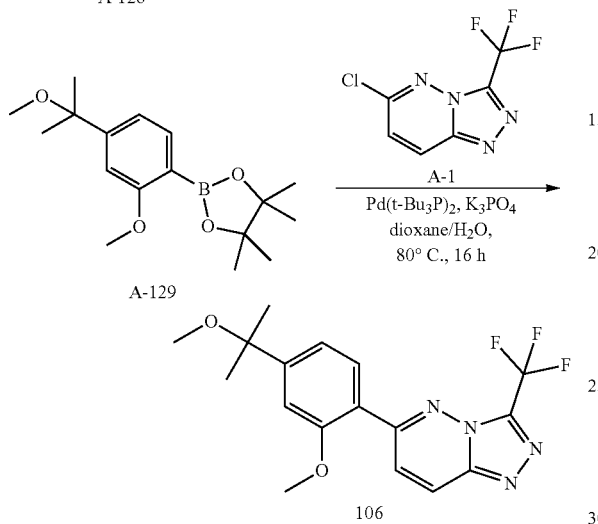

Synthesis of A-127: To a solution of methyl 4-bromo-3-methoxy-benzoate (1.00 g, 4.08 mmol) in THF (30 mL) was added MeMgBr (3 M, 10.88 mL) dropwise at −30° C. The reaction mixture was allowed to warm to 25° C. and stirred for 8 hours. The mixture was quenched with sat.NH$_4$Cl (200 mL) at 0° C. and extracted with EtOAc (200 mL×2). The organic layers were concentrated to afford A-127 (960.00 mg) as a solid. $^1$H NMR (400 MHz DMSO-d$_6$) $\delta_H$=7.45 (d, 1H), 7.19 (d, 1H), 6.95 (dd, 1H), 5.12 (s, 1H), 3.84 (s, 3H), 1.42 (s, 6H).

Synthesis of A-128: To a mixture of A-127 (960.00 mg, 3.92 mmol) in THF (20 mL) was added NaH (313.60 mg, 7.84 mmol, 60% purity) and CH$_3$I (1.11 g, 7.84 mmol) at 0° C., then the mixture was stirred at 25° C. for 16 hours. The mixture was quenched with a sat. NH$_4$Cl (50 mL) and extracted with EtOAc (100 mL×2). The combined organic phase was washed with brine (50 mL), dried over Na$_2$SO$_4$, filtered and concentrated to afford A-128 (950.00 mg, 3.67 mmol) as an oil. $^1$H NMR (400 MHz, DMSO-d$_6$) $\delta_H$=7.51 (d, 1H), 7.04 (d, 1H), 6.89 (dd, 1H), 3.85 (s, 3H), 2.99 (s, 3H), 1.44 (s, 6H).

Synthesis of A-129: A mixture of A-128 (500.00 mg, 1.93 mmol), 4,4,5,5-tetramethyl-2-(4,4,5,5-tetramethyl-1,3,2-dioxaborolan-2-yl)-1,3,2-dioxaborolane (1.47 g, 5.79 mmol), Pd(dppf)Cl$_2$.CH$_2$Cl$_2$ (157.61 mg, 193.00 μmol) and KOAc (378.82 mg, 3.86 mmol) in dioxane (10 mL) was stirred at 90° C. for 16 hours. After cooling to room temperature, the mixture was concentrated to give the crude product, which was by flash chromatography on silica gel (EtOAc:PE=0 to 1:50 to 1:30 to 1:20 to 1:10) to afford A-129 (460.00 mg) as a solid. $^1$H NMR (400 MHz, CDCl$_3$) $\delta_H$=7.65 (d, 1H), 6.97-6.92 (m, 2H), 3.86 (s, 3H), 3.08 (s, 3H), 1.52 (s, 6H), 1.36 (s, 12H).

Synthesis of Compound 106: A mixture of A-129 (309.56 mg, 1.01 mmol), A-1 (150.00 mg, 673.98 μmol), Pd(t-Bu$_3$P)$_2$ (68.89 mg, 134.80 μmol) and K$_3$PO$_4$ (286.13 mg, 1.35 mmol) in dioxane (8 mL) and H$_2$O (1 mL) was stirred at 80° C. for 16 hours. After cooling to room temperature, the mixture was concentrated and purified by prep-HPLC (Waters Xbridge (150 mm×25 mm, 5 μm) A=H$_2$O (10 mM NH$_4$OH) and B=CH$_3$CN; 45-75% B over 10 minutes) to afford Compound 106 (110.05 mg, 297.94 μmol) as a solid. $^1$H NMR (400 MHz, DMSO-d$_6$) $\delta_H$=8.55 (d, 1H), 7.93 (d, 1H), 7.58 (d, 1H), 7.23-7.14 (m, 2H), 3.90 (s, 3H), 3.07 (s, 3H), 1.50 (s, 6H). LCMS R$_t$=1.16 min using Method A, MS ESI calcd. for C$_{17}$H$_{18}$F$_3$N$_4$O$_2$ [M+H]$^+$ 367.1, found 367.0.

Example 101: Synthesis of Compound 107

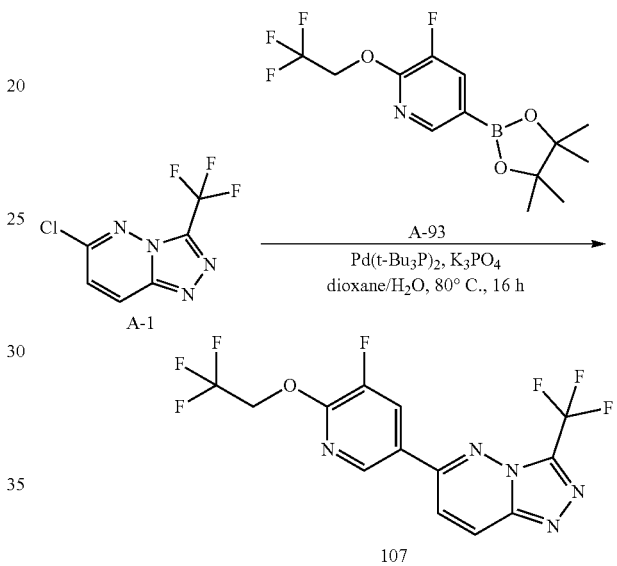

Synthesis of Compound 107: A mixture of A-93 (250.00 mg, 778.62 μmol), A-1 (115.53 mg, 519.08 μmol), Pd(t-Bu$_3$P)$_2$ (26.53 mg, 51.91 μmol) and K$_3$PO$_4$ (220.37 mg, 1.04 mmol) was stirred at 80° C. for 16 hours. After cooling to room temperature, the mixture was concentrated to give the crude product, which was purified by prep-HPLC (Waters Xbridge (150 mm×25 mm, 5 μm) A=H$_2$O (10 mM NH$_4$OH) and B=CH$_3$CN; 40-70% B over 10 minutes) to afford Compound 107 (35.63 mg, 92.96 μmol) as a solid. $^1$H NMR (400 MHz, CDCl$_3$) $\delta_H$=8.58 (d, 1H), 8.37 (d, 1H), 8.16 (dd, 1H), 7.75 (d, 1H), 4.95 (q, 2H). LCMS R$_t$=1.30 min in 2.0 min chromatography, MS ESI calcd. for C$_{13}$H$_7$F$_7$N$_5$O [M+H]$^+$ 382.0, found 381.9.

Example 102: Synthesis of Compound 108

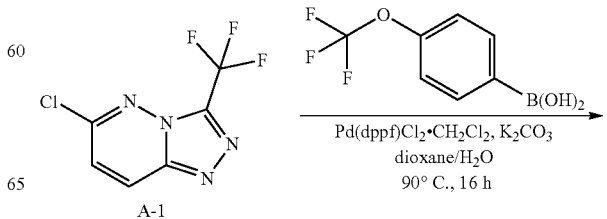

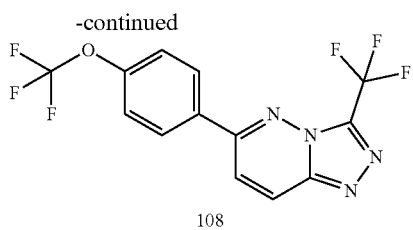

108

A mixture of A-1 (100.00 mg, 449.32 umol), [4-(trifluoromethoxy)phenyl]boronic acid (111.03 mg, 539.18 umol), $K_2CO_3$ (124.20 mg, 898.64 μmol) and $Pd(dppf)Cl_2\cdot CH_2Cl_2$ (55.04 mg, 67.40 μmol) in dioxane (6 mL) and water (600 uL) under $N_2$ was heated to 90° C. and stirred for 16 hours. The reaction was diluted with EtOAc (10 mL), and the mixture was filtered and concentrated. The residue was purified by prep-HPLC (Kromasil (150 mm×25 mm, 10 μm) A=$H_2O$ (0.05% $NH_4OH$) and B=$CH_3CN$; 42-72% B over 8 minutes) to afford Compound 108 (18.00 mg) as a solid. $^1H$ NMR (400 MHz, $CDCl_3$) $\delta_H$=8.33 (d, 1H), 8.08 (d, 2H), 7.75 (d, 1H), 7.43 (d, 2H). LCMS $R_t$=1.16 min using Method A, MS ESI calcd. for $C_{13}H_7F_6N_4O$ [M+H]$^+$ 349.0, found 349.1.

Example 103: Synthesis of Compound 111

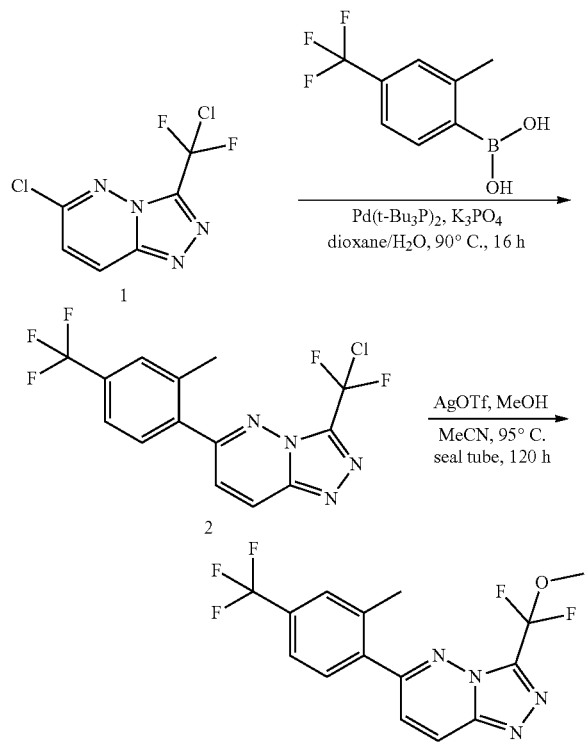

A mixture of 6-chloro-3-[chloro(difluoro)methyl]-[1,2,4]triazolo[4,3-b]pyridazine (200 mg, 0.84 mmol), [2-methyl-4-(trifluoromethyl)phenyl]boronic acid (204.79 mg, 1 mmol), $Pd(t-Bu_3P)_2$ (51.32 mg, 0.1 mmol) and $K_3PO_4$ (355.3 mg, 1.67 mmol) in 1,4-Dioxane (3 mL) and water (0.3 mL) under $N_2$ was stirred at 90° C. for 16 hours. After cooling, the reaction mixture was diluted with EtOAc (10 mL), and filtered through a Celite pad, eluted with EtOAc (10 mL). The filtrate was concentrated. The residue was purified by flash chromatography on silica gel (EtOAc in PE=0% to 15% to 30%) to give the product (200 mg, 0.5514 mmol) as a solid. $^1H$ NMR (400 MHz, $CDCl_3$) $\delta_H$=8.36 (d, 1H), 7.70-7.58 (m, 3H), 7.50 (d, 1H), 2.57 (s, 3H).

A mixture of 3-[chloro(difluoro)methyl]-6-[2-methyl-4-(trifluoromethyl)phenyl]-[1,2,4]triazolo[4,3-b]pyridazine (200 mg, 0.55 mmol) and AgOTf (1.42 g, 5.51 mmol) in MeCN (2 mL) and methanol (2 mL) was sealed and stirred at 95° C. for 120. After cooling, the mixture was diluted with $H_2O$ (15 mL), and the mixture was extracted with EtOAc (30 mL×2). The combined organic phase was washed with brine (20 mL), dried over $Na_2SO_4$, filtered and concentrated. The residue was purified by flash chromatography on silica gel (EtOAc in PE=0% to 20% to 40%) to give the product (77.92 mg, 0.2133 mmol) as a solid. $^1H$ NMR (400 MHz, $CDCl_3$) $\delta_H$=8.29 (d, 1H), 7.67-7.60 (m, 3H), 7.41 (d, 1H), 3.89 (s, 3H), 2.55 (s, 3H). LCMS $R_t$=1.185 min in 2.0 min chromatography, 10-80AB, purity 100%, MS ESI calcd. for $C_{15}H_{12}F_5N_4O$ [M+H]$^+$ 359.1, found 359.0.

Example 104: Synthesis of Compound 112

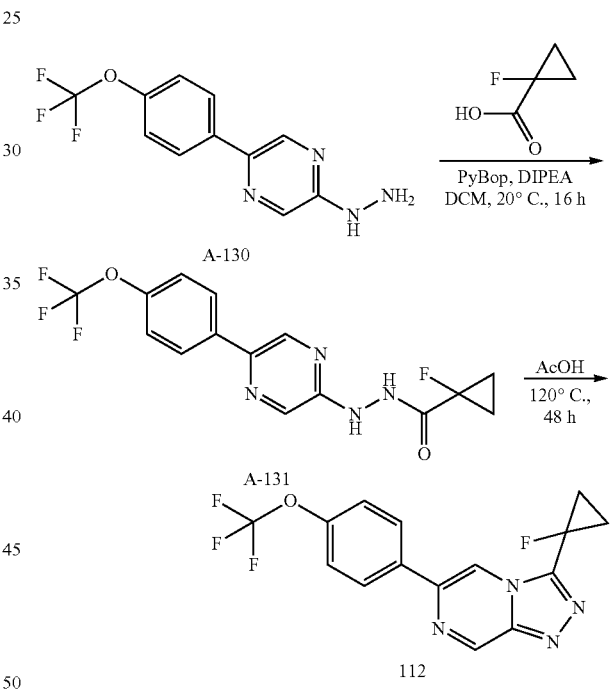

To a mixture of [5-[4-(trifluoromethoxy)phenyl]pyrazin-2-yl]hydrazine (150 mg, 0.56 mmol), 1-fluorocyclopropanecarboxylic acid (57.78 mg, 0.5600 mmol) and PyBop (433.32 mg, 0.83 mmol) in DCM (5 mL) was added DIPEA (0.29 mL, 1.67 mmol). The reaction mixture was stirred at 20° C. for 2 hours. The reaction was quenched with sat.$NH_4Cl$ (10 mL), extracted with EtOAc (10 mL×3). The combined organic phase was washed with brine (10 mL), dried over $Na_2SO_4$, filtered and concentrated to give the crude product (300 mg, 0.2878 mmol) as an oil. LCMS $R_t$=0.790 min in 1.5 min chromatography, 5-95AB, purity 34.18%, MS ESI calcd. for $C_{15}H_{13}F_4N_4O_2$ [M+H]$^+$ 357.1, found 356.9.

A mixture of 1-fluoro-N'-[5-[4-(trifluoromethoxy)phenyl]pyrazin-2-yl]cyclopropanecarbohydrazide (300 mg, 0.84 mmol) in acetic acid (3 mL) was stirred at 120° C. for 48 hours. After cooling, the reaction mixture was concentrated to remove most of the AcOH, then diluted with sat.NaHCO₃ (10 mL). The mixture was extracted with EtOAc (10 mL×2). The combined organic phase was washed with brine (10 mL), dried over Na₂SO₄, filtered and concentrated. The residue was purified by Prep-HPLC (column: Phenomenex Gemini C18 250*50 mm*10 um; mobile phase: [water (0.05% ammonia hydroxide v/v)-ACN]; B %: 48%-78%, 8 min) to give the product (37.43 mg, 0.1107 mmol) as a solid. ¹H NMR (400 MHz, CDCl₃) δ$_H$=9.46 (d, 1H), 8.56 (d, 1H), 8.03 (d, 2H), 7.39 (d, 2H), 1.82-1.72 (m, 2H), 1.66-1.60 (m, 2H). LCMS R$_t$=1.172 min in 2.0 min chromatography, 10-80AB, purity 100%, MS ESI calcd. for C₁₅H₁₁F₄N₄O [M+H]⁺ 339.1, found 338.9.

Example 105 Synthesis of Compound 113

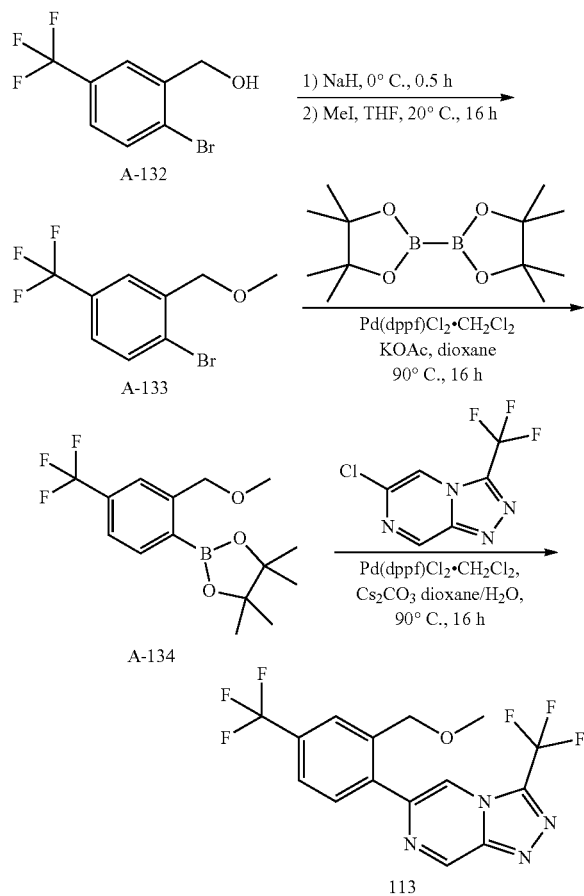

To a solution of [2-bromo-5-(trifluoromethyl)phenyl]methanol (2 g, 7.84 mmol) in THF (40 mL) was added NaH (470.53 mg, 11.76 mmol) at 0° C. and stirred at 0° C. for 0.5 hours. To the resulting mixture was added MeI (1.46 mL, 23.53 mmol). The resulting mixture was stirred at 20° C. for 16 hours. Saturated NH₄Cl aqueous (100 mL) and EtOAc (150 mL) were added to the reaction mixture. After separation, the organic layer was washed with brine (50 mL×2), dried over anhydrous Na₂SO₄, filtered and concentrated to give the crude product. The crude product was purified by flash chromatography on silica gel (EtOAc in PE=0% to 10%) to give the product (1500 mg) as oil. ¹H NMR (400 MHZ CDCl₃) δ$_H$=7.76 (s, 1H), 7.66 (d, 1H), 7.41 (d, 1H), 4.55 (s, 2H), 3.52 (s, 3H).

A mixture of 1-bromo-2-(methoxymethyl)-4-(trifluoromethyl)benzene (1.5 g, 5.57 mmol), 4,4,5,5-tetramethyl-2-(4,4,5,5-tetramethyl-1,3,2-dioxaborolan-2-yl)-1,3,2-dioxaborolane (1.84 g, 7.25 mmol) and Pd(dppf)Cl₂·CH₂Cl₂ (427.36 mg, 0.84 mmol) and KOAc (1094.25 mg, 11.15 mmol) in 1,4-Dioxane (8 mL) was stirred at 90° C. under N₂ for 16 hours. The mixture was filtered through silica gel, eluted with EtOAc (20 mL×2), and the filtrate was concentrated to give the crude product. The crude product was purified by flash chromatography on silica gel (PE: EtOAc=100:1 to 10:1) to give the product (1100 mg, 3.4797 mmol) as an oil. ¹H NMR (400 MHz, CDCl₃) δ$_H$=7.88 (d, 1H), 7.70 (s, 1H), 7.51 (d, 1H), 4.73 (s, 2H), 3.45 (s, 3H), 1.37 (s, 12H).

A mixture of 6-chloro-3-(trifluoromethyl)-[1,2,4]triazolo[4,3-a]pyrazine (100 mg, 0.45 mmol), Cs₂CO₃ (292.77 mg, 0.9 mmol), 2-[2-(methoxymethyl)-4-(trifluoromethyl)phenyl]-4,4,5,5-tetramethyl-1,3,2-dioxaborolane (213.06 mg, 0.67 mmol), and Pd(dppf)Cl₂·CH₂Cl₂ (55.04 mg, 0.07 mmol) and in 1,4-dioxane (3 mL) and water (0.3 mL) was stirred at 90° C. for 16 hours under N₂. The mixture was cooled to r.t., diluted with EtOAc (20 mL), filtered through silica gel and eluted with EtOAc (20 mL). The filtrate was concentrated to give the crude product. The crude product was purified by flash chromatography on silica gel (PE: EtOAc=5:1 to 3:1) to give the product (88.03 mg, 0.2304 mmol) as a solid. ¹H NMR (400 MHz, CDCl₃) δ$_H$=9.61 (d, 1H), 8.77 (s, 1H), 7.89-7.85 (m, 2H), 7.81-7.75 (m, 1H), 4.52 (s, 2H), 3.47 (s, 3H). LCMS R$_t$=1.181 min in 2.0 min chromatography, 10-80AB, purity 98.98%, MS ESI calcd. for C₁₅H₁₁F₆N₄O [M+H]⁺ 377.1, found 377.0.

Example 106: Synthesis of Compound 114

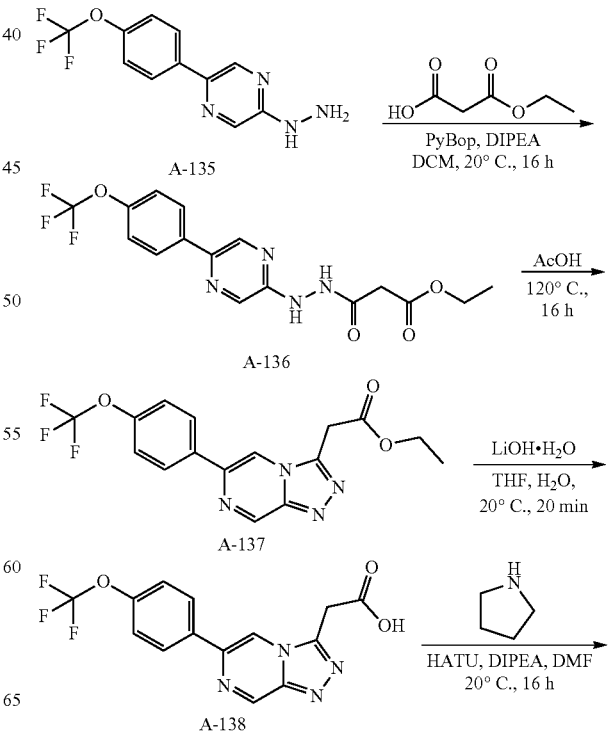

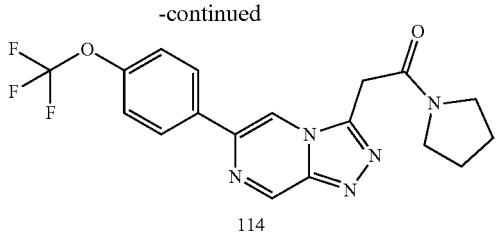

114

To a mixture of [5-[4-(trifluoromethoxy)phenyl]pyrazin-2-yl]hydrazine (1 g, 3.7 mmol), 3-ethoxy-3-oxo-propanoic acid (488.92 mg, 3.7 mmol) in DCM (5 mL) was added PyBOP (2.89 g, 5.55 mmol) and DIPEA (1.94 mL, 11.1 mmol) at 20° C. for 16 hours. The reaction mixture was concentrated to remove most of the DCM, diluted with sat.NH$_4$Cl (30 mL) and extracted with EtOAc (20 mL×2). The combined organic phase was washed with brine (10 mL), dried over Na$_2$SO$_4$, and concentrated to give the crude product (1200 mg, 3.12 mmol). The product was used directly without any further purification. LCMS R$_t$=0.78 min in 1.5 min chromatography, 5-95AB, purity 68.12%, MS ESI calcd. for C$_{16}$H$_{16}$F$_3$N$_4$O$_4$ [M+H]$^+$ 385.1, found 385.0.

A solution of Ethyl 3-oxo-3-[2-[5-[4-(trifluoromethoxy)phenyl]pyrazin-2-yl]hydrazino]propanoate (1.2 g, 3.12 mmol) in acetic acid (10 mL) was stirred at 120° C. for 16 hours. After cooling to r.t., the mixture was concentrated, and the residue was neutralized with sat.NaHCO$_3$ to pH=8-10 and extracted with EtOAc (20 mL×2). Then the combined organic phase was washed with brine (15 mL), dried over Na$_2$SO$_4$ and concentrated to give the crude product. The crude product was purified by flash chromatography on silica gel (EtOAc in PE=20% to 70%) to give the product (340 mg, 0.93 mmol) as a solid. $^1$H NMR (400 MHz, CDCl$_3$) δ$_H$=9.44 (d, 1H), 8.35 (d, 1H), 8.00 (d, 2H), 7.37 (d, 2H), 4.37 (s, 2H), 4.26 (q, 2H), 1.31 (t, 3H).

To a solution of ethyl 2-[6-[4-(trifluoromethoxy)phenyl]-[1,2,4]triazolo[4,3-a]pyrazin-3-yl]acetate (340 mg, 0.93 mmol) in THF (1 mL) and Water (1 mL) was added LiOH.H$_2$O (46.74 mg, 1.11 mmol) and the mixture was stirred at 20° C. for 20 minutes. The reaction mixture was acidified with HCl to pH=3 and extracted with EtOAc (10 mL×2). The combined organic phase was washed with brine (10 mL), dried over Na$_2$SO$_4$, filtered and concentrated to give the crude product (150 mg, 0.44 mmol) as an oil which was used directly without any purification. LCMS R$_t$=0.74 min in 1.5 min chromatography, 5-95AB, purity 80.54%, MS ESI calcd. for C$_{14}$H$_{10}$F$_3$N$_4$O$_3$ [M+H]$^+$ 339.1, found 338.9.

To the mixture of 2-[6-[4-(trifluoromethoxy)phenyl]-[1,2,4]triazolo[4,3-a]pyrazin-3-yl]acetic acid (150 mg, 0.44 mmol), pyrrolidine (37.85 mg, 0.53 mmol) and HATU (252.93 mg, 0.67 mmol) in DMF (5 mL) was added DIPEA (0.15 mL, 0.89 mmol), and the mixture was stirred at 20° C. for 16 h. The mixture was diluted with NH$_4$Cl (20 mL) and extracted with EtOAc (20 mL×2). The combined organic phase was washed with brine (10 mL), dried over Na$_2$SO$_4$, filtered and concentrated to give the crude product. The crude product was purified by Prep-HPLC (Column: Waters Xbridge 150*25 5 u, mobile phase: water (10 mM NH$_4$HCO$_3$)-ACN, B %: 30%-50%, 8 min) to give the product (30.28 mg, 0.25 mmol) as a solid. $^1$H NMR (400 MHz, CDCl$_3$) δ$_H$=9.40 (d, 1H), 8.82 (d, 1H), 8.03 (d, 2H), 7.35 (d, 2H), 4.33 (s, 2H), 3.77 (t, 2H), 3.47 (t, 2H), 2.07-2.00 (m, 2H), 1.93-1.87 (m, 2H). LCMS R$_t$=1.10 min in 2.0 min chromatography, 10-80AB, purity 100%, MS ESI calcd. for C$_{18}$H$_{17}$F$_3$N$_5$O$_2$ [M+H]$^+$ 392.1, found 392.1.

Example 107: Synthesis of Compound 115

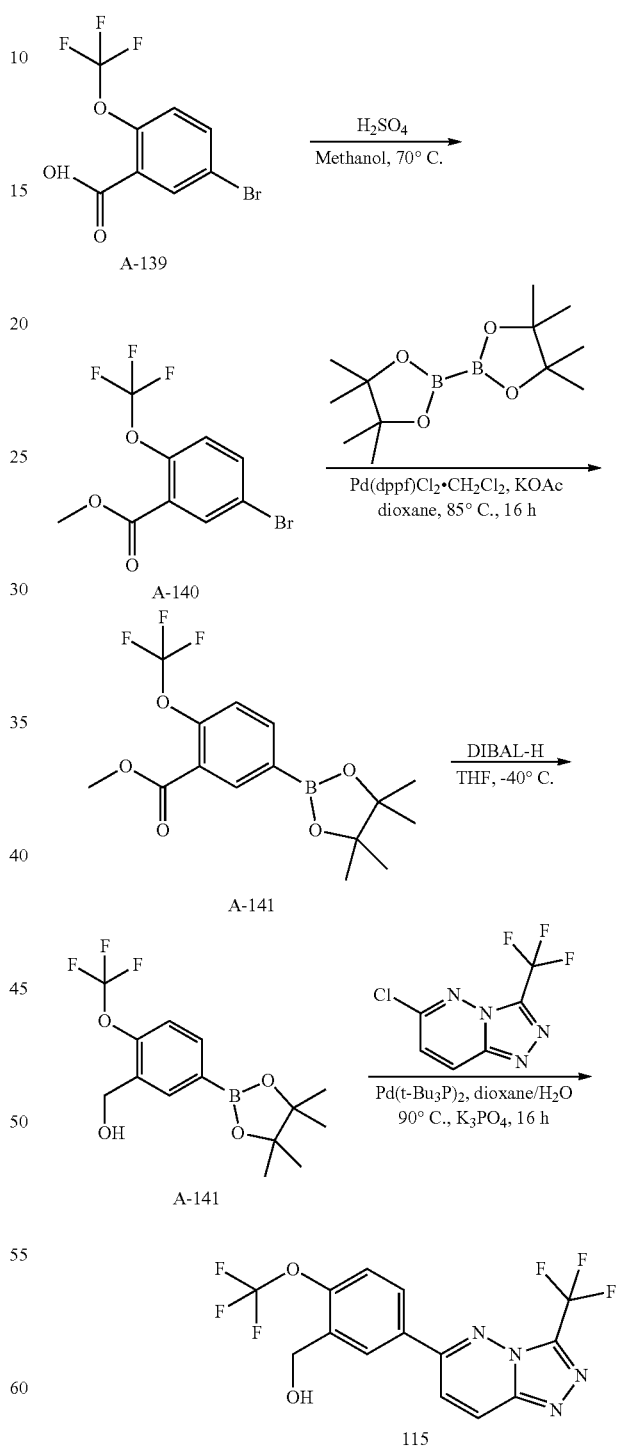

To a mixture of 5-bromo-2-(trifluoromethoxy)benzoic acid (1.22 g, 4.28 mmol) in methanol (5 mL) was added $H_2SO_4$ (0.68 mL, 12.84 mmol). The mixture was stirred at 70° C. for 16 hours. After cooling to r.t., the mixture was concentrated, the residue was diluted with $H_2O$ (50 mL) and extracted with EtOAc (100 mL×2). The combined organic phase was washed with brine (50 mL), dried over $Na_2SO_4$, filtered and concentrated to give the crude product. The crude product was purified by flash chromatography on silica gel (EtOAc in PE=0 to 20%) to give the product (1250 mg, 4.18 mmol) as an oil. $^1H$ NMR (400 MHz, $CDCl_3$) $\delta_H$=8.10 (d, 1H), 7.69 (dd, 1H), 7.22 (dd, 1H), 3.95 (s, 3H).

A mixture of methyl 5-bromo-2-(trifluoromethoxy)benzoate (1.1 g, 3.68 mmol), 4,4,5,5-tetramethyl-2-(4,4,5,5-tetramethyl-1,3,2-dioxaborolan-2-yl)-1,3,2-dioxaborolane (2.8 g, 11.04 mmol), KOAc (722 mg, 7.36 mmol) and $Pd(dppf)Cl_2.CH_2Cl_2$ (300.4 mg, 0.37 mmol) in 1,4-dioxane (25 mL) was stirred at 85° C. for 16 hours under $N_2$. After cooling to r.t., the mixture was diluted with $H_2O$ (50 mL) and extracted with EtOAc (100 mL×2). The combined organic phase was washed with brine (50 mL), dried over $Na_2SO_4$, filtered and concentrated to give the crude product. The crude product was purified by flash chromatography on silica gel (EtOAc in PE=0 to 5%) to give the product (2000 mg, 3.69 mmol) as an colorless oil. H NMR (400 MHz, $CDCl_3$) $\delta_H$=8.37 (d, 1H), 7.98 (dd, 1H), 7.32 (dd, 1H), 3.93 (s, 3H), 1.36 (s, 12H) LCMS $R_t$=0.93 min in 1.5 min chromatography, 5-95AB, purity 63.86%, MS ESI calcd. for $C_{15}H_{19}BF_3O_5$ $[M+H]^+$ 347.1, found 346.9.

To a mixture of methyl 5-(4,4,5,5-tetramethyl-1,3,2-dioxaborolan-2-yl)-2-(trifluoromethoxy)benzoate (1 g, 2.89 mmol) in THF (30 mL) was added DiBAl-H (2.05 g, 14.45 mmol) at −40° C. under $N_2$, and the mixture was stirred until the reaction was completed. After warming to r.t., the reaction was quenched with $Na_2SO_4.H_2O$, filtered through Celite and eluted with THF (10 mL). The filtrate was diluted with $H_2O$ (10 mL) and extracted with EtOAc (20 mL×2). The combined organic phase was washed with brine (10 mL), dried over $Na_2SO_4$, filtered and concentrated to give the crude product (810 mg, 2.04 mmol) as a colorless oil. $^1H$ NMR (400 MHz, DMSO-$d_6$) $\delta_H$=7.95-7.92 (m, 1H), 7.67 (dd, 1H), 7.31 (dd, 1H), 5.39 (t, 1H), 4.56 (d, 2H), 1.30 (s, 12H).

A mixture of [5-(4,4,5,5-tetramethyl-1,3,2-dioxaborolan-2-yl)-2-(trifluoromethoxy)phenyl]methanol (400 mg, 1.26 mmol), 6-chloro-3-(trifluoromethyl)-[1,2,4]triazolo[4,3-b]pyridazine (215.28 mg, 0.97 mmol), $Pd(t-Bu_3P)_2$ (74.15 mg, 0.15 mmol) and $K_3PO_4$ (410.71 mg, 1.93 mmol) in 1,4-dioxane (10 mL) and water (2 mL) was stirred at 90° C. for 16 hours under $N_2$. After cooling to r.t., the mixture was diluted with $H_2O$ (20 mL) and extracted with EtOAc (40 mL×2). The combined organic phase was washed with brine (20 mL), dried over $Na_2SO_4$, filtered and concentrated to give the crude product. The crude product was purified by flash chromatography on silica gel (EtOAc in PE=0 to 50% to 80%) to give the product (160 mg, 0.3718 mmol) a solid.

The impure product (50 mg) was purified by Prep-HPLC (column: Waters Xbridge 150*25 5 um; mobile phase: [water (0.05% ammonia hydroxide v/v)-ACN]; B %: 35%-60%, 9 min) to give the product (17.18 mg) as a solid. $^1H$ NMR (400 MHz, DMSO-$d_6$) $\delta_H$=8.72 (d, 1H), 8.34 (s, 1H), 8.21 (d, 1H), 8.16-8.11 (m, 1H), 7.59 (d, 1H), 5.59 (t, 1H), 4.67 (d, 2H). LCMS $R_t$=1.08 min in 2.0 min chromatography, 10-80AB, purity 100.00%, MS ESI calcd. for $C_{14}H_9F_6N_4O_2$ $[M+H]^+$ 379.1, found 379.0.

Example 108: Synthesis of Compound 116

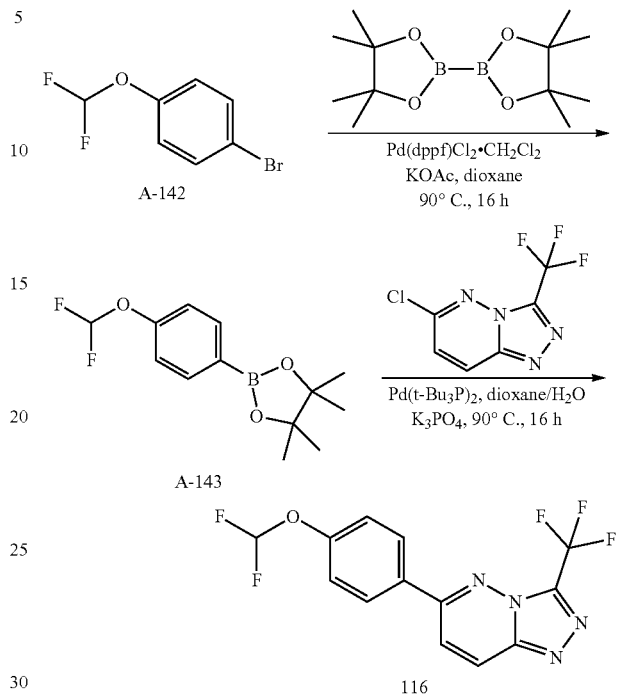

To a mixture of 1-bromo-4-(difluoromethoxy)benzene (200 mg, 0.90 mmol), 4,4,5,5-tetramethyl-2-(4,4,5,5-tetramethyl-1,3,2-dioxaborolan-2-yl)-1,3,2-dioxaborolane (683.22 mg, 2.69 mmol), $Pd(dppf)Cl_2.CH_2Cl_2$ (146.48 mg, 0.18 mmol) and KOAc (176.03 mg, 1.79 mmol) in 1,4-Dioxane (5 mL) was stirred at 90° C. for 16 hours under $N_2$. After cooling to r.t., the mixture was concentrated to give the crude product. The crude product was purified by flash chromatography on silica gel (PE) to give the product (300 mg, 1.11 mmol) as colorless oil. $^1H$ NMR (400 MHz, $CDCl_3$) $\delta_H$=7.82 (d, 2H), 7.10 (d, 2H), 6.55 (t, 1H), 1.35 (s, 12H).

A mixture of 2-[4-(difluoromethoxy)phenyl]-4,4,5,5-tetramethyl-1,3,2-dioxaborolane (300 mg, 1.11 mmol), 6-chloro-3-(trifluoromethyl)-[1,2,4]triazolo[4,3-b]pyridazine (100 mg, 0.45 mmol), $Pd(t-Bu_3P)_2$ (45.92 mg, 0.09 mmol) and $K_3PO_4$ (190.78 mg, 0.90 mmol) in 1,4-dioxane (10 mL) and water (1.5 mL) was stirred at 90° C. for 16 hours under $N_2$. After cooling to r.t., the mixture was filtered through silica gel and eluted with EtOAc (20 mL×2). The filtrate was concentrated and diluted with EtOAc (30 mL), washed with water (10 mL×2) and brine (10 mL), dried over $Na_2SO_4$, filtered and concentrated to give the crude product. The crude product was purified by Prep-HPLC (column: Phenomenex Gemini C18 250*50 10 um; mobile phase: [water (0.05% ammonia hydroxide v/v)-ACN]; B %: 53%-63%, 8 min) to give the product (62.52 mg, 0.19 mmol) as a solid. $^1H$ NMR (400 MHz, $CDCl_3$) $\delta_H$=8.32 (d, 1H), 8.06 (d, 2H), 7.76 (d, 1H), 7.33 (d, 2H), 6.64 (t, 1H). LCMS $R_t$=1.14 min in 2 min chromatography, 10-80AB, purity 100.00%, MS ESI calcd. for $C_{13}H_8F_5N_4O$ $[M+H]^+$ 331.1, found 330.9.

Example 109: Synthesis of Compound 117

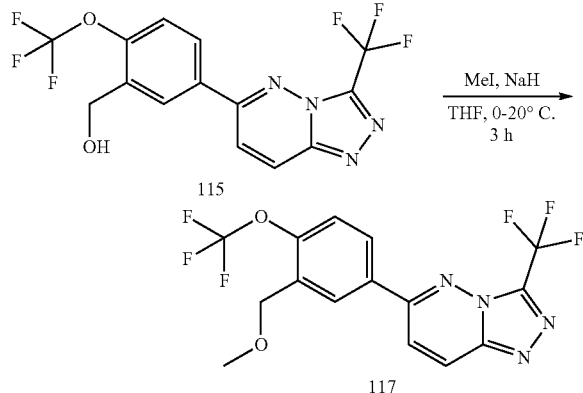

To a mixture of [2-(trifluoromethoxy)-5-[3-(trifluoromethyl)-[1,2,4]triazolo[4,3-b]pyridazin-6-yl]phenyl]methanol (110 mg, 0.29 mmol) in THF (3 mL) was added NaH (10.47 mg, 0.44 mmol) and then MeI (123.84 mg, 0.87 mmol) at 0° C., then the mixture was stirred at 20° C. for 3 hours. The mixture was diluted with H$_2$O (20 mL) and extracted with EtOAc (40 mL×2). The combined organic phase was washed with brine (20 mL), dried over Na$_2$SO$_4$, filtered and concentrated to give the crude product. The crude product was purified by Prep-TLC (silica gel, PE:EtOAc=3:1) to give the product (28.15 mg, 0.07 mmol) as a solid. $^1$H NMR (400 MHz CDCl$_3$) $\delta_H$=8.32 (d, 1H), 8.16 (s, 1H), 8.05 (d, 1H), 7.80 (d, 1H), 7.45 (d, 1H), 4.64 (s, 2H), 3.53 (s, 3H). LCMS R$_t$=1.18 min in 2.0 min chromatography, 10-80AB, purity 100.00%, MS ESI calcd. for C$_{15}$H$_{11}$F$_6$N$_4$O$_2$ [M+H]$^+$ 393.1, found 393.0.

Example 110: Synthesis of Compound 118

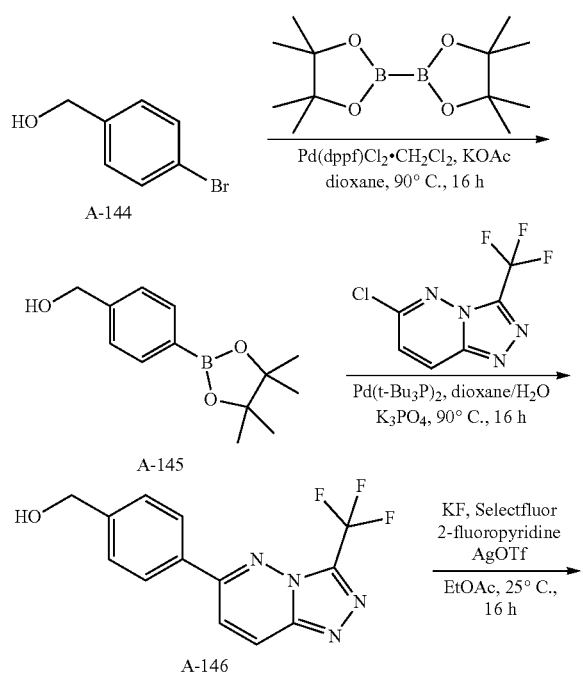

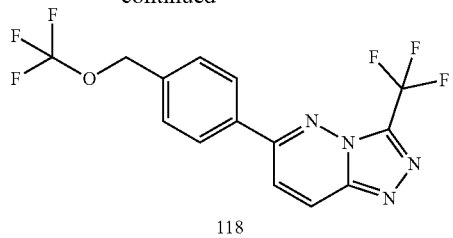

A mixture of (4-bromophenyl)methanol (1 g, 5.35 mmol), 4,4,5,5-tetramethyl-2-(4,4,5,5-tetramethyl-1,3,2-dioxaborolan-2-yl)-1,3,2-dioxaborolane (4.07 g, 16.04 mmol), KOAc (1.05 g, 10.69 mmol) and Pd(dppf)Cl$_2$·CH$_2$Cl$_2$ (873.27 mg, 1.07 mmol) in 1,4-Dioxane (20 mL) was stirred at 90° C. for 16 hours. After cooling to r.t., the mixture was concentrated to give the crude product. The crude product was purified by flash chromatography on silica gel (EtOAc in PE=0 to 50%) to give the product (1500 mg) as oil. $^1$H NMR (400 MHz DMSO-d$_6$) $\delta_H$=7.63 (d, 2H), 7.32 (d, 2H), 5.23 (t, 1H), 4.51 (d, 2H), 1.29 (s, 12H).

A mixture of [4-(4,4,5,5-tetramethyl-1,3,2-dioxaborolan-2-yl)phenyl]methanol (1.5 g, 6.41 mmol), 6-chloro-3-(trifluoromethyl)-[1,2,4]triazolo[4,3-b]pyridazine (1 g, 4.49 mmol), Pd(t-Bu$_3$P)$_2$ (459.25 mg, 0.90 mmol) and K$_3$PO$_4$ (1.91 g, 8.99 mmol) in 1,4-dioxane (60 mL) and water (10 mL) was stirred at 90° C. for 16 hours. After cooling to r.t., the mixture was concentrated to give the crude product. The crude product was purified by flash chromatography on silica gel (EtOAc in PE=0 to 100%) to give the product (670 mg, 2.28 mmol) as a solid. $^1$H NMR (400 MHz, DMSO-d$_6$) $\delta_H$=8.67 (d, 1H), 8.22 (d, 1H), 8.11 (d, 2H), 7.56 (d, 2H), 5.39 (t, 1H), 4.61 (d, 2H).

To a mixture of AgOTf (1309.89 mg, 5.1 mmol), KF (394.93 mg, 6.8 mmol), Selectfluor (903.02 mg, 2.55 mmol) and [4-[3-(trifluoromethyl)-[1,2,4]triazolo[4,3-b]pyridazin-6-yl]phenyl]methanol (100 mg, 0.34 mmol) in ethyl acetate (6 mL) was added 2-fluoropyridine (494.97 mg, 5.1 mmol) and trimethyl(trifluoromethyl)silane (483.26 mg, 3.4 mmol) under N$_2$, then the mixture was stirred at 25° C. for 16 hours. The mixture was concentrated to give the crude product. The crude product was purified by Prep-HPLC (Waters Xbridge (150 mm×25 mm, 5 µm), A=H$_2$O (10 mM NH$_4$HCO$_3$) and B=CH$_3$CN, 47-67% B over 8 minutes) to give the impure product. The impure product was purified by Prep-TLC (silica gel, PE:EtOAc=3:1) to give the product (20.13 mg, 0.06 mmol) as a solid. $^1$H NMR (400 MHz, CDCl$_3$) $\delta_H$=8.33 (d, 1H), 8.07 (d, 2H), 7.79 (d, 1H), 7.59 (d, 2H), 5.11 (s, 2H). LCMS R$_t$=1.38 min in 2 min chromatography, 10-80AB, purity 100%, MS ESI calcd. for C$_{14}$H$_9$F$_6$N$_4$O [M+H]$^+$ 363.1, found 363.0.

Example 111: Synthesis of Compound 119

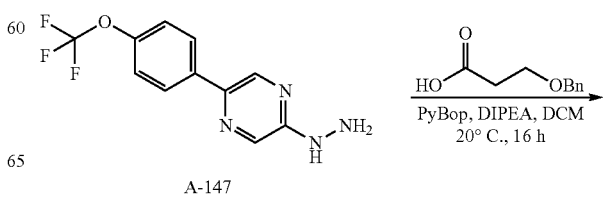

-continued

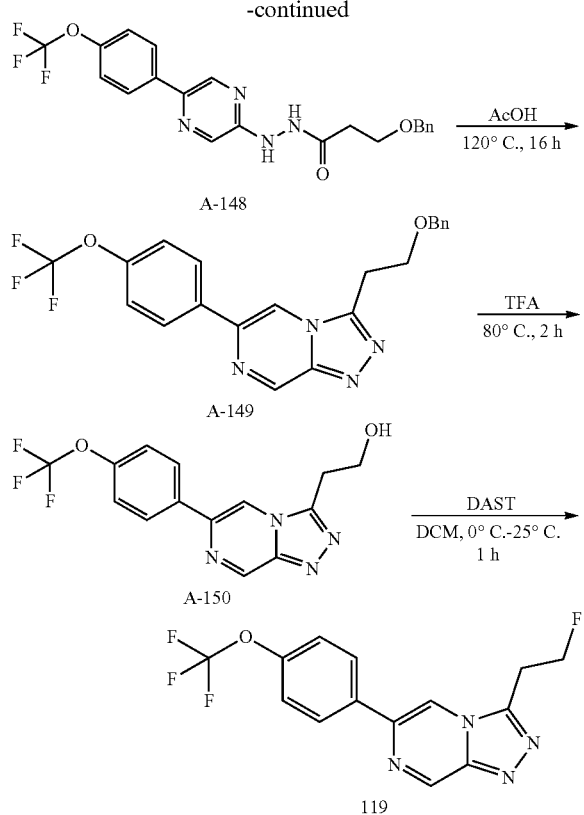

To a mixture of [5-[4-(trifluoromethoxy)phenyl]pyrazin-2-yl]hydrazine (1 g, 3.7 mmol), 3-benzyloxypropanoic acid (733.58 mg, 4.07 mmol) in DCM (20 mL) was added PyBOP (2.89 g, 5.55 mmol) and DIPEA (1.94 mL, 11.1 mmol), the mixture was stirred at 20° C. for 16 hours. The mixture was diluted with NH₄Cl (40 mL), extracted with CH₂Cl₂ (20 mL×2). The combined organic phase was washed with brine (10 mL), dried over Na₂SO₄, filtered and concentrated to give the crude product (4000 mg, 9.25 mmol, crude) as solid. The crude product was used directly purified without any further purification. LCMS $R_t$=0.84 min in 1.5 min chromatography, 5-95AB, purity 13.49%, MS ESI calcd. for $C_{21}H_{20}F_3N_4O_3$ [M+H]⁺ 433.1, found 433.1.

A mixture of 3-benzyloxy-N'-[5-[4-(trifluoromethoxy)phenyl]pyrazin-2-yl]propanehydrazide (4000 mg, 9.25 mmol) in acetic acid (15 mL) was stirred at 120° C. for 16 hours. After cooling to r.t., the mixture was concentrated, the residue was diluted with EtOAc (20 mL), neutralized with sat.NaHCO₃ to pH=9 and extracted with EtOAc (20 mL×2). Then the combined organic phase was washed with brine (15 mL), dried over Na₂SO₄ and concentrated to give the crude product. The crude product was purified by flash chromatography on silica gel (EtOAc in PE=20% to 100%) to give the product (600 mg, 1.45 mmol) as a solid. LCMS $R_t$=0.86 min in 1.5 min chromatography, 5-95AB, purity 26.18%, MS ESI calcd. for $C_{21}H_{18}F_3N_4O_2$ [M+H]⁺ 414.1, found 415.1.

A mixture of 3-(2-benzyloxyethyl)-6-[4-(trifluoromethoxy)phenyl]-[1,2,4]triazolo[4,3-a]pyrazine (520 mg, 1.25 mmol) and TFA (10 mL) was stirred at 80° C. for 2 hours. After cooling to r.t., the mixture was concentrated, the residue was diluted with EtOAc (30 mL), neutralized with sat.NaHCO₃ to pH=9 and extracted with EtOAc (25 mL×2). Then the combined organic phase was washed with brine (15 mL), dried over Na₂SO₄ and concentrated to give the crude product. The crude product was purified by flash chromatography on silica gel (MeOH in DCM=10% to 20%) to give the product (217 mg, 0.67 mmol) as a solid. ¹H NMR (400 MHz, CDCl₃) $δ_H$=9.40 (s, 1H), 8.36 (s, 1H), 8.00 (d, 2H), 7.37 (d, 2H), 4.38-4.20 (m, 2H), 3.50-3.30 (m, 2H).

To a solution of 2-[6-[4-(trifluoromethoxy)phenyl]-[1,2,4]triazolo[4,3-a]pyrazin-3-yl]ethanol (100 mg, 0.31 mmol) in DCM (2 mL) was added DAST (497.10 mg, 3.08 mmol). The reaction mixture was stirred at 25° C. for 1 hour. The mixture was diluted with H₂O (10 mL), extracted with EtOAc (20 mL×2). The combined organic phase was washed with brine (10 mL), dried over Na₂SO₄, filtered and concentrated to give the crude product. The crude product was purified by flash chromatography on silica gel (EtOAc in PE=50% to 100%) to give product (13.80 mg, 0.04 mmol) as a solid. ¹H NMR (400 MHz DMSO-d₆) $δ_H$=9.50 (d, 1H), 9.15 (d, 1H), 8.25 (d, 2H), 7.55 (d, 2H), 5.14-4.74 (m, 2H), 3.80-3.61 (m, 2H). LCMS $R_t$=1.12 min in 2.0 min chromatography, 10-80AB, purity 98.74%, MS ESI calcd. for $C_{14}H_{11}F_4N_4O$ [M+H]⁺ 327.1, found 326.9.

Example 112: Synthesis of Compound 120

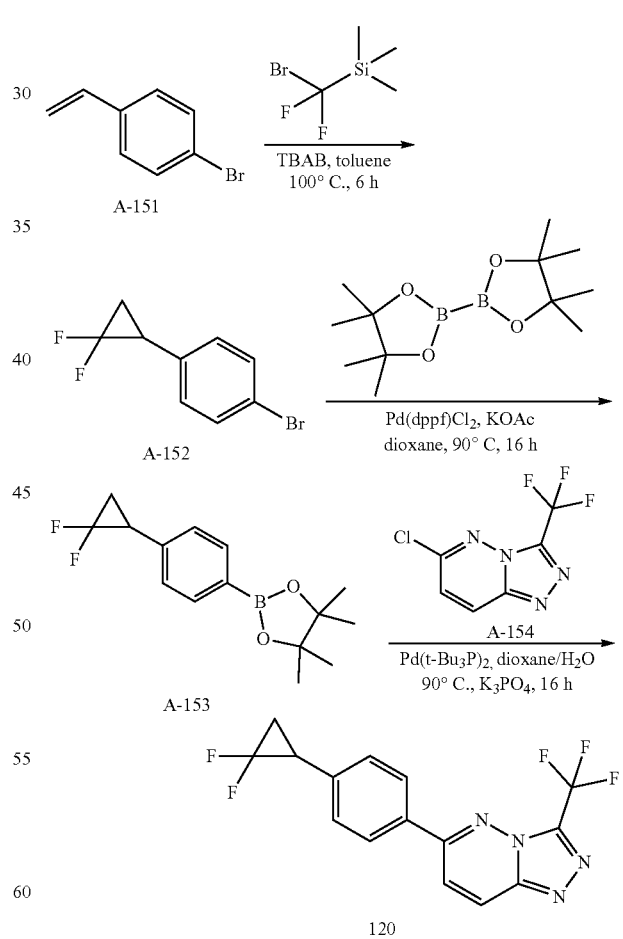

A mixture of 1-bromo-4-vinyl-benzene (500 mg, 2.73 mmol), [bromo(difluoro)methyl]-trimethyl-silane (832.15 mg, 4.1 mmol) and TBAB (26.42 mg, 0.08 mmol) in toluene (5 mL) was stirred at 110° C. for 6 hours. After cooling to r.t., the mixture was diluted with H₂O (10 mL) and extracted with EtOAc (10 mL×2). The combined organic phase was washed with brine (10 mL), dried over Na₂SO₄, filtered and concentrated to give the crude product. The crude product was purified by flash chromatography on silica gel (EtOAc in PE=0% to 50%) to give the product (400 mg, 1.72 mmol) as an oil. ¹H NMR (400 MHz, CDCl₃) δ$_H$=7.31-7.27 (m, 2H), 6.93 (d, 2H), 2.53 (dt, 1H), 1.91-1.77 (m, 1H), 1.47-1.39 (m, 1H).

A mixture of 1-bromo-4-(2,2-difluorocyclopropyl)benzene (400 mg, 1.72 mmol), 4,4,5,5-tetramethyl-2-(4,4,5,5-tetramethyl-1,3,2-dioxaborolan-2-yl)-1,3,2-dioxaborolane (1.31 g, 5.15 mmol), Pd(dppf)Cl₂ (251.17 mg, 0.34 mmol) and KOAc (336.89 mg, 3.43 mmol) in 1,4-dioxane (20 mL) was stirred at 90° C. for 16 hours under N₂. After cooling to r.t., the mixture was concentrated. The residue was diluted with H₂O (20 mL) and extracted with EtOAc (20 mL×2). The combined organic phase was washed with brine (50 mL), dried over Na₂SO₄, filtered and concentrated to give the crude product. The crude product was purified by flash chromatography on silica gel (PE) to give the product (450 mg, 1.61 mmol) as oil. ¹H NMR (400 MHz CDCl₃) δ$_H$=7.78 (d, 2H), 7.24 (d, 2H), 2.77 (dt, 1H), 1.91-1.78 (m, 1H), 1.72-1.60 (m, 1H), 1.35 (s, 12H).

A mixture of 2-[4-(2,2-difluorocyclopropyl)phenyl]-4,4,5,5-tetramethyl-1,3,2-dioxaborolane (450 mg, 1.61 mmol), 6-chloro-3-(trifluoromethyl)-[1,2,4]triazolo[4,3-b]pyridazine (300 mg, 1.35 mmol), Pd(t-Bu₃P)₂ (137.77 mg, 0.27 mmol) and K₃PO₄ (572.34 mg, 2.7 mmol) in 1,4-dioxane (20 mL) and water (3 mL) was stirred at 90° C. for 16 hours. After cooling to r.t., the mixture was concentrated to the residue. The residue was diluted with H₂O (50 mL) and extracted with EtOAc (50 mL×2). The combined organic phase was washed with brine (50 mL), dried over Na₂SO₄, filtered and concentrated to give the crude product. The crude product was purified by flash chromatography on silica gel (EtOAc in PE=0% to 50% to 100%) to give the impure product (180 mg). A part of impure product (40 mg) was purified by Prep-TLC (silica gel, PE:EtOAc=1:1) to give the product (9.2 mg, 0.03 mmol) as a solid. ¹H NMR (400 MHz CDCl₃) δ$_H$=8.30 (d, 1H), 8.00 (d, 2H), 7.77 (d, 1H), 7.44 (d, 2H), 2.85 (dt, 1H), 2.02-1.90 (m, 1H), 1.78-1.67 (m, 1H). LCMS R$_t$=1.21 min in 2 min chromatography, 10-80AB, purity 100.00%, MS ESI calcd. for C₁₅H₁₀F₅N₄ [M+H]⁺ 341.1, found 340.8.

Example 113: Synthesis of Compound 121 and 122

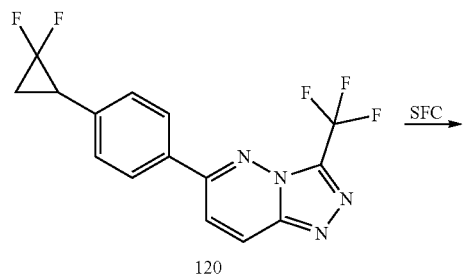

120

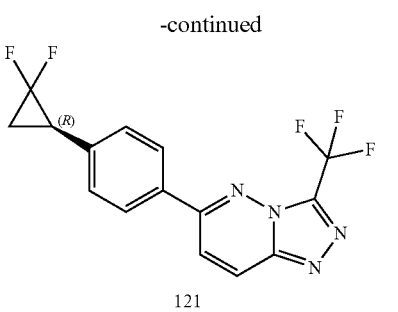

121

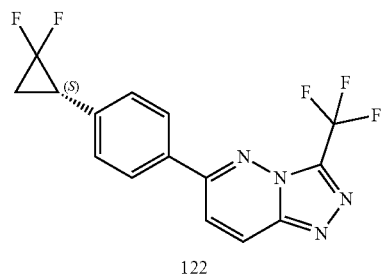

122

The impure product of 6-[4-(2,2-difluorocyclopropyl)phenyl]-3-(trifluoromethyl)-[1,2,4]triazolo[4,3-b]pyridazine (140 mg, 0.41 mmol) was purified by Prep-TLC (silica gel, PE:EtOAc=1:1) to give the product (40 mg). The product was analyzed by SFC to show two peaks (Peak 1: Rt=3.16 min, Peak 2: Rt=3.32 min). Method: Chiralpak AD-3 150×4.6 mm I.D., 3 μm Mobile phase: A: CO₂ B:methanol (0.05% DEA) Gradient: from 5% to 40% of B in 5 min and hold 40% for 2.5 min, then 5% of B for 2.5 min Flow rate: 2.5 mL/min Column temp: 35° C.

The product was purified by SFC (Chiralpak AD (250 mm×30 mm, 5 μm); A=CO₂ and B=methanol (0.05% DEA); 38° C.; 50 mL/min; 40% B; 10 min run; 21 injections, Rt of peak 1=7.5 min, Rt of Peak 2=8.5 min) to give 6-[4-[(1R)-2,2-difluorocyclopropyl]phenyl]-3-(trifluoromethyl)-[1,2,4]triazolo[4,3-b]pyridazine (Peak 1, Rt=3.16 min in SFC) as a solid and 6-[4-[(1S)-2,2-difluorocyclopropyl]phenyl]-3-(trifluoromethyl)-[1,2,4]triazolo[4,3-b]pyridazine (Peak 2: Rt=3.32 min in SFC) as a solid.

Note: the enantiomers were randomly assigned.

Compound 121 (peak 1):

¹H NMR (400 MHz CDCl₃) δ$_H$=8.30 (d, 1H), 8.00 (d, 2H), 7.77 (d, 1H), 7.44 (d, 2H), 2.85 (dt, 1H), 2.01-1.90 (m, 1H), 1.79-1.68 (m, 1H).

LCMS R$_t$=1.27 min in 2 min chromatography, 10-80AB, purity 100.00%, MS ESI calcd. for C₁₅H₁₀F₅N₄ [M+H]⁺ 341.1, found 341.1.

Compound 122 (peak 2):

¹H NMR (400 MHz CDCl₃) δ$_H$=8.22 (d, 1H), 7.92 (d, 2H), 7.70 (d, 1H), 7.36 (d, 2H), 2.78 (dt, 1H), 1.93-1.82 (m, 1H), 1.71-1.61 (m, 1H).

LCMS R$_t$=1.27 min in 2 min chromatography, 10-80AB, purity 98.33%, MS ESI calcd. for C₁₅H₁₀F₅N₄ [M+H]⁺ 341.1, found 341.0.

Example 116 Synthesis of Compound 123

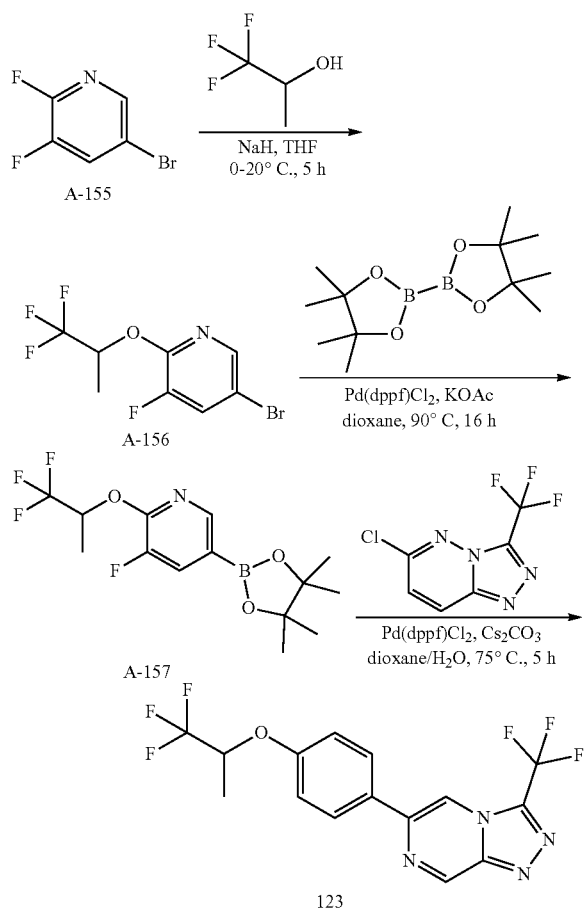

To a suspension of NaH (701.32 mg, 17.53 mmol) in THF (100 mL) was added 1,1,1-trifluoropropan-2-ol (2 g, 17.53 mmol) at 0° C., and the mixture was stirred at 20° C. for 1 hour. Then to the mixture was added 5-bromo-2,3-difluoro-pyridine (3.09 g, 15.94 mmol), and the mixture was stirred at 20° C. for another 4 hours. The reaction was quenched with sat.NH$_4$Cl (15 mL), and the mixture was extracted with EtOAc (40 mL×2). The combined organic phase was washed with brine (15 mL), dried over Na$_2$SO$_4$, filtered and concentrated to give the crude product. The crude product was purified by flash chromatography on silica gel (PE) to give the product (4580 mg, 15.90 mmol) as colorless oil. $^1$H NMR (400 MHz, CDCl$_3$) $\delta_H$=7.99 (d, 1H), 7.56 (dd, 1H), 5.82-5.68 (m, 1H), 1.54 (d, 3H).

A mixture of 5-bromo-3-fluoro-2-(2,2,2-trifluoro-1-methyl-ethoxy)pyridine (4.58 g, 15.9 mmol), 4,4,5,5-tetramethyl-2-(4,4,5,5-tetramethyl-1,3,2-dioxaborolan-2-yl)-1,3,2-dioxaborolane (8.08 g, 31.8 mmol), KOAc (3.12 g, 31.8 mmol) and Pd(dppf)Cl$_2$ (1.16 g, 1.59 mmol) in 1,4-dioxane (100 mL) was stirred at 90° C. for 16 hours under N$_2$. After cooling to r.t., the mixture was diluted with H$_2$O (80 mL) and extracted with EtOAc (160 mL×2). The combined organic phase was washed with brine (80 mL), dried over Na$_2$SO$_4$, filtered and concentrated to give the crude product. The crude product was purified by flash chromatography on silica gel (PE) to give the product (3050 mg, 5.66 mmol) as oil. $^1$H NMR (400 MHz, CDCl$_3$) $\delta_H$=8.25 (d, 1H), 7.70 (dd, 1H), 5.96-5.78 (m, 1H), 1.54 (d, 3H), 1.34 (s, 12H).

A mixture of 3-fluoro-5-(4,4,5,5-tetramethyl-1,3,2-dioxaborolan-2-yl)-2-(2,2,2-trifluoro-1-methyl-ethoxy)pyridine (425.92 mg, 1.27 mmol), 6-chloro-3-(difluoromethyl)-[1.2.4]triazolo[4,3-a]pyrazine (200 mg, 0.98 mmol), Pd(dppf)Cl$_2$ (107.31 mg, 0.15 mmol) and Cs$_2$CO$_3$ (637.07 mg, 1.96 mmol) in 1,4-dioxane (20 mL) and water (4 mL) was stirred at 75° C. for 5 hours. After cooling to r.t, the mixture was diluted with H$_2$O (30 mL) and extracted with EtOAc (60 mL×2). The combined organic phase was washed with brine (30 mL), dried over Na$_2$SO$_4$, filtered and concentrated to give the crude product. The crude product was purified by flash chromatography on silica gel (EtOAc in PE=0 to 30%) to give the impure product. The impure product was purified by prep-HPLC (Waters Xbridge (150 mm×25 mm, 5 μm), A=H$_2$O (0.05% NH$_4$OH) and B=CH$_3$CN; 45-75% B over 8 minutes) to give the product (58.12 mg, 0.15 mmol) as a solid. $^1$H NMR (400 MHz, DMSO-d$_6$) $\delta_H$=9.69 (d, 1H), 9.28 (d, 1H), 8.78 (d, 1H), 8.52 (dd, 1H), 7.80 (t, 1H), 6.09-5.98 (m, 1H), 1.55 (d, 3H). LCMS R$_t$=1.26 min in 2.0 min chromatography, 10-80AB, purity 100%, MS ESI calcd. for C$_{14}$H$_{10}$F$_6$N$_5$O [M+H]$^+$ 378.1, found 378.0.

Example 114: Synthesis of Compounds 124 and 125

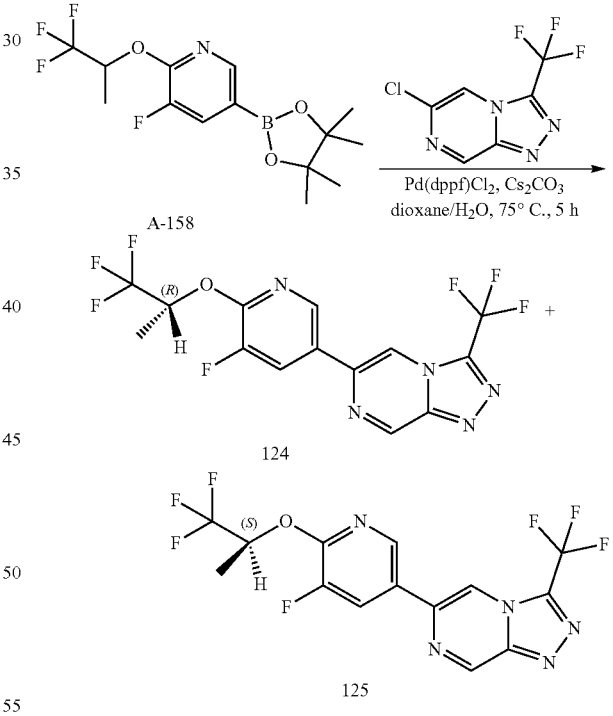

A mixture of 3-fluoro-5-(4,4,5,5-tetramethyl-1,3,2-dioxaborolan-2-yl)-2-(2,2,2-trifluoro-1-methyl-ethoxy)pyridine (489.34 mg, 1.46 mmol), 6-chloro-3-(trifluoromethyl)-[1.2.4]triazolo[4,3-a]pyrazine (250 mg, 1.12 mmol), Pd(dppf)Cl$_2$ (123.29 mg, 0.17 mmol) and Cs$_2$CO$_3$ (731.94 mg, 2.25 mmol) in 1,4-Dioxane (20 mL) and Water (4 mL) was stirred at 75° C. for 5 hours. After cooling to r.t., the mixture was diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 20%) to give the product. The product was analyzed by SFC show two peaks (Peak 1: Rt=1.90 min, Peak 2: Rt=2.02 min). Method: Column: Chiralpak OJ-H 150×4.6 mm I.D., 5 μm Mobile phase: A: $CO_2$ B: Ethanol (0.05% DEA), Gradient: from 5% to 40% of B in 5.5 min and hold 40% for 3 min, then 5% of B for 1.5 min Flow rate: 2.5 mL/min Column temp.: 40° C.

The product was separated by SFC (OJ (250 mm×30 mm, 5 μm); A=$CO_2$ and B=EtOH (0.1% $NH_3H_2O$); 38° C.; 50 mL/min; 15% B; 8 min run; 25 injections, Rt of peak 1=6.48 min, Rt of Peak 2=6.87 min) to give the impure Peak 1 (30 mg) and impure Peak 2 (50 mg).

The impure Peak 1 (30 mg) was purified by SFC (OJ (250 mm×30 mm, 5 μm); A=$CO_2$ and B=EtOH (0.1% $NH_3H_2O$); 38° C.; 50 mL/min; 15% B; 8 min run; 12 injections, Rt of peak 1=6.36 min, Rt of Peak 2=6.72 min) to give 6-[5-fluoro-6-[(1R)-2,2,2-trifluoro-1-methyl-ethoxy]-3-pyridyl]-3-(trifluoromethyl)-[1,2,4]triazolo[4,3-a]pyrazine (12.71 mg, 0.03 mmol) (Peak 1, Rt=1.90 min in SFC) as a solid.

The impure Peak 2 (50 mg) was purified by SFC (OJ (250 mm×30 mm, 5 μm); A=$CO_2$ and B=EtOH (0.1% $NH_3H_2O$); 38° C.; 50 mL/min; 15% B; 8 min run; 15 injections, Rt of peak 1=6.32 min, Rt of Peak 2=6.69 min) to give 6-[5-fluoro-6-[(1S)-2,2,2-trifluoro-1-methyl-ethoxy]-3-pyridyl]-3-(trifluoromethyl)-[1,2,4]triazolo[4,3-a]pyrazine (30.36 mg, 0.08 mmol) (Peak 2: Rt=2.02 min in SFC) as a solid.

Note: the enantiomers were randomly assigned.

Compound 124 (peak 1): $^1$H NMR (400 MHz, DMSO-$d_6$) $\delta_H$=9.78 (s, 1H), 9.16 (s, 1H), 8.83 (d, 1H), 8.63 (dd, 1H), 6.09-5.98 (m, 1H), 1.55 (d, 3H). LCMS $R_t$=1.21 min in 2.0 min chromatography, 10-80AB, purity 100%, MS ESI calcd. for $C_{14}H_9F_7N_5O$ [M+H]$^+$ 396.1, found 395.9.

Compound 125 (peak 2): $^1$H NMR (400 MHz DMSO-$d_6$) $\delta_H$=9.78 (s, 1H), 9.16 (s, 1H), 8.82 (d, 1H), 8.63 (dd, 1H), 6.12-5.93 (m, 1H), 1.55 (d, 3H). LCMS $R_t$=1.21 min in 2.0 min chromatography, 10-80AB, purity 100%, MS ESI calcd. for $C_{14}H_9F_7N_5O$ [M+H]$^+$ 396.1, found 396.0.

Example 115: Synthesis of Compounds 126 and 127

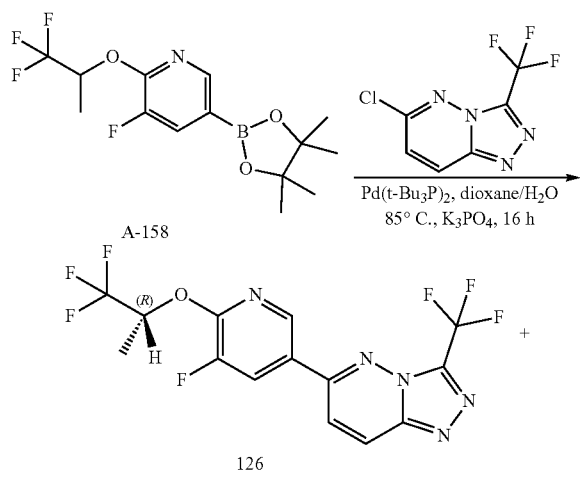

126

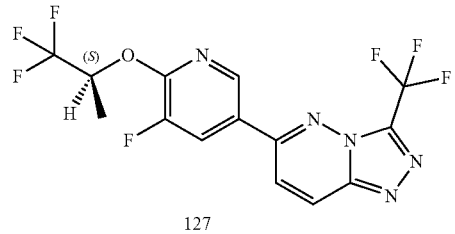

127

A mixture of 3-fluoro-5-(4,4,5,5-tetramethyl-1,3,2-dioxaborolan-2-yl)-2-(2,2,2-trifluoro-1-methyl-ethoxy)pyridine (391.47 mg, 1.17 mmol), 6-chloro-3-(trifluoromethyl)-[1,2,4]triazolo[4,3-b]pyridazine (200 mg, 0.90 mmol), $K_3PO_4$ (381.56 mg, 1.8 mmol) and Pd(t-$Bu_3$P)$_2$ (68.89 mg, 0.13 mmol) in 1,4-Dioxane (10 mL) and Water (2 mL) was stirred at 85° C. for 16 hours. After cooling to r.t., the mixture was diluted with $H_2O$ (10 mL) and extracted with EtOAc (20 mL×2). The combined organic phase was washed with brine (10 mL), dried over $Na_2SO_4$, filtered and concentrated to give the crude product. The crude product was purified by Prep-HPLC (Waters Xbridge (150 mm×25 mm, 5 μm), A=$H_2O$ (0.05% $NH_4OH$) and B=$CH_3CN$; 57-87% B over 7 minutes) to give the product. The product was analyzed by SFC and showed two peaks (Peak 1: Rt=4.80 min, Peak 2: Rt=4.89 min). Method: Column: Chiralpak OD-H 150×4.6 mm I.D., 5 μm Mobile phase: A: $CO_2$ B: IPA (0.05% DEA), Gradient: from 5% to 40% of B in 5.5 min and hold 40% for 3 min, then 5% of B for 1.5 min Flow rate: 2.5 mL/min Column temp.: 40° C.

The product was purified by SFC (OD (250 mm×30 mm, 5 μm); A=$CO_2$ and B=IPA (0.1% $NH_3H_2O$); 38° C.; 60 mL/min; 25% B; 12 min run; 35 injections, Rt of peak 1=10.5 min, Rt of Peak 2=10.9 min) to give 6-[5-fluoro-6-[(1R)-2,2,2-trifluoro-1-methyl-ethoxy]-3-pyridyl]-3-(trifluoromethyl)-[1,2,4]triazolo[4,3-b]pyridazine (23.12 mg, 0.06 mmol) (Peak 1, Rt=4.80 min in SFC) as a solid and impure Peak 2 (30 mg).

The impure Peak 2 (30 mg) was purified by SFC (OD (250 mm×30 mm, 5 μm); A=$CO_2$ and B=IPA (0.1% $NH_3H_2O$); 38° C.; 60 mL/min; 20% B; 13 min run; 10 injections, Rt of peak 1=10.7 min, Rt of Peak 2=11.0 min) to give 6-[5-fluoro-6-[(1S)-2,2,2-trifluoro-1-methyl-ethoxy]-3-pyridyl]-3-(trifluoromethyl)-[1,2,4]triazolo[4,3-b]pyridazine (13.73 mg, 0.03 mmol) (Peak 2: Rt=4.89 min in SFC) as a solid.

Note: the enantiomers were randomly assigned.

Compound 126 (peak 1): $^1$H NMR (400 MHz DMSO-$d_6$) $\delta_H$=8.74 (d, 1H), 8.61 (d, 1H), 8.38 (dd, 1H), 8.16 (d, 1H), 6.07-5.98 (m, 1H), 1.53 (d, 3H).

LCMS $R_t$=1.29 min in 2.0 min chromatography, 10-80AB, purity 98.45%, MS ESI calcd. for $C_{14}H_9F_7N_5O$ [M+H]$^+$ 396.1, found 395.8.

Compound 127 (peak 2): $^1$H NMR (400 MHz DMSO-$d_6$) $\delta_H$=8.82 (d, 1H), 8.77 (d, 1H), 8.46 (dd, 1H), 8.28 (d, 1H), 6.14-6.03 (m, 1H), 1.56 (d, 3H).

LCMS $R_t$=1.35 min in 2.0 min chromatography, 10-80AB, purity 100%, MS ESI calcd. for $C_{14}H_9F_7N_5O$ [M+H]$^+$ 396.1, found 396.0.

Example 116: Synthesis of Compound 128

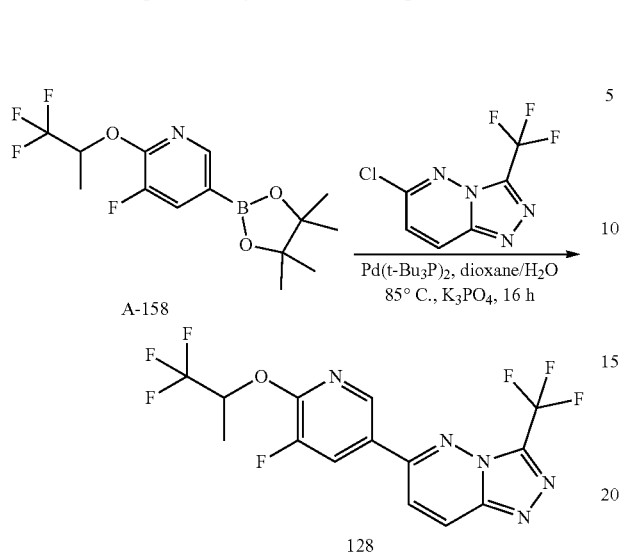

A mixture of 3-fluoro-5-(4,4,5,5-tetramethyl-1,3,2-dioxaborolan-2-yl)-2-(2,2,2-trifluoro-1-methyl-ethoxy)pyridine (97.87 mg, 0.29 mmol), 6-chloro-3-(trifluoromethyl)-[1,2,4]triazolo[4,3-b]pyridazine (50 mg, 0.22 mmol), Pd(t-Bu$_3$P)$_2$ (17.22 mg, 0.03 mmol) and K$_3$PO$_4$ (95.39 mg, 0.45 mmol) in 1,4-dioxane (4 mL) and water (1 mL) was stirred at 85° C. under N$_2$ for 16 hours. After cooling to r.t., the mixture was diluted with H$_2$O (10 mL) and extracted with EtOAc (10 mL×2). The combined organic phase was washed with brine (10 mL), dried over Na$_2$SO$_4$, filtered and concentrated to give the crude product. The crude product was purified by prep-HPLC (Waters Xbridge (150 mm×25 mm, 5 μm) A=H$_2$O (0.05% NH$_4$OH) and B=CH$_3$CN; 55-85% B over 7 minutes) to give the product (36.45 mg, 0.09 mmol) as a solid. $^1$H NMR (400 MHz, DMSO-d$_6$) δ$_H$=8.81 (d, 1H), 8.76 (d, 1H), 8.45 (dd, 1H), 8.27 (d, 1H), 6.10-6.02 (m, 1H), 1.56 (d, 3H). LCMS R$_t$=1.20 min in 2.0 min chromatography, 10-80AB, purity 100%, MS ESI calcd. for C$_{14}$H$_9$F$_7$N$_5$O [M+H]$^+$ 396.1, found 396.0.

Example 117: Synthesis of Compounds 129 and 130

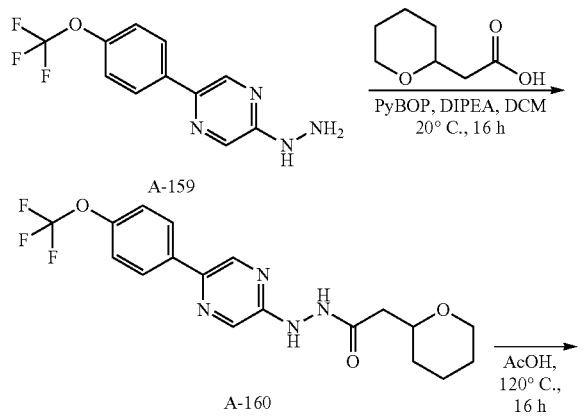

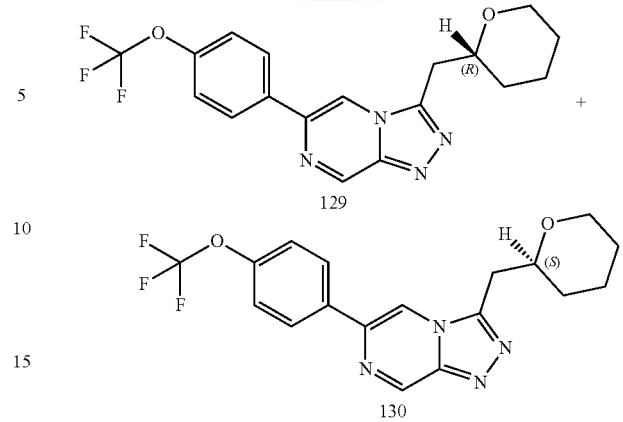

To a mixture of 2-tetrahydropyran-2-ylacetic acid (205.42 mg, 1.42 mmol), DIPEA (0.68 mL, 3.89 mmol) and PyBOP (1.01 g, 1.94 mmol) in DCM (20 mL) was added [5-[4-(trifluoromethoxy)phenyl]pyrazin-2-yl]hydrazine (350 mg, 1.3 mmol), and the mixture was stirred at 20° C. for 16 hours. The mixture was diluted with sat.NH$_4$Cl (80 mL), extracted with DCM (80 mL×2). The combined organic phase was washed with brine (40 mL), dried over Na$_2$SO$_4$, filtered. The filtrate was concentrated to give the crude product (800 mg). The crude product was used directly in next step without any purification. LCMS R$_t$=0.84 min in 1.5 min chromatography, 5-95AB, purity 43.38%, MS ESI calcd. for C$_{18}$H$_{20}$F$_3$N$_4$O$_3$ [M+H]$^+$ 397.1, found 396.9.

A mixture of 2-tetrahydropyran-2-yl-N'-[5-[4-(trifluoromethoxy)phenyl]pyrazin-2-yl]acetohydrazide (800 mg, 2.02 mmol) in acetic acid (6 mL) was stirred at 120° C. for 16 hours. After cooling to r.t., the mixture was concentrated, diluted with EtOAc (10 mL), basified with 1N NaHCO$_3$ to pH=8~9, and extracted with EtOAc (20 mL×2). The combined organic phase was concentrated to give the crude product. The crude product was purified by flash chromatography on silica gel (EtOAc in PE=20% to 50% to 100%) to give the product (200 mg, 0.53 mmol) as a solid. The product was analyzed by SFC to show two peaks (Peak 1: Rt=3.40 min, Peak 2: Rt=3.48 min). Method: (Column: Chiralcel OD-3 150 mm×4.6 mm I.D., 3 μm Mobile phase: A: CO$_2$ B: ethanol (0.05% DEA), Gradient: from 5% to 40% of B in 5 min and hold 40% for 2.5 min, then 5% of B for 2.5 min Flow rate: 2.5 mL/min Column temp.: 35° C.).

The product was purified by SFC (DAICEL CHIRALCEL OD-H (250 mm×30 mm, 5 μm); A=CO$_2$ and B=EtOH (0.1% NH$_3$H$_2$O); 38° C.; 60 mL/min; 25% B; 8 min run; 6 injections, Rt of Peak 1=5.40 min, Rt of Peak 2=6.20 min) to give 3-[[(2R)-tetrahydropyran-2-yl]methyl]-6-[4-(trifluoromethoxy)phenyl]-[1,2,4]triazolo[4,3-a]pyrazine (77.43 mg, 0.20 mmol) (Peak 1, Rt=3.40 min in SFC) and 3-[[(2S)-tetrahydropyran-2-yl]methyl]-6-[4-(trifluoromethoxy)phenyl]-[1,2,4]triazolo[4,3-a]pyrazine (86.11 mg, 0.23 mmol) (Peak 2, Rt=3.68 min in SFC).

Note: the enantiomers were randomly assigned.

Compound 129 (peak 1): $^1$H NMR (400 MHz, DMSO-d$_6$+D$_2$O) δ$_H$=9.39 (s, 1H), 8.92 (s, 1H), 8.15 (d, 2H), 7.50 (d, 2H), 3.79-3.70 (m, 2H), 3.42-3.31 (m, 2H), 3.30-3.21 (m, 1H), 1.78-1.66 (m, 2H), 1.51-1.26 (m, 4H). LCMS R$_t$=1.19 min in 2.0 min chromatography, 10-80AB, purity 100%, MS ESI calcd. for C$_{18}$H$_{18}$F$_3$N$_4$O$_2$ [M+H]$^+$ 379.1, found 379.1.

Compound 130 (peak 2): $^1$H NMR (400 MHz, DMSO-d$_6$+D$_2$O) δ$_H$=9.37 (s, 1H), 8.86 (s, 1H), 8.12 (d, 2H), 7.48 (d, 2H), 3.81-3.66 (m, 2H), 3.40-3.28 (m, 2H), 3.29-3.21 (m, 1H), 1.78-1.65 (m, 2H), 1.46-1.27 (m, 4H). LCMS $R_t$=1.17 min in 2.0 min chromatography, 10-80AB, purity 100%, MS ESI calcd. for $C_{18}H_{18}F_3N_4O_2$ [M+H]$^+$ 379.1, found 379.1.

Example 118: Synthesis of Compound 131

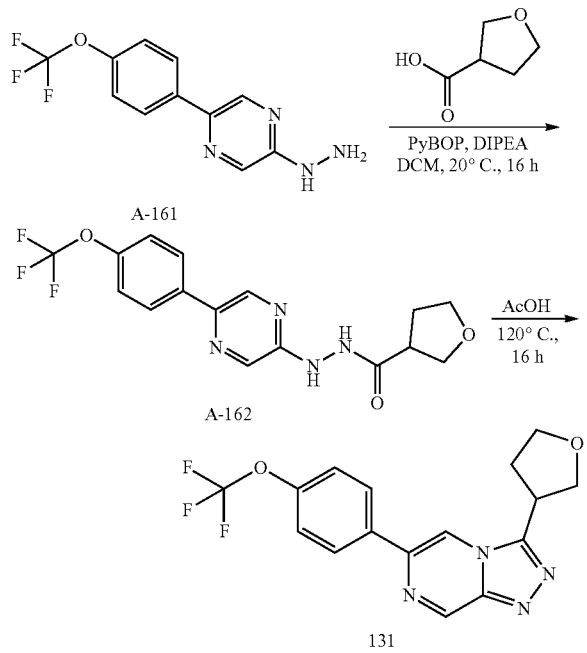

A mixture of [5-[4-(trifluoromethoxy)phenyl]pyrazin-2-yl]hydrazine (200 mg, 0.74 mmol), PyBOP (0.58 g, 1.11 mmol), tetrahydrofuran-2-carboxylic acid (103.14 mg, 0.89 mmol) and DIPEA (0.39 mL, 2.22 mmol) in DCM (10 mL) was stirred at 20° C. for 16 hours to give the brown mixture. The mixture was diluted with H$_2$O (10 mL) and extracted with DCM (10 mL×2). The combined organic phase was washed with brine (10 mL), dried over Na$_2$SO$_4$, filtered and concentrated to give the crude product (300 mg, 0.78 mmol) as oil. LCMS $R_t$=0.75 min in 1.5 min chromatography, 5-95AB, purity 42.43%, MS ESI calcd. for $C_{16}H_{16}F_3N_4O_3$ [M+H]$^+$369.1, found 369.0.

A mixture of N'-[5-[4-(trifluoromethoxy)phenyl]pyrazin-2-yl]tetrahydrofuran-3-carbohydrazide (250 mg, 0.68 mmol) in acetic acid (10 mL) was stirred at 120° C. for 16 hours. After cooling to r.t., the reaction was quenched with sat.NaHCO$_3$ (10 mL), and the mixture was extracted with EtOAc (20 mL×2). The combined organic phase was washed with brine (10 mL), dried over Na$_2$SO$_4$, filtered and concentrated to give the crude product The crude product was purified by flash chromatography on silica gel (EtOAc in PE=0 to 70% to 100%) to give the product (22.57 mg, 62.7 μmol) as solid. $^1$H NMR (400 MHZ, CDCl$_3$) $\delta_H$=9.43 (d, 1H), 8.36 (d, 1H), 8.00 (d, 2H), 7.38 (d, 2H), 4.33-4.22 (m, 3H), 4.15-3.97 (m, 2H), 2.66-2.53 (m, 1H), 2.51-2.38 (m, 1H). LCMS $R_t$=1.05 min in 2 min chromatography, 10-80AB, purity 100%, MS ESI calcd. for $C_{16}H_{14}F_3N_4O_2$ [M+H]$^+$ 351.1, found 351.0.

Example 119: Synthesis of Compound 132

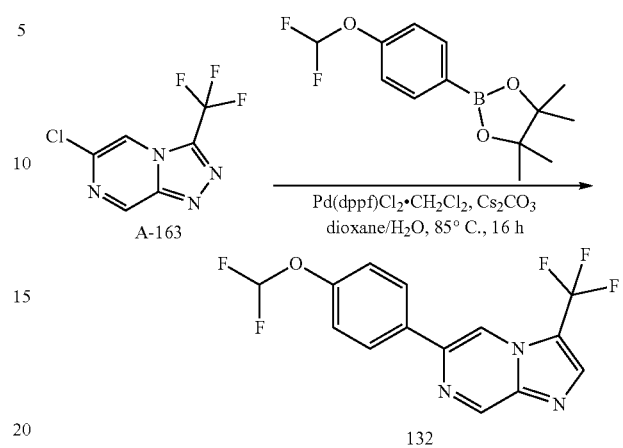

A mixture of 6-chloro-3-(trifluoromethyl)-[1,2,4]triazolo[4,3-a]pyrazine (100 mg, 0.45 mmol), 2-[4-(difluoromethoxy)phenyl]-4,4,5,5-tetramethyl-1,3,2-dioxaborolane (133.49 mg, 0.49 mmol), Pd(dppf)Cl$_2$ (49.31 mg, 0.07 mmol) and Cs$_2$CO$_3$ (292.77 mg, 0.9 mmol) in 1,4-Dioxane (2 mL) and Water (0.2 mL) was stirred at 85° C. for 16 hours. After cooling to r.t., the mixture was concentrated, diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0% to 15% to 25% to 50%) to give the product (36.9 mg, 0.11 mmol) as a solid. $^1$H NMR (400 MHz DMSO-d$_6$) $\delta_H$=9.76 (d, 1H), 9.02 (s, 1H), 8.25 (d, 2H), 7.57-7.16 (m, 3H). LCMS $R_t$=1.09 min in 2 min chromatography, 10-80AB, purity 100%, MS ESI calcd. for $C_{13}H_8F_5N_4O$ [M+H]$^+$ 331.1, found 330.9.

Example 120: Synthesis of Compound 133

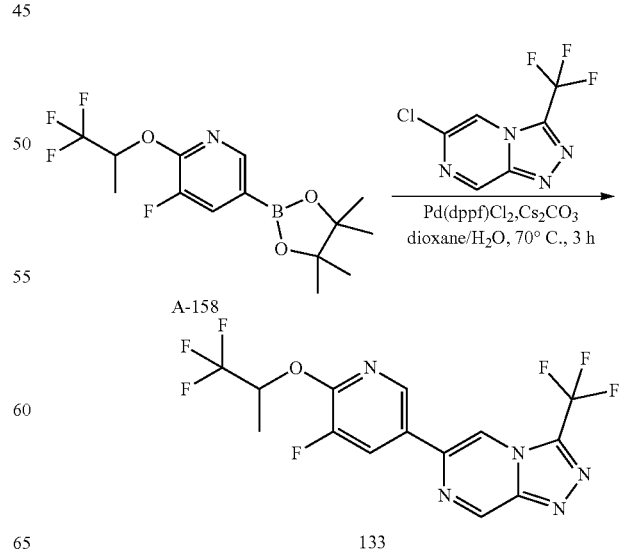

A mixture of 3-fluoro-5-(4,4,5,5-tetramethyl-1,3,2-dioxaborolan-2-yl)-2-(2,2,2-trifluoro-1-methyl-ethoxy)pyridine (180.68 mg, 0.54 mmol), 6-chloro-3-(trifluoromethyl)-[1,2,4]triazolo[4,3-a]pyrazine (80 mg, 0.36 mmol), Pd(dppf)Cl$_2$ (39.45 mg, 0.05 mmol) and Cs$_2$CO$_3$ (234.22 mg, 0.72 mmol) in 1,4-dioxane (5 mL) and water (1 mL) was stirred at 70° C. for 3 hours under N$_2$. After cooling to r.t, the mixture was diluted with H$_2$O (30 mL) and extracted with EtOAc (50 mL×2). The combined organic phase was washed with brine (30 mL), dried over Na$_2$SO$_4$, filtered and concentrated to give the crude product. The product was purified by Prep-TLC (silica gel, PE:EtOAc=4:1) to give the product (47.38 mg, 0.12 mmol). $^1$H NMR (400 MHz DMSO-d$_6$) δ$_H$=9.78 (d, 1H), 9.17 (s, 1H), 8.83 (d, 1H), 8.64 (dd, 1H), 6.10-5.92 (m, 1H), 1.55 (d, 3H). LCMS R$_t$=1.20 min in 2.0 min chromatography, 10-80AB, purity 100%, MS ESI calcd. for C$_{14}$H$_9$F$_7$N$_5$O [M+H]$^+$ 396.1, found 396.0.

Example 121: Synthesis of Compound 134

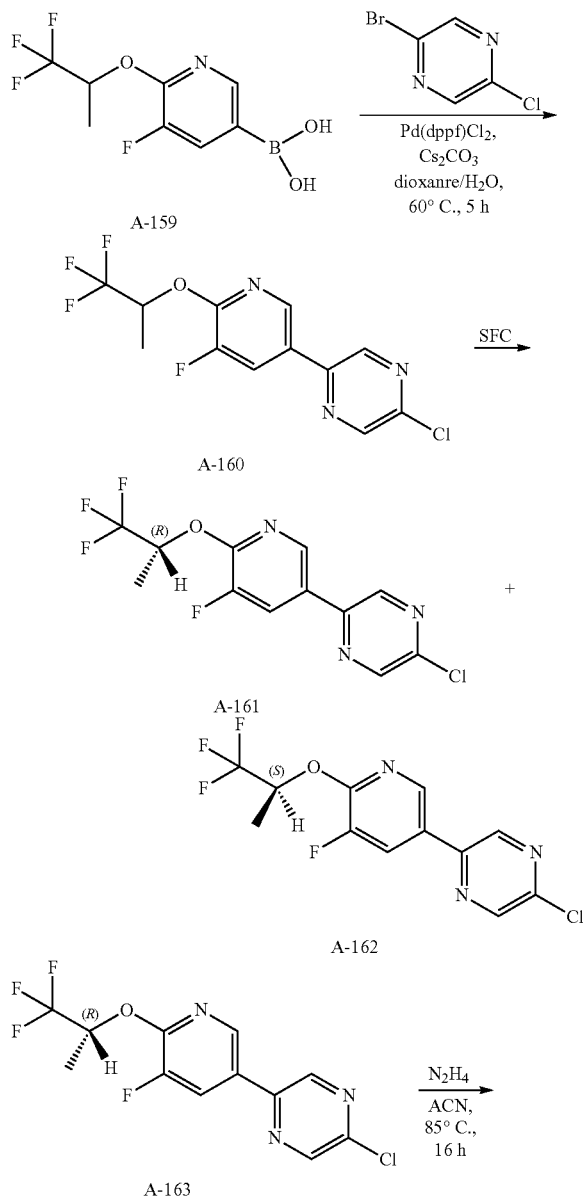

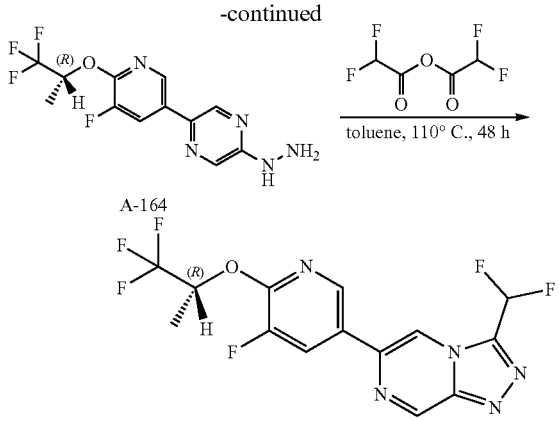

A mixture of 2-bromo-5-chloro-pyrazine (229.4 mg, 1.19 mmol), [5-fluoro-6-(2,2,2-trifluoro-1-methyl-ethoxy)-3-pyridyl]boronic acid (300 mg, 1.19 mmol), Pd(dppf)Cl$_2$ (130.16 mg, 0.18 mmol) and Cs$_2$CO$_3$ (772.77 mg, 2.37 mmol) in 1,4-dioxane (10 mL) and water (1 mL) was stirred at 60° C. for 5 hours under N$_2$. After cooling to r.t., the mixture was diluted with H$_2$O (30 mL), and the mixture was extracted with EtOAc (50 mL×2). The combined organic phase was washed with water (20 mL×2) and brine (20 mL), dried over Na$_2$SO$_4$, filtered and concentrated to give the crude product. The crude product was purified by flash chromatography on silica gel (EtOAc in PE=0% to 1% to 3%) to give the product (210 mg, 0.64 mmol) as a solid.

The product was analyzed by SFC to show two peaks (Peak 1: Rt=2.02 min, Peak 2: Rt=2.28 min).

Method: Column: Chiralpak AD-3 150×4.6 mm I.D, 3 µm Mobile phase: A: CO$_2$ B:ethanol (0.05% DEA), Gradient: from 5% to 40% of B in 5 min and hold 40% for 2.5 min, then 5% of B for 2.5 min Flow rate: 2.5 mL/min Column temp.: 35° C.

$^1$H NMR (400 MHz CDCl$_3$) δ$_H$=8.77 (d, 1H), 8.65 (d, 1H), 8.53 (d, 1H), 8.08 (dd, 1H), 5.95-5.85 (m, 1H), 1.63-1.48 (m, 3H). LCMS Rt=0.92 min in 1.5 min chromatography, 5-95AB, purity 98.54%, MS ESI calcd. for C$_{12}$H$_9$ClF$_4$N$_3$O [M+H]$^+$ 322.0, found 321.9.

The 2-chloro-5-[5-fluoro-6-(2,2,2-trifluoro-1-methyl-ethoxy)-3-pyridyl]pyrazine (150 mg, 0.46 mmol) was purified by SFC (DAICEL CHIRALPAK AD-H (250 mm×30 mm, 5 µm); A=CO$_2$ and B=EtOH (0.1% NH$_3$H$_2$O); 38° C.; 50 mL/min; 15% B; 8.8 min run; 15 injections, Rt of Peak 1=6.27 min, Rt of Peak 2=7.28 min) to give 2-chloro-5-[5-fluoro-6-[(1R)-2,2,2-trifluoro-1-methyl-ethoxy]-3-pyridyl]pyrazine (70 mg, 0.21 mmol) (Peak 1, Rt=2.02 min in SFC) as a solid and 2-chloro-5-[5-fluoro-6-[(1S)-2,2,2-trifluoro-1-methyl-ethoxy]-3-pyridyl]pyrazine (70 mg, 0.22 mmol) (Peak 2, Rt=2.28 min in SFC) as a solid.

Note: the enantiomers were randomly assigned.

LCMS R$_t$=1.27 min in 2.0 min chromatography, 10-80AB, purity 98.05%, MS ESI calcd. for C$_{12}$H$_9$ClF$_4$N$_3$O [M+H]$^+$ 322.0, found 321.9.

LCMS R$_t$=1.25 min in 2.0 min chromatography, 10-80AB, purity 100%, MS ESI calcd. for C$_{12}$H$_9$ClF$_4$N$_3$O [M+H]$^+$ 322.0, found 321.9.

A mixture of 2-chloro-5-[5-fluoro-6-[(1R)-2,2,2-trifluoro-1-methyl-ethoxy]-3-pyridyl]pyrazine (70 mg, 0.22 mmol) and hydrazine (139.5 mg, 4.35 mmol) in MeCN (5 mL) was stirred at 85° C. for 16 hours. After cooling to r.t., the mixture was concentrated to give the crude product (65 mg, 0.20 mmol) as a solid, which was used directly without any further purification. LCMS Rt=0.72 min in 1.5 min chromatography, 5-95AB, purity 67.77%, MS ESI calcd. for $C_{12}H_{12}F_4N_5O$ [M+H]$^+$ 318.1, found 317.9.

To a mixture of [5-[5-fluoro-6-[(1R)-2,2,2-trifluoro-1-methyl-ethoxy]-3-pyridyl]pyrazin-2-yl]hydrazine (65 mg, 0.20 mmol) in toluene (3 mL) was added (2,2-difluoroacetyl) 2,2-difluoroacetate (71.32 mg, 0.41 mmol), then the mixture was stirred at 110° C. for 48 hours. After cooling to r.t., the mixture was diluted with H$_2$O (20 mL), and the mixture was extracted with EtOAc (30 mL×2). The combined organic phase was washed with water (10 mL) and brine (20 mL), dried over Na$_2$SO$_4$, filtered and concentrated to give the crude product. The crude product was purified by Prep-TLC (silica gel, PE:EtOAc=4:1) to give the product (46 mg, 0.12 mmol) as a solid. $^1$H NMR (400 MHz, DMSO-d$_6$) $\delta_H$=9.69 (d, 1H), 9.28 (d, 1H), 8.78 (d, 1H), 8.52 (dd, 1H), 7.80 (t, 1H), 6.10-5.95 (m, 1H), 1.55 (d, 3H). LCMS R$_t$=1.21 min in 2.0 min chromatography, 10-80AB, purity 100%, MS ESI calcd. for $C_{14}H_{10}F_6N_5O$ [M+H]$^+$ 378.1, found 377.9.

further purification. LCMS Rt=0.71 min in 1.5 min chromatography, 5-95AB, purity 75.34%, MS ESI calcd. for $C_{12}H_{12}F_4N_5O$ [M+H]$^+$ 318.1, found 317.9.

To a mixture of [5-[5-fluoro-6-[(1S)-2,2,2-trifluoro-1-methyl-ethoxy]-3-pyridyl]pyrazin-2-yl]hydrazine (65 mg, 0.20 mmol) in toluene (3 mL) was added (2,2-difluoroacetyl) 2,2-difluoroacetate (71.32 mg, 0.41 mmol), then the mixture was stirred at 110° C. for 48 hours. After cooling to r.t., the mixture was diluted with H$_2$O (20 mL), and the mixture was extracted with EtOAc (30 mL×2). The combined organic phase was washed with water (10 mL) and brine (20 mL), dried over Na$_2$SO$_4$, filtered and concentrated to give the crude product. The crude product was purified by Prep-TLC (silica gel, PE:EtOAc=4:1) to give the product (48 mg, 0.13 mmol) as a solid. $^1$H NMR (400 MHz, DMSO-d$_6$) $\delta_H$=9.69 (d, 1H), 9.28 (d, 1H), 8.78 (d, 1H), 8.52 (dd, 1H), 7.80 (t, 1H), 6.10-5.94 (m, 1H), 1.55 (d, 3H). LCMS R$_t$=1.20 min in 2.0 min chromatography, 10-80AB, purity 100%, MS ESI calcd. for $C_{14}H_{10}F_6N_5O$ [M+H]$^+$ 378.1, found 378.0.

Example 122: Synthesis of Compound 135

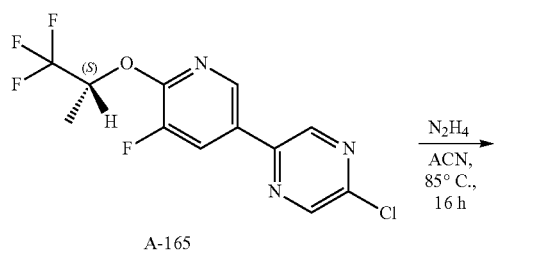

Example 123: Synthesis of Compound 136

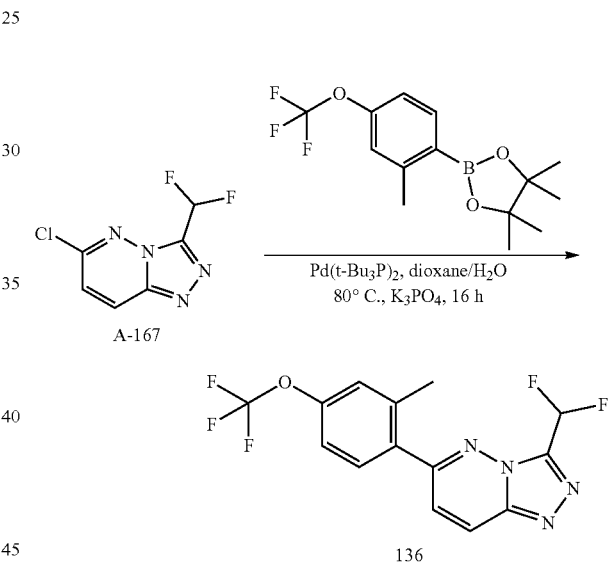

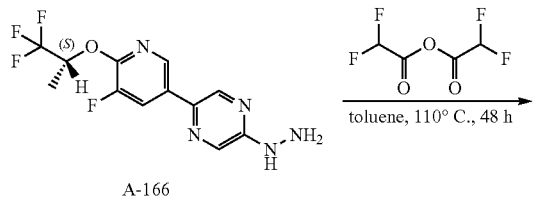

A mixture of 2-chloro-5-[5-fluoro-6-[(1S)-2,2,2-trifluoro-1-methyl-ethoxy]-3-pyridyl]pyrazine (70 mg, 0.22 mmol) and hydrazine (139.5 mg, 4.35 mmol) in MeCN (5 mL) was stirred at 85° C. for 16 hours. After cooling to r.t., the mixture was concentrated to give the crude product (65 mg, 0.20 mmol) as a solid, which was used directly without any A mixture of 6-chloro-3-(difluoromethyl)-[1,2,4]triazolo[4,3-b]pyridazine (100 mg, 0.49 mmol), 4,4,5,5-tetramethyl-2-[2-methyl-4-(trifluoromethoxy)phenyl]-1,3,2-dioxaborolane (177.22 mg, 0.59 mmol), K$_3$PO$_4$ (207.57 mg, 0.98 mmol) and Pd(t-Bu$_3$P)$_2$ (37.47 mg, 0.07 mmol) in 1,4-dioxane (5 mL) and water (0.50 mL) was stirred at 80° C. under N$_2$ for 16 hours to give a suspension. The mixture was cooled to room temperature and filtered through Celite. The filtrate was concentrated to give a residue. The residue was re-dissolved in EtOAc (20 mL), washed with water (10 mL×2), brine (10 mL×2), dried over anhydrous Na$_2$SO$_4$, filtered and concentrated to give the crude product. The crude product was purified by flash chromatography on silica gel (EtOAc in PE=10% to 30% to 50%) to give the product (87.09 mg, 0.25 mmol) as a solid. $^1$H NMR (400 MHz, MeOD-d$_4$) $\delta_H$=8.41 (d, 1H), 7.75-7.64 (m, 2H), 7.61-7.29 (m, 3H), 2.51 (s, 3H). LCMS R$_t$=1.13 min in 2.0 min chromatography, 10-80AB, purity 98.84%, MS ESI calcd. for $C_{14}H_{10}F_5N_4O$ [M+H]$^+$ 345.1, found 344.9.

Example 124: Synthesis of Compound 137

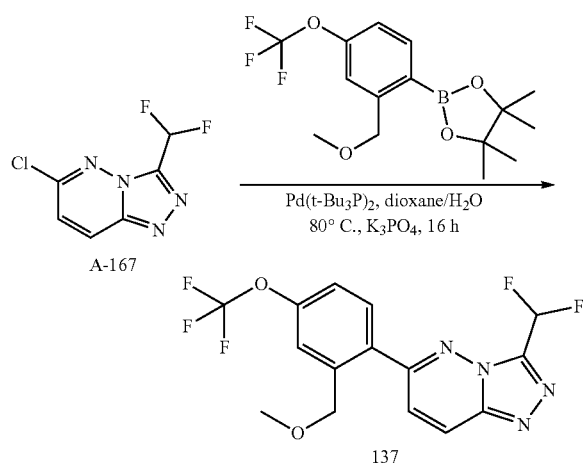

A mixture of 6-chloro-3-(difluoromethyl)-[1,2,4]triazolo[4,3-b]pyridazine (100 mg, 0.49 mmol), 2-[2-(methoxymethyl)-4-(trifluoromethoxy)phenyl]-4,4,5,5-tetramethyl-1,3,2-dioxaborolane (194.83 mg, 0.59 mmol), $K_3PO_4$ (207.57 mg, 0.98 mmol) and $Pd(t-Bu_3P)_2$ (37.47 mg, 0.07 mmol) in 1,4-dioxane (5 mL) and water (0.50 mL) was stirred at 80° C. under $N_2$ for 16 hours to give a suspension. The mixture was cooled to room temperature and filtered through Celite. The filtrate was concentrated to give a residue. The residue was re-dissolved in EtOAc (20 mL), washed with water (10 mL×2), brine (10 mL×2), dried over anhydrous $Na_2SO_4$, filtered and concentrated to give the crude product. The crude product was purified by flash chromatography on silica gel (EtOAc in PE=10% to 30% to 50%) to give the product (22.42 mg, 59.9 μmol) as a solid. $^1$H NMR (400 MHz, DMSO-$d_6$) $\delta_H$=8.62 (d, 1H), 7.88-7.51 (m, 5H), 4.67 (s, 2H), 3.23 (s, 3H). LCMS $R_t$=1.12 min in 2.0 min chromatography, 10-80AB, purity 100%, MS ESI calcd. for $C_{15}H_{12}F_5N_4O_2$ [M+H]$^+$ 375.1, found 375.1.

Example 125: Synthesis of Compound 138

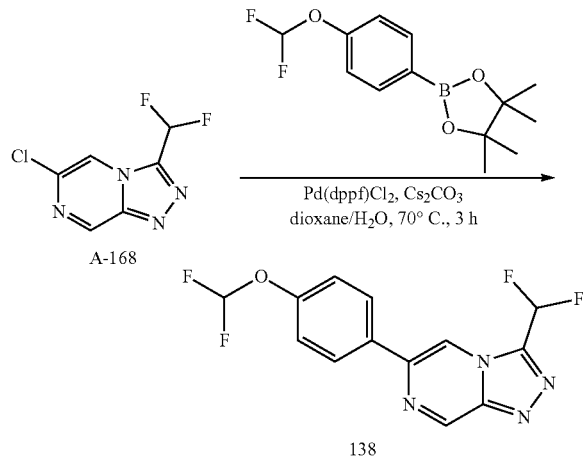

A mixture of 6-chloro-3-(difluoromethyl)-[1,2,4]triazolo[4,3-a]pyrazine (100 mg, 0.49 mmol), 2-[4-(difluoromethoxy)phenyl]-4,4,5,5-tetramethyl-1,3,2-dioxaborolane (158.44 mg, 0.59 mmol), $Cs_2CO_3$ (318.54 mg, 0.98 mmol) and $Pd(dppf)Cl_2$ (53.65 mg, 0.07 mmol) in 1,4-Dioxane (5 mL) and Water (0.50 mL) was stirred under $N_2$ at 70° C. for 3 hours to give a suspension. The mixture was cooled to room temperature and filtered through Celite. The filtrate was concentrated to give a residue. The residue was dissolved in EtOAc (20 mL), washed with water (10 mL×2), brine (10 mL×2), dried over anhydrous $Na_2SO_4$, filtered and concentrated to give the crude product. The crude product was purified by flash chromatography on silica gel (EtOAc in PE=10% to 30% to 50%) to give the product (90.42 mg, 0.29 mmol) as a solid. $^1$H NMR (400 MHz, DMSO-$d_6$) $\delta_H$=9.67 (s, 1H), 9.18 (d, 1H), 8.19 (d, 2H), 7.85 (t, 1H), 7.58-7.16 (m, 3H). LCMS $R_t$=1.02 min in 2.0 min chromatography, 10-80AB, purity 100%, MS ESI calcd. for $C_{13}H_9F_4N_4O$ [M+H]$^+$ 313.1, found 312.9.

Example 126: Synthesis of Compound 139

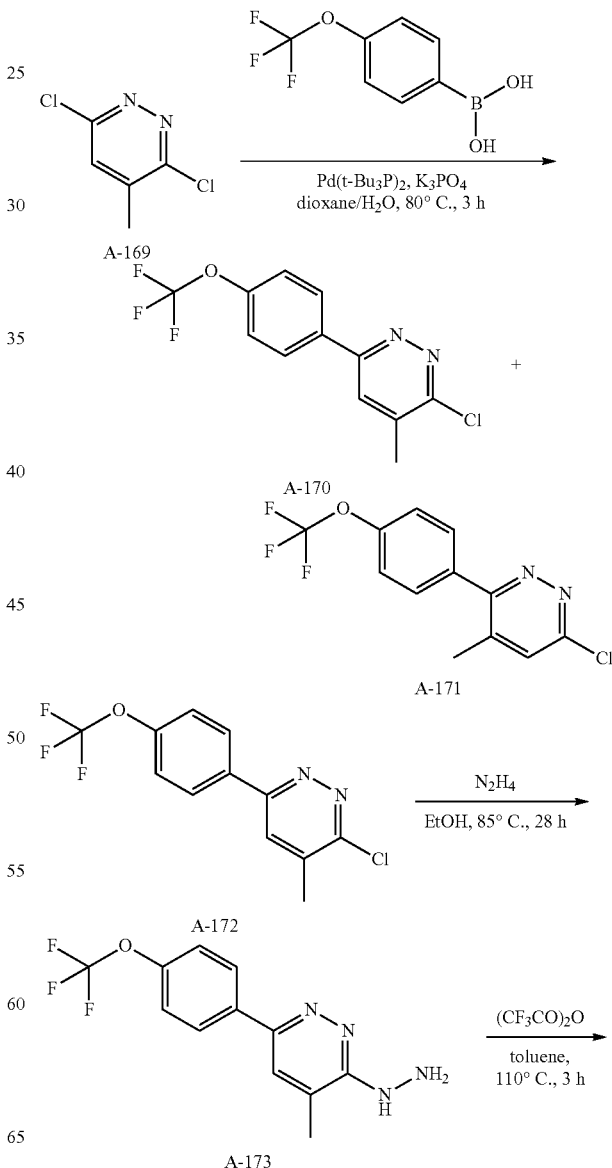

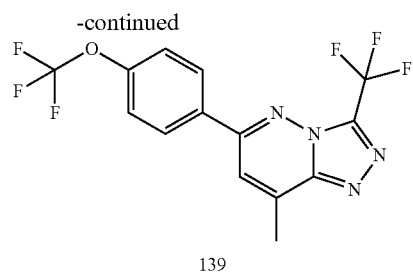

139

A mixture of 3,6-dichloro-4-methyl-pyridazine (1.4 g, 8.59 mmol), [4-(trifluoromethoxy)phenyl]boronic acid (1.65 g, 8.01 mmol), Pd(t-Bu$_3$P)$_2$ (265 mg, 0.52 mmol) and K$_3$PO$_4$ (3.1 g, 14.6 mmol) in 1,4-dioxane (80 mL) and water (15 mL) was stirred at 80° C. for 3 hours under N$_2$. After cooling to r.t., the mixture was concentrated. The residue was diluted with H$_2$O (50 mL), and the mixture was extracted with EtOAc (100 mL×2). The combined organic phase was washed with water (50 mL) and brine (50 mL), dried over Na$_2$SO$_4$, filtered and concentrated to give the crude product. The crude product was purified by flash chromatography on silica gel (EtOAc in PE=0% to 4% to 8%) to give impure 3-chloro-4-methyl-6-[4-(trifluoromethoxy)phenyl] pyridazine (1400 mg, 2.23 mmol) as a solid and 6-chloro-4-methyl-3-[4-(trifluoromethoxy)phenyl]pyridazine (600 mg, 1.87 mmol) as a solid.

3-chloro-4-methyl-6-[4-(trifluoromethoxy)phenyl] pyridazine LCMS Rt=2.68 min in 4.0 min chromatography, 10-80AB, purity 46.02%, MS ESI calcd. for C$_{12}$H$_9$ClF$_3$N$_2$O [M+H]$^+$ 289.0, found 288.9.

6-chloro-4-methyl-3-[4-(trifluoromethoxy)phenyl] pyridazine $^1$H NMR (400 MHz, CDCl$_3$) $\delta_H$=8.62 (d, 2H), 8.46 (s, 1H), 8.37 (d, 2H), 2.40 (s, 3H). LCMS Rt=2.54 min in 4.0 min chromatography, 10-80AB, purity 89.88%, MS ESI calcd. for C$_{12}$H$_9$ClF$_3$N$_2$O [M+H]$^+$ 289.0, found 288.9.

To a mixture of 3-chloro-4-methyl-6-[4-(trifluoromethoxy)phenyl]pyridazine (700 mg, 2.43 mmol) in ethanol (20 mL) was added hydrazine (2.33 g, 72.75 mmol), then the mixture was stirred at 85° C. for 28 hours. After cooling to r.t., the mixture was concentrated to give the crude product (680 mg, 2.39 mmol as a solid, which was used directly without any further purification. LCMS Rt=0.71 min in 1.5 min chromatography, 5-95AB, purity 21.62%, MS ESI calcd. for C$_{12}$H$_{12}$F$_3$N$_4$O [M+H]$^+$ 285.1, found 284.9.

To a mixture of [4-methyl-6-[4-(trifluoromethoxy)phenyl]pyridazin-3-yl]hydrazine (680 mg, 2.39 mmol) in toluene (15 mL) was added (2,2,2-trifluoroacetyl) 2,2,2-trifluoroacetate (1.0 g, 4.78 mmol), then the mixture was stirred at 110° C. for 3 hours. After cooling to r.t., the mixture was diluted with H$_2$O (20 mL) and sat.Na$_2$CO$_3$ (10 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 25% to 50%) to give the impure product (310 mg, 0.43 mmol) as a solid.

The impure product (80 mg, 0.22 mmol) was purified by purified by prep-HPLC [Waters Xbridge (150 mm×25 mm, 5 μm) A=H$_2$O (0.05% NH$_4$OH) and B=CH$_3$CN; 55-85% B over 7 minutes] to give the product (27.05 mg, 74.7 μmol) as a solid. $^1$H NMR (400 MHz, CDCl$_3$) $\delta_H$=8.07 (d, 2H), 7.52 (d, 1H), 7.42 (d, 2H), 2.88 (d, 3H). LCMS R$_t$=1.23 min in 2.0 min chromatography, 10-80AB, purity 100%, MS ESI calcd. for C$_{14}$H$_9$F$_6$N$_4$O [M+H]$^+$ 363.1, found 363.0.

Example 127: Synthesis of Compound 140

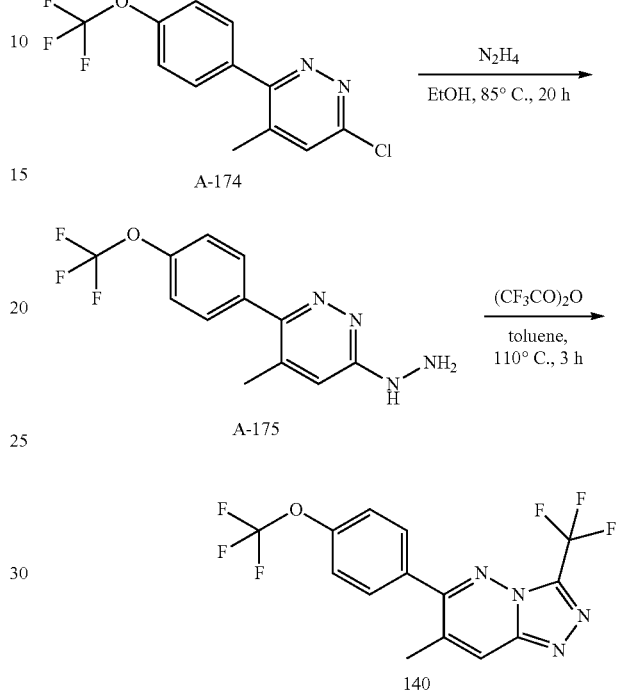

To a mixture of 6-chloro-4-methyl-3-[4-(trifluoromethoxy)phenyl]pyridazine (300 mg, 1.04 mmol) in rthanol (10 mL) was added hydrazine (666.2 mg, 20.79 mmol), then the mixture was stirred at 85° C. for 20 hours. After cooling to r.t., the mixture was concentrated to give the crude product (290 mg, 0.73 mmol) as a solid. LCMS Rt=0.70 min in 1.5 min chromatography, 5-95AB, purity 71.37%, MS ESI calcd. for C$_{12}$H$_{12}$F$_3$N$_4$O [M+H]$^+$ 285.1, found 284.9.

To a mixture of [5-methyl-6-[4-(trifluoromethoxy)phenyl]pyridazin-3-yl]hydrazine (290 mg, 1.02 mmol) in toluene (10 mL) was added (2,2,2-trifluoroacetyl) 2,2,2-trifluoroacetate (428.57 mg, 2.04 mmol), then the mixture was stirred at 110° C. for 3 hours. After cooling to r.t., the mixture was diluted with H$_2$O (20 mL) and sat.Na$_2$CO$_3$ (10 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 25% to 50%) to give the product (220 mg, 0.59 mmol) as a solid.

The impure product (50 mg, 0.14 mmol) was triturated from i-Pr$_2$O (2 mL) and dried in oven to give the pure product (32.72 mg, 90.3 μmol) as a solid. $^1$H NMR (400 MHz CDCl$_3$) $\delta_H$=8.09 (d, 1H), 7.61 (d, 2H), 7.42 (d, 2H), 2.46 (d, 3H). LCMS R$_t$=1.25 min in 2.0 min chromatography, 10-80AB, purity 100%, MS ESI calcd. for C$_{14}$H$_9$F$_6$N$_4$O [M+H]$^+$ 363.1, found 363.1.

Example 128: Synthesis of Compound 141

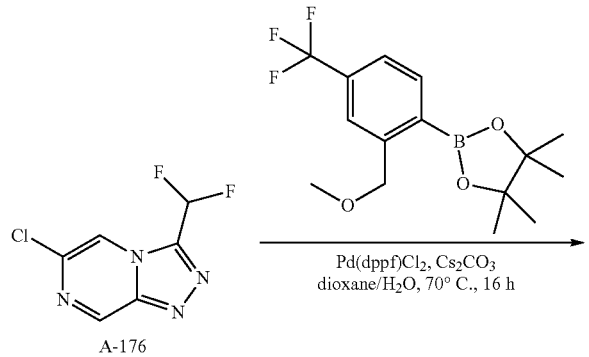

A mixture of 6-chloro-3-(difluoromethyl)-[1,2,4]triazolo[4,3-a]pyrazine (100 mg, 0.49 mmol), 2-[2-(methoxymethyl)-4-(trifluoromethyl)phenyl]-4,4,5,5-tetramethyl-1,3,2-dioxaborolane (185.44 mg, 0.59 mmol), Cs$_2$CO$_3$ (318.54 mg, 0.98 mmol) and Pd(dppf)Cl$_2$ (53.65 mg, 0.07 mmol) in 1,4-dioxane (3 mL) and water (0.50 mL) was stirred at 70° C. under N$_2$ for 16 hours. After cooling to r.t., the suspension was diluted with EtOAc (10 mL), filtered through silica gel, eluted with EtOAc (20 mL). The combined filtrates were concentrated to give the crude product. The crude product was purified by flash chromatography on silica gel (EtOAc in PE=70% to 100%) to give the product (88.81 mg, 0.25 mmol) as a solid. $^1$H NMR (400 MHz, DMSO-d$_6$+D$_2$O) $\delta_H$=9.65 (d, 1H), 8.88 (d, 1H), 7.95-7.65 (m, 4H), 4.57 (s, 2H), 3.30 (s, 3H). LCMS R$_t$=1.08 min in 2 min chromatography, 10-80AB, purity 100%, MS ESI calcd. for C$_{15}$H$_{12}$F$_5$N$_4$O [M+H]$^+$ 359.1, found 359.0.

Example 129: Synthesis of Compound 142

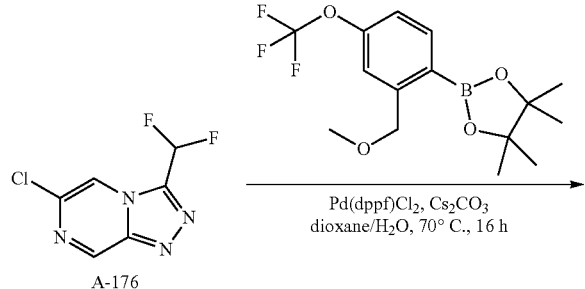

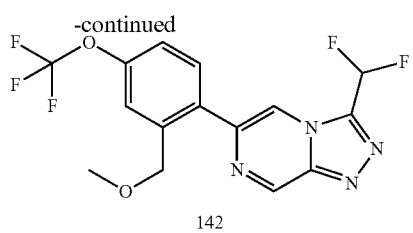

A mixture of 6-chloro-3-(difluoromethyl)-[1,2,4]triazolo[4,3-a]pyrazine (100 mg, 0.49 mmol), 2-[2-(methoxymethyl)-4-(trifluoromethoxy)phenyl]-4,4,5,5-tetramethyl-1,3,2-dioxaborolane (194.83 mg, 0.59 mmol), Cs$_2$CO$_3$ (318.54 mg, 0.98 mmol) and Pd(dppf)Cl$_2$ (53.65 mg, 0.07 mmol) in 1,4-dioxane (3 mL) and water (0.50 mL) was stirred at 70° C. under N$_2$ for 16 hours. After cooling to r.t., the suspension was diluted with EtOAc (10 mL), filtered through silica gel, eluted with EtOAc (20 mL). The combined filtrates were concentrated to give the crude product. The crude product was purified by flash chromatography on silica gel (EtOAc in PE=70% to 100%) to give the product (48.50 mg, 0.13 mmol) as a solid. $^1$H NMR (400 MHz, DMSO-d$_6$+D$_2$O) $\delta_H$=9.52 (s, 1H), 8.72 (s, 1H), 7.81-7.52 (m, 2H), 7.50-7.38 (m, 2H), 4.45 (s, 2H), 3.24 (s, 3H). LCMS R$_t$=1.10 min in 2 min chromatography, 10-80AB, purity 100%, MS ESI calcd. for C$_{15}$H$_{12}$F$_5$N$_4$O$_2$ [M+H]$^+$ 375.1, found 375.0.

Example 130: Synthesis of Compound 143

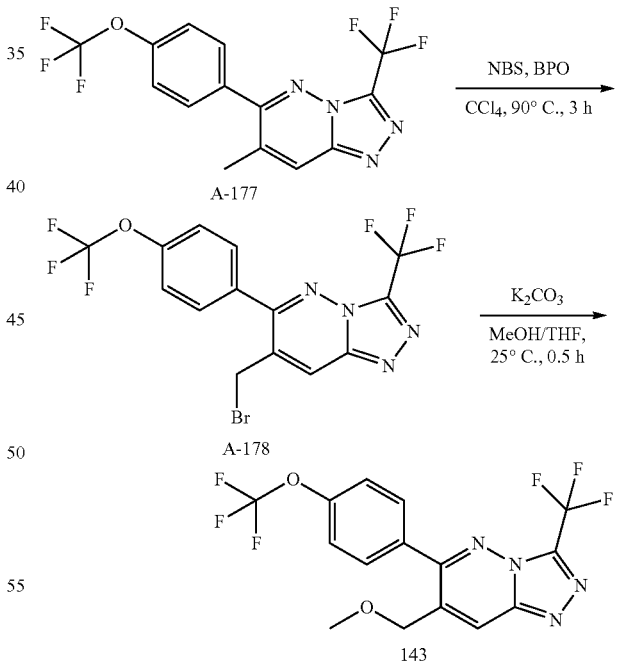

To a mixture of 7-methyl-6-[4-(trifluoromethoxy)phenyl]-3-(trifluoromethyl)-[1,2,4]triazolo[4,3-b]pyridazine (150 mg, 0.41 mmol) and NBS (110.55 mg, 0.62 mmol) in carbon tetrachloride (5 mL) was added BPO (100.31 mg, 0.41 mmol) at 90° C., then the mixture was stirred at 90° C. for 3 hours. After cooling to r.t., the mixture was diluted with H$_2$O (20 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by Prep-TLC (silica gel, PE:EtOAc=2:1) to give the impure product (85 mg, 0.17 mmol) as a solid. LCMS Rt=1.28 min in 2.0 min chromatography, 10-80AB, purity 90.79%, MS ESI calcd. for C$_{14}$H$_8$BrF$_6$N$_4$O [M+H+2]$^+$443.0, found 443.1.

The mixture of 7-(bromomethyl)-6-[4-(trifluoromethoxy) phenyl]-3-(trifluoromethyl)-[1,2,4]triazolo[4,3-b]pyridazine (80 mg, 0.18 mmol) and K$_2$CO$_3$ (50.13 mg, 0.36 mmol) in THF (3 mL) and Methanol (3 mL) was stirred at 25° C. for 0.5 hour. The mixture was quenched with sat. NH$_4$Cl (10 mL) and extracted with EtOAc (30 mL×2). The combined organic phase was washed with brine (15 mL), dried over Na$_2$SO$_4$, filtered and concentrated to give the crude product. The crude product was purified by Prep-TLC (silica gel, PE:EtOAc=2:1) to give the product (29.75 mg, 75.8 μmol) as a solid. $^1$H NMR (400 MHz, CDCl$_3$) δ$_H$=8.42 (t, 1H), 7.63 (d, 2H), 7.42 (d, 2H), 4.39 (d, 2H), 3.49 (s, 3H). LCMS R$_t$=1.17 min in 2.0 min chromatography, 10-80AB, purity 100%, MS ESI calcd. for C$_{15}$H$_{11}$F$_6$N$_4$O$_2$ [M+H]$^+$ 393.1, found 393.0.

Example 131: Synthesis of Compound 144

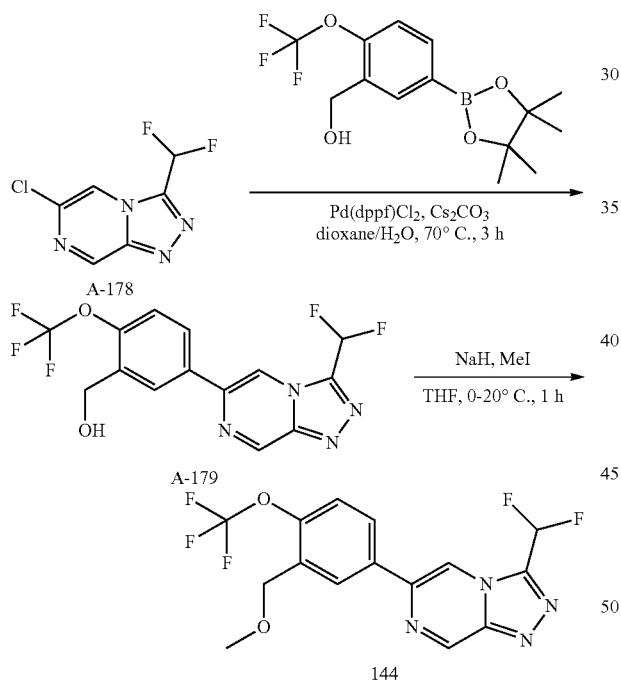

144

A mixture of 6-chloro-3-(difluoromethyl)-[1,2,4]triazolo [4,3-a]pyrazine (100 mg, 0.49 mmol), [5-(4,4,5,5-tetramethyl-1,3,2-dioxaborolan-2-yl)-2-(trifluoromethoxy)phenyl] methanol (233.26 mg, 0.73 mmol), Cs$_2$CO$_3$ (318.54 mg, 0.98 mmol) and Pd(dppf)Cl$_2$ (53.65 mg, 0.07 mmol) in 1,4-dioxane (5 mL) and water (0.50 mL) was stirred at 70° C. under N$_2$ for 3 hours to give a suspension. The mixture was cooled to room temperature and filtered through Celite. The filtrate was concentrated to give a residue. The residue was re-dissolved in EtOAc (20 mL), washed with water (10 mL×2), brine (10 mL×2), dried over anhydrous Na$_2$SO$_4$, filtered and concentrated to give the crude product. The crude product was purified by flash chromatography on silica gel (EtOAc in PE=10% to 30% to 50%) to give the product (90 mg, 0.24 mmol) as a solid. $^1$H NMR (400 MHz DMSO-d$_6$) δ$_H$=9.69 (d, 1H), 9.20 (d, 1H), 8.37 (d, 1H), 8.13 (dd, 1H), 7.88 (t, 1H), 7.51 (dd, 1H), 5.54 (t, 1H), 4.66 (d, 2H). LCMS R$_t$=0.76 min in 1.5 min chromatography, 5-95AB, purity 97.04%, MS ESI calcd. for C$_{14}$H$_{10}$F$_5$N$_4$O$_2$ [M+H]$^+$ 361.1, found 361.0.

To a mixture of [5-[3-(difluoromethyl)-[1,2,4]triazolo[4, 3-a]pyrazin-6-yl]-2-(trifluoromethoxy)phenyl]methanol (80 mg, 0.22 mmol) in THF (3 mL) was added NaH (13.32 mg, 0.33 mmol) at 0° C. To the mixture was added iodomethane (94.56 mg, 0.67 mmol). The resulting mixture was stirred at 20° C. for 1 hour. To the reaction mixture was added saturated NH$_4$Cl aqueous (20 mL). The resulting mixture was extracted with EtOAc (20 mL×2). After separation, the combined organic phase was washed with water (20 mL×2), brine (20 mL×2), dried over anhydrous Na$_2$SO$_4$, filtered and concentrated to give the crude product. The crude product was purified by flash chromatography on silica gel (EtOAc in PE=0% to 10% to 20%) to give the product (42.34 mg, 113.1 μmol) as a solid. $^1$H NMR (400 MHz, DMSO-d$_6$) δ$_H$=9.69 (s, 1H), 9.25 (d, 1H), 8.31 (d, 1H), 8.19 (dd, 1H), 7.87 (t, 1H), 7.56 (dd, 1H), 4.58 (s, 2H), 3.39 (s, 3H). LCMS R$_t$=1.12 min in 2.0 min chromatography, 10-80AB, purity 100.00%, MS ESI calcd. for C$_{15}$H$_{12}$F$_5$N$_4$O$_2$ [M+H]$^+$ 375.1, found 375.0.

Example 132: Synthesis of Compound 145

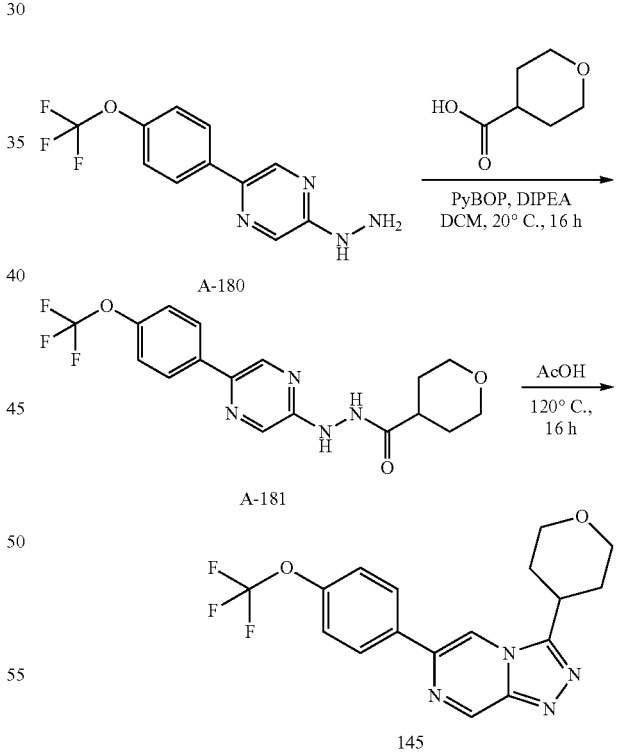

145

A mixture of [5-[4-(trifluoromethoxy)phenyl]pyrazin-2-yl]hydrazine (100 mg, 0.37 mmol), PyBOP (0.29 g, 0.56 mmol) in DCM (3 mL) was added tetrahydropyran-4-carboxylic acid (48.16 mg, 0.37 mmol) and DIPEA (0.19 mL, 1.11 mmol). The reaction mixture was stirred at 20° C. for 16 hours. The mixture was diluted with NH$_4$Cl (15 mL×2) and extracted with CH$_2$Cl$_2$ (20 mL). The combined organic phase was washed with brine (10 mL), dried over Na$_2$SO$_4$, filtered and concentrated to give the crude product (290 mg, 0.55 mmol). The crude product was used directly without any purification. LCMS $R_f$=0.76 min in 1.5 min chromatography, 5-95 AB, purity 72.15%, MS ESI calcd. for $C_{17}H_{18}F_3N_4O_3$ [M+H]$^+$ 383.1, found 383.0.

A mixture of N'-[5-[4-(trifluoromethoxy)phenyl]pyrazin-2-yl]tetrahydropyran-4-carbohydrazide (290 mg, 0.76 mmol) in acetic acid (8 mL) was stirred at 120° C. for 16 hours. After cooling to r.t., the mixture was concentrated, the residue was diluted with EtOAc (20 mL), neutralized with sat.NaHCO$_3$ to pH=9 and extracted with EtOAc (20 mL×2). Then the combined organic phase was washed with brine (15 mL), dried over Na$_2$SO$_4$ and concentrated to give the crude product. The crude product was purified by flash chromatography on silica gel (EtOAc in PE=50% to 100%) to give the impure product. The impure product was purified by Prep-TLC (silica gel, PE:EA=1:7) to give the product (28.60 mg, 0.08 mmol) as a solid. $^1$H NMR (400 MHz DMSO-d$_6$) $\delta_H$=9.48 (d, 1H), 9.14 (d, 1H), 8.26 (d, 2H), 7.54 (d, 2H), 4.04-3.99 (m, 2H), 3.81-3.70 (m, 1H), 3.63-3.54 (m, 2H), 2.03-1.87 (m, 4H). LCMS $R_f$=1.08 min in 2 min chromatography, 10-80AB, purity 96.37%, MS ESI calcd. for $C_{17}H_{16}F_3N_4O_2$ [M+H]$^+$ 365.1, found 365.1.

Example 133: Synthesis of Compound 146

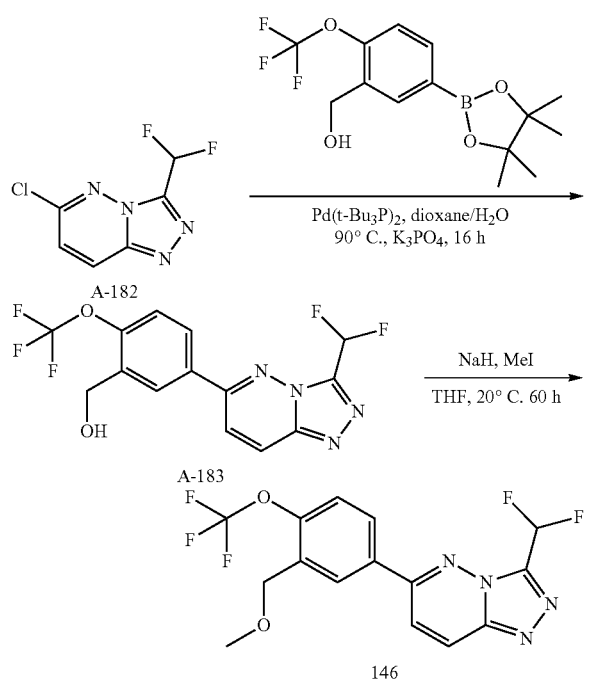

A mixture of 6-chloro-3-(difluoromethyl)-[1,2,4]triazolo[4,3-b]pyridazine (100 mg, 0.49 mmol), [5-(4,4,5,5-tetramethyl-1,3,2-dioxaborolan-2-yl)-2-(trifluoromethoxy)phenyl]methanol (155.50 mg, 0.49 mmol), Pd(t-Bu$_3$P)$_2$ (37.47 mg, 0.07 mmol) and K$_3$PO$_4$ (207.57 mg, 0.98 mmol) in water (0.2 mL) and 1,4-dioxane (2 mL) was stirred at 90° C. for 16 hours. After cooling to r.t., the suspension was diluted with EtOAc (10 mL), filtered through silica gel and eluted with EtOAc (20 mL). The combined filtrates were concentrated to give the crude product. The crude product was purified by flash chromatography on silica gel (EtOAc in PE=20% to 70% to 100%) to give the product (55 mg, 0.15 mmol) as a solid. $^1$H NMR (400 MHz DMSO-d$_6$) $\delta_H$=8.63 (d, 1H), 8.33 (d, 1H), 8.18-8.09 (m, 2H), 7.77 (t, 1H), 7.62-7.55 (m, 1H), 5.59 (t, 1H), 4.67 (d, 2H).

To a mixture of [5-[3-(difluoromethyl)-[1,2,4]triazolo[4,3-b]pyridazin-6-yl]-2-(trifluoromethoxy)phenyl]methanol (45 mg, 0.12 mmol) in THF (2 mL) was added the NaH (6 mg, 0.15 mmol) at 0° C., and the mixture was stirred for 30 minutes. Then iodomethane (53.19 mg, 0.37 mmol) was added. The mixture was stirred at 20° C. for 16 hours to give the brown mixture. The mixture was concentrated, the residue was diluted with EtOAc (20 mL), neutralized with HCl to pH=3 and extracted with EtOAc (20 mL×2). Then the combined organic phase was washed with brine (15 mL), dried over Na$_2$SO$_4$ and concentrated to give the crude product. The crude product was triturated from i-Pr$_2$O (5 mL) to give the product (20.93 mg, 0.05 mmol) as a solid. $^1$H NMR (400 MHz, DMSO-d$_6$+D$_2$O) $\delta_H$=8.57 (d, 1H), 8.24 (d, 1H), 8.20-8.15 (m, 1H), 8.11 (d, 1H), 7.91-7.58 (m, 2H), 4.56 (s, 2H), 3.37 (s, 3H). LCMS $R_f$=1.13 min in 2 min chromatography, 10-80AB, purity 100%, MS ESI calcd. for $C_{15}H_{12}F_5N_4O_2$ [M+H]$^+$ 375.1, found 375.0.

Example 134: Synthesis of Compound 147

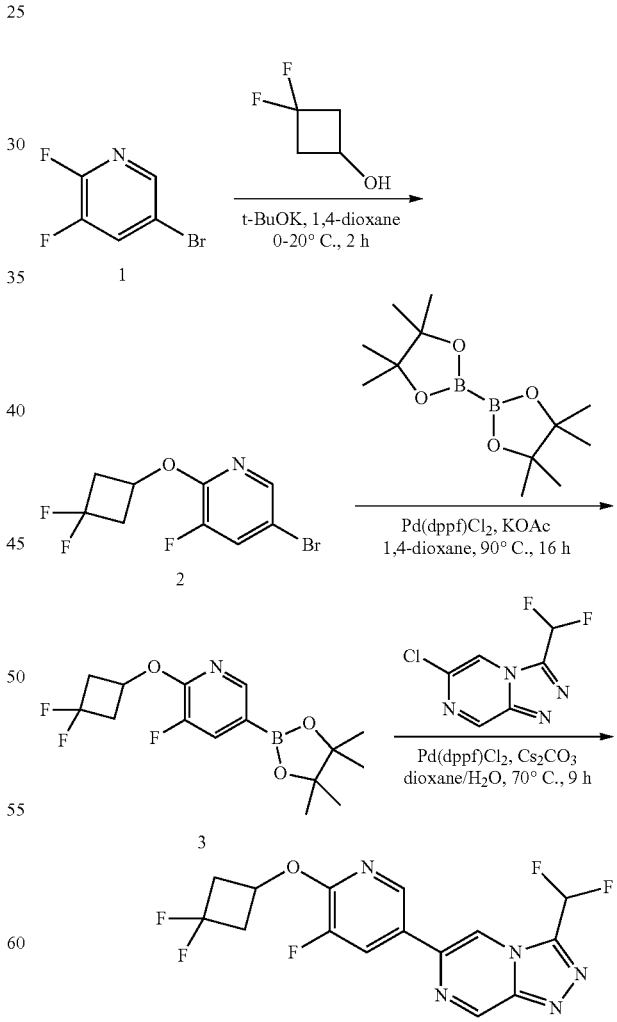

To a mixture of 5-bromo-2,3-difluoro-pyridine (750 mg, 3.87 mmol) and 3,3-difluorocyclobutanol (501.5 mg, 4.64 mmol) in 1,4-dioxane (10 mL) was added t-BuOK (867.69 mg, 7.73 mmol) under 0° C. Then the mixture was stirred at 20° C. for 2 hours. The reaction was quenched with sat.NH₄Cl (10 mL), and the mixture was extracted with EtOAc (20 mL×2). The combined organic phase was washed with brine (10 mL×2), dried over anhydrous Na₂SO₄, filtered and concentrated to give the crude product. The crude product was purified by flash chromatography on silica gel (PE) to give the product (930 mg, 3.29 mmol) as colorless oil. ¹H NMR (400 MHz, CDCl₃) δ$_H$=7.98 (d, 1H), 7.57-7.47 (m, 1H), 5.21-5.09 (m, 1H), 3.24-3.05 (m, 2H), 2.88-2.70 (m, 2H).

A mixture of 5-bromo-2-(3,3-difluorocyclobutoxy)-3-fluoro-pyridine (930 mg, 3.3 mmol), 4,4,5,5-tetramethyl-2-(4,4,5,5-tetramethyl-1,3,2-dioxaborolan-2-yl)-1,3,2-dioxaborolane (2.5 g, 9.89 mmol), KOAc (647.17 mg, 6.59 mmol) and Pd(dppf)Cl₂ (361.88 mg, 0.49 mmol) in 1,4-dioxane (20 mL) was stirred at 90° C. under N₂ for 16 hours to give a suspension. The mixture was cooled to room temperature and filtered through Celite. The filtrate was concentrated to give a residue. The residue was re-dissolved in EtOAc (50 mL), washed with water (30 mL×2), brine (30 mL×2), dried over anhydrous Na₂SO₄, filtered and concentrated to give the crude product. The crude product was purified by flash chromatography on silica gel (EtOAc in PE=0% to 3%) to give the product (1000 mg, 3.03 mmol) as a solid. ¹H NMR (400 MHz, CDCl₃) δ$_H$=8.25 (s, 1H), 7.66 (dd, 1H), 5.32-5.16 (m, 1H), 3.23-3.07 (m, 2H), 2.88-2.71 (m, 2H), 1.34 (s, 12H).

A mixture of 6-chloro-3-(difluoromethyl)-[1,2,4]triazolo[4,3-a]pyrazine (100 mg, 0.49 mmol), 2-(3,3-difluorocyclobutoxy)-3-fluoro-5-(4,4,5,5-tetramethyl-1,3,2-dioxaborolan-2-yl)pyridine (241.34 mg, 0.73 mmol), Cs₂CO₃ (318.54 mg, 0.98 mmol) and Pd(dppf)Cl₂ (53.65 mg, 0.07 mmol) in 1,4-dioxane (5 mL) and water (0.50 mL) was stirred at 70° C. under N₂ for 9 hours to give a suspension. The mixture was cooled to room temperature and filtered through Celite. The filtrate was concentrated to give a residue. The residue was re-dissolved in EtOAc (20 mL), washed with water (10 mL×2) and brine (10 mL×2), dried over anhydrous Na₂SO₄, filtered and concentrated to give the crude product. The crude product was purified by flash chromatography on silica gel (EtOAc in PE=10% to 30% to 50%) to give the impure product. The impure product was purified again by Prep-HPLC [Waters Xbridge (150 mm×25 mm, 5 μm) A=H₂O (10 mM NH₄HCO₃) and B=CH₃CN; 40-70% B over 6 minutes] to give the product (108.25 mg, 291.6 μmol) as a solid. ¹H NMR (400 MHz, DMSO-d₆) δ$_H$=9.68 (s, 1H), 9.25 (d, 1H), 8.74 (s, 1H), 8.44 (dd, 1H), 7.80 (t, 1H), 5.35-5.20 (m, 1H), 3.29-3.15 (m, 2H), 2.92-2.79 (m, 2H). LCMS R$_t$=1.16 min in 2.0 min chromatography, 10-80AB, purity 98.90%, MS ESI calcd. for C₁₅H₁₁F₅N₅O [M+H]⁺ 372.1, found 372.1.

Example 135: Synthesis of Compound 148

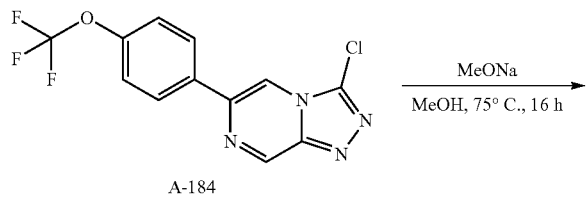

A-184

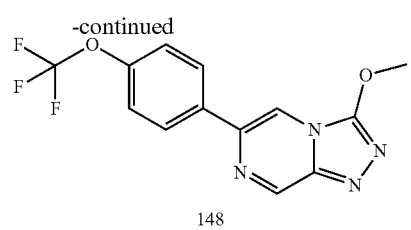

148

A mixture of sodium methoxide (15.45 mg, 0.29 mmol) and 3-chloro-6-[4-(trifluoromethoxy)phenyl]-[1,2,4]triazolo[4,3-a]pyrazine (30 mg, 0.10 mmol) in Methanol (3 mL) was stirred at 75° C. for 16 hours. After cooling to r.t., the mixture was concentrated, the residue was diluted with EtOAc (10 mL) and sat.NH₄Cl (10 mL), and extracted with EtOAc (10 mL×2). Then the combined organic phase was washed with brine (10 mL), dried over Na₂SO₄ and concentrated to give the crude product. The crude product was purified by Prep-HPLC (Waters Xbridge (150 mm×25 mm, 5 μm) A=H₂O (0.05% NH₄OH) and B=CH₃CN; 41-65% B over 6 minutes) to give the product (3.16 mg, 0.01 mmol) as a solid. ¹H NMR (400 MHz, DMSO-d₆) δ$_H$=9.31 (s, 1H), 8.72 (s, 1H), 8.22 (d, 2H), 7.48 (d, 2H), 4.32 (s, 3H). LCMS R$_t$=1.07 min in 2 min chromatography, 10-80AB, purity 100%, MS ESI calcd. for C₁₃H₁₀F₃N₄O₂ [M+H]⁺ 311.1, found 310.9.

Example 136: Synthesis of Compound 149

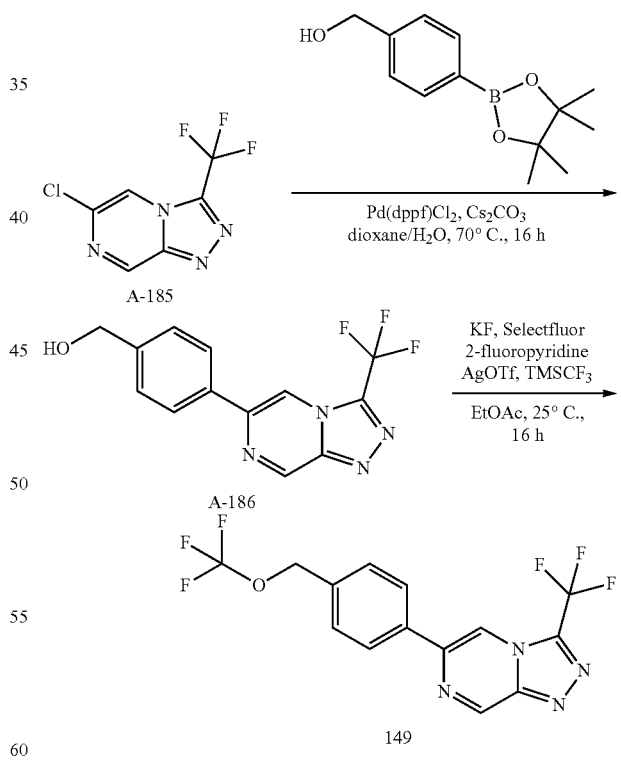

149

A mixture of 6-chloro-3-(trifluoromethyl)-[1,2,4]triazolo[4,3-a]pyrazine (100 mg, 0.45 mmol), [4-(4,4,5,5-tetramethyl-1,3,2-dioxaborolan-2-yl)phenyl]methanol (210.37 mg, 0.90 mmol), Pd(dppf)Cl₂ (32.88 mg, 0.04 mmol) and Cs₂CO₃ (292.77 mg, 0.90 mmol) in 1,4-dioxane (3 mL) and water (0.15 mL) was stirred at 70° C. for 16 hours. After cooling to r.t., the mixture was filtered through Celite, and eluted with EtOAc (10 mL×2). The filtrate was concentrated and diluted with EtOAc (10 mL), washed with water (10 mL×2) and brine (10 mL), dried over Na₂SO₄, filtered and concentrated to give the crude product. The crude product was purified by flash chromatography on silica gel (EtOAc in PE=30% to 80%) to give the product (29 mg, 0.10 mmol) as a solid. ¹H NMR (400 MHz DMSO-d₆) δ$_H$=9.76 (d, 1H), 8.96 (s, 1H), 8.15 (d, 2H), 7.49 (d, 2H), 5.31 (t, 1H), 4.58 (d, 2H). LCMS Rt=0.68 min in 1.5 min chromatography, 5-95AB, purity 100%, MS ESI calcd. for C$_{13}$H$_{10}$F$_3$N$_4$O [M+H]⁺ 295.1, found 294.9.

To a mixture of AgOTf (558.89 mg, 2.18 mmol), KF (157.97 mg, 2.72 mmol), Selectfluor (385.29 mg, 1.09 mmol) and [4-[3-(trifluoromethyl)-[1,2,4]triazolo[4,3-a] pyrazin-6-yl]phenyl]methanol (80 mg, 0.27 mmol) in ethyl acetate (6 mL) was added 2-fluoropyridine (211.19 mg, 2.18 mmol) and trimethyl(trifluoromethyl)silane (193.3 mg, 1.36 mmol) under N₂, then the mixture was stirred at 25° C. for 16 hours. The mixture was filtered through Celite, eluted with EtOAc (30 mL×2), the filtrate was concentrated to give the crude product. The crude product was purified by flash chromatography on silica gel (EtOAc in PE=0% to 50%) to give the impure product. The impure product was purified by Prep-HPLC (Waters Xbridge (150 mm×25 mm, 5 μm) A=H₂O (10 mM NH₄HCO₃) and B=CH₃CN; 42-72% B over 7 minutes) to give the product (3.34 mg, 9.2 μmol) as a solid. ¹H NMR (400 MHz CDCl₃) δ$_H$=9.61 (d, 1H), 8.44 (s, 1H), 8.03 (d, 2H), 7.56 (d, 2H), 5.09 (s, 2H). LCMS R$_t$=1.18 min in 2.0 min chromatography, 10-80AB, purity 100%, MS ESI calcd. for C$_{14}$H$_9$F$_6$N$_4$O [M+H]⁺ 363.1, found 363.0.

Example 137: Synthesis of Compound 150

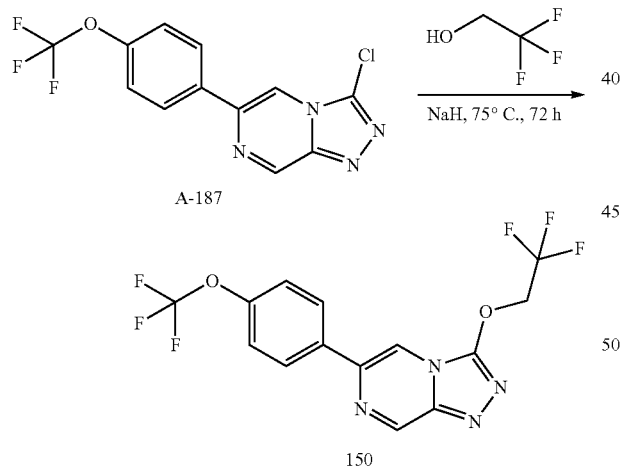

A solution of 2,2,2-trifluoroethanol (0.8 mL, 0.50 mmol) in THF (0.50 mL) was added NaH (59.98 mg, 1.50 mmol) at 0° C. Then 3-chloro-6-[4-(trifluoromethoxy)phenyl]-[1,2,4]triazolo[4,3-a]pyrazine (50 mg, 0.16 mmol) was added. The mixture was stirred at 75° C. for 72 hours. After cooling to r.t., the mixture was concentrated, the residue was diluted with EtOAc (15 mL) and NH₄Cl (15 mL), and extracted with EtOAc (15 mL×2). Then the combined organic phase was washed with brine (10 mL), dried over Na₂SO₄ and concentrated to give the crude product. The crude product was purified by Prep-HPLC (Waters Xbridge (150 mm×25 mm, 5 μm) A=H₂O (0.05% NH₄OH) and B=CH₃CN; 47-67% B over 6 minutes) to give the product (21.12 mg, 55.80 μmol) as a solid. ¹H NMR (400 MHz, DMSO-d₆) δ$_H$=9.38 (d, 1H), 8.79 (d, 1H), 8.26 (d, 2H), 7.49 (br d, 2H), 5.41 (q, 2H). LCMS R$_t$=1.18 min in 2 min chromatography, 10-80AB, purity 100%, MS ESI calcd. for C$_{14}$H$_9$F$_6$N$_4$O$_2$ [M+H]⁺ 379.1, found 379.0.

Example 138: Synthesis of Compounds 151 and 152

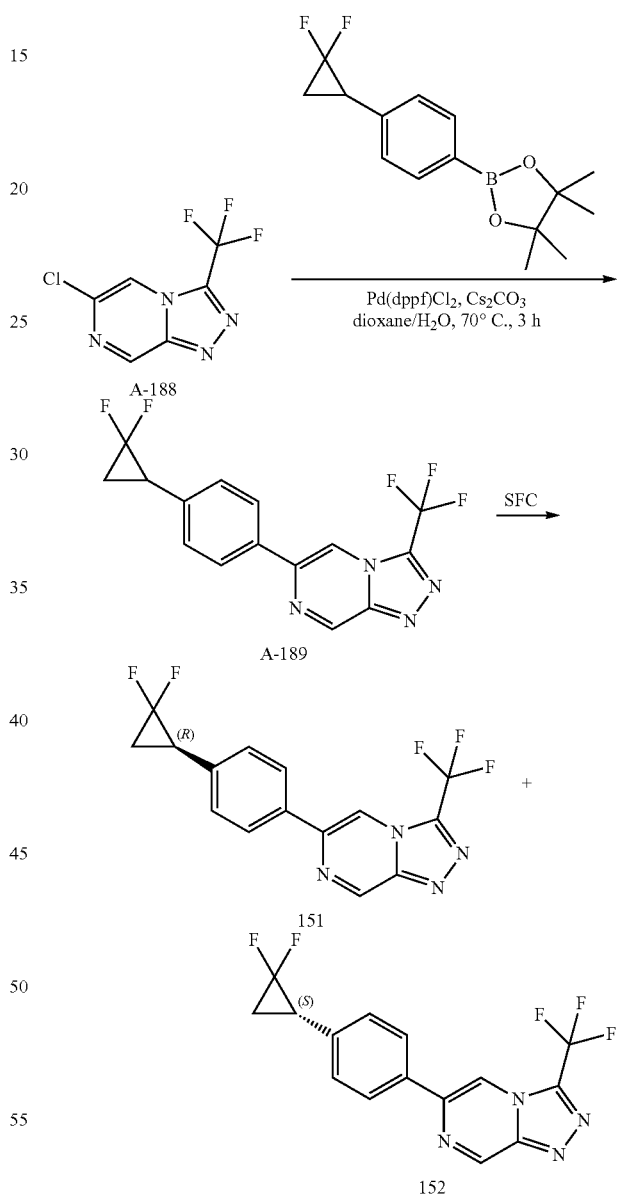

A mixture of 2-[4-(2,2-difluorocyclopropyl)phenyl]-4,4,5,5-tetramethyl-1,3,2-dioxaborolane (453.11 mg, 1.62 mmol), 6-chloro-3-(trifluoromethyl)-[1,2,4]triazolo[4,3-a]pyrazine (300 mg, 1.35 mmol), Pd(dppf)Cl₂ (197.26 mg, 0.27 mmol) and Cs₂CO₃ (878.32 mg, 2.7 mmol) in 1,4-dioxane (15 mL) and water (3 mL) was stirred at 70° C. for 3 hours. After cooling to r.t., the mixture was concentrated to a residue. The residue was diluted with H₂O (50 mL) and extracted with EtOAc (50 mL×2). The combined organic phase was washed with brine (50 mL), dried over Na₂SO₄, filtered and concentrated to give the crude product. The crude product was purified by flash chromatography on silica gel (EtOAc in PE=0% to 30%) to give the impure product. The impure product was purified by TLC (silica gel, PE:EtOAc=3:1) to give the product (50 mg). The product was analyzed by SFC and showed two peaks (Peak 1: Rt=2.96 min, Peak 2: Rt=3.30 min).

Method: Column: Chiralpak AD-3 150×4.6 mm I.D., 3 μm Mobile phase: A: $CO_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C.

The product was separated by SFC (DAICEL CHIRAL-PAK AD-H (250 mm×30 mm, 5 μm); A=$CO_2$ and B=methanol (0.1% $NH_3H_2O$ MeOH); 38° C.; 50 mL/min; 30% B; 12 min run; 15 injections, Rt of peak 1=8.47 min, Rt of Peak 2=10.63 min) to give the product of 6-[4-[(1R)-2,2-difluorocyclopropyl]phenyl]-3-(trifluoromethyl)-[1,2,4]triazolo[4,3-a]pyrazine (10.35 mg, 0.03 mmol, 20.7% yield, 100% purity) (Peak 1, Rt=2.96 min in SFC) as a solid and 6-[4-[(1S)-2,2-difluorocyclopropyl]phenyl]-3-(trifluoromethyl)-[1,2,4]triazolo[4,3-a]pyrazine (7.36 mg, 0.02 mmol, 14.56% yield, 98.94% purity) (Peak 2: Rt=3.30 min in SFC) as a solid.

Compound 151 (peak 1): ¹H NMR (400 MHz, CDCl₃) $δ_H$=9.60 (d, 1H), 8.41 (s, 1H), 7.95 (d, 2H), 7.41 (d, 2H), 2.90-2.79 (m, 1H), 1.98-1.88 (m, 1H), 1.77-1.68 (m, 1H). LCMS $R_t$=1.12 min in 2 min chromatography, 10-80AB, purity 100.00%, MS ESI calcd. for $C_{15}H_{10}F_5N_4$ [M+H]⁺ 341.1, found 341.0.

Compound 152 (peak 2): ¹H NMR (400 MHz, CDCl₃) $δ_H$=9.60 (d, 1H), 8.41 (s, 1H), 7.95 (d, 2H), 7.41 (d, 2H), 2.89-2.79 (m, 1H), 1.99-1.87 (m, 1H), 1.77-1.67 (m, 1H). LCMS $R_t$=1.13 min in 2 min chromatography, 10-80AB, purity 100.00%, MS ESI calcd. for $C_{15}H_{10}F_5N_4$ [M+H]⁺ 341.1, found 341.0.

Example 139: Synthesis of Compound 153

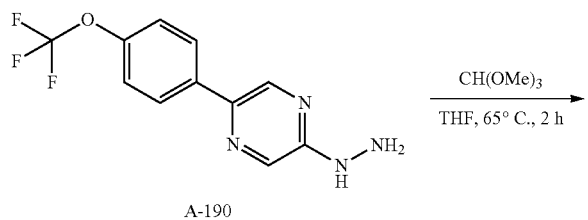

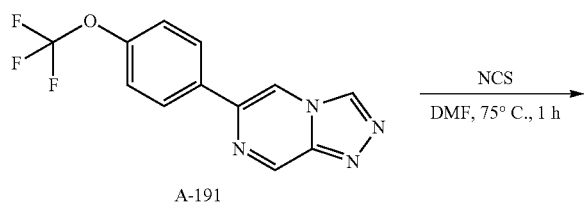

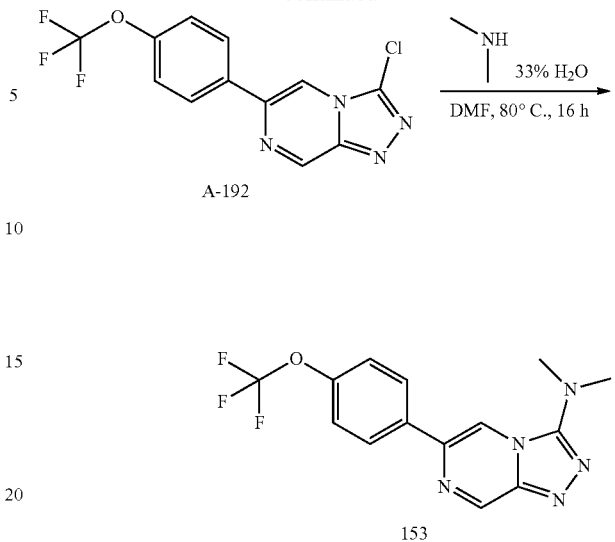

To a solution of [5-[4-(trifluoromethoxy)phenyl]pyrazin-2-yl]hydrazine (2 g, 7.40 mmol) in THF (20 mL) was added trimethoxymethane (3.93 g, 37.01 mmol) and TFA (0.55 mL, 7.40 mmol). The reaction mixture was stirred at 65° C. for 2 hours. After cooling to r.t., the reaction mixture was concentrated to remove most of THF, then diluted with sat.NaHCO₃ (30 mL). The mixture was extracted with EtOAc (30 mL×2). The combined organic phase was washed with brine (20 mL), dried over Na₂SO₄, filtered and concentrated to give the product (1600 mg, 5.71 mmol) as a solid. ¹H NMR (400 MHz DMSO-d₆) $δ_H$=9.54 (d, 1H), 9.46 (s, 1H), 9.23 (d, 1H), 8.16 (d, 2H), 7.54 (d, 2H).

A mixture of 6-[4-(trifluoromethoxy)phenyl]-[1,2,4]triazolo[4,3-a]pyrazine (1 g, 3.57 mmol) and NCS (619.50 mg, 4.64 mmol) in DMF (10 mL) was stirred at 75° C. for 1 hour. After cooling to r.t., the mixture was diluted with H₂O (20 mL), and the mixture was extracted with EtOAc (20 mL×2). The combined organic phase was washed with brine (20 mL), dried over Na₂SO₄, filtered and concentrated. The residue was purified by flash chromatography on silica gel (EtOAc in PE=0% to 10% to 30%) to give the product (105 mg, 0.33 mmol) as a solid. ¹H NMR (400 MHz, DMSO-d₆) $δ_H$=9.57 (d, 1H), 9.01 (d, 1H), 8.30 (d, 2H), 7.53 (d, 2H).

A solution of 3-chloro-6-[4-(trifluoromethoxy)phenyl]-[1,2,4]triazolo[4,3-a]pyrazine (60 mg, 0.19 mmol) in DMF (1 mL) was added N-methylmethanamine (1 mL, 0.19 mmol, 33% in H₂O). The mixture was stirred at 80° C. for 16 hours. After cooling to r.t., the mixture was concentrated, the residue was diluted with EtOAc (15 mL) and NH₄Cl (15 mL), then extracted with EtOAc (15 mL×2). Then the combined organic phase was washed with brine (15 mL), dried over Na₂SO₄ and concentrated to give the crude product. The crude product was purified by Prep-HPLC (Waters Xbridge (150 mm×25 mm, 5 μm) A=H₂O (0.05% NH₄OH) and B=CH₃CN; 47-57% B over 6 minutes) to give the product (7.29 mg, 22.60 μmol) as a solid. ¹H NMR (400 MHz, DMSO-d₆) $δ_H$=9.50 (d, 1H), 9.01 (d, 1H), 8.21 (d, 2H), 7.48 (d, 2H), 3.11 (s, 6H). LCMS $R_t$=1.18 min in 2 min chromatography, 10-80AB, purity 100%, MS ESI calcd. for $C_{14}H_{13}F_3N_5O$ [M+H]⁺ 324.1, found 324.0.

Example 140: Synthesis of Compound 154 and 155

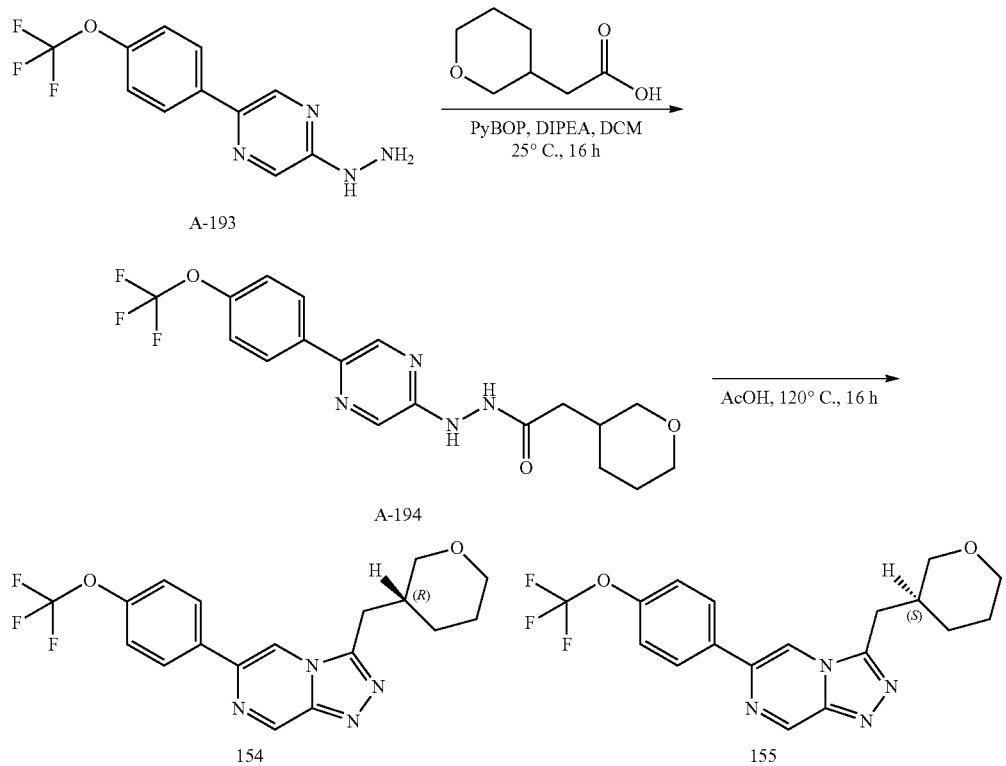

To a mixture of [5-[4-(trifluoromethoxy)phenyl]pyrazin-2-yl]hydrazine (200 mg, 0.74 mmol) and PyBOP (0.58 g, 1.11 mmol) in DCM (20 mL) was added the 2-tetrahydropyran-3-ylacetic acid (117.38 mg, 0.81 mmol) and DIPEA (0.39 mL, 2.22 mmol), and the mixture was stirred at 25° C. for 16 hours. The mixture was diluted with sat.NH$_4$Cl (80 mL), extracted with DCM (80 mL×2). The combined organic phase was washed with brine (40 mL), dried over Na$_2$SO$_4$ and filtered. The filtrate was concentrated to give the crude product (460 mg, 0.70 mmol) as oil, which was used directly in next step without any purification. LCMS R$_t$=0.84 min in 1.5 min chromatography, 5-95AB, purity 60.12%, MS ESI calcd. for C$_{18}$H$_{20}$F$_3$N$_4$O$_3$ [M+H]$^+$ 397.1, found 397.3.

A mixture of 2-tetrahydropyran-3-yl-N'-[5-[4-(trifluoromethoxy)phenyl]pyrazin-2-yl]acetohydrazide (460 mg, 1.16 mmol) in acetic acid (20 mL) was stirred at 120° C. for 16 hours. The mixture was cooled to r.t., and concentrated to give the crude product. The crude product was diluted with EtOAc (10 mL), then basified with sat.NaHCO$_3$ to pH=8-9, and extracted with EtOAc (20 mL×2). The combined organic phase was washed with brine (15 mL), dried over Na$_2$SO$_4$, filtered and concentrated to give the crude product. The crude product was purified by Prep-HPLC (Waters Xbridge 150 mm×25 mm, 5 μm, A=H$_2$O (10 mM NH$_4$HCO$_3$) and B=CH$_3$CN; 40-70% B over 6 minutes) to give the product (90 mg, 0.24 mmol) as a solid. The product was analysed by SFC and showed two peaks (Peak 1 Rt=3.67 min, Peak 2 Rt=4.25 min).

Method: Column: Chiralcel OJ-H 150 mm×4.6 mm I.D., 5 μm, Mobile phase: A:CO$_2$ B: ethanol (0.05% DEA), Gradient: hold 5% for 0.5 min, then from 5% to 40% of B in 3.5 min and hold 40% for 2.5 min, then 5% of B for 1.5 min, Flow rate: 3 mL/min Column temp:40° C.

The product was separated by SFC (DAICEL CHIRALCEL OJ-H (250 mm×30 mm, 5 μm); A=CO$_2$ and B=EtOH (0.1% NH$_3$H$_2$O); 35° C.; 60 mL/min; 40% B; 9 min run; 14 injections, Rt of peak 1=4.80 min, Rt of Peak 2=7.10 min) to give the product of 3-[[(3R)-tetrahydropyran-3-yl]methyl]-6-[4-(trifluoromethoxy)phenyl]-[1,2,4]triazolo[4,3-a]pyrazine (44.32 mg, 0.12 mmol) (Peak 1, Rt=3.67 min in SFC) as a solid and 3-[[(3S)-tetrahydropyran-3-yl]methyl]-6-[4-(trifluoromethoxy)phenyl]-[1,2,4]triazolo[4,3-a]pyrazine (32.91 mg, 86.6 μmol) (Peak 2, Rt=4.25 min in SFC) as a solid.

Note: the enantiomers were randomly assigned.

Compound 154 (peak 1): $^1$H NMR (400 MHz, DMSO-d$_6$+D$_2$O) δ$_H$=9.35 (d, 1H), 8.86 (d, 1H), 8.13 (d, 2H), 7.45 (d, 2H), 3.83-3.76 (m, 1H), 3.72-3.65 (m, 1H), 3.36-3.28 (m, 1H), 3.23-3.16 (m, 1H), 3.14-3.01 (m, 2H), 2.18-2.08 (m, 1H), 1.77-1.69 (m, 1H), 1.60-1.52 (m, 1H), 1.48-1.38 (m, 1H), 1.34-1.24 (m, 1H).

LCMS R$_t$=1.10 min in 2.0 min chromatography, 10-80AB, purity 100%, MS ESI calcd. for C$_{18}$H$_{18}$F$_3$N$_4$O$_2$ [M+H]$^+$ 379.1, found 379.1.

Compound 155 (peak 2): $^1$H NMR (400 MHz, DMSO-d$_6$+D$_2$O) δ$_H$=9.37 (d, 1H), 8.89 (d, 1H), 8.15 (d, 2H), 7.47 (d, 2H), 3.83-3.76 (m, 1H), 3.74-3.65 (m, 1H), 3.36-3.28 (m, 1H), 3.23-3.16 (m, 1H), 3.15-3.02 (m, 2H), 2.19-2.06 (m, 1H), 1.79-1.69 (m, 1H), 1.60-1.52 (m, 1H), 1.49-1.38 (m, 1H), 1.35-1.24 (m, 1H).

LCMS R$_t$=1.10 min in 2.0 min chromatography, 10-80AB, purity 100%, MS ESI calcd. for C$_{18}$H$_{18}$F$_3$N$_4$O$_2$ [M+H]$^+$ 379.1, found 379.0.

Example 141: Synthesis of Compound 156

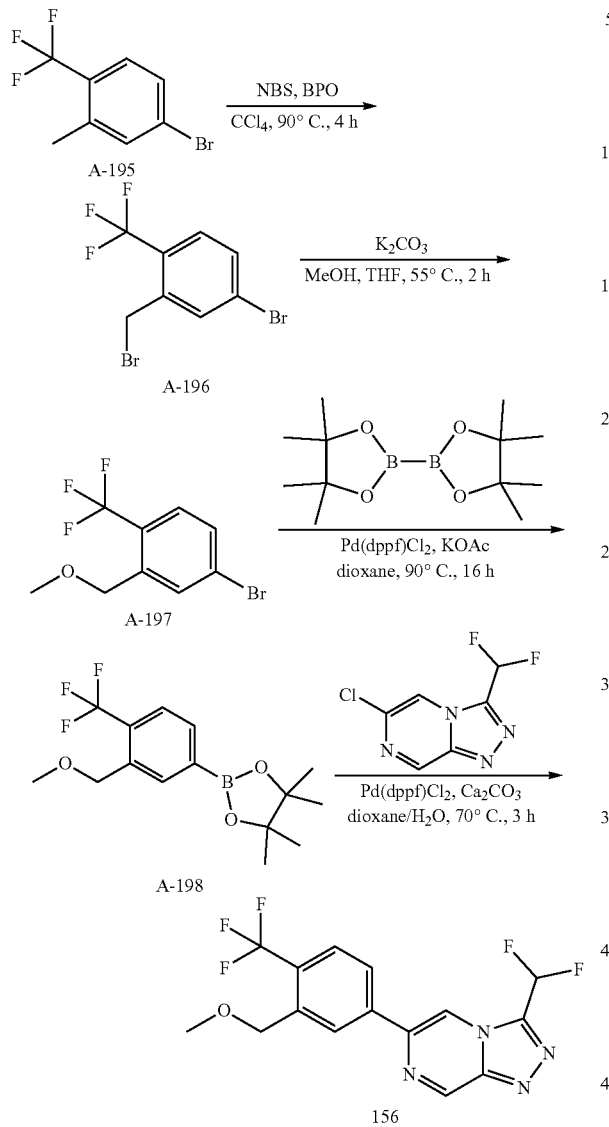

A mixture of 4-bromo-2-methyl-1-(trifluoromethyl)benzene (3 g, 12.55 mmol), NBS (2.23 g, 12.55 mmol) and BPO (152.01 mg, 0.63 mmol) in carbon tetrachloride (40 mL) was stirred at 90° C. for 4 hours. After cooling to 0° C., the mixture was filtered through Celite and elute with $CH_2Cl_2$ (20 mL×2). The filtrate was concentrated to give the crude product. The crude product was purified by flash chromatography (PE) to give the product (3400 mg, 10.69 mmol) as colorless oil. $^1$H NMR (400 MHz, CDCl$_3$) δ$_H$=7.76 (s, 1H), 7.59-7.54 (m, 1H), 7.53-7.50 (m, 1H), 4.58 (s, 2H).

A mixture of $K_2CO_3$ (2.61 g, 18.87 mmol) and 4-bromo-2-(bromomethyl)-1-(trifluoromethyl)benzene (3 g, 9.44 mmol) in THF (60 mL) and methanol (60 mL) was stirred at 55° C. for 2 hours. After cooling to r.t., the mixture was concentrated to a residue. The residue was diluted with $H_2O$ (50 mL) and extracted with EtOAc (50 mL×2). The combined organic phase was washed with brine (50 mL), dried over $Na_2SO_4$, filtered and concentrated to give the crude product. The crude product was purified by flash chromatography on silica gel (PE) to give the product (1500 mg, 5.57 mmol) as colorless oil. $^1$H NMR (400 MHz, CDCl$_3$) δ$_H$=7.87 (s, 1H), 7.55-7.47 (m, 2H), 4.62 (s, 2H), 3.48 (s, 3H).

A mixture of 4-bromo-2-(methoxymethyl)-1-(trifluoromethyl)benzene (1500 mg, 5.57 mmol), 4,4,5,5-tetramethyl-2-(4,4,5,5-tetramethyl-1,3,2-dioxaborolan-2-yl)-1,3,2-dioxaborolane (4247.12 mg, 16.72 mmol), Pd(dppf)Cl$_2$ (815.84 mg, 1.11 mmol) and KOAc (1094.25 mg, 11.15 mmol) in 1,4-Dioxane (50 mL) was stirred at 90° C. for 16 hours. After cooling to r.t., the mixture was concentrated to a residue. The residue was diluted with $H_2O$ (100 mL) and extracted with EtOAc (100 mL×2). The combined organic phase was washed with brine (50 mL), dried over $Na_2SO_4$, filtered and concentrated to give the crude product. The crude product was purified by flash chromatography on silica gel (EtOAc in PE=0 to 2%) to give the product (800 mg, 2.5307 mmol) as oil. $^1$H NMR (400 MHz, CDCl$_3$) δ$_H$=8.00 (s, 1H), 7.73 (d, 1H), 7.56 (d, 1H), 4.56 (s, 2H), 3.38 (s, 3H), 1.28 (s, 12H).

A mixture of 2-[3-(methoxymethyl)-4-(trifluoromethyl)phenyl]-4,4,5,5-tetramethyl-1,3,2-dioxaborolane (154.54 mg, 0.49 mmol), 6-chloro-3-(difluoromethyl)-[1,2,4]triazolo[4,3-a]pyrazine (100 mg, 0.49 mmol), Pd(dppf)Cl$_2$ (71.54 mg, 0.10 mmol) and Cs$_2$CO$_3$ (318.54 mg, 0.98 mmol) in water (0.50 mL) and 1,4-dioxane (3 mL) was stirred at 70° C. for 3 hours under N$_2$. After cooling to r.t, the mixture was filtered through silica gel and eluted with EtOAc (5 mL×2). The filtrate was concentrated and diluted with EtOAc (20 mL), washed with water (10 mL×2) and brine (10 mL), dried over Na$_2$SO$_4$, filtered and concentrated to give the crude product. The crude product was purified by Prep-HPLC [Waters Xbridge (150 mm×25 mm, 5 μm) A=H$_2$O (0.05% NH$_3$H$_2$O) and B=CH$_3$CN; 47-77% B over 7 minutes] to give the product (35.94 mg, 0.10 mmol) as a solid. $^1$H NMR (400 MHz, DMSO-d$_6$) δ$_H$=9.72 (d, 1H), 9.35 (s, 1H), 8.45 (s, 1H), 8.26 (br d, 1H), 8.03-7.73 (m, 2H), 4.67 (s, 2H), 3.42 (s, 3H). LCMS R$_t$=1.09 min in 2.0 min chromatography, 10-80AB, purity 100.00%, MS ESI calcd. for C$_{15}$H$_{12}$F$_5$N$_4$O [M+H]$^+$359.1, found 359.0.

Example 142: Synthesis of Compound 157

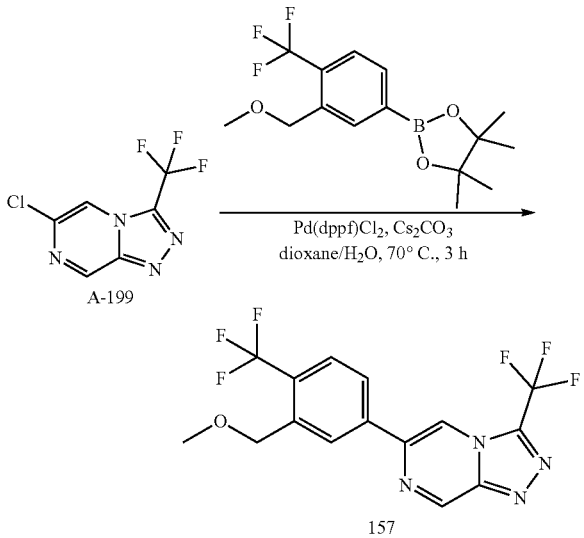

A mixture of 2-[3-(methoxymethyl)-4-(trifluoromethyl)phenyl]-4,4,5,5-tetramethyl-1,3,2-dioxaborolane (142.04 mg, 0.45 mmol), 6-chloro-3-(trifluoromethyl)-[1,2,4]triazolo[4,3-a]pyrazine (100 mg, 0.45 mmol), Pd(dppf)Cl$_2$ (65.75 mg, 0.09 mmol) and Cs$_2$CO$_3$ (292.77 mg, 0.90 mmol) in 1,4-dioxane (3 mL) and water (0.50 mL) was stirred at 70° C. for 3 hours. After cooling to r.t., the mixture was filtered through silica gel and eluted with EtOAc (5 mL×2). The filtrate was concentrated and diluted with EtOAc (20 mL), washed with water (10 mL×2) and brine (10 mL), dried over Na$_2$SO$_4$, filtered and concentrated to give the crude product. The crude product was purified by Prep-HPLC [Waters Xbridge (150 mm×25 mm, 5 μm) A=H$_2$O (0.05% NH$_3$H$_2$O) and B=CH$_3$CN; 50-80% B over 7 minutes] to give the product (48.22 mg, 0.12 mmol) as a solid. $^1$H NMR (400 MHz, CDCl$_3$) δ$_H$=9.63 (d, 1H), 8.51 (s, 1H), 8.30 (s, 1H), 8.03 (d, 1H), 7.83 (d, 1H), 4.75 (s, 2H), 3.55 (s, 3H). LCMS R$_t$=1.14 min in 2.0 min chromatography, 10-80AB, purity 98.25%, MS ESI calcd. for C$_{15}$H$_{11}$F$_6$N$_4$O [M+H]$^+$ 377.1, found 377.0.

Example 143: Synthesis of Compound 158

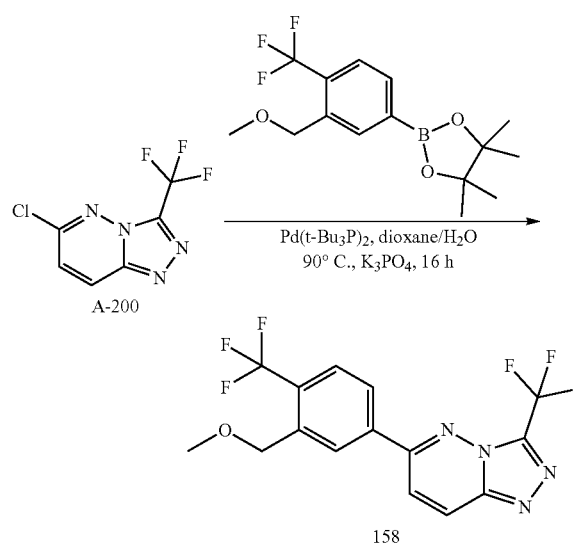

A mixture of 6-chloro-3-(trifluoromethyl)-[1,2,4]triazolo[4,3-b]pyridazine (100 mg, 0.45 mmol), 2-[3-(methoxymethyl)-4-(trifluoromethyl)phenyl]-4,4,5,5-tetramethyl-1,3,2-dioxaborolane (142.04 mg, 0.45 mmol), Pd(t-Bu$_3$P)$_2$ (45.92 mg, 0.09 mmol) and K$_3$PO$_4$ (190.78 mg, 0.90 mmol) in 1,4-dioxane (3 mL) and water (0.50 mL) was stirred at 90° C. for 16 hours. After cooling to r.t., the mixture was filtered through silica gel and eluted with EtOAc (5 mL×2). The filtrate was concentrated and diluted with EtOAc (20 mL), washed with water (10 mL×2) and brine (10 mL), dried over Na$_2$SO$_4$, filtered and concentrated to give the crude product. The crude product was purified by Prep-HPLC [Xtimate C18 (150 mm×25 mm, 5 μm) A=H$_2$O (0.04% NH$_3$H$_2$O+10 mM NH$_4$HCO$_3$) and B=CH$_3$CN; 43-73% B over 8.5 minutes] to give the product (64.83 mg, 0.17 mmol) as a solid. $^1$H NMR (400 MHz, CDCl$_3$) δ$_H$=8.36 (d, 1H), 8.31 (s, 1H), 8.08 (d, 1H), 7.88-7.80 (m, 2H), 4.76 (s, 2H), 3.55 (s, 3H). LCMS R$_t$=1.16 min in 2.0 min chromatography, 10-80AB, purity 100.00%, MS ESI calcd. for C$_{15}$H$_{11}$F$_6$N$_4$O [M+H]$^+$ 377.1, found 377.1.

Example 144: Synthesis of Compound 159

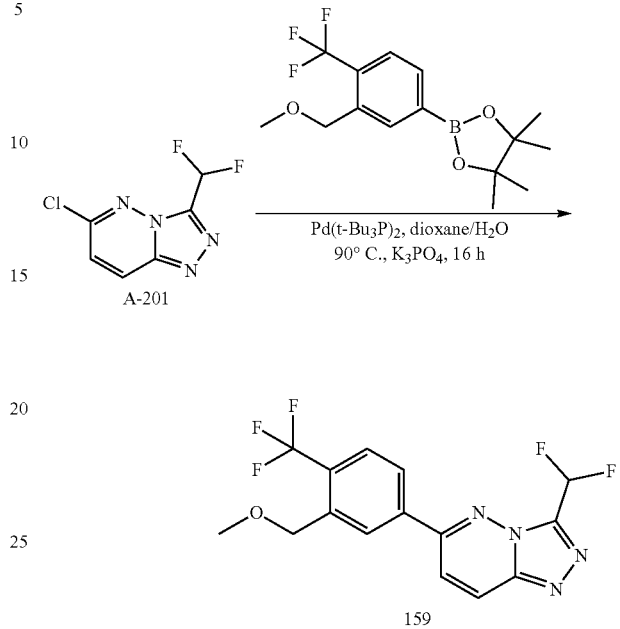

A mixture of 6-chloro-3-(difluoromethyl)-[1,2,4]triazolo[4,3-b]pyridazine (100 mg, 0.49 mmol), 2-[3-(methoxymethyl)-4-(trifluoromethyl)phenyl]-4,4,5,5-tetramethyl-1,3,2-dioxaborolane (154.54 mg, 0.49 mmol), Pd(t-Bu$_3$P)$_2$ (49.97 mg, 0.10 mmol) and K$_3$PO$_4$ (207.57 mg, 0.98 mmol) in 1,4-dioxane (3 mL) and water (0.50 mL) was stirred at 90° C. for 16 hours. After cooling to r.t., the mixture was filtered through silica gel and eluted with EtOAc (5 mL×2). The filtrate was concentrated and diluted with EtOAc (20 mL), washed with water (10 mL×2) and brine (10 mL), dried over Na$_2$SO$_4$, filtered and concentrated to give the crude product. The crude product was purified by Prep-HPLC [Xtimate C18 (150 mm×25 mm, 5 μm) A=H$_2$O (0.04% NH$_3$H$_2$O+10 mM NH$_4$HCO$_3$) and B=CH$_3$CN; 35-65% B over 8.5 minutes] to give the product (58.03 mg, 0.16 mmol) as a solid. $^1$H NMR (400 MHz, DMSO-d$_6$) δ$_H$=8.67 (d, 1H), 8.38 (s, 1H), 8.25 (br d, 1H), 8.19 (d, 1H), 7.99 (d, 1H), 7.80 (t, 1H), 4.69 (s, 2H), 3.42 (s, 3H). LCMS R$_t$=1.09 min in 2.0 min chromatography, 10-80AB, purity 100.00%, MS ESI calcd. for C$_{15}$H$_{12}$F$_5$N$_4$O [M+H]$^+$ 359.1, found 359.0.

Example 145: Synthesis of Compounds 160 and 161

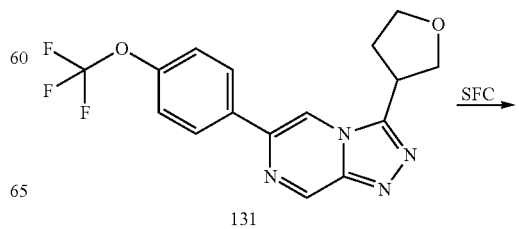

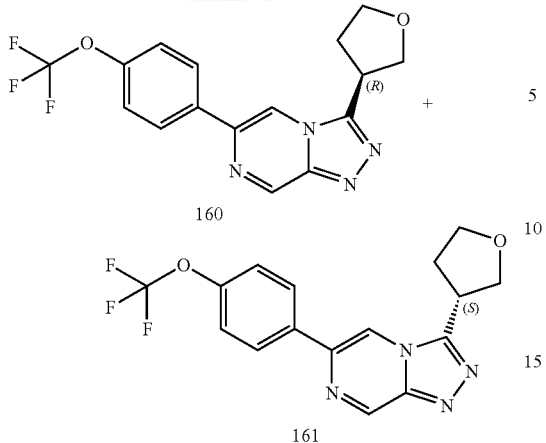

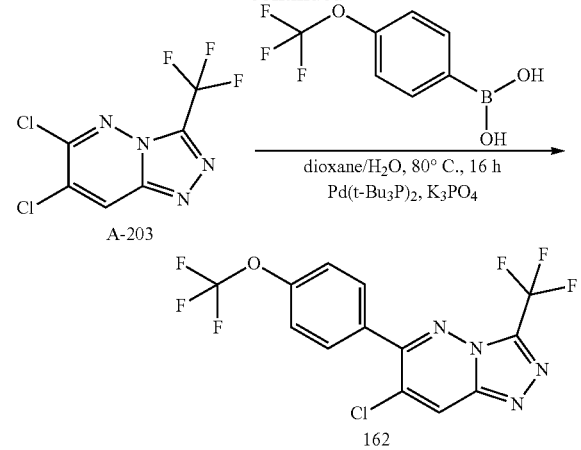

The product of 3-tetrahydrofuran-3-yl-6-[4-(trifluoromethoxy)phenyl]-[1,2,4]triazolo[4,3-a]pyrazine (110 mg, 0.31 mmol) was analyzed by SEC which showed two peaks (Peak 1: Rt=3.96 min, Peak 2: Rt=5.29 min).

(Method: Column: Chiralpak AD-3, 150×4.6 mm I.D., 3 μm; Mobile phase: 40% of EtOH (0.05% DEA) in $CO_2$, Flow rate: 2.5 mL/min Column temperature: 35° C.).

The product was purified by SFC (YMC CHIRAL (250 mm×30 mm I.D., 5 μm); A=$CO_2$ and B=EtOH (0.1% $NH_3H_2O$); 38° C.; 60 mL/min; 35% B; 8 min run; 7 injections, Rt of Peak 1=3.9 min, Rt of Peak 2=6.4 min) to give the product of 3-[(3R)-tetrahydrofuran-3-yl]-6-[4-(trifluoromethoxy)phenyl]-[1,2,4]triazolo[4,3-a]pyrazine (26.81 mg, 0.08 mmol) (Peak 1, Rt=3.96 min in SFC) as a solid, and 3-[(3S)-tetrahydrofuran-3-yl]-6-[4-(trifluoromethoxy)phenyl]-[1,2,4]triazolo[4,3-a]pyrazine (39.04 mg, 0.11 mmol) (Peak 2: Rt=5.29 min in SFC) as a solid.

Note: the enantiomers were randomly assigned.

Compound 160 (peak 1): $^1$H NMR (400 MHz, $CDCl_3$) $δ_H$=9.42 (d, 1H), 8.36 (d, 1H), 8.03-7.98 (m, 2H), 7.38 (d, 2H), 4.31-4.23 (m, 3H), 4.14-3.95 (m, 2H), 2.66-2.53 (m, 1H), 2.51-2.35 (m, 1H).

LCMS $R_t$=1.05 min in 2.0 min chromatography, 10-80AB, purity 100%, MS ESI calcd. for $C_{16}H_{14}F_3N_4O_2$ [M+H]$^+$ 351.1, found 351.0.

Compound 161 (peak 2): $^1$H NMR (400 MHz, $CDCl_3$) $δ_H$=9.43 (d, 1H), 8.36 (d, 1H), 8.07-7.90 (m, 2H), 7.38 (d, 2H), 4.33-4.22 (m, 3H), 4.15-3.97 (m, 2H), 2.67-2.54 (m, 1H), 2.51-2.32 (m, 1H).

LCMS $R_t$=1.06 min in 2.0 min chromatography, 10-80AB, purity 100%, MS ESI calcd. for $C_{16}H_{14}F_3N_4O_2$ [M+H]$^+$ 351.1, found 351.0.

Example 146: Synthesis of Compound 162

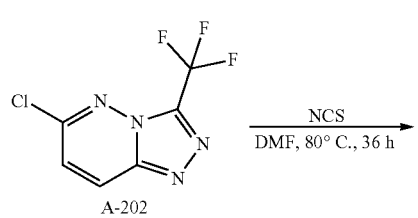

To a mixture of 6-chloro-3-(trifluoromethyl)-[1,2,4]triazolo[4,3-b]pyridazine (3 g, 13.48 mmol) in DMF (45 mL) was added NCS (14.4 g, 107.84 mmol), then the mixture was stirred at 80° C. for 36 hours. After cooling to r.t., the mixture was diluted with $H_2O$ (100 mL), and the mixture was extracted with EtOAc (100 mL×2). The combined organic phase was washed with water (50 mL×2) and brine (50 mL), dried over $Na_2SO_4$, filtered and concentrated to give the crude product. The crude product was purified by flash chromatography on silica gel (EtOAc in PE=0% to 10% to 20%) to give the product (480 mg, 1.83 mmol) as a solid. LCMS $R_t$=0.72 min in 1.5 min chromatography, 5-95AB, purity 98.13%, MS ESI calcd. for $C_6H_2Cl_2F_3N_4$ [M+H]$^+$ 257.0, found 256.9.

A mixture of 6,7-dichloro-3-(trifluoromethyl)-[1,2,4]triazolo[4,3-b]pyridazine (200 mg, 0.78 mmol), [4-(trifluoromethoxy)phenyl]boronic acid (144.23 mg, 0.70 mmol), $K_3PO_4$ (330.43 mg, 1.56 mmol) and Pd(t-$Bu_3P$)$_2$ (59.66 mg, 0.12 mmol) in 1,4-dioxane (15 mL) and water (1.5 mL) was stirred at 80° C. under $N_2$ for 16 hours to give a suspension. After cooling to room temperature, the mixture was filtered through Celite. The filtrate was concentrated to give a residue. The residue was diluted with water (20 mL), extracted with EtOAc (20 mL×2). The combined organic layer was washed with water (10 mL×2), brine (15 mL×2), dried over anhydrous $Na_2SO_4$, filtered and concentrated to give the crude product. The crude product was purified by Prep-TLC (silica gel, PE:EtOAc=1:1) to give the product (43.58 mg, 112.9 μmol) as a solid. $^1$H NMR (400 MHz, $CDCl_3$) $δ_H$=8.39 (s, 1H), 7.79 (d, 2H), 7.42 (d, 2H). LCMS Rt=1.19 min in 2.0 min chromatography, 10-80AB, purity 100.00%, MS ESI calcd. for $C_{13}H_6ClF_6N_4O$ [M+H]$^+$ 383.0, found 383.0.

Example 147: Synthesis of Compound 163

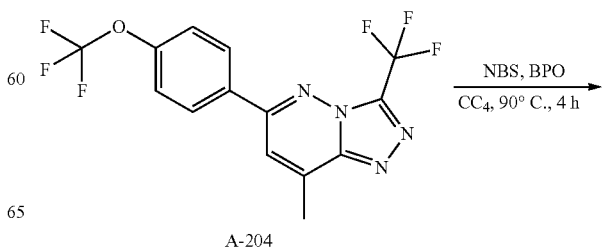

-continued

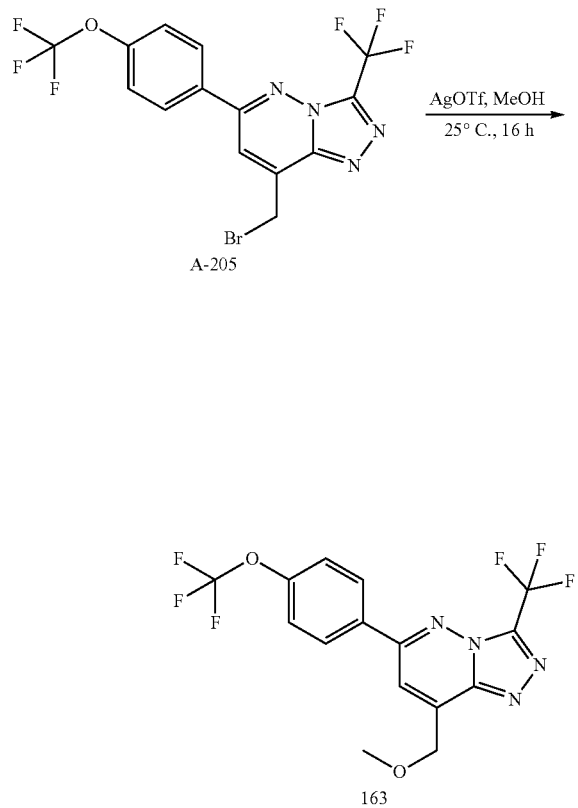

Example 148: Synthesis of Compounds 164 and 165

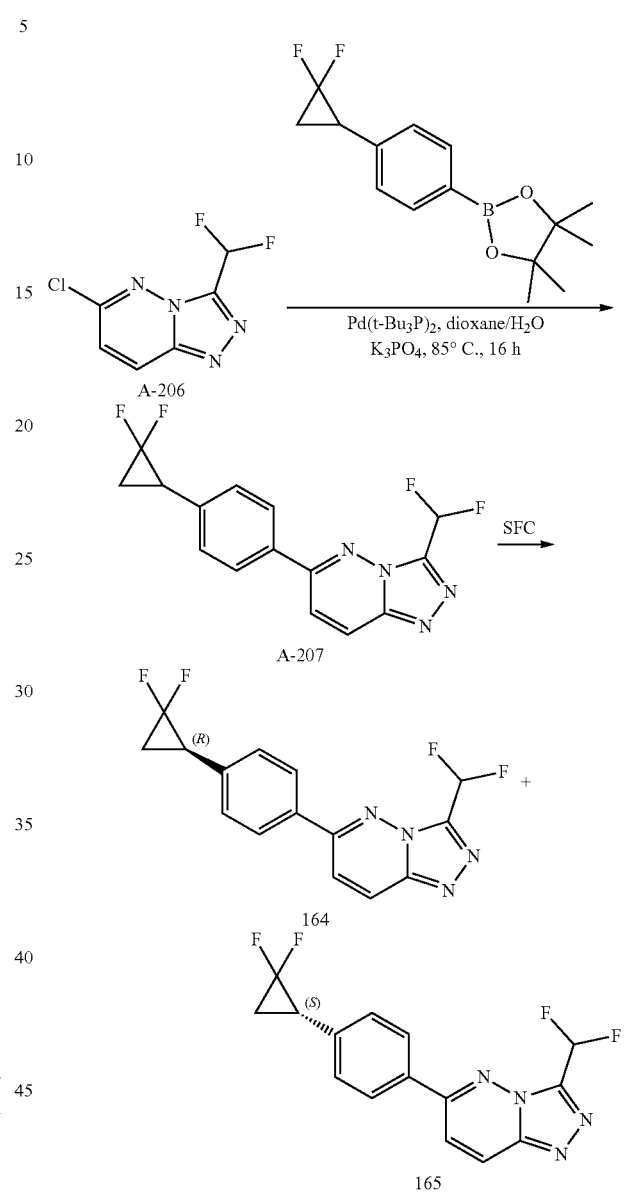

To a mixture of 8-methyl-6-[4-(trifluoromethoxy)phenyl]-3-(trifluoromethyl)-[1,2,4]triazolo[4,3-b]pyridazine (420 mg, 1.16 mmol) in carbon tetrachloride (10 mL) was added NBS (309.55 mg, 1.74 mmol) and BPO (280.86 mg, 1.16 mmol), then the mixture was stirred at 90° C. for 4 hours. After cooling to r.t., the mixture was diluted with H$_2$O (30 mL), and the mixture was extracted with EtOAc (50 mL×2). The combined organic phase was washed with water (20 mL) and brine (20 mL), dried over Na$_2$SO$_4$, filtered and concentrated to give the crude product. The crude product was purified by Prep-TLC (silica gel, PE:EtOAc=2:1) to give the impure product (160 mg, 0.33 mmol) as a solid. LCMS Rt=0.89 min in 1.5 min chromatography, 5-95AB, purity 92.18%, MS ESI calcd. for C$_{14}$H$_8$BrF$_6$N$_4$O [M+H+2]$^+$443.0, found 442.8.

The mixture of 8-(bromomethyl)-6-[4-(trifluoromethoxy)phenyl]-3-(trifluoromethyl)-[1,2,4]triazolo[4,3-b]pyridazine (65 mg, 0.15 mmol) and AgOTf (567.9 mg, 2.21 mmol) in Methanol (6 mL) was stirred at 25° C. for 16 hours. The mixture was filtered through Celite, eluted with EtOAc (10 mL×2), the organic phase was washed with sat.NaHCO$_3$ (20 mL), water (20 mL) and brine (20 mL), dried over Na$_2$SO$_4$, filtered and concentrated to give the crude product. The crude product was purified by Prep-TLC (silica gel, PE:EtOAc=2:1) to give the product (40.89 mg, 104.2 μmol) as a solid. $^1$H NMR (400 MHz, CDCl$_3$) δ$_H$=8.12 (d, 2H), 7.86 (t, 1H), 7.42 (d, 2H), 5.08 (d, 2H), 3.66 (s, 3H). LCMS R$_t$=1.32 min in 2.0 min chromatography, 10-80AB, purity 100%, MS ESI calcd. for C$_{15}$H$_{11}$F$_6$N$_4$O$_2$ [M+H]$^+$ 393.1, found 392.9.

A mixture of 6-chloro-3-(difluoromethyl)-[1,2,4]triazolo[4,3-b]pyridazine (200 mg, 0.98 mmol), 2-[4-(2,2-difluorocyclopropyl)phenyl]-4,4,5,5-tetramethyl-1,3,2-dioxaborolane (328.65 mg, 1.17 mmol), Pd(t-Bu$_3$P)$_2$ (74.95 mg, 0.15 mmol) and K$_3$PO$_4$ (415.13 mg, 1.96 mmol) in 1,4-Dioxane (4 mL) and Water (0.4 mL) was stirred at 85° C. for 16 hours under N$_2$. After cooling to r.t., the mixture was concentrated and diluted with H$_2$O (10 mL), and the mixture was extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 35% to 70% to 100%) to give the product (90 mg, 0.27 mmol) as a solid. The product was analyzed by SFC, and showed two peaks (Peak 1: Rt=7.65 min, Peak 2: Rt=8.6 min).

Method: Chiralcel AD-3 150×4.6 mm I.D., 3 μm, mobile phase: A: CO₂ B: methanol (0.05% DEA), Flow rate: 2.5 mL/min Column temperature: 35° C.

LCMS R$_t$=1.07 min in 2.0 min chromatography, 10-80AB, purity 95.93%, MS ESI calcd. for C$_{15}$H$_{11}$F$_4$N$_4$ [M+H]⁺ 323.1, found 323.0.

The product was separated by SFC (DAICEL CHIRAL-PAK AD-H (250 mm×30 mm, 5 μm); A=CO₂ and B=MeOH (0.1% NH₃H₂O); 38° C.; 50 mL/min; 30% B; 10 min run; 24 injections, Rt of Peak 1=7.65 min, Rt of Peak 2=8.6 min) to give 6-[4-[(1R)-2,2-difluorocyclopropyl]phenyl]-3-(difluoromethyl)-[1,2,4]triazolo[4,3-b]pyridazine (22.39 mg, 0.07 mmol) (Peak 1, Rt=3.90 min in SFC) as a solid and 6-[4-[(1S)-2,2-difluorocyclopropyl]phenyl]-3-(difluoromethyl)-[1,2,4]triazolo[4,3-b]pyridazine (29.99 mg, 0.09 mmol) (Peak 2: Rt=4.17 min in SFC) as a solid.

Note: the enantiomers were randomly assigned.

Compound 164 (peak 1): ¹H NMR (400 MHz, DMSO-d₆) δ$_H$=8.60 (d, 1H), 8.20-8.07 (m, 3H), 7.78 (t, 1H), 7.52 (d, 2H), 3.23-3.06 (m, 1H), 2.21-1.96 (m, 2H). LCMS R$_t$=1.07 min in 2.0 min chromatography, 10-80AB, purity 100%, MS ESI calcd. for C$_{15}$H$_{11}$F$_4$N$_4$ [M+H]⁺ 323.1, found 322.9.

Compound 165 (peak 2): ¹H NMR (400 MHz, DMSO-d₆) δ$_H$=8.61 (d, 1H), 8.19-8.06 (m, 3H), 7.78 (t, 1H), 7.53 (d, 2H), 3.23-3.08 (m, 1H), 2.18-2.00 (m, 2H). LCMS R$_t$=1.06 min in 2.0 min chromatography, 10-80AB, purity 100%, MS ESI calcd. for C$_{15}$H$_{11}$F$_4$N$_4$ [M+H]⁺ 323.1, found 323.0.

Example 149: Synthesis of Compounds 166 and 167

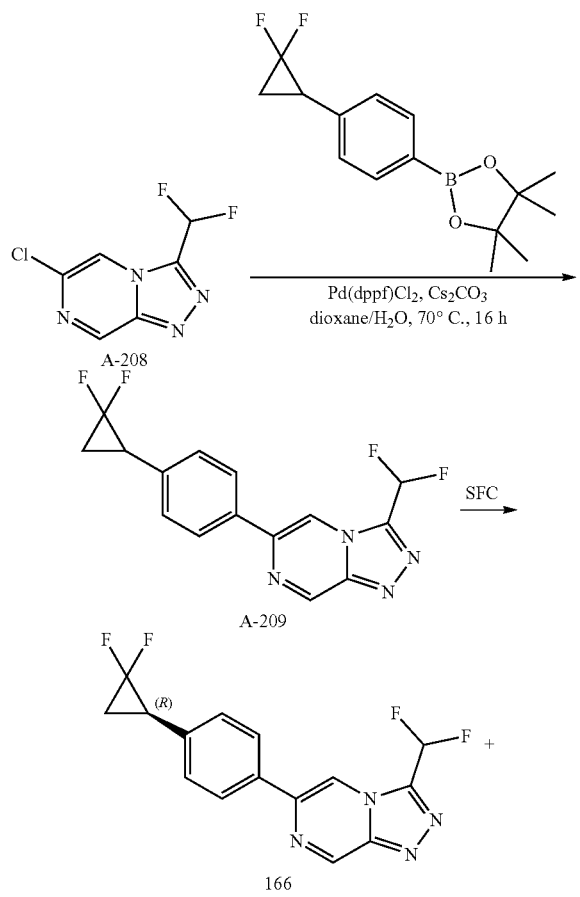

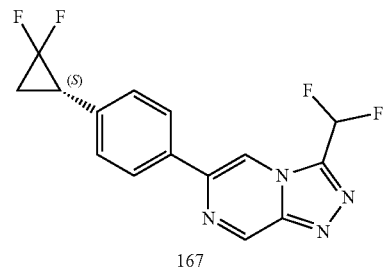

A mixture of 6-chloro-3-(difluoromethyl)-[1,2,4]triazolo[4,3-a]pyrazine (200 mg, 0.98 mmol), 2-[4-(2,2-difluorocyclopropyl)phenyl]-4,4,5,5-tetramethyl-1,3,2-dioxaborolane (301.26 mg, 1.08 mmol), Pd(dppf)Cl₂ (107.31 mg, 0.15 mmol) and Cs₂CO₃ (637.07 mg, 1.96 mmol) in 1,4-dioxane (4 mL) and water (0.4 mL) was stirred at 70° C. for 16 hours under N₂. After cooling to r.t., the mixture was concentrated and diluted with H₂O (10 mL) and the mixture was extracted with EtOAc (20 mL×2). The combined organic phase was washed with brine (10 mL), dried over Na₂SO₄, filtered and concentrated to give the crude product. The crude product was purified by prep-HPLC (Waters Xbridge (150 mm×25 mm, 5 μm) A=H₂O (0.05% NH₄OH) and B=CH₃CN; 35-75% B over 7 minutes) to give the product (90 mg, 0.28 mmol) as a solid, which was confirmed by LCMS. The product was analyzed by SFC, and showed two peaks (Peak 1: Rt=3.35 min, Peak 2: Rt=3.73 min).

Method: Chiralcel AD-3 250×30 mm I.D., 5 μm, mobile phase: A: CO₂ B: ethanol (0.05% DEA), Flow rate: 2.5 mL/min Column temperature: 35° C.

LCMS R$_t$=0.78 min in 1.5 min chromatography, 5-95AB, purity 100%, MS ESI calcd. for C$_{15}$H$_{11}$F$_4$N$_4$ [M+H]⁺ 323.1, found 322.9.

The product was separated by SFC (DAICEL CHIRAL-PAK AD-H (250 mm×30 mm, 5 μm); A=CO₂ and B=EtOH (0.1% NH₃H₂O); 38° C.; 50 mL/min; 25% B; 11 min run; 13 injections, Rt of Peak 1=7.7 min, Rt of Peak 2=9.28 min) to give 6-[4-[(1R)-2,2-difluorocyclopropyl]phenyl]-3-(difluoromethyl)-[1,2,4]triazolo[4,3-a]pyrazine (21.72 mg, 0.07 mmol) (Peak 1, Rt=3.35 min in SFC) as a solid and 6-[4-[(1S)-2,2-difluorocyclopropyl]phenyl]-3-(difluoromethyl)-[1,2,4]triazolo[4,3-a]pyrazine (23.15 mg, 0.07 mmol) (Peak 2: Rt=3.73 min in SFC) as a solid.

Note: the enantiomers were randomly assigned.

Compound 166 (peak 1): ¹H NMR (400 MHz DMSO-d₆) δ$_H$=9.66 (d, 1H), 9.16 (d, 1H), 8.10 (d, 2H), 7.85 (t, 1H), 7.46 (d, 2H), 3.17-3.04 (m, 1H), 2.10-2.00 (m, 2H). LCMS R$_t$=1.07 min in 2.0 min chromatography, 10-80AB, purity 100%, MS ESI calcd. for C$_{15}$H$_{11}$F$_4$N$_4$ [M+H]⁺323.1, found 322.9.

Compound 167 (peak 2): ¹H NMR (400 MHz DMSO-d₆) δ$_H$=9.67 (d, 1H), 9.16 (d, 1H), 8.10 (d, 2H), 7.85 (t, 1H), 7.46 (d, 2H), 3.18-3.02 (m, 1H), 2.12-1.98 (m, 2H). LCMS R$_t$=1.08 min in 2.0 min chromatography, 10-80AB, purity 100%, MS ESI calcd. for C$_{15}$H$_{11}$F$_4$N$_4$ [M+H]⁺323.1, found 322.9.

Example 150: Synthesis of Compounds 168

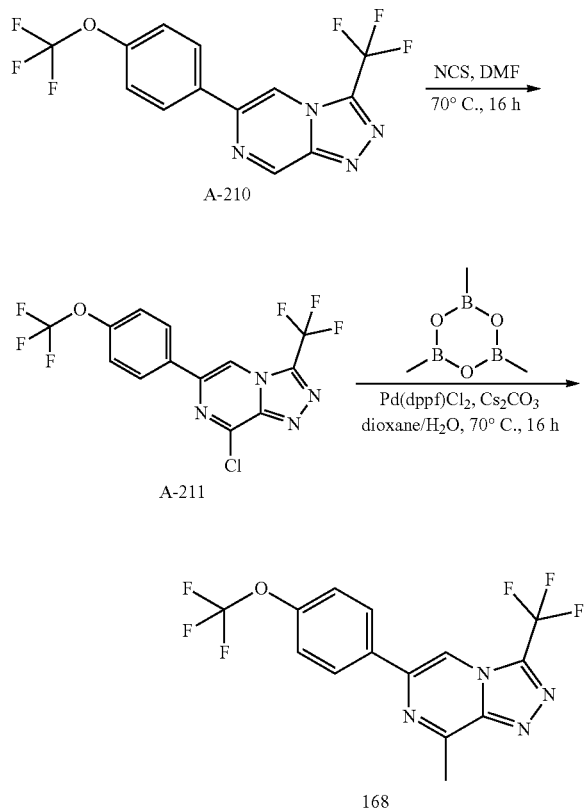

A mixture of 6-[4-(trifluoromethoxy)phenyl]-3-(trifluoromethyl)-[1,2,4]triazolo[4,3-a]pyrazine (200 mg, 0.57 mmol) and NCS (92.04 mg, 0.69 mmol) in DMF (2 mL) was stirred at 70° C. for 16 hours. After cooling to r.t., the mixture was diluted with H$_2$O (15 mL), and the mixture was extracted with EtOAc (15 mL×2). The combined organic phase was washed with brine (10 mL), dried over Na$_2$SO$_4$, filtered and concentrated. The residue was purified by flash chromatography on silica gel (EtOAc in PE=0 to 10% to 30%) to give the product (97 mg, 0.25 mmol) as a solid. $^1$H NMR (400 MHz, DMSO-d$_6$) $\delta_H$=9.15 (s, 1H), 8.32-8.22 (m, 2H), 7.56 (d, 2H).

A mixture of 8-chloro-6-[4-(trifluoromethoxy)phenyl]-3-(trifluoromethyl)-[1,2,4]triazolo[4,3-a]pyrazine (150 mg, 0.39 mmol), 2,4,6-trimethyl-1,3,5,2,4,6-trioxatriborinane (54.13 mg, 0.43 mmol), Pd(dppf)Cl$_2$ (57.37 mg, 0.08 mmol) and Cs$_2$CO$_3$ (255.43 mg, 0.78 mmol) in 1,4-Dioxane (3 mL) and Water (0.3 mL) was stirred at 70° C. for 16 hours. After cooling to r.t., the mixture was concentrated and diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 20% to 50%) to give the product (17.42 mg, 0.05 mmol) as a solid. $^1$H NMR (400 MHz DMSO-d$_6$) $\delta_H$=8.94 (s, 1H), 8.29 (d, 2H), 7.53 (d, 2H), 2.98 (s, 3H). LCMS R$_t$=1.21 min in 2 min chromatography, 10-80AB, purity 99.05%, MS ESI calcd. for C$_{14}$H$_9$F$_6$N$_4$O [M+H]$^+$ 363.1, found 363.0.

Example 151: Synthesis of Compounds 169

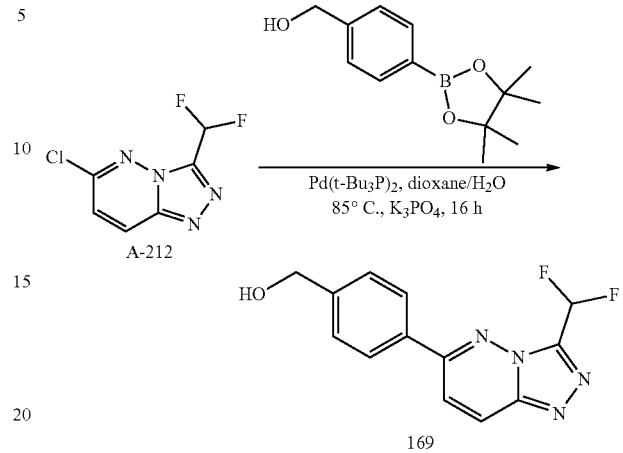

To a mixture of 6-chloro-3-(difluoromethyl)-[1,2,4]triazolo[4,3-b]pyridazine (200 mg, 0.98 mmol), [4-(4,4,5,5-tetramethyl-1,3,2-dioxaborolan-2-yl)phenyl]methanol (686.64 mg, 2.93 mmol), K$_3$PO$_4$ (415.13 mg, 1.96 mmol) and Pd(t-Bu$_3$P)$_2$ (99.93 mg, 0.2 mmol) in 1,4-dioxane (4 mL) and water (0.4 mL) was stirred at 85° C. for 16 hours under N$_2$. After cooling to r.t., the mixture was concentrated and diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by Prep-HPLC (Kromasil (150 mm×25 mm, 5 µm) A=H$_2$O (0.05% NH$_4$OH) and B=CH$_3$CN; 13-43% B over 8 minutes) to give the product (21.79 mg, 0.08 mmol) as a solid. $^1$H NMR (400 MHz, DMSO-d$_6$) $\delta_H$=8.59 (d, 1H), 8.18-8.07 (m, 3H), 7.77 (t, 1H), 7.55 (d, 2H), 5.39 (t, 1H), 4.61 (d, 2H). LCMS R$_t$=1.07 min in 2 min chromatography, 0-60AB, purity 100%, MS ESI calcd. for C$_{13}$H$_{11}$F$_2$N$_4$O [M+H]$^+$ 277.1, found 276.9.

Example 152: Synthesis of Compounds 170

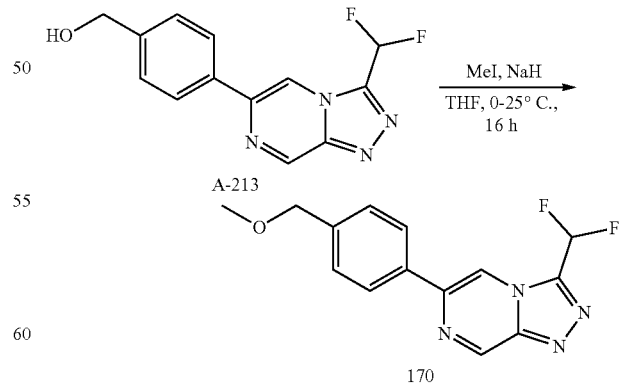

To a mixture of [4-[3-(difluoromethyl)-[1,2,4]triazolo[4,3-a]pyrazin-6-yl]phenyl]methanol (100 mg, 0.36 mmol) in THF (2 mL) was added NaH (17.38 mg, 0.43 mmol) at 0° C., and the mixture was stirred for 30 min. Then iodomethane (154.15 mg, 1.09 mmol) was added. The mixture was stirred at 25° C. for 16 hours. The mixture was diluted with H₂O (50 mL), and extracted with EtOAc (50 mL×2). The combined organic phase was washed with brine (20 mL), dried over Na₂SO₄, filtered and concentrated to give the crude product. The crude product was purified by Prep-HPLC (Waters Xbridge (150 mm×25 mm, 5 μm), A=H₂O (10 mM NH₄HCO₃) and B=CH₃CN; 30-60% B over 6 minutes) to give the product (27.6 mg, 95.1 mmol) as a solid. ¹H NMR (400 MHz, DMSO-d₆+D₂O) δ$_H$=9.60 (d, 1H), 9.05 (d, 1H), 8.06 (d, 2H), 7.78 (t, 1H), 7.47 (d, 2H), 4.46 (s, 2H), 3.31 (s, 3H). LCMS R$_f$=0.96 min in 2.0 min chromatography, 10-80AB, purity 100%, MS ESI calcd. for C₁₄H₁₃F₂N₄O [M+H]⁺ 291.1, found 290.9.

Example 153: Synthesis of Compounds 171

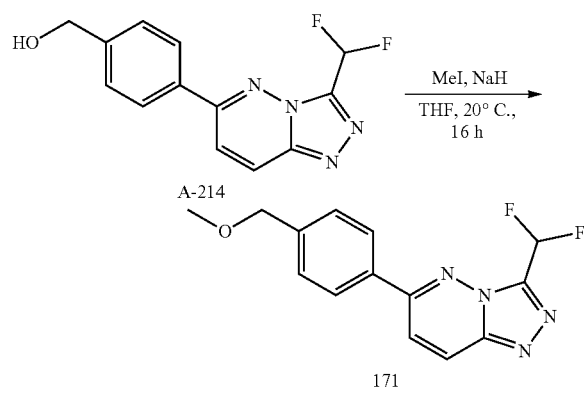

A mixture of [4-[3-(difluoromethyl)-[1,2,4]triazolo[4,3-b]pyridazin-6-yl]phenyl]methanol (50 mg, 0.18 mmol), NaH (14.48 mg, 0.36 mmol) and MeI (102.77 mg, 0.72 mmol) in THF (2 mL) was stirred at 20° C. for 16 hours. The mixture was concentrated and diluted with H₂O (10 mL) and extracted with EtOAc (20 mL×2). The combined organic phase was washed with brine (10 mL), dried over Na₂SO₄, filtered and concentrated to give the crude product. The crude product was purified by prep-HPLC (Kromasil (150 mm×25 mm, 5 μm) A=H₂O (0.05% NH₄OH) and B=CH₃CN; 30-60% B over 7 minutes) to give the product (3.54 mg, 10 μmol) as a solid. ¹H NMR (400 MHz, DMSO-d₆+D₂O) δ$_H$=8.53 (d, 1H), 8.13-8.07 (m, 3H), 7.74 (t, 1H), 7.54 (d, 2H), 4.51 (s, 2H), 3.32 (s, 3H). LCMS R$_f$=0.98 min in 2 min chromatography, 10-80AB, purity 100%, MS ESI calcd. for C₁₄H₁₃F₂N₄O [M+H]⁺ 291.1, found 290.9.

Example 154: Synthesis of Compounds 172

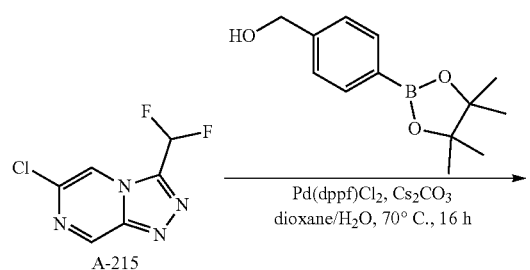

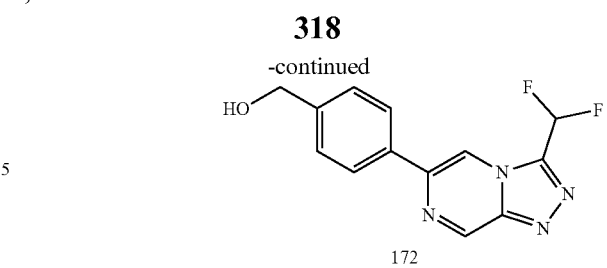

A mixture of 6-chloro-3-(difluoromethyl)-[1,2,4]triazolo[4,3-a]pyrazine (300 mg, 1.47 mmol), [4-(4,4,5,5-tetramethyl-1,3,2-dioxaborolan-2-yl)phenyl]methanol (1.03 g, 4.40 mmol), Cs₂CO₃ (955.61 mg, 2.93 mmol) and Pd(dppf)Cl₂ (160.96 mg, 0.22 mmol) in 1,4-dioxane (10 mL) and water (0.50 mL) was stirred at 70° C. under N₂. The mixture was cooled to room temperature and filtered through Celite. The filtrate was concentrated to give a residue. The residue was diluted in EtOAc (20 mL), washed with water (20 mL×2) and brine (10 mL), dried over anhydrous Na₂SO₄, filtered and concentrated to give the crude product. The crude product was purified by flash chromatography on silica gel (EtOAc in PE=30% to 80%) to give the product (330 mg).

The impure product (100 mg) was purified by Prep-HPLC (Waters Xbridge (150 mm×25 mm, 5 μm) A=H₂O (10 mM NH₄HCO₃) and B=CH₃CN; 20-40% B over 6 minutes) to give the product (29.12 mg, 0.11 mmol) as a solid. ¹H NMR (400 MHz DMSO-d₆) δ$_H$=9.66 (s, 1H), 9.13 (s, 1H), 8.09 (d, 2H), 7.85 (t, 1H), 7.49 (d, 2H), 5.31 (t, 1H), 4.58 (d, 2H). LCMS R$_f$=1.04 min in 2.0 min chromatography, 0-60AB, purity 100%, MS ESI calcd. for C₁₃H₁₁F₂N₄O [M+H]⁺ 277.1, found 276.9.

Example 155: Synthesis of Compound 173

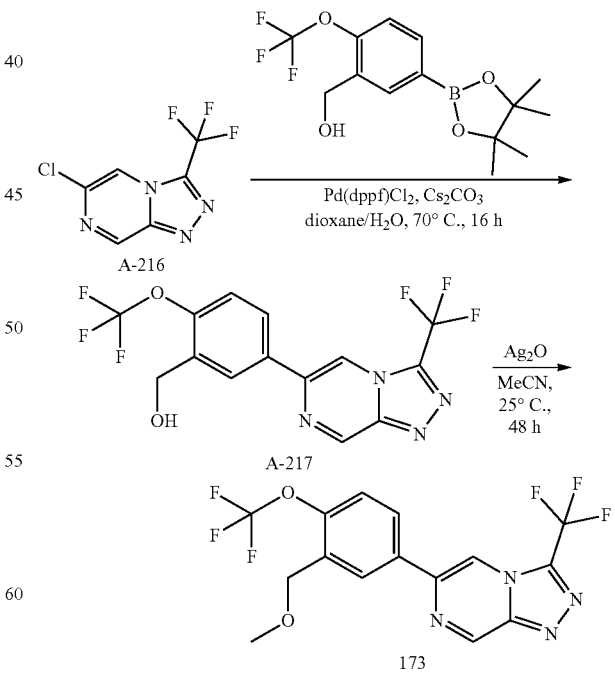

A mixture of 6-chloro-3-(trifluoromethyl)-[1,2,4]triazolo[4,3-a]pyrazine (150 mg, 0.67 mmol), [5-(4,4,5,5-tetramethyl-1,3,2-dioxaborolan-2-yl)-2-(trifluoromethoxy)phenyl]

methanol (321.59 mg, 1.01 mmol), Pd(dppf)Cl$_2$ (73.97 mg, 0.10 mmol) and Cs$_2$CO$_3$ (439.16 mg, 1.35 mmol) in 1,4-dioxane (12 mL) and water (2 mL) was stirred at 70° C. for 16 hours. The mixture was cooled to r.t., diluted with EtOAc (10 mL), filtered through silica gel and eluted with EtOAc (20 mL). The filtrate was concentrated to give the crude product. The crude product was purified by flash chromatography on silica gel (EtOAc in PE=20% to 50%) to give the product (70 mg, 0.19 mmol) as a solid. $^1$H NMR (400 MHz, DMSO-d$_6$) δ$_H$=9.79 (d, 1H), 9.03 (d, 1H), 8.39 (d, 1H), 8.18 (dd, 1H), 7.49 (dd, 1H), 5.52 (t, 1H), 4.65 (d, 2H).

To a mixture of [2-(trifluoromethoxy)-5-[3-(trifluoromethyl)-[1,2,4]triazolo[4,3-a]pyrazin-6-yl]phenyl]methanol (70 mg, 0.19 mmol) in MeCN (2 mL) was added Ag$_2$O (214.44 mg, 0.93 mmol), followed by iodomethane (131.35 mg, 0.93 mmol), and the mixture was keep out of the light and stirred at 25° C. for 48 hours. The mixture was diluted with MeCN (10 mL), filtered through Celite, eluted with MeCN (20 mL) and the filtrate was concentrated to give the crude product. The crude product was purified by Prep-HPLC (Waters Xbridge (150 mm×25 mm, 5 μm), A=H$_2$O (10 mM NH$_4$HCO$_3$) and B=CH$_3$CN; 48-68% B over 7 minutes) to give the product (12 mg, 30.6 μmol) as a solid. $^1$H NMR (400 MHz DMSO-d$_6$) δ$_H$=(d, 1H), 9.09 (s, 1H), 8.35 (d, 1H), 8.25 (dd, 1H), 7.54 (dd, 1H), 4.57 (s, 2H), 3.38 (s, 3H). LCMS R$_t$=1.16 min in 2.0 min chromatography, 10-80AB, purity 100%, MS ESI calcd. for C$_{15}$H$_{11}$F$_6$N$_4$O$_2$ [M+H]$^+$393.1, found 393.0.

Example 156: Synthesis of Compounds 174

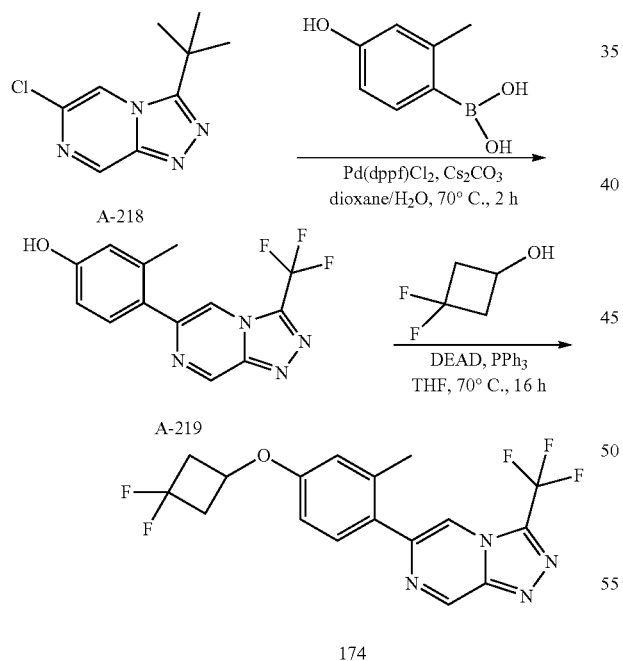

174

A mixture of 6-chloro-3-(trifluoromethyl)-[1,2,4]triazolo[4,3-a]pyrazine (200 mg, 0.9 mmol), (4-hydroxy-2-methylphenyl)boronic acid (204.83 mg, 1.35 mmol), Pd(dppf)Cl$_2$ (98.63 mg, 0.13 mmol) and Cs$_2$CO$_3$ (585.55 mg, 1.8 mmol) in 1,4-dioxane (4 mL) and water (0.4 mL) was stirred at 70° C. for 2 hours. The mixture was cooled to r.t., diluted with EtOAc (10 mL), filtered with silica gel, eluted with EtOAc (20 mL) and concentrated to give the crude product. The crude product was purified by flash chromatograph on silica gel (EtOAc in PE=20% to 60%) to give the product (150 mg, 0.51 mmol) as a solid. $^1$H NMR (400 MHz, DMSO-d$_6$) δ$_H$=9.75-9.60 (m, 2H), 8.51 (s, 1H), 7.32 (d, 1H), 6.81-6.68 (m, 2H), 2.30 (s, 3H).

To a mixture of 3-methyl-4-[3-(trifluoromethyl)-[1,2,4]triazolo[4,3-a]pyrazin-6-yl]phenol (80 mg, 0.27 mmol), 3,3-difluorocyclobutanol (88.17 mg, 0.82 mmol) and Ph$_3$P (142.64 mg, 0.54 mmol) in THF (2 mL) was added DEAD (94.7 mg, 0.54 mmol) at 0° C. under N$_2$. Then the mixture was stirred at 70° C. for 16 hours. The mixture was concentrated to give the crude product. The crude product was purified by Prep-HPLC (Waters Xbridge (150 mm×25 mm, 5 μm) A=H$_2$O (10 mM NH$_4$HCO$_3$) and B=CH$_3$CN; 43-73% B over 6 minutes) to give the product (4.22 mg, 11.0 μmol) as a solid. $^1$H NMR (400 MHz, CDCl$_3$) δ$_H$=9.57 (d, 1H), 8.13 (s, 1H), 7.38 (d, 1H), 6.84-6.80 (m, 1H), 6.77 (dd, 1H), 4.78-4.66 (m, 1H), 3.20-3.09 (m, 2H), 2.86-2.74 (m, 2H), 2.41 (s, 3H). LCMS R$_t$=1.16 min in 2.0 min chromatography, 10-80AB, purity 100%, MS ESI calcd. for C$_{17}$H$_{14}$F$_5$N$_4$O [M+H]$^+$ 385.1, found 385.1.

Example 157: Synthesis of Compounds 175

Route I

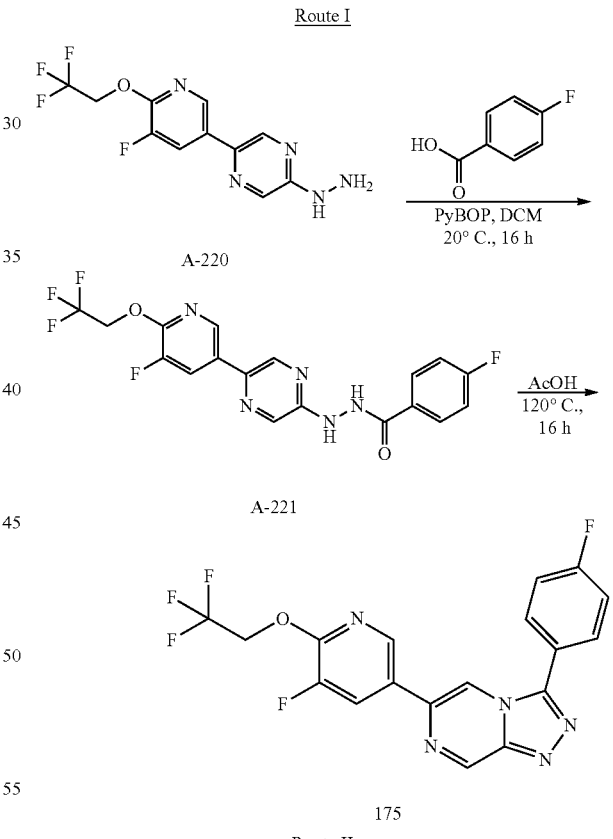

175

Route II

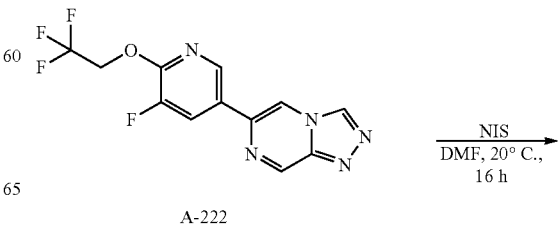

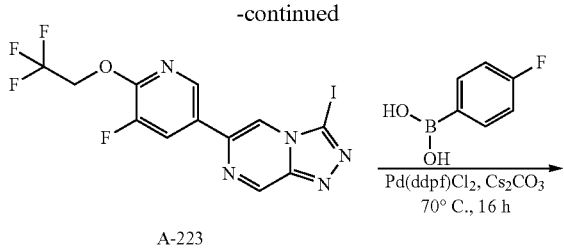

A-223

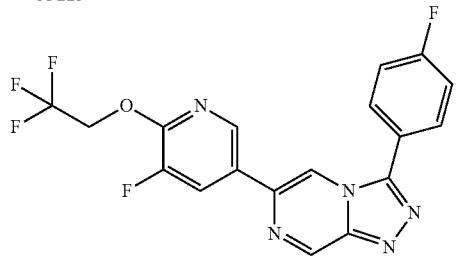

175

A mixture of 6-[5-fluoro-6-(2,2,2-trifluoroethoxy)-3-pyridyl]-[1,2,4]triazolo[4,3-a]pyrazine (200 mg, 0.64 mmol) and NIS (158.03 mg, 0.7 mmol) in THF (2 mL) was stirred at 20° C. for 16 hours. The mixture was diluted with H$_2$O (20 mL), and the mixture was extracted with EtOAc (20 mL×2). The combined organic phase was washed with brine (20 mL), dried over Na$_2$SO$_4$, filtered and concentrated. The residue was purified by flash chromatography on silica gel (EtOAc in PE=0% to 30% to 70%) to give the product (105 mg, 0.24 mmol) as a solid. $^1$H NMR (400 MHz DMSO-d$_6$) $\delta_H$=9.48 (d, 1H), 8.87 (d, 1H), 8.81 (d, 1H), 8.63 (dd, 1H), 5.18 (q, 2H).

A mixture of 6-[5-fluoro-6-(2,2,2-trifluoroethoxy)-3-pyridyl]-3-iodo-[1,2,4]triazolo[4,3-a]pyrazine (100 mg, 0.23 mmol), (4-fluorophenyl)boronic acid (35.05 mg, 0.25 mmol), Cs$_2$CO$_3$ (148.39 mg, 0.46 mmol) and Pd(dppf)Cl$_2$ (24.99 mg, 0.03 mmol) in 1,4-dioxane (3 mL) and water (0.5 mL) was stirred at 70° C. for 16 hours. After cooling to r.t. the mixture was concentrated and diluted with H$_2$O (10 mL) and extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 30% to 60% to 100%) to give the impure product (35 mg). The impure product was purified by Prep-TLC (silica gel, PE:EtOAc=1:1) to give the product (10 mg, 24.6 μmol) as a solid.

To a mixture of 4-fluorobenzoic acid (157.11 mg, 1.12 mmol) and PyBOP (875.27 mg, 1.68 mmol) in DCM (15 mL) was added [5-[5-fluoro-6-(2,2,2-trifluoroethoxy)-3-pyridyl]pyrazin-2-yl]hydrazine (170 mg, 0.56 mmol) and DIPEA (0.49 mL, 2.8 mmol) and was stirred at 20° C. for 16 hours. The mixture was diluted with H$_2$O (10 mL) and extracted with DCM (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 50% to 100%) to give the product (155 mg, 0.09 mmol) as a solid. LCMS R$_t$=0.80 min in 1.5 min chromatography, 5-95AB, purity 26.03%, MS ESI calcd. for C$_{18}$H$_{13}$F$_5$N$_5$O$_2$ [M+H]$^+$ 426.1, found 426.0.

A mixture of 4-fluoro-N'-[5-[5-fluoro-6-(2,2,2-trifluoroethoxy)-3-pyridyl]pyrazin-2-yl]benzohydrazide (150 mg, 0.35 mmol) in acetic acid (15 mL) was stirred at 120° C. for 16 hours. After cooling to r.t., the reaction was concentrated and diluted with sat.NaHCO$_3$ (15 mL), and the mixture was extracted with EtOAc (20 mL×2). The combined organic phase was washed with brine (10 mL), dried over Na$_2$SO$_4$, filtered and concentrated to give the crude product. The crude product was purified by purified by prep-HPLC (Kromasil (150 mm×25 mm, 5 μm) A=H$_2$O (0.05% NH$_4$OH) and B=CH$_3$CN; 47-62% B over 7 minutes) to give the product (~5 mg, 100% purity) as a solid.

The 2 batches of the product described above were combined and triturated from DCM/haxane (0.5 ml 73 mL) to give the product (8.57 mg, 0.02 mmol) as a solid. $^1$H NMR (400 MHz, DMSO-d$_6$) $\delta_H$=9.50 (d, 1H), 8.47 (d, 1H), 8.41 (d, 1H), 8.05 (dd, 1H), 7.90 (dd, 2H), 7.39 (t, 2H), 4.91 (q, 2H). LCMS R$_t$=1.15 min in 2 min chromatography, 10-80AB, purity 100%, MS ESI calcd. for C$_{18}$H$_{11}$F$_5$N$_5$O [M+H]$^+$ 408.1, found 408.0.

Example 158: Synthesis of Compound 176

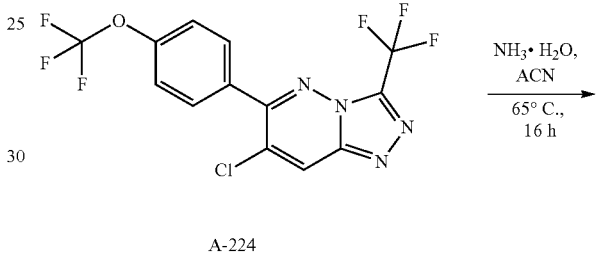

A-224

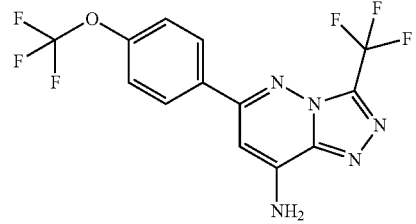

176

A mixture of 7-chloro-6-[4-(trifluoromethoxy)phenyl]-3-(trifluoromethyl)-[1,2,4]triazolo[4,3-b]pyridazine (500 mg, 1.31 mmol) in NH$_3$.H$_2$O (100 mL) and MeCN (40 mL) was stirred at 65° C. for 24 hours. After cooling to r.t., the mixture was concentrated. The residue was diluted with H$_2$O (30 mL), and the mixture was extracted with EtOAc (100 mL×2). The combined organic phase was washed with water (30 mL) and brine (30 mL), dried over Na$_2$SO$_4$, filtered and concentrated to give the crude product. The crude product was purified by TLC (silica gel, PE:EtOAc=1:1) to give the product (10.26 mg, 28.2 μmol) as a solid. $^1$H NMR (400 MHz, DMSO-d$_6$) $\delta_H$=8.11-7.96 (m, 4H), 7.58 (d, 2H), 6.78 (s, 1H). LCMS R$_t$=1.19 min in 2.0 min chromatography, 10-80AB, purity 100.00%, MS ESI calcd. for C$_{13}$H$_8$F$_6$N$_5$O [M+H]$^+$ 364.1, found 364.0.

Example 159: Synthesis of Compounds 177

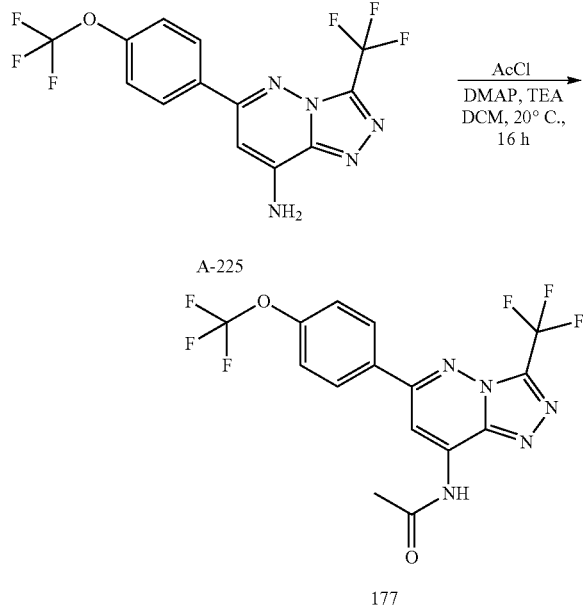

To a mixture of 6-[4-(trifluoromethoxy)phenyl]-3-(trifluoromethyl)-[1,2,4]triazolo[4,3-b]pyridazin-8-amine (50 mg, 0.14 mmol), DMAP (33.64 mg, 0.28 mmol) and TEA (41.79 mg, 0.41 mmol) in DCM (5 mL) was added acetyl chloride (21.61 mg, 0.28 mmol). The mixture was stirred at 20° C. for 16 hours. The mixture was diluted with DCM (10 mL), washed with water (5 mL×2) and brine (5 mL), dried over Na$_2$SO$_4$, filtered and concentrated to give the crude product. The crude product was purified by TLC (silica gel, PE:EtOAc=1:1) to give the product (17.32 mg, 41.9 μmol) as a solid. $^1$H NMR (400 MHz, CDCl$_3$) δ$_H$=8.99 (br s, 1H), 8.69 (s, 1H), 8.08 (d, 2H), 7.40 (d, 2H), 2.44 (s, 3H). LCMS R$_t$=1.21 min in 2.0 min chromatography, 10-80AB, purity 97.61%, MS ESI calcd. for C$_{15}$H$_{10}$F$_6$N$_5$O$_2$ [M+H]$^+$ 406.1, found 406.0.

Example 160: Synthesis of Compounds 178

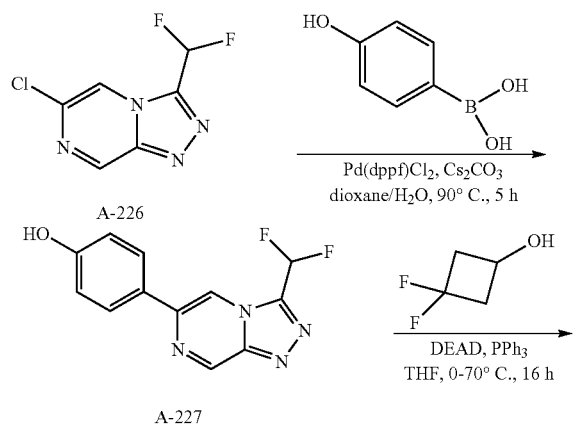

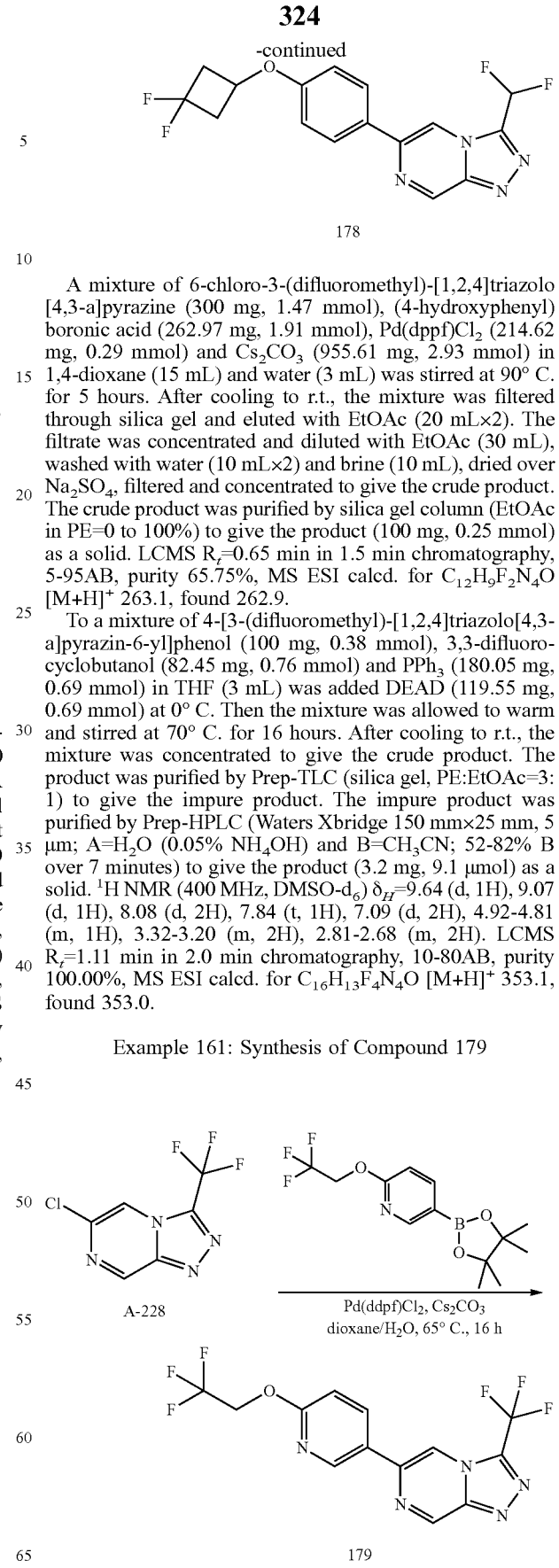

A mixture of 6-chloro-3-(difluoromethyl)-[1,2,4]triazolo[4,3-a]pyrazine (300 mg, 1.47 mmol), (4-hydroxyphenyl)boronic acid (262.97 mg, 1.91 mmol), Pd(dppf)Cl$_2$ (214.62 mg, 0.29 mmol) and Cs$_2$CO$_3$ (955.61 mg, 2.93 mmol) in 1,4-dioxane (15 mL) and water (3 mL) was stirred at 90° C. for 5 hours. After cooling to r.t., the mixture was filtered through silica gel and eluted with EtOAc (20 mL×2). The filtrate was concentrated and diluted with EtOAc (30 mL), washed with water (10 mL×2) and brine (10 mL), dried over Na$_2$SO$_4$, filtered and concentrated to give the crude product. The crude product was purified by silica gel column (EtOAc in PE=0 to 100%) to give the product (100 mg, 0.25 mmol) as a solid. LCMS R$_t$=0.65 min in 1.5 min chromatography, 5-95AB, purity 65.75%, MS ESI calcd. for C$_{12}$H$_9$F$_2$N$_4$O [M+H]$^+$ 263.1, found 262.9.

To a mixture of 4-[3-(difluoromethyl)-[1,2,4]triazolo[4,3-a]pyrazin-6-yl]phenol (100 mg, 0.38 mmol), 3,3-difluorocyclobutanol (82.45 mg, 0.76 mmol) and PPh$_3$ (180.05 mg, 0.69 mmol) in THF (3 mL) was added DEAD (119.55 mg, 0.69 mmol) at 0° C. Then the mixture was allowed to warm and stirred at 70° C. for 16 hours. After cooling to r.t., the mixture was concentrated to give the crude product. The product was purified by Prep-TLC (silica gel, PE:EtOAc=3:1) to give the impure product. The impure product was purified by Prep-HPLC (Waters Xbridge 150 mm×25 mm, 5 μm; A=H$_2$O (0.05% NH$_4$OH) and B=CH$_3$CN; 52-82% B over 7 minutes) to give the product (3.2 mg, 9.1 μmol) as a solid. $^1$H NMR (400 MHz, DMSO-d$_6$) δ$_H$=9.64 (d, 1H), 9.07 (d, 1H), 8.08 (d, 2H), 7.84 (t, 1H), 7.09 (d, 2H), 4.92-4.81 (m, 1H), 3.32-3.20 (m, 2H), 2.81-2.68 (m, 2H). LCMS R$_t$=1.11 min in 2.0 min chromatography, 10-80AB, purity 100.00%, MS ESI calcd. for C$_{16}$H$_{13}$F$_4$N$_4$O [M+H]$^+$ 353.1, found 353.0.

Example 161: Synthesis of Compound 179

A mixture of 5-(4,4,5,5-tetramethyl-1,3,2-dioxaborolan-2-yl)-2-(2,2,2-trifluoroethoxy)pyridine (149.8 mg, 0.49 mmol), 6-chloro-3-(trifluoromethyl)-[1,2,4]triazolo[4,3-a]pyrazine (100 mg, 0.45 mmol), Pd(dppf)Cl$_2$ (65.75 mg, 0.09 mmol) and Cs$_2$CO$_3$ (292.77 mg, 0.9 mmol) in 1,4-dioxane (3 mL) and water (0.3 mL) was stirred at 65° C. for 16 hours. After cooling to r.t., the mixture was concentrated and diluted with H$_2$O (10 mL), and the mixture was extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=0 to 10% to 30% to 60% to 100%) to give the product (23.24 mg, 0.06 mmol) as a solid. $^1$H NMR (400 MHz, CDCl$_3$) $\delta_H$=9.60 (d, 1H), 8.77 (d, 1H), 8.39 (s, 1H), 8.26 (dd, 1H), 7.06 (d, 1H), 4.87 (q, 2H). LCMS R$_t$=1.21 min in 2 min chromatography, 10-80AB, purity 100%, MS ESI calcd. for C$_{13}$H$_8$F$_6$N$_5$O [M+H]$^+$ 364.1, found 363.9.

Example 162: Synthesis of Compound 180

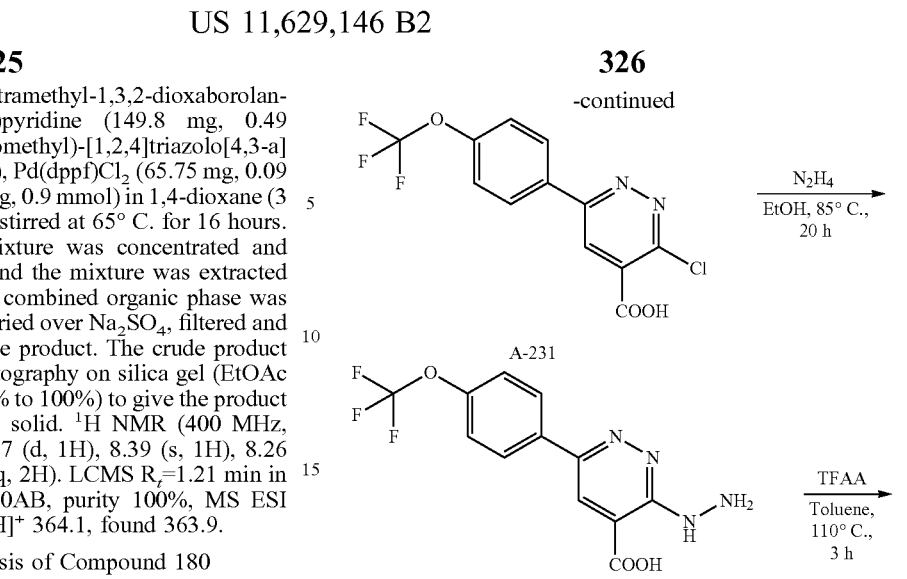

A mixture of [4-[3-(trifluoromethyl)-[1,2,4]triazolo[4,3-a]pyrazin-6-yl]phenyl]methanol (50 mg, 0.17 mmol), Ag$_2$O (196.90 mg, 0.85 mmol) and CH$_3$I (0.05 mL, 0.85 mmol) in MeCN (3 mL) was keep out of the light and stirred at 20° C. for 72 hours. The mixture was filtered through Celite, and eluted with EtOAc (15 mL×2). The filtrate was concentrated and diluted with EtOAc (20 mL), washed with water (15 mL×2) and brine (10 mL), dried over Na$_2$SO$_4$, filtered and concentrated to give the crude product. The crude product was purified by Prep-TLC (silica gel, PE:EtOAc=2:1) to give the product (18.97 mg, 0.06 mmol). $^1$H NMR (400 MHz, CDCl$_3$) $\delta_H$=9.60 (d, 1H), 8.42 (s, 1H), 7.97 (d, 2H), 7.53 (d, 2H), 4.56 (s, 2H), 3.46 (s, 3H). LCMS R$_t$=1.02 min in 2.0 min chromatography, 10-80AB, purity 100%, MS ESI calcd. for C$_{14}$H$_{12}$F$_3$N$_4$O [M+H]$^+$ 309.1, found 308.9.

Example 163: Synthesis of Compound 181

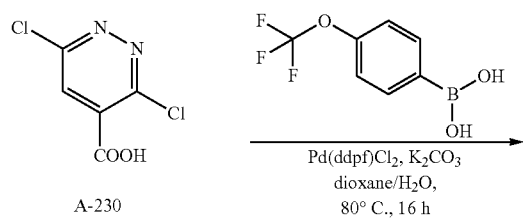

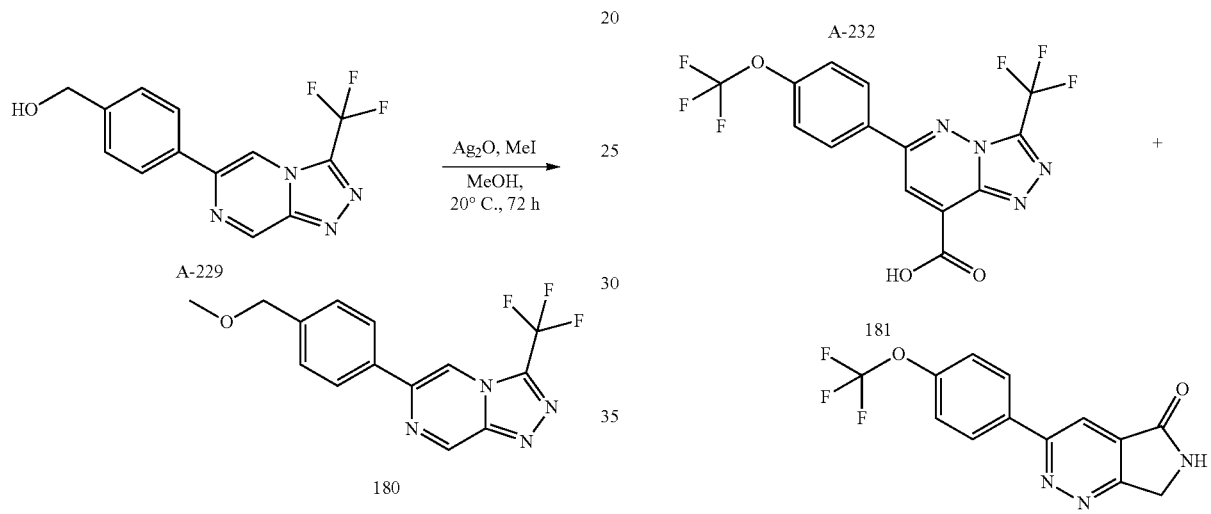

A mixture of 3,6-dichloropyridazine-4-carboxylic acid (2 g, 10.36 mmol), [4-(trifluoromethoxy)phenyl]boronic acid (1.99 g, 9.67 mmol), Pd(dppf)Cl$_2$ (758.28 mg, 1.04 mmol) and K$_2$CO$_3$ (2.86 g, 20.73 mmol) in 1,4-dioxane (50 mL) and water (10 mL) was stirred at 80° C. for 16 hours under N$_2$. After cooling to r.t., the mixture was concentrated. The residue was diluted with H$_2$O (50 mL), and acidified with 1 N HCl to pH ~2. The mixture was extracted with EtOAc (100 mL×3). The combined organic phase was washed with brine (50 mL), dried over Na$_2$SO$_4$, filtered and concentrated to give the crude product (3300 mg, 3.46 mmol) as a solid. The crude product was used directly without any further purification. LCMS Rt=0.79 min in 1.5 min chromatography, 5-95AB, purity 33.38%, MS ESI calcd. for C$_{12}$H$_7$ClF$_3$N$_2$O$_3$ [M+H]$^+$ 319.0, found 318.9.

To a mixture of and 3-chloro-6-[4-(trifluoromethoxy)phenyl]pyridazine-4-carboxylic acid (3.3 g, 4.77 mmol) in Ethanol (50 mL) was added hydrazine (3.06 g, 95.32 mmol), then the mixture was stirred at 85° C. for 20 hours. After cooling to r.t., the mixture was concentrated to give the crude product (3000 mg, 9.55 mmol) as a solid, which was used directly without any further purification. LCMS Rt=0.68 min in 1.5 min chromatography, 5-95AB, purity 28.33%, MS ESI calcd. for C$_{12}$H$_{10}$F$_3$N$_4$O$_3$ [M+H]$^+$ 315.1, found 314.9.

To a mixture of 3-hydrazino-6-[4-(trifluoromethoxy)phenyl]pyridazine-4-carboxylic acid (3 g, 9.55 mmol) in toluene (30 mL) was added TFAA (4.01 g, 19.09 mmol), then the mixture was stirred at 110° C. for 3 hours. After cooling to r.t., the mixture was concentrated. The residue was poured into water (50 mL), basified with NaOH (solid) to pH~9 and washed with EtOAc (50 mL×2). The aqueous layer was acidified with 1N HCl solution to pH=2, then the mixture was extracted with EtOAc (100 mL×2). The combined organic phase was washed with brine (20 mL), dried over $Na_2SO_4$, filtered and concentrated to give the crude product. The crude product was purified by flash chromatography on silica gel (EtOAc in PE=0% to 50% to 100%) to give the impure product, which was triturated from EtOAc (5 mL) to give the byproduct 5-[4-(trifluoromethoxy)phenyl]-1,2-dihydropyrazolo[3,4-c]pyridazin-3-one (75.11 mg, 0.25 mmol) as a solid.

Meanwhile, the crude product was purified by flash chromatography on silica gel (MeOH in EtOAc=0% to 5% to 10%) to give the impure product, which was further purified by prep-HPLC [Kromasil (150 mm×25 mm, 10 μm) A=$H_2O$ (0.05% $NH_4OH$) and B=$CH_3CN$; 50-80% B over 8 minutes] to give the product, 6-[4-(trifluoromethoxy)phenyl]-3-(trifluoromethyl)-[1,2,4]triazolo[4,3-b]pyridazine-8-carboxylic acid (45.79 mg) as a solid.

$^1$H NMR (400 MHz, DMSO-$d_6$) $\delta_H$=8.34-8.17 (m, 3H), 7.62 (d, 2H). LCMS $R_t$=1.14 min in 2.0 min chromatography, 10-80AB, purity 100%, MS ESI calcd. for $C_{14}H_7F_6N_4O_3$ [M+H]$^+$393.0, found 393.0.

Example 164: Synthesis of Compound 183

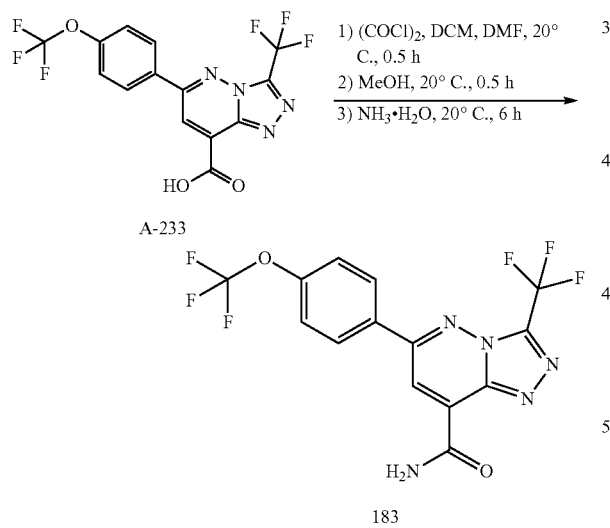

To a mixture of 6-[4-(trifluoromethoxy)phenyl]-3-(trifluoromethyl)-[1,2,4]triazolo[4,3-b]pyridazine-8-carboxylic acid (25 mg, 0.06 mmol) in DCM (5 mL) was added $(COCl)_2$ (16.18 mg, 0.13 mmol) and DMF (2.33 mg, 0.03 mmol), then the mixture was stirred at 20° C. for 0.5 hours. To the mixture was added Methanol (1 mL), then the mixture was stirred at 20° C. for 0.5 hour. The mixture was concentrated. To $NH_3 \cdot H_2O$ (10 mL) was added the solution of the residue in Methanol (1 mL) at 0° C., then the mixture was stirred at 20° C. for 6 hours. The mixture was diluted with $H_2O$ (20 mL), and the mixture was extracted with EtOAc (30 mL×2). The combined organic phase was washed with water (20 mL×2) and brine (20 mL), dried over $Na_2SO_4$, filtered and concentrated to give the crude product. The crude product was triturated from i-$Pr_2O$/hexane (1 mL/2 mL) and dried in oven to give the product (14.17 mg, 36.2 μmol) as a solid.

$^1$H NMR (400 MHz, CDCl$_3$) $\delta_H$=9.04 (brs, 1H), 8.58 (s, 1H), 8.18 (d, 2H), 7.45 (d, 2H), 6.27 (brs, 1H). LCMS $R_t$=1.17 min in 2.0 min chromatography, 10-80AB, purity 100%, MS ESI calcd. for $C_{14}H_8F_6N_5O_2$ [M+H]$^+$ 392.1, found 392.0.

Example 165: Synthesis of Compound 184

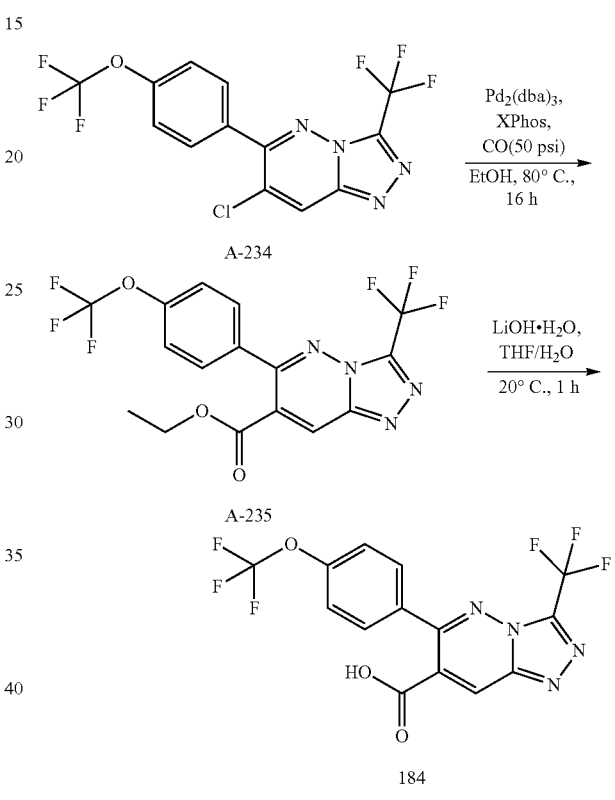

A mixture of 7-chloro-6-[4-(trifluoromethoxy)phenyl]-3-(trifluoromethyl)-[1.2.4]triazolo[4,3-b]pyridazine (100 mg, 0.26 mmol), $Pd_2(dba)_3$ (47.82 mg, 0.05 mmol), XPhos (49.79 mg, 0.10 mmol) and $Et_3N$ (0.11 mL, 0.78 mmol) in ethanol (20 mL) was stirred at 80° C. under CO (50 psi) for 16 hours. The reaction mixture was concentrated to give a residue. The residue was diluted with water (20 mL), extracted with EtOAc (20 mL×2). The combined organic layer was washed with water (10 mL×2) and brine (10 mL×2), dried over anhydrous $Na_2SO_4$, filtered and concentrated to give the crude product. The crude product was purified by flash chromatography on silica gel (EtOAc in PE=0% to 15% to 30%) to give the product (80 mg, 164.8 μmol) as a solid. LCMS $R_t$=0.87 min in 1.5 min chromatography, 5-95AB, purity 86.56%, MS ESI calcd. for $C_{16}H_{11}F_6N_4O_3$ [M+H]$^+$ 421.1, found 421.0.

To a mixture of ethyl 6-[4-(trifluoromethoxy)phenyl]-3-(trifluoromethyl)-[1.2.4]triazolo[4,3-b]pyridazine-7-carboxylate (80 mg, 0.19 mmol) in THF (1 mL) and water (1 mL) was added LiOH·$H_2O$ (23.96 mg, 0.57 mmol). The resulting mixture was stirred at 20° C. for 1 hour. To the mixture was added 1N HCl aqueous (4 mL) to adjusted the pH=2. Then the mixture was extracted with EtOAc (5 mL×2). The combined organic layer was washed with water (5 mL×2), brine (5 mL×2), dried over anhydrous Na$_2$SO$_4$, filtered and concentrated to give the crude product (40 mg). The crude product (40 mg) was purified by triturating from n-hexane (1 mL) and i-Pr$_2$O (1 mL) to give the product (26.44 mg, 66.1 μmol) as a solid. $^1$H NMR (400 MHz, DMSO-d$_6$) δ$_H$=9.00 (s, 1H), 7.73 (d, 2H), 7.56 (d, 2H). LCMS R$_t$=1.16 min in 2.0 min chromatography, 10-80AB, purity 97.85%, MS ESI calcd. for C$_{14}$H$_7$F$_6$N$_4$O$_3$ [M+H]$^+$ 393.0, found 392.9.

Example 166: Synthesis of Compound 185

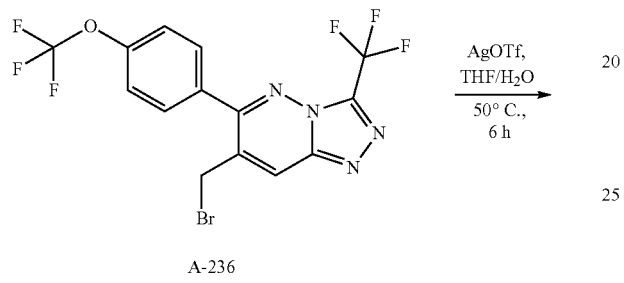

A-236

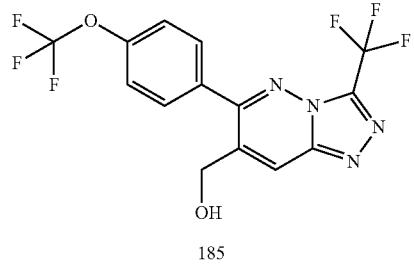

185

To a mixture of 8-(bromomethyl)-6-[4-(trifluoromethoxy)phenyl]-3-(trifluoromethyl)-[1,2,4]triazolo[4,3-b]pyridazine (155 mg, 0.32 mmol) in THF (15 mL) and Water (15 mL) was added AgOTf (1.55 g, 6.03 mmol), then the mixture was stirred at 50° C. for 6 hours. To the mixture was added saturated NaCl aqueous (20 mL), and the mixture was extracted with EtOAc (20 mL×2). The combined organic phase was washed with water (20 mL), brine (20 mL), dried over anhydrous Na$_2$SO$_4$, filtered and concentrated to give the crude product. The crude product was purified by Prep-HPLC [Waters Xbridge (150 mm×25 mm, 5 μm) A=H$_2$O (10 mM NH$_4$HCO$_3$) and B=CH$_3$CN; 46-66% B over 6 minutes] to give the product (7.06 mg, 18.7 μmol) as a solid. $^1$H NMR (400 MHz, CDCl$_3$) δ$_H$=8.55 (s, 1H), 7.64 (d, 2H), 7.43 (d, 2H), 4.75 (d, 2H), 2.30-2.20 (m, 1H). LCMS R$_t$=1.10 min in 2.0 min chromatography, 10-80AB, purity 100.00%, MS ESI calcd. for C$_{14}$H$_9$F$_6$N$_4$O$_2$ [M+H]$^+$ 379.1, found 379.0.

Example 167: Synthesis of Compound 186

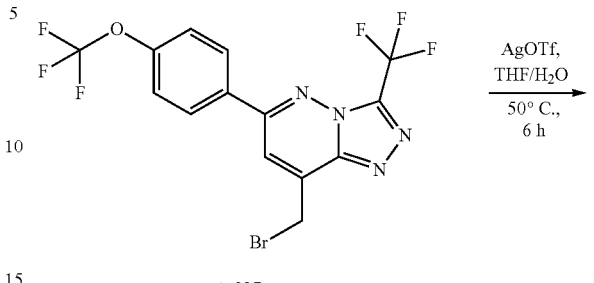

A-237

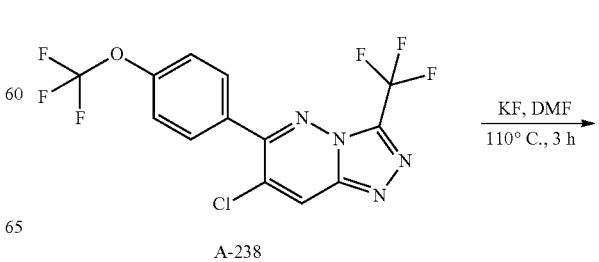

186

To a mixture of 8-(bromomethyl)-6-[4-(trifluoromethoxy)phenyl]-3-(trifluoromethyl)-[1,2,4]triazolo[4,3-b]pyridazine (80 mg, 0.17 mmol) in THF (15 mL) and water (15 mL) was added AgOTf (800 mg, 3.11 mmol), then the mixture was stirred at 50° C. for 6 hours. To the mixture was added saturated NaCl aqueous (20 mL), and the mixture was extracted with EtOAc (20 mL×2). The combined organic phase was washed with water (20 mL) and brine (20 mL), dried over anhydrous Na$_2$SO$_4$, filtered and concentrated to give the crude product. The crude product was purified by Prep-HPLC [Waters Xbridge (150 mm×25 mm, 5 μm) A=H$_2$O (10 mM NH$_4$HCO$_3$) and B=CH$_3$CN; 50-70% B over 6 minutes] to give the product (18.67 mg, 49.2 μmol) as a solid. $^1$H NMR (400 MHz, CDCl$_3$) δ$_H$=8.12 (d, 2H), 7.89 (s, 1H), 7.43 (d, 2H), 5.34 (d, 2H), 2.76 (t, 1H). LCMS R$_t$=1.14 min in 2.0 min chromatography, 10-80AB, purity 100.00%, MS ESI calcd. for C$_{14}$H$_9$F$_6$N$_4$O$_2$ [M+H]$^+$ 379.1, found 379.0.

Example 168: Synthesis of Compound 187

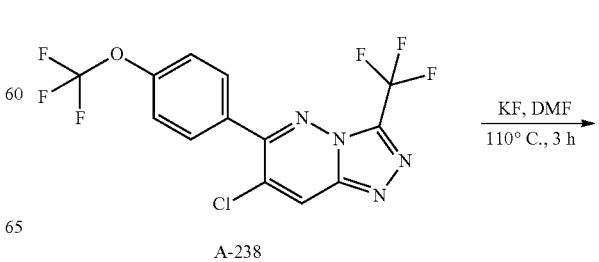

A-238

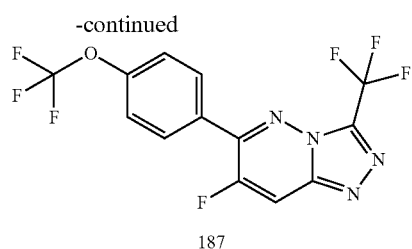

187

To a mixture of 7-chloro-6-[4-(trifluoromethoxy)phenyl]-3-(trifluoromethyl)-[1,2,4]triazolo[4,3-b]pyridazine (45 mg, 0.12 mmol) in DMF (1 mL) was added KF (68.33 mg, 1.18 mmol), then the mixture was stirred at 110° C. for 3 hours under $N_2$. After cooling to r.t., the mixture was diluted with $H_2O$ (10 mL), and the mixture was extracted with EtOAc (20 mL×2). The combined organic phase was washed with water (10 mL×2) and brine (10 mL), dried over $Na_2SO_4$, filtered and concentrated to give the crude product. The crude product was purified by Prep-TLC (silica gel, PE:EtOAc=3:1) to give the product (13.64 mg, 37.1 µmol) as a solid. $^1$H NMR (400 MHz, DMSO-4) $δ_H$=8.83 (d, 1H), 7.99 (d, 2H), 7.66 (d, 2H). LCMS $R_t$=1.19 min in 2.0 min chromatography, 10-80AB, purity 100%, MS ESI calcd. for $C_{13}H_6F_7N_4O$ [M+H]$^+$ 367.0, found 367.0.

Example 169: Synthesis of Compound 188

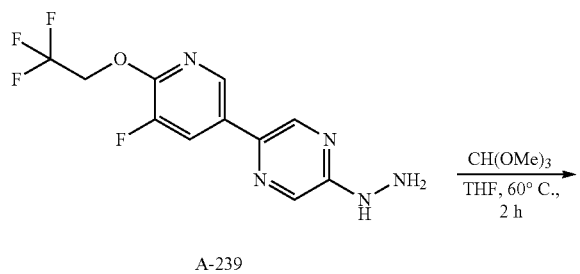

A-239

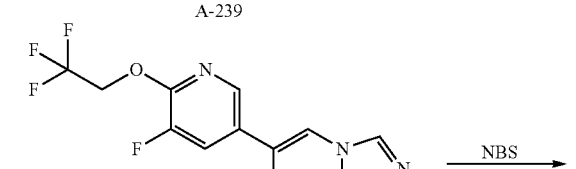

A-240

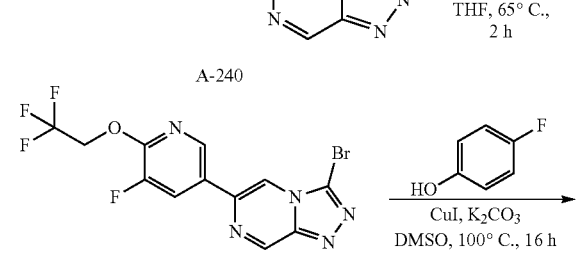

A-241

188

To a solution of [5-[5-fluoro-6-(2,2,2-trifluoroethoxy)-3-pyridyl]pyrazin-2-yl]hydrazine (1 g, 3.3 mmol) in THF (10 mL) was added trimethoxymethane (1.75 g, 16.49 mmol) and TFA (0.24 mL, 3.3 mmol). The reaction mixture was stirred at 60° C. for 2 hours. After cooling to r.t., the reaction mixture was concentrated to remove most of THF and diluted with sat.NaHCO$_3$ (30 mL). The mixture was extracted with EtOAc (30 mL×2). The combined organic phase was washed with brine (20 mL), dried over $Na_2SO_4$, filtered and concentrated to give the product (980 mg, 3.13 mmol) as a solid. $^1$H NMR (400 MHz DMSO-d$_6$) $δ_H$=9.56 (d, 1H), 9.50 (s, 1H), 9.26 (d, 1H), 8.69 (d, 1H), 8.40 (dd, 1H), 5.18 (q, 2H).

A mixture of 6-[5-fluoro-6-(2,2,2-trifluoroethoxy)-3-pyridyl]-[1,2,4]triazolo[4,3-a]pyrazine (600 mg, 1.92 mmol) and NBS (375.04 mg, 2.11 mmol) in THF (20 mL) was stirred at 65° C. for 2 hours. The mixture was diluted with $H_2O$ (20 mL), and the mixture was extracted with EtOAc (20 mL×2). The combined organic phase was washed with brine (20 mL), dried over $Na_2SO_4$, filtered and concentrated. The residue was purified by flash chromatography on silica gel (EtOAc in PE=0% to 30% to 70%) to give the product (280 mg, 0.71 mmol) as a solid. $^1$H NMR (400 MHz, DMSO-d$_6$) $δ_H$=9.55 (d, 1H), 9.01 (d, 1H), 8.82 (d, 1H), 8.62 (dd, 1H), 5.18 (q, 2H).

A mixture of 3-bromo-6-[5-fluoro-6-(2,2,2-trifluoroethoxy)-3-pyridyl]-[1,2,4]triazolo[4,3-a]pyrazine (100 mg, 0.26 mmol), 4-fluorophenol (42.88 mg, 0.38 mmol), $K_2CO_3$ (140.99 mg, 1.02 mmol) and CuI (29.14 mg, 0.15 mmol) in DMSO (1 mL) under $N_2$ was stirred at 100° C. for 16 hours. The mixture was cooled to r.t., diluted with EtOAc (10 mL), filtered through Celite and eluted with EtOAc (20 mL×2), then the filtrate was washed with $H_2O$ (20 mL) and brine (10 mL) and concentrated to give the crude product. The crude product was purified by Prep-HPLC (Waters Xbridge (150 mm×25 mm, 5 µm), A=$H_2O$ (10 mM NH$_4$HCO$_3$) and B=CH$_3$CN; 45-75% B over 6 minutes) to give the product (6.2 mg, 14.6 µmol as a solid. $^1$H NMR (400 MHz, DMSO-d$_6$) $δ_H$=9.43 (d, 1H), 9.09 (d, 1H), 8.80 (d, 1H), 8.54 (dd, 1H), 7.59-7.54 (m, 2H), 7.39-7.33 (m, 2H), 5.17 (q, 2H). LCMS $R_t$=1.20 min in 2.0 min chromatography, 10-80AB, purity 96.20%, MS ESI calcd. for $C_{18}H_{11}F_5N_5O_2$ [M+H]$^+$ 424.1, found 424.0.

Example 170: Synthesis of Compound 189

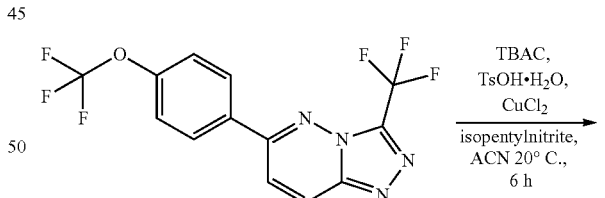

A-242

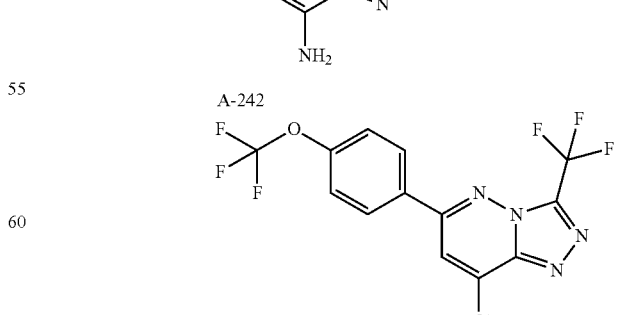

189

To a mixture of 6-[4-(trifluoromethoxy)phenyl]-3-(trifluoromethyl)-[1,2,4]triazolo[4,3-b]pyridazin-8-amine (60 mg, 0.17 mmol), TBAC (137.14 mg, 0.49 mmol) and TsOH.H$_2$O (47.14 mg, 0.25 mmol) in MeCN (6 mL) was added isopentylnitrite (29.14 mg, 0.25 mmol) and CuCl$_2$ (4.29 mg, 0.03 mmol), then the mixture was stirred at 20° C. for 6 hours. The mixture was diluted with H$_2$O (20 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by Prep-TLC (silica gel, PE:EtOAc=3:1) to give the product (7.24 mg, 18.8 μmol) as a solid. $^1$H NMR (400 MHz, CDCl$_3$) $\delta_H$=8.06 (d, 2H), 7.82 (s, 1H), 7.44 (d, 2H). LCMS R$_t$=1.24 min in 2.0 min chromatography, 10-80AB, purity 99.16%, MS ESI calcd. for C$_{13}$H$_6$ClF$_6$N$_4$O [M+H]$^+$ 383.0, found 382.9.

Example 171: Synthesis of Compound 190

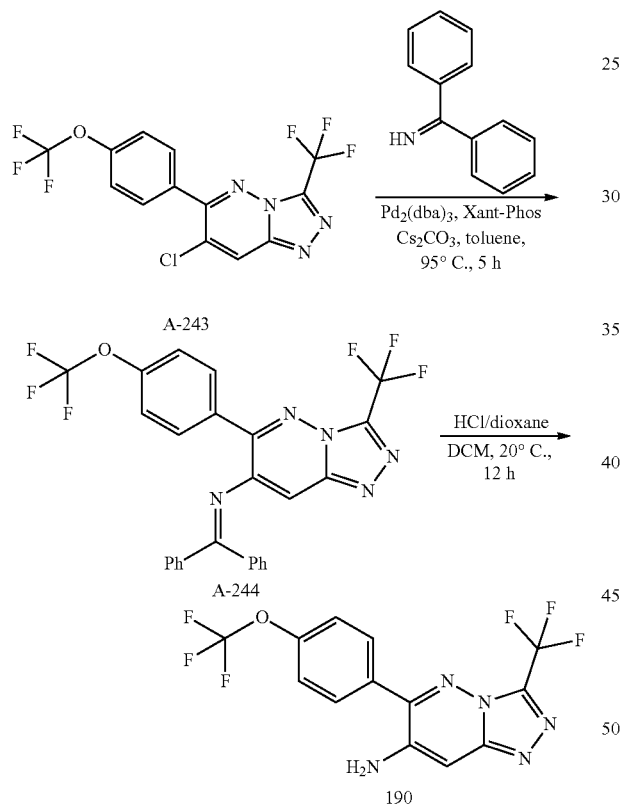

A mixture of 7-chloro-6-[4-(trifluoromethoxy)phenyl]-3-(trifluoromethyl)-[1,2,4]triazolo[4,3-b]pyridazine (250 mg, 0.65 mmol), diphenylmethanimine (355.21 mg, 1.96 mmol), Pd$_2$(dba)$_3$ (89.74 mg, 0.10 mmol), XantPhos (132.31 mg, 0.23 mmol) and Cs$_2$CO$_3$ (532.14 mg, 1.63 mmol) in toluene (8 mL) was stirred at 95° C. for 5 hours under N$_2$. After cooling to r.t., the mixture was concentrated. The residue was diluted with H$_2$O (30 mL), and the mixture was extracted with EtOAc (50 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 10% to 20%) to give the product (380 mg, 0.62 mmol) as a solid. LCMS Rt=0.96 min in 1.5 min chromatography, 5-95AB, purity 85.69%, MS ESI calcd. for C$_{26}$H$_{16}$F$_6$N$_5$O [M+H]$^+$ 528.1, found 528.1.

To a mixture of 1,1-diphenyl-N-[6-[4-(trifluoromethoxy)phenyl]-3-(trifluoromethyl)-[1,2,4]triazolo[4,3-b]pyridazin-7-yl]methanimine (80 mg, 0.15 mmol) in DCM (2 mL) was added HCl/dioxane (0.15 mL, 0.61 mmol), then the mixture was stirred at 20° C. for 12 hours. The mixture was diluted with water (5 mL), basified with Na$_2$CO$_3$ (solid) to pH~8, then extracted with DCM (20 mL×2). The combined organic phase was washed with brine (10 mL), dried over Na$_2$SO$_4$, filtered and concentrated to give the crude product. The crude product was purified by flash chromatography on silica gel (EtOAc in PE=0% to 50% to 100%) to give the product (38.97 mg, 107.3 μmol) as a solid. $^1$H NMR (400 MHZ DMSO-d$_6$) $\delta_H$=7.79 (d, 2H), 7.59 (d, 2H), 7.09 (s, 1H), 6.37 (br s, 2H). LCMS R$_t$=1.18 min in 2.0 min chromatography, 10-80AB, purity 100%, MS ESI calcd. for C$_{13}$H$_8$F$_6$N$_5$O [M+H]$^+$ 364.1, found 364.1.

Example 172: Synthesis of Compound 191

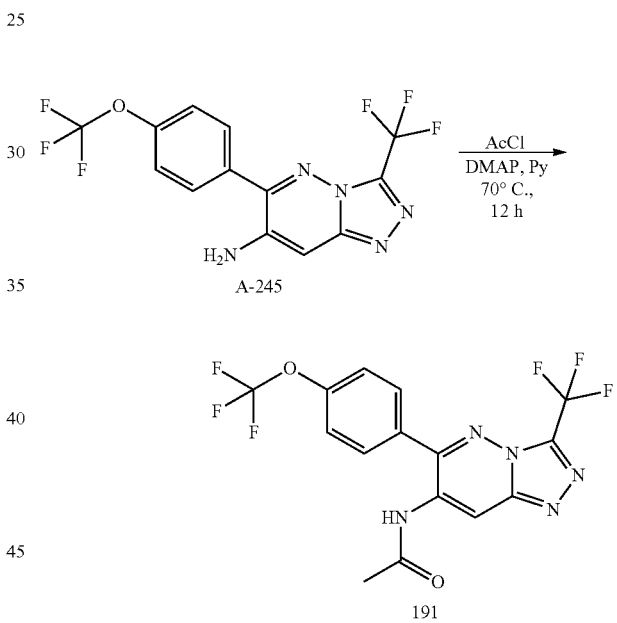

A mixture of 6-[4-(trifluoromethoxy)phenyl]-3-(trifluoromethyl)-[1,2,4]triazolo[4,3-b]pyridazin-7-amine (70 mg, 0.19 mmol) in pyridine (1 mL) was added acetyl chloride (45.39 mg, 0.58 mmol) and DMAP (23.54 mg, 0.19 mmol), then the mixture was stirred at 70° C. for 12 hours. After cooling to r.t., the mixture was concentrated to give the residue. The residue was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-TLC (silica gel, PE:EtOAc=1:5) to give the product (17.05 mg, 42.1 μmol) as a solid. $^1$H NMR (400 MHz, DMSO-d$_6$) $\delta_H$=9.90 (s, 1H), 8.77 (s, 1H), 7.81 (d, 2H), 7.59 (d, 2H), 2.05 (s, 3H). LCMS R$_t$=1.13 min in 2.0 min chromatography, 10-80AB, purity 100%, MS ESI calcd. for C$_{15}$H$_{10}$F$_6$N$_5$O$_2$ [M+H]$^+$ 406.1, found 406.0.

Example 173: Synthesis of Compound 192

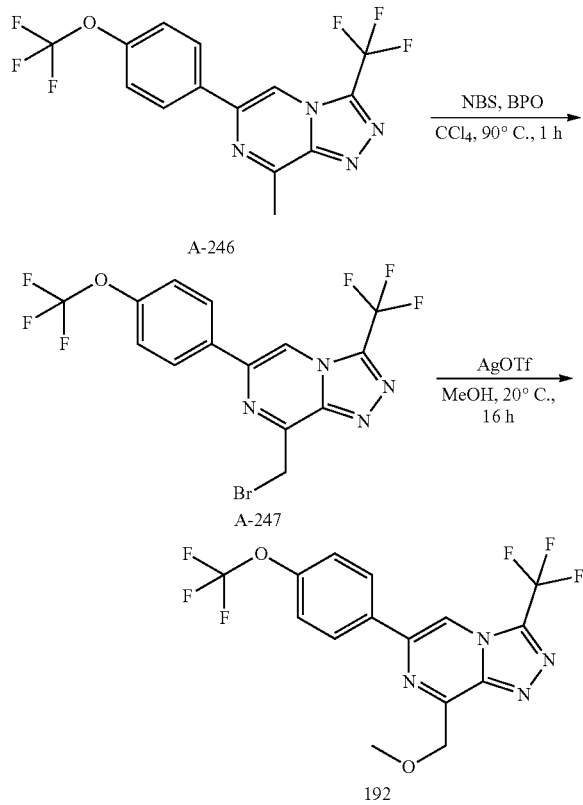

To a mixture of 8-methyl-6-[4-(trifluoromethoxy)phenyl]-3-(trifluoromethyl)-[1.2.4]triazolo[4,3-a]pyrazine (120 mg, 0.33 mmol) and NBS (76.65 mg, 0.43 mmol) in carbon tetrachloride (2 mL) was added BPO (80.25 mg, 0.33 mmol), then the mixture was stirred at 90° C. under $N_2$ for 1 hour. After cooling to r.t., the mixture was diluted with $H_2O$ (20 mL), and the mixture was extracted with EtOAc (10 mL×2). The combined organic phase was washed with water (10 mL) and brine (10 mL), dried over $Na_2SO_4$, filtered and concentrated to give the crude product. The crude product was purified by Prep-TLC (silica gel, PE:EtOAc=5:1) to give the impure product (45 mg, 49.9 µmol) as a solid. LCMS $R_t$=0.89 min in 1.5 min chromatography, 5-95AB, purity 48.87%, MS ESI calcd. for $C_{14}H_8BrF_6N_4O$ $[M+H+2]^+$443.0, found 442.9.

A mixture of 8-(bromomethyl)-6-[4-(trifluoromethoxy)phenyl]-3-(trifluoromethyl)-[1.2.4]triazolo[4,3-a]pyrazine (40 mg, 0.08 mmol) and AgOTf (192.77 mg, 0.75 mmol) in methanol (5 mL) was stirred at 20° C. for 16 hours. The reaction mixture was diluted with EtOAc (20 mL), and treated with brine (20 mL). The organic phase was separated and concentrated. The residue was purified by Prep-TLC (silica gel, PE:EA=3:1) to give the product (4.93 mg, 12.5 µmol) as a solid. $^1$H NMR (400 MHz, DMSO-$d_6$) $\delta_H$=9.04 (s, 1H), 8.32 (d, 2H), 7.56 (d, 2H), 5.08 (s, 2H), 3.52 (s, 3H). LCMS $R_t$=1.17 min in 2.0 min chromatography, 10-80AB, purity 98.51%, MS ESI calcd. for $C_{15}H_{11}F_6N_4O_2$ $[M+H]^+$ 393.1, found 393.0.

Example 174: Synthesis of Compound 193

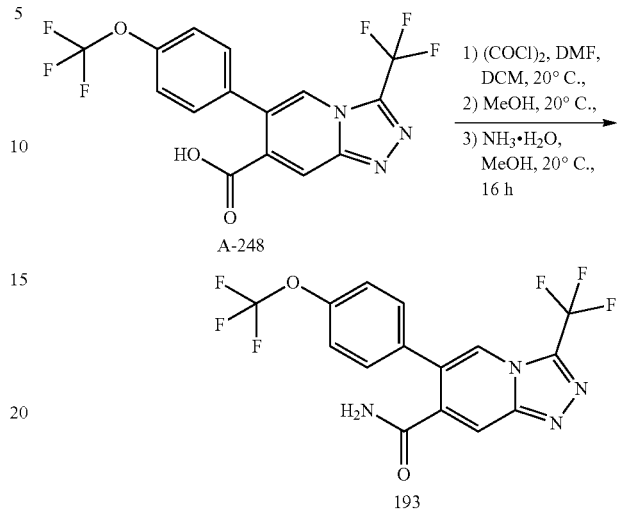

To a mixture of 6-[4-(trifluoromethoxy)phenyl]-3-(trifluoromethyl)-[1,2,4]triazolo[4,3-b]pyridazine-7-carboxylic acid (37 mg, 0.09 mmol) in DCM (5 mL) was added $(COCl)_2$ (23.95 mg, 0.19 mmol) and DMF (3.45 mg, 0.05 mmol), then the mixture was stirred at 20° C. for 0.5 hours. To the mixture was added methanol (2 mL), then the mixture was stirred at 20° C. for 0.5 hour. The mixture was diluted with EtOAc (30 mL), washed with water (10 mL) and brine (10 mL), dried over anhydrous $Na_2SO_4$, filtered and concentrated to give the residue. To $NH_3.H_2O$ (10 mL, 0.29 mmol) was added the solution of the residue in THF (2 mL) at 0° C., then the mixture was stirred at 20° C. for 16 hours. To the mixture was added water (15 mL), and extracted with EtOAc (15 mL×2). The combined organic phase was washed with water (10 mL×2) and brine (10 mL×2), dried over anhydrous $Na_2SO_4$, filtered and concentrated to give the crude product. The crude product was purified by Prep-TLC (silica gel, PE:EtOAc=1:3) to give the product (5.67 mg, 14.5 µmol) as a solid. $^1$H NMR (400 MHz, DMSO-$d_6$) $\delta_H$=8.80 (s, 1H), 8.32 (s, 1H), 8.02 (s, 1H), 7.78 (d, 2H), 7.58 (d, 2H). LCMS $R_t$=1.14 min in 2.0 min chromatography, 10-80AB, purity 100.00%, MS ESI calcd. for $C_{14}H_8F_6N_5O_2$ $[M+H]^+$ 392.1, found 391.9.

Example 175: Synthesis of Compound 194

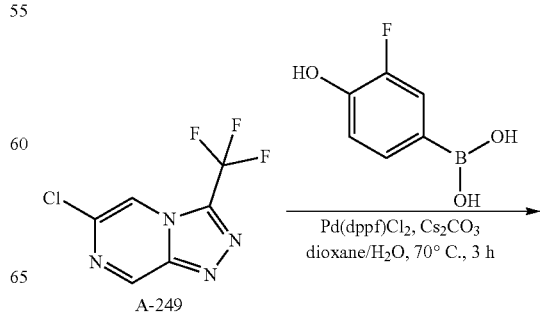

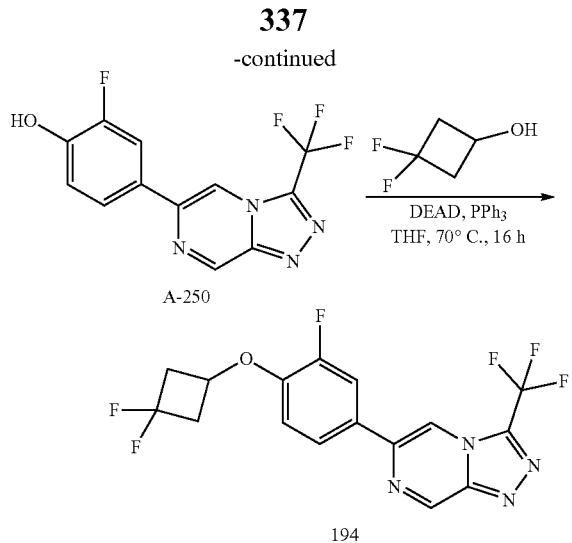

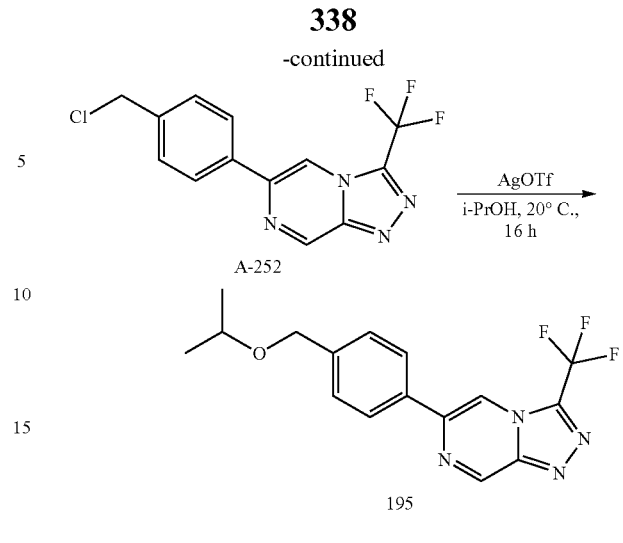

A mixture of 6-chloro-3-(trifluoromethyl)-[1,2,4]triazolo[4,3-a]pyrazine (150 mg, 0.67 mmol), (3-fluoro-4-hydroxyphenyl)boronic acid (157.63 mg, 1.01 mmol), Pd(dppf)Cl$_2$ (73.97 mg, 0.10 mmol) and Cs$_2$CO$_3$ (439.16 mg, 1.35 mmol) in 1,4-dioxane (4 mL) and water (0.40 mL) was stirred at 70° C. for 3 hours. After cooling to r.t., the mixture was diluted with EtOAc (10 mL), filtered through silica gel, eluted with EtOAc (20 mL) and concentrated to give the crude product. The crude product was purified by flash chromatograph on silica gel (EtOAc in PE=0% to 40%) to give the product (40 mg, 0.12 mmol) as a solid. LCMS R$_t$=0.70 min in 1.5 min chromatography, 5-95AB, purity 93.52%, MS ESI calcd. for C$_{12}$H$_7$F$_4$N$_4$O [M+H]$^+$ 299.0, found 298.9.

To a mixture of 2-fluoro-4-[3-(trifluoromethyl)-[1,2,4]triazolo[4,3-a]pyrazin-6-yl]phenol (40 mg, 0.13 mmol), 3,3-difluorocyclobutanol (43.5 mg, 0.40 mmol) and PPh$_3$ (63.33 mg, 0.24 mmol) in THF (3 mL) was added DEAD (42.05 mg, 0.24 mmol) at 0° C. Then the mixture was allowed to be warmed to 70° C. and stirred for 16 hours. After cooling to r.t., the mixture was concentrated to give the crude product. The product was purified by Prep-TLC (PE:EtOAc=3:1) to give the impure product. The impure product was purified by Prep-HPLC [Xtimate C18 (150 mm×25 mm, 5 μm) A=H$_2$O (0.05% ammonia hydroxide) and B=CH$_3$CN; 43-73% B over 8 minutes] to give the product (1.78 mg, 4.5 μmol) as a solid. $^1$H NMR (400 MHz, CDCl$_3$) δ$_H$=9.57 (d, 1H), 8.34 (s, 1H), 7.79 (dd, 1H), 7.73-7.69 (m, 1H), 6.95 (t, 1H), 4.84-4.73 (m, 1H), 3.22-3.09 (m, 2H), 2.96-2.81 (m, 2H). LCMS R$_t$=1.18 min in 2.0 min chromatography, 10-80AB, purity 100.00%, MS ESI calcd. for C$_{16}$H$_{11}$F$_6$N$_4$O [M+H]$^+$ 389.1, found 389.1.

Example 176: Synthesis of Compound 195

A mixture of [4-[3-(trifluoromethyl)-[1,2,4]triazolo[4,3-a]pyrazin-6-yl]phenyl]methanol (50 mg, 0.17 mmol) and SOCl$_2$ (0.06 mL, 0.85 mmol) in DCM (2 mL) was stirred at 20° C. for 16 hours. The mixture was quenched with sat.NaHCO$_3$ (20 mL), and the mixture was extracted with DCM (20 mL×2). The combined organic phase was washed with brine (10 mL), dried over Na$_2$SO$_4$, filtered and concentrated to give the crude product (30 mg, 0.06 mmol) as oil. The crude product was used directly in next step without any purification. LCMS R$_t$=0.84 min in 1.5 min chromatography, 5-95AB, purity 64.26%, MS ESI calcd. for C$_{13}$H$_9$ClF$_3$N$_4$ [M+H]$^+$313.0, found 312.9.

To a solution of 6-[4-(chloromethyl)phenyl]-3-(trifluoromethyl)-[1,2,4]triazolo[4,3-a]pyrazine (50 mg, 0.16 mmol) in IPA (3 mL) was added AgOTf (410.87 mg, 1.60 mmol), and the mixture was stirred at 20° C. for 16 hours. The mixture was filtered through Celite, and eluted with EtOAc (15 mL×2). The filtrate was concentrated and diluted with EtOAc (20 mL), washed with water (15 mL×2) and brine (10 mL), dried over Na$_2$SO$_4$, filtered and concentrated to give the crude product. The crude product was purified by Prep-TLC (silica gel, PE:EtOAc=3:1) to give the product (24.73 mg, 0.07 mmol) as a solid. $^1$H NMR (400 MHz, CDCl$_3$) δ$_H$=9.60 (d, 1H), 8.41 (s, 1H), 7.96 (d, 2H), 7.54 (d, 2H), 4.61 (s, 2H), 3.80-3.66 (m, 1H), 1.26 (d, 6H). LCMS R$_t$=1.22 min in 2 min chromatography, 10-80AB, purity 100%, MS ESI calcd. for C$_{16}$H$_{16}$F$_3$N$_4$O [M+H]$^+$ 337.1, found 336.9.

Example 177: Synthesis of Compound 196

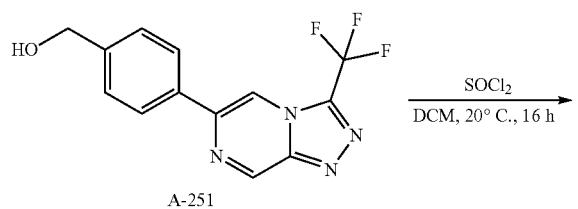

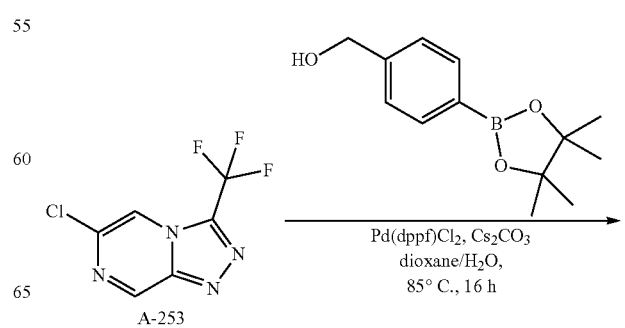

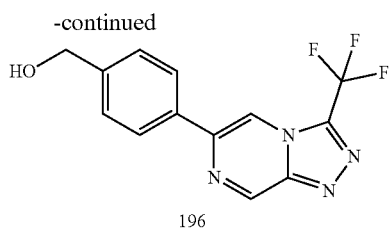

196

A mixture of 6-chloro-3-(trifluoromethyl)-[1,2,4]triazolo[4,3-a]pyrazine (300 mg, 1.35 mmol), [4-(hydroxymethyl)phenyl]boronic acid (307.25 mg, 2.02 mmol), Pd(dppf)Cl$_2$ (147.94 mg, 0.20 mmol) and Cs$_2$CO$_3$ (878.32 mg, 2.7 mmol) in 1,4-dioxane (10 mL) and water (1 mL) was stirred at 85° C. for 16 hours. After cooling to r.t., the mixture was filtered through Celite, and eluted with EtOAc (10 mL×2). The filtrate was concentrated and diluted with EtOAc (10 mL), washed with water (10 mL×2) and brine (10 mL), dried over Na$_2$SO$_4$, filtered and concentrated to give the crude product. The crude product was purified by flash chromatography on silica gel (EtOAc in PE=30% to 80%) to give impure product. The impure product was purified by Prep-HPLC (Waters Xbridge (150 mm×25 mm, 5 μm), A=water (10 mM NH$_4$HCO$_3$) and B=CH$_3$CN; 18-48% B over 6 minutes) to give the product (21.13 mg, 0.07 mmol) as a solid. $^1$H NMR (400 MHz, DMSO-d$_6$) δ$_H$=9.76 (d, 1H), 8.96 (s, 1H), 8.15 (d, 2H), 7.49 (d, 2H), 5.32 (t, 1H), 4.59 (d, 2H). LCMS R$_t$=0.83 min in 2.0 min chromatography, 10-80AB, purity 100%, MS ESI calcd. for C$_{13}$H$_{10}$F$_3$N$_4$O [M+H]$^+$ 295.1, found 294.9.

Example 178: Synthesis of Compound 197

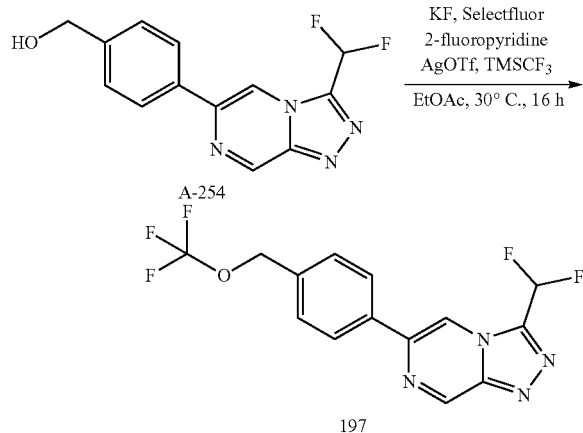

To a mixture of AgOTf (781.31 mg, 3.04 mmol), KF (235.56 mg, 4.05 mmol), Selectfluor (538.62 mg, 1.52 mmol) and [4-[3-(difluoromethyl)-[1,2,4]triazolo[4,3-a]pyrazin-6-yl]phenyl]methanol (140 mg, 0.51 mmol) in ethyl acetate (6 mL) was added 2-fluoropyridine (295.23 mg, 3.04 mmol) and trimethyl(trifluoromethyl)silane (432.38 mg, 3.04 mmol) under N$_2$, and the mixture was stirred at 30° C. for 16 hours. The mixture was diluted with sat.NH$_4$Cl (10 mL), filtered through Celite and eluted with EtOAc (30 mL×2). The filtrate was concentrated to give the crude product. The crude product was purified by Prep-TLC (silica gel, PE:EtOAc=3:1) to give the product (8.36 mg, 24.3 μmol) as a solid. $^1$H NMR (400 MHz, DMSO-d$_6$) δ$_H$=9.68 (d, 1H), 9.21 (d, 1H), 8.19 (d, 2H), 7.86 (t, 1H), 7.62 (d, 2H), 5.26 (s, 2H). LCMS R$_t$=1.19 min in 2.0 min chromatography, 10-80AB, purity 100%, MS ESI calcd. for C$_{14}$H$_{10}$F$_5$N$_4$O [M+H]$^+$ 345.1, found 344.9.

Example 179: Synthesis of Compound 198

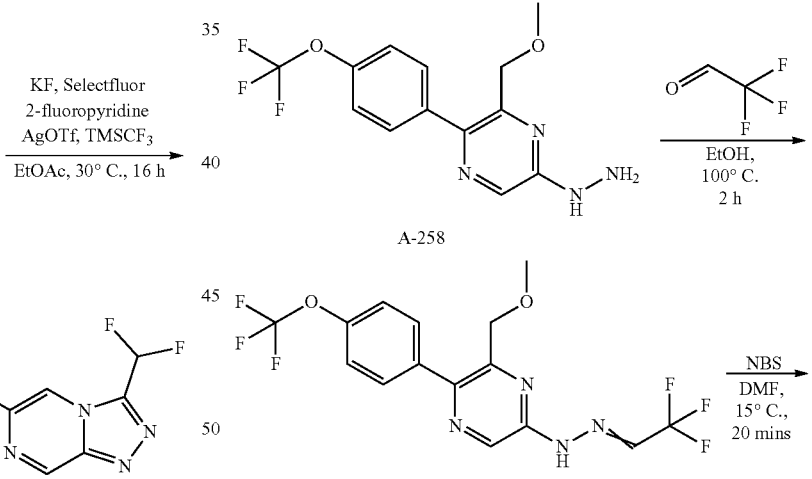

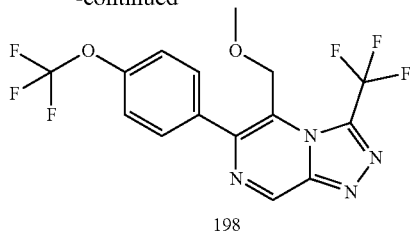

198

A mixture of [6-chloro-3-[4-(trifluoromethoxy)phenyl]pyrazin-2-yl]methanol (500 mg, 1.64 mmol) and SOCl$_2$ (5 mL) was stirred at 60° C. for 1 hour. After cooling to r.t., the mixture was concentrated. The residue was poured into sat.Na$_2$CO$_3$ (20 mL), and the mixture was extracted with EtOAc (50 mL×2). The combined organic phase was washed with brine (20 mL), dried over Na$_2$SO$_4$, filtered and concentrated to give the crude product (600 mg, 1.86 mmol, crude) as oil, which was used directly without any further purification. LCMS R$_t$=0.97 min in 1.5 min chromatography, 5-95AB, purity 47.74%, MS ESI calcd. for C$_{12}$H$_8$Cl$_2$F$_3$N$_2$O [M+H]$^+$ 323.0, found 323.0.

A mixture of 5-chloro-3-(chloromethyl)-2-[4-(trifluoromethoxy)phenyl]pyrazine (600 mg, 1.86 mmol) and AgOTf (4771.4 mg, 18.57 mmol) in methanol (15 mL) was stirred at 50° C. for 6 hours. After cooling to r.t., the mixture was quenched with sat.NH$_4$Cl (20 mL), and the mixture was filtered through Celite and eluted with EtOAc (30 mL×2). The filtrate was concentrated to give the crude product (700 mg, 1.41 mmol) as an oil. The crude product was used directly without any further purification. LCMS R$_t$=0.88 min in 1.5 min chromatography, 5-95AB, purity 64.30%, MS ESI calcd. for C$_{13}$H$_{11}$ClF$_3$N$_2$O$_2$ [M+H]$^+$ 319.0, found 318.9.

A mixture of 5-chloro-3-(methoxymethyl)-2-[4-(trifluoromethoxy)phenyl]pyrazine (700 mg, 2.2 mmol) and N$_2$H$_4$ (2.11 g, 65.9 mmol) in MeCN (10 mL) was stirred at 90° C. for 1 hour. The mixture was stirred at 90° C. for another 30 mins. After cooling to r.t., the mixture was diluted with H$_2$O (20 mL) and extracted with EtOAc (40 mL×2). The combined organic phase was washed with H$_2$O (20 mL) and brine (20 mL), dried over Na$_2$SO$_4$, filtered and concentrated to give the crude product (350 mg, 0.57 mmol, crude) as a solid. The crude product was used directly without any further purification. LCMS R$_t$=0.94 min in 2.0 min chromatography, 10-80AB, purity 50.92%, MS ESI calcd. for C$_{13}$H$_{14}$F$_3$N$_4$O$_2$ [M+H]$^+$ 315.1, found 315.1.

A mixture of [6-(methoxymethyl)-5-[4-(trifluoromethoxy)phenyl]pyrazin-2-yl]hydrazine (350 mg, 1.11 mmol) and 2,2,2-trifluoroacetaldehyde (582.23 mg, 4.45 mmol) in ethanol (1 mL) was stirred at 100° C. for 2 hours. After cooling to r.t., the mixture was diluted with H$_2$O (20 mL) and extracted with EtOAc (30 mL×2). The combined organic phase was washed with brine (20 mL), dried over Na$_2$SO$_4$, filtered and concentrated to give the crude product (400 mg, 1.01 mmol, crude) as an oil, which was used directly without any further purification. LCMS R$_t$=0.89 min in 1.5 min chromatography, 5-95AB, purity 52.48%, MS ESI calcd. for C$_{15}$H$_{13}$F$_6$N$_4$O$_2$ [M+H]$^+$ 395.1, found 395.4.

To a solution of 6-(methoxymethyl)-N-(2,2,2-trifluoroethylideneamino)-5-[4-(trifluoromethoxy)phenyl]pyrazin-2-amine (400 mg, 1.01 mmol) in DMF (5 mL) was added NBS (180.57 mg, 1.01 mmol), and the mixture was stirred at 15° C. for 20 minutes. The mixture was diluted with H$_2$O (20 mL) and extracted with EtOAc (50 mL×2). The combined organic phase was washed with H$_2$O (30 mL) and brine (30 mL), dried over Na$_2$SO$_4$, filtered and concentrated to give the crude product (500 mg, 1.06 mmol, crude) as oil, which was used directly without any further purification. LCMS R$_t$=0.99 min in 1.5 min chromatography, 5-95AB, purity 17.37%, MS ESI calcd. for C$_{15}$H$_{12}$BrF$_6$N$_4$O$_2$ [M+H+2]$^+$475.0, found 475.0.

To a solution of 2,2,2-trifluoro-N-[6-(methoxymethyl)-5-[4-(trifluoromethoxy)phenyl]pyrazin-2-yl]ethanehydrazonoyl bromide (500 mg, 1.06 mmol) in toluene (10 mL) was added Et$_3$N (0.73 mL, 5.28 mmol), and the mixture was stirred at 15° C. for 30 mins. The mixture was diluted with H$_2$O (10 mL) and extracted with EtOAc (30 mL×2). The combined organic phase was washed with brine (20 mL), dried over Na2SO4, filtered and concentrated to give the crude product. The crude product was purified by flash chromatography on silica gel (EtOAc in PE=20% to 40% to 60%) to give the impure product (~100 mg). The impure product was purified by prep-TLC (silica gel, PE:EtOAc=2:1) to give the product (24.86 mg, 0.06 mmol) as a solid. $^1$H NMR (400 MHz, CDCl$_3$) δ$_H$=9.54 (s, 1H), 7.77 (d, 2H), 7.40 (d, 2H), 4.68 (s, 2H), 3.44 (s, 3H). LCMS R$_t$=1.17 min in 2 min chromatography, 10-80AB, purity 100%, MS ESI calcd. for C$_{15}$H$_{11}$F$_6$N$_4$O$_2$ [M+H]$^+$ 393.1, found 393.0.

Example 180: Synthesis of Compounds 199 and 200

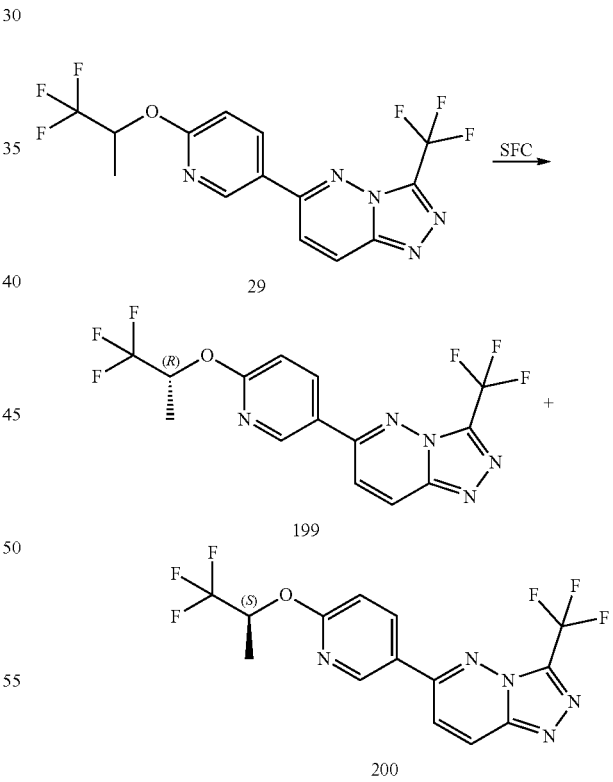

The sample was analyzed by SFC to show two peaks (Peak 1: Rt=2.35 min, Peak 2: Rt=2.49 min).

Method: Column: ChiralCel OJ-H 150×4.6 mm I.D., 5 μm Mobile phase: A: CO$_2$ B: IPA (0.05% DEA) Gradient: from 5% to 40% of B in 5.5 min and hold 40% for 3 min, then 5% of B for 1.5 min Flow rate: 2.5 mL/min Column temperature: 40° C.

The product was separated by SFC (DAICEL CHIRAL-CEL OJ-H (250 mm×30 mm, 5 μm)); A=CO$_2$ and B=IPA (0.1% NH$_3$H$_2$O); 35° C.; 50 mL/min; 15% B; 10 min run; 20 injections, Rt of peak 1=7.33 min, Rt of peak 2=8.3 min) to give 3-(trifluoromethyl)-6-[6-[(1R)-2,2,2-trifluoro-1-methyl-ethoxy]-3-pyridyl]-[1,2,4]triazolo[4,3-b]pyridazine (6.76 mg, 17.9 μmol) (Peak 1, Rt=2.35 min in SFC) as a solid, and 3-(trifluoromethyl)-6-[6-[(1S)-2,2,2-trifluoro-1-methyl-ethoxy]-3-pyridyl]-[1,2,4]triazolo[4,3-b]pyridazine (16.41 mg, 43.5 μmol) (Peak 2: Rt=2.49 min in SFC) as a solid.

Note: the enantiomers were randomly assigned.

Compound 201 (peak 1): $^1$H NMR (400 MHz, CDCl$_3$+D$_2$O) $\delta_H$=8.79 (d, 1H), 8.36-8.31 (m, 2H), 7.74 (d, 1H), 7.03 (d, 1H), 5.95-5.82 (m, 1H), 1.56 (d, 3H) LCMS R$_t$=1.20 min in 2 min chromatography, 10-80AB, purity 100%, MS ESI calcd. for C$_{14}$H$_{10}$F$_6$N$_5$O [M+H]$^+$ 378.1, found 378.0.

Compound 202 (peak 2): $^1$H NMR (400 MHz, CDCl$_3$+D$_2$O)=8.79 (d, 1H), 8.37-8.31 (m, 2H), 7.74 (d, 1H), 7.03 (d, 1H), 5.96-5.81 (m, 1H), 1.56 (d, 3H). LCMS R$_t$=1.18 min in 2 min chromatography, 10-80AB, purity 100%, MS ESI calcd. for C$_{14}$H$_{10}$F$_6$N$_5$O [M+H]$^+$ 378.1, found 378.0.

Example 181: Synthesis of Compound 201

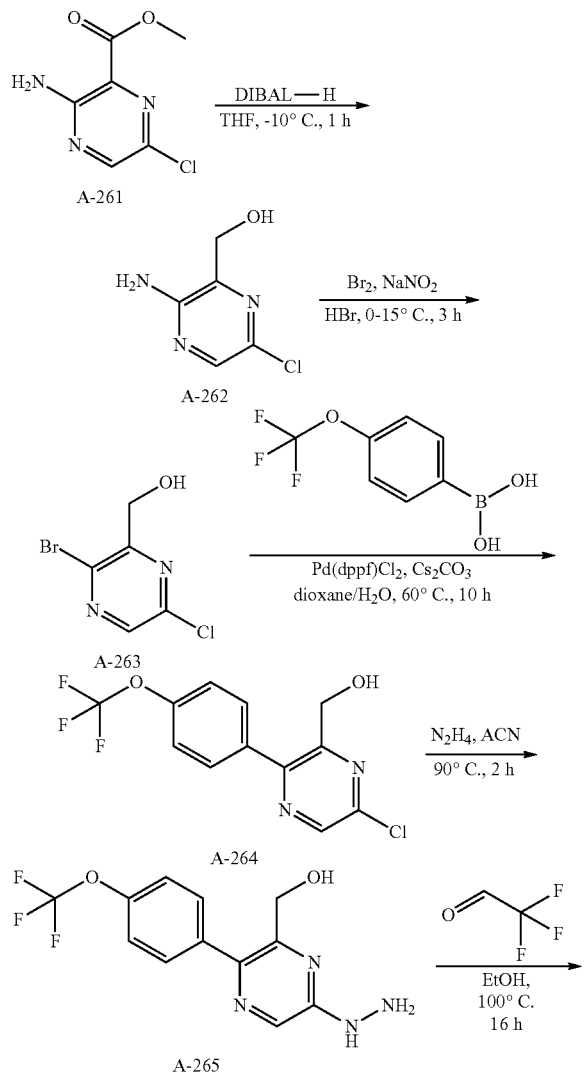

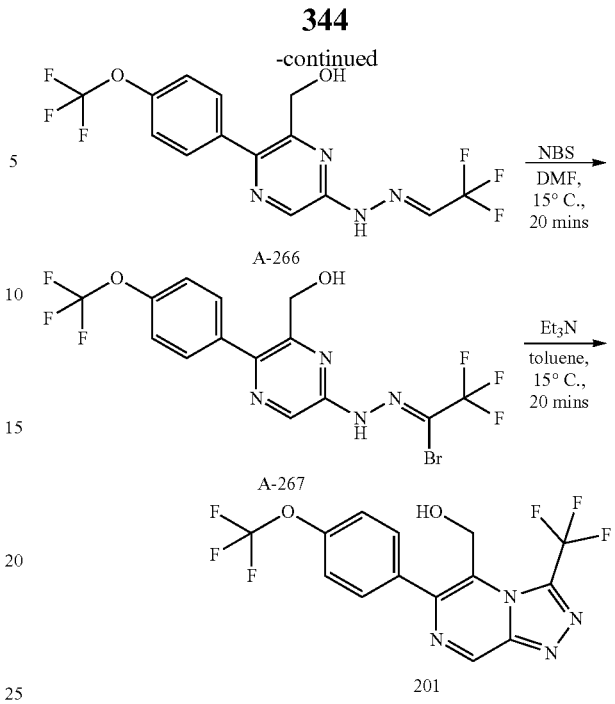

To a solution of methyl 3-amino-6-chloro-pyrazine-2-carboxylate (3 g, 15.99 mmol) in THF (150 mL) was added DIBAL-H (63.97 mL, 63.97 mmol) at −40° C. and the mixture was allowed to warmed to −10° C. and stirred for 1 hour. To the mixture was added potassium sodium tartrate (sat. aq., ~100 mL) slowly, and the mixture was stirred at r.t. for 2 hours. The mixture was extracted with EtOAc (150 mL×2), and the combined organic phase was washed with brine (50 mL), dried over Na$_2$SO$_4$, filtered and concentrated to give the crude product (2400 mg, 15.04 mmol) as a solid. $^1$H NMR (400 MHz, CDCl$_3$) $\delta_H$=7.98 (s, 1H), 5.00 (br s, 2H), 4.72 (s, 2H), 2.73 (br s, 1H).

To a mixture of (3-amino-6-chloro-pyrazin-2-yl)methanol (2.4 g, 15.04 mmol) in HBr (20 mL) was added Br$_2$ (2.31 mL, 45.12 mmol) at 0° C., followed by NaNO$_2$ (2.59 g, 37.6 mmol) in water (5 mL), and the mixture was stirred at 15° C. for 3 hours. The mixture was diluted with H$_2$O (20 mL) and quenched by NaHSO$_3$ (solid, ~5 g). The mixture extracted with EtOAc (100 mL×2), and the combined organic phase was washed with sat.Na$_2$CO$_3$ (50 mL) and brine (50 mL), dried over Na$_2$SO$_4$, filtered and concentrated to give the crude product. The crude product was purified by flash chromatography on silica gel (EtOAc in PE=5% to 10% to 15% to 20% to 30%) to give the product (1100 mg, 4.92 mmol) as colorless oil. $^1$H NMR (400 MHz, CDCl$_3$) $\delta_H$=8.34 (s, 1H), 4.82 (dd, 2H), 3.32 (t, 1H).

A mixture of (3-bromo-6-chloro-pyrazin-2-yl)methanol (1.1 g, 4.92 mmol), [4-(trifluoromethoxy)phenyl]boronic acid (1.06 g, 5.17 mmol), Cs$_2$CO$_3$ (3.21 g, 9.85 mmol) and Pd(dppf)Cl$_2$ (360.19 mg, 0.49 mmol) in 1,4-dioxane (20 mL) and water (2 mL) was stirred at 60° C. for 10 hours. After cooling to r.t., the mixture was concentrated to give the crude product. The crude product was purified by flash chromatography on silica gel (EtOAc in PE=20% to 40% to 50%) to give the pure product (600 mg, 1.97 mmol) as a colorless oil. $^1$H NMR (400 MHz, CDCl$_3$) $\delta_H$=8.63 (s, 1H), 7.65 (d, 2H), 7.37 (d, 2H), 4.80 (d, 2H), 3.40 (t, 1H).

A mixture of [6-chloro-3-[4-(trifluoromethoxy)phenyl]pyrazin-2-yl]methanol (600 mg, 1.97 mmol) and N$_2$H$_4$ (1890.69 mg, 59.08 mmol) in MeCN (20 mL) was stirred at 90° C. for 2 hours. After cooling to r.t., the mixture was diluted with H₂O (30 mL) and extracted with EtOAc (50 mL×2). The combined organic phase was washed with H₂O (20 mL) and brine (20 mL), dried over Na₂SO₄, filtered and concentrated to give the crude product (460 mg, 1.53 mmol) as a solid, which was used directly without any further purification. LCMS $R_t$=0.67 min in 1.5 min chromatography, 5-95AB, purity 59.13%, MS ESI calcd. for $C_{12}H_{12}F_3N_4O_2$ [M+H]⁺ 301.1, found 301.0.

A mixture of [6-hydrazino-3-[4-(trifluoromethoxy)phenyl]pyrazin-2-yl]methanol (460 mg, 1.53 mmol) and 2,2,2-trifluoroacetaldehyde (250.3 mg, 1.92 mmol) in ethanol (2 mL) was stirred at 100° C. for 16 hours. After cooling to r.t., the mixture was diluted with H₂O (20 mL) and extracted with EtOAc (40 mL×2). The combined organic phase was washed with brine (30 mL), dried over Na₂SO₄, filtered and concentrated to give the crude product (600 mg, 1.58 mmol, crude) as oil. The crude product was used directly without any further purification. LCMS $R_t$=0.85 min in 1.5 min chromatography, 5-95AB, purity 35.73%, MS ESI calcd. for $C_{14}H_{11}F_6N_4O_2$ [M+H]⁺ 381.1, found 381.0.

To a solution of [6-[2-(2,2,2-trifluoroethylidene)hydrazino]-3-[4-(trifluoromethoxy)phenyl]pyrazin-2-yl]methanol (600 mg, 1.58 mmol) in DMF (5 mL) was added NBS (294.88 mg, 1.66 mmol), and the mixture was stirred at 15° C. for 20 mins. The mixture was diluted with H₂O (20 mL) and extracted with EtOAc (50 mL×2). The combined organic phase was washed with H₂O (30 mL) and brine (30 mL), dried over Na₂SO₄, filtered and concentrated to give the crude product (800 mg, 1.74 mmol) as oil, which was used directly for next step without any further purification. LCMS $R_t$=0.91 min in 1.5 min chromatography, 5-95AB, MS ESI calcd. for $C_{14}H_{10}BrF_6N_4O_2$ [M+H]⁺ 459.0, found 459.0.

A mixture of 2,2,2-trifluoro-N-[6-(hydroxymethyl)-5-[4-(trifluoromethoxy)phenyl]pyrazin-2-yl]ethanehydrazonoyl bromide (800 mg, 1.74 mmol) and Et₃N (0.72 mL, 5.23 mmol) in Toluene (5 mL) was stirred at 15° C. for 20 mins. The mixture was diluted with H₂O (20 mL) and extracted with EtOAc (50 mL×2). The combined organic phase was washed with brine (20 mL), dried over Na₂SO₄, filtered and concentrated to give the crude product. The crude product was purified by flash chromatography on silica gel (EtOAc in PE=20% to 40% to 60%) to give the impure product (400 mg).

A part of the impure product (30 mg) was by prep-TLC (silica gel, PE:EtOAc=1:1) to give the product (12.8 mg, 33.8 μmol) as a solid. ¹H NMR (400 MHz, DMSO-d₆) $δ_H$=9.55 (s, 1H), 7.82 (d, 2H), 7.40 (d, 2H), 5.06 (d, 2H), 2.43-2.31 (m, 1H). LCMS $R_t$=1.04 min in 2.0 min chromatography, 10-80AB, purity 100.00%, MS ESI calcd. for $C_{14}H_9F_6N_4O_2$ [M+H]⁺ 379.1, found 379.0.

Example 182: Synthesis of Compound 202

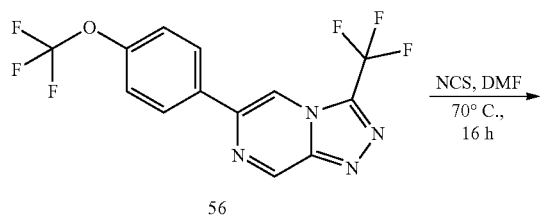

56

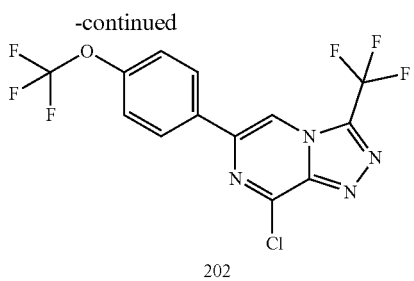

202

A mixture of 6-[4-(trifluoromethoxy)phenyl]-3-(trifluoromethyl)-[1,2,4]triazolo[4,3-a]pyrazine (920 mg, 2.64 mmol) and NCS (529.21 mg, 3.96 mmol) in DMF (30 mL) was stirred at 70° C. for 16 hours to give a brown mixture. After cooling to r.t., the mixture was diluted with H₂O (50 mL), and the mixture was extracted with EtOAc (100 mL×2). The combined organic phase was washed with water (50 mL×2) and brine (50 mL), dried over Na₂SO₄, filtered and concentrated. The residue was purified by flash chromatography on silica gel (EtOAc in PE=0% to 10% to 20%) to give the impure product (580 mg) as a solid.

A part of the impure product (30 mg) was triturated from hexane (1 mL) and dried in an oven to give the product (11 mg) as an off-white solid ¹H NMR (400 MHz, CDCl₃) $δ_H$=8.37 (s, 1H), 8.02 (d, 2H), 7.41 (dd, 2H). LCMS $R_t$=1.21 min in 2.0 min chromatography, 10-80AB, purity 100%, MS ESI calcd. for $C_{13}H_6ClF_6N_4O$ [M+H]⁺ 383.0, found 382.9.

Example 183: Synthesis of Compound 203

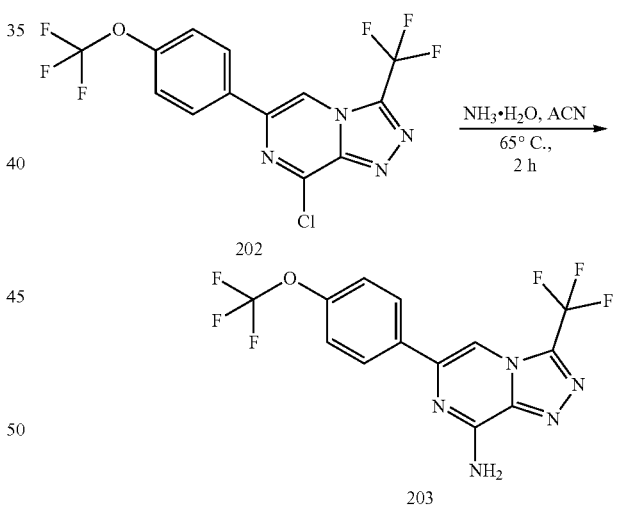

A mixture of 8-chloro-6-[4-(trifluoromethoxy)phenyl]-3-(trifluoromethyl)-[1,2,4]triazolo[4,3-a]pyrazine (480 mg, 1.25 mmol) in NH₃.H₂O (100 mL) and MeCN (50 mL) was stirred at 65° C. for 2 hours. After cooling to r.t., the mixture was concentrated. The residue was diluted with H₂O (30 mL), and the mixture was extracted with EtOAc (50 mL×2). The combined organic phase was washed with water (30 mL) and brine (30 mL), dried over Na₂SO₄, filtered and concentrated to give the crude product (430 mg, 94% yield) as a solid.

A part of the crude product (30 mg) was purified by Prep-TLC (silica gel, PE:EtOAc=2:1) to give 6-[4-(trifluoromethoxy)phenyl]-3-(trifluoromethyl)-[1,2,4]triazolo[4,3- a]pyrazin-8-amine (17.28 mg) as a solid. ¹H NMR (400 MHz, CDCl₃) $\delta_H$=7.92 (d, 2H), 7.88 (s, 1H), 7.34 (d, 2H), 6.04 (br s, 2H). LCMS $R_t$=1.23 min in 2.0 min chromatography, 10-80AB, purity 100%, MS ESI calcd. for $C_{13}H_8F_6N_5O$ [M+H]⁺ 364.1, found 363.9.

Example 184: Synthesis of Compound 204

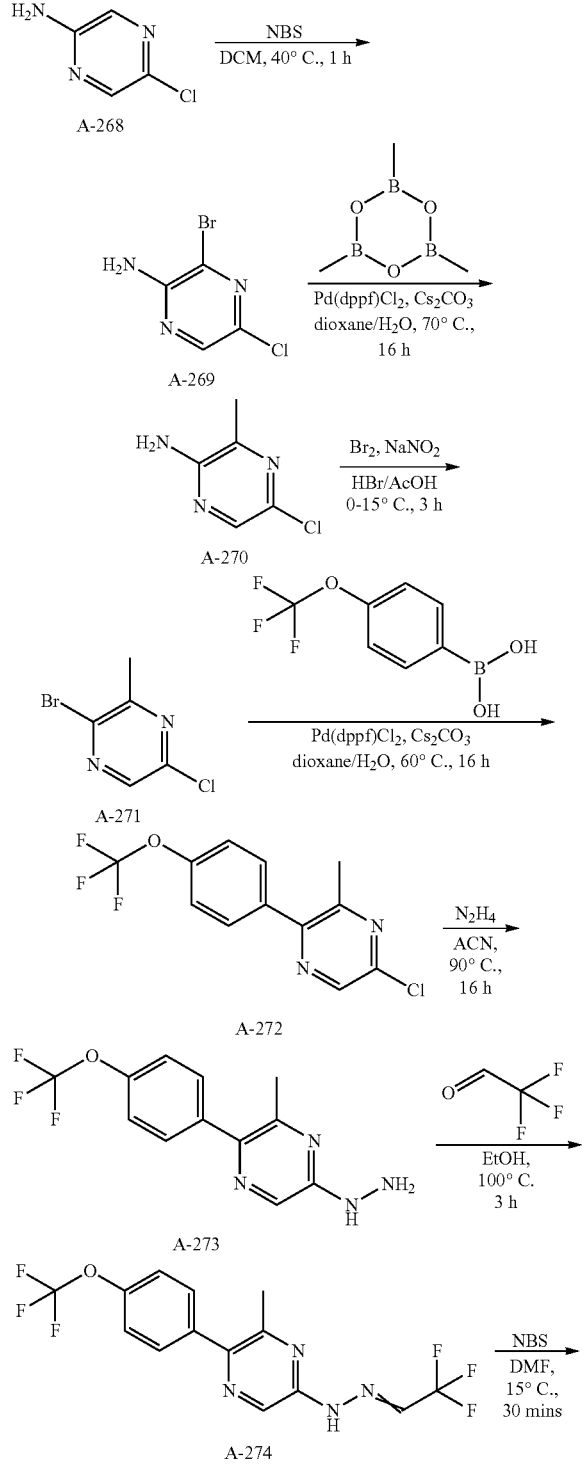

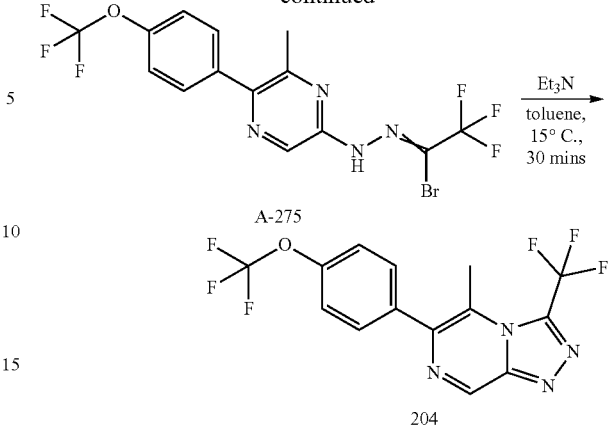

To a solution of 5-chloropyrazin-2-amine (500 mg, 3.86 mmol) in DCM (5 mL) was added NBS (686.92 mg, 3.86 mmol), and the brown mixture was stirred at 40° C. for 1 hour. After cooling to r.t., the mixture was filtered through silica gel and eluted with EtOAc (20 mL×3), and the filtrate was concentrated to give the crude product. The crude product was purified by flash chromatography on silica gel (EtOAc in PE=20% to 40% to 50%) to give the product (600 mg) as a solid. ¹H NMR (400 MHz, CDCl₃) $\delta_H$=7.98 (s, 1H), 5.05 (br s, 2H).

A mixture of 3-bromo-5-chloro-pyrazin-2-amine (600 mg, 2.88 mmol), 2,4,6-trimethyl-1,3,5,2,4,6-trioxatriborinane (397.48 mg, 3.17 mmol), Cs₂CO₃ (1.88 g, 5.76 mmol) and Pd(dppf)Cl₂ (210.62 mg, 0.29 mmol) in 1,4-Dioxane (5 mL) and Water (0.50 mL) was stirred at 70° C. for 16 hours. After cooling to r.t., the mixture was concentrated to give the crude product. The crude product was purified by flash chromatography on silica gel (EtOAc in PE=20% to 40% to 60% to 80%) to give the product (200 mg) as a solid. ¹H NMR (400 MHZ, CDCl₃) $\delta_H$=7.90 (s, 1H), 4.55 (br s, 2H), 2.40 (s, 3H).

To a mixture of 5-chloro-3-methyl-pyrazin-2-amine (200 mg, 1.39 mmol) in Acetic acid (3 mL) and HBr (3 mL) was added Br₂ (0.18 mL, 3.48 mmol) at 0° C., followed by NaNO₂ (288.34 mg, 4.18 mmol) in Water (0.5 mL), and the mixture was stirred at 15° C. for 3 hours. The mixture was quenched with NaHSO₃ (solid, 3 g) and the mixture was basified with Na₂CO₃ (solid) to pH ~8. The mixture was extracted with EtOAc (40 mL×2), and the combined organic phase was washed with sat.Na₂CO₃ (30 mL) and brine (30 mL), dried over Na₂SO₄, filtered and concentrated to give the crude product (40 mg) as an oil LCMS $R_t$=0.72 min in 1.5 min chromatography, 5-95AB, purity 94.05%, A mixture of 2-bromo-5-chloro-3-methyl-pyrazine (40 mg, 0.19 mmol), [4-(trifluoromethoxy)phenyl]boronic acid (43.68 mg, 0.21 mmol), Cs₂CO₃ (125.63 mg, 0.39 mmol) and Pd(dppf)Cl₂ (14.11 mg, 0.02 mmol) in 1,4-Dioxane (2 mL) and Water (0.2 mL) was stirred at 60° C. for 16 hours. After cooling to r.t., the mixture was concentrated to give the crude product. The crude product was purified by flash chromatography on silica gel (EtOAc in PE=10% to 20% to 40% to 50%) to give the product (40 mg) as an oil. LCMS $R_t$=0.89 min in 1.5 min chromatography, MS ESI calcd. for $C_{12}H_9ClF_3N_2O$ [M+H]⁺ 289.0, found 288.9.

A mixture of 5-chloro-3-methyl-2-[4-(trifluoromethoxy)phenyl]pyrazine (40 mg, 0.14 mmol) and N₂H₄ (88.69 mg, 2.77 mmol) in MeCN (2 mL) was stirred at 90° C. for 16 hours. After cooling to r.t., the mixture was diluted with EtOAc (40 mL), washed with H$_2$O (10 mL) and brine (10 mL), dried over Na$_2$SO$_4$, filtered and concentrated to give the crude product (40 mg) as a solid. LCMS R$_t$=0.70 min in 1.5 min chromatography, MS ESI calcd. for C$_{12}$H$_{12}$F$_3$N$_4$O [M+H]$^+$ 285.1, found 284.9.

A mixture of [6-methyl-5-[4-(trifluoromethoxy)phenyl]pyrazin-2-yl]hydrazine (40 mg, 0.14 mmol) and 2,2,2-trifluoroacetaldehyde (18.39 mg, 0.14 mmol, 75% in H$_2$O) in Ethanol (1 mL) was stirred at 100° C. for 3 hours. After cooling to r.t., the mixture was diluted with EtOAc (20 mL) and washed with H$_2$O (10 mL) and brine (10 mL), dried over Na$_2$SO$_4$, filtered and concentrated to give the crude (40 mg) as an oil, which was used directly without any further purification. LCMS R$_t$=0.91 min in 1.5 min chromatography, MS ESI calcd. for C$_{14}$H$_{11}$F$_6$N$_4$O [M+H]$^+$ 365.1, found 365.0.

To a solution of 6-methyl-N-(2,2,2-trifluoroethylideneamino)-5-[4-(trifluoromethoxy)phenyl]pyrazin-2-amine (40 mg, 0.11 mmol) in DMF (2 mL) was added NBS (21.5 mg, 0.12 mmol), and the mixture was stirred at 15° C. for 30 mins. The mixture was diluted with EtOAc (50 mL), washed with H$_2$O (10 mL×2) and brine (20 mL), dried over Na$_2$SO$_4$, filtered and concentrated to give the crude (50 mg) as an oil, which was used directly without any further purification. LCMS R$_t$=0.97 min in 1.5 min chromatography, 5-95AB, MS ESI calcd. for C$_{14}$H$_{10}$BrF$_6$N$_4$O [M+H+2]$^+$445.0, found 444.9.

To a solution of 2,2,2-trifluoro-N-[6-methyl-5-[4-(trifluoromethoxy)phenyl]pyrazin-2-yl]ethanehydrazonoyl bromide (50 mg, 0.11 mmol) in toluene (2 mL) was added Et$_3$N (0.08 mL, 0.56 mmol), and the solution was stirred at 15° C. for 30 mins. The mixture was diluted with EtOAc (40 mL), washed with H$_2$O (10 mL) and brine (20 mL), dried over Na$_2$SO$_4$, filtered and concentrated to give the crude product. The crude product was purified by Prep-TLC (silica gel, PE:EtOAc=3:1) to give the product (8.8 mg) as a solid. $^1$H NMR (400 MHZ, CDCl$_3$), δ$_H$=9.47 (s, 1H), 7.62 (d, 2H), 7.40 (d, 2H), 2.84 (d, 3H). LCMS R$_t$=1.15 min in 2.0 min chromatography, MS ESI calcd. for C$_{14}$H$_9$F$_6$N$_4$O [M+H]$^+$ 363.1, found 363.0.

Example 185: Efficacy of Exemplary Compounds in the Modulation of Late (Persistent) Sodium Current (INaL)

Functional characterization of exemplary compounds to modulate INaL expressed by the Nay 1.6 voltage-gated sodium channel was accomplished using the PatchXpress™ high throughput electrophysiology platform (Molecular Devices, Sunnyvale, Calif.). HEK-293 cells expressing recombinant, human Na$_V$1.6 (hNa$_V$1.6) were grown in DMEM/high-glucose Dulbecco's modified, 10% FBS, 2 mM sodium pyruvate, 10 mM HEPES and 400 μg/mL G418. Cells were grown to 50%-80% confluency prior to harvesting. Trypsinized cells were washed, allowed to recover for 1 hour and then resuspended in extracellular recording solution at a concentration of 1×10$^6$ cells/ml. The onboard liquid handling facility of the PatchXpress was used for dispensing cells and applying test compounds. Nay late currents were evoked by the application of 300 nM ATX-II. INaL was evoked by depolarizing pulses to 0 mV for 200 ms from a non-inactivating holding potential (e.g., −120 mV) at a frequency of 0.1 Hz. INaL amplitude and stability were determined by analyzing the mean current amplitude over the final 20 ms of the test pulse. Following steady state block with exemplary compounds (e.g., as described herein), a Na$^+$ free solution containing an impermeant cation (e.g., Choline or NDMG) was added to confirm the identify of the sodium current. Percent steady-state inhibition of INaL was calculated as: [(INaL_compound)/(INaL_control)]*100, where INaL_compound and INaL_control represent INaL recorded in the presence or absence of compound, respectively.

Results from this assay relating to percent inhibition of INaL at hNa$_V$1.5 (measured using procedure similar to described above but using HEK-293 cells expressing recombinant, human Na$_V$1.5 (hNa$_V$1.5) at 1 μM are summarized in Table 1 below. In this table, "A" indicates inhibition between less than 0% to 50% and "B" indicates inhibition of greater than 50%.

TABLE 1

| Compound | INaL v1.5 (1 μM, % Inhibition) |
|---|---|
| 1 | B |
| 2 | B |
| 3 | B |
| 6 | B |
| 7 | A |
| 8 | B |
| 9 | B |
| 10 | A |
| 11 | A |
| 12 | B |
| 13 | B |
| 14 | B |
| 15 | B |
| 16 | B |
| 17 | A |
| 18 | A |
| 19 | A |
| 21 | A |
| 22 | B |
| 23 | B |
| 24 | B |
| 25 | B |
| 26 | B |
| 27 | B |
| 28 | B |
| 29 | B |
| 30 | B |
| 31 | B |

Results from this assay relating to percent inhibition of INaL at hNaV1.6 at 1 μM are summarized in Table 2 below. In this table, "A" indicates inhibition of less than 30%; "B" indicates inhibition of between about 30% to about 70%; and "C" indicates inhibition of greater than 70%.

TABLE 2

| Compound | INaL v1.6 (1 μM, % Inhibition) |
|---|---|
| 1 | C |
| 2 | C |
| 3 | C |
| 4 | A |
| 5 | C |
| 6 | B |
| 7 | B |
| 8 | B |
| 9 | B |
| 10 | B |
| 11 | A |
| 12 | C |
| 13 | C |
| 14 | C |
| 15 | C |
| 16 | C |
| 17 | B |
| 18 | A |
| 19 | A |

TABLE 2-continued

| Compound | INaL v1.6 (1 µM, % Inhibition) |
|---|---|
| 20 | A |
| 21 | A |
| 22 | C |
| 23 | C |
| 24 | C |
| 25 | B |
| 26 | C |
| 27 | C |
| 28 | C |
| 29 | C |
| 30 | C |
| 31 | C |
| 32 | B |
| 33 | C |
| 34 | C |
| 35 | A |
| 36 | A |
| 37 | C |
| 38 | B |
| 39 | A |
| 40 | A |
| 41 | C |
| 42 | B |
| 43 | B |
| 44 | C |
| 45 | A |
| 46 | C |
| 47 | B |
| 48 | A |
| 49 | C |
| 50 | B |
| 51 | A |
| 52 | B |
| 54 | A |
| 55 | A |
| 56 | C |
| 57 | A |
| 58 | B |
| 59 | B |
| 60 | B |
| 61 | C |
| 62 | B |
| 63 | C |
| 64 | A |
| 65 | C |
| 66 | C |
| 67 | A |
| 68 | B |
| 69 | B |
| 70 | B |
| 71 | B |
| 72 | A |
| 73 | B |
| 74 | A |
| 75 | A |
| 76 | B |
| 77 | C |
| 78 | B |
| 79 | C |
| 80 | B |
| 81 | B |
| 82 | B |
| 83 | B |
| 84 | C |
| 85 | A |
| 86 | B |
| 87 | A |
| 88 | B |
| 89 | C |
| 91 | B |
| 92 | A |
| 93 | C |
| 94 | B |
| 95 | A |
| 96 | C |
| 97 | C |
| 98 | C |
| 99 | A |
| 100 | B |
| 101 | B |
| 102 | A |
| 103 | B |
| 104 | A |
| 105 | B |
| 106 | C |
| 107 | C |
| 108 | C |
| 111 | C |
| 112 | B |
| 113 | C |
| 114 | B |
| 115 | B |
| 116 | C |
| 117 | C |
| 118 | C |
| 119 | A |
| 120 | C |
| 121 | C |
| 122 | C |
| 123 | C |
| 124 | C |
| 125 | C |
| 126 | C |
| 127 | C |
| 128 | C |
| 129 | A |
| 130 | B |
| 131 | A |
| 132 | A |
| 133 | C |
| 134 | C |
| 135 | C |
| 136 | C |
| 137 | B |
| 138 | A |
| 139 | A |
| 140 | B |
| 141 | B |
| 142 | C |
| 143 | A |
| 144 | A |
| 145 | A |
| 146 | B |
| 147 | C |
| 148 | A |
| 149 | C |
| 150 | A |
| 151 | B |
| 152 | C |
| 153 | A |
| 154 | A |
| 155 | A |
| 156 | A |
| 157 | B |
| 158 | B |
| 159 | B |
| 160 | A |
| 161 | A |
| 162 | C |
| 163 | A |
| 164 | B |
| 165 | C |
| 166 | B |
| 167 | B |
| 168 | B |
| 169 | A |
| 170 | A |
| 171 | A |
| 172 | A |
| 173 | B |
| 174 | B |
| 175 | C |
| 176 | A |
| 177 | A |
| 178 | B |
| 179 | B |

TABLE 2-continued

| Compound | INaL v1.6 (1 µM, % Inhibition) |
|---|---|
| 180 | A |
| 181 | A |
| 183 | A |
| 184 | A |
| 185 | A |
| 186 | A |
| 187 | C |
| 188 | B |
| 189 | A |
| 190 | A |
| 191 | A |
| 192 | A |
| 193 | A |
| 194 | B |
| 195 | A |
| 196 | A |
| 197 | B |
| 198 | B |
| 199 | C |
| 200 | C |
| 201 | A |

Example 186: PK Rat Clearance Experiment

The IV dosing solution was prepared freshly on the dosing day. Test article (0.5 mg/kg) was prepared in a vehicle, for example, consisting of 5% DMSO/5% solutol/90% water. The concentrations of test article in all dosing solutions were determined by HPLC/UV. Three male Sprague-Dawley rats were used in this study. The animals were confirmed healthy before being assigned to the study. Each animal was given a unique identification number which was marked on the tail or the ear, and written on the cage card. All animals were fasted overnight before dosing and the food was returned at 4 hours post dosing. Water was provided to all animals ad libitum during the fasting period. Animals were weighed prior to dose administration on the day of dosing for calculating the actual dose volume. The body weights were in the range from 212 g to 223 g for males. All animals received test article by single intravenous bolus administration at 0.5 mg/kg. Approximately 0.2 mL blood was collected at each time point via jugular vein from each study animal. The actual time for each sample collection was recorded (0.0833, 0.250, 0.500, 1.00, 2.00, 4.00, 8.00, 12.0, 24.0 hrs). All blood samples were transferred into pre-labeled plastic micro centrifuge tubes and mixed with the pre-loaded anti-coagulant K2EDTA (5 µL, 0.5 M). Plasma samples were then prepared by centrifuging the blood samples. All plasma samples were then quickly frozen over dry ice and kept at −60° C. or lower until LC/MS/MS analysis. The concentrations of test article in plasma were determined by using a quantitative bioanalytical LC/MS/MS method. The lower limit of quantitation (LLOQ) for test article in plasma was 1 ng/mL, and the upper limit of quantitation (ULOQ) in plasma was 3000 ng/mL. The plasma concentration of test article in rats was subjected to a non compartmental pharmacokinetic analysis by using the Phoenix WinNonlin software (version 6.3, Pharsight, Mountain View, Calif.). The linear/log trapezoidal rule was applied in obtaining the PK parameters. The results are summarized in Table 3.

TABLE 3

| Rat Clearance and half life Data | | |
|---|---|---|
| Compound No. | Clearance (mL/min/kg) | $T_{1/2}$ (h) |
| 23 | 1.4 | 21.9 |
| 61 | 1.6 | 15.2 |
| 31 | 2 | 15.4 |
| 46 | 4.7 | 4.5 |
| 12 | 5.1 | 1.4 |
| 3 | 6 | 6.7 |
| 49 | 7.6 | 8.1 |
| 63 | 8.8 | 10.2 |
| 6 | 9.2 | 3.2 |
| 134 | 10.9 | 2.6 |
| 107 | 13.9 | 1.9 |
| 68 | 15.8 | 1.5 |
| 124 | 15.9 | 6.5 |
| 22 | 16.6 | 0.6 |
| 84 | 21.9 | 2.1 |
| 69 | 28.3 | 2.5 |
| 30 | 29 | 0.36 |
| 65 | 31 | 0.55 |
| 14 | 32.8 | 1.4 |
| 59 | 39.8 | 0.8 |
| 16 | 52.3 | 0.49 |
| 27 | 88.1 | 0.7 |
| 26 | 89.2 | 0.7 |

Example 187: CYP1A2 Inhibition in Human Liver Microsomes

Pooled human liver microsomes were incubated with individual CYP, CYP1A2, isozyme-specific marker substrate (Phenacetin) in the presence of test compound at various concentrations (0.05, 0.15, 0.5, 1.5, 5, 15, 50 uM). The specific marker metabolites are measured with LC/MS/MS. The remaining enzymatic activities and inhibitory potency IC50 are determined.

Procedure:

Microsomes are removed out of the −80° C. freezer to thaw on ice and 20 µL of the substrates solution added to the corresponding wells. Then 20 µL PB was added to blank wells and 2 µL of the test compounds and positive control working solution added to the corresponding wells. 2 µL of solvent was added to No Inhibitor wells and Blank wells. Then 158 µL of the HLM working solution was added to all wells of the incubation plate. The plate was pre-warmed for about 10 min using a 37° C. water bath. Then 20 µL of the NADPH cofactor solution was added to all incubation wells, mixed and incubated for 10 minutes at 37° C. water bath. The reaction is terminated by adding 400 µL cold stop solution (200 ng/mL Tolbutamide and 200 ng/mL Labetalol in ACN). The samples were centrifuged at 4000 rpm for 20 minutes to precipitate protein. Finally 200 µL of the supernatant was transferred to 100 µL HPLC water, shaken for 10 min and analyzed by LC/MS/MS.

Data Analysis

SigmaPlot (V.11) was used to plot % control activity versus the test compound concentrations, and for non-linear regression analysis of the data. IC50 values were determined using 3-parameter logistic equation. IC50 values are reported as ">50 µM" when % inhibition at highest concentration (50 µM) is less than 50%. Equation for three parameters logistic sigmoidal curve:

$$y = \frac{max}{1 + \left(\frac{x}{IC_{50}}\right)^{-hillslope}}$$

Results from this assay are summarized in Table 4 below. In this table, "A" indicates inhibition of less than 1 µM; "B" indicates inhibition of between about 1 µM to about 15 µM; "C" indicates inhibition of between about 15 µM to about 30 µM; and "D" indicates inhibition of greater than 30 µM.

TABLE 4

CYP1A2 Inhibition in Human Liver Microsomes

| Compound No. | CYP1A2 IC$_{50}$ mean |
|---|---|
| 62 | A |
| 98 | A |
| 1 | A |
| 76 | A |
| 48 | A |
| 70 | A |
| 116 | A |
| 79 | A |
| 97 | A |
| 122 | A |
| 41 | A |
| 118 | A |
| 56 | A |
| 47 | A |
| 112 | B |
| 46 | B |
| 52 | B |
| 108 | B |
| 113 | B |
| 73 | B |
| 72 | B |
| 6 | B |
| 3 | B |
| 12 | B |
| 66 | B |
| 77 | B |
| 84 | B |
| 136 | B |
| 117 | C |
| 49 | C |
| 63 | C |
| 105 | C |
| 30 | C |
| 134 | D |
| 126 | D |
| 125 | D |
| 124 | D |
| 96 | D |
| 78 | D |
| 42 | D |
| 107 | D |
| 127 | D |
| 135 | D |
| 65 | D |
| 43 | D |
| 59 | D |
| 68 | D |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:
1. A compound of Formula (VII):

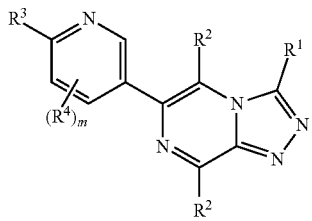

or a pharmaceutically acceptable salt thereof,
wherein:
  $R^1$ is hydrogen, $CH_3$, $C_{1-6}$ haloalkyl, O-phenyl, $C_{3-8}$ carbocyclyl, or phenyl, wherein the $CH_3$, $C_{1-6}$ haloalkyl, O-phenyl, $C_{3-8}$ carbocyclyl, or phenyl is optionally substituted with one or more substituents independently selected from the group consisting of halo, $OR^c$, and 3-8 membered heterocyclyl;
  each $R^2$ is independently hydrogen, halo, or $C_{1-6}$ alkyl;
  $R^3$ is halo, cyano, nitro, $C_{1-6}$ alkyl, $C(O)R^c$, $C(O)N(R^d)_2$, $C(O)OR^c$, $N(R^d)_2$, $OR^7$, $C_{3-8}$ carbocyclyl, or 3-8 membered heterocyclyl, wherein the $C_{1-6}$ alkyl, $C_{3-8}$ carbocyclyl, or 3-8 membered heterocyclyl is optionally substituted with one or more independently selected $R^5$ substituents;
  $R^4$ is cyano, nitro, $C_{1-6}$ alkyl, $C(O)R^c$, $C(O)N(R^d)_2$, $C(O)OR^c$, $N(R^d)_2$, $OR^c$, $C_{3-8}$ carbocyclyl, or 3-8 membered heterocyclyl, wherein the $C_{1-6}$ alkyl, $C_{3-8}$ carbocyclyl, or 3-8 membered heterocyclyl is optionally substituted with one or more independently selected $R^5$ substituents;
  each $R^5$ is independently halo, cyano, nitro, $C_{1-6}$ alkyl, $C(O)N(R^d)_2$, $N(R^d)_2$, $NR^dC(O)R^c$, $OR^c$, $S(O)_2R^c$, $S(O)_2N(R^d)_2$, $S(O)_2OR^c$, $C_{3-8}$ carbocyclyl, or 3-8 membered heterocyclyl;
  each $R^c$ is independently hydrogen or $C_{1-6}$ alkyl, wherein each $C_{1-6}$ alkyl is optionally and independently substituted with one or more independently selected $R^6$ substituents;
  each $R^d$ is independently hydrogen or $C_{1-6}$ alky];
  each $R^6$ is independently halo, cyano, $C_{3-8}$ carbocyclyl, or 3-8 membered heterocyclyl, wherein each $C_{3-8}$ carbocyclyl is optionally and independently substituted with one or more substituents independently selected from the group consisting of halo and cyano;
  $R^7$ is $C_{1-6}$ alkyl or $C_{3-8}$ carbocyclyl, wherein the $C_{1-6}$ alkyl or $C_{3-8}$ carbocyclyl is optionally substituted with one or more independently selected $R^6$ substituents; and
  m is 0, 1, or 2.

2. The compound of claim 1, or a pharmaceutically acceptable salt thereof, wherein $R^1$ is hydrogen, $CH_3$, $C_{1-6}$ haloalkyl, or $C_{3-8}$ carbocyclyl, wherein the $CH_3$, $C_{1-6}$ haloalkyl, or $C_{3-8}$ carbocyclyl is optionally substituted with one or more substituents independently selected from the group consisting of halo, $OR^c$, and 3-8 membered heterocyclyl.

3. The compound of claim 1, or a pharmaceutically acceptable salt thereof, wherein $R^1$ is $CHF_2$ or $CF_3$.

4. The compound of claim 1, or a pharmaceutically acceptable salt thereof, wherein at least one $R^2$ is hydrogen.

5. The compound of claim 1, or a pharmaceutically acceptable salt thereof, wherein $R^3$ is $OR^7$.

6. The compound of claim 1, or a pharmaceutically acceptable salt thereof, wherein $R^4$ is $C_{1-6}$ alkyl or $OR^c$.

7. The compound of claim 1, or a pharmaceutically acceptable salt thereof, wherein $R^4$ is $CH_3$.

8. The compound of claim 1, or a pharmaceutically acceptable salt thereof, wherein $R^7$ is:
  (i) $C_{1-6}$ alkyl, wherein the $C_{1-6}$ alkyl is optionally substituted with one, two, or three substituents independently selected from the group consisting of halo and cyano; or
  (ii) $C_{1-6}$ alkyl, wherein the $C_{1-6}$ alkyl is optionally substituted with one $C_{3-8}$ carbocyclyl, and further wherein the $C_{3-8}$ carbocyclyl is optionally substituted with one, two, or three substituents independently selected from the group consisting of halo and cyano; or
  (iii) $C_{3-8}$ carbocyclyl, wherein the $C_{3-8}$ carbocyclyl is optionally substituted with one, two, or three substituents independently selected from the group consisting of halo and cyano.

9. The compound of claim 1, or a pharmaceutically acceptable salt thereof, wherein $R^7$ is $C_{1-6}$ alkyl, wherein the $C_{1-6}$ alkyl is optionally substituted with one, two, or three independently selected halo substituents.

10. The compound of claim 1, or a pharmaceutically acceptable salt thereof, wherein m is 1 or 2.

11. The compound of claim 1, or a pharmaceutically acceptable salt thereof, wherein m is 1.

12. The compound of claim 1, wherein the compound is selected from the group consisting of:

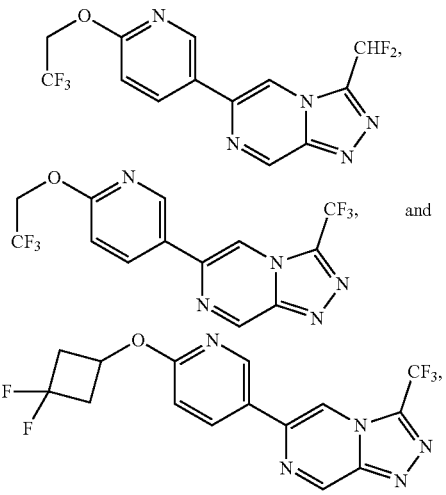

or a pharmaceutically acceptable salt thereof.

13. A pharmaceutical composition comprising a compound of claim 1, or a pharmaceutically acceptable salt thereof, and a pharmaceutically acceptable carrier.

14. A method for treating a neurological disorder or a psychiatric disorder in a subject, wherein the method comprises administering to a subject in need thereof a compound of claim 1, or a pharmaceutically acceptable salt thereof.

* * * * *

UNITED STATES PATENT AND TRADEMARK OFFICE
CERTIFICATE OF CORRECTION

PATENT NO. : 11,629,146 B2
APPLICATION NO. : 16/464468
DATED : April 18, 2023
INVENTOR(S) : Kiran Reddy et al.

It is certified that error appears in the above-identified patent and that said Letters Patent is hereby corrected as shown below:

In the Claims

In Column 357, Claim 1, Line 45, please replace "each $R^d$ is independently hydrogen or $C_{1-6}$ alky];" with --each $R^d$ is independently hydrogen or $C_{1-6}$ alkyl;--.

Signed and Sealed this
Fifteenth Day of August, 2023

Katherine Kelly Vidal
*Director of the United States Patent and Trademark Office*